US012606623B2

(12) United States Patent
Zhang et al.

(10) Patent No.: US 12,606,623 B2
(45) Date of Patent: *Apr. 21, 2026

(54) DLL3 TARGETING CHIMERIC ANTIGEN RECEPTORS AND BINDING AGENTS

(71) Applicants: ALLOGENE THERAPEUTICS, INC., South San Francisco, CA (US); PFIZER INC., New York, NY (US)

(72) Inventors: Yi Zhang, Foster City, CA (US); Thomas John Van Blarcom, Oakland, CA (US); Siler Panowski, Berkeley, CA (US); Silvia K. Tacheva-Grigorova, Redwood City, CA (US); Barbra Johnson Sasu, San Francisco, CA (US)

(73) Assignees: ALLOGENE THERAPEUTICS, INC., South San Francisco, CA (US); PFIZER INC., New York, NY (US)

( * ) Notice: Subject to any disclaimer, the term of this patent is extended or adjusted under 35 U.S.C. 154(b) by 579 days.

This patent is subject to a terminal disclaimer.

(21) Appl. No.: 18/308,143

(22) Filed: Apr. 27, 2023

(65) Prior Publication Data

US 2023/0287120 A1 Sep. 14, 2023

Related U.S. Application Data

(62) Division of application No. 16/802,822, filed on Feb. 27, 2020, now Pat. No. 11,673,953.

(60) Provisional application No. 62/969,976, filed on Feb. 4, 2020, provisional application No. 62/812,585, filed on Mar. 1, 2019.

(51) Int. Cl.
| | |
|---|---|
| *C07K 16/28* | (2006.01) |
| *A61K 40/11* | (2025.01) |
| *A61K 40/31* | (2025.01) |
| *A61K 40/42* | (2025.01) |
| *A61P 35/00* | (2006.01) |
| *C12N 5/0783* | (2010.01) |
| *C12N 15/63* | (2006.01) |
| *A61K 39/00* | (2006.01) |

(52) U.S. Cl.
CPC .......... *C07K 16/2809* (2013.01); *A61K 40/11* (2025.01); *A61K 40/31* (2025.01); *A61K 40/4202* (2025.01); *A61K 40/4204* (2025.01); *A61P 35/00* (2018.01); *C07K 16/2887* (2013.01); *C12N 5/0636* (2013.01); *C12N 15/63* (2013.01); *A61K 2039/505* (2013.01); *A61K 2239/31* (2023.05); *A61K 2239/38* (2023.05); *A61K 2239/55* (2023.05); *C07K 2317/24* (2013.01); *C07K 2317/565* (2013.01); *C07K 2317/622* (2013.01); *C07K 2319/70* (2013.01)

(58) Field of Classification Search
CPC ............ C07K 16/2809; C07K 16/2887; C07K 2317/24; C07K 2317/565; C07K 2317/622; C07K 2319/70; C07K 2319/03; C07K 2319/33; C07K 16/28; C07K 14/705; C07K 14/7051; C07K 14/70578; C07K 14/70596; C07K 16/18; A61K 40/11; A61K 40/31; A61K 40/4202; A61K 40/4204; A61K 2039/505; A61K 2239/31; A61K 2239/38; A61K 2239/55; A61K 2121/00; A61K 2300/00; A61K 40/42; A61P 35/00; C12N 5/0636; C12N 15/63; C12N 2510/00
See application file for complete search history.

(56) References Cited

U.S. PATENT DOCUMENTS

| | | | |
|---|---|---|---|
| 4,816,567 | A | 3/1989 | Cabilly et al. |
| 5,571,894 | A | 11/1996 | Wels et al. |
| 5,587,458 | A | 12/1996 | King et al. |
| 5,641,870 | A | 6/1997 | Rinderknecht |
| 5,821,337 | A | 10/1998 | Carter et al. |
| 5,827,642 | A | 10/1998 | Ridell et al. |
| 5,830,462 | A | 11/1998 | Crabtree et al. |
| 5,834,266 | A | 11/1998 | Crabtree et al. |
| 5,869,046 | A | 2/1999 | Presta et al. |
| 5,869,337 | A | 2/1999 | Crabtree et al. |
| 6,040,177 | A | 3/2000 | Ridell et al. |
| 6,075,181 | A | 6/2000 | Kucherlapati et al. |
| 6,165,787 | A | 12/2000 | Crabtree et al. |
| 6,248,516 | B1 | 6/2001 | Winter et al. |
| 6,319,494 | B1 | 11/2001 | Capon et al. |
| 6,797,514 | B2 | 9/2004 | Brenson et al. |
| 6,867,041 | B2 | 3/2005 | Berenson et al. |
| 6,905,874 | B2 | 6/2005 | Berenson et al. |
| 6,982,321 | B2 | 1/2006 | Winter et al. |

(Continued)

FOREIGN PATENT DOCUMENTS

| | | |
|---|---|---|
| EP | 404097 B1 | 9/1996 |
| JP | 2018506981 A | 3/2018 |

(Continued)

OTHER PUBLICATIONS

Examination Report issued in Singapore Application No. 11202108011U, mailed on Jul. 28, 2025, 2 pages.

(Continued)

*Primary Examiner* — Chun W Dahle
*Assistant Examiner* — Grace H Lunde
(74) *Attorney, Agent, or Firm* — Allogene Therapeutics, Inc.

(57) ABSTRACT

Provided herein are DLL3 binding agents and chimeric antigen receptors (CARs) comprising a DLL3 binding molecule that specifically binds to DLL3; and immune cells comprising these DLL3-specific CARs, e.g., CAR-T cells. Also provided are methods of making and using DLL3-specific CARs, and immune cells comprising DLL3-specific CARs.

26 Claims, 39 Drawing Sheets

Specification includes a Sequence Listing.

(56)     References Cited

U.S. PATENT DOCUMENTS

| | | | |
|---|---|---|---|
| 7,087,409 | B2 | 8/2006 | Barbas et al. |
| 7,527,791 | B2 | 5/2009 | Adams et al. |
| 7,709,226 | B2 | 5/2010 | Foote |
| 7,741,465 | B1 | 6/2010 | Eshhar et al. |
| 8,486,693 | B2 | 7/2013 | Park et al. |
| 11,673,953 | B2 | 6/2023 | Zhang et al. |
| 2003/0130496 | A1 | 7/2003 | Winter et al. |
| 2011/0286980 | A1 | 11/2011 | Brenner |
| 2012/0130076 | A1 | 5/2012 | Holt et al. |
| 2013/0209475 | A1 | 8/2013 | Richards et al. |
| 2014/0171649 | A1 | 6/2014 | Li et al. |
| 2014/0286987 | A1 | 9/2014 | Spencer et al. |
| 2014/0364590 | A1 | 12/2014 | Stull et al. |
| 2015/0266973 | A1 | 9/2015 | Jarjour et al. |
| 2016/0046700 | A1 | 2/2016 | Foster et al. |
| 2017/0088620 | A1 | 3/2017 | Nioi et al. |
| 2017/0283500 | A1 | 10/2017 | Wiltzius et al. |
| 2018/0044415 | A1 | 2/2018 | Escarpe et al. |
| 2018/0237511 | A1 | 8/2018 | Beil et al. |
| 2018/0296601 | A1 | 10/2018 | Rossi et al. |
| 2021/0107979 | A1 | 4/2021 | Zhang et al. |

FOREIGN PATENT DOCUMENTS

| | | |
|---|---|---|
| KR | 20170120158 A | 10/2017 |
| WO | WO9301161 A1 | 1/1993 |
| WO | WO1994025591 A1 | 11/1994 |
| WO | 2012058393 A2 | 5/2012 |
| WO | WO2012079000 A1 | 6/2012 |
| WO | WO2012129514 A1 | 9/2012 |
| WO | 2013126746 A2 | 8/2013 |
| WO | WO2014127261 A1 | 8/2014 |
| WO | WO2015090229 A1 | 6/2015 |
| WO | WO2015120096 A2 | 8/2015 |
| WO | WO2015127407 A1 | 8/2015 |
| WO | WO2016014565 A2 | 1/2016 |
| WO | WO2016090034 A2 | 6/2016 |
| WO | WO2016120218 A1 | 8/2016 |
| WO | WO2016126608 A1 | 8/2016 |
| WO | WO2016138038 A1 | 9/2016 |
| WO | 2016179319 A1 | 11/2016 |
| WO | 2017031458 A2 | 2/2017 |
| WO | WO2017021349 A1 | 2/2017 |
| WO | 2017172981 A2 | 10/2017 |
| WO | 2018017827 A1 | 1/2018 |
| WO | 2018073394 A2 | 4/2018 |
| WO | 2018195348 A1 | 10/2018 |
| WO | 2020180591 A1 | 9/2020 |

OTHER PUBLICATIONS

Saunders et al., A DLL3-targeted antibody-drug conjugate eradicates high-grade pulmonary neuroendocrine tumor-initiating cells in vivo, Sci Transl Med. Aug. 26, 2015;7(302):302ra136. doi: 10.1126/scitranslmed.aac9459.

Koshkin et al. (Jan. 1, 2019) "Transcriptomic and Protein Analysis of Small-cell Bladder Cancer (SCBC) Identifies Prognostic Biomarkers and DLL3 as a Relevant Therapeutic Target", Clinical Cancer Research, 25(1):210-221.

Puca et al. (Mar. 20, 2019) "Delta-like protein 3 Expression and Therapeutic Targeting in Neuroendocrine Prostate Cancer", Science Translational Medicine, 11(484):1-12.

Spino et al. (Feb. 2019) "Cell Surface Notch Ligand DLL3 is a Therapeutic Target in Isocitrate Dehydrogenase-mutant Glioma", Clinical Cancer Research, 25(4):1261-1271 (22 pages).

Saunders LR, et al., A DLL3-targeted antibody-drug conjugate eradicates high-grade pulmonary neuroendocrine tumor-initiating cells in vivo. Sci Transl Med. Aug. 26, 2015;7(302):302ra136; "Generation and characterization of DLL3-specific monoclonal antibodies" (Year: 2015).

Van Dijk, Marc A., et al., "Human antibodies as next generation therapeutics", Curr Opin Chem Biol, vol. 5, No. 4, pp. 368-374, (2001).

Vollmers, H. P., et al., "Death by Stress: Natural IgM-Induced Apoptosis", Methods Find Exp Clin Pharmacol 2005, 27(3): 185-191.

Vollmers, H. P., et al., "The "early birds": natural IgM antibodies and immune surveillance", Review, Histol Histopathol (2005) 20: 927-937.

Li et al., Increasing the safety and efficacy of chimeric antigen receptor T cell therapy. Protein Cell 2017, 8(8):573-589.

Novikova M.V. et al., The role of Notch pathway in carcinogenesis, Advances in Molecular Oncology, 2015, vol. 2, No. 3. (Russian language article with English language abstract).

Owonikiko et al. Two Novel Immunotherapy Agents Targeting DLL3 in SCLC: Trials in Progress of AMG 757 and AMG 119 (Abstract).

Sai Kiran Sharma et al., Non-invasive Interrogation of DLL3 Expression in Metastatic Small Cell Lung Cancer, Cancer Res, Jul. 15, 2017; 77(14): 3931-3941.

Al-Lazikani, Bissan , et al., "Standard Conformations for the Canonical Structures of Immunoglobulins", J. Mol. Biol. (1997) 273, 927-948.

Almagro , et al., "Humanization of antibodies", Frontiers in Bioscience, vol. 13, pp. 1619-1633, (2008).

Baca, Manuel , et al., "Antibody Humanization Using Monovalent Phage Display", The Journal of Biological Chemistry.

Basu, Sreemanti , et al., "Purification of Specific Cell Population by Fluorescence Activated Cell Sorting (FACS)", Journal of Visualized Experiments, (41), e1546, doi:10.3791/1546 (2010).

Brenner, Malcom K., et al., "Adoptive T Cell Therapy of Cancer", Curr Opin Immunol. Apr. 2010 ; 22(2): 251-257. doi:10.1016/j.coi. 2010.01.020.

Brinkmann, Ulrich , et al., "The making of bispecific antibodies", MABS, 2017, vol. 9, No. 2, 182-212.

Brodeur, Bernart R., et al., "Mouse-Human Myeloma Partners for the production of Heterohybridomas", Monoclonal Antibody Production Techniques and Applications, pp. 51-56, 3Mercel Dekker Inc, (1987).

Carter, Robert H., et al., "CD19: Lowering the Threshold for Antigen Receptor Stimulation of B Lymphocytes", Reports, Science, vol. 256 pp. 105-107.

Chothia, Cyrus , et al., "Conformations of immunoglobulin hypervariable regions", Nature. vol 342 . Dec. 21-28, 1989.

Chothia, Cyrus , et al., "Structural Repertoire of the Human VH Segments", J. Mol. Biol. (1992) 227, 799-917.

Courtois, Anthony , et al., "Complement dependent cytotoxicity activity of therapeutic antibody fragments is acquired by immunogenic glycan coupling", Research Article, Biotechnology of Human Disorders, Electronic Journal of Biotechnology, vol. 15 No. 5, Issue of Sep. 15, 2012.

Dall'Acqua, William F., et al., "Antibody humanization by framework shuffling", Methods, vol. 36, pp. 43-60, (2005).

EPO , "International Search Report & Written Opinion", mailed Aug. 5, 2020 for PCT/US2020/020042.

Eshhar, Zelig , et al., "Specific activation and targeting of cytotoxic lymphocytes through chimeric single chains consisting of antibody-binding domains and the gamma or zeta subunits of the immunoglobulin and T-cell receptors.", Immunology; Proc Natl Acad Sci U S A. Jan. 15, 1993; 90(2): 720-724.

Finney, Helen , et al., "Chimeric Receptors Providing Both Primary and Costimulatory Signaling in T Cells from a Single Gene Product", J Immunol Sep. 15, 1998, 161 (6) 2791-2797.

Flatman, Stephen , et al., "Process analytics for purification of monoclonal antibodies", J. Chromatogr. B 848 (2007) 79-87.

Gross, Gideon , et al., "Therapeutic Potential of T Cell Chimeric Antigen Receptors (CARs) in Cancer Treatment: Counteracting Off-Tumor Toxicities for Safe Car T Cell Therapy", Annual Review of Pharmacology and Toxicology; vol. 56:59-83 (Volume publication date Jan. 2016) https://doi.org/10.1146/annurev-pharmtox-010814-124844.

Holliger, Philipp , et al., ""Diabodies": Small bivalent and bispecific antibody fragments", Proc. Natl. Acad. Sci. USA, vol. 90, pp. 6444-6448, Jul. 1993, Biophysics.

Hudson, Peter J., et al., "Engineered antibodies", Review, National Medicine, vol. 9, No. 1, (2003).

(56)          References Cited

OTHER PUBLICATIONS

Kalos, Michael , et al., "T Cells with Chimeric Antigen Receptors Have Potent Antitumor Effects and Can Establish Memory in Patients with Advanced Leukemia", Science Transnational Medicine, vol. 3 Issue 95 95ra73, 2011.

Kam, Nadine Wong, et al., "Carbon nanotubes as multifunctional biological transporters and near-infrared agents for selective cancer cell destruction", PNAS, vol. 102, No. 33, pp. 11600-11605.

Karlsson, Robert , et al., "Kinetic and Concentration Analysis Using BIA Technology", Methods: A Companion to Methods in Enzymology 6, 99-110 (1994).

Kashmiri, Syed V.S., et al., "SDR grafting—a new approach to antibody humanization", Methods, vol. 36, pp. 25-34, (2005).

Klimka, A. , et al., "Human anti-CD30 recombinant antibodies by guided phage antibody selection using cell panning", British Journal of Cancer, vol. 83, No. 2, pp. 252-260, (2000).

Kozbor, Danuta , et al., "A Human Hybrid Myeloma for Production of Human Monoclonal Antibodies", The Journal of Immunology, vol. 133, No. 6 (1984).

Krause, Anja , et al., "Antigen-dependent CD28 Signaling Selectively Enhances Survival and Proliferation in Genetically Modified Activated Human Primary T Lymphocytes", The Journal of experimental medicine vol. 188,4 (1998): 619-26. doi:10.1084/jem.188.4.619.

Li, Jian , et al., "Human antibodies for immunotherapy development generated via a human B cell hybridoma technology", PNAS, vol. 103, No. 10, pp. 3557-3562.

Lonberg, Nils , "Fully human antibodies from transgenic mouse and phage display platforms", Current Opinion in Immunology, 2008, 20:450-459.

Lonberg, Nils , "Human antibodies from transgenic animals", Review, Nature Biotechnology, vol. 23, No. 9, pp. 1117-1125 (2005).

Morrison, Sherie L., et al., "Chimeric human antibody molecules: Mouse antigen-binding domains with human constant region domains", Proc. Natl. Acad. Sci., USA, vol. 81, pp. 6851-6855, (1984).

Muller, Dafne , et al., "Bispecific Antibodies for Cancer Immunotherapy", Review Article, Biodrugs 2010; 24 (2): 89-98.

Niculescu-Duvaz, I. , et al., "Antibody-directed enzyme prodrug therapy (ADEPT): a review", Advanced Drug Delivery Reviews 26 (1997) 151-172.

Osbourn, Jane , et al., "From rodent reagents to human therapeutics using antibody guided selection", , Methods, vol. 36, pp. 61-68, (2005).

Padlan, Eduardo A., et al., "A Possible Procedure for Reducing the Immunogenicity of Antibody Variable Domains While Preserving Their Ligand-Binding Properties", Mol. Immunol, vol. 28, pp. 489-498, (1991).

Payne, Gillian , "Progress in immunoconjugate cancer therapeutics", Pipeline, Cancer Cell, vol. 3, pp. 207-212, (2003).

Pluckthun, A. , "Antibodies from *Escherichia Coli*", The Pharmacology of Monoclonal Antibodies, Chapter 11, pp. 269-315 (1994).

Porter, David L., et al., "Chimeric Antigen Receptor-Modified T Cells in Chronic Lymphoid Leukemia", N Engl J Med 2011;365:725-33.

Presta, L. G., et al., "Humanization of an antibody directed against IgE.", J Immunol 1993; 151:2623-2632.

Riechmann, Lutz , et al., "Reshaping human antibodies for therapy", Nature, vol. 332, pp. 323-327, (1998).

Rosenberg, Steven A., et al., "Adoptive cell transfer: a clinical path to effective cancer immunotherapy", Nat Rev Cancer. Apr. 2008 ; 8(4): 299-308. doi:10.1038/nrc2355.

Rosok, Mae Joanne, et al., "A Combinatorial Library Strategy for the Rapid Humanization of Anticarcinoma BR96 Fab", The Journal of Biological Chemistry, vol. 271, No. 37, Issue of Sep. 13, pp. 22611-22618, 1996.

Sadelain, Michel , et al., "The promise and potential pitfalls of chimeric antigen receptors", Current Opinion in Immunology 2009, 21:215-223.

Sims, M. J., et al., "A humanized CD18 antibody can block function without cell destruction", J Immunol 1993; 151:2296-2308.

Song, De-Gang , et al., "CD27 costimulation augments the survival and antitumor activity of redirected human T cells in vivo", Blood (2012) 119 (3): 696-706.

Stockmeyer, Bernhard , et al., "Triggering FCa-Receptor I (CD89) Recruits Neutrophils as Effector Cells for CD20-Directed Antibody Therapy", J Immunol 2000; 165:5954-5961.

Syrigos, Konstantinos , et al., "Antibody Directed Enzyme Prodrug Therapy (ADEPT): A Review of the Experimental and Clinical Considerations", Review, Anticancer Re~Earch 19: 605-614 (1999).

Trail, Pamela A., et al., "Monoclonal antibody drug immunoconjugates for targeted treatment of cancer", Symposium in Writing, Cancer Immunol Immunother (2003) 52: 328-337.

Tramontano, Anna , et al., "Framework Residue 71 is a Major Determinant of the Position and Conformation of the Second Hypervariable Region in the V H Domains of Immunoglobulins", J. Mol. Biol. (1990) 215, 175-182.

Murphy et al. (Journal of Immunological Methods, vol. 463, p. 127-133, 2018) (Year: 2018).

Edwards et al. 2003. The remarkable flexibility of the human antibody repertoire; isolation of over one thousand different antibodies to a single protein, BlyS. Journal of Molecular Biology 334:103-118 (Year: 2003).

Canadian Office Action for Canadian Patent Application No. 3131908, mailed on May 24, 2023, 4 pages.

Canadian Office Action for Canadian Patent Application No. 3131908, mailed on Oct. 15, 2024, 6 pages.

European Office Action issued in European Application No. 20715560.7, mailed on Apr. 11, 2024, 5 pages.

European Office Action issued in European Application No. 20715560.7, mailed on Dec. 19, 2024, 5 pages.

International Preliminary Report on Patentability received for PCT Application No. PCT/US2020/020042, mailed on Sep. 16, 2021, 14 pages.

Invitation to Pay Additional Fees for International Application No. PCT/US2020/020042, mailed on Jun. 15, 2020, 13 pages.

Non-Final Office Action in U.S. Appl. No. 16/802,822, mailed on Jul. 1, 2022, 14 pages.

Notice of Allowance issued in U.S. Appl. No. 16/802,822, mailed on Feb. 1, 2023, 12 pages.

Caldas et al. (May 1, 2003) "Humanization of the Anti-CD18 Antibody 6.7: an Unexpected Effect of a Framework Residue in Binding to Antigen", Molecular Immunology, 39(15):941-952.

Dondelinger et al. (Oct. 16, 2018) "Understanding the Significance and Implications of Antibody Numbering and Antigen-Binding Surface/Residue Definition", Frontiers in Immunology, 9(2278): 1-15.

Du et al. (2008) "Molecular Basis of Recognition of Human Osteopontin by 23C3, a Potential Therapeutic Antibody for Treatment of Rheumatoid Arthritis", Journal of Molecular Biology, 382(4):835-842.

Sela-Culang et al. (Oct. 8, 2013) "The Structural Basis of Antibody-Antigen Recognition", Frontiers in Immunology, 4(302):1-13.

Torres et al. (Feb. 2008) "The Immunoglobulin Constant Region Contributes to Affinity and Specificity", Trends in Immunology, 29(2):91-97.

Winkler et al. (Oct. 15, 2000) "Changing the Antigen Binding Specificity by Single Point Mutations of an Anti-p24 (HIV-1) Antibody", The Journal of Immunology, 165(8):4505-4514.

Colombian Office Action for Colombian Patent Application No. NC2021/0011326, mailed on Jan. 7, 2025, p. 15.

FIG. 2B

| SEQ ID NO | Name/Compon ent | Sequence |
|---|---|---|
| 556 | Human DLL3 complete ECD | METDTLLLWVLLLWVPGSTGYPYDVPDYAGMLAGVFELQIHSFGPGPGPAPRSPCSARL PCRLFFRVCLKPGLSEEAAESPCALGAALSARGPVYTEQPGAPAPDLPLPDGLLQVPFRD AWPGTFSFIIETWREELGDQIGGPAWSLLARVAGRRRLAAGGPWARDIQRAGAWELRFSY RARCEPPAVGTACTRLCRPRSAPSRCGPGLRPCAPLEDECEAPLVCRAGCSPEHGFCEQP GECRCLEGWTGPLCTVPVSTSSCLSPRGPSSATTGCLVPGPGPCDGNPCANGGSCSETPR SFECTCPRGFYGLRCEVSGVTCADGPCFNGGLCVGGADPDSAYICHCPPGFQGSNCEKRV DRCSLQPCRNGGLCLDLGHALRCRCRAGFAGPRCEHDLDDCAGRACANGGTCVEGGAHR CSCALGFGGRDCRERADPCAARPCAHGGRCYAHFSGLVCACAPGYMGARCEFPVHPDGAS ALPAAPPGLRPGDPQRYLLPPALGLLVAAGVAGAALLLVHVRRRGHSQDAGSRLLAGTPE PSVHALPDALNNLRTQEGSGDGPSSSVDWNRPEDVDPQGIYVISAPSIYAREVATPLFPP LHTGRAGQRQHLLFPYPSSILSVK |
| 557 | Human DLL3 DSL-EGF6 | METDTLLLWVLLLWVPGSTGYPYDVPDYAGMLGSARCEPPAVGTACTRLCRPRSAPSRCG PGLRPCAPLEDECEAPLVCRAGCSPEHGFCEQPGECRCLEGWTGPLCTVPVSTSSCLSPR GPSSATTGCLVPGPGPCDGNPCANGGSCSETPRSFECTCPRGFYGLRCEVSGVTCADGPC FNGGLCVGGADPDSAYICHCPPGFQGSNCEKRVDRCSLQPCRNGGLCLDLGHALRCRCRA GFAGPRCEHDLDDCAGRACANGGTCVEGGAHRCSCALGFGGRDCRERADPCAARPCAHG GRCYAHFSGLVCACAPGYMGARCEFPVHPDGASALPAAPPGLRPGDPQRYLLPPALGLLV AAGVAGAALLLVHVRRRGHSQDAGSRLLAGTPEPSVHALPDALNNLRTQEGSGDGPSSSV DWNRPEDVDPQGIYVISAPSIYAREVATPLFPPLHTGRAGQRQHLLFPYPSSILSVK |
| 558 | Human DLL3 EGF1- EGF6 | METDTLLLWVLLLWVPGSTGYPYDVPDYAGMLGSAPLVCRAGCSPEHGFCEQPGECRCLE GWTGPLCTVPVSTSSCLSPRGPSSATTGCLVPGPGPCDGNPCANGGSCSETPRSFECTCP RGFYGLRCEVSGVTCADGPCFNGGLCVGGADPDSAYICHCPPGFQGSNCEKRVDRCSLQP CRNGGLCLDLGHALRCRCRAGFAGPRCEHDLDDCAGRACANGGTCVEGGAHRCSCALGF GGRDCRERADPCAARPCAHGGRCYAHFSGLVCACAPGYMGARCEFPVHPDGASALPAAPP GLRPGDPQRYLLPPALGLLVAAGVAGAALLLVHVRRRGHSQDAGSRLLAGTPEPSVHALP DALNNLRTQEGSGDGPSSSVDWNRPEDVDPQGIYVISAPSIYAREVATPLFPPLHTGRAG QRQHLLFPYPSSILSVK |

FIG. 2C

| SEQ. ID. NO. | Name/ Component | Sequence |
|---|---|---|
| 559 | Human DLL3 EGF2- EGF6 | METDTLLLWVLLLWVPGSTGYPYDVPDYAGMLGSGPGPCDGNPCANGGSCSETPRSFECT CPRGFYGLRCEVSGVTCADGPCFNGGLCVGGADPDSAYICHCPPGFQGSNCEKRVDRCSL QPCRNGGLCLDLGHALRCRCRAGFAGPRCEHDLDDCAGRACANGGTCVEGGAHRCSCAL GFGGRDCRERADPCAARPCAHGGRCYAHFSGLVCACAPGYMGARCEFPVHPDGASALPAA PPGLRPGDPQRYLLPPALGLLVAAGVAGAALLLVHVRRRGHSQDAGSRLLAGTPEPSVHA LPDALNNLRTQEGSGDGPSSSVDWNRPEDVDPQGIYVISAPSIYAREVATPLFPPLHTGR AGQRQHLLFPYPSSILSVK |
| 560 | Human DLL3 EGF3- EGF6 | METDTLLLWVLLLWVPGSTGYPYDVPDYAGMLGSSGVTCADGPCFNGGLCVGGADPDSAY ICHCPPGFQGSNCEKRVDRCSLQPCRNGGLCLDLGHALRCRCRAGFAGPRCEHDLDDCAG RACANGGTCVEGGAHRCSCALGFGGRDCRERADPCAARPCAHGGRCYAHFSGLVCACAP GYMGARCEFPVHPDGASALPAAPPGLRPGDPQRYLLPPALGLLVAAGVAGAALLLVHVRR RGHSQDAGSRLLAGTPEPSVHALPDALNNLRTQEGSGDGPSSSVDWNRPEDVDPQGIYVI SAPSIYAREVATPLFPPLHTGRAGQRQHLLFPYPSSILSVK |
| 561 | Human DLL3 EGF4- EGF6 | METDTLLLWVLLLWVPGSTGYPYDVPDYAGMLGSRVDRCSLQPCRNGGLCLDLGHALRCR CRAGFAGPRCEHDLDDCAGRACANGGTCVEGGAHRCSCALGFGGRDCRERADPCAARPC AHGGRCYAHFSGLVCACAPGYMGARCEFPVHPDGASALPAAPPGLRPGDPQRYLLPPALG LLVAAGVAGAALLLVHVRRRGHSQDAGSRLLAGTPEPSVHALPDALNNLRTQEGSGDGPS SSVDWNRPEDVDPQGIYVISAPSIYAREVATPLFPPLHTGRAGQRQHLLFPYPSSILSVK |
| 562 | Human DLL3 EGF5- EGF6 | METDTLLLWVLLLWVPGSTGYPYDVPDYAGMLGSDLDDCAGRACANGGTCVEGGAHRCS CALGFGGRDCRERADPCAARPCAHGGRCYAHFSGLVCACAPGYMGARCEFPVHPDGASAL PAAPPGLRPGDPQRYLLPPALGLLVAAGVAGAALLLVHVRRRGHSQDAGSRLLAGTPEPS VHALPDALNNLRTQEGSGDGPSSSVDWNRPEDVDPQGIYVISAPSIYAREVATPLFPPLH TGRAGQRQHLLFPYPSSILSVK |
| 563 | Human DLL3 EGF6 | METDTLLLWVLLLWVPGSTGYPYDVPDYAGMLGSRADPCAARPCAHGGRCYAHFSGLVCA CAPGYMGARCEFPVHPDGASALPAAPPGLRPGDPQRYLLPPALGLLVAAGVAGAALLLVH VRRRGHSQDAGSRLLAGTPEPSVHALPDALNNLRTQEGSGDGPSSSVDWNRPEDVDPQGI YVISAPSIYAREVATPLFPPLHTGRAGQRQHLLFPYPSSILSVK |

DLL3 CAR domain structure

FIG. 3C

| Clone | Transduction efficiency (Donor 116) | Transduction efficiency (Donor 419) |
|---|---|---|
| 2C3 | 31.0 % | 22.7 % |
| 2G1 | 66.9 % | 49.1 % |
| 3E4 | 58.3 % | 46.4 % |
| 3F2 | 16.3 % | 12.2 % |
| 4F9 | 67.5 % | 49.4 % |
| 4G9 | 48.9 % | 35.2 % |
| 6H1 | 5.81 % | 2.70 % |
| 6H5 | <0.1% | <0.1% |
| 10D1 | <0.1% | <0.1% |
| 11F6 | 15.2 % | 4.08 % |
| 11H7 | 52.4 % | 40.2 % |
| 16H7 | 42.7 % | 27.1 % |
| 17A2 | 68.6 % | 43.3 % |

| Clone | Transduction efficiency (Donor 116) | Transduction efficiency (Donor 117) |
|---|---|---|
| 2A6.C5 | 37.2 % | 37.7 % |
| 2D3 | 46.1 % | 47.4 % |
| 5A2 | 49.1 % | 47.4 % |
| 5C1.A4 | 0.31 % | NA |
| 5E12 | 53.8 % | 49.1 % |
| 6D8 | 32.4 % | 34.8 % |
| 7F9 | 42.2 % | 37.4 % |
| 8E11 | 39.1 % | 41.4 % |
| 9D3 | 52.4 % | 50.8 % |
| 9F7 | 0.24 % | 0.15 % |
| 26C8 | 48.9 % | 46.9 % |

FIG. 3D

| Clone | Transduction efficiency (Donor 503) | Transduction efficiency (Donor 772) |
|---|---|---|
| 4H5 | <0.1% | <0.1% |
| 6F8 | 59.4% | 26.7% |
| 3G6 - L1 | 35% | 14.2% |
| 3G6 - L2 | 33.5% | 16.9% |
| 4C6 | 56.9% | 25.2% |
| 3B9 | <0.1% | <0.1% |
| 4E6 | 37.8% | 24.8% |
| 3F9-L | 19.5% | 13.8% |
| 4H8 | 39.3% | 27.2% |
| 3E10 | <0.1% | 0.43% |
| 3C3 | <0.1% | 0.14% |
| 11F4 | <0.1% | 0.43% |
| 9H12-K | 41.4% | 35.6% |
| 10E12 | <0.1% | 0.98% |
| 10G1-K | 53.7% | 33.7% |
| 11A3 | 42.1% | 20% |

| Clone | Transduction efficiency (Donor 419) | Transduction efficiency (Donor 503) |
|---|---|---|
| 3B11 | 57.3% | 65.8% |
| 4E1 | 2.35% | 3.18% |
| 5G2 | 36.7% | 42.8% |
| 2404.6H1 | 6.01% | 6.41% |
| 2A8-K | <0.1% | <0.1% |
| 3B1 | 6.15% | 7.95% |
| 9B5 | <0.1% | <0.1% |
| 11E4 | 54.8% | 62.8% |
| 2404.8E11 | NA | 58.9% |
| 11A5 | NA | 0.11% |
| 10A2 | 58.5% | 67.6% |
| 11A8 | 33.4% | 45.1% |

NA, not available

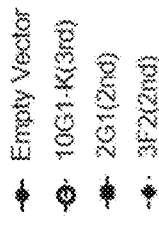
FIG. 4C
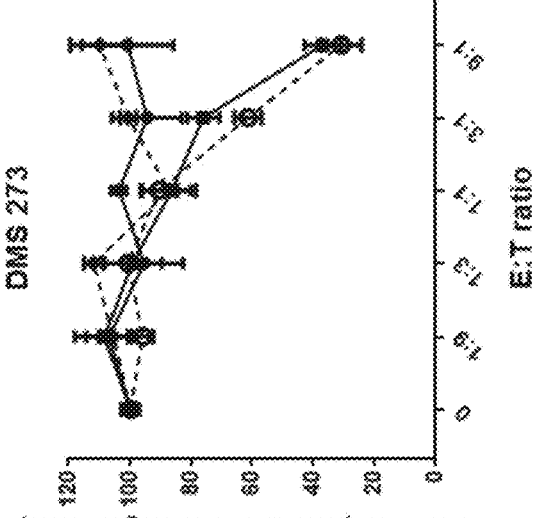
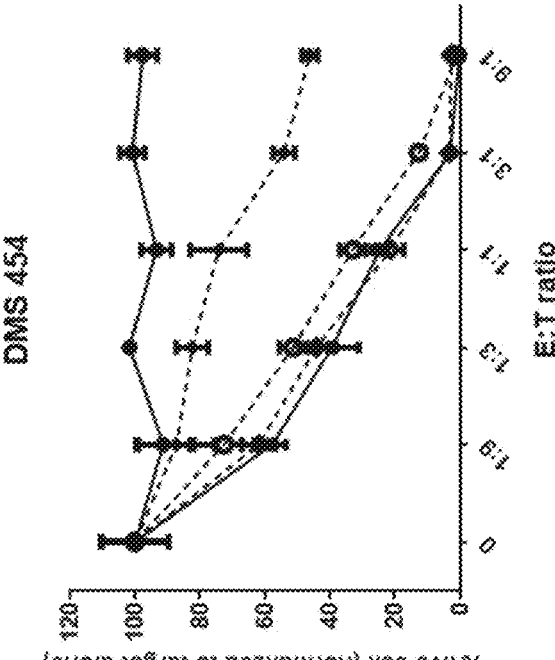

Non-transduced T Cells     10G1-K     2G1

Spleen

Pituitary

Brain

LN229-mDLL3 Subcutaneous tumor

Non-transduced T cells

DLL3 CAR-T

NSG mice

AAV (IL-7 & IL-15)    SC Tumor    CAR T (IV)    Tox evaluation

Day    -3    0    22    49

Non-transduced T cells

DLL3 CAR-T

CAR T dosing

Tumor volume (mm3)

Human CD3 Staining Score (Day 49)

| Group | Animal | Brain | Pituitary |
|---|---|---|---|
| Non-transduced T cells | #1 | 1 | 1 |
| | #2 | 1 | 1 |
| | #3 | 1 | 1 |
| DLL3 CAR T | #4 | 2 | 3 |
| | #5 | 1 | 3 |
| | #6 | 1 | 3 |

Staining score:
0 = No staining
1 = Sparse-to-moderately low staining
2 = Moderate-to-moderately high staining
3 = Abundant staining

FIG. 14D

Histopathology Analysis (Day 49)

| Group | Animal | Brain | Pituitary |
|---|---|---|---|
| Non-transduced T cells | #1 | NSML | NSML |
| | #2 | NSML | NSML |
| | #3 | NSML | NSML |
| DLL3 CAR T | #4 | NSML | Infiltrate, mixed cell (severity*=3) |
| | #5 | NSML | Infiltrate, mononuclear cell(severity=2) |
| | #6 | NSML | Infiltrate, mononuclear cell(severity=2) |

NSML=No Significant Microscopic Lesions
*Severity: 1=Minimal; 2=Mild; 3=Moderate

FIG. 15C

Human CD45 Staining Score (Day 36 or 38)

| Group | Animal | Brain | Pituitary | Spleen |
|---|---|---|---|---|
| Non-transduced T cells | #1 | 1 | 1 | 3 |
| | #2 | 1 | 1 | 3 |
| | #3 | 1 | 1 | 3 |
| | #4 | 1 | 1 | 3 |
| | #5 | 1 | 1 | 3 |
| DLL3 CAR T | #6 | 1 | 2 | 3 |
| | #7 | 1/2 | 1/2 | 3 |
| | #8 | 1 | 1/2 | 3 |
| | #9 | 1 | 1/2 | 3 |
| | #10 | 1 | 1/2 | 2 |
| EGFRvIII CAR T | #11 | 1 | 1 | 2 |
| | #12 | 1 | 1 | 3 |
| | #13 | 1 | 1 | 2 |
| | #14 | 1 | 1 | 3 |
| | #15 | 1 | 1 | 3 | hCD45 Staining score:
0 = No staining
1 = Rare/Sparse staining
2 = Sparse-to-moderately low staining
3 = Moderate-to-moderately high staining
4 = Abundant staining

FIG. 15D

Histopathology Analysis (Day 36 or 38)

| Group | Animal | Brain | Pituitary |
|---|---|---|---|
| Non-transduced T cells | #1 | NSML | NSML |
| | #2 | Tumor present | NSML |
| | #3 | Tumor present | NSML |
| | #4 | Tumor present | NSML |
| | #5 | Tumor present | NSML |
| | #6 | Tumor present | Infiltrate, mononuclear cell (severity=2) |
| | #7 | Tumor present | Infiltrate, mononuclear cell (severity=2) |
| DLL3 CAR T | #8 | Tumor present | Infiltrate, mononuclear cell (severity=1) |
| | #9 | NSML | Infiltrate, mononuclear cell (severity=2) |
| | #10 | NSML | Infiltrate, mononuclear cell (severity=2) |
| EGFRvIII CAR T | #11 | NSML | NSML |
| | #12 | NSML | NSML |
| | #13 | NSML | NSML |
| | #14 | NSML | NSML |
| | #15 | NSML | NSML |

NSML=No Significant Microscopic Lesions
**Severity: 1=Minimal; 2=Mild; 3=Moderate

SEQUENCE LISTING

```
Sequence total quantity: 696
SEQ ID NO: 1          moltype = AA  length = 9
FEATURE               Location/Qualifiers
source                1..9
                      mol_type = protein
```

-continued

```
                          organism = synthetic construct
                          note = Description of Artificial Sequence: Synthetic peptide
SEQUENCE: 1
NSISNYYWS                                                          9

SEQ ID NO: 2              moltype = AA   length = 12
FEATURE                   Location/Qualifiers
source                    1..12
                          mol_type = protein
                          organism = synthetic construct
                          note = Description of Artificial Sequence: Synthetic peptide
SEQUENCE: 2
AYIYYSGTTN YN                                                     12

SEQ ID NO: 3              moltype = AA   length = 14
FEATURE                   Location/Qualifiers
source                    1..14
                          mol_type = protein
                          organism = synthetic construct
                          note = Description of Artificial Sequence: Synthetic peptide
SEQUENCE: 3
CARLFNWGFA FDIW                                                   14

SEQ ID NO: 4              moltype = AA   length = 11
FEATURE                   Location/Qualifiers
source                    1..11
                          mol_type = protein
                          organism = synthetic construct
                          note = Description of Artificial Sequence: Synthetic peptide
SEQUENCE: 4
RASQSVSSNL A                                                      11

SEQ ID NO: 5              moltype = AA   length = 7
FEATURE                   Location/Qualifiers
source                    1..7
                          mol_type = protein
                          organism = synthetic construct
                          note = Description of Artificial Sequence: Synthetic peptide
SEQUENCE: 5
GASTRAT                                                           7

SEQ ID NO: 6              moltype = AA   length = 11
FEATURE                   Location/Qualifiers
source                    1..11
                          mol_type = protein
                          organism = synthetic construct
                          note = Description of Artificial Sequence: Synthetic peptide
SEQUENCE: 6
CQQYNNWPLT F                                                      11

SEQ ID NO: 7              moltype = AA   length = 118
FEATURE                   Location/Qualifiers
source                    1..118
                          mol_type = protein
                          organism = synthetic construct
                          note = Description of Artificial Sequence: Synthetic
                           polypeptide
SEQUENCE: 7
QVQLQESGPG LVKPSETLSL TCTVSDNSIS NYYWSWIRQP PGKGLEWIAY IYYSGTTNYN  60
PSLKSRVTIS LDTSKNQFSL KLSSVTAADT AVYYCARLFN WGFAFDIWGQ GTMVTVSS    118

SEQ ID NO: 8              moltype = AA   length = 107
FEATURE                   Location/Qualifiers
source                    1..107
                          mol_type = protein
                          organism = synthetic construct
                          note = Description of Artificial Sequence: Synthetic
                           polypeptide
SEQUENCE: 8
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPLTFGG GTKVEIK               107

SEQ ID NO: 9              moltype = AA   length = 245
FEATURE                   Location/Qualifiers
source                    1..245
                          mol_type = protein
                          organism = synthetic construct
                          note = Description of Artificial Sequence: Synthetic
                           polypeptide
```

```
SEQUENCE: 9
QVQLQESGPG LVKPSETLSL TCTVSDNSIS NYYWSWIRQP PGKGLEWIAY IYYSGTTNYN    60
PSLKSRVTIS LDTSKNQFSL KLSSVTAADT AVYYCARLFN WGFAFDIWGQ GTMVTVSSGG   120
GGSGGGGSGG GGSGGGGSEI VMTQSPATLS VSPGERATLS CRASQSVSSN LAWYQQKPGQ   180
APRLLIYGAS TRATGIPARF SGSGSGTEFT LTISSLQSED FAVYYCQQYN NWPLTFGGGT   240
KVEIK                                                               245

SEQ ID NO: 10          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 10
GSISSSYWS                                                             9

SEQ ID NO: 11          moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 11
GYIYYSGTTN YN                                                        12

SEQ ID NO: 12          moltype = AA  length = 14
FEATURE                Location/Qualifiers
source                 1..14
                       mol_type = protein
                       organism = synthetic construct
                       note = Description of Artificial Sequence: Synthetic peptide
SEQUENCE: 12
CARVAPTGFW FDYW                                                      14

SEQ ID NO: 13          moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 13
RASQRVSSRY LA                                                        12

SEQ ID NO: 14          moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 14
GASSRAT                                                               7

SEQ ID NO: 15          moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 15
CQQYGTSPLT F                                                         11

SEQ ID NO: 16          moltype = AA  length = 118
FEATURE                Location/Qualifiers
source                 1..118
                       mol_type = protein
                       organism = synthetic construct
                       note = Description of Artificial Sequence: Synthetic
                        polypeptide
SEQUENCE: 16
QVQLQESGPG LMKPSETLSL TCTVSGGSIS SSYWSCIRQP PGKGLEWIGY IYYSGTTNYN    60
PSLKSRVTLS LDTSKNQFSL RLTSVTAADT AVYYCARVAP TGFWFDYWGQ GTLVTVSS     118

SEQ ID NO: 17          moltype = AA  length = 108
FEATURE                Location/Qualifiers
source                 1..108
                       mol_type = protein
                       organism = synthetic construct
                       note = Description of Artificial Sequence: Synthetic
                        polypeptide
```

```
SEQUENCE: 17
EIVLTQSPGT LSLSPGERAT LSCRASQRVS SRYLAWYQQK PGQAPRLLIY GASSRATGIP  60
DRFSGSGSGT DFTLTISRLE PEEFAVYYCQ QYGTSPLTFG GGTKVEIK                108

SEQ ID NO: 18          moltype = AA  length = 246
FEATURE                Location/Qualifiers
source                 1..246
                       mol_type = protein
                       organism = synthetic construct
                       note = Description of Artificial Sequence: Synthetic
                        polypeptide
SEQUENCE: 18
QVQLQESGPG LMKPSETLSL TCTVSGGSIS SSYWSCIRQP PGKGLEWIGY IYYSGTTNYN  60
PSLKSRVTLS LDTSKNQFSL RLTSVTAADT AVYYCARVAP TGFWFDYWGQ GTLVTVSSGG  120
GGSGGGGSGG GGSGGGGSEI VLTQSPGTLS LSPGERATLS CRASQRVSSR YLAWYQQKPG  180
QAPRLLIYGA SSRATGIPDR FSGSGSGTDF TLTISRLEPE EFAVYYCQQY GTSPLTFGGG  240
TKVEIK                                                             246

SEQ ID NO: 19          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 19
FTFSSHDMH                                                          9

SEQ ID NO: 20          moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 20
SAIGIAGDTY YS                                                      12

SEQ ID NO: 21          moltype = AA  length = 14
FEATURE                Location/Qualifiers
source                 1..14
                       mol_type = protein
                       organism = synthetic construct
                       note = Description of Artificial Sequence: Synthetic peptide
SEQUENCE: 21
CARANWGEGA FDIW                                                    14

SEQ ID NO: 22          moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 22
RASQGISDYL A                                                       11

SEQ ID NO: 23          moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 23
AASTLQS                                                            7

SEQ ID NO: 24          moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 24
CQKYNSVPLT F                                                       11

SEQ ID NO: 25          moltype = AA  length = 118
FEATURE                Location/Qualifiers
source                 1..118
                       mol_type = protein
                       organism = synthetic construct
                       note = Description of Artificial Sequence: Synthetic
                        polypeptide
```

-continued

```
SEQUENCE: 25
EVQLVESGGG LVQPGGSLRL SCAASGFTFS SHDMHWVRQA TGKGLEWVSA IGIAGDTYYS    60
GSVKGRFTIS RENAKNSLYL QMNSLRAGDT AVYYCARANW GEGAFDIWGQ GTMVTVSS     118

SEQ ID NO: 26          moltype = AA  length = 107
FEATURE                Location/Qualifiers
source                 1..107
                       mol_type = protein
                       organism = synthetic construct
                       note = Description of Artificial Sequence: Synthetic
                        polypeptide
SEQUENCE: 26
DIQMTQSPSS LSASVGDRVT ITCRASQGIS DYLAWYQQKP GKIPKLLIYA ASTLQSGVPS    60
RFSGSGSGTD FTLTISSLQP EDVATYYCQK YNSVPLTFGG GTKVEIK              107

SEQ ID NO: 27          moltype = AA  length = 245
FEATURE                Location/Qualifiers
source                 1..245
                       mol_type = protein
                       organism = synthetic construct
                       note = Description of Artificial Sequence: Synthetic
                        polypeptide
SEQUENCE: 27
EVQLVESGGG LVQPGGSLRL SCAASGFTFS SHDMHWVRQA TGKGLEWVSA IGIAGDTYYS    60
GSVKGRFTIS RENAKNSLYL QMNSLRAGDT AVYYCARANW GEGAFDIWGQ GTMVTVSSGG   120
GGSGGGGSGG GGSGGGGSDI QMTQSPSSLS ASVGDRVTIT CRASQGISDY LAWYQQKPGK   180
IPKLLIYAAS TLQSGVPSRF SGSGSGTDFT LTISSLQPED VATYYCQKYN SVPLTFGGGT   240
KVEIK                                                               245

SEQ ID NO: 28          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 28
DSISNYYWS                                                             9

SEQ ID NO: 29          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 29
DSISNYYWS                                                             9

SEQ ID NO: 30          moltype = AA  length = 14
FEATURE                Location/Qualifiers
source                 1..14
                       mol_type = protein
                       organism = synthetic construct
                       note = Description of Artificial Sequence: Synthetic peptide
SEQUENCE: 30
CARVFNWGFA FDIW                                                      14

SEQ ID NO: 31          moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 31
RASQRISRTY LA                                                        12

SEQ ID NO: 32          moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 32
GASSRAT                                                               7

SEQ ID NO: 33          moltype = AA  length = 11
FEATURE                Location/Qualifiers
source                 1..11
                       mol_type = protein
                       organism = synthetic construct
```

-continued

```
                        note = Description of Artificial Sequence: Synthetic peptide
SEQUENCE: 33
CQQYGTSPLT F                                                    11

SEQ ID NO: 34         moltype = AA  length = 118
FEATURE               Location/Qualifiers
source                1..118
                      mol_type = protein
                      organism = synthetic construct
                      note = Description of Artificial Sequence: Synthetic
                       polypeptide
SEQUENCE: 34
QVQLQESGPG LVKPSETLSL TCTVSDDSIS NYYWSWIRQP PGKGLEWIGY IFYSGTTNHN  60
PSLKSRLTIS LDKAKNQFSL RLSSVTAADT AVYYCARVFN WGFAFDIWGQ GTMVTVSS    118

SEQ ID NO: 35         moltype = AA  length = 108
FEATURE               Location/Qualifiers
source                1..108
                      mol_type = protein
                      organism = synthetic construct
                      note = Description of Artificial Sequence: Synthetic
                       polypeptide
SEQUENCE: 35
EIVLTQSPGT LSLSPGERAT LSCRASQRIS RTYLAWYQQK PGQAPRLLIY GASSRATGIP  60
DRFTGSGSGT DFTLTISRLE PEDFAVYYCQ QYGTSPLTFG GGTKVEIN              108

SEQ ID NO: 36         moltype = AA  length = 246
FEATURE               Location/Qualifiers
source                1..246
                      mol_type = protein
                      organism = synthetic construct
                      note = Description of Artificial Sequence: Synthetic
                       polypeptide
SEQUENCE: 36
QVQLQESGPG LVKPSETLSL TCTVSDDSIS NYYWSWIRQP PGKGLEWIGY IFYSGTTNHN  60
PSLKSRLTIS LDKAKNQFSL RLSSVTAADT AVYYCARVFN WGFAFDIWGQ GTMVTVSSGG  120
GGSGGGGSGG GGSGGGGSEI VLTQSPGTLS LSPGERATLS CRASQRISRT YLAWYQQKPG  180
QAPRLLIYGA SSRATGIPDR FTGSGSGTDF TLTISRLEPE DFAVYYCQQY GTSPLTFGGG  240
TKVEIN                                                            246

SEQ ID NO: 37         moltype = AA  length = 9
FEATURE               Location/Qualifiers
source                1..9
                      mol_type = protein
                      organism = synthetic construct
                      note = Description of Artificial Sequence: Synthetic peptide
SEQUENCE: 37
NSISNYYWS                                                         9

SEQ ID NO: 38         moltype = AA  length = 12
FEATURE               Location/Qualifiers
source                1..12
                      mol_type = protein
                      organism = synthetic construct
                      note = Description of Artificial Sequence: Synthetic peptide
SEQUENCE: 38
AYIYYSGTTN YN                                                     12

SEQ ID NO: 39         moltype = AA  length = 14
FEATURE               Location/Qualifiers
source                1..14
                      mol_type = protein
                      organism = synthetic construct
                      note = Description of Artificial Sequence: Synthetic peptide
SEQUENCE: 39
CARVFHWGFA FDIW                                                   14

SEQ ID NO: 40         moltype = AA  length = 12
FEATURE               Location/Qualifiers
source                1..12
                      mol_type = protein
                      organism = synthetic construct
                      note = Description of Artificial Sequence: Synthetic peptide
SEQUENCE: 40
RASQRVSNTY LA                                                     12

SEQ ID NO: 41         moltype = AA  length = 7
FEATURE               Location/Qualifiers
source                1..7
```

```
                            mol_type = protein
                            organism = synthetic construct
                            note = Description of Artificial Sequence: Synthetic peptide
SEQUENCE: 41
GASSRAT                                                                      7

SEQ ID NO: 42           moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 42
CQQYGTSPLT F                                                                11

SEQ ID NO: 43           moltype = AA   length = 118
FEATURE                 Location/Qualifiers
source                  1..118
                        mol_type = protein
                        organism = synthetic construct
                        note = Description of Artificial Sequence: Synthetic
                         polypeptide
SEQUENCE: 43
QVQLQESGPG LVKPSETLSL TCTVSDNSIS NYYWSWIRQP PGKGLEWIAY IYYSGTTNYN  60
PSLKSRVTIS LDTSKNQFSL QLSSVTAADA AVYYCARVFH WGFAFDIWGQ GTMVTVSS    118

SEQ ID NO: 44           moltype = AA   length = 108
FEATURE                 Location/Qualifiers
source                  1..108
                        mol_type = protein
                        organism = synthetic construct
                        note = Description of Artificial Sequence: Synthetic
                         polypeptide
SEQUENCE: 44
EIVLTQSPGT LSLSPGERAT LSCRASQRVS NTYLAWYQQN PGQAPRLLIY GASSRATGIP  60
DRFSGSGSGT DFTLTISRLE PEDFAVYYCQ QYGTSPLTFG GGTKVEIK              108

SEQ ID NO: 45           moltype = AA   length = 246
FEATURE                 Location/Qualifiers
source                  1..246
                        mol_type = protein
                        organism = synthetic construct
                        note = Description of Artificial Sequence: Synthetic
                         polypeptide
SEQUENCE: 45
QVQLQESGPG LVKPSETLSL TCTVSDNSIS NYYWSWIRQP PGKGLEWIAY IYYSGTTNYN  60
PSLKSRVTIS LDTSKNQFSL QLSSVTAADA AVYYCARVFH WGFAFDIWGQ GTMVTVSSGG  120
GGSGGGGSGG GGSGGGGSEI VLTQSPGTLS LSPGERATLS CRASQRVSNT YLAWYQQNPG  180
QAPRLLIYGA SSRATGIPDR FSGSGSGTDF TLTISRLEPE DFAVYYCQQY GTSPLTFGGG  240
TKVEIK                                                              246

SEQ ID NO: 46           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 46
VSISSYYWS                                                                    9

SEQ ID NO: 47           moltype = AA   length = 12
FEATURE                 Location/Qualifiers
source                  1..12
                        mol_type = protein
                        organism = synthetic construct
                        note = Description of Artificial Sequence: Synthetic peptide
SEQUENCE: 47
GYIYYSGTTN YN                                                               12

SEQ ID NO: 48           moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 48
CARLSNWGFA FDIW                                                             14

SEQ ID NO: 49           moltype = AA   length = 12
```

-continued

```
FEATURE              Location/Qualifiers
source               1..12
                     mol_type = protein
                     organism = synthetic construct
                     note = Description of Artificial Sequence: Synthetic peptide
SEQUENCE: 49
RASQTISSSY LA                                                      12

SEQ ID NO: 50        moltype = AA  length = 7
FEATURE              Location/Qualifiers
source               1..7
                     mol_type = protein
                     organism = synthetic construct
                     note = Description of Artificial Sequence: Synthetic peptide
SEQUENCE: 50
GASSRAT                                                            7

SEQ ID NO: 51        moltype = AA  length = 11
FEATURE              Location/Qualifiers
source               1..11
                     mol_type = protein
                     organism = synthetic construct
                     note = Description of Artificial Sequence: Synthetic peptide
SEQUENCE: 51
CQQYGWSPIT F                                                       11

SEQ ID NO: 52        moltype = AA  length = 118
FEATURE              Location/Qualifiers
source               1..118
                     mol_type = protein
                     organism = synthetic construct
                     note = Description of Artificial Sequence: Synthetic
                      polypeptide
SEQUENCE: 52
QVQLQESGPG LVKPSETLSL TCTVSNVSIS SYYWSWIRQP PGKGLEWIGY IYYSGTTNYN  60
PSLKSRVTMS VDTSKNQFSL KLSSVTAADT AVYFCARLSN WGFAFDIWGQ GTMVTFSS    118

SEQ ID NO: 53        moltype = AA  length = 108
FEATURE              Location/Qualifiers
source               1..108
                     mol_type = protein
                     organism = synthetic construct
                     note = Description of Artificial Sequence: Synthetic
                      polypeptide
SEQUENCE: 53
EIVLTQSPGT LSLSPGERAT LSCRASQTIS SSYLAWYQQK PGQAPRLLIY GASSRATGIP  60
DRFSGSGSGT EFTLTISRLE PEDFAVYYCQ QYGWSPITFG QGTRLEIK              108

SEQ ID NO: 54        moltype = AA  length = 246
FEATURE              Location/Qualifiers
source               1..246
                     mol_type = protein
                     organism = synthetic construct
                     note = Description of Artificial Sequence: Synthetic
                      polypeptide
SEQUENCE: 54
QVQLQESGPG LVKPSETLSL TCTVSNVSIS SYYWSWIRQP PGKGLEWIGY IYYSGTTNYN  60
PSLKSRVTMS VDTSKNQFSL KLSSVTAADT AVYFCARLSN WGFAFDIWGQ GTMVTFSSGG  120
GGSGGGGSGG GGSGGGGSEI VLTQSPGTLS LSPGERATLS CRASQTISSS YLAWYQQKPG  180
QAPRLLIYGA SSRATGIPDR FSGSGSGTEF TLTISRLEPE DFAVYYCQQY GWSPITFGQG  240
TRLEIK                                                            246

SEQ ID NO: 55        moltype = AA  length = 9
FEATURE              Location/Qualifiers
source               1..9
                     mol_type = protein
                     organism = synthetic construct
                     note = Description of Artificial Sequence: Synthetic peptide
SEQUENCE: 55
FTFSSYDMH                                                          9

SEQ ID NO: 56        moltype = AA  length = 12
FEATURE              Location/Qualifiers
source               1..12
                     mol_type = protein
                     organism = synthetic construct
                     note = Description of Artificial Sequence: Synthetic peptide
SEQUENCE: 56
SAIGPAGDTY YP                                                      12
```

-continued

```
SEQ ID NO: 57          moltype = AA   length = 16
FEATURE                Location/Qualifiers
source                 1..16
                       mol_type = protein
                       organism = synthetic construct
                       note = Description of Artificial Sequence: Synthetic peptide
SEQUENCE: 57
CARADPPYYY YGMDVW                                                 16

SEQ ID NO: 58          moltype = AA   length = 16
FEATURE                Location/Qualifiers
source                 1..16
                       mol_type = protein
                       organism = synthetic construct
                       note = Description of Artificial Sequence: Synthetic peptide
SEQUENCE: 58
RSSQSLLHSN EYNYLD                                                 16

SEQ ID NO: 59          moltype = AA   length = 7
FEATURE                Location/Qualifiers
source                 1..7
                       mol_type = protein
                       organism = synthetic construct
                       note = Description of Artificial Sequence: Synthetic peptide
SEQUENCE: 59
LGSNRAS                                                           7

SEQ ID NO: 60          moltype = AA   length = 11
FEATURE                Location/Qualifiers
source                 1..11
                       mol_type = protein
                       organism = synthetic construct
                       note = Description of Artificial Sequence: Synthetic peptide
SEQUENCE: 60
CMQALEIPLT F                                                      11

SEQ ID NO: 61          moltype = AA   length = 120
FEATURE                Location/Qualifiers
source                 1..120
                       mol_type = protein
                       organism = synthetic construct
                       note = Description of Artificial Sequence: Synthetic
                        polypeptide
SEQUENCE: 61
EVQLVESGGG LVQPGGSLRL SCAASGFTFS SYDMHWVRQA TGKGLEWVSA IGPAGDTYYP  60
GSVKGRFTIS RENAKNSLYL QMNSLRAGDT AVYYCARADP PYYYYGMDVW GQGTTVTVSS  120

SEQ ID NO: 62          moltype = AA   length = 112
FEATURE                Location/Qualifiers
source                 1..112
                       mol_type = protein
                       organism = synthetic construct
                       note = Description of Artificial Sequence: Synthetic
                        polypeptide
SEQUENCE: 62
DIVMTQSPLS LPVTPGEPAS ISCRSSQSLL HSNEYNYLDW YLQKPGQSPQ LLIYLGSNRA  60
SGVPDRFSGS GSGTDFILKI SRVEAEDVGV YYCMQALEIP LTFGGGTKVE IK          112

SEQ ID NO: 63          moltype = AA   length = 252
FEATURE                Location/Qualifiers
source                 1..252
                       mol_type = protein
                       organism = synthetic construct
                       note = Description of Artificial Sequence: Synthetic
                        polypeptide
SEQUENCE: 63
EVQLVESGGG LVQPGGSLRL SCAASGFTFS SYDMHWVRQA TGKGLEWVSA IGPAGDTYYP  60
GSVKGRFTIS RENAKNSLYL QMNSLRAGDT AVYYCARADP PYYYYGMDVW GQGTTVTVSS  120
GGGGSGGGGS GGGGSGGGGS DIVMTQSPLS LPVTPGEPAS ISCRSSQSLL HSNEYNYLDW  180
YLQKPGQSPQ LLIYLGSNRA SGVPDRFSGS GSGTDFILKI SRVEAEDVGV YYCMQALEIP  240
LTFGGGTKVE IK                                                     252

SEQ ID NO: 64          moltype = AA   length = 11
FEATURE                Location/Qualifiers
source                 1..11
                       mol_type = protein
                       organism = synthetic construct
                       note = Description of Artificial Sequence: Synthetic peptide
```

```
SEQUENCE: 64
FSLSTRGVGV G                                                            11

SEQ ID NO: 65          moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 65
ALIYWNDDKR YS                                                           12

SEQ ID NO: 66          moltype = AA  length = 14
FEATURE                Location/Qualifiers
source                 1..14
                       mol_type = protein
                       organism = synthetic construct
                       note = Description of Artificial Sequence: Synthetic peptide
SEQUENCE: 66
CARSNWGNWY FALW                                                         14

SEQ ID NO: 67          moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 67
RASQSVSSYL A                                                            11

SEQ ID NO: 68          moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 68
DAFYRAT                                                                 7

SEQ ID NO: 69          moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 69
CQHRSNWPIT F                                                            11

SEQ ID NO: 70          moltype = AA  length = 120
FEATURE                Location/Qualifiers
source                 1..120
                       mol_type = protein
                       organism = synthetic construct
                       note = Description of Artificial Sequence: Synthetic
                        polypeptide
SEQUENCE: 70
QITLKESGPT LVKPTQTLTL TCTFSGFSLS TRGVGVGWIR QPPGKALEWL ALIYWNDDKR  60
YSPSLQTRLT ITKDTPKNQV VLTMTNMDPV DTATYYCARS NWGNWYFALW GRGTLVTVSS  120

SEQ ID NO: 71          moltype = AA  length = 107
FEATURE                Location/Qualifiers
source                 1..107
                       mol_type = protein
                       organism = synthetic construct
                       note = Description of Artificial Sequence: Synthetic
                        polypeptide
SEQUENCE: 71
EIVLTQSPAT LSLSPGERAT LSCRASQSVS SYLAWYQQKP GQAPRLLIYD AFYRATGIPA  60
RFSGSGSGTD FTLTISSLEP EDFAVYYCQH RSNWPITFGQ GTRLEIK           107

SEQ ID NO: 72          moltype = AA  length = 247
FEATURE                Location/Qualifiers
source                 1..247
                       mol_type = protein
                       organism = synthetic construct
                       note = Description of Artificial Sequence: Synthetic
                        polypeptide
SEQUENCE: 72
QITLKESGPT LVKPTQTLTL TCTFSGFSLS TRGVGVGWIR QPPGKALEWL ALIYWNDDKR  60
```

-continued

```
YSPSLQTRLT ITKDTPKNQV VLTMTNMDPV DTATYYCARS NWGNWYFALW GRGTLVTVSS 120
GGGGSGGGGS GGGGSGGGGS EIVLTQSPAT LSLSPGERAT LSCRASQSVS SYLAWYQQKP 180
GQAPRLLIYD AFYRATGIPA RFSGSGSGTD FTLTISSLEP EDFAVYYCQH RSNWPITFGQ 240
GTRLEIK                                                         247

SEQ ID NO: 73            moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 73
DSISNYYWT                                                       9

SEQ ID NO: 74            moltype = AA  length = 12
FEATURE                  Location/Qualifiers
source                   1..12
                         mol_type = protein
                         organism = synthetic construct
                         note = Description of Artificial Sequence: Synthetic peptide
SEQUENCE: 74
GYIYYSGTTN SN                                                   12

SEQ ID NO: 75            moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 75
CARVFNRGFA FDIW                                                 14

SEQ ID NO: 76            moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 76
CARVFNRGFA FDIW                                                 14

SEQ ID NO: 77            moltype = AA  length = 7
FEATURE                  Location/Qualifiers
source                   1..7
                         mol_type = protein
                         organism = synthetic construct
                         note = Description of Artificial Sequence: Synthetic peptide
SEQUENCE: 77
GASSRAT                                                         7

SEQ ID NO: 78            moltype = AA  length = 11
FEATURE                  Location/Qualifiers
source                   1..11
                         mol_type = protein
                         organism = synthetic construct
                         note = Description of Artificial Sequence: Synthetic peptide
SEQUENCE: 78
CQQYDTSPLT F                                                    11

SEQ ID NO: 79            moltype = AA  length = 118
FEATURE                  Location/Qualifiers
source                   1..118
                         mol_type = protein
                         organism = synthetic construct
                         note = Description of Artificial Sequence: Synthetic
                          polypeptide
SEQUENCE: 79
QVQLQESGPG LVKPSETLSL TCTVSGDSIS NYYWTWIRQP PGKGLEWIGY IYYSGTTNSN 60
PSLKSRVTVS LDTSKSQFSL NLSSVTAADT AVYYCARVFN RGFAFDIWGQ GTMVTVSS   118

SEQ ID NO: 80            moltype = AA  length = 108
FEATURE                  Location/Qualifiers
source                   1..108
                         mol_type = protein
                         organism = synthetic construct
                         note = Description of Artificial Sequence: Synthetic
                          polypeptide
SEQUENCE: 80
EIVLTQSPGT LSLSPGERAT LSCRASQRIS NTYLAWYQQK PGQAPRLLIY GASSRATGIP 60
```

-continued

```
DRFSGSGSGT DFTLTISRLE PEDFAAYYCQ QYDTSPLTFG GGTKVEIK              108

SEQ ID NO: 81              moltype = AA   length = 246
FEATURE                    Location/Qualifiers
source                     1..246
                           mol_type = protein
                           organism = synthetic construct
                           note = Description of Artificial Sequence: Synthetic
                            polypeptide
SEQUENCE: 81
QVQLQESGPG LVKPSETLSL TCTVSGDSIS NYYWTWIRQP PGKGLEWIGY IYYSGTTNSN  60
PSLKSRVTVS LDTSKSQFSL NLSSVTAADT AVYYCARVFN RGFAFDIWGQ GTMVTVSSGG  120
GGSGGGGSGG GGSGGGGSEI VLTQSPGTLS LSPGERATLS CRASQRISNT YLAWYQQKPG  180
QAPRLLIYGA SSRATGIPDR FSGSGSGTDF TLTISRLEPE DFAAYYCQQY DTSPLTFGGG  240
TKVEIK                                                            246

SEQ ID NO: 82              moltype = AA   length = 11
FEATURE                    Location/Qualifiers
source                     1..11
                           mol_type = protein
                           organism = synthetic construct
                           note = Description of Artificial Sequence: Synthetic peptide
SEQUENCE: 82
VSLSTSGMCV S                                                       11

SEQ ID NO: 83              moltype = AA   length = 12
FEATURE                    Location/Qualifiers
source                     1..12
                           mol_type = protein
                           organism = synthetic construct
                           note = Description of Artificial Sequence: Synthetic peptide
SEQUENCE: 83
GFIDWDDDKY YN                                                      12

SEQ ID NO: 84              moltype = AA   length = 17
FEATURE                    Location/Qualifiers
source                     1..17
                           mol_type = protein
                           organism = synthetic construct
                           note = Description of Artificial Sequence: Synthetic peptide
SEQUENCE: 84
CARIRGYSGS YDAFDIW                                                 17

SEQ ID NO: 85              moltype = AA   length = 16
FEATURE                    Location/Qualifiers
source                     1..16
                           mol_type = protein
                           organism = synthetic construct
                           note = Description of Artificial Sequence: Synthetic peptide
SEQUENCE: 85
RSSQSLLHSN GYNHLD                                                  16

SEQ ID NO: 86              moltype = AA   length = 7
FEATURE                    Location/Qualifiers
source                     1..7
                           mol_type = protein
                           organism = synthetic construct
                           note = Description of Artificial Sequence: Synthetic peptide
SEQUENCE: 86
LGSNRAS                                                            7

SEQ ID NO: 87              moltype = AA   length = 11
FEATURE                    Location/Qualifiers
source                     1..11
                           mol_type = protein
                           organism = synthetic construct
                           note = Description of Artificial Sequence: Synthetic peptide
SEQUENCE: 87
CMQALQTPLT F                                                       11

SEQ ID NO: 88              moltype = AA   length = 123
FEATURE                    Location/Qualifiers
source                     1..123
                           mol_type = protein
                           organism = synthetic construct
                           note = Description of Artificial Sequence: Synthetic
                            polypeptide
SEQUENCE: 88
QVTLRESGPA LVKPTQTLTL TCTVSGVSLS TSGMCVSWIR QPLGKALEWL GFIDWDDDKY  60
```

```
YNTSLKTRLT ISKDTSKNQV VLTMTNMDPV DTATYYCARI RGYSGSYDAF DIWGQGTVVI  120
VSS                                                                 123

SEQ ID NO: 89           moltype = AA  length = 112
FEATURE                 Location/Qualifiers
source                  1..112
                        mol_type = protein
                        organism = synthetic construct
                        note = Description of Artificial Sequence: Synthetic
                         polypeptide
SEQUENCE: 89
DIVMTQSPLS LPVTPGEPAS ISCRSSQSLL HSNGYNHLDW YLQKPGQSPQ VLIYLGSNRA  60
SGVPDRFSGS GSGTDFTLKI SRVEAEDVGV YFCMQALQTP LTFGGGTKVE IK           112

SEQ ID NO: 90           moltype = AA  length = 255
FEATURE                 Location/Qualifiers
source                  1..255
                        mol_type = protein
                        organism = synthetic construct
                        note = Description of Artificial Sequence: Synthetic
                         polypeptide
SEQUENCE: 90
QVTLRESGPA LVKPTQTLTL TCTVSGVSLS TSGMCVSWIR QPLGKALEWL GFIDWDDDKY  60
YNTSLKTRLT ISKDTSKNQV VLTMTNMDPV DTATYYCARI RGYSGSYDAF DIWGQGTVVI  120
VSSGGGGSGG GGSGGGGSGG GGSDIVMTQS PLSLPVTPGE PASISCRSSQ SLLHSNGYNH  180
LDWYLQKPGQ SPQVLIYLGS NRASGVPDRF SGSGSGTDFT LKISRVEAED VGVYFCMQAL  240
QTPLTFGGGT KVEIK                                                    255

SEQ ID NO: 91           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 91
GSISSYYWS                                                           9

SEQ ID NO: 92           moltype = AA  length = 12
FEATURE                 Location/Qualifiers
source                  1..12
                        mol_type = protein
                        organism = synthetic construct
                        note = Description of Artificial Sequence: Synthetic peptide
SEQUENCE: 92
GYMYYSGTTN YN                                                       12

SEQ ID NO: 93           moltype = AA  length = 14
FEATURE                 Location/Qualifiers
source                  1..14
                        mol_type = protein
                        organism = synthetic construct
                        note = Description of Artificial Sequence: Synthetic peptide
SEQUENCE: 93
CARVGLTGFF FDYW                                                     14

SEQ ID NO: 94           moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 94
RASQGIRNDL G                                                        11

SEQ ID NO: 95           moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 95
AASSLQS                                                             7

SEQ ID NO: 96           moltype = AA  length = 11
FEATURE                 Location/Qualifiers
source                  1..11
                        mol_type = protein
                        organism = synthetic construct
                        note = Description of Artificial Sequence: Synthetic peptide
```

-continued

```
SEQUENCE: 96
CLQDYNYPYT F                                                          11

SEQ ID NO: 97            moltype = AA   length = 118
FEATURE                  Location/Qualifiers
source                   1..118
                         mol_type = protein
                         organism = synthetic construct
                         note = Description of Artificial Sequence: Synthetic
                          polypeptide
SEQUENCE: 97
QVQLQVSGPG LVKPSETLSL TCSVSGGSIS SYYWSWIRQS PGKGLDWIGY MYYSGTTNYN   60
PSLKSRVTIS VDTSKNQFSL KLSSVTATDT AVYYCARVGL TGFFFDYWGQ GTLVTVSS    118

SEQ ID NO: 98            moltype = AA   length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 98
AIQMTQSPSS LSASVGDRVT ITCRASQGIR NDLGWYQQKP GKAPKLLIYA ASSLQSGVPS   60
RFSGSGSGTD FTLTVSSLQP EDFATYYCLQ DYNYPYTFGQ GTKLEIK               107

SEQ ID NO: 99            moltype = AA   length = 245
FEATURE                  Location/Qualifiers
source                   1..245
                         mol_type = protein
                         organism = synthetic construct
                         note = Description of Artificial Sequence: Synthetic
                          polypeptide
SEQUENCE: 99
QVQLQVSGPG LVKPSETLSL TCSVSGGSIS SYYWSWIRQS PGKGLDWIGY MYYSGTTNYN   60
PSLKSRVTIS VDTSKNQFSL KLSSVTATDT AVYYCARVGL TGFFFDYWGQ GTLVTVSSGG  120
GGSGGGGSGG GGSGGGGSAI QMTQSPSSLS ASVGDRVTIT CRASQGIRND LGWYQQKPGK  180
APKLLIYAAS SLQSGVPSRF SGSGSGTDFT LTVSSLQPED FATYYCLQDY NYPYTFGQGT  240
KLEIK                                                              245

SEQ ID NO: 100           moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 100
GSSSGNYWS                                                            9

SEQ ID NO: 101           moltype = AA   length = 12
FEATURE                  Location/Qualifiers
source                   1..12
                         mol_type = protein
                         organism = synthetic construct
                         note = Description of Artificial Sequence: Synthetic peptide
SEQUENCE: 101
GEINHSGTTS YN                                                        12

SEQ ID NO: 102           moltype = AA   length = 12
FEATURE                  Location/Qualifiers
source                   1..12
                         mol_type = protein
                         organism = synthetic construct
                         note = Description of Artificial Sequence: Synthetic peptide
SEQUENCE: 102
CARGELGIAD SW                                                        12

SEQ ID NO: 103           moltype = AA   length = 11
FEATURE                  Location/Qualifiers
source                   1..11
                         mol_type = protein
                         organism = synthetic construct
                         note = Description of Artificial Sequence: Synthetic peptide
SEQUENCE: 103
RASQSISRWL A                                                         11

SEQ ID NO: 104           moltype = AA   length = 7
FEATURE                  Location/Qualifiers
source                   1..7
                         mol_type = protein
```

-continued

```
                             organism = synthetic construct
                             note = Description of Artificial Sequence: Synthetic peptide
SEQUENCE: 104
KASSLES                                                                       7

SEQ ID NO: 105               moltype = AA   length = 10
FEATURE                      Location/Qualifiers
source                       1..10
                             mol_type = protein
                             organism = synthetic construct
                             note = Description of Artificial Sequence: Synthetic peptide
SEQUENCE: 105
CQQYNSYSTF                                                                    10

SEQ ID NO: 106               moltype = AA   length = 116
FEATURE                      Location/Qualifiers
source                       1..116
                             mol_type = protein
                             organism = synthetic construct
                             note = Description of Artificial Sequence: Synthetic
                              polypeptide
SEQUENCE: 106
QVQLQQWGGG LLKPSETLSL TCAVYGGSSS GNYWSWIRQP PGKRLEWIGE INHSGTTSYN  60
PSLKSRVTIS VDTSKNQFSL KLSSVTAADT AVYYCARGEL GIADSWGQGT LVTVSS       116

SEQ ID NO: 107               moltype = AA   length = 106
FEATURE                      Location/Qualifiers
source                       1..106
                             mol_type = protein
                             organism = synthetic construct
                             note = Description of Artificial Sequence: Synthetic
                              polypeptide
SEQUENCE: 107
DIQMTQSPST LSASVGDRVT ITCRASQSIS RWLAWYQQKP GKAPKLLIYK ASSLESGVPS  60
RFSGSGSGTE FTLTISSLQP DDFATYYCQQ YNSYSTFGQG TKVEIK                 106

SEQ ID NO: 108               moltype = AA   length = 242
FEATURE                      Location/Qualifiers
source                       1..242
                             mol_type = protein
                             organism = synthetic construct
                             note = Description of Artificial Sequence: Synthetic
                              polypeptide
SEQUENCE: 108
QVQLQQWGGG LLKPSETLSL TCAVYGGSSS GNYWSWIRQP PGKRLEWIGE INHSGTTSYN  60
PSLKSRVTIS VDTSKNQFSL KLSSVTAADT AVYYCARGEL GIADSWGQGT LVTVSSGGGG  120
SGGGGSGGGG SGGGGSDIQM TQSPSTLSAS VGDRVTITCR ASQSISRWLA WYQQKPGKAP  180
KLLIYKASSL ESGVPSRFSG SGSGTEFTLT ISSLQPDDFA TYYCQQYNSY STFGQGTKVE  240
IK                                                                242

SEQ ID NO: 109               moltype = AA   length = 11
FEATURE                      Location/Qualifiers
source                       1..11
                             mol_type = protein
                             organism = synthetic construct
                             note = Description of Artificial Sequence: Synthetic peptide
SEQUENCE: 109
GSISSSSYYW G                                                                  11

SEQ ID NO: 110               moltype = AA   length = 12
FEATURE                      Location/Qualifiers
source                       1..12
                             mol_type = protein
                             organism = synthetic construct
                             note = Description of Artificial Sequence: Synthetic peptide
SEQUENCE: 110
GSIYYSGNIY HN                                                                 12

SEQ ID NO: 111               moltype = AA   length = 15
FEATURE                      Location/Qualifiers
source                       1..15
                             mol_type = protein
                             organism = synthetic construct
                             note = Description of Artificial Sequence: Synthetic peptide
SEQUENCE: 111
CAREIIVGAT HFDYW                                                              15

SEQ ID NO: 112               moltype = AA   length = 11
FEATURE                      Location/Qualifiers
```

-continued

```
source                    1..11
                          mol_type = protein
                          organism = synthetic construct
                          note = Description of Artificial Sequence: Synthetic peptide
SEQUENCE: 112
RASQGIRNDL G                                                                        11

SEQ ID NO: 113            moltype = AA  length = 7
FEATURE                   Location/Qualifiers
source                    1..7
                          mol_type = protein
                          organism = synthetic construct
                          note = Description of Artificial Sequence: Synthetic peptide
SEQUENCE: 113
AASSLQS                                                                             7

SEQ ID NO: 114            moltype = AA  length = 11
FEATURE                   Location/Qualifiers
source                    1..11
                          mol_type = protein
                          organism = synthetic construct
                          note = Description of Artificial Sequence: Synthetic peptide
SEQUENCE: 114
CLQDYNYPLT F                                                                        11

SEQ ID NO: 115            moltype = AA  length = 121
FEATURE                   Location/Qualifiers
source                    1..121
                          mol_type = protein
                          organism = synthetic construct
                          note = Description of Artificial Sequence: Synthetic
                           polypeptide
SEQUENCE: 115
QLQLQESGPG LVKPSETLSL TCTVSGGSIS SSSYYWGWIR QPPGKGLEWI GSIYYSGNIY    60
HNPSLKSRVS ISVDTSKNQF SLRLSSVTAA DTAVYYCARE IIVGATHFDY WGQGTLVTVS    120
S                                                                   121

SEQ ID NO: 116            moltype = AA  length = 107
FEATURE                   Location/Qualifiers
source                    1..107
                          mol_type = protein
                          organism = synthetic construct
                          note = Description of Artificial Sequence: Synthetic
                           polypeptide
SEQUENCE: 116
AIQMTQSPSS LSASVGDRVT ITCRASQGIR NDLGWYQQKP GKAPELLIYA ASSLQSGVPS    60
RFSGSGSGTD FTLTISSLQP EDFATYYCLQ DYNYPLTFGP GTKVDIK                  107

SEQ ID NO: 117            moltype = AA  length = 248
FEATURE                   Location/Qualifiers
source                    1..248
                          mol_type = protein
                          organism = synthetic construct
                          note = Description of Artificial Sequence: Synthetic
                           polypeptide
SEQUENCE: 117
QLQLQESGPG LVKPSETLSL TCTVSGGSIS SSSYYWGWIR QPPGKGLEWI GSIYYSGNIY    60
HNPSLKSRVS ISVDTSKNQF SLRLSSVTAA DTAVYYCARE IIVGATHFDY WGQGTLVTVS    120
SGGGGSGGGG SGGGGSGGGG SAIQMTQSPS SLSASVGDRV TITCRASQGI RNDLGWYQQK    180
PGKAPELLIY AASSLQSGVP SRFSGSGSGT DFTLTISSLQ PEDFATYYCL QDYNYPLTFG    240
PGTKVDIK                                                            248

SEQ ID NO: 118            moltype = AA  length = 9
FEATURE                   Location/Qualifiers
source                    1..9
                          mol_type = protein
                          organism = synthetic construct
                          note = Description of Artificial Sequence: Synthetic peptide
SEQUENCE: 118
GSFSGYYWS                                                                           9

SEQ ID NO: 119            moltype = AA  length = 12
FEATURE                   Location/Qualifiers
source                    1..12
                          mol_type = protein
                          organism = synthetic construct
                          note = Description of Artificial Sequence: Synthetic peptide
SEQUENCE: 119
GEIIHSGSSN YN                                                                       12
```

-continued

```
SEQ ID NO: 120          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 120
CSRGEYGSGS RFDYW                                             15

SEQ ID NO: 121          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 121
RASQGIRDDL G                                                 11

SEQ ID NO: 122          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 122
AASSLQS                                                      7

SEQ ID NO: 123          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 123
CLQDYDYPLT F                                                 11

SEQ ID NO: 124          moltype = AA   length = 119
FEATURE                 Location/Qualifiers
source                  1..119
                        mol_type = protein
                        organism = synthetic construct
                        note = Description of Artificial Sequence: Synthetic
                         polypeptide
SEQUENCE: 124
QVQLQQWGAG LLKPSETLSL TCAVYGGSFS GYYWSWIRQP PGKGLEWIGE IIHSGSSNYN 60
PSLKSRVSIS VDTSKNQFSL KLSSVTAADT AVYYCSRGEY GSGSRFDYWG QGTLVTVSS   119

SEQ ID NO: 125          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 125
AIQMTQSPSS LSASVGDRVA ITCRASQGIR DDLGWYQQKP GKAPKLLIYA ASSLQSGVPS 60
RFSGSRSDTD FTLTISSLQP EDFATYYCLQ DYDYPLTFGG GTKVEIK            107

SEQ ID NO: 126          moltype = AA   length = 246
FEATURE                 Location/Qualifiers
source                  1..246
                        mol_type = protein
                        organism = synthetic construct
                        note = Description of Artificial Sequence: Synthetic
                         polypeptide
SEQUENCE: 126
QVQLQQWGAG LLKPSETLSL TCAVYGGSFS GYYWSWIRQP PGKGLEWIGE IIHSGSSNYN 60
PSLKSRVSIS VDTSKNQFSL KLSSVTAADT AVYYCSRGEY GSGSRFDYWG QGTLVTVSSG 120
GGGSGGGGSG GGGSGGGGSA IQMTQSPSSL SASVGDRVAI TCRASQGIRD DLGWYQQKPG 180
KAPKLLIYAA SSLQSGVPSR FSGSRSDTDF TLTISSLQPE DFATYYCLQD YDYPLTFGGG 240
TKVEIK                                                       246

SEQ ID NO: 127          moltype = AA   length = 10
FEATURE                 Location/Qualifiers
source                  1..10
                        mol_type = protein
                        organism = synthetic construct
                        note = Description of Artificial Sequence: Synthetic peptide
```

-continued

```
SEQUENCE: 127
GSISSNNWWS                                                              10

SEQ ID NO: 128         moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 128
GDIHHSGSTN YK                                                           12

SEQ ID NO: 129         moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 129
CAREAGGYFD YW                                                           12

SEQ ID NO: 130         moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 130
RASQSISSWL A                                                            11

SEQ ID NO: 131         moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 131
KASSLES                                                                 7

SEQ ID NO: 132         moltype = AA  length = 10
FEATURE                Location/Qualifiers
source                 1..10
                       mol_type = protein
                       organism = synthetic construct
                       note = Description of Artificial Sequence: Synthetic peptide
SEQUENCE: 132
CQQYNSYSTF                                                              10

SEQ ID NO: 133         moltype = AA  length = 117
FEATURE                Location/Qualifiers
source                 1..117
                       mol_type = protein
                       organism = synthetic construct
                       note = Description of Artificial Sequence: Synthetic
                        polypeptide
SEQUENCE: 133
QVQLQESGPG LVKPSGTLSL TCAVSGGSIS SNNWWSWVRQ PPGKGLEWIG DIHHSGSTNY   60
KPSLKSRVTI SVDKSKNQFS LNLISVTAAD TAVYYCAREA GGYFDYWGQG ILVTVSS       117

SEQ ID NO: 134         moltype = AA  length = 106
FEATURE                Location/Qualifiers
source                 1..106
                       mol_type = protein
                       organism = synthetic construct
                       note = Description of Artificial Sequence: Synthetic
                        polypeptide
SEQUENCE: 134
DIQMTQSPST LSASVGDRVT ITCRASQSIS SWLAWYQQKP GKAPKLLISK ASSLESGVPS   60
RFSGSGSGPE FTLTISSLQP ADFATYYCQQ YNSYSTFGQG TKLEIK                  106

SEQ ID NO: 135         moltype = AA  length = 243
FEATURE                Location/Qualifiers
source                 1..243
                       mol_type = protein
                       organism = synthetic construct
                       note = Description of Artificial Sequence: Synthetic
                        polypeptide
SEQUENCE: 135
QVQLQESGPG LVKPSGTLSL TCAVSGGSIS SNNWWSWVRQ PPGKGLEWIG DIHHSGSTNY   60
```

-continued

```
KPSLKSRVTI SVDKSKNQFS LNLISVTAAD TAVYYCAREA GGYFDYWGQG ILVTVSSGGG  120
GSGGGGSGGG GSGGGGSDIQ MTQSPSTLSA SVGDRVTITC RASQSISSWL AWYQQKPGKA  180
PKLLISKASS LESGVPSRFS GSGSGPEFTL TISSLQPADF ATYYCQQYNS YSTFGQGTKL  240
EIK                                                                243

SEQ ID NO: 136           moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 136
GSFSGYYWT                                                          9

SEQ ID NO: 137           moltype = AA  length = 12
FEATURE                  Location/Qualifiers
source                   1..12
                         mol_type = protein
                         organism = synthetic construct
                         note = Description of Artificial Sequence: Synthetic peptide
SEQUENCE: 137
GEITHSGSTN YN                                                      12

SEQ ID NO: 138           moltype = AA  length = 15
FEATURE                  Location/Qualifiers
source                   1..15
                         mol_type = protein
                         organism = synthetic construct
                         note = Description of Artificial Sequence: Synthetic peptide
SEQUENCE: 138
CARGEYGSGS RFDYW                                                   15

SEQ ID NO: 139           moltype = AA  length = 11
FEATURE                  Location/Qualifiers
source                   1..11
                         mol_type = protein
                         organism = synthetic construct
                         note = Description of Artificial Sequence: Synthetic peptide
SEQUENCE: 139
RASQGIRDDL G                                                       11

SEQ ID NO: 140           moltype = AA  length = 7
FEATURE                  Location/Qualifiers
source                   1..7
                         mol_type = protein
                         organism = synthetic construct
                         note = Description of Artificial Sequence: Synthetic peptide
SEQUENCE: 140
AASSLQS                                                            7

SEQ ID NO: 141           moltype = AA  length = 11
FEATURE                  Location/Qualifiers
source                   1..11
                         mol_type = protein
                         organism = synthetic construct
                         note = Description of Artificial Sequence: Synthetic peptide
SEQUENCE: 141
CLQDYDYPLT F                                                       11

SEQ ID NO: 142           moltype = AA  length = 119
FEATURE                  Location/Qualifiers
source                   1..119
                         mol_type = protein
                         organism = synthetic construct
                         note = Description of Artificial Sequence: Synthetic
                          polypeptide
SEQUENCE: 142
QVQLQQWGAG LLKPSETLSL TCAVYGGSFS GYYWTWIRQP PGKGLEWIGE ITHSGSTNYN  60
PSLKSRVSIS VDTSKNQFSL KLSSVTAADT AVYYCARGEY GSGSRFDYWG QGTLVTVSS   119

SEQ ID NO: 143           moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 143
AIQMTQSPSS LSASVGDRVA ITCRASQGIR DDLGWYQQKP GKAPKLLIYA ASSLQSGVPS  60
```

-continued

```
RFSGSGSDTD FTLTISSLQP EDFATYYCLQ DYDYPLTFGG GTKVEIK                        107

SEQ ID NO: 144            moltype = AA   length = 246
FEATURE                   Location/Qualifiers
source                    1..246
                          mol_type = protein
                          organism = synthetic construct
                          note = Description of Artificial Sequence: Synthetic
                           polypeptide
SEQUENCE: 144
QVQLQQWGAG LLKPSETLSL TCAVYGGSFS GYYWTWIRQP PGKGLEWIGE ITHSGSTNYN   60
PSLKSRVSIS VDTSKNQFSL KLSSVTAADT AVYYCARGEY GSGSRFDYWG QGTLVTVSSG   120
GGGSGGGGSG GGGSGGGGSA IQMTQSPSSL SASVGDRVAI TCRASQGIRD DLGWYQQKPG   180
KAPKLLIYAA SSLQSGVPSR FSGSGSDTDF TLTISSLQPE DFATYYCLQD YDYPLTFGGG   240
TKVEIK                                                             246

SEQ ID NO: 145            moltype = AA   length = 9
FEATURE                   Location/Qualifiers
source                    1..9
                          mol_type = protein
                          organism = synthetic construct
                          note = Description of Artificial Sequence: Synthetic peptide
SEQUENCE: 145
GSFSGYYWS                                                           9

SEQ ID NO: 146            moltype = AA   length = 12
FEATURE                   Location/Qualifiers
source                    1..12
                          mol_type = protein
                          organism = synthetic construct
                          note = Description of Artificial Sequence: Synthetic peptide
SEQUENCE: 146
GEITHSGSTN YN                                                       12

SEQ ID NO: 147            moltype = AA   length = 15
FEATURE                   Location/Qualifiers
source                    1..15
                          mol_type = protein
                          organism = synthetic construct
                          note = Description of Artificial Sequence: Synthetic peptide
SEQUENCE: 147
CARGEYGSGS RFDYW                                                    15

SEQ ID NO: 148            moltype = AA   length = 11
FEATURE                   Location/Qualifiers
source                    1..11
                          mol_type = protein
                          organism = synthetic construct
                          note = Description of Artificial Sequence: Synthetic peptide
SEQUENCE: 148
RASQGIRDDL G                                                        11

SEQ ID NO: 149            moltype = AA   length = 7
FEATURE                   Location/Qualifiers
source                    1..7
                          mol_type = protein
                          organism = synthetic construct
                          note = Description of Artificial Sequence: Synthetic peptide
SEQUENCE: 149
AASSLQS                                                             7

SEQ ID NO: 150            moltype = AA   length = 11
FEATURE                   Location/Qualifiers
source                    1..11
                          mol_type = protein
                          organism = synthetic construct
                          note = Description of Artificial Sequence: Synthetic peptide
SEQUENCE: 150
CLQDYDYPLT F                                                        11

SEQ ID NO: 151            moltype = AA   length = 119
FEATURE                   Location/Qualifiers
source                    1..119
                          mol_type = protein
                          organism = synthetic construct
                          note = Description of Artificial Sequence: Synthetic
                           polypeptide
SEQUENCE: 151
QVQLQQWGAG LLKPSETLSL TCAVYGGSFS GYYWSWIRQP PGKGLEWIGE ITHSGSTNYN   60
```

```
PSLKSRVSIS VDTSKNQFSL KLSSVTAADT AVYYCARGEY GSGSRFDYWG QGTLVTVSS    119

SEQ ID NO: 152          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 152
AIQMTQSPSS LSASVGDRVA LTCRASQGIR DDLGWYQQKP GKAPKLLIYA ASSLQSGVPS    60
RFSGSGSDTD FTLTISSLQP EDFATYYCLQ DYDYPLTFGG GTKVEIK                 107

SEQ ID NO: 153          moltype = AA  length = 246
FEATURE                 Location/Qualifiers
source                  1..246
                        mol_type = protein
                        organism = synthetic construct
                        note = Description of Artificial Sequence: Synthetic
                         polypeptide
SEQUENCE: 153
QVQLQQWGAG LLKPSETLSL TCAVYGGSFS GYYWSWIRQP PGKGLEWIGE ITHSGSTNYN    60
PSLKSRVSIS VDTSKNQFSL KLSSVTAADT AVYYCARGEY GSGSRFDYWG QGTLVTVSSG   120
GGGSGGGGSG GGGSGGGGSA IQMTQSPSSL SASVGDRVAL TCRASQGIRD DLGWYQQKPG   180
KAPKLLIYAA SSLQSGVPSR FSGSGSDTDF TLTISSLQPE DFATYYCLQD YDYPLTFGGG   240
TKVEIK                                                             246

SEQ ID NO: 154          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 154
GSFSAYYWN                                                            9

SEQ ID NO: 155          moltype = AA  length = 12
FEATURE                 Location/Qualifiers
source                  1..12
                        mol_type = protein
                        organism = synthetic construct
                        note = Description of Artificial Sequence: Synthetic peptide
SEQUENCE: 155
GEINHSGSTN YN                                                       12

SEQ ID NO: 156          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 156
CARGLDSSGW YPFDYW                                                   16

SEQ ID NO: 157          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 157
RASQGISSWL A                                                        11

SEQ ID NO: 158          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 158
AASSLQS                                                              7

SEQ ID NO: 159          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 159
```

```
CQQADSFPFT F                                                              11

SEQ ID NO: 160          moltype = AA  length = 120
FEATURE                 Location/Qualifiers
source                  1..120
                        mol_type = protein
                        organism = synthetic construct
                        note = Description of Artificial Sequence: Synthetic
                         polypeptide
SEQUENCE: 160
QVQLQQWGAG LLKPSETLSL TCAVYGGSFS AYYWNWIRQP PGKGLEWIGE INHSGSTNYN  60
PSLKSRVTIS VDTSKNQFSL NLTSLTAADT AVYYCARGLD SSGWYPFDYW GQGTLVTVSS  120

SEQ ID NO: 161          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 161
DIQMTQSPSS VSASVGDRVT ITCRASQGIS SWLAWYQQKP GKAPKLLIYA ASSLQSGVPS  60
RFSGSGSGTD FTLTISSLQP EDFATYYCQQ ADSFPFTFGP GTKVDIK            107

SEQ ID NO: 162          moltype = AA  length = 247
FEATURE                 Location/Qualifiers
source                  1..247
                        mol_type = protein
                        organism = synthetic construct
                        note = Description of Artificial Sequence: Synthetic
                         polypeptide
SEQUENCE: 162
QVQLQQWGAG LLKPSETLSL TCAVYGGSFS AYYWNWIRQP PGKGLEWIGE INHSGSTNYN  60
PSLKSRVTIS VDTSKNQFSL NLTSLTAADT AVYYCARGLD SSGWYPFDYW GQGTLVTVSS  120
GGGGSGGGGS GGGGSGGGGS DIQMTQSPSS VSASVGDRVT ITCRASQGIS SWLAWYQQKP  180
GKAPKLLIYA ASSLQSGVPS RFSGSGSGTD FTLTISSLQP EDFATYYCQQ ADSFPFTFGP  240
GTKVDIK                                                            247

SEQ ID NO: 163          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 163
GSFSGDYWS                                                          9

SEQ ID NO: 164          moltype = AA  length = 12
FEATURE                 Location/Qualifiers
source                  1..12
                        mol_type = protein
                        organism = synthetic construct
                        note = Description of Artificial Sequence: Synthetic peptide
SEQUENCE: 164
GEINHSGITS FN                                                      12

SEQ ID NO: 165          moltype = AA  length = 12
FEATURE                 Location/Qualifiers
source                  1..12
                        mol_type = protein
                        organism = synthetic construct
                        note = Description of Artificial Sequence: Synthetic peptide
SEQUENCE: 165
CARGELGIPD NW                                                      12

SEQ ID NO: 166          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 166
RASQSISRWL A                                                       11

SEQ ID NO: 167          moltype = AA  length = 7
FEATURE                 Location/Qualifiers
source                  1..7
                        mol_type = protein
                        organism = synthetic construct
```

```
                            note = Description of Artificial Sequence: Synthetic peptide
SEQUENCE: 167
KASSLES                                                                      7

SEQ ID NO: 168              moltype = AA   length = 10
FEATURE                     Location/Qualifiers
source                      1..10
                            mol_type = protein
                            organism = synthetic construct
                            note = Description of Artificial Sequence: Synthetic peptide
SEQUENCE: 168
CQQYNSYSTF                                                                   10

SEQ ID NO: 169              moltype = AA   length = 116
FEATURE                     Location/Qualifiers
source                      1..116
                            mol_type = protein
                            organism = synthetic construct
                            note = Description of Artificial Sequence: Synthetic
                             polypeptide
SEQUENCE: 169
QVQLQQWGAG LLKPSETLSL TCAVFGGSFS GDYWSWIRQP PGKGLEWIGE INHSGITSFN  60
PSLKSRVTIS VDTSKNQFSL KLSSVTAADT AVYYCARGEL GIPDNWGQGT LVTVSS      116

SEQ ID NO: 170              moltype = AA   length = 106
FEATURE                     Location/Qualifiers
source                      1..106
                            mol_type = protein
                            organism = synthetic construct
                            note = Description of Artificial Sequence: Synthetic
                             polypeptide
SEQUENCE: 170
DIQMTQSPST LSASVGDRVT ITCRASQSIS RWLAWYQQKP GKAPKLLIYK ASSLESGVPS  60
RFSGSGSGTE FTLTISSLQP DDFATYYCQQ YNSYSTFGQG TKVEIK               106

SEQ ID NO: 171              moltype = AA   length = 242
FEATURE                     Location/Qualifiers
source                      1..242
                            mol_type = protein
                            organism = synthetic construct
                            note = Description of Artificial Sequence: Synthetic
                             polypeptide
SEQUENCE: 171
QVQLQQWGAG LLKPSETLSL TCAVFGGSFS GDYWSWIRQP PGKGLEWIGE INHSGITSFN  60
PSLKSRVTIS VDTSKNQFSL KLSSVTAADT AVYYCARGEL GIPDNWGQGT LVTVSSGGGG  120
SGGGGSGGGG SGGGGSDIQM TQSPSTLSAS VGDRVTITCR ASQSISRWLA WYQQKPGKAP  180
KLLIYKASSL ESGVPSRFSG SGSGTEFTLT ISSLQPDDFA TYYCQQYNSY STFGQGTKVE  240
IK                                                                 242

SEQ ID NO: 172              moltype = AA   length = 10
FEATURE                     Location/Qualifiers
source                      1..10
                            mol_type = protein
                            organism = synthetic construct
                            note = Description of Artificial Sequence: Synthetic peptide
SEQUENCE: 172
DSISSSNWWS                                                                   10

SEQ ID NO: 173              moltype = AA   length = 12
FEATURE                     Location/Qualifiers
source                      1..12
                            mol_type = protein
                            organism = synthetic construct
                            note = Description of Artificial Sequence: Synthetic peptide
SEQUENCE: 173
GEVFHSGSTN YN                                                                12

SEQ ID NO: 174              moltype = AA   length = 13
FEATURE                     Location/Qualifiers
source                      1..13
                            mol_type = protein
                            organism = synthetic construct
                            note = Description of Artificial Sequence: Synthetic peptide
SEQUENCE: 174
CARAAVAGAL DYW                                                               13

SEQ ID NO: 175              moltype = AA   length = 17
FEATURE                     Location/Qualifiers
source                      1..17
```

```
                        mol_type = protein
                        organism = synthetic construct
                        note = Description of Artificial Sequence: Synthetic peptide
SEQUENCE: 175
KSSQSVLYSS NNKNYLA                                                      17

SEQ ID NO: 176          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 176
WASTRES                                                                 7

SEQ ID NO: 177          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 177
CQQYYGTSWT F                                                            11

SEQ ID NO: 178          moltype = AA   length = 118
FEATURE                 Location/Qualifiers
source                  1..118
                        mol_type = protein
                        organism = synthetic construct
                        note = Description of Artificial Sequence: Synthetic
                         polypeptide
SEQUENCE: 178
QVQLQESGPG LVKPSGTLSL TCVVFGDSIS SSNWWSWVRQ PPGKGLEWIG EVFHSGSTNY  60
NPSLKSRVTI SVDKSKNQFS LKLSSVTAAD TAVYYCARAA VAGALDYWGQ GTLVTVSS    118

SEQ ID NO: 179          moltype = AA   length = 113
FEATURE                 Location/Qualifiers
source                  1..113
                        mol_type = protein
                        organism = synthetic construct
                        note = Description of Artificial Sequence: Synthetic
                         polypeptide
SEQUENCE: 179
DIVMTQSPDS LAVSLGERAT INCKSSQSVL YSSNNKNYLA WYQQKPGQPP NLLVYWASTR  60
ESGVPDRFSG AGSGTDFTLT ISSLQAEDVA VYYCQQYYGT SWTFGQGTKV EIK         113

SEQ ID NO: 180          moltype = AA   length = 251
FEATURE                 Location/Qualifiers
source                  1..251
                        mol_type = protein
                        organism = synthetic construct
                        note = Description of Artificial Sequence: Synthetic
                         polypeptide
SEQUENCE: 180
QVQLQESGPG LVKPSGTLSL TCVVFGDSIS SSNWWSWVRQ PPGKGLEWIG EVFHSGSTNY  60
NPSLKSRVTI SVDKSKNQFS LKLSSVTAAD TAVYYCARAA VAGALDYWGQ GTLVTVSSGG  120
GGSGGGGSGG GGSGGGGSDI VMTQSPDSLA VSLGERATIN CKSSQSVLYS SNNKNYLAWY  180
QQKPGQPPNL LVYWASTRES GVPDRFSGAG SGTDFTLTIS SLQAEDVAVY YCQQYYGTSW  240
TFGQGTKVEI K                                                       251

SEQ ID NO: 181          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 181
FSLSTSGLGV G                                                           11

SEQ ID NO: 182          moltype = AA   length = 12
FEATURE                 Location/Qualifiers
source                  1..12
                        mol_type = protein
                        organism = synthetic construct
                        note = Description of Artificial Sequence: Synthetic peptide
SEQUENCE: 182
ALIYWNDDKR YS                                                          12

SEQ ID NO: 183          moltype = AA   length = 14
```

-continued

```
FEATURE             Location/Qualifiers
source              1..14
                    mol_type = protein
                    organism = synthetic construct
                    note = Description of Artificial Sequence: Synthetic peptide
SEQUENCE: 183
CVHRRIAAPG SVYW                                                     14

SEQ ID NO: 184      moltype = AA  length = 11
FEATURE             Location/Qualifiers
source              1..11
                    mol_type = protein
                    organism = synthetic construct
                    note = Description of Artificial Sequence: Synthetic peptide
SEQUENCE: 184
RASQGISSWL A                                                        11

SEQ ID NO: 185      moltype = AA  length = 7
FEATURE             Location/Qualifiers
source              1..7
                    mol_type = protein
                    organism = synthetic construct
                    note = Description of Artificial Sequence: Synthetic peptide
SEQUENCE: 185
AASSLQS                                                             7

SEQ ID NO: 186      moltype = AA  length = 11
FEATURE             Location/Qualifiers
source              1..11
                    mol_type = protein
                    organism = synthetic construct
                    note = Description of Artificial Sequence: Synthetic peptide
SEQUENCE: 186
CHQANSFPFT F                                                        11

SEQ ID NO: 187      moltype = AA  length = 120
FEATURE             Location/Qualifiers
source              1..120
                    mol_type = protein
                    organism = synthetic construct
                    note = Description of Artificial Sequence: Synthetic
                     polypeptide
SEQUENCE: 187
QITLRESGPT LVKPTQTLTL TCTFSGFSLS TSGLGVGWIR QPPGEALEWL ALIYWNDDKR   60
YSPSLKSRLS ITKDTSKNQV VLIMTNMDPV DTATYYCVHR RIAAPGSVYW GQGTLVTVSS   120

SEQ ID NO: 188      moltype = AA  length = 107
FEATURE             Location/Qualifiers
source              1..107
                    mol_type = protein
                    organism = synthetic construct
                    note = Description of Artificial Sequence: Synthetic
                     polypeptide
SEQUENCE: 188
DIQMTQSPSS VSASVGDRVT ITCRASQGIS SWLAWYQQKP GKAPKLLISA ASSLQSGVPS   60
RFSGSGSGTD FTLTISSLQP EDFATYYCHQ ANSFPFTFGQ GTKLEIK               107

SEQ ID NO: 189      moltype = AA  length = 247
FEATURE             Location/Qualifiers
source              1..247
                    mol_type = protein
                    organism = synthetic construct
                    note = Description of Artificial Sequence: Synthetic
                     polypeptide
SEQUENCE: 189
QITLRESGPT LVKPTQTLTL TCTFSGFSLS TSGLGVGWIR QPPGEALEWL ALIYWNDDKR   60
YSPSLKSRLS ITKDTSKNQV VLIMTNMDPV DTATYYCVHR RIAAPGSVYW GQGTLVTVSS   120
GGGGSGGGGS GGGGSGGGGS DIQMTQSPSS VSASVGDRVT ITCRASQGIS SWLAWYQQKP   180
GKAPKLLISA ASSLQSGVPS RFSGSGSGTD FTLTISSLQP EDFATYYCHQ ANSFPFTFGQ   240
GTKLEIK                                                            247

SEQ ID NO: 190      moltype = AA  length = 9
FEATURE             Location/Qualifiers
source              1..9
                    mol_type = protein
                    organism = synthetic construct
                    note = Description of Artificial Sequence: Synthetic peptide
SEQUENCE: 190
YTLTELSMH                                                           9
```

-continued

SEQ ID NO: 191          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 191
GGFDPEDGKT IYA                                                      13

SEQ ID NO: 192          moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 192
CATLLRGLDA FDVW                                                     14

SEQ ID NO: 193          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 193
RASQGIRNDL G                                                        11

SEQ ID NO: 194          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 194
AASSLQS                                                             7

SEQ ID NO: 195          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 195
CLQHNSYPRT F                                                        11

SEQ ID NO: 196          moltype = AA   length = 119
FEATURE                 Location/Qualifiers
source                  1..119
                        mol_type = protein
                        organism = synthetic construct
                        note = Description of Artificial Sequence: Synthetic
                         polypeptide
SEQUENCE: 196
QVQLVQSGAE VKKPGASVKV SCKVSGYTLT ELSMHWVRQA PGKGPEGMGG FDPEDGKTIY  60
AQKFQGRVTM TEDTSADTAY MELNSLRSED TAVYYCATLL RGLDAFDVWG QGTMVTVSS   119

SEQ ID NO: 197          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 197
DIQMTQSPSS LSASVGDRVT ITCRASQGIR NDLGWYQQKP GKAPKRLIYA ASSLQSGVPS  60
RFSGSGSGTE FTLTISTLQP EDFATYYCLQ HNSYPRTFGQ GTKVEIK                107

SEQ ID NO: 198          moltype = AA   length = 246
FEATURE                 Location/Qualifiers
source                  1..246
                        mol_type = protein
                        organism = synthetic construct
                        note = Description of Artificial Sequence: Synthetic
                         polypeptide
SEQUENCE: 198
QVQLVQSGAE VKKPGASVKV SCKVSGYTLT ELSMHWVRQA PGKGPEGMGG FDPEDGKTIY  60
AQKFQGRVTM TEDTSADTAY MELNSLRSED TAVYYCATLL RGLDAFDVWG QGTMVTVSSG  120
GGGSGGGGSG GGGSGGGGSD IQMTQSPSSL SASVGDRVTI TCRASQGIRN DLGWYQQKPG  180

-continued

```
KAPKRLIYAA SSLQSGVPSR FSGSGSGTEF TLTISTLQPE DFATYYCLQH NSYPRTFGQG  240
TKVEIK                                                              246

SEQ ID NO: 199        moltype = AA  length = 9
FEATURE               Location/Qualifiers
source                1..9
                      mol_type = protein
                      organism = synthetic construct
                      note = Description of Artificial Sequence: Synthetic peptide
SEQUENCE: 199
GSFSGYYWR                                                           9

SEQ ID NO: 200        moltype = AA  length = 12
FEATURE               Location/Qualifiers
source                1..12
                      mol_type = protein
                      organism = synthetic construct
                      note = Description of Artificial Sequence: Synthetic peptide
SEQUENCE: 200
GEISHSGSTN YN                                                       12

SEQ ID NO: 201        moltype = AA  length = 16
FEATURE               Location/Qualifiers
source                1..16
                      mol_type = protein
                      organism = synthetic construct
                      note = Description of Artificial Sequence: Synthetic peptide
SEQUENCE: 201
CAVRGYSYGY PLFDYW                                                   16

SEQ ID NO: 202        moltype = AA  length = 11
FEATURE               Location/Qualifiers
source                1..11
                      mol_type = protein
                      organism = synthetic construct
                      note = Description of Artificial Sequence: Synthetic peptide
SEQUENCE: 202
RASQGIRNDL G                                                        11

SEQ ID NO: 203        moltype = AA  length = 7
FEATURE               Location/Qualifiers
source                1..7
                      mol_type = protein
                      organism = synthetic construct
                      note = Description of Artificial Sequence: Synthetic peptide
SEQUENCE: 203
AASSLQS                                                             7

SEQ ID NO: 204        moltype = AA  length = 11
FEATURE               Location/Qualifiers
source                1..11
                      mol_type = protein
                      organism = synthetic construct
                      note = Description of Artificial Sequence: Synthetic peptide
SEQUENCE: 204
CLQYNSYPRT F                                                        11

SEQ ID NO: 205        moltype = AA  length = 120
FEATURE               Location/Qualifiers
source                1..120
                      mol_type = protein
                      organism = synthetic construct
                      note = Description of Artificial Sequence: Synthetic
                       polypeptide
SEQUENCE: 205
QVQLQQWGAG LLKPSETLSL TCAVYGGSFS GYYWRWIRQP PGKGLEWIGE ISHSGSTNYN  60
PSLKSRVTIS VDTSKNQFSL KLSSVTAADT AVYYCAVRGY SYGYPLFDYW GQGTLVTVSS  120

SEQ ID NO: 206        moltype = AA  length = 107
FEATURE               Location/Qualifiers
source                1..107
                      mol_type = protein
                      organism = synthetic construct
                      note = Description of Artificial Sequence: Synthetic
                       polypeptide
SEQUENCE: 206
DIQMTQSPSS LSASVGDRVT ITCRASQGIR NDLGWYQQKL GKAPKRLIYA ASSLQSGVPS  60
RFSGSGSGTE FTLTISSLQP EDFATYYCLQ YNSYPRTFGQ GTKVEIK                107
```

-continued

```
SEQ ID NO: 207           moltype = AA   length = 247
FEATURE                  Location/Qualifiers
source                   1..247
                         mol_type = protein
                         organism = synthetic construct
                         note = Description of Artificial Sequence: Synthetic
                          polypeptide
SEQUENCE: 207
QVQLQQWGAG LLKPSETLSL TCAVYGGSFS GYYWRWIRQP PGKGLEWIGE ISHSGSTNYN   60
PSLKSRVTIS VDTSKNQFSL KLSSVTAADT AVYYCAVRGY SYGYPLFDYW GQGTLVTVSS   120
GGGGSGGGGS GGGGSGGGGS DIQMTQSPSS LSASVGDRVT ITCRASQGIR NDLGWYQQKL   180
GKAPKRLIYA ASSLQSGVPS RFSGSGSGTE FTLTISSLQP EDFATYYCLQ YNSYPRTFGQ   240
GTKVEIK                                                             247

SEQ ID NO: 208           moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 208
DSISSNWWT                                                           9

SEQ ID NO: 209           moltype = AA   length = 12
FEATURE                  Location/Qualifiers
source                   1..12
                         mol_type = protein
                         organism = synthetic construct
                         note = Description of Artificial Sequence: Synthetic peptide
SEQUENCE: 209
GDIHHSGSTN YN                                                       12

SEQ ID NO: 210           moltype = AA   length = 12
FEATURE                  Location/Qualifiers
source                   1..12
                         mol_type = protein
                         organism = synthetic construct
                         note = Description of Artificial Sequence: Synthetic peptide
SEQUENCE: 210
CARDGGGTLD YW                                                       12

SEQ ID NO: 211           moltype = AA   length = 11
FEATURE                  Location/Qualifiers
source                   1..11
                         mol_type = protein
                         organism = synthetic construct
                         note = Description of Artificial Sequence: Synthetic peptide
SEQUENCE: 211
RASQSISSWL A                                                        11

SEQ ID NO: 212           moltype = AA   length = 7
FEATURE                  Location/Qualifiers
source                   1..7
                         mol_type = protein
                         organism = synthetic construct
                         note = Description of Artificial Sequence: Synthetic peptide
SEQUENCE: 212
KASTLES                                                             7

SEQ ID NO: 213           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 213
CQQYNGYSTF                                                          10

SEQ ID NO: 214           moltype = AA   length = 116
FEATURE                  Location/Qualifiers
source                   1..116
                         mol_type = protein
                         organism = synthetic construct
                         note = Description of Artificial Sequence: Synthetic
                          polypeptide
SEQUENCE: 214
QVQLQESGPG LVKPSGTLSL TCAVSGDSIS SNWWTWVRQP PGKGLEWIGD IHHSGSTNYN   60
PSLKSRVTMS VDKSENQFSL KLSSVTAADT AVFYCARDGG GTLDYWGQGT LVTVSS       116
```

-continued

```
SEQ ID NO: 215          moltype = AA   length = 106
FEATURE                 Location/Qualifiers
source                  1..106
                        mol_type = protein
                        organism = synthetic construct
                        note = Description of Artificial Sequence: Synthetic
                         polypeptide
SEQUENCE: 215
DIQMTQSPST LSASVGDRVT ITCRASQSIS SWLAWYQQKP GKAPKLLIYK ASTLESGVPS   60
RFSGSGSGTE FTLTISSLQP DDFATYYCQQ YNGYSTFGQG TKVEIK                 106

SEQ ID NO: 216          moltype = AA   length = 242
FEATURE                 Location/Qualifiers
source                  1..242
                        mol_type = protein
                        organism = synthetic construct
                        note = Description of Artificial Sequence: Synthetic
                         polypeptide
SEQUENCE: 216
QVQLQESGPG LVKPSGTLSL TCAVSGDSIS SNWWTWVRQP PGKGLEWIGD IHHSGSTNYN   60
PSLKSRVTMS VDKSENQFSL KLSSVTAADT AVFYCARDGG GTLDYWGQGT LVTVSSGGGG  120
SGGGGSGGGG SGGGGSDIQM TQSPSTLSAS VGDRVTITCR ASQSISSWLA WYQQKPGKAP  180
KLLIYKASTL ESGVPSRFSG SGSGTEFTLT ISSLQPDDFA TYYCQQYNGY STFGQGTKVE  240
IK                                                                242

SEQ ID NO: 217          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 217
GTFTNYCIS                                                           9

SEQ ID NO: 218          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 218
GGIIPIFGTT NYA                                                     13

SEQ ID NO: 219          moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 219
CARDNGDRYY YDMDVW                                                  16

SEQ ID NO: 220          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 220
SGSSSNIGNN YVS                                                     13

SEQ ID NO: 221          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 221
DNNKRPS                                                            7

SEQ ID NO: 222          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 222
CGTWDSSLSA VVF                                                     13
```

```
SEQ ID NO: 223              moltype = AA  length = 121
FEATURE                     Location/Qualifiers
source                      1..121
                            mol_type = protein
                            organism = synthetic construct
                            note = Description of Artificial Sequence: Synthetic
                             polypeptide
SEQUENCE: 223
QVQLVQSGAE VKKPGSSVKV SCKASGGTFT NYCISWVRQA PGQGLEWMGG IIPIFGTTNY  60
AQTFQGRVTI TADKSTSTAY MELSSLRSED TAVYYCARDN GDRYYYDMDV WGQGTTVTVS  120
S                                                                 121

SEQ ID NO: 224              moltype = AA  length = 110
FEATURE                     Location/Qualifiers
source                      1..110
                            mol_type = protein
                            organism = synthetic construct
                            note = Description of Artificial Sequence: Synthetic
                             polypeptide
SEQUENCE: 224
QSVLTQPPSV SAAPGQKVTI SCSGSSSNIG NNYVSWYQQL PGTAPKLLIY DNNKRPSGIP  60
DRFSGSKSGT SATLGITGLQ TGDEADYYCG TWDSSLSAVV FGGGTKLTVL            110

SEQ ID NO: 225              moltype = AA  length = 251
FEATURE                     Location/Qualifiers
source                      1..251
                            mol_type = protein
                            organism = synthetic construct
                            note = Description of Artificial Sequence: Synthetic
                             polypeptide
SEQUENCE: 225
QVQLVQSGAE VKKPGSSVKV SCKASGGTFT NYCISWVRQA PGQGLEWMGG IIPIFGTTNY  60
AQTFQGRVTI TADKSTSTAY MELSSLRSED TAVYYCARDN GDRYYYDMDV WGQGTTVTVS  120
SGGGGSGGGG SGGGGSGGGG SQSVLTQPPS VSAAPGQKVT ISCSGSSSNI GNNYVSWYQQ  180
LPGTAPKLLI YDNNKRPSGI PDRFSGSKSG TSATLGITGL QTGDEADYYC GTWDSSLSAV  240
VFGGGTKLTV L                                                      251

SEQ ID NO: 226              moltype = AA  length = 9
FEATURE                     Location/Qualifiers
source                      1..9
                            mol_type = protein
                            organism = synthetic construct
                            note = Description of Artificial Sequence: Synthetic peptide
SEQUENCE: 226
GTFSTYSIS                                                          9

SEQ ID NO: 227              moltype = AA  length = 13
FEATURE                     Location/Qualifiers
source                      1..13
                            mol_type = protein
                            organism = synthetic construct
                            note = Description of Artificial Sequence: Synthetic peptide
SEQUENCE: 227
GGIIPIFGTT NYA                                                     13

SEQ ID NO: 228              moltype = AA  length = 18
FEATURE                     Location/Qualifiers
source                      1..18
                            mol_type = protein
                            organism = synthetic construct
                            note = Description of Artificial Sequence: Synthetic peptide
SEQUENCE: 228
CARDGEGSYY YYYGMDVW                                                18

SEQ ID NO: 229              moltype = AA  length = 13
FEATURE                     Location/Qualifiers
source                      1..13
                            mol_type = protein
                            organism = synthetic construct
                            note = Description of Artificial Sequence: Synthetic peptide
SEQUENCE: 229
SGSSSNIGNN YVS                                                     13

SEQ ID NO: 230              moltype = AA  length = 7
FEATURE                     Location/Qualifiers
source                      1..7
                            mol_type = protein
                            organism = synthetic construct
                            note = Description of Artificial Sequence: Synthetic peptide
```

```
SEQUENCE: 230
DNNKRPS                                                                    7

SEQ ID NO: 231        moltype = AA  length = 13
FEATURE               Location/Qualifiers
source                1..13
                      mol_type = protein
                      organism = synthetic construct
                      note = Description of Artificial Sequence: Synthetic peptide
SEQUENCE: 231
CGTWDSSLSA VVF                                                             13

SEQ ID NO: 232        moltype = AA  length = 123
FEATURE               Location/Qualifiers
source                1..123
                      mol_type = protein
                      organism = synthetic construct
                      note = Description of Artificial Sequence: Synthetic
                       polypeptide
SEQUENCE: 232
QVPLVQSGAE VKKPGSSVKV SCKASGGTFS TYSISWVRQA PGQGLEWMGG IIPIFGTTNY  60
AQKFQGRVTI TADKSTSTAY MELSSLRSED TAVYYCARDG EGSYYYYYGM DVWGQGTTVT  120
VSS                                                                       123

SEQ ID NO: 233        moltype = AA  length = 110
FEATURE               Location/Qualifiers
source                1..110
                      mol_type = protein
                      organism = synthetic construct
                      note = Description of Artificial Sequence: Synthetic
                       polypeptide
SEQUENCE: 233
QSVLTQPPSV SAAPGQKVTI SCSGSSSNIG NNYVSWYQQL PGTAPKLLIY DNNKRPSGIP  60
DRFFGSKFGT SATLGITGLQ TGDEADYYCG TWDSSLSAVV FGGGTKLTVL             110

SEQ ID NO: 234        moltype = AA  length = 253
FEATURE               Location/Qualifiers
source                1..253
                      mol_type = protein
                      organism = synthetic construct
                      note = Description of Artificial Sequence: Synthetic
                       polypeptide
SEQUENCE: 234
QVPLVQSGAE VKKPGSSVKV SCKASGGTFS TYSISWVRQA PGQGLEWMGG IIPIFGTTNY  60
AQKFQGRVTI TADKSTSTAY MELSSLRSED TAVYYCARDG EGSYYYYYGM DVWGQGTTVT  120
VSSGGGGSGG GGSGGGGSGG GGSQSVLTQP PSVSAAPGQK VTISCSGSSS NIGNNYVSWY  180
QQLPGTAPKL LIYDNNKRPS GIPDRFFGSK FGTSATLGIT GLQTGDEADY YCGTWDSSLS  240
AVVFGGGTKL TVL                                                             253

SEQ ID NO: 235        moltype = AA  length = 9
FEATURE               Location/Qualifiers
source                1..9
                      mol_type = protein
                      organism = synthetic construct
                      note = Description of Artificial Sequence: Synthetic peptide
SEQUENCE: 235
DSISSYYWS                                                                  9

SEQ ID NO: 236        moltype = AA  length = 12
FEATURE               Location/Qualifiers
source                1..12
                      mol_type = protein
                      organism = synthetic construct
                      note = Description of Artificial Sequence: Synthetic peptide
SEQUENCE: 236
GYMYYSGITN YN                                                              12

SEQ ID NO: 237        moltype = AA  length = 14
FEATURE               Location/Qualifiers
source                1..14
                      mol_type = protein
                      organism = synthetic construct
                      note = Description of Artificial Sequence: Synthetic peptide
SEQUENCE: 237
CARLSVAGFY FDYW                                                            14

SEQ ID NO: 238        moltype = AA  length = 12
FEATURE               Location/Qualifiers
source                1..12
```

```
                           mol_type = protein
                           organism = synthetic construct
                           note = Description of Artificial Sequence: Synthetic peptide
SEQUENCE: 238
RASQSVTRSY LA                                                       12

SEQ ID NO: 239             moltype = AA  length = 7
FEATURE                    Location/Qualifiers
source                     1..7
                           mol_type = protein
                           organism = synthetic construct
                           note = Description of Artificial Sequence: Synthetic peptide
SEQUENCE: 239
GASSRAT                                                             7

SEQ ID NO: 240             moltype = AA  length = 11
FEATURE                    Location/Qualifiers
source                     1..11
                           mol_type = protein
                           organism = synthetic construct
                           note = Description of Artificial Sequence: Synthetic peptide
SEQUENCE: 240
CQQYGTSPLT F                                                        11

SEQ ID NO: 241             moltype = AA  length = 118
FEATURE                    Location/Qualifiers
source                     1..118
                           mol_type = protein
                           organism = synthetic construct
                           note = Description of Artificial Sequence: Synthetic
                            polypeptide
SEQUENCE: 241
QVQLQESGPG LVKPSETLSL TCTVSGDSIS SYYWSWIRQP PGKGLEWIGY MYYSGITNYN   60
PSLKSRVNIS LDTSKNQFSL KLGSVTAADT AVYYCARLSV AGFYFDYWGQ GTLVTVSS     118

SEQ ID NO: 242             moltype = AA  length = 108
FEATURE                    Location/Qualifiers
source                     1..108
                           mol_type = protein
                           organism = synthetic construct
                           note = Description of Artificial Sequence: Synthetic
                            polypeptide
SEQUENCE: 242
EIVLTQSPGT LSLSPGERAT LSCRASQSVT RSYLAWYQQK PGQAPRLLIY GASSRATDIP   60
DRFSGSGSGT DFTLTINRLE PEDFAVYYCQ QYGTSPLTFG GGTKVEIK               108

SEQ ID NO: 243             moltype = AA  length = 246
FEATURE                    Location/Qualifiers
source                     1..246
                           mol_type = protein
                           organism = synthetic construct
                           note = Description of Artificial Sequence: Synthetic
                            polypeptide
SEQUENCE: 243
QVQLQESGPG LVKPSETLSL TCTVSGDSIS SYYWSWIRQP PGKGLEWIGY MYYSGITNYN   60
PSLKSRVNIS LDTSKNQFSL KLGSVTAADT AVYYCARLSV AGFYFDYWGQ GTLVTVSSGG   120
GGSGGGGSGG GGSGGGGSEI VLTQSPGTLS LSPGERATLS CRASQSVTRS YLAWYQQKPG   180
QAPRLLIYGA SSRATDIPDR FSGSGSGTDF TLTINRLEPE DFAVYYCQQY GTSPLTFGGG   240
TKVEIK                                                             246

SEQ ID NO: 244             moltype = AA  length = 9
FEATURE                    Location/Qualifiers
source                     1..9
                           mol_type = protein
                           organism = synthetic construct
                           note = Description of Artificial Sequence: Synthetic peptide
SEQUENCE: 244
DSISSYYWS                                                           9

SEQ ID NO: 245             moltype = AA  length = 12
FEATURE                    Location/Qualifiers
source                     1..12
                           mol_type = protein
                           organism = synthetic construct
                           note = Description of Artificial Sequence: Synthetic peptide
SEQUENCE: 245
SYIYYSGISN YN                                                       12

SEQ ID NO: 246             moltype = AA  length = 14
```

-continued

```
FEATURE            Location/Qualifiers
source             1..14
                   mol_type = protein
                   organism = synthetic construct
                   note = Description of Artificial Sequence: Synthetic peptide
SEQUENCE: 246
CARISVAGFF FDNW                                                           14

SEQ ID NO: 247     moltype = AA  length = 12
FEATURE            Location/Qualifiers
source             1..12
                   mol_type = protein
                   organism = synthetic construct
                   note = Description of Artificial Sequence: Synthetic peptide
SEQUENCE: 247
RASQSVSSSY LA                                                             12

SEQ ID NO: 248     moltype = AA  length = 7
FEATURE            Location/Qualifiers
source             1..7
                   mol_type = protein
                   organism = synthetic construct
                   note = Description of Artificial Sequence: Synthetic peptide
SEQUENCE: 248
GASSRAA                                                                    7

SEQ ID NO: 249     moltype = AA  length = 11
FEATURE            Location/Qualifiers
source             1..11
                   mol_type = protein
                   organism = synthetic construct
                   note = Description of Artificial Sequence: Synthetic peptide
SEQUENCE: 249
CQQYGISPLT F                                                             11

SEQ ID NO: 250     moltype = AA  length = 118
FEATURE            Location/Qualifiers
source             1..118
                   mol_type = protein
                   organism = synthetic construct
                   note = Description of Artificial Sequence: Synthetic
                    polypeptide
SEQUENCE: 250
QVQLQESGPG LVKPSETLSL TCTVSSDSIS SYYWSWIRQP PGKGLEWISY IYYSGISNYN  60
PSLKSRVSIS VDTSKNQFSL RLSSVTAADT AVYYCARISV AGFFFDNWGQ GTLVTVSS    118

SEQ ID NO: 251     moltype = AA  length = 108
FEATURE            Location/Qualifiers
source             1..108
                   mol_type = protein
                   organism = synthetic construct
                   note = Description of Artificial Sequence: Synthetic
                    polypeptide
SEQUENCE: 251
EIMLTQSPDT LSLSPGERAT LSCRASQSVS SSYLAWYQQK PGQAPRLLIY GASSRAAGVP  60
DRFSGSGSGT DFTLTISRLA PEDFVVYYCQ QYGISPLTFG GGTKVEIK            108

SEQ ID NO: 252     moltype = AA  length = 246
FEATURE            Location/Qualifiers
source             1..246
                   mol_type = protein
                   organism = synthetic construct
                   note = Description of Artificial Sequence: Synthetic
                    polypeptide
SEQUENCE: 252
QVQLQESGPG LVKPSETLSL TCTVSSDSIS SYYWSWIRQP PGKGLEWISY IYYSGISNYN  60
PSLKSRVSIS VDTSKNQFSL RLSSVTAADT AVYYCARISV AGFFFDNWGQ GTLVTVSSGG  120
GGSGGGGSGG GGSGGGGSEI MLTQSPDTLS LSPGERATLS CRASQSVSSS YLAWYQQKPG  180
QAPRLLIYGA SSRAAGVPDR FSGSGSGTDF TLTISRLAPE DFVVYYCQQY GISPLTFGGG  240
TKVEIK                                                             246

SEQ ID NO: 253     moltype = AA  length = 11
FEATURE            Location/Qualifiers
source             1..11
                   mol_type = protein
                   organism = synthetic construct
                   note = Description of Artificial Sequence: Synthetic peptide
SEQUENCE: 253
DSVSSNSATW N                                                             11
```

```
SEQ ID NO: 254        moltype = AA   length = 14
FEATURE               Location/Qualifiers
source                1..14
                      mol_type = protein
                      organism = synthetic construct
                      note = Description of Artificial Sequence: Synthetic peptide
SEQUENCE: 254
GRTYYRSKWY DDYA                                              14

SEQ ID NO: 255        moltype = AA   length = 16
FEATURE               Location/Qualifiers
source                1..16
                      mol_type = protein
                      organism = synthetic construct
                      note = Description of Artificial Sequence: Synthetic peptide
SEQUENCE: 255
CAGGGLVGAP DGFDVW                                            16

SEQ ID NO: 256        moltype = AA   length = 13
FEATURE               Location/Qualifiers
source                1..13
                      mol_type = protein
                      organism = synthetic construct
                      note = Description of Artificial Sequence: Synthetic peptide
SEQUENCE: 256
SGSSSNIGSD PVN                                               13

SEQ ID NO: 257        moltype = AA   length = 7
FEATURE               Location/Qualifiers
source                1..7
                      mol_type = protein
                      organism = synthetic construct
                      note = Description of Artificial Sequence: Synthetic peptide
SEQUENCE: 257
SNNQRPS                                                      7

SEQ ID NO: 258        moltype = AA   length = 13
FEATURE               Location/Qualifiers
source                1..13
                      mol_type = protein
                      organism = synthetic construct
                      note = Description of Artificial Sequence: Synthetic peptide
SEQUENCE: 258
CSAWDDSLNG YVF                                               13

SEQ ID NO: 259        moltype = AA   length = 124
FEATURE               Location/Qualifiers
source                1..124
                      mol_type = protein
                      organism = synthetic construct
                      note = Description of Artificial Sequence: Synthetic
                       polypeptide
SEQUENCE: 259
QVQLQQSGPG LVKPSQTLSL TCAISGDSVS SNSATWNWIR QSPSRGLEWL GRTYYRSKWY  60
DDYAVSVKSR ITINPDTSKN HLSLHLNSVT PEDTAVYYCA GGGLVGAPDG FDVWGQGTMV  120
TVSS                                                         124

SEQ ID NO: 260        moltype = AA   length = 110
FEATURE               Location/Qualifiers
source                1..110
                      mol_type = protein
                      organism = synthetic construct
                      note = Description of Artificial Sequence: Synthetic
                       polypeptide
SEQUENCE: 260
QSVLTQPPSA SGTPGQRVTI SCSGSSSNIG SDPVNWYQQL PGTAPKLLIY SNNQRPSGVP  60
DRFSGSKSGT SASLAISGLQ SEDEADYYCS AWDDSLNGYV FGTGTKVTVL            110

SEQ ID NO: 261        moltype = AA   length = 254
FEATURE               Location/Qualifiers
source                1..254
                      mol_type = protein
                      organism = synthetic construct
                      note = Description of Artificial Sequence: Synthetic
                       polypeptide
SEQUENCE: 261
QVQLQQSGPG LVKPSQTLSL TCAISGDSVS SNSATWNWIR QSPSRGLEWL GRTYYRSKWY  60
DDYAVSVKSR ITINPDTSKN HLSLHLNSVT PEDTAVYYCA GGGLVGAPDG FDVWGQGTMV  120
```

-continued

```
TVSSGGGGSG GGGSGGGGSG GGGSQSVLTQ PPSASGTPGQ RVTISCSGSS SNIGSDPVNW  180
YQQLPGTAPK LLIYSNNQRP SGVPDRFSGS KSGTSASLAI SGLQSEDEAD YYCSAWDDSL  240
NGYVFGTGTK VTVL                                                    254

SEQ ID NO: 262          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 262
YTFTGYSIH                                                          9

SEQ ID NO: 263          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 263
GWINPNSGGT FYA                                                     13

SEQ ID NO: 264          moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 264
CARDGWGDYY YYGLDVW                                                 17

SEQ ID NO: 265          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 265
RASQDISSWL A                                                       11

SEQ ID NO: 266          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 266
TASSLQG                                                            7

SEQ ID NO: 267          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 267
CQQANVFPYT F                                                       11

SEQ ID NO: 268          moltype = AA  length = 122
FEATURE                 Location/Qualifiers
source                  1..122
                        mol_type = protein
                        organism = synthetic construct
                        note = Description of Artificial Sequence: Synthetic
                         polypeptide
SEQUENCE: 268
QVQLVQSGAE VKKPGASVKV SCKASGYTFT GYSIHWVRQA PGQGLEWMGW INPNSGGTFY  60
AQKFQGRVTM TRDTSISTVY MELSRLRSDD TAVYYCARDG WGDYYYYGLD VWGQGTTVTV  120
SL                                                                122

SEQ ID NO: 269          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 269
DIQMTQSPSS VSASVGDRVT ITCRASQDIS SWLAWYQQKP GKAPKLLIYT ASSLQGGVPS  60
```

-continued

```
RFSGSGSGTD FTLTISSLQP EDLATYSCQQ ANVFPYTFGQ GTKLEIK            107

SEQ ID NO: 270         moltype = AA   length = 249
FEATURE                Location/Qualifiers
source                 1..249
                       mol_type = protein
                       organism = synthetic construct
                       note = Description of Artificial Sequence: Synthetic
                        polypeptide
SEQUENCE: 270
QVQLVQSGAE VKKPGASVKV SCKASGYTFT GYSIHWVRQA PGQGLEWMGW INPNSGGTFY  60
AQKFQGRVTM TRDTSISTVY MELSRLRSDD TAVYYCARDG WGDYYYYGLD VWGQGTTVTV  120
SLGGGGSGGG GSGGGGSGGG GSDIQMTQSP SSVSASVGDR VTITCRASQD ISSWLAWYQQ  180
KPGKAPKLLI YTASSLQGGV PSRFSGSGSG TDFTLTISSL QPEDLATYSC QQANVFPYTF  240
GQGTKLEIK                                                       249

SEQ ID NO: 271         moltype = AA   length = 9
FEATURE                Location/Qualifiers
source                 1..9
                       mol_type = protein
                       organism = synthetic construct
                       note = Description of Artificial Sequence: Synthetic peptide
SEQUENCE: 271
FTFSSYAMN                                                        9

SEQ ID NO: 272         moltype = AA   length = 13
FEATURE                Location/Qualifiers
source                 1..13
                       mol_type = protein
                       organism = synthetic construct
                       note = Description of Artificial Sequence: Synthetic peptide
SEQUENCE: 272
STISGSGGST YYA                                                   13

SEQ ID NO: 273         moltype = AA   length = 17
FEATURE                Location/Qualifiers
source                 1..17
                       mol_type = protein
                       organism = synthetic construct
                       note = Description of Artificial Sequence: Synthetic peptide
SEQUENCE: 273
CAIDPEYYDI LTGGDYW                                               17

SEQ ID NO: 274         moltype = AA   length = 11
FEATURE                Location/Qualifiers
source                 1..11
                       mol_type = protein
                       organism = synthetic construct
                       note = Description of Artificial Sequence: Synthetic peptide
SEQUENCE: 274
RASQGISNYL A                                                     11

SEQ ID NO: 275         moltype = AA   length = 7
FEATURE                Location/Qualifiers
source                 1..7
                       mol_type = protein
                       organism = synthetic construct
                       note = Description of Artificial Sequence: Synthetic peptide
SEQUENCE: 275
AASSLQS                                                          7

SEQ ID NO: 276         moltype = AA   length = 11
FEATURE                Location/Qualifiers
source                 1..11
                       mol_type = protein
                       organism = synthetic construct
                       note = Description of Artificial Sequence: Synthetic peptide
SEQUENCE: 276
CLQHDSFPLT F                                                     11

SEQ ID NO: 277         moltype = AA   length = 122
FEATURE                Location/Qualifiers
source                 1..122
                       mol_type = protein
                       organism = synthetic construct
                       note = Description of Artificial Sequence: Synthetic
                        polypeptide
SEQUENCE: 277
EVQLLESGGG LVQPGGSLRL SCAASGFTFS SYAMNWVRQA PGKGLEWVST ISGSGGSTYY  60
```

-continued

```
ADSVKGRFTI SRDNSKNTLY LQMNSLRAED TAVFYCAIDP EYYDILTGGD YWGQGTLVTV   120
SS                                                                  122

SEQ ID NO: 278          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 278
DIQMTQSPSA MSASVGDRVT ITCRASQGIS NYLAWFQQKP GKVPKRLIYA ASSLQSGVPS   60
RFSGSGSGTE FTLTISSLQP EDFATYFCLQ HDSFPLTFGG GTKVEIK                 107

SEQ ID NO: 279          moltype = AA   length = 250
FEATURE                 Location/Qualifiers
source                  1..250
                        mol_type = protein
                        organism = synthetic construct
                        note = Description of Artificial Sequence: Synthetic
                         polypeptide
SEQUENCE: 279
EVQLLESGGG LVQPGGSLRL SCAASGFTFS SYAMNWVRQA PGKGLEWVST ISGSGGSTYY   60
ADSVKGRFTI SRDNSKNTLY LQMNSLRAED TAVFYCAIDP EYYDILTGGD YWGQGTLVTV   120
SSGGGGSGGG GSGGGGSGG GGSDIQMTQS PSAMSASVGD RVTITCRASQ GISNYLAWFQ    180
QKPGKVPKRL IYAASSLQSG VPSRFSGSGS GTEFTLTISS LQPEDFATYF CLQHDSFPLT   240
FGGGTKVEIK                                                          250

SEQ ID NO: 280          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 280
DSISNYYWS                                                           9

SEQ ID NO: 281          moltype = AA   length = 12
FEATURE                 Location/Qualifiers
source                  1..12
                        mol_type = protein
                        organism = synthetic construct
                        note = Description of Artificial Sequence: Synthetic peptide
SEQUENCE: 281
SYIYYSGITN YN                                                       12

SEQ ID NO: 282          moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 282
CARITVTGFY FDYW                                                     14

SEQ ID NO: 283          moltype = AA   length = 12
FEATURE                 Location/Qualifiers
source                  1..12
                        mol_type = protein
                        organism = synthetic construct
                        note = Description of Artificial Sequence: Synthetic peptide
SEQUENCE: 283
RASQSISRSY LA                                                       12

SEQ ID NO: 284          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 284
GASSRAT                                                             7

SEQ ID NO: 285          moltype = AA   length = 11
FEATURE                 Location/Qualifiers
source                  1..11
                        mol_type = protein
                        organism = synthetic construct
                        note = Description of Artificial Sequence: Synthetic peptide
```

```
SEQUENCE: 285
CQQYDTSPLT F                                                          11

SEQ ID NO: 286          moltype = AA  length = 118
FEATURE                 Location/Qualifiers
source                  1..118
                        mol_type = protein
                        organism = synthetic construct
                        note = Description of Artificial Sequence: Synthetic
                         polypeptide
SEQUENCE: 286
QVQLQESGPG LVKPSETLSL TCTVSSDSIS NYYWSWIRQP PGKGLEWISY IYYSGITNYN  60
PSLKSRVTIS VDTSKNQFSL KLSSVTAADT AVYYCARITV TGFYFDYWGQ GTLVTVSS    118

SEQ ID NO: 287          moltype = AA  length = 108
FEATURE                 Location/Qualifiers
source                  1..108
                        mol_type = protein
                        organism = synthetic construct
                        note = Description of Artificial Sequence: Synthetic
                         polypeptide
SEQUENCE: 287
EIVLTQSPGT LSLSPGERAT LSCRASQSIS RSYLAWYQQK PGQAPRHLIY GASSRATGIP  60
DRFSGSGSGT DFILTISRLE PEDFAVYYCQ QYDTSPLTFG GGTKVEIK              108

SEQ ID NO: 288          moltype = AA  length = 246
FEATURE                 Location/Qualifiers
source                  1..246
                        mol_type = protein
                        organism = synthetic construct
                        note = Description of Artificial Sequence: Synthetic
                         polypeptide
SEQUENCE: 288
QVQLQESGPG LVKPSETLSL TCTVSSDSIS NYYWSWIRQP PGKGLEWISY IYYSGITNYN  60
PSLKSRVTIS VDTSKNQFSL KLSSVTAADT AVYYCARITV TGFYFDYWGQ GTLVTVSSGG  120
GGSGGGGSGG GGSGGGGSEI VLTQSPGTLS LSPGERATLS CRASQSISRS YLAWYQQKPG  180
QAPRHLIYGA SSRATGIPDR FSGSGSGTDF ILTISRLEPE DFAVYYCQQY DTSPLTFGGG  240
TKVEIK                                                             246

SEQ ID NO: 289          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 289
DSVSSNSVVW N                                                         11

SEQ ID NO: 290          moltype = AA  length = 14
FEATURE                 Location/Qualifiers
source                  1..14
                        mol_type = protein
                        organism = synthetic construct
                        note = Description of Artificial Sequence: Synthetic peptide
SEQUENCE: 290
GRTYYRSKWY DDYA                                                      14

SEQ ID NO: 291          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 291
CARGGIVGAP DAFDIW                                                    16

SEQ ID NO: 292          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 292
SGSSSNIGSD PVS                                                       13

SEQ ID NO: 293          moltype = AA  length = 7
FEATURE                 Location/Qualifiers
source                  1..7
                        mol_type = protein
```

-continued

```
                              organism = synthetic construct
                              note = Description of Artificial Sequence: Synthetic peptide
SEQUENCE: 293
TNNQRPS                                                                    7

SEQ ID NO: 294         moltype = AA   length = 13
FEATURE                Location/Qualifiers
source                 1..13
                       mol_type = protein
                       organism = synthetic construct
                       note = Description of Artificial Sequence: Synthetic peptide
SEQUENCE: 294
CAAWDDSLNG HVF                                                              13

SEQ ID NO: 295         moltype = AA   length = 124
FEATURE                Location/Qualifiers
source                 1..124
                       mol_type = protein
                       organism = synthetic construct
                       note = Description of Artificial Sequence: Synthetic
                        polypeptide
SEQUENCE: 295
QVQLQQSGPG LVKPSQTLSL TCAISGDSVS SNSVVWNWIR QSPSRGLEWL GRTYYRSKWY  60
DDYAVSVKSR ITINPDTSKN QFSLQLNSVT PEDTAVYHCA RGGIVGAPDA FDIWGQGTMV  120
TVSS                                                              124

SEQ ID NO: 296         moltype = AA   length = 110
FEATURE                Location/Qualifiers
source                 1..110
                       mol_type = protein
                       organism = synthetic construct
                       note = Description of Artificial Sequence: Synthetic
                        polypeptide
SEQUENCE: 296
QSVLTQPPSA SGTPGQRVTI SCSGSSSNIG SDPVSWYQQF PGTAPKLLIY TNNQRPSGVP  60
DRFSGSKSGT SASLAISGLQ SEDEADYYCA AWDDSLNGHV FGTGTKVTVL            110

SEQ ID NO: 297         moltype = AA   length = 254
FEATURE                Location/Qualifiers
source                 1..254
                       mol_type = protein
                       organism = synthetic construct
                       note = Description of Artificial Sequence: Synthetic
                        polypeptide
SEQUENCE: 297
QVQLQQSGPG LVKPSQTLSL TCAISGDSVS SNSVVWNWIR QSPSRGLEWL GRTYYRSKWY  60
DDYAVSVKSR ITINPDTSKN QFSLQLNSVT PEDTAVYHCA RGGIVGAPDA FDIWGQGTMV  120
TVSSGGGGSG GGGSGGGGSG GGGSQSVLTQ PPSASGTPGQ RVTISCSGSS SNIGSDPVSW  180
YQQFPGTAPK LLIYTNNQRP SGVPDRFSGS KSGTSASLAI SGLQSEDEAD YYCAAWDDSL  240
NGHVFGTGTK VTVL                                                   254

SEQ ID NO: 298         moltype = AA   length = 11
FEATURE                Location/Qualifiers
source                 1..11
                       mol_type = protein
                       organism = synthetic construct
                       note = Description of Artificial Sequence: Synthetic peptide
SEQUENCE: 298
DSVSSNSAVW N                                                       11

SEQ ID NO: 299         moltype = AA   length = 14
FEATURE                Location/Qualifiers
source                 1..14
                       mol_type = protein
                       organism = synthetic construct
                       note = Description of Artificial Sequence: Synthetic peptide
SEQUENCE: 299
GWTYYRSKYY NDYA                                                    14

SEQ ID NO: 300         moltype = AA   length = 16
FEATURE                Location/Qualifiers
source                 1..16
                       mol_type = protein
                       organism = synthetic construct
                       note = Description of Artificial Sequence: Synthetic peptide
SEQUENCE: 300
CTRGGIVGAP DGFDIW                                                  16

SEQ ID NO: 301         moltype = AA   length = 13
```

```
FEATURE            Location/Qualifiers
source             1..13
                   mol_type = protein
                   organism = synthetic construct
                   note = Description of Artificial Sequence: Synthetic peptide
SEQUENCE: 301
SGSNSNIGSN PIN                                          13

SEQ ID NO: 302     moltype = AA  length = 7
FEATURE            Location/Qualifiers
source             1..7
                   mol_type = protein
                   organism = synthetic construct
                   note = Description of Artificial Sequence: Synthetic peptide
SEQUENCE: 302
SNNQRPS                                                 7

SEQ ID NO: 303     moltype = AA  length = 13
FEATURE            Location/Qualifiers
source             1..13
                   mol_type = protein
                   organism = synthetic construct
                   note = Description of Artificial Sequence: Synthetic peptide
SEQUENCE: 303
CAAWDDSLNG HVF                                          13

SEQ ID NO: 304     moltype = AA  length = 124
FEATURE            Location/Qualifiers
source             1..124
                   mol_type = protein
                   organism = synthetic construct
                   note = Description of Artificial Sequence: Synthetic
                    polypeptide
SEQUENCE: 304
QVQLQQSGPG LVKPSQTLSL TCAISGDSVS SNSAVWNWIR QSPSRGLEWL GWTYYRSKYY  60
NDYAVSLKSR ITINPDTSKN QFSLQLNSLT PEDTAVYYCT RGGIVGAPDG FDIWGQGTMV  120
TVSS                                                   124

SEQ ID NO: 305     moltype = AA  length = 110
FEATURE            Location/Qualifiers
source             1..110
                   mol_type = protein
                   organism = synthetic construct
                   note = Description of Artificial Sequence: Synthetic
                    polypeptide
SEQUENCE: 305
QSALTQPPSA SGTPGQRVTI SCSGSNSNIG SNPINWYQQL PGTAPKLLIY SNNQRPSGVP  60
DRFSGSKSGT SASLAISGLQ SEDEADYYCA AWDDSLNGHV FGTGTKVTVL           110

SEQ ID NO: 306     moltype = AA  length = 254
FEATURE            Location/Qualifiers
source             1..254
                   mol_type = protein
                   organism = synthetic construct
                   note = Description of Artificial Sequence: Synthetic
                    polypeptide
SEQUENCE: 306
QVQLQQSGPG LVKPSQTLSL TCAISGDSVS SNSAVWNWIR QSPSRGLEWL GWTYYRSKYY  60
NDYAVSLKSR ITINPDTSKN QFSLQLNSLT PEDTAVYYCT RGGIVGAPDG FDIWGQGTMV  120
TVSSGGGGSG GGGSGGGGSG GGGSQSALTQ PPSASGTPGQ RVTISCSGSN SNIGSNPINW  180
YQQLPGTAPK LLIYSNNQRP SGVPDRFSGS KSGTSASLAI SGLQSEDEAD YYCAAWDDSL  240
NGHVFGTGTK VTVL                                         254

SEQ ID NO: 307     moltype = AA  length = 9
FEATURE            Location/Qualifiers
source             1..9
                   mol_type = protein
                   organism = synthetic construct
                   note = Description of Artificial Sequence: Synthetic peptide
SEQUENCE: 307
GSISSYYWS                                               9

SEQ ID NO: 308     moltype = AA  length = 12
FEATURE            Location/Qualifiers
source             1..12
                   mol_type = protein
                   organism = synthetic construct
                   note = Description of Artificial Sequence: Synthetic peptide
SEQUENCE: 308
```

-continued

```
GYVYYSDITN YN                                          12

SEQ ID NO: 309         moltype = AA   length = 14
FEATURE                Location/Qualifiers
source                 1..14
                       mol_type = protein
                       organism = synthetic construct
                       note = Description of Artificial Sequence: Synthetic peptide
SEQUENCE: 309
CARIGVAGFY FDYW                                        14

SEQ ID NO: 310         moltype = AA   length = 12
FEATURE                Location/Qualifiers
source                 1..12
                       mol_type = protein
                       organism = synthetic construct
                       note = Description of Artificial Sequence: Synthetic peptide
SEQUENCE: 310
RASQSVSRRY LA                                          12

SEQ ID NO: 311         moltype = AA   length = 7
FEATURE                Location/Qualifiers
source                 1..7
                       mol_type = protein
                       organism = synthetic construct
                       note = Description of Artificial Sequence: Synthetic peptide
SEQUENCE: 311
GASSRAT                                                7

SEQ ID NO: 312         moltype = AA   length = 11
FEATURE                Location/Qualifiers
source                 1..11
                       mol_type = protein
                       organism = synthetic construct
                       note = Description of Artificial Sequence: Synthetic peptide
SEQUENCE: 312
CQQYGTSPIT F                                           11

SEQ ID NO: 313         moltype = AA   length = 118
FEATURE                Location/Qualifiers
source                 1..118
                       mol_type = protein
                       organism = synthetic construct
                       note = Description of Artificial Sequence: Synthetic
                        polypeptide
SEQUENCE: 313
QVQLQESGPG LVKPSETLSL TCTVSGGSIS SYYWSWIRQS PGKGLEWIGY VYYSDITNYN  60
PSLKSRVTIS VDTSKNQFSL NLNSVTAADT AFYFCARIGV AGFYFDYWGQ GTLVTVSS   118

SEQ ID NO: 314         moltype = AA   length = 108
FEATURE                Location/Qualifiers
source                 1..108
                       mol_type = protein
                       organism = synthetic construct
                       note = Description of Artificial Sequence: Synthetic
                        polypeptide
SEQUENCE: 314
EIVLTQSPDT LSLSPGERAT LSCRASQSVS RRYLAWYQQK PGQAPRLLIY GASSRATGIP  60
DRFSGSGSGT DFTLTISRLE PEDFEVYYCQ QYGTSPITFG QGTRLEIK             108

SEQ ID NO: 315         moltype = AA   length = 246
FEATURE                Location/Qualifiers
source                 1..246
                       mol_type = protein
                       organism = synthetic construct
                       note = Description of Artificial Sequence: Synthetic
                        polypeptide
SEQUENCE: 315
QVQLQESGPG LVKPSETLSL TCTVSGGSIS SYYWSWIRQS PGKGLEWIGY VYYSDITNYN  60
PSLKSRVTIS VDTSKNQFSL NLNSVTAADT AFYFCARIGV AGFYFDYWGQ GTLVTVSSGG 120
GGSGGGGSGG GGSGGGGSEI VLTQSPDTLS LSPGERATLS CRASQSVSRR YLAWYQQKPG 180
QAPRLLIYGA SSRATGIPDR FSGSGSGTDF TLTISRLEPE DFEVYYCQQY GTSPITFGQG 240
TRLEIK                                                            246

SEQ ID NO: 316         moltype = AA   length = 11
FEATURE                Location/Qualifiers
source                 1..11
                       mol_type = protein
                       organism = synthetic construct
```

-continued

```
                         note = Description of Artificial Sequence: Synthetic peptide
SEQUENCE: 316
DSVSSNSAVW N                                                     11

SEQ ID NO: 317           moltype = AA   length = 14
FEATURE                  Location/Qualifiers
source                   1..14
                         mol_type = protein
                         organism = synthetic construct
                         note = Description of Artificial Sequence: Synthetic peptide
SEQUENCE: 317
GRTYYRSKWY NDYA                                                  14

SEQ ID NO: 318           moltype = AA   length = 16
FEATURE                  Location/Qualifiers
source                   1..16
                         mol_type = protein
                         organism = synthetic construct
                         note = Description of Artificial Sequence: Synthetic peptide
SEQUENCE: 318
FTRGGIVGAP DAFDIW                                                16

SEQ ID NO: 319           moltype = AA   length = 13
FEATURE                  Location/Qualifiers
source                   1..13
                         mol_type = protein
                         organism = synthetic construct
                         note = Description of Artificial Sequence: Synthetic peptide
SEQUENCE: 319
SGSSSNIGSD PIN                                                   13

SEQ ID NO: 320           moltype = AA   length = 7
FEATURE                  Location/Qualifiers
source                   1..7
                         mol_type = protein
                         organism = synthetic construct
                         note = Description of Artificial Sequence: Synthetic peptide
SEQUENCE: 320
SNNQRPS                                                          7

SEQ ID NO: 321           moltype = AA   length = 13
FEATURE                  Location/Qualifiers
source                   1..13
                         mol_type = protein
                         organism = synthetic construct
                         note = Description of Artificial Sequence: Synthetic peptide
SEQUENCE: 321
CAAWDDSLNG YVF                                                   13

SEQ ID NO: 322           moltype = AA   length = 124
FEATURE                  Location/Qualifiers
source                   1..124
                         mol_type = protein
                         organism = synthetic construct
                         note = Description of Artificial Sequence: Synthetic
                          polypeptide
SEQUENCE: 322
QIQLQQSGPG LVKPSQTLSL TCAISGDSVS SNSAVWNWIR QSPSRGLEWL GRTYYRSKWY  60
NDYAVSVKSR ITIKPDTAKN QFSLQLNSVT PEDTAVYYFT RGGIVGAPDA FDIWGQGTMV 120
TVSS                                                            124

SEQ ID NO: 323           moltype = AA   length = 110
FEATURE                  Location/Qualifiers
source                   1..110
                         mol_type = protein
                         organism = synthetic construct
                         note = Description of Artificial Sequence: Synthetic
                          polypeptide
SEQUENCE: 323
QSVLTQPPSA SGTPGQRVTI SCSGSSSNIG SDPINWYQQV PGTAPKLLIY SNNQRPSGVP  60
DRFSGSKSGT SASLAISGLQ SEDEADYYCA AWDDSLNGYV FGTGTKVTVL          110

SEQ ID NO: 324           moltype = AA   length = 254
FEATURE                  Location/Qualifiers
source                   1..254
                         mol_type = protein
                         organism = synthetic construct
                         note = Description of Artificial Sequence: Synthetic
                          polypeptide
```

```
SEQUENCE: 324
QIQLQQSGPG LVKPSQTLSL TCAISGDSVS SNSAVWNWIR QSPSRGLEWL GRTYYRSKWY    60
NDYAVSVKSR ITIKPDTAKN QFSLQLNSVT PEDTAVYYFT RGGIVGAPDA FDIWGQGTMV   120
TVSSGGGGSG GGGSGGGGSG GGGSQSVLTQ PPSASGTPGQ RVTISCSGSS SNIGSDPINW   180
YQQVPGTAPK LLIYSNNQRP SGVPDRFSGS KSGTSASLAI SGLQSEDEAD YYCAAWDDSL   240
NGYVFGTGTK VTVL                                                    254

SEQ ID NO: 325          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 325
DSVSSNSATW N                                                        11

SEQ ID NO: 326          moltype = AA  length = 14
FEATURE                 Location/Qualifiers
source                  1..14
                        mol_type = protein
                        organism = synthetic construct
                        note = Description of Artificial Sequence: Synthetic peptide
SEQUENCE: 326
GRTYYRSEWY NDYA                                                     14

SEQ ID NO: 327          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 327
CAGGGIVGAP DGFDVW                                                   16

SEQ ID NO: 328          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 328
SGSSSNIGSD PVI                                                      13

SEQ ID NO: 329          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 329
SNNQRPS                                                              7

SEQ ID NO: 330          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 330
CAAWDDSLNG YVF                                                      13

SEQ ID NO: 331          moltype = AA  length = 124
FEATURE                 Location/Qualifiers
source                  1..124
                        mol_type = protein
                        organism = synthetic construct
                        note = Description of Artificial Sequence: Synthetic
                         polypeptide
SEQUENCE: 331
QVQLQQSGPG LVKPSETLSL TCAISGDSVS SNSATWNWIR QSPSRGLEWL GRTYYRSEWY    60
NDYAVSVKSR ITINPDTSKN HLSLHLNSVT PEDTAVYYCA GGGIVGAPDG FDVWGQGTMV   120
TVSS                                                               124

SEQ ID NO: 332          moltype = AA  length = 110
FEATURE                 Location/Qualifiers
source                  1..110
                        mol_type = protein
                        organism = synthetic construct
                        note = Description of Artificial Sequence: Synthetic
```

-continued

```
                         polypeptide
SEQUENCE: 332
QSVLTQPPSA SGTPGQRVTI SCSGSSSNIG SDPVIWYQQL PRTAPKLLIY SNNQRPSGVP   60
DRFSGSKSGT SASLAISGLQ SEDEADYYCA AWDDSLNGYV FGTGTKVTVL            110

SEQ ID NO: 333          moltype = AA  length = 254
FEATURE                 Location/Qualifiers
source                  1..254
                        mol_type = protein
                        organism = synthetic construct
                        note = Description of Artificial Sequence: Synthetic
                         polypeptide
SEQUENCE: 333
QVQLQQSGPG LVKPSETLSL TCAISGDSVS SNSATWNWIR QSPSRGLEWL GRTYYRSEWY   60
NDYAVSVKSR ITINPDTSKN HLSLHLNSVT PEDTAVYYCA GGGIVGAPDG FDVWGQGTMV  120
TVSSGGGGSG GGGSGGGGSG GGGSQSVLTQ PPSASGTPGQ RVTISCSGSS SNIGSDPVIW  180
YQQLPRTAPK LLIYSNNQRP SGVPDRFSGS KSGTSASLAI SGLQSEDEAD YYCAAWDDSL  240
NGYVFGTGTK VTVL                                                   254

SEQ ID NO: 334          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 334
DSVSSNSATW N                                                       11

SEQ ID NO: 335          moltype = AA  length = 14
FEATURE                 Location/Qualifiers
source                  1..14
                        mol_type = protein
                        organism = synthetic construct
                        note = Description of Artificial Sequence: Synthetic peptide
SEQUENCE: 335
ARTYYRSKWY NDYE                                                    14

SEQ ID NO: 336          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 336
CARGGIVGAP DAFDIW                                                  16

SEQ ID NO: 337          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 337
SGSSSNIGSN PVN                                                     13

SEQ ID NO: 338          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 338
SNNQRPS                                                            7

SEQ ID NO: 339          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 339
CSAWDDWLNG YVF                                                     13

SEQ ID NO: 340          moltype = AA  length = 124
FEATURE                 Location/Qualifiers
source                  1..124
                        mol_type = protein
                        organism = synthetic construct
                        note = Description of Artificial Sequence: Synthetic
```

```
                           polypeptide
SEQUENCE: 340
QVQLQQSGPG LVKPSQTLSL TCAISGDSVS SNSATWNWIR QSPSTGLEWL ARTYYRSKWY   60
NDYEVSVKSQ ITINPDTSKN QFSLQLNSVT PEDTAVYYCA RGGIVGAPDA FDIWGQGTMV  120
TVSS                                                              124

SEQ ID NO: 341          moltype = AA   length = 110
FEATURE                 Location/Qualifiers
source                  1..110
                        mol_type = protein
                        organism = synthetic construct
                        note = Description of Artificial Sequence: Synthetic
                         polypeptide
SEQUENCE: 341
QSVLTQPPSA SGTPGQGVTI SCSGSSSNIG SNPVNWYQQL PGTAPKLLIY SNNQRPSGVP   60
DRFSDSKSGT SASLAISGLQ SEDEADYYCS AWDDWLNGYV FGTGTKVTVL            110

SEQ ID NO: 342          moltype = AA   length = 254
FEATURE                 Location/Qualifiers
source                  1..254
                        mol_type = protein
                        organism = synthetic construct
                        note = Description of Artificial Sequence: Synthetic
                         polypeptide
SEQUENCE: 342
QVQLQQSGPG LVKPSQTLSL TCAISGDSVS SNSATWNWIR QSPSTGLEWL ARTYYRSKWY   60
NDYEVSVKSQ ITINPDTSKN QFSLQLNSVT PEDTAVYYCA RGGIVGAPDA FDIWGQGTMV  120
TVSSGGGGSG GGGSGGGGSG GGGSQSVLTQ PPSASGTPGQ GVTISCSGSS SNIGSNPVNW  180
YQQLPGTAPK LLIYSNNQRP SGVPDRFSDS KSGTSASLAI SGLQSEDEAD YYCSAWDDWL  240
NGYVFGTGTK VTVL                                                   254

SEQ ID NO: 343          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 343
DSINNYFWS                                                           9

SEQ ID NO: 344          moltype = AA   length = 12
FEATURE                 Location/Qualifiers
source                  1..12
                        mol_type = protein
                        organism = synthetic construct
                        note = Description of Artificial Sequence: Synthetic peptide
SEQUENCE: 344
GYFYHRGGNN YN                                                       12

SEQ ID NO: 345          moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 345
CARLALAGFF FDYW                                                     14

SEQ ID NO: 346          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 346
RASQSISSWL A                                                        11

SEQ ID NO: 347          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 347
KASSLES                                                             7

SEQ ID NO: 348          moltype = AA   length = 11
FEATURE                 Location/Qualifiers
source                  1..11
```

-continued

```
                          mol_type = protein
                          organism = synthetic construct
                          note = Description of Artificial Sequence: Synthetic peptide
SEQUENCE: 348
CQQYNSYSRT F                                                    11

SEQ ID NO: 349           moltype = AA   length = 118
FEATURE                  Location/Qualifiers
source                   1..118
                          mol_type = protein
                          organism = synthetic construct
                          note = Description of Artificial Sequence: Synthetic
                           polypeptide
SEQUENCE: 349
QVQLQESGPG LVKPSETLSL TCTVSGDSIN NYFWSWIRQP PGKGLEWIGY FYHRGGNNYN  60
PSLKSRVTIS IDTSKNQFSL NLNSVTSADT AVYYCARLAL AGFFFDYWGQ GTLVTVSS   118

SEQ ID NO: 350           moltype = AA   length = 107
FEATURE                  Location/Qualifiers
source                   1..107
                          mol_type = protein
                          organism = synthetic construct
                          note = Description of Artificial Sequence: Synthetic
                           polypeptide
SEQUENCE: 350
DIQMTQSPST LSASVGDRVT ITCRASQSIS SWLAWYQQKP GKAPKLLIYK ASSLESGVPS  60
RFSGSGSGTE FTLTISSLQP DDFATYYCQQ YNSYSRTFGQ GTKVEIK              107

SEQ ID NO: 351           moltype = AA   length = 245
FEATURE                  Location/Qualifiers
source                   1..245
                          mol_type = protein
                          organism = synthetic construct
                          note = Description of Artificial Sequence: Synthetic
                           polypeptide
SEQUENCE: 351
QVQLQESGPG LVKPSETLSL TCTVSGDSIN NYFWSWIRQP PGKGLEWIGY FYHRGGNNYN  60
PSLKSRVTIS IDTSKNQFSL NLNSVTSADT AVYYCARLAL AGFFFDYWGQ GTLVTVSSGG 120
GGSGGGGSGG GGSGGGGSDI QMTQSPSTLS ASVGDRVTIT CRASQSISSW LAWYQQKPGK 180
APKLLIYKAS SLESGVPSRF SGSGSGTEFT LTISSLQPDD FATYYCQQYN SYSRTFGQGT 240
KVEIK                                                          245

SEQ ID NO: 352           moltype = AA   length = 9
FEATURE                  Location/Qualifiers
source                   1..9
                          mol_type = protein
                          organism = synthetic construct
                          note = Description of Artificial Sequence: Synthetic peptide
SEQUENCE: 352
GTFSTYSIS                                                        9

SEQ ID NO: 353           moltype = AA   length = 13
FEATURE                  Location/Qualifiers
source                   1..13
                          mol_type = protein
                          organism = synthetic construct
                          note = Description of Artificial Sequence: Synthetic peptide
SEQUENCE: 353
GGIIPIFGTT NYA                                                   13

SEQ ID NO: 354           moltype = AA   length = 18
FEATURE                  Location/Qualifiers
source                   1..18
                          mol_type = protein
                          organism = synthetic construct
                          note = Description of Artificial Sequence: Synthetic peptide
SEQUENCE: 354
CARDGEGSYY YYYGMDVW                                              18

SEQ ID NO: 355           moltype = AA   length = 13
FEATURE                  Location/Qualifiers
source                   1..13
                          mol_type = protein
                          organism = synthetic construct
                          note = Description of Artificial Sequence: Synthetic peptide
SEQUENCE: 355
SGSSSNIGSN YVY                                                   13

SEQ ID NO: 356           moltype = AA   length = 7
```

-continued

```
FEATURE              Location/Qualifiers
source               1..7
                     mol_type = protein
                     organism = synthetic construct
                     note = Description of Artificial Sequence: Synthetic peptide
SEQUENCE: 356
SNNQRPS                                                              7

SEQ ID NO: 357       moltype = AA  length = 13
FEATURE              Location/Qualifiers
source               1..13
                     mol_type = protein
                     organism = synthetic construct
                     note = Description of Artificial Sequence: Synthetic peptide
SEQUENCE: 357
CAAWDDSLSG WVF                                                       13

SEQ ID NO: 358       moltype = AA  length = 123
FEATURE              Location/Qualifiers
source               1..123
                     mol_type = protein
                     organism = synthetic construct
                     note = Description of Artificial Sequence: Synthetic
                      polypeptide
SEQUENCE: 358
QVPLVQSGAE VKKPGSSVKV SCKASGGTFS TYSISWVRQA PGQGLEWMGG IIPIFGTTNY  60
AQKFQGRVTI TADKSTSTAY MELSSLRSED TAVYYCARDG EGSYYYYYGM DVWGQGTTVT  120
VSS                                                                 123

SEQ ID NO: 359       moltype = AA  length = 110
FEATURE              Location/Qualifiers
source               1..110
                     mol_type = protein
                     organism = synthetic construct
                     note = Description of Artificial Sequence: Synthetic
                      polypeptide
SEQUENCE: 359
QSVLTQPPSA SGTPGQRVTI SCSGSSSNIG SNYVYWYQQL PGTAPKLLIY SNNQRPSGVP  60
DRFSGSKSGT SASLAISGLR SEDEADYYCA AWDDSLSGWV FGGGTKLTVL             110

SEQ ID NO: 360       moltype = AA  length = 253
FEATURE              Location/Qualifiers
source               1..253
                     mol_type = protein
                     organism = synthetic construct
                     note = Description of Artificial Sequence: Synthetic
                      polypeptide
SEQUENCE: 360
QVPLVQSGAE VKKPGSSVKV SCKASGGTFS TYSISWVRQA PGQGLEWMGG IIPIFGTTNY  60
AQKFQGRVTI TADKSTSTAY MELSSLRSED TAVYYCARDG EGSYYYYYGM DVWGQGTTVT  120
VSSGGGGSGG GGSGGGGSGG GGSQSVLTQP PSASGTPGQR VTISCSGSSS NIGSNYVYWY  180
QQLPGTAPKL LIYSNNQRPS GVPDRFSGSK SGTSASLAIS GLRSEDEADY YCAAWDDSLS  240
GWVFGGGTKL TVL                                                      253

SEQ ID NO: 361       moltype = AA  length = 9
FEATURE              Location/Qualifiers
source               1..9
                     mol_type = protein
                     organism = synthetic construct
                     note = Description of Artificial Sequence: Synthetic peptide
SEQUENCE: 361
FTFSSYSMN                                                            9

SEQ ID NO: 362       moltype = AA  length = 13
FEATURE              Location/Qualifiers
source               1..13
                     mol_type = protein
                     organism = synthetic construct
                     note = Description of Artificial Sequence: Synthetic peptide
SEQUENCE: 362
SYISSSSSTI YYA                                                       13

SEQ ID NO: 363       moltype = AA  length = 17
FEATURE              Location/Qualifiers
source               1..17
                     mol_type = protein
                     organism = synthetic construct
                     note = Description of Artificial Sequence: Synthetic peptide
SEQUENCE: 363
```

-continued

```
CARDKERRYY YYGMDVW                                                      17

SEQ ID NO: 364          moltype = AA  length = 12
FEATURE                 Location/Qualifiers
source                  1..12
                        mol_type = protein
                        organism = synthetic construct
                        note = Description of Artificial Sequence: Synthetic peptide
SEQUENCE: 364
RASQSVSRRY LA                                                           12

SEQ ID NO: 365          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 365
GASSRAT                                                                 7

SEQ ID NO: 366          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 366
CQQFGTSPIT F                                                            11

SEQ ID NO: 367          moltype = AA  length = 122
FEATURE                 Location/Qualifiers
source                  1..122
                        mol_type = protein
                        organism = synthetic construct
                        note = Description of Artificial Sequence: Synthetic
                         polypeptide
SEQUENCE: 367
EVQLVESGGG LVQPGGSLRL SCAASGFTFS SYSMNWVRQA PGKGLEWVSY ISSSSSTIYY       60
ADSVKGRFTI SRDNAKNSLY LQMNSLRDED TAVYYCARDK ERRYYYGMD VWGQGTTVTV        120
SS                                                                      122

SEQ ID NO: 368          moltype = AA  length = 108
FEATURE                 Location/Qualifiers
source                  1..108
                        mol_type = protein
                        organism = synthetic construct
                        note = Description of Artificial Sequence: Synthetic
                         polypeptide
SEQUENCE: 368
EIVLTQSPDT LSLSPGERAT LSCRASQSVS RRYLAWYQQK PGQAPRLLIY GASSRATGIP       60
DRFSGSGSGT DFTLTISRLE PEDFAVYYCQ QFGTSPITFG QGTRLEIK                    108

SEQ ID NO: 369          moltype = AA  length = 250
FEATURE                 Location/Qualifiers
source                  1..250
                        mol_type = protein
                        organism = synthetic construct
                        note = Description of Artificial Sequence: Synthetic
                         polypeptide
SEQUENCE: 369
EVQLVESGGG LVQPGGSLRL SCAASGFTFS SYSMNWVRQA PGKGLEWVSY ISSSSSTIYY       60
ADSVKGRFTI SRDNAKNSLY LQMNSLRDED TAVYYCARDK ERRYYYGMD VWGQGTTVTV        120
SSGGGGSGGG GSGGGGSGGG GSEIVLTQSP DTLSLSPGER ATLSCRASQS VSRRYLAWYQ       180
QKPGQAPRLL IYGASSRATG IPDRFSGSGS GTDFTLTISR LEPEDFAVYY CQQFGTSPIT       240
FGQGTRLEIK                                                              250

SEQ ID NO: 370          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 370
DSVSSNSAIW N                                                            11

SEQ ID NO: 371          moltype = AA  length = 14
FEATURE                 Location/Qualifiers
source                  1..14
                        mol_type = protein
```

-continued

```
                        organism = synthetic construct
                        note = Description of Artificial Sequence: Synthetic peptide
SEQUENCE: 371
GGTYYRSMWY NDYA                                              14

SEQ ID NO: 372          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 372
CSRGGIVGVP DAFDIW                                            16

SEQ ID NO: 373          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 373
SGSSSNIGSN TAN                                               13

SEQ ID NO: 374          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 374
RNNQRPS                                                      7

SEQ ID NO: 375          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 375
CAAWDDSLNG YVF                                               13

SEQ ID NO: 376          moltype = AA  length = 124
FEATURE                 Location/Qualifiers
source                  1..124
                        mol_type = protein
                        organism = synthetic construct
                        note = Description of Artificial Sequence: Synthetic
                         polypeptide
SEQUENCE: 376
QVQLQQSGPG LVKPSQTLSL ACAISGDSVS SNSAIWNWIR QSPSRGLEWL GGTYYRSMWY   60
NDYAVSVKSR ITINPDTSKN QLSLQLNSVT PEDTAVYYCS RGGIVGVPDA FDIWGQGTMV  120
TVSS                                                        124

SEQ ID NO: 377          moltype = AA  length = 110
FEATURE                 Location/Qualifiers
source                  1..110
                        mol_type = protein
                        organism = synthetic construct
                        note = Description of Artificial Sequence: Synthetic
                         polypeptide
SEQUENCE: 377
QSVLTQPPSA SGTPGQRVTI SCSGSSSNIG SNTANWYQQL PGTAPRLLIY RNNQRPSGVP   60
DRFSGSKSGT SASLAISGLQ SEDEADYYCA AWDDSLNGYV FGTGTKVTVL           110

SEQ ID NO: 378          moltype = AA  length = 254
FEATURE                 Location/Qualifiers
source                  1..254
                        mol_type = protein
                        organism = synthetic construct
                        note = Description of Artificial Sequence: Synthetic
                         polypeptide
SEQUENCE: 378
QVQLQQSGPG LVKPSQTLSL ACAISGDSVS SNSAIWNWIR QSPSRGLEWL GGTYYRSMWY   60
NDYAVSVKSR ITINPDTSKN QLSLQLNSVT PEDTAVYYCS RGGIVGVPDA FDIWGQGTMV  120
TVSSGGGGSG GGGSGGGGSG GGGSQSVLTQ PPSASGTPGQ RVTISCSGSS SNIGSNTANW  180
YQQLPGTAPR LLIYRNNQRP SGVPDRFSGS KSGTSASLAI SGLQSEDEAD YYCAAWDDSL  240
NGYVFGTGTK VTVL                                             254

SEQ ID NO: 379          moltype = AA  length = 9
```

-continued

```
FEATURE               Location/Qualifiers
source                1..9
                      mol_type = protein
                      organism = synthetic construct
                      note = Description of Artificial Sequence: Synthetic peptide
SEQUENCE: 379
GSISSYYWT                                                            9

SEQ ID NO: 380        moltype = AA  length = 12
FEATURE               Location/Qualifiers
source                1..12
                      mol_type = protein
                      organism = synthetic construct
                      note = Description of Artificial Sequence: Synthetic peptide
SEQUENCE: 380
GYIFYSGTTN YN                                                        12

SEQ ID NO: 381        moltype = AA  length = 14
FEATURE               Location/Qualifiers
source                1..14
                      mol_type = protein
                      organism = synthetic construct
                      note = Description of Artificial Sequence: Synthetic peptide
SEQUENCE: 381
CARISEKSFY FDYW                                                      14

SEQ ID NO: 382        moltype = AA  length = 13
FEATURE               Location/Qualifiers
source                1..13
                      mol_type = protein
                      organism = synthetic construct
                      note = Description of Artificial Sequence: Synthetic peptide
SEQUENCE: 382
SGSSSNIGSN YVY                                                       13

SEQ ID NO: 383        moltype = AA  length = 7
FEATURE               Location/Qualifiers
source                1..7
                      mol_type = protein
                      organism = synthetic construct
                      note = Description of Artificial Sequence: Synthetic peptide
SEQUENCE: 383
SNNQRPS                                                              7

SEQ ID NO: 384        moltype = AA  length = 13
FEATURE               Location/Qualifiers
source                1..13
                      mol_type = protein
                      organism = synthetic construct
                      note = Description of Artificial Sequence: Synthetic peptide
SEQUENCE: 384
CAPWDDSLSG RVF                                                       13

SEQ ID NO: 385        moltype = AA  length = 118
FEATURE               Location/Qualifiers
source                1..118
                      mol_type = protein
                      organism = synthetic construct
                      note = Description of Artificial Sequence: Synthetic
                       polypeptide
SEQUENCE: 385
QVQLQESGPG LVKPSETLSL TCNVSDGSIS SYYWTWIRQP PGKGLDWIGY IFYSGTTNYN   60
PSLKSRVTIS LDTSKNQFSL KLTSMTAADT AVYYCARISE KSFYFDYWGQ GTLVTVSS     118

SEQ ID NO: 386        moltype = AA  length = 110
FEATURE               Location/Qualifiers
source                1..110
                      mol_type = protein
                      organism = synthetic construct
                      note = Description of Artificial Sequence: Synthetic
                       polypeptide
SEQUENCE: 386
QSVLTQPPSA SGTPGQRVTI SCSGSSSNIG SNYVYWYQQL PGTAPKLLIY SNNQRPSGVP   60
DRFSGSKSGT SASLAISGLR SEDEADYYCA PWDDSLSGRV FGGGTKLTVL             110

SEQ ID NO: 387        moltype = AA  length = 248
FEATURE               Location/Qualifiers
source                1..248
                      mol_type = protein
```

-continued

```
                            organism = synthetic construct
                            note = Description of Artificial Sequence: Synthetic
                             polypeptide
SEQUENCE: 387
QVQLQESGPG LVKPSETLSL TCNVSDGSIS SYYWTWIRQP PGKGLDWIGY IFYSGTTNYN  60
PSLKSRVTIS LDTSKNQFSL KLTSMTAADT AVYYCARISE KSFYFDYWGQ GTLVTVSSGG  120
GGSGGGGSGG GGSGGGGSQS VLTQPPSASG TPGQRVTISC SGSSSNIGSN YVYWYQQLPG  180
TAPKLLIYSN NQRPSGVPDR FSGSKSGTSA SLAISGLRSE DEADYYCAPW DDSLSGRVFG  240
GGTKLTVL                                                           248

SEQ ID NO: 388        moltype = AA  length = 9
FEATURE               Location/Qualifiers
source                1..9
                      mol_type = protein
                      organism = synthetic construct
                      note = Description of Artificial Sequence: Synthetic peptide
SEQUENCE: 388
YTFTSYYIH                                                          9

SEQ ID NO: 389        moltype = AA  length = 13
FEATURE               Location/Qualifiers
source                1..13
                      mol_type = protein
                      organism = synthetic construct
                      note = Description of Artificial Sequence: Synthetic peptide
SEQUENCE: 389
GVIVPSGGSI SYA                                                     13

SEQ ID NO: 390        moltype = AA  length = 17
FEATURE               Location/Qualifiers
source                1..17
                      mol_type = protein
                      organism = synthetic construct
                      note = Description of Artificial Sequence: Synthetic peptide
SEQUENCE: 390
CARDRYYGDY YYGLDVW                                                 17

SEQ ID NO: 391        moltype = AA  length = 11
FEATURE               Location/Qualifiers
source                1..11
                      mol_type = protein
                      organism = synthetic construct
                      note = Description of Artificial Sequence: Synthetic peptide
SEQUENCE: 391
RASQGINNFL A                                                       11

SEQ ID NO: 392        moltype = AA  length = 7
FEATURE               Location/Qualifiers
source                1..7
                      mol_type = protein
                      organism = synthetic construct
                      note = Description of Artificial Sequence: Synthetic peptide
SEQUENCE: 392
AASSLQS                                                            7

SEQ ID NO: 393        moltype = AA  length = 11
FEATURE               Location/Qualifiers
source                1..11
                      mol_type = protein
                      organism = synthetic construct
                      note = Description of Artificial Sequence: Synthetic peptide
SEQUENCE: 393
CQHYNSYPIT F                                                       11

SEQ ID NO: 394        moltype = AA  length = 122
FEATURE               Location/Qualifiers
source                1..122
                      mol_type = protein
                      organism = synthetic construct
                      note = Description of Artificial Sequence: Synthetic
                       polypeptide
SEQUENCE: 394
QVQLVQSGAE VKRPGASVKV SCKASGYTFT SYYIHWVRQA PGQGLEWMGV IVPSGGSISY  60
AQKFQGRVTM TRDTSTNIVY MELSSLRSED TAVYYCARDR YYGDYYYGLD VWGQGTTVTV  120
SS                                                                 122

SEQ ID NO: 395        moltype = AA  length = 107
FEATURE               Location/Qualifiers
source                1..107
```

-continued

```
                          mol_type = protein
                          organism = synthetic construct
                          note = Description of Artificial Sequence: Synthetic
                           polypeptide
SEQUENCE: 395
DIQMTQSPSS LSASVGDRVT ITCRASQGIN NFLAWFQQKP GKAPKSLIYA ASSLQSGVPS   60
KFSGSGSGTD FTLTIRSLQP EDFATYYCQH YNSYPITFGQ GTRLEIK                 107

SEQ ID NO: 396           moltype = AA  length = 249
FEATURE                  Location/Qualifiers
source                   1..249
                          mol_type = protein
                          organism = synthetic construct
                          note = Description of Artificial Sequence: Synthetic
                           polypeptide
SEQUENCE: 396
QVQLVQSGAE VKRPGASVKV SCKASGYTFT SYYIHWVRQA PGQGLEWMGV IVPSGGSISY   60
AQKFQGRVTM TRDTSTNIVY MELSSLRSED TAVYYCARDR YYGDYYYGLD VWGQGTTVTV  120
SSGGGGSGGG GSGGGGSGGG GSDIQMTQSP SSLSASVGDR VTITCRASQG INNFLAWFQQ  180
KPGKAPKSLI YAASSLQSGV PSKFSGSGSG TDFTLTIRSL QPEDFATYYC QHYNSYPITF  240
GQGTRLEIK                                                          249

SEQ ID NO: 397           moltype = AA  length = 9
FEATURE                  Location/Qualifiers
source                   1..9
                          mol_type = protein
                          organism = synthetic construct
                          note = Description of Artificial Sequence: Synthetic peptide
SEQUENCE: 397
GSISHYYWT                                                            9

SEQ ID NO: 398           moltype = AA  length = 12
FEATURE                  Location/Qualifiers
source                   1..12
                          mol_type = protein
                          organism = synthetic construct
                          note = Description of Artificial Sequence: Synthetic peptide
SEQUENCE: 398
GYIYYSGITN FS                                                       12

SEQ ID NO: 399           moltype = AA  length = 14
FEATURE                  Location/Qualifiers
source                   1..14
                          mol_type = protein
                          organism = synthetic construct
                          note = Description of Artificial Sequence: Synthetic peptide
SEQUENCE: 399
CAGISLAGFY FDYW                                                     14

SEQ ID NO: 400           moltype = AA  length = 12
FEATURE                  Location/Qualifiers
source                   1..12
                          mol_type = protein
                          organism = synthetic construct
                          note = Description of Artificial Sequence: Synthetic peptide
SEQUENCE: 400
RASQSVSRSY LA                                                       12

SEQ ID NO: 401           moltype = AA  length = 7
FEATURE                  Location/Qualifiers
source                   1..7
                          mol_type = protein
                          organism = synthetic construct
                          note = Description of Artificial Sequence: Synthetic peptide
SEQUENCE: 401
GASSRAT                                                             7

SEQ ID NO: 402           moltype = AA  length = 11
FEATURE                  Location/Qualifiers
source                   1..11
                          mol_type = protein
                          organism = synthetic construct
                          note = Description of Artificial Sequence: Synthetic peptide
SEQUENCE: 402
CQQYSISPLT F                                                        11

SEQ ID NO: 403           moltype = AA  length = 118
FEATURE                  Location/Qualifiers
source                   1..118
```

```
                          mol_type = protein
                          organism = synthetic construct
                          note = Description of Artificial Sequence: Synthetic
                           polypeptide
SEQUENCE: 403
QVHLQESGPG LVKPSETLSL TCTVSGGSIS HYYWTWIRQP PGKGLEWIGY IYYSGITNFS   60
PSLKSRVSIS VDSSKNQFSL NLNSVTAADT AVYYCAGISL AGFYFDYWVQ GTLVTVSS     118

SEQ ID NO: 404           moltype = AA  length = 108
FEATURE                  Location/Qualifiers
source                   1..108
                          mol_type = protein
                          organism = synthetic construct
                          note = Description of Artificial Sequence: Synthetic
                           polypeptide
SEQUENCE: 404
EIVLTQSPGT LSLSPGERAT LSCRASQSVS RSYLAWYQQK PGQAPRLLIY GASSRATGVP   60
DRFSGSGSGT DFTLTISRLE PEDFAVFYCQ QYSISPLTFG GGTKVEIK              108

SEQ ID NO: 405           moltype = AA  length = 246
FEATURE                  Location/Qualifiers
source                   1..246
                          mol_type = protein
                          organism = synthetic construct
                          note = Description of Artificial Sequence: Synthetic
                           polypeptide
SEQUENCE: 405
QVHLQESGPG LVKPSETLSL TCTVSGGSIS HYYWTWIRQP PGKGLEWIGY IYYSGITNFS   60
PSLKSRVSIS VDSSKNQFSL NLNSVTAADT AVYYCAGISL AGFYFDYWVQ GTLVTVSSGG  120
GGSGGGGSGG GGSGGGGSEI VLTQSPGTLS LSPGERATLS CRASQSVSRS YLAWYQQKPG  180
QAPRLLIYGA SSRATGVPDR FSGSGSGTDF TLTISRLEPE DFAVFYCQQY SISPLTFGGG  240
TKVEIK                                                         246

SEQ ID NO: 406           moltype = AA  length = 9
FEATURE                  Location/Qualifiers
source                   1..9
                          mol_type = protein
                          organism = synthetic construct
                          note = Description of Artificial Sequence: Synthetic peptide
SEQUENCE: 406
VSISSYYWS                                                        9

SEQ ID NO: 407           moltype = AA  length = 12
FEATURE                  Location/Qualifiers
source                   1..12
                          mol_type = protein
                          organism = synthetic construct
                          note = Description of Artificial Sequence: Synthetic peptide
SEQUENCE: 407
AYIYYSGNTN YS                                                    12

SEQ ID NO: 408           moltype = AA  length = 15
FEATURE                  Location/Qualifiers
source                   1..15
                          mol_type = protein
                          organism = synthetic construct
                          note = Description of Artificial Sequence: Synthetic peptide
SEQUENCE: 408
CTRGGSGTID VFDIW                                                 15

SEQ ID NO: 409           moltype = AA  length = 13
FEATURE                  Location/Qualifiers
source                   1..13
                          mol_type = protein
                          organism = synthetic construct
                          note = Description of Artificial Sequence: Synthetic peptide
SEQUENCE: 409
SGSSSNIGNN YVS                                                   13

SEQ ID NO: 410           moltype = AA  length = 7
FEATURE                  Location/Qualifiers
source                   1..7
                          mol_type = protein
                          organism = synthetic construct
                          note = Description of Artificial Sequence: Synthetic peptide
SEQUENCE: 410
DNNKRPS                                                          7

SEQ ID NO: 411           moltype = AA  length = 13
```

-continued

```
FEATURE              Location/Qualifiers
source               1..13
                     mol_type = protein
                     organism = synthetic construct
                     note = Description of Artificial Sequence: Synthetic peptide
SEQUENCE: 411
CETWDSSLSA VVF                                               13

SEQ ID NO: 412       moltype = AA  length = 119
FEATURE              Location/Qualifiers
source               1..119
                     mol_type = protein
                     organism = synthetic construct
                     note = Description of Artificial Sequence: Synthetic
                      polypeptide
SEQUENCE: 412
QVQLQESGPG LVKPSETLSL TCTVSGVSIS SYYWSWIRQP PGKGLEWIAY IYYSGNTNYS  60
PSLKSRVTIS VDTSKDQLSL KLSSVTAADT AVYYCTRGGS GTIDVFDIWG QGTMVAVSS   119

SEQ ID NO: 413       moltype = AA  length = 110
FEATURE              Location/Qualifiers
source               1..110
                     mol_type = protein
                     organism = synthetic construct
                     note = Description of Artificial Sequence: Synthetic
                      polypeptide
SEQUENCE: 413
QSVLTQPPSV SAAPGQKVTI SCSGSSSNIG NNYVSWYQQL PGTAPKLLIY DNNKRPSGIP  60
DRFSGSKSGT SATLGITGLQ TGDEADYYCE TWDSSLSAVV FGGGTKLTVL            110

SEQ ID NO: 414       moltype = AA  length = 249
FEATURE              Location/Qualifiers
source               1..249
                     mol_type = protein
                     organism = synthetic construct
                     note = Description of Artificial Sequence: Synthetic
                      polypeptide
SEQUENCE: 414
QVQLQESGPG LVKPSETLSL TCTVSGVSIS SYYWSWIRQP PGKGLEWIAY IYYSGNTNYS  60
PSLKSRVTIS VDTSKDQLSL KLSSVTAADT AVYYCTRGGS GTIDVFDIWG QGTMVAVSSG  120
GGGSGGGGSG GGGSGGGGSQ SVLTQPPSVS AAPGQKVTIS CSGSSSNIGN NYVSWYQQLP  180
GTAPKLLIYD NNKRPSGIPD RFSGSKSGTS ATLGITGLQT GDEADYYCET WDSSLSAVVF  240
GGGTKLTVL                                                   249

SEQ ID NO: 415       moltype = AA  length = 11
FEATURE              Location/Qualifiers
source               1..11
                     mol_type = protein
                     organism = synthetic construct
                     note = Description of Artificial Sequence: Synthetic peptide
SEQUENCE: 415
DNVSTNSAAW N                                                 11

SEQ ID NO: 416       moltype = AA  length = 14
FEATURE              Location/Qualifiers
source               1..14
                     mol_type = protein
                     organism = synthetic construct
                     note = Description of Artificial Sequence: Synthetic peptide
SEQUENCE: 416
GWTYYRSKWY NDYA                                              14

SEQ ID NO: 417       moltype = AA  length = 13
FEATURE              Location/Qualifiers
source               1..13
                     mol_type = protein
                     organism = synthetic construct
                     note = Description of Artificial Sequence: Synthetic peptide
SEQUENCE: 417
CARWVNRDVF DIW                                               13

SEQ ID NO: 418       moltype = AA  length = 14
FEATURE              Location/Qualifiers
source               1..14
                     mol_type = protein
                     organism = synthetic construct
                     note = Description of Artificial Sequence: Synthetic peptide
SEQUENCE: 418
TGTSSDVGSY NLVS                                              14
```

```
SEQ ID NO: 419          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 419
EGSKRPS                                                              7

SEQ ID NO: 420          moltype = AA   length = 12
FEATURE                 Location/Qualifiers
source                  1..12
                        mol_type = protein
                        organism = synthetic construct
                        note = Description of Artificial Sequence: Synthetic peptide
SEQUENCE: 420
CCSYAGSSTW VF                                                        12

SEQ ID NO: 421          moltype = AA   length = 121
FEATURE                 Location/Qualifiers
source                  1..121
                        mol_type = protein
                        organism = synthetic construct
                        note = Description of Artificial Sequence: Synthetic
                         polypeptide
SEQUENCE: 421
QVQLQQSGPG LVKPSQTLSL TCAISGDNVS TNSAAWNWIR QSPSRGLEWL GWTYYRSKWY   60
NDYAVSLKSR ININPDTSKN QFSLQLNSVT PEDTAVYYCA RWVNRDVFDI WGQGTMVTVS  120
S                                                                  121

SEQ ID NO: 422          moltype = AA   length = 110
FEATURE                 Location/Qualifiers
source                  1..110
                        mol_type = protein
                        organism = synthetic construct
                        note = Description of Artificial Sequence: Synthetic
                         polypeptide
SEQUENCE: 422
QSALTQPASV SGSPGQSITI SCTGTSSDVG SYNLVSWYQQ HPGKAPKLMI YEGSKRPSGV   60
SNRFSGSKSG NTASLTISGL QAEDEADYYC CSYAGSSTWV FGGGTKLTVL            110

SEQ ID NO: 423          moltype = AA   length = 251
FEATURE                 Location/Qualifiers
source                  1..251
                        mol_type = protein
                        organism = synthetic construct
                        note = Description of Artificial Sequence: Synthetic
                         polypeptide
SEQUENCE: 423
QVQLQQSGPG LVKPSQTLSL TCAISGDNVS TNSAAWNWIR QSPSRGLEWL GWTYYRSKWY   60
NDYAVSLKSR ININPDTSKN QFSLQLNSVT PEDTAVYYCA RWVNRDVFDI WGQGTMVTVS  120
SGGGGSGGGG SGGGGSGGGG SQSALTQPAS VSGSPGQSIT ISCTGTSSDV GSYNLVSWYQ  180
QHPGKAPKLM IYEGSKRPSG VSNRFSGSKS GNTASLTISG LQAEDEADYY CCSYAGSSTW  240
VFGGGTKLTV L                                                      251

SEQ ID NO: 424          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 424
FTFSSYGMH                                                            9

SEQ ID NO: 425          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 425
AVISYDGNSN YYA                                                       13

SEQ ID NO: 426          moltype = AA   length = 19
FEATURE                 Location/Qualifiers
source                  1..19
                        mol_type = protein
                        organism = synthetic construct
```

-continued

```
                        note = Description of Artificial Sequence: Synthetic peptide
SEQUENCE: 426
CARDGATVTS YYYYGMDVW                                          19

SEQ ID NO: 427          moltype = AA   length = 12
FEATURE                 Location/Qualifiers
source                  1..12
                        mol_type = protein
                        organism = synthetic construct
                        note = Description of Artificial Sequence: Synthetic peptide
SEQUENCE: 427
RASQSVSRTY LA                                                 12

SEQ ID NO: 428          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 428
GASSRAT                                                       7

SEQ ID NO: 429          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 429
CQQYGTSPIT F                                                  11

SEQ ID NO: 430          moltype = AA   length = 124
FEATURE                 Location/Qualifiers
source                  1..124
                        mol_type = protein
                        organism = synthetic construct
                        note = Description of Artificial Sequence: Synthetic
                         polypeptide
SEQUENCE: 430
QVQLVESGGG VVQPGRSLRL SCAASGFTFS SYGMHWVRQT PGKGLEWVAV ISYDGNSNYY   60
ADSVKGRFTI SRDNSKNTLY LQMNSLRAED TAVYYCARDG ATVTSYYYYG MDVWGQGTTV  120
TVSS                                                        124

SEQ ID NO: 431          moltype = AA   length = 108
FEATURE                 Location/Qualifiers
source                  1..108
                        mol_type = protein
                        organism = synthetic construct
                        note = Description of Artificial Sequence: Synthetic
                         polypeptide
SEQUENCE: 431
EIVLTQSPGT LSLSPGERAT LSCRASQSVS RTYLAWYHQK PGQAPRLLIY GASSRATGIS   60
DRFSGSGSGT DFTLTISRLE PEDFAVYYCQ QYGTSPITFG QGTRLEIK            108

SEQ ID NO: 432          moltype = AA   length = 252
FEATURE                 Location/Qualifiers
source                  1..252
                        mol_type = protein
                        organism = synthetic construct
                        note = Description of Artificial Sequence: Synthetic
                         polypeptide
SEQUENCE: 432
QVQLVESGGG VVQPGRSLRL SCAASGFTFS SYGMHWVRQT PGKGLEWVAV ISYDGNSNYY   60
ADSVKGRFTI SRDNSKNTLY LQMNSLRAED TAVYYCARDG ATVTSYYYYG MDVWGQGTTV  120
TVSSGGGSG GGGSGGGGSG GGGSEIVLTQ SPGTLSLSPG ERATLSCRAS QSVSRTYLAW  180
YHQKPGQAPR LLIYGASSRA TGISDRFSGS GSGTDFTLTI SRLEPEDFAV YYCQQYGTSP  240
ITFGQGTRLE IK                                                252

SEQ ID NO: 433          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 433
DSVSSNSAVW N                                                  11

SEQ ID NO: 434          moltype = AA   length = 14
FEATURE                 Location/Qualifiers
```

-continued

```
source               1..14
                     mol_type = protein
                     organism = synthetic construct
                     note = Description of Artificial Sequence: Synthetic peptide
SEQUENCE: 434
GRTYYRSKWY NDYA                                            14

SEQ ID NO: 435       moltype = AA  length = 16
FEATURE              Location/Qualifiers
source               1..16
                     mol_type = protein
                     organism = synthetic construct
                     note = Description of Artificial Sequence: Synthetic peptide
SEQUENCE: 435
CARGGIVGAP DGFDIW                                          16

SEQ ID NO: 436       moltype = AA  length = 17
FEATURE              Location/Qualifiers
source               1..17
                     mol_type = protein
                     organism = synthetic construct
                     note = Description of Artificial Sequence: Synthetic peptide
SEQUENCE: 436
KSSQSVLDSS NNNNYFA                                         17

SEQ ID NO: 437       moltype = AA  length = 7
FEATURE              Location/Qualifiers
source               1..7
                     mol_type = protein
                     organism = synthetic construct
                     note = Description of Artificial Sequence: Synthetic peptide
SEQUENCE: 437
WASSRES                                                    7

SEQ ID NO: 438       moltype = AA  length = 11
FEATURE              Location/Qualifiers
source               1..11
                     mol_type = protein
                     organism = synthetic construct
                     note = Description of Artificial Sequence: Synthetic peptide
SEQUENCE: 438
CQQYYSTPYT F                                               11

SEQ ID NO: 439       moltype = AA  length = 124
FEATURE              Location/Qualifiers
source               1..124
                     mol_type = protein
                     organism = synthetic construct
                     note = Description of Artificial Sequence: Synthetic
                      polypeptide
SEQUENCE: 439
QVQLQQSGPG LVKPSQTLSL TCAISGDSVS SNSAVWNWIR QSPSRGLEWL GRTYYRSKWY  60
NDYAVSVKSR ITINPDTSRN QFSLQLNSVT PEDTAVYYCA RGGIVGAPDG FDIWGQGTMV  120
TVSS                                                      124

SEQ ID NO: 440       moltype = AA  length = 113
FEATURE              Location/Qualifiers
source               1..113
                     mol_type = protein
                     organism = synthetic construct
                     note = Description of Artificial Sequence: Synthetic
                      polypeptide
SEQUENCE: 440
DIVMTQSPDS LAVSLGERAT INCKSSQSVL DSSNNNNYFA WYQQRPGQPP HLLIYWASSR  60
ESGVPDRFSG SGSGTDFTLT ISSLQAEDVA VYYCQQYYST PYTFGQGTKL EIK         113

SEQ ID NO: 441       moltype = AA  length = 257
FEATURE              Location/Qualifiers
source               1..257
                     mol_type = protein
                     organism = synthetic construct
                     note = Description of Artificial Sequence: Synthetic
                      polypeptide
SEQUENCE: 441
QVQLQQSGPG LVKPSQTLSL TCAISGDSVS SNSAVWNWIR QSPSRGLEWL GRTYYRSKWY  60
NDYAVSVKSR ITINPDTSRN QFSLQLNSVT PEDTAVYYCA RGGIVGAPDG FDIWGQGTMV  120
TVSSGGGGSG GGGSGGGGSG GGGSDIVMTQ SPDSLAVSLG ERATINCKSS QSVLDSSNNN  180
NYFAWYQQRP GQPPHLLIYW ASSRESGVPD RFSGSGSGTD FTLTISSLQA EDVAVYYCQQ  240
YYSTPYTFGQ GTKLEIK                                        257
```

-continued

```
SEQ ID NO: 442          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 442
DSVSSNTTAW K                                                  11

SEQ ID NO: 443          moltype = AA  length = 14
FEATURE                 Location/Qualifiers
source                  1..14
                        mol_type = protein
                        organism = synthetic construct
                        note = Description of Artificial Sequence: Synthetic peptide
SEQUENCE: 443
GWTYYRSKWY YDYT                                               14

SEQ ID NO: 444          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 444
CARWIFHDAF DIW                                                13

SEQ ID NO: 445          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 445
SGSSSNIGSN TVN                                                13

SEQ ID NO: 446          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 446
TNNQRPS                                                       7

SEQ ID NO: 447          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 447
CSTWDDSLNG PVF                                                13

SEQ ID NO: 448          moltype = AA  length = 121
FEATURE                 Location/Qualifiers
source                  1..121
                        mol_type = protein
                        organism = synthetic construct
                        note = Description of Artificial Sequence: Synthetic
                         polypeptide
SEQUENCE: 448
QVQLQQSGPG LVKPSQTLSL TCAISGDSVS SNTTAWKWSR QSPSKGLEWL GWTYYRSKWY  60
YDYTVSVKSR ITINPDTSKN QFSLQLNSVT PEDTAVYYCA RWIFHDAFDI WGQGTMVTVS  120
S                                                            121

SEQ ID NO: 449          moltype = AA  length = 110
FEATURE                 Location/Qualifiers
source                  1..110
                        mol_type = protein
                        organism = synthetic construct
                        note = Description of Artificial Sequence: Synthetic
                         polypeptide
SEQUENCE: 449
QSALTQPPSA SGTPGQRVTI SCSGSSSNIG SNTVNWYQQL PGTAPKLLIY TNNQRPSGVP  60
DRFSGSKSGT SASLAISGLQ SEDEADYFCS TWDDSLNGPV FGGGTKLTVL          110

SEQ ID NO: 450          moltype = AA  length = 251
```

-continued

```
FEATURE                Location/Qualifiers
source                 1..251
                       mol_type = protein
                       organism = synthetic construct
                       note = Description of Artificial Sequence: Synthetic
                        polypeptide
SEQUENCE: 450
QVQLQQSGPG LVKPSQTLSL TCAISGDSVS SNTTAWKWSR QSPSKGLEWL GWTYYRSKWY  60
YDYTVSVKSR ITINPDTSKN QFSLQLNSVT PEDTAVYYCA RWIFHDAFDI WGQGTMVTVS  120
SGGGGSGGGG SGGGGSGGGG SQSALTQPPS ASGTPGQRVT ISCSGSSSNI GSNTVNWYQQ  180
LPGTAPKLLI YTNNQRPSGV PDRFSGSKSG TSASLAISGL QSEDEADYFC STWDDSLNGP  240
VFGGGTKLTV L                                                       251

SEQ ID NO: 451         moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 451
DSISSLSWS                                                          9

SEQ ID NO: 452         moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 452
GYLYYSGSTD YN                                                      12

SEQ ID NO: 453         moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 453
CARGRRAFDI W                                                       11

SEQ ID NO: 454         moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 454
RGSQGISNYL A                                                       11

SEQ ID NO: 455         moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 455
AASSLES                                                            7

SEQ ID NO: 456         moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 456
CQQYYNYPIT F                                                       11

SEQ ID NO: 457         moltype = AA  length = 115
FEATURE                Location/Qualifiers
source                 1..115
                       mol_type = protein
                       organism = synthetic construct
                       note = Description of Artificial Sequence: Synthetic
                        polypeptide
SEQUENCE: 457
QVQLQESGPG LVKPSETLSL TCTVSGDSIS SLSWSWIRQT PGEGLEWIGY LYYSGSTDYN  60
PSLKSRVTIS VDTSKNQFSL KLRSVAAADT ALYYCARGRR AFDIWGQGTM VTVSS       115

SEQ ID NO: 458         moltype = AA  length = 107
```

-continued

```
FEATURE               Location/Qualifiers
source                1..107
                      mol_type = protein
                      organism = synthetic construct
                      note = Description of Artificial Sequence: Synthetic
                       polypeptide
SEQUENCE: 458
DIQMTQSPSS LSASVGDRVT ITCRGSQGIS NYLAWFQQRP GKAPKSLIYA ASSLESGVPS    60
KFSGSGSGTD FTLTIISLQP EDFATYYCQQ YYNYPITFGQ GTRLEIK               107

SEQ ID NO: 459        moltype = AA  length = 242
FEATURE               Location/Qualifiers
source                1..242
                      mol_type = protein
                      organism = synthetic construct
                      note = Description of Artificial Sequence: Synthetic
                       polypeptide
SEQUENCE: 459
QVQLQESGPG LVKPSETLSL TCTVSGDSIS SLSWSWIRQT PGEGLEWIGY LYYSGSTDYN    60
PSLKSRVTIS VDTSKNQFSL KLRSVAADT ALYYCARGRR AFDIWGQGTM VTVSSGGGGS    120
GGGGSGGGGS GGGGSDIQMT QSPSSLSASV GDRVTITCRG SQGISNYLAW FQQRPGKAPK   180
SLIYAASSLE SGVPSKFSGS GSGTDFTLTI ISLQPEDFAT YYCQQYYNYP ITFGQGTRLE   240
IK                                                                 242

SEQ ID NO: 460        moltype = AA  length = 9
FEATURE               Location/Qualifiers
source                1..9
                      mol_type = protein
                      organism = synthetic construct
                      note = Description of Artificial Sequence: Synthetic peptide
SEQUENCE: 460
YTFTGYYMH                                                            9

SEQ ID NO: 461        moltype = AA  length = 13
FEATURE               Location/Qualifiers
source                1..13
                      mol_type = protein
                      organism = synthetic construct
                      note = Description of Artificial Sequence: Synthetic peptide
SEQUENCE: 461
GWINPNSGGT NYA                                                      13

SEQ ID NO: 462        moltype = AA  length = 17
FEATURE               Location/Qualifiers
source                1..17
                      mol_type = protein
                      organism = synthetic construct
                      note = Description of Artificial Sequence: Synthetic peptide
SEQUENCE: 462
CAKDGGGDFY FYGMDVW                                                  17

SEQ ID NO: 463        moltype = AA  length = 14
FEATURE               Location/Qualifiers
source                1..14
                      mol_type = protein
                      organism = synthetic construct
                      note = Description of Artificial Sequence: Synthetic peptide
SEQUENCE: 463
GLSSGSVSTS YYPS                                                     14

SEQ ID NO: 464        moltype = AA  length = 7
FEATURE               Location/Qualifiers
source                1..7
                      mol_type = protein
                      organism = synthetic construct
                      note = Description of Artificial Sequence: Synthetic peptide
SEQUENCE: 464
STDTRSS                                                              7

SEQ ID NO: 465        moltype = AA  length = 12
FEATURE               Location/Qualifiers
source                1..12
                      mol_type = protein
                      organism = synthetic construct
                      note = Description of Artificial Sequence: Synthetic peptide
SEQUENCE: 465
CVLYMGSGIS VF                                                       12

SEQ ID NO: 466        moltype = AA  length = 122
```

-continued

```
FEATURE                 Location/Qualifiers
source                  1..122
                        mol_type = protein
                        organism = synthetic construct
                        note = Description of Artificial Sequence: Synthetic
                         polypeptide
SEQUENCE: 466
QVQLVQSGAE VKKPGASVKV SCKASGYTFT GYYMHWVRQA PGQGLEWMGW INPNSGGTNY  60
AQKFQGRVTM TRDTSVSTAY MELSRLTSDD TAIYYCAKDG GGDFYFYGMD VWGQGTTVTV  120
SS                                                                 122

SEQ ID NO: 467          moltype = AA  length = 110
FEATURE                 Location/Qualifiers
source                  1..110
                        mol_type = protein
                        organism = synthetic construct
                        note = Description of Artificial Sequence: Synthetic
                         polypeptide
SEQUENCE: 467
QTVVTQEPSF SVSPGGTVTL TCGLSSGSVS TSYYPSCFQQ TPGQAPRTLI YSTDTRSSGV  60
PDRFSGSILG NKAALTITGA QADDESDYYC VLYMGSGISV FGGGTKLTVL             110

SEQ ID NO: 468          moltype = AA  length = 252
FEATURE                 Location/Qualifiers
source                  1..252
                        mol_type = protein
                        organism = synthetic construct
                        note = Description of Artificial Sequence: Synthetic
                         polypeptide
SEQUENCE: 468
QVQLVQSGAE VKKPGASVKV SCKASGYTFT GYYMHWVRQA PGQGLEWMGW INPNSGGTNY  60
AQKFQGRVTM TRDTSVSTAY MELSRLTSDD TAIYYCAKDG GGDFYFYGMD VWGQGTTVTV  120
SSGGGGSGGG GSGGGGSGGG GSQTVVTQEP SFSVSPGGTV TLTCGLSSGS VSTSYYPSCF  180
QQTPGQAPRT LIYSTDTRSS GVPDRFSGSI LGNKAALTIT GAQADDESDY YCVLYMGSGI  240
SVFGGGTKLT VL                                                      252

SEQ ID NO: 469          moltype = AA  length = 113
FEATURE                 Location/Qualifiers
source                  1..113
                        mol_type = protein
                        organism = synthetic construct
                        note = Description of Artificial Sequence: Synthetic
                         polypeptide
SEQUENCE: 469
LRVKFSRSAD APAYKQGQNQ LYNELNLGRR EEYDVLDKRR GRDPEMGGKP RRKNPQEGLY  60
NELQKDKMAE AYSEIGMKGE RRRGKGHDGL YQGLSTATKD TYDALHMQAL PPR         113

SEQ ID NO: 470          moltype = AA  length = 25
FEATURE                 Location/Qualifiers
source                  1..25
                        mol_type = protein
                        organism = synthetic construct
                        note = Description of Artificial Sequence: Synthetic peptide
VARIANT                 1..25
                        note = MISC_FEATURE - This sequence may encompass 1-5 GGGGS
                         repeating units
REGION                  1..25
                        note = See specification as filed for detailed description
                         of substitutions and preferred embodiments
SEQUENCE: 470
GGGGSGGGGS GGGGSGGGGS GGGGS                                              25

SEQ ID NO: 471          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 471
ELPTQGTFSN VSTNVS                                                        16

SEQ ID NO: 472          moltype = AA  length = 15
FEATURE                 Location/Qualifiers
source                  1..15
                        mol_type = protein
                        organism = synthetic construct
                        note = Description of Artificial Sequence: Synthetic peptide
SEQUENCE: 472
GGGGSGGGGS GGGGS                                                         15
```

SEQ ID NO: 473          moltype = AA   length = 8
FEATURE                 Location/Qualifiers
source                  1..8
                        mol_type = protein
                        organism = synthetic construct
                        note = Description of Artificial Sequence: Synthetic 8xHis
                         tag
SEQUENCE: 473
HHHHHHHH                                                                              8

SEQ ID NO: 474          moltype = AA   length = 571
FEATURE                 Location/Qualifiers
source                  1..571
                        mol_type = protein
                        organism = synthetic construct
                        note = Description of Artificial Sequence: Synthetic
                         polypeptide
SEQUENCE: 474
MALPVTALLL PLALLLHAAR PGGGGSCPYS NPSLCSGGGG SGGGGSEVQL LESGGGLVQP    60
GGSLRLSCAA SGFTFSSYAM NWVRQAPGKG LEWVSTISGS GGSTYYADSV KGRFTISRDN   120
SKNTLYLQMN SLRAEDTAVF YCAIDPEYYD ILTGGDYWGQ GTLVTVSSGG GGSGGGGSGG   180
GGGSGGGGSD IQMTQSPSAM SASVGDRVTI TCRASQGISN YLAWFQQKPG KVPKRLIYAA   240
SSLQSGVPSR FSGSGSGTEF TLTISSLQPE DFATYFCLQH DSFPLTFGGG TKVEIKGSGG   300
GGSCPYSNPS LCSGGGGSEL PTQGTFSNVS TNVSPAKPTT TACPYSNPSL CTTTPAPRPP   360
TPAPTIASQP LSLRPEACRP AAGGAVHTRG LDFACDIYIW APLAGTCGVL LLSLVITKRG   420
RKKLLYIFKQ PFMRPVQTTQ EEDGCSCRFP EEEEGGCELR VKFSRSADAP AYQQGQNQLY   480
NELNLGRREE YDVLDKRRGR DPEMGGKPRR KNPQEGLYNE LQKDKMAEAY SEIGMKGERR   540
RGKGHDGLYQ GLSTATKDTY DALHMQALPP R                                  571

SEQ ID NO: 475          moltype = AA   length = 541
FEATURE                 Location/Qualifiers
source                  1..541
                        mol_type = protein
                        organism = synthetic construct
                        note = Description of Artificial Sequence: Synthetic
                         polypeptide
SEQUENCE: 475
MALPVTALLL PLALLLHAAR PEVQLLESGG GLVQPGGSLR LSCAASGFTF SSYAMNWVRQ    60
APGKGLEWVS TISGSGGSTY YADSVKGRFT ISRDNSKNTL YLQMNSLRAE DTAVFYCAID   120
PEYYDILTGG DYWGQGTLVT VSSGGGGSGG GGSGGGGSG GGGSDIQMTQ SPSAMSASVG    180
DRVTITCRAS QGISNYLAWF QQKPGKVPKR LIYAASSLQS GVPSRFSGSG SGTEFTLTIS   240
SLQPEDFATY FCLQHDSFPL TFGGGTKVEI KGSGGGGSCP YSNPSLCSGG GGSCPYSNPS   300
LCSGGGGSTT TACPYSNPSL CTTTPAPRPP TPAPTIASQP LSLRPEACRP AAGGAVHTRG   360
LDFACDIYIW APLAGTCGVL LLSLVITKRG RKKLLYIFKQ PFMRPVQTTQ EEDGCSCRFP   420
EEEEGGCELR VKFSRSADAP AYQQGQNQLY NELNLGRREE YDVLDKRRGR DPEMGGKPRR   480
KNPQEGLYNE LQKDKMAEAY SEIGMKGERR RGKGHDGLYQ GLSTATKDTY DALHMQALPP   540
R                                                                  541

SEQ ID NO: 476          moltype = AA   length = 529
FEATURE                 Location/Qualifiers
source                  1..529
                        mol_type = protein
                        organism = synthetic construct
                        note = Description of Artificial Sequence: Synthetic
                         polypeptide
SEQUENCE: 476
MALPVTALLL PLALLLHAAR PGGGGSCPYS NPSLCGGGGS EVQLLESGGG LVQPGGSLRL    60
SCAASGFTFS SYAMNWVRQA PGKGLEWVST ISGSGGSTYY ADSVKGRFTI SRDNSKNTLY   120
LQMNSLRAED TAVFYCAIDP EYYDILTGGD YWGQGTLVTV SSGGGGSGGG GSGGGGGSGG   180
GGSDIQMTQS PSAMSASVGD RVTITCRASQ GISNYLAWFQ QKPGKVPKRL IYAASSLQSG   240
VPSRFSGSGS GTEFTLTISS LQPEDFATYF CLQHDSFPLT FGGGTKVEIK GGGGSCPYSN   300
PSLCGGGGST TPAPRPPTP APTIASQPLS LRPEACRPAA GGAVHTRGLD FACDIYIWAP   360
LAGTCGVLLL SLVITKRGRK KLLYIFKQPF MRPVQTTQEE DGCSCRFPEE EEGGCELRVK   420
FSRSADAPAY QQGQNQLYNE LNLGRREEYD VLDKRRGRDP EMGGKPRRKN PQEGLYNELQ   480
KDKMAEAYSE IGMKGERRRG KGHDGLYQGL STATKDTYDA LHMQALPPR              529

SEQ ID NO: 477          moltype = AA   length = 21
FEATURE                 Location/Qualifiers
source                  1..21
                        mol_type = protein
                        organism = Homo sapiens
SEQUENCE: 477
MALPVTALLL PLALLLHAAR P                                             21

SEQ ID NO: 478          moltype = AA   length = 20
FEATURE                 Location/Qualifiers
source                  1..20
                        mol_type = protein -continued

```
                          organism = synthetic construct
                          note = Description of Artificial Sequence: Synthetic peptide
SEQUENCE: 478
GGGGSGGGGS GGGGSGGGGS                                                 20

SEQ ID NO: 479            moltype = AA  length = 66
FEATURE                   Location/Qualifiers
source                    1..66
                          mol_type = protein
                          organism = Homo sapiens
SEQUENCE: 479
TTTPAPRPPT PAPTIASQPL SLRPEACRPA AGGAVHTRGL DFACDIYIWA PLAGTCGVLL  60
LSLVIT                                                                66

SEQ ID NO: 480            moltype = AA  length = 42
FEATURE                   Location/Qualifiers
source                    1..42
                          mol_type = protein
                          organism = Homo sapiens
SEQUENCE: 480
KRGRKKLLYI FKQPFMRPVQ TTQEEDGCSC RFPEEEEGGC EL                        42

SEQ ID NO: 481            moltype = AA  length = 113
FEATURE                   Location/Qualifiers
source                    1..113
                          mol_type = protein
                          organism = Homo sapiens
SEQUENCE: 481
LRVKFSRSAD APAYQQGQNQ LYNELNLGRR EEYDVLDKRR GRDPEMGGKP RRKNPQEGLY  60
NELQKDKMAE AYSEIGMKGE RRRGKGHDGL YQGLSTATKD TYDALHMQAL PPR          113

SEQ ID NO: 482            moltype = AA  length = 486
FEATURE                   Location/Qualifiers
source                    1..486
                          mol_type = protein
                          organism = synthetic construct
                          note = Description of Artificial Sequence: Synthetic
                          polypeptide
SEQUENCE: 482
MALPVTALLL PLALLLHAAR PQVQLQESGP GLVKPSETLS LTCTVSDNSI SNYYWSWIRQ  60
PPGKGLEWIA YIYYSGTTNY NPSLKSRVTI SLDTSKNQFS LKLSSVTAAD TAVYYCARLF  120
NWGFAFDIWG QGTMVTVSSG GGGSGGGGSG GGGSGGGGSE IVMTQSPATL SVSPGERATL  180
SCRASQSVSS NLAWYQQKPG QAPRLLIYGA STRATGIPAR FSGSGSGTEF TLTISSLQSE  240
DFAVYYCQQY NNWPLTFGGG TKVEIKTTTP APRPPTPAPT IASQPLSLRP EACRPAAGGA  300
VHTRGLDFAC DIYIWAPLAG TCGVLLLSLV ITKRGRKKLL YIFKQPFMRP VQTTQEEDGC  360
SCRFPEEEEG GCELRVKFSR SADAPAYQQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                               486

SEQ ID NO: 483            moltype = AA  length = 487
FEATURE                   Location/Qualifiers
source                    1..487
                          mol_type = protein
                          organism = synthetic construct
                          note = Description of Artificial Sequence: Synthetic
                          polypeptide
SEQUENCE: 483
MALPVTALLL PLALLLHAAR PQVQLQESGP GLMKPSETLS LTCTVSGGSI SSSYWSCIRQ  60
PPGKGLEWIG YIYYSGTTNY NPSLKSRVTL SLDTSKNQFS LRLTSVTAAD TAVYYCARVA  120
PTGFWFDYWG QGTLVTVSSG GGGSGGGGSG GGGSGGGGSE IVLTQSPGTL SLSPGERATL  180
SCRASQRVSS RYLAWYQQKP GQAPRLLIYG ASSRATGIPD RFSGSGSGTD FTLTISRLEP  240
EEFAVYYCQQ YGTSPLTFGG GTKVEIKTTT PAPRPPTPAP TIASQPLSLR PEACRPAAGG  300
AVHTRGLDFA CDIYIWAPLA GTCGVLLLSL VITKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                              487

SEQ ID NO: 484            moltype = AA  length = 486
FEATURE                   Location/Qualifiers
source                    1..486
                          mol_type = protein
                          organism = synthetic construct
                          note = Description of Artificial Sequence: Synthetic
                          polypeptide
SEQUENCE: 484
MALPVTALLL PLALLLHAAR PEVQLVESGG GLVQPGGSLR LSCAASGFTF SSHDMHWVRQ  60
ATGKGLEWVS AIGIAGDTYY SGSVKGRFTI SRENAKNSLY LQMNSLRAGD TAVYYCARAN  120
WGEGAFDIWG QGTMVTVSSG GGGSGGGGSG GGGSGGGGSI QMTQSPSSL SASVGDRVTI  180
TCRASQGISD YLAWYQQKPG KIPKLLIYAA STLQSGVPSR FSGSGSGTDF TLTISSLQPE  240
```

-continued

```
DVATYYCQKY NSVPLTFGGG TKVEIKTTTP APRPPTPAPT IASQPLSLRP EACRPAAGGA   300
VHTRGLDFAC DIYIWAPLAG TCGVLLLSLV ITKRGRKKLL YIFKQPFMRP VQTTQEEDGC   360
SCRFPEEEG GCELRVKFSR SADAPAYQQG QNQLYNELNL GRREEYDVLD KRRGRDPEMG    420
GKPRRKNPQE GLYNELQKDK MAEAYSEIGM KGERRRGKGH DGLYQGLSTA TKDTYDALHM   480
QALPPR                                                             486

SEQ ID NO: 485          moltype = AA  length = 487
FEATURE                 Location/Qualifiers
source                  1..487
                        mol_type = protein
                        organism = synthetic construct
                        note = Description of Artificial Sequence: Synthetic
                         polypeptide
SEQUENCE: 485
MALPVTALLL PLALLLHAAR PQVQLQESGP GLVKPSETLS LTCTVSDDSI SNYYWSWIRQ   60
PPGKGLEWIG YIFYSGTTNH NPSLKSRLTI SLDKAKNQFS LRLSSVTAAD TAVYYCARVF   120
NWGFAFDIWG QGTMVTVSSG GGGSGGGGSG GGGSGGGGSE IVLTQSPGTL SLSPGERATL   180
SCRASQRISR TYLAWYQQKP GQAPRLLIYG ASSRATGIPD RFTGSGSGTD FTLTISRLEP   240
EDFAVYYCQQ YGTSPLTFGG GTKVEINTTT PAPRPPTPAP TIASQPLSLR PEACRPAAGG   300
AVHTRGLDFA CDIYIWAPLA GTCGVLLLSL VITKRGRKKL LYIFKQPFMR PVQTTQEEDG   360
CSCRFPEEE GGCELRVKFS RSADAPAYQQ GQNQLYNELN LGRREEYDVL DKRRGRDPEM    420
GGKPRRKNPQ EGLYNELQKD KMAEAYSEIG MKGERRRGKG HDGLYQGLST ATKDTYDALH   480
MQALPPR                                                            487

SEQ ID NO: 486          moltype = AA  length = 487
FEATURE                 Location/Qualifiers
source                  1..487
                        mol_type = protein
                        organism = synthetic construct
                        note = Description of Artificial Sequence: Synthetic
                         polypeptide
SEQUENCE: 486
MALPVTALLL PLALLLHAAR PQVQLQESGP GLVKPSETLS LTCTVSDNSI SNYYWSWIRQ   60
PPGKGLEWIA YIYYSGTTNY NPSLKSRVTI SLDTSKNQFS LQLSSVTAAD AAVYYCARVF   120
HWGFAFDIWG QGTMVTVSSG GGGSGGGGSG GGGSGGGGSE IVLTQSPGTL SLSPGERATL   180
SCRASQRVSN TYLAWYQQNP GQAPRLLIYG ASSRATGIPD RFSGSGSGTD FTLTISRLEP   240
EDFAVYYCQQ YGTSPLTFGG GTKVEIKTTT PAPRPPTPAP TIASQPLSLR PEACRPAAGG   300
AVHTRGLDFA CDIYIWAPLA GTCGVLLLSL VITKRGRKKL LYIFKQPFMR PVQTTQEEDG   360
CSCRFPEEE GGCELRVKFS RSADAPAYQQ GQNQLYNELN LGRREEYDVL DKRRGRDPEM    420
GGKPRRKNPQ EGLYNELQKD KMAEAYSEIG MKGERRRGKG HDGLYQGLST ATKDTYDALH   480
MQALPPR                                                            487

SEQ ID NO: 487          moltype = AA  length = 487
FEATURE                 Location/Qualifiers
source                  1..487
                        mol_type = protein
                        organism = synthetic construct
                        note = Description of Artificial Sequence: Synthetic
                         polypeptide
SEQUENCE: 487
MALPVTALLL PLALLLHAAR PQVQLQESGP GLVKPSETLS LTCTVSNVSI SSYYWSWIRQ   60
PPGKGLEWIG YIYYSGTTNY NPSLKSRVTM SVDTSKNQFS LKLSSVTAAD TAVYFCARLS   120
NWGFAFDIWG QGTMVTFSSG GGGSGGGGSG GGGSGGGGSE IVLTQSPGTL SLSPGERATL   180
SCRASQTISS SYLAWYQQKP GQAPRLLIYG ASSRATGIPD RFSGSGSGTE FTLTISRLEP   240
EDFAVYYCQQ YGWSPITFGQ GTRLEIKTTT PAPRPPTPAP TIASQPLSLR PEACRPAAGG   300
AVHTRGLDFA CDIYIWAPLA GTCGVLLLSL VITKRGRKKL LYIFKQPFMR PVQTTQEEDG   360
CSCRFPEEE GGCELRVKFS RSADAPAYQQ GQNQLYNELN LGRREEYDVL DKRRGRDPEM    420
GGKPRRKNPQ EGLYNELQKD KMAEAYSEIG MKGERRRGKG HDGLYQGLST ATKDTYDALH   480
MQALPPR                                                            487

SEQ ID NO: 488          moltype = AA  length = 493
FEATURE                 Location/Qualifiers
source                  1..493
                        mol_type = protein
                        organism = synthetic construct
                        note = Description of Artificial Sequence: Synthetic
                         polypeptide
SEQUENCE: 488
MALPVTALLL PLALLLHAAR PEVQLVESGG GLVQPGGSLR LSCAASGFTF SSYDMHWVRQ   60
ATGKGLEWVS AIGPAGDTYY PGSVKGRFTI SRENAKNSLY LQMNSLRAGD TAVYYCARAD   120
PPYYYYGMDV WGQGTTVTVS SGGGGSGGGG SGGGGSGGGG SDIVMTQSPL SLPVTPGEPA   180
SISCRSSQSL LHSNEYNYLD WYLQKPGQSP QLLIYLGSNR ASGVPDRFSG SGSGTDFILK   240
ISRVEAEDVG VYYCMQALEI PLTFGGGTKV EIKTTTPAPR PPTPAPTIAS QPLSLRPEAC   300
RPAAGGAVHT RGLDFACDIY IWAPLAGTCG VLLLSLVITK RGRKKLLYIF KQPFMRPVQT   360
TQEEDGCSCR FPEEEGGCE LRVKFSRSAD APAYQQGQNQ LYNELNLGRR EEYDVLDKRR    420
GRDPEMGGKP RRKNPQEGLY NELQKDKMAE AYSEIGMKGE RRRGKGHDGL YQGLSTATKD   480
TYDALHMQAL PPR                                                     493

SEQ ID NO: 489          moltype = AA  length = 488
```

-continued

```
FEATURE                 Location/Qualifiers
source                  1..488
                        mol_type = protein
                        organism = synthetic construct
                        note = Description of Artificial Sequence: Synthetic
                          polypeptide
SEQUENCE: 489
MALPVTALLL PLALLLHAAR PQITLKESGP TLVKPTQTLT LTCTFSGFSL STRGVGVGWI   60
RQPPGKALEW LALIYWNDDK RYSPSLQTRL TITKDTPKNQ VVLTMTNMDP VDTATYYCAR  120
SNWGNWYFAL WGRGTLVTVS SGGGGSGGGG SGGGGSGGGG SEIVLTQSPA TLSLSPGERA  180
TLSCRASQSV SSYLAWYQQK PGQAPRLLIY DAFYRATGIP ARFSGSGSGT DFTLTISSLE  240
PEDFAVYYCQ HRSNWPITFG QGTRLEIKTT TPAPRPPTPA PTIASQPLSL RPEACRPAAG  300
GAVHTRGLDF ACDIYIWAPL AGTCGVLLLS LVITKRGRKK LLYIFKQPFM RPVQTTQEED  360
GCSCRFPEEE EGGCELRVKF SRSADAPAYQ QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPR                                                          488

SEQ ID NO: 490          moltype = AA   length = 487
FEATURE                 Location/Qualifiers
source                  1..487
                        mol_type = protein
                        organism = synthetic construct
                        note = Description of Artificial Sequence: Synthetic
                          polypeptide
SEQUENCE: 490
MALPVTALLL PLALLLHAAR PQVQLQESGP GLVKPSETLS LTCTVSGDSI SNYYWTWIRQ   60
PPGKGLEWIG YIYYSGTTNS NPSLKSRVTV SLDTSKSQFS LNLSSVTAAD TAVYYCARVF  120
NRGFAFDIWG QGTMVTVSSG GGGSGGGGSG GGGSGGGGSE IVLTQSPGTL SLSPGERATL  180
SCRASQRISN TYLAWYQQKP GQAPRLLIYG ASSRATGIPD RFSGSGSGTD FTLTISRLEP  240
EDFAAYYCQQ YDTSPLTFGG GTKVEIKTTT PAPRPPTPAP TIASQPLSLR PEACRPAAGG  300
AVHTRGLDFA CDIYIWAPLA GTCGVLLLSL VITKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                           487

SEQ ID NO: 491          moltype = AA   length = 496
FEATURE                 Location/Qualifiers
source                  1..496
                        mol_type = protein
                        organism = synthetic construct
                        note = Description of Artificial Sequence: Synthetic
                          polypeptide
SEQUENCE: 491
MALPVTALLL PLALLLHAAR PQVTLRESGP ALVKPTQTLT LTCTVSGVSL STSGMCVSWI   60
RQPLGKALEW LGFIDWDDDK YYNTSLKTRL TISKDTSKNQ VVLTMTNMDP VDTATYYCAR  120
IRGYSGSYDA FDIWGQGTVV IVSSGGGGSG GGGSGGGGSG GGGSDIVMTQ SPLSLPVTPG  180
EPASISCRSS QSLLHSNGYN HLDWYLQKPG QSPQVLIYLG SNRASGVPDR FSGSGSGTDF  240
TLKISRVEAE DVGVYFCMQA LQTPLTFGGG TKVEIKTTTP APRPPTPAPT IASQPLSLRP  300
EACRPAAGGA VHTRGLDFAC DIYIWAPLAG TCGVLLLSLV ITKRGRKKLL YIFKQPFMRP  360
VQTTQEEDGC SCRFPEEEEG GCELRVKFSR SADAPAYQQG QNQLYNELNL GRREEYDVLD  420
KRRGRDPEMG GKPRRKNPQE GLYNELQKDK MAEAYSEIGM KGERRRGKGH DGLYQGLSTA  480
TKDTYDALHM QALPPR                                                  496

SEQ ID NO: 492          moltype = AA   length = 486
FEATURE                 Location/Qualifiers
source                  1..486
                        mol_type = protein
                        organism = synthetic construct
                        note = Description of Artificial Sequence: Synthetic
                          polypeptide
SEQUENCE: 492
MALPVTALLL PLALLLHAAR PQVQLQVSGP GLVKPSETLS LTCSVSGGSI SSYYWSWIRQ   60
SPGKGLDWIG YMYYSGTTNY NPSLKSRVTI SVDTSKNQFS LKLSSVTATD TAVYYCARVG  120
LTGFFFDYWG QGTLVTVSSG GGGSGGGGSG GGGSGGGGSA IQMTQSPSSL SASVGDRVTI  180
TCRASQGIRN DLGWYQQKPG KAPKLLIYAA SSLQSGVPSR FSGSGSGTDF TLTVSSLQPE  240
DFATYYCLQD YNYPYTFGQG TKLEIKTTTP APRPPTPAPT IASQPLSLRP EACRPAAGGA  300
VHTRGLDFAC DIYIWAPLAG TCGVLLLSLV ITKRGRKKLL YIFKQPFMRP VQTTQEEDGC  360
SCRFPEEEEG GCELRVKFSR SADAPAYQQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                            486

SEQ ID NO: 493          moltype = AA   length = 483
FEATURE                 Location/Qualifiers
source                  1..483
                        mol_type = protein
                        organism = synthetic construct
                        note = Description of Artificial Sequence: Synthetic
                          polypeptide
SEQUENCE: 493
```

```
MALPVTALLL PLALLLHAAR PQVQLQQWGG GLLKPSETLS LTCAVYGGSS SGNYWSWIRQ  60
PPGKRLEWIG EINHSGTTSY NPSLKSRVTI SVDTSKNQFS LKLSSVTAAD TAVYYCARGE  120
LGIADSWGQG TLVTVSSGGG GSGGGGSGGG GSGGGGSDIQ MTQSPSTLSA SVGDRVTITC  180
RASQSISRWL AWYQQKPGKA PKLLIYKASS LESGVPSRFS GSGSGTEFTL TISSLQPDDF  240
ATYYCQQYNS YSTFGQGTKV EIKTTTPAPR PPTPAPTIAS QPLSLRPEAC RPAAGGAVHT  300
RGLDFACDIY IWAPLAGTCG VLLLSLVITK RGRKKLLYIF KQPFMRPVQT TQEEDGCSCR  360
FPEEEEGGCE LRVKFSRSAD APAYQQGQNQ LYNELNLGRR EEYDVLDKRR GRDPEMGGKP  420
RRKNPQEGLY NELQKDKMAE AYSEIGMKGE RRRGKGHDGL YQGLSTATKD TYDALHMQAL  480
PPR                                                                483

SEQ ID NO: 494          moltype = AA  length = 489
FEATURE                 Location/Qualifiers
source                  1..489
                        mol_type = protein
                        organism = synthetic construct
                        note = Description of Artificial Sequence: Synthetic
                        polypeptide
SEQUENCE: 494
MALPVTALLL PLALLLHAAR PQLQLQESGP GLVKPSETLS LTCTVSGGSI SSSSYYWGWI  60
RQPPGKGLEW IGSIYYSGNI YHNPSLKSRV SISVDTSKNQ FSLRLSSVTA ADTAVYYCAR  120
EIIVGATHFD YWGQGTLVTV SSGGGGSGGG GSGGGGSGGG GSAIQMTQSP SSLSASVGDR  180
VTITCRASQG IRNDLGWYQQ KPGKAPELLI YAASSLQSGV PSRFSGSGSG TDFTLTISSL  240
QPEDFATYYC LQDYNYPLTF GPGTKVDIKT TTPAPRPPTP APTIASQPLS LRPEACRPAA  300
GGAVHTRGLD FACDIYIWAP LAGTCGVLLL SLVITKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 495          moltype = AA  length = 487
FEATURE                 Location/Qualifiers
source                  1..487
                        mol_type = protein
                        organism = synthetic construct
                        note = Description of Artificial Sequence: Synthetic
                        polypeptide
SEQUENCE: 495
MALPVTALLL PLALLLHAAR PQVQLQQWGA GLLKPSETLS LTCAVYGGSF SGYYWSWIRQ  60
PPGKGLEWIG EIIHSGSSNY NPSLKSRVSI SVDTSKNQFS LKLSSVTAAD TAVYYCSRGE  120
YGSGSRFDYW GQGTLVTVSS GGGGSGGGGS GGGGSGGGGS AIQMTQSPSS LSASVGDRVA  180
ITCRASQGIR DDLGWYQQKP GKAPKLLIYA ASSLQSGVPS RFSGSRSDTD FTLTISSLQP  240
EDFATYYCLQ DYDYPLTFGG GTKVEIKTTT PAPRPPTPAP TIASQPLSLR PEACRPAAGG  300
AVHTRGLDFA CDIYIWAPLA GTCGVLLLSL VITKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                            487

SEQ ID NO: 496          moltype = AA  length = 484
FEATURE                 Location/Qualifiers
source                  1..484
                        mol_type = protein
                        organism = synthetic construct
                        note = Description of Artificial Sequence: Synthetic
                        polypeptide
SEQUENCE: 496
MALPVTALLL PLALLLHAAR PQVQLQESGP GLVKPSGTLS LTCAVSGGSI SSNNWWSWVR  60
QPPGKGLEWI GDIHHSGSTN YKPSLKSRVT ISVDKSKNQF SLNLISVTAA DTAVYYCARE  120
AGGYFDYWGQ GILVTVSSGG GGSGGGGSGG GSGGGGSDI QMTQSPSTLS ASVGDRVTIT  180
CRASQSISSW LAWYQQKPGK APKLLISKAS SLESGVPSRF SGSGSGPEFT LTISSLQPAD  240
FATYYCQQYN SYSTFGQGTK LEIKTTTPAP RPPTPAPTIA SQPLSLRPEA CRPAAGGAVH  300
TRGLDFACDI YIWAPLAGTC GVLLLSLVIT KRGRKKLLYI FKQPFMRPVQ TTQEEDGCSC  360
RFPEEEEGGC ELRVKFSRSA DAPAYQQGQN QLYNELNLGR REEYDVLDKR RGRDPEMGGK  420
PRRKNPQEGL YNELQKDKMA EAYSEIGMKG ERRRGKGHDG LYQGLSTATK DTYDALHMQA  480
LPPR                                                               484

SEQ ID NO: 497          moltype = AA  length = 487
FEATURE                 Location/Qualifiers
source                  1..487
                        mol_type = protein
                        organism = synthetic construct
                        note = Description of Artificial Sequence: Synthetic
                        polypeptide
SEQUENCE: 497
MALPVTALLL PLALLLHAAR PQVQLQQWGA GLLKPSETLS LTCAVYGGSF SGYYWTWIRQ  60
PPGKGLEWIG EITHSGSTNY NPSLKSRVSI SVDTSKNQFS LKLSSVTAAD TAVYYCARGE  120
YGSGSRFDYW GQGTLVTVSS GGGGSGGGGS GGGGSGGGGS AIQMTQSPSS LSASVGDRVA  180
ITCRASQGIR DDLGWYQQKP GKAPKLLIYA ASSLQSGVPS RFSGSGSDTD FTLTISSLQP  240
EDFATYYCLQ DYDYPLTFGG GTKVEIKTTT PAPRPPTPAP TIASQPLSLR PEACRPAAGG  300
AVHTRGLDFA CDIYIWAPLA GTCGVLLLSL VITKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
```

```
GGKPRRKNPQ EGLYNELQKD KMAEAYSEIG MKGERRRGKG HDGLYQGLST ATKDTYDALH  480
MQALPPR                                                            487

SEQ ID NO: 498        moltype = AA  length = 487
FEATURE               Location/Qualifiers
source                1..487
                      mol_type = protein
                      organism = synthetic construct
                      note = Description of Artificial Sequence: Synthetic
                      polypeptide
SEQUENCE: 498
MALPVTALLL PLALLLHAAR PQVQLQQWGA GLLKPSETLS LTCAVYGGSF SGYYWSWIRQ  60
PPGKGLEWIG EITHSGSTNY NPSLKSRVSI SVDTSKNQFS LKLSSVTAAD TAVYYCARGE  120
YGSGSRFDYW GQGTLVTVSS GGGGSGGGGS GGGGSGGGGS AIQMTQSPSS LSASVGDRVA  180
LTCRASQGIR DDLGWYQQKP GKAPKLLIYA ASSLQSGVPS RFSGSGSDTD FTLTISSLQP  240
EDFATYYCLQ DYDYPLTFGG GTKVEIKTTT PAPRPPTPAP TIASQPLSLR PEACRPAAGG  300
AVHTRGLDFA CDIYIWAPLA GTCGVLLLSL VITKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                            487

SEQ ID NO: 499        moltype = AA  length = 488
FEATURE               Location/Qualifiers
source                1..488
                      mol_type = protein
                      organism = synthetic construct
                      note = Description of Artificial Sequence: Synthetic
                      polypeptide
SEQUENCE: 499
MALPVTALLL PLALLLHAAR PQVQLQQWGA GLLKPSETLS LTCAVYGGSF SAYYWNWIRQ  60
PPGKGLEWIG EINHSGSTNY NPSLKSRVTI SVDTSKNQFS LNLTSLTAAD TAVYYCARGL  120
DSSGWYPFDY WGQGTLVTVS SGGGGSGGGG SGGGGSGGGG SDIQMTQSPS SVSASVGDRV  180
TITCRASQGI SSWLAWYQQK PGKAPKLLIY AASSLQSGVP SRFSGSGSGT DFTLTISSLQ  240
PEDFATYYCQ QADSFPFTFG PGTKVDIKTT TPAPRPPTPA PTIASQPLSL RPEACRPAAG  300
GAVHTRGLDF ACDIYIWAPL AGTCGVLLLS LVITKRGRKK LLYIFKQPFM RPVQTTQEED  360
GCSCRFPEEE EGGCELRVKF SRSADAPAYQ QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPR                                                           488

SEQ ID NO: 500        moltype = AA  length = 483
FEATURE               Location/Qualifiers
source                1..483
                      mol_type = protein
                      organism = synthetic construct
                      note = Description of Artificial Sequence: Synthetic
                      polypeptide
SEQUENCE: 500
MALPVTALLL PLALLLHAAR PQVQLQQWGA GLLKPSETLS LTCAVFGGSF SGDYWSWIRQ  60
PPGKGLEWIG EINHSGITSF NPSLKSRVTI SVDTSKNQFS LKLSSVTAAD TAVYYCARGE  120
LGIPDNWGQG TLVTVSSGGG GSGGGGSGGG GSGGGGSDIQ MTQSPSTLSA SVGDRVTITC  180
RASQSISRWL AWYQQKPGKA PKLLIYKASS LESGVPSRFS GSGSGTEFTL TISSLQPDDF  240
ATYYCQQYNS YSTFGQGTKV EIKTTTPAPR PPTPAPTIAS QPLSLRPEAC RPAAGGAVHT  300
RGLDFACDIY IWAPLAGTCG VLLLSLVITK RGRKKLLYIF KQPFMRPVQT TQEEDGCSCR  360
FPEEEEGGCE LRVKFSRSAD APAYQQGQNQ LYNELNLGRR EEYDVLDKRR GRDPEMGGKP  420
RRKNPQEGLY NELQKDKMAE AYSEIGMKGE RRRGKGHDGL YQGLSTATKD TYDALHMQAL  480
PPR                                                                483

SEQ ID NO: 501        moltype = AA  length = 492
FEATURE               Location/Qualifiers
source                1..492
                      mol_type = protein
                      organism = synthetic construct
                      note = Description of Artificial Sequence: Synthetic
                      polypeptide
SEQUENCE: 501
MALPVTALLL PLALLLHAAR PQVQLQESGP GLVKPSGTLS LTCVVFGDSI SSSNWWSWVR  60
QPPGKGLEWI GEVFHSGSTN YNPSLKSRVT ISVDKSKNQF SLKLSSVTAA DTAVYYCARA  120
AVAGALDYWG QGTLVTVSSG GGGSGGGGSG GGGSGGGGSD IVMTQSPDSL AVSLGERATI  180
NCKSSQSVLY SSNNKNYLAW YQQKPGQPPN LLVYWASTRE SGVPDRFSGA GSGTDFTLTI  240
SSLQAEDVAV YYCQQYYGTS WTFGQGTKVE IKTTTPAPRP PTPAPTIASQ PLSLRPEACR  300
PAAGGAVHTR GLDFACDIYI WAPLAGTCGV LLLSLVITKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                      492

SEQ ID NO: 502        moltype = AA  length = 488
FEATURE               Location/Qualifiers
source                1..488
                      mol_type = protein
```

```
                   organism = synthetic construct
                   note = Description of Artificial Sequence: Synthetic
                     polypeptide
SEQUENCE: 502
MALPVTALLL PLALLLHAAR PQITLRESGP TLVKPTQTLT LTCTFSGFSL STSGLGVGWI    60
RQPPGEALEW LALIYWNDDK RYSPSLKSRL SITKDTSKNQ VVLIMTNMDP VDTATYYCVH   120
RRIAAPGSVY WGQGTLVTVS SGGGGSGGGG SGGGGSGGGG SDIQMTQSPS SVSASVGDRV   180
TITCRASQGI SSWLAWYQQK PGKAPKLLIS AASSLQSGVP SRFSGSGSGT DFTLTISSLQ   240
PEDFATYYCH QANSFPFTFG QGTKLEIKTT TPAPRPPTPA PTIASQPLSL RPEACRPAAG   300
GAVHTRGLDF ACDIYIWAPL AGTCGVLLLS LVITKRGRKK LLYIFKQPFM RPVQTTQEED   360
GCSCRFPEEE EGGCELRVKF SRSADAPAYQ QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                            488

SEQ ID NO: 503          moltype = AA  length = 487
FEATURE                 Location/Qualifiers
source                  1..487
                        mol_type = protein
                        organism = synthetic construct
                        note = Description of Artificial Sequence: Synthetic
                          polypeptide
SEQUENCE: 503
MALPVTALLL PLALLLHAAR PQVQLVQSGA EVKKPGASVK VSCKVSGYTL TELSMHWVRQ    60
APGKGPEGMG GFDPEDGKTI YAQKFQGRVT MTEDTSADTA YMELNSLRSE DTAVYYCATL   120
LRGLDAFDVW GQGTMVTVSS GGGGSGGGGS GGGGSGGGGS DIQMTQSPSS LSASVGDRVT   180
ITCRASQGIR NDLGWYQQKP GKAPKRLIYA ASSLQSGVPS RFSGSGSGTE FTLTISTLQP   240
EDFATYYCLQ HNSYPRTFGQ GTKVEIKTTT PAPRPPTPAP TIASQPLSLR PEACRPAAGG   300
AVHTRGLDFA CDIYIWAPLA GTCGVLLLSL VITKRGRKKL LYIFKQPFMR PVQTTQEEDG   360
CSCRFPEEEE GGCELRVKFS RSADAPAYQQ GQNQLYNELN LGRREEYDVL DKRRGRDPEM   420
GGKPRRKNPQ EGLYNELQKD KMAEAYSEIG MKGERRRGKG HDGLYQGLST ATKDTYDALH   480
MQALPPR                                                             487

SEQ ID NO: 504          moltype = AA  length = 488
FEATURE                 Location/Qualifiers
source                  1..488
                        mol_type = protein
                        organism = synthetic construct
                        note = Description of Artificial Sequence: Synthetic
                          polypeptide
SEQUENCE: 504
MALPVTALLL PLALLLHAAR PQVQLQQWGA GLLKPSETLS LTCAVYGGSF SGYYWRWIRQ    60
PPGKGLEWIG EISHSGSTNY NPSLKSRVTI SVDTSKNQFS LKLSSVTAAD TAVYYCAVRG   120
YSYGYPLFDY WGQGTLVTVS SGGGGSGGGG SGGGGSGGGG SDIQMTQSPS SLSASVGDRV   180
TITCRASQGI RNDLGWYQQK LGKAPKRLIY AASSLQSGVP SRFSGSGSGT EFTLTISSLQ   240
PEDFATYYCL QYNSYPRTFG QGTKVEIKTT TPAPRPPTPA PTIASQPLSL RPEACRPAAG   300
GAVHTRGLDF ACDIYIWAPL AGTCGVLLLS LVITKRGRKK LLYIFKQPFM RPVQTTQEED   360
GCSCRFPEEE EGGCELRVKF SRSADAPAYQ QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                            488

SEQ ID NO: 505          moltype = AA  length = 483
FEATURE                 Location/Qualifiers
source                  1..483
                        mol_type = protein
                        organism = synthetic construct
                        note = Description of Artificial Sequence: Synthetic
                          polypeptide
SEQUENCE: 505
MALPVTALLL PLALLLHAAR PQVQLQESGP GLVKPSGTLS LTCAVSGDSI SSNWWTWVRQ    60
PPGKGLEWIG DIHHSGSTNY NPSLKSRVTM SVDKSENQFS LKLSSVTAAD TAVFYCARDG   120
GGTLDYWGQG TLVTVSSGGG GSGGGGSGGG GSGGGGSDIQ MTQSPSTLSA SVGDRVTITC   180
RASQSISSWL AWYQQKPGKA PKLLIYKAST LESGVPSRFS GSGSGTEFTL TISSLQPDDF   240
ATYYCQQYNG YSTFGQGTKV EIKTTTPAPR PPTPAPTIAS QPLSLRPEAC RPAAGGAVHT   300
RGLDFACDIY IWAPLAGTCG VLLLSLVITK RGRKKLLYIF KQPFMRPVQT TQEEDGCSCR   360
FPEEEEGGCE LRVKFSRSAD APAYQQGQNQ LYNELNLGRR EEYDVLDKRR GRDPEMGGKP   420
RRKNPQEGLY NELQKDKMAE AYSEIGMKGE RRRGKGHDGL YQGLSTATKD TYDALHMQAL   480
PPR                                                                 483

SEQ ID NO: 506          moltype = AA  length = 492
FEATURE                 Location/Qualifiers
source                  1..492
                        mol_type = protein
                        organism = synthetic construct
                        note = Description of Artificial Sequence: Synthetic
                          polypeptide
SEQUENCE: 506
MALPVTALLL PLALLLHAAR PQVQLVQSGA EVKKPGSSVK VSCKASGGTF TNYCISWVRQ    60
APGQGLEWMG GIIPIFGTTN YAQTFQGRVT ITADKSTSTA YMELSSLRSE DTAVYYCARD   120
NGDRYYYDMD VWGQGTTVTV SSGGGGSGGG GSGGGGSGGG GSQSVLTQPP SVSAAPGQKV   180
```

-continued

```
TISCSGSSSN IGNNYVSWYQ QLPGTAPKLL IYDNNKRPSG IPDRFSGSKS GTSATLGITG  240
LQTGDEADYY CGTWDSSLSA VVFGGGTKLT VLTTTPAPRP PTPAPTIASQ PLSLRPEACR  300
PAAGGAVHTR GLDFACDIYI WAPLAGTCGV LLLSLVITKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                      492
```

```
SEQ ID NO: 507            moltype = AA  length = 494
FEATURE                   Location/Qualifiers
source                    1..494
                          mol_type = protein
                          organism = synthetic construct
                          note = Description of Artificial Sequence: Synthetic
                            polypeptide
SEQUENCE: 507
MALPVTALLL PLALLLHAAR PQVPLVQSGA EVKKPGSSVK VSCKASGGTF STYSISWVRQ  60
APGQGLEWMG GIIPIFGTTN YAQKFQGRVT ITADKSTSTA YMELSSLRSE DTAVYYCARD  120
GEGSYYYYG MDVWGQGTTV TVSSGGGGSG GGGSGGGGSG GGGSQSVLTQ PPSVSAAPGQ  180
KVTISCSGSS SNIGNNYVSW YQQLPGTAPK LLIYDNNKRP SGIPDRFFGS KFGTSATLGI  240
TGLQTGDEAD YYCGTWDSSL SAVVFGGGTK LTVLTTTPAP RPPTPAPTIA SQPLSLRPEA  300
CRPAAGGAVH TRGLDFACDI YIWAPLAGTC GVLLLSLVIT KRGRKKLLYI FKQPFMRPVQ  360
TTQEEDGCSC RFPEEEEGGC ELRVKFSRSA DAPAYQQGQN QLYNELNLGR REEYDVLDKR  420
RGRDPEMGGK PRRKNPQEGL YNELQKDKMA EAYSEIGMKG ERRRGKGHDG LYQGLSTATK  480
DTYDALHMQA LPPR                                                    494
```

```
SEQ ID NO: 508            moltype = AA  length = 487
FEATURE                   Location/Qualifiers
source                    1..487
                          mol_type = protein
                          organism = synthetic construct
                          note = Description of Artificial Sequence: Synthetic
                            polypeptide
SEQUENCE: 508
MALPVTALLL PLALLLHAAR PQVQLQESGP GLVKPSETLS LTCTVSGDSI SSYYWSWIRQ  60
PPGKGLEWIG YMYYSGITNY NPSLKSRVNI SLDTSKNQFS LKLGSVTAAD TAVYYCARLS  120
VAGFYFDYWG QGTLVTVSSG GGGSGGGGSG GGGSGGGGSE IVLTQSPGTL SLSPGERATL  180
SCRASQSVTR SYLAWYQQKP GQAPRLLIYG ASSRATDIPD RFSGSGSGTD FTLTINRLEP  240
EDFAVYYCQQ YGTSPLTFGG GTKVEIKTTT PAPRPPTPAP TIASQPLSLR PEACRPAAGG  300
AVHTRGLDFA CDIYIWAPLA GTCGVLLLSL VITKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                            487
```

```
SEQ ID NO: 509            moltype = AA  length = 487
FEATURE                   Location/Qualifiers
source                    1..487
                          mol_type = protein
                          organism = synthetic construct
                          note = Description of Artificial Sequence: Synthetic
                            polypeptide
SEQUENCE: 509
MALPVTALLL PLALLLHAAR PQVQLQESGP GLVKPSETLS LTCTVSSDSI SSYYWSWIRQ  60
PPGKGLEWIS YIYYSGISNY NPSLKSRVSI SVDTSKNQFS LRLSSVTAAD TAVYYCARIS  120
VAGFFFDNWG QGTLVTVSSG GGGSGGGGSG GGGSGGGGSE IMLTQSPDTL SLSPGERATL  180
SCRASQSVSS SYLAWYQQKP GQAPRLLIYG ASSRAAGVPD RFSGSGSGTD FTLTISRLAP  240
EDFVVYYCQQ YGISPLTFGG GTKVEIKTTT PAPRPPTPAP TIASQPLSLR PEACRPAAGG  300
AVHTRGLDFA CDIYIWAPLA GTCGVLLLSL VITKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                            487
```

```
SEQ ID NO: 510            moltype = AA  length = 495
FEATURE                   Location/Qualifiers
source                    1..495
                          mol_type = protein
                          organism = synthetic construct
                          note = Description of Artificial Sequence: Synthetic
                            polypeptide
SEQUENCE: 510
MALPVTALLL PLALLLHAAR PQVQLQQSGP GLVKPSQTLS LTCAISGDSV SSNSATWNWI  60
RQSPSRGLEW LGRTYYRSKW YDDYAVSVKS RITINPDTSK NHLSLHLNSV TPEDTAVYYC  120
AGGGLVGAPD GFDVWGQGTM VTVSSGGGGS GGGGSGGGGS GGGGSQSVLT QPPSASGTPG  180
QRVTISCSGS SSNIGSDPVN WYQQLPGTAP KLLIYSNNQR PSGVPDRFSG SKSGTSASLA  240
ISGLQSEDEA DYYCSAWDDS LNGYVFGTGT KVTVLTTTPA PRPPTPAPTI ASQPLSLRPE  300
ACRPAAGGAV HTRGLDFACD IYIWAPLAGT CGVLLLSLVI TKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                   495
```

-continued

```
SEQ ID NO: 511          moltype = AA   length = 490
FEATURE                 Location/Qualifiers
source                  1..490
                        mol_type = protein
                        organism = synthetic construct
                        note = Description of Artificial Sequence: Synthetic
                         polypeptide
SEQUENCE: 511
MALPVTALLL PLALLLHAAR PQVQLVQSGA EVKKPGASVK VSCKASGYTF TGYSIHWVRQ   60
APGQGLEWMG WINPNSGGTF YAQKFQGRVT MTRDTSISTV YMELSRLRSD DTAVYYCARD  120
GWGDYYYYGL DVWGQGTTVT VSLGGGGSGG GGSGGGGSGG GGSDIQMTQS PSSVSASVGD  180
RVTITCRASQ DISSWLAWYQ QKPGKAPKLL IYTASSLQGG VPSRFSGSGS GTDFTLTISS  240
LQPEDLATYS CQQANVFPYT FGQGTKLEIK TTTPAPRPPT PAPTIASQPL SLRPEACRPA  300
AGGAVHTRGL DFACDIYIWA PLAGTCGVLL LSLVITKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 512          moltype = AA   length = 491
FEATURE                 Location/Qualifiers
source                  1..491
                        mol_type = protein
                        organism = synthetic construct
                        note = Description of Artificial Sequence: Synthetic
                         polypeptide
SEQUENCE: 512
MALPVTALLL PLALLLHAAR PEVQLLESGG GLVQPGGSLR LSCAASGFTF SSYAMNWVRQ   60
APGKGLEWVS TISGSGGSTY YADSVKGRFT ISRDNSKNTL YLQMNSLRAE DTAVFYCAID  120
PEYYDILTGG DYWGQGTLVT VSSGGGGSGG GGSGGGGSG  GGGSDIQMTQ SPSAMSASVG  180
DRVTITCRAS QGISNYLAWF QQKPGKVPKR LIYAASSLQS GVPSRFSGSG SGTEFTLTIS  240
SLQPEDFATY FCLQHDSFPL TFGGGTKVEI KTTTPAPRPP TPAPTIASQP LSLRPEACRP  300
AAGGAVHTRG LDFACDIYIW APLAGTCGVL LLSLVITKRG RKKLLYIFKQ PPMRPVQTTQ  360
EEDGCSCRFP EEEEGGCELR VKFSRSADAP AYQQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                       491

SEQ ID NO: 513          moltype = AA   length = 487
FEATURE                 Location/Qualifiers
source                  1..487
                        mol_type = protein
                        organism = synthetic construct
                        note = Description of Artificial Sequence: Synthetic
                         polypeptide
SEQUENCE: 513
MALPVTALLL PLALLLHAAR PQVQLQESGP GLVKPSETLS LTCTVSSDSI SNYYWSWIRQ   60
PPGKGLEWIS YIYYSGITNY NPSLKSRVTI SVDTSKNQFS LKLSSVTAAD TAVYYCARIT  120
VTGFYFDYWG QGTLVTVSSG GGGSGGGGSG GGGSGGGGSG IVLTQSPGTL SLSPGERATL  180
SCRASQSISR SYLAWYQQKP GQAPRHLIYG ASSRATGIPD RFSGSGSGTD FILTISRLEP  240
EDFAVYYCQQ YDTSPLTFGG GTKVEIKTTT PAPRPPTPAP TIASQPLSLR PEACRPAAGG  300
AVHTRGLDFA CDIYIWAPLA GTCGVLLLSL VITKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                            487

SEQ ID NO: 514          moltype = AA   length = 495
FEATURE                 Location/Qualifiers
source                  1..495
                        mol_type = protein
                        organism = synthetic construct
                        note = Description of Artificial Sequence: Synthetic
                         polypeptide
SEQUENCE: 514
MALPVTALLL PLALLLHAAR PQVQLQQSGP GLVKPSQTLS LTCAISGDSV SSNSVVWNWI   60
RQSPSRGLEW LGRTYYRSKW YDDYAVSVKS RITINPDTSK NQFSLQLNSV TPEDTAVYHC  120
ARGGIVGAPD AFDIWGQGTM VTVSSGGGGS GGGGSGGGGS GGGGSQSVLT QPPSASGTPG  180
QRVTISCSGS SSNIGSDPVS WYQQFPGTAP KLLIYTNNQR PSGVPDRFSG SKSGTSASLA  240
ISGLQSEDEA DYYCAAWDDS LNGHVFGTGT KVTVLTTTPA PRPPTPAPTI ASQPLSLRPE  300
ACRPAAGGAV HTRGLDFACD IYIWAPLAGT CGVLLLSLVI TKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                   495

SEQ ID NO: 515          moltype = AA   length = 495
FEATURE                 Location/Qualifiers
source                  1..495
                        mol_type = protein
                        organism = synthetic construct
                        note = Description of Artificial Sequence: Synthetic
                         polypeptide
```

```
SEQUENCE: 515
MALPVTALLL PLALLLHAAR PQVQLQQSGP GLVKPSQTLS LTCAISGDSV SSNSAVWNWI   60
RQSPSRGLEW LGWTYYRSKY YNDYAVSLKS RITINPDTSK NQFSLQLNSL TPEDTAVYYC  120
TRGGIVGAPD GFDIWGQGTM VTVSSGGGGS GGGGSGGGGS GGGGSQSALT QPPSASGTPG  180
QRVTISCSGS NSNIGSNPIN WYQQLPGTAP KLLIYSNNQR PSGVPDRFSG SKSGTSASLA  240
ISGLQSEDEA DYYCAAWDDS LNGHVFGTGT KVTVLTTTPA PRPPTPAPTI ASQPLSLRPE  300
ACRPAAGGAV HTRGLDFACD IYIWAPLAGT CGVLLLSLVI TKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                  495

SEQ ID NO: 516          moltype = AA  length = 487
FEATURE                 Location/Qualifiers
source                  1..487
                        mol_type = protein
                        organism = synthetic construct
                        note = Description of Artificial Sequence: Synthetic
                         polypeptide
SEQUENCE: 516
MALPVTALLL PLALLLHAAR PQVQLQESGP GLVKPSETLS LTCTVSGGSI SSYYWSWIRQ   60
SPGKGLEWIG YVYYSDITNY NPSLKSRVTI SVDTSKNQFS LNLNSVTAAD TAFYFCARIG  120
VAGFYFDYWG QGTLVTVSSG GGGSGGGGSG GGGSGGGGSE IVLTQSPDTL SLSPGERATL  180
SCRASQSVSR RYLAWYQQKP GQAPRLLIYG ASSRATGIPD RFSGSGSGTD FTLTISRLEP  240
EDFEVYYCQQ YGTSPITFGQ GTRLEIKTTT PAPRPPTPAP TIASQPLSLR PEACRPAAGG  300
AVHTRGLDFA CDIYIWAPLA GTCGVLLLSL VITKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                           487

SEQ ID NO: 517          moltype = AA  length = 495
FEATURE                 Location/Qualifiers
source                  1..495
                        mol_type = protein
                        organism = synthetic construct
                        note = Description of Artificial Sequence: Synthetic
                         polypeptide
SEQUENCE: 517
MALPVTALLL PLALLLHAAR PQIQLQQSGP GLVKPSQTLS LTCAISGDSV SSNSAVWNWI   60
RQSPSRGLEW LGRTYYRSKW YNDYAVSVKS RITIKPDTAK NQFSLQLNSV TPEDTAVYYF  120
TRGGIVGAPD AFDIWGQGTM VTVSSGGGGS GGGGSGGGGS GGGGSQSVLT QPPSASGTPG  180
QRVTISCSGS SSNIGSDPIN WYQQVPGTAP KLLIYSNNQR PSGVPDRFSG SKSGTSASLA  240
ISGLQSEDEA DYYCAAWDDS LNGYVFGTGT KVTVLTTTPA PRPPTPAPTI ASQPLSLRPE  300
ACRPAAGGAV HTRGLDFACD IYIWAPLAGT CGVLLLSLVI TKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                  495

SEQ ID NO: 518          moltype = AA  length = 495
FEATURE                 Location/Qualifiers
source                  1..495
                        mol_type = protein
                        organism = synthetic construct
                        note = Description of Artificial Sequence: Synthetic
                         polypeptide
SEQUENCE: 518
MALPVTALLL PLALLLHAAR PQVQLQQSGP GLVKPSETLS LTCAISGDSV SSNSATWNWI   60
RQSPSRGLEW LGRTYYRSEW YNDYAVSVKS RITINPDTSK NHLSLHLNSV TPEDTAVYYC  120
AGGGIVGAPD GFDVWGQGTM VTVSSGGGGS GGGGSGGGGS GGGGSQSVLT QPPSASGTPG  180
QRVTISCSGS SSNIGSDPVI WYQQLPRTAP KLLIYSNNQR PSGVPDRFSG SKSGTSASLA  240
ISGLQSEDEA DYYCAAWDDS LNGYVFGTGT KVTVLTTTPA PRPPTPAPTI ASQPLSLRPE  300
ACRPAAGGAV HTRGLDFACD IYIWAPLAGT CGVLLLSLVI TKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                  495

SEQ ID NO: 519          moltype = AA  length = 495
FEATURE                 Location/Qualifiers
source                  1..495
                        mol_type = protein
                        organism = synthetic construct
                        note = Description of Artificial Sequence: Synthetic
                         polypeptide
SEQUENCE: 519
MALPVTALLL PLALLLHAAR PQVQLQQSGP GLVKPSQTLS LTCAISGDSV SSNSATWNWI   60
RQSPSTGLEW LARTYYRSKW YNDYEVSVKS QITINPDTSK NQFSLQLNSV TPEDTAVYYC  120
ARGGIVGAPD AFDIWGQGTM VTVSSGGGGS GGGGSGGGGS GGGGSQSVLT QPPSASGTPG  180
QGVTISCSGS SSNIGSNPVN WYQQLPGTAP KLLIYSNNQR PSGVPDRFSD SKSGTSASLA  240
ISGLQSEDEA DYYCSAWDDW LNGYVFGTGT KVTVLTTTPA PRPPTPAPTI ASQPLSLRPE  300
ACRPAAGGAV HTRGLDFACD IYIWAPLAGT CGVLLLSLVI TKRGRKKLLY IFKQPFMRPV  360
```

```
QTTQEEDGCS CRFPEEEEGG CELRVKFSRS ADAPAYQQGQ NQLYNELNLG RREEYDVLDK   420
RRGRDPEMGG KPRRKNPQEG LYNELQKDKM AEAYSEIGMK GERRRGKGHD GLYQGLSTAT   480
KDTYDALHMQ ALPPR                                                   495

SEQ ID NO: 520              moltype = AA   length = 486
FEATURE                     Location/Qualifiers
source                      1..486
                            mol_type = protein
                            organism = synthetic construct
                            note = Description of Artificial Sequence: Synthetic
                             polypeptide
SEQUENCE: 520
MALPVTALLL PLALLLHAAR PQVQLQESGP GLVKPSETLS LTCTVSGDSI NNYFWSWIRQ    60
PPGKGLEWIG YFYHRGGNNY NPSLKSRVTI SIDTSKNQFS LNLNSVTSAD TAVYYCARLA   120
LAGFFFDYWG QGTLVTVSSG GGGSGGGGSG GGGSGGGGSD IQMTQSPSTL SASVGDRVTI   180
TCRASQSISS WLAWYQQKPG KAPKLLIYKA SSLESGVPSR FSGSGSGTEF TLTISSLQPD   240
DFATYYCQQY NSYSRTFGQG TKVEIKTTTP APRPPTPAPT IASQPLSLRP EACRPAAGGA   300
VHTRGLDFAC DIYIWAPLAG TCGVLLLSLV ITKRGRKKLL YIFKQPFMRP VQTTQEEDGC   360
SCRFPEEEEG GCELRVKFSR SADAPAYQQG QNQLYNELNL GRREEYDVLD KRRGRDPEMG   420
GKPRRKNPQE GLYNELQKDK MAEAYSEIGM KGERRRGKGH DGLYQGLSTA TKDTYDALHM   480
QALPPR                                                             486

SEQ ID NO: 521              moltype = AA   length = 494
FEATURE                     Location/Qualifiers
source                      1..494
                            mol_type = protein
                            organism = synthetic construct
                            note = Description of Artificial Sequence: Synthetic
                             polypeptide
SEQUENCE: 521
MALPVTALLL PLALLLHAAR PQVPLVQSGA EVKKPGSSVK VSCKASGGTF STYSISWVRQ    60
APGQGLEWMG GIIPIFGTTN YAQKFQGRVT ITADKSTSTA YMELSSLRSE DTAVYYCARD   120
GEGSYYYYYG MDVWGQGTTV TVSSGGGGSG GGGSGGGGSG GGGSQSVLTQ PPSASGTPGQ   180
RVTISCSGSS SNIGSNYVYW YQQLPGTAPK LLIYSNNQRP SGVPDRFSGS KSGTSASLAI   240
SGLRSEDEAD YYCAAWDDSL SGWVFGGGTK LTVLTTTPAP RPPTPAPTIA SQPLSLRPEA   300
CRPAAGGAVH TRGLDFACDI YIWAPLAGTC GVLLLSLVIT KRGRKKLLYI FKQPFMRPVQ   360
TTQEEDGCSC RFPEEEEGGC ELRVKFSRSA DAPAYQQGQN QLYNELNLGR REEYDVLDKR   420
RGRDPEMGGK PRRKNPQEGL YNELQKDKMA EAYSEIGMKG ERRRGKGHDG LYQGLSTATK   480
DTYDALHMQA LPPR                                                    494

SEQ ID NO: 522              moltype = AA   length = 491
FEATURE                     Location/Qualifiers
source                      1..491
                            mol_type = protein
                            organism = synthetic construct
                            note = Description of Artificial Sequence: Synthetic
                             polypeptide
SEQUENCE: 522
MALPVTALLL PLALLLHAAR PEVQLVESGG GLVQPGGSLR LSCAASGFTF SSYSMNWVRQ    60
APGKGLEWVS YISSSSSTIY YADSVKGRFT ISRDNAKNSL YLQMNSLRDE DTAVYYCARD   120
KERRYYYYGM DVWGQGTTVT VSSGGGGSGG GGSGGGGSGG GGSEIVLTQS PDTLSLSPGE   180
RATLSCRASQ SVSRRYLAWY QQKPGQAPRL LIYGASSRAT GIPDRFSGSG SGTDFTLTIS   240
RLEPEDFAVY YCQQFGTSPI TFGQGTRLEI KTTTPAPRPP TPAPTIASQP LSLRPEACRP   300
AAGGAVHTRG LDFACDIYIW APLAGTCGVL LLSLVITKRG RKKLLYIFKQ PFMRPVQTTQ   360
EEDGCSCRFP EEEEGGCELR VKFSRSADAP AYQQGQNQLY NELNLGRREE YDVLDKRRGR   420
DPEMGGKPRR KNPQEGLYNE LQKDKMAEAY SEIGMKGERR RGKGHDGLYQ GLSTATKDTY   480
DALHMQALPP R                                                       491

SEQ ID NO: 523              moltype = AA   length = 495
FEATURE                     Location/Qualifiers
source                      1..495
                            mol_type = protein
                            organism = synthetic construct
                            note = Description of Artificial Sequence: Synthetic
                             polypeptide
SEQUENCE: 523
MALPVTALLL PLALLLHAAR PQVQLQQSGP GLVKPSQTLS LACAISGDSV SSNSAIWNWI    60
RQSPSRGLEW LGGTYYRSMW YNDYAVSVKS RITINPDTSK NQLSLQLNSV TPEDTAVYYC   120
SRGGIVGVPD AFDIWGQGTM VTVSSGGGGS GGGGSGGGGS GGGGSQSVLT QPPSASGTPG   180
QRVTISCSGS SSNIGSNTAN WYQQLPGTAP RLLIYRNNQR PSGVPDRFSG SKSGTSASLA   240
ISGLQSEDEA DYYCAAWDDS LNGYVFGTGT KVTVLTTTPA PRPPTPAPTI ASQPLSLRPE   300
ACRPAAGGAV HTRGLDFACD IYIWAPLAGT CGVLLLSLVI TKRGRKKLLY IFKQPFMRPV   360
QTTQEEDGCS CRFPEEEEGG CELRVKFSRS ADAPAYQQGQ NQLYNELNLG RREEYDVLDK   420
RRGRDPEMGG KPRRKNPQEG LYNELQKDKM AEAYSEIGMK GERRRGKGHD GLYQGLSTAT   480
KDTYDALHMQ ALPPR                                                   495

SEQ ID NO: 524              moltype = AA   length = 489
FEATURE                     Location/Qualifiers
source                      1..489
```

```
                        mol_type = protein
                        organism = synthetic construct
                        note = Description of Artificial Sequence: Synthetic
                          polypeptide
SEQUENCE: 524
MALPVTALLL PLALLLHAAR PQVQLQESGP GLVKPSETLS LTCNVSDGSI SSYYWTWIRQ    60
PPGKGLDWIG YIFYSGTTNY NPSLKSRVTI SLDTSKNQFS LKLTSMTAAD TAVYYCARIS   120
EKSFYFDYWG QGTLVTVSSG GGGSGGGGSG GGGSGGGGSQ SVLTQPPSAS GTPGQRVTIS   180
CSGSSSNIGS NYVYWYQQLP GTAPKLLIYS NNQRPSGVPD RFSGSKSGTS ASLAISGLRS   240
EDEADYYCAP WDDSLSGRVF GGGTKLTVLT TTPAPRPPTP APTIASQPLS LRPEACRPAA   300
GGAVHTRGLD FACDIYIWAP LAGTCGVLLL SLVITKRGRK KLLYIFKQPF MRPVQTTQEE   360
DGCSCRFPEE EEGGCELRVK FSRSADAPAY QQGQNQLYNE LNLGRREEYD VLDKRRGRDP   420
EMGGKPRRKN PQEGLYNELQ KDKMAEAYSE IGMKGERRRG KGHDGLYQGL STATKDTYDA   480
LHMQALPPR                                                          489

SEQ ID NO: 525          moltype = AA  length = 490
FEATURE                 Location/Qualifiers
source                  1..490
                        mol_type = protein
                        organism = synthetic construct
                        note = Description of Artificial Sequence: Synthetic
                          polypeptide
SEQUENCE: 525
MALPVTALLL PLALLLHAAR PQVQLVQSGA EVKRPGASVK VSCKASGYTF TSYYIHWVRQ    60
APGQGLEWMG VIVPSGGSIS YAQKFQGRVT MTRDTSTNIV YMELSSLRSE DTAVYYCARD   120
RYYGDYYYGL DVWGQGTTVT VSSGGGGSGG GGSGGGGSGG GGSDIQMTQS PSSLSASVGD   180
RVTITCRASQ GINNFLAWFQ QKPGKAPKSL IYAASSLQSG VPSKFSGSGS GTDFTLTIRS   240
LQPEDFATYY CQHYNSYPIT FGQGTRLEIK TTTPAPRPPT PAPTIASQPL SLRPEACRPA   300
AGGAVHTRGL DFACDIYIWA PLAGTCGVLL LSLVITKRGR KKLLYIFKQP FMRPVQTTQE   360
EDGCSCRFPE EEEGGCELRV KFSRSADAPA YQQGQNQLYN ELNLGRREEY DVLDKRRGRD   420
PEMGGKPRRK NPQEGLYNEL QKDKMAEAYS EIGMKGERRR GKGHDGLYQG LSTATKDTYD   480
ALHMQALPPR                                                         490

SEQ ID NO: 526          moltype = AA  length = 487
FEATURE                 Location/Qualifiers
source                  1..487
                        mol_type = protein
                        organism = synthetic construct
                        note = Description of Artificial Sequence: Synthetic
                          polypeptide
SEQUENCE: 526
MALPVTALLL PLALLLHAAR PQVHLQESGP GLVKPSETLS LTCTVSGGSI SHYYWTWIRQ    60
PPGKGLEWIG YIYYSGITNF SPSLKSRVSI SVDSSKNQFS LNLNSVTAAD TAVYYCAGIS   120
LAGFYFDYWV QGTLVTVSSG GGGSGGGGSG GGGSGGGGSE IVLTQSPGTL SLSPGERATL   180
SCRASQSVSR SYLAWYQQKP GQAPRLLIYG ASSRATGVPD RFSGSGSGTD FTLTISRLEP   240
EDFAVFYCQQ YSISPLTFGG GTKVEIKTTT PAPRPPTPAP TIASQPLSLR PEACRPAAGG   300
AVHTRGLDFA CDIYIWAPLA GTCGVLLLSL VITKRGRKKL LYIFKQPFMR PVQTTQEEDG   360
CSCRFPEEEE GGCELRVKFS RSADAPAYQQ GQNQLYNELN LGRREEYDVL DKRRGRDPEM   420
GGKPRRKNPQ EGLYNELQKD KMAEAYSEIG MKGERRRGKG HDGLYQGLST ATKDTYDALH   480
MQALPPR                                                            487

SEQ ID NO: 527          moltype = AA  length = 490
FEATURE                 Location/Qualifiers
source                  1..490
                        mol_type = protein
                        organism = synthetic construct
                        note = Description of Artificial Sequence: Synthetic
                          polypeptide
SEQUENCE: 527
MALPVTALLL PLALLLHAAR PQVQLQESGP GLVKPSETLS LTCTVSGVSI SSYYWSWIRQ    60
PPGKGLEWIA YIYYSGNTNY SPSLKSRVTI SVDTSKDQLS LKLSSVTAAD TAVYYCTRGG   120
SGTIDVFDIW GQGTMVAVSS GGGGSGGGGS GGGGSGGGGS QSVLTQPPSV SAAPGQKVTI   180
SCSGSSSNIG NNYVSWYQQL PGTAPKLLIY DNNKRPSGIP DRFSGSKSGT SATLGITGLQ   240
TGDEADYYCE TWDSSLSAVV FGGGTKLTVL TTTPAPRPPT PAPTIASQPL SLRPEACRPA   300
AGGAVHTRGL DFACDIYIWA PLAGTCGVLL LSLVITKRGR KKLLYIFKQP FMRPVQTTQE   360
EDGCSCRFPE EEEGGCELRV KFSRSADAPA YQQGQNQLYN ELNLGRREEY DVLDKRRGRD   420
PEMGGKPRRK NPQEGLYNEL QKDKMAEAYS EIGMKGERRR GKGHDGLYQG LSTATKDTYD   480
ALHMQALPPR                                                         490

SEQ ID NO: 528          moltype = AA  length = 492
FEATURE                 Location/Qualifiers
source                  1..492
                        mol_type = protein
                        organism = synthetic construct
                        note = Description of Artificial Sequence: Synthetic
                          polypeptide
SEQUENCE: 528
MALPVTALLL PLALLLHAAR PQVQLQQSGP GLVKPSQTLS LTCAISGDNV STNSAAWNWI    60
RQSPSRGLEW LGWTYYRSKW YNDYAVSLKS RININPDTSK NQFSLQLNSV TPEDTAVYYC   120
```

-continued

```
ARWVNRDVFD IWGQGTMVTV SSGGGGSGGG GSGGGGSGGG GSQSALTQPA SVSGSPGQSI  180
TISCTGTSSD VGSYNLVSWY QQHPGKAPKL MIYEGSKRPS GVSNRFSGSK SGNTASLTIS  240
GLQAEDEADY YCCSYAGSST WVFGGGTKLT VLTTTPAPRP PTPAPTIASQ PLSLRPEACR  300
PAAGGAVHTR GLDFACDIYI WAPLAGTCGV LLLLSLVITKR GRKKLLYIFK QPFMRPVQTT  360
QEEDGCSCRF PEEEEGGCEL RVKFSRSADA PAYQQGQNQL YNELNLRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                         492
```

SEQ ID NO: 529          moltype = AA  length = 493
FEATURE                 Location/Qualifiers
source                  1..493
                        mol_type = protein
                        organism = synthetic construct
                        note = Description of Artificial Sequence: Synthetic
                         polypeptide
SEQUENCE: 529
```
MALPVTALLL PLALLLHAAR PQVQLVESGG GVVQPGRSLR LSCAASGFTF SSYGMHWVRQ  60
TPGKGLEWVA VISYDGNSNY YADSVKGRFT ISRDNSKNTL YLQMNSLRAE DTAVYYCARD  120
GATVTSYYYY GMDVWGQGTT VTVSSGGGGS GGGGSGGGGS GGGGSEIVLT QSPGTLSLSP  180
GERATLSCRA SQSVSRTYLA WYHQKPGQAP RLLIYGASSR ATGISDRFSG SGSGTDFTLT  240
ISRLEPEDFA VYYCQQYGTS PITFGQGTRL EIKTTTPAPR PPTPAPTIAS QPLSLRPEAC  300
RPAAGGAVHT RGLDFACDIY IWAPLAGTCG VLLLSLVITK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                        493
```

SEQ ID NO: 530          moltype = AA  length = 498
FEATURE                 Location/Qualifiers
source                  1..498
                        mol_type = protein
                        organism = synthetic construct
                        note = Description of Artificial Sequence: Synthetic
                         polypeptide
SEQUENCE: 530
```
MALPVTALLL PLALLLHAAR PQVQLQQSGP GLVKPSQTLS LTCAISGDSV SSNSAVWNWI  60
RQSPSRGLEW LGRTYYRSKW YNDYAVSVKS RITINPDTSR NQFSLQLNSV TPEDTAVYYC  120
ARGGIVGAPD GFDIWGQGTM VTVSSGGGGS GGGGSGGGGS GGGGSDIVMT QSPDSLAVSL  180
GERATINCKS SQSVLDSSNN NNYFAWYQQR PGQPPHLLIY WASSRESGVP DRFSGSGSGT  240
DFTLTISSLQ AEDVAVYYCQ QYYSTPYTFG QGTKLEIKTT TPAPRPPTPA PTIASQPLSL  300
RPEACRPAAG GAVHTRGLDF ACDIYIWAPL AGTCGVLLLS LVITKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRRGK GHDGLYQGLS  480
TATKDTYDAL HMQALPPR                                                   498
```

SEQ ID NO: 531          moltype = AA  length = 492
FEATURE                 Location/Qualifiers
source                  1..492
                        mol_type = protein
                        organism = synthetic construct
                        note = Description of Artificial Sequence: Synthetic
                         polypeptide
SEQUENCE: 531
```
MALPVTALLL PLALLLHAAR PQVQLQQSGP GLVKPSQTLS LTCAISGDSV SSNTTAWKWS  60
RQSPSKGLEW LGWTYYRSKW YYDYTVSVKS RITINPDTSK NQFSLQLNSV TPEDTAVYYC  120
ARWIFHDAFD IWGQGTMVTV SSGGGGSGGG GSGGGGSGGG GSQSALTQPP SASGTPGQRV  180
TISCSGSSSN IGSNTVNWYQ QLPGTAPKLL IYTNNQRPSG VPDRFSGSKS GTSASLAISG  240
LQSEDEADYF CSTWDDSLNG PVFGGGTKLT VLTTTPAPRP PTPAPTIASQ PLSLRPEACR  300
PAAGGAVHTR GLDFACDIYI WAPLAGTCGV LLLLSLVITKR GRKKLLYIFK QPFMRPVQTT  360
QEEDGCSCRF PEEEEGGCEL RVKFSRSADA PAYQQGQNQL YNELNLRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                         492
```

SEQ ID NO: 532          moltype = AA  length = 483
FEATURE                 Location/Qualifiers
source                  1..483
                        mol_type = protein
                        organism = synthetic construct
                        note = Description of Artificial Sequence: Synthetic
                         polypeptide
SEQUENCE: 532
```
MALPVTALLL PLALLLHAAR PQVQLQESGP GLVKPSETLS LTCTVSGDSI SSLSWSWIRQ  60
TPGEGLEWIG YLYYSGSTDY NPSLKSRVTI SVDTSKNQFS LKLRSVAAAD TALYYCARGR  120
RAFDIWGQGT MVTVSSGGGG SGGGGSGGGG SGGGGSDIQM TQSPSSLSAS VGDRVTITCR  180
GSQGISNYLA WFQQRPGKAP KSLIYAASSL ESGVPSKFSG SGSGTDFTLT IISLQPEDFA  240
TYYCQQYYNY PITFGQGTRL EIKTTTPAPR PPTPAPTIAS QPLSLRPEAC RPAAGGAVHT  300
RGLDFACDIY IWAPLAGTCG VLLLSLVITK RGRKKLLYIF KQPFMRPVQT TQEEDGCSCR  360
FPEEEEGGCE LRVKFSRSAD APAYQQGQNQ LYNELNLGRR EEYDVLDKRR GRDPEMGGKP  420
RRKNPQEGLY NELQKDKMAE AYSEIGMKGE RRRGKGHDGL YQGLSTATKD TYDALHMQAL  480
PPR                                                                    483
```

-continued

```
SEQ ID NO: 533            moltype = AA   length = 493
FEATURE                   Location/Qualifiers
source                    1..493
                          mol_type = protein
                          organism = synthetic construct
                          note = Description of Artificial Sequence: Synthetic
                           polypeptide
SEQUENCE: 533
MALPVTALLL PLALLLHAAR PQVQLVQSGA EVKKPGASVK VSCKASGYTF TGYYMHWVRQ   60
APGQGLEWMG WINPNSGGTN YAQKFQGRVT MTRDTSVSTA YMELSRLTSD DTAIYYCAKD  120
GGGDFYFYGM DVWGQGTTVT VSSGGGGSGG GGSGGGGSGG GGSQTVVTQE PSFSVSPGGT  180
VTLTCGLSSG SVSTSYYPSC FQQTPGQAPR TLIYSTDTRS SGVPDRFSGS ILGNKAALTI  240
TGAQADDESD YYCVLYMGSG ISVFGGGTKL TVLTTTPAPR PPTPAPTIAS QPLSLRPEAC  300
RPAAGGAVHT RGLDFACDIY IWAPLAGTCG VLLLSLVITK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                     493

SEQ ID NO: 534            moltype = AA   length = 15
FEATURE                   Location/Qualifiers
source                    1..15
                          mol_type = protein
                          organism = synthetic construct
                          note = Description of Artificial Sequence: Synthetic peptide
SEQUENCE: 534
GGGGSGGGGS GGGGS                                                    15

SEQ ID NO: 535            moltype = AA   length = 18
FEATURE                   Location/Qualifiers
source                    1..18
                          mol_type = protein
                          organism = synthetic construct
                          note = Description of Artificial Sequence: Synthetic peptide
SEQUENCE: 535
GSTSGSGKPG SGEGSTKG                                                 18

SEQ ID NO: 536            moltype = AA   length = 9
FEATURE                   Location/Qualifiers
source                    1..9
                          mol_type = protein
                          organism = synthetic construct
                          note = Description of Artificial Sequence: Synthetic peptide
SEQUENCE: 536
CPYSNPSLC                                                           9

SEQ ID NO: 537            moltype = AA   length = 24
FEATURE                   Location/Qualifiers
source                    1..24
                          mol_type = protein
                          organism = synthetic construct
                          note = Description of Artificial Sequence: Synthetic peptide
SEQUENCE: 537
NSELLSLIND MPITNDQKKL MSNN                                          24

SEQ ID NO: 538            moltype = AA   length = 12
FEATURE                   Location/Qualifiers
source                    1..12
                          mol_type = protein
                          organism = synthetic construct
                          note = Description of Artificial Sequence: Synthetic peptide
SEQUENCE: 538
CQFDLSTRRL KC                                                       12

SEQ ID NO: 539            moltype = AA   length = 12
FEATURE                   Location/Qualifiers
source                    1..12
                          mol_type = protein
                          organism = synthetic construct
                          note = Description of Artificial Sequence: Synthetic peptide
SEQUENCE: 539
CQYNLSSRAL KC                                                       12

SEQ ID NO: 540            moltype = AA   length = 12
FEATURE                   Location/Qualifiers
source                    1..12
                          mol_type = protein
                          organism = synthetic construct
                          note = Description of Artificial Sequence: Synthetic peptide
```

-continued

```
SEQUENCE: 540
CVWQRWQKSY VC                                                          12

SEQ ID NO: 541         moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 541
CMWDRFSRWY KC                                                          12

SEQ ID NO: 542         moltype = AA  length = 25
FEATURE                Location/Qualifiers
source                 1..25
                       mol_type = protein
                       organism = synthetic construct
                       note = Description of Artificial Sequence: Synthetic peptide
SEQUENCE: 542
SFVLNWYRMS PSNQTDKLAA FPEDR                                            25

SEQ ID NO: 543         moltype = AA  length = 19
FEATURE                Location/Qualifiers
source                 1..19
                       mol_type = protein
                       organism = synthetic construct
                       note = Description of Artificial Sequence: Synthetic peptide
SEQUENCE: 543
SGTYLCGAIS LAPKAQIKE                                                   19

SEQ ID NO: 544         moltype = AA  length = 24
FEATURE                Location/Qualifiers
source                 1..24
                       mol_type = protein
                       organism = synthetic construct
                       note = Description of Artificial Sequence: Synthetic peptide
SEQUENCE: 544
ELPTQGTFSN VSTNVSPAKP TTTA                                             24

SEQ ID NO: 545         moltype = AA  length = 12
FEATURE                Location/Qualifiers
source                 1..12
                       mol_type = protein
                       organism = synthetic construct
                       note = Description of Artificial Sequence: Synthetic peptide
SEQUENCE: 545
GQNDTSQTSS PS                                                          12

SEQ ID NO: 546         moltype = AA  length = 16
FEATURE                Location/Qualifiers
source                 1..16
                       mol_type = protein
                       organism = Homo sapiens
SEQUENCE: 546
GLAVSTISSF FPPGYQ                                                      16

SEQ ID NO: 547         moltype = AA  length = 45
FEATURE                Location/Qualifiers
source                 1..45
                       mol_type = protein
                       organism = Homo sapiens
SEQUENCE: 547
TTTPAPRPPT PAPTIASQPL SLRPEACRPA AGGAVHTRGL DFACD                      45

SEQ ID NO: 548         moltype = AA  length = 231
FEATURE                Location/Qualifiers
source                 1..231
                       mol_type = protein
                       organism = Homo sapiens
SEQUENCE: 548
EPKSPDKTHT CPPCPAPPVA GPSVFLFPPK PKDTLMIART PEVTCVVVDV SHEDPEVKFN      60
WYVDGVEVHN AKTKPREEQY NSTYRVVSVL TVLHQDWLNG KEYKCKVSNK ALPAPIEKTI     120
SKAKGQPREP QVYTLPPSRD ELTKNQVSLT CLVKGFYPSD IAVEWESNGQ PENNYKTTPP     180
VLDSDGSFFL YSKLTVDKSR WQQGNVFSCS VMHEALHNHY TQKSLSLSPG K              231

SEQ ID NO: 549         moltype = AA  length = 21
FEATURE                Location/Qualifiers
source                 1..21
                       mol_type = protein
```

```
                          organism = Homo sapiens
SEQUENCE: 549
IYIWAPLAGT CGVLLLSLVI T                                                        21

SEQ ID NO: 550           moltype = AA  length = 27
FEATURE                  Location/Qualifiers
source                   1..27
                         mol_type = protein
                         organism = Homo sapiens
SEQUENCE: 550
FWVLVVVGGV LACYSLLVTV AFIIFWV                                                  27

SEQ ID NO: 551           moltype = AA  length = 41
FEATURE                  Location/Qualifiers
source                   1..41
                         mol_type = protein
                         organism = Homo sapiens
SEQUENCE: 551
RSKRSRLLHS DYMNMTPRRP GPTRKHYQPY APPRDFAAYR S                                  41

SEQ ID NO: 552           moltype = AA  length = 136
FEATURE                  Location/Qualifiers
source                   1..136
                         mol_type = protein
                         organism = synthetic construct
                         note = Description of Artificial Sequence: Synthetic
                          polypeptide
SEQUENCE: 552
CPYSNPSLCS GGGGSELPTQ GTFSNVSTNV SPAKPTTTAC PYSNPSLCSG GGGSPAPRPP  60
TPAPTIASQP LSLRPEACRP AAGGAVHTRG LDFACDIYIW APLAGTCGVL LLSLVITLYC  120
NHRNRRRVCK CPRPVV                                                  136

SEQ ID NO: 553           moltype = AA  length = 21
FEATURE                  Location/Qualifiers
source                   1..21
                         mol_type = protein
                         organism = synthetic construct
                         note = Description of Artificial Sequence: Synthetic peptide
SEQUENCE: 553
MGTSLLCWMA LCLLGADHAD A                                                        21

SEQ ID NO: 554           moltype = AA  length = 157
FEATURE                  Location/Qualifiers
source                   1..157
                         mol_type = protein
                         organism = synthetic construct
                         note = Description of Artificial Sequence: Synthetic
                          polypeptide
SEQUENCE: 554
MGTSLLCWMA LCLLGADHAD ACPYSNPSLC SGGGGSELPT QGTFSNVSTN VSPAKPTTTA  60
CPYSNPSLCS GGGGSPAPRP PTPAPTIASQ PLSLRPEACR PAAGGAVHTR GLDFACDIYI  120
WAPLAGTCGV LLLSLVITLY CNHRNRRRVC KCPRPVV                           157

SEQ ID NO: 555           moltype = DNA  length = 63
FEATURE                  Location/Qualifiers
source                   1..63
                         mol_type = unassigned DNA
                         organism = Homo sapiens
SEQUENCE: 555
atggcactcc ccgtaactgc tctgctgctg ccgttggcat tgctcctgca cgccgcacgc  60
ccg                                                               63

SEQ ID NO: 556           moltype = AA  length = 624
FEATURE                  Location/Qualifiers
source                   1..624
                         mol_type = protein
                         organism = Homo sapiens
SEQUENCE: 556
METDTLLLWV LLLWVPGSTG YPYDVPDYAG MLAGVFELQI HSFGPGPGPG APRSPCSARL  60
PCRLFFRVCL KPGLSEEAAE SPCALGAALS ARGPVYTEQP GAPAPDLPLP DGLLQVPFRD  120
AWPGTFSFII ETWREELGDQ IGGPAWSLLA RVAGRRRLAA GGPWARDIQR AGAWELRFSY  180
RARCEPPAVG TACTRLCRPR SAPSRCGPGL RPCAPLEDEC EAPLVCRAGC SPEHGFCEQP  240
GECRCLEGWT GPLCTVPVST SSCLSPRGPS SATTGCLVPG PGPCDGNPCA NGGSCSETPR  300
SFECTCPRGF YGLRCEVSGV TCADGPCFNG GLCVGGADPD SAYICHCPPG FQGSNCEKRV  360
DRCSLQPCRN GGLCLDLGHA LRCRCRAGFA GPRCEHDLDD CAGRACANGG TCVEGGGAHR  420
CSCALGFGGR DCRERADPCA ARPCAHGGRC YAHFSGLVCA CAPGYMGARC EFPVHPDGAS  480
ALPAAPPGLR PGDPQRYLLP PALGLLVAAG VAGAALLLVH VRRRGHSQDA GSRLLAGTPE  540
PSVHALPDAL NNLRTQEGSG DGPSSSVDWN RPEDVDPQGI YVISAPSIYA REVATPLFPP  600
LHTGRAGQRQ HLLFPYPSSI LSVK                                         624
```

```
SEQ ID NO: 557            moltype = AA  length = 477
FEATURE                   Location/Qualifiers
source                    1..477
                          mol_type = protein
                          organism = synthetic construct
                          note = Description of Artificial Sequence: Synthetic
                          polypeptide
SEQUENCE: 557
METDTLLLWV LLLWVPGSTG YPYDVPDYAG MLGSARCEPP AVGTACTRLC RPRSAPSRCG   60
PGLRPCAPLE DECEAPLVCR AGCSPEHGFC EQPGECRCLE GWTGPLCTVP VSTSSCLSPR  120
GPSSATTGCL VPGPGPCDGN PCANGGSCSE TPRSFECTCP RGFYGLRCEV SGVTCADGPC  180
FNGGLCVGGA DPDSAYICHC PPGFQGSNCE KRVDRCSLQP CRNGGLCLDL GHALRCRCRA  240
GFAGPRCEHD LDDCAGRACA NGGTCVEGGG AHRCSCALGF GGRDCRERAD PCAARPCAHG  300
GRCYAHFSGL VCACAPGYMG ARCEFPVHPD GASALPAAPP GLRPGDPQRY LLPPALGLLV  360
AAGVAGAALL LVHVRRRGHS QDAGSRLLAG TPEPSVHALP DALNNLRTQE GSGDGPSSSV  420
DWNRPEDVDP QGIYVISAPS IYAREVATPL FPPLHTGRAG QRQHLLFPYP SSILSVK     477

SEQ ID NO: 558            moltype = AA  length = 437
FEATURE                   Location/Qualifiers
source                    1..437
                          mol_type = protein
                          organism = synthetic construct
                          note = Description of Artificial Sequence: Synthetic
                          polypeptide
SEQUENCE: 558
METDTLLLWV LLLWVPGSTG YPYDVPDYAG MLGSAPLVCR AGCSPEHGFC EQPGECRCLE   60
GWTGPLCTVP VSTSSCLSPR GPSSATTGCL VPGPGPCDGN PCANGGSCSE TPRSFECTCP  120
RGFYGLRCEV SGVTCADGPC FNGGLCVGGA DPDSAYICHC PPGFQGSNCE KRVDRCSLQP  180
CRNGGLCLDL GHALRCRCRA GFAGPRCEHD LDDCAGRACA NGGTCVEGGG AHRCSCALGF  240
GGRDCRERAD PCAARPCAHG GRCYAHFSGL VCACAPGYMG ARCEFPVHPD GASALPAAPP  300
GLRPGDPQRY LLPPALGLLV AAGVAGAALL LVHVRRRGHS QDAGSRLLAG TPEPSVHALP  360
DALNNLRTQE GSGDGPSSSV DWNRPEDVDP QGIYVISAPS IYAREVATPL FPPLHTGRAG  420
QRQHLLFPYP SSILSVK                                                437

SEQ ID NO: 559            moltype = AA  length = 379
FEATURE                   Location/Qualifiers
source                    1..379
                          mol_type = protein
                          organism = synthetic construct
                          note = Description of Artificial Sequence: Synthetic
                          polypeptide
SEQUENCE: 559
METDTLLLWV LLLWVPGSTG YPYDVPDYAG MLGSGPGPCD GNPCANGGSC SETPRSFECT   60
CPRGFYGLRC EVSGVTCADG PCFNGGLCVG GADPDSAYIC HCPPGFQGSN CEKRVDRCSL  120
QPCRNGGLCL DLGHALRCRC RAGFAGPRCE HDLDDCAGRA CANGGTCVEG GGAHRCSCAL  180
GFGGRDCRER ADPCAARPCA HGGRCYAHFS GLVCACAPGY MGARCEFPVH PDGASALPAA  240
PPGLRPGDPQ RYLLPPALGL LVAAGVAGAA LLLVHVRRRG HSQDAGSRLL AGTPEPSVHA  300
LPDALNNLRT QEGSGDGPSS SVDWNRPEDV DPQGIYVISA PSIYAREVAT PLFPPLHTGR  360
AGQRQHLLFP YPSSILSVK                                              379

SEQ ID NO: 560            moltype = AA  length = 341
FEATURE                   Location/Qualifiers
source                    1..341
                          mol_type = protein
                          organism = synthetic construct
                          note = Description of Artificial Sequence: Synthetic
                          polypeptide
SEQUENCE: 560
METDTLLLWV LLLWVPGSTG YPYDVPDYAG MLGSSGVTCA DGPCFNGGLC VGGADPDSAY   60
ICHCPPGFQG SNCEKRVDRC SLQPCRNGGL CLDLGHALRC RCRAGFAGPR CEHDLDDCAG  120
RACANGGTCV EGGGAHRCSC ALGFGGRDCR ERADPCAARP CAHGGRCYAH FSGLVCACAP  180
GYMGARCEFP VHPDGASALP AAPPGLRPGD PQRYLLPPAL GLLVAAGVAG AALLLVHVRR  240
RGHSQDAGSR LLAGTPEPSV HALPDALNNL RTQEGSGDGP SSSVDWNRPE DVDPQGIYVI  300
SAPSIYAREV ATPLFPPLHT GRAGQRQHLL FPYPSSILSV K                     341

SEQ ID NO: 561            moltype = AA  length = 300
FEATURE                   Location/Qualifiers
source                    1..300
                          mol_type = protein
                          organism = synthetic construct
                          note = Description of Artificial Sequence: Synthetic
                          polypeptide
SEQUENCE: 561
METDTLLLWV LLLWVPGSTG YPYDVPDYAG MLGSRVDRCS LQPCRNGGLC LDLGHALRCR   60
CRAGFAGPRC EHDLDDCAGR ACANGGTCVE GGGAHRCSCA LGFGGRDCRE RADPCAARPC  120
AHGGRCYAHF SGLVCACAPG YMGARCEFPV HPDGASALPA APPGLRPGDP QRYLLPPALG  180
LLVAAGVAGA ALLLVHVRRR GHSQDAGSRL LAGTPEPSVH ALPDALNNLR TQEGSGDGPS  240
SSVDWNRPED VDPQGIYVIS APSIYAREVA TPLFPPLHTG RAGQRQHLLF PYPSSILSVK  300
```

-continued

```
SEQ ID NO: 562          moltype = AA   length = 262
FEATURE                 Location/Qualifiers
source                  1..262
                        mol_type = protein
                        organism = synthetic construct
                        note = Description of Artificial Sequence: Synthetic
                        polypeptide
SEQUENCE: 562
METDTLLLWV LLLWVPGSTG YPYDVPDYAG MLGSDLDDCA GRACANGGTC VEGGGAHRCS   60
CALGFGGRDC RERADPCAAR PCAHGGRCYA HFSGLVCACA PGYMGARCEF PVHPDGASAL  120
PAAPPGLRPG DPQRYLLPPA LGLLVAAGVA GAALLLVHVR RRGHSQDAGS RLLAGTPEPS  180
VHALPDALNN LRTQEGSGDG PSSSVDWNRP EDVDPQGIYV ISAPSIYARE VATPLFPPLH  240
TGRAGQRQHL LFPYPSSILS VK                                           262

SEQ ID NO: 563          moltype = AA   length = 224
FEATURE                 Location/Qualifiers
source                  1..224
                        mol_type = protein
                        organism = synthetic construct
                        note = Description of Artificial Sequence: Synthetic
                        polypeptide
SEQUENCE: 563
METDTLLLWV LLLWVPGSTG YPYDVPDYAG MLGSRADPCA ARPCAHGGRC YAHFSGLVCA   60
CAPGYMGARC EFPVHPDGAS ALPAAPPGLR PGDPQRYLLP PALGLLVAAG VAGAALLLVH  120
VRRRGHSQDA GSRLLAGTPE PSVHALPDAL NNLRTQEGSG DGPSSSVDWN RPEDVDPQGI  180
YVISAPSIYA REVATPLFPP LHTGRAGQRQ HLLFPYPSSI LSVK                   224

SEQ ID NO: 564          moltype = DNA   length = 45
FEATURE                 Location/Qualifiers
source                  1..45
                        mol_type = other DNA
                        organism = synthetic construct
                        note = Description of Artificial Sequence: Synthetic
                        oligonucleotide
SEQUENCE: 564
ggcggtggag ctccggagg gggggctct ggcggagggg gctcc                     45

SEQ ID NO: 565          moltype = AA   length = 524
FEATURE                 Location/Qualifiers
source                  1..524
                        mol_type = protein
                        organism = synthetic construct
                        note = Description of Artificial Sequence: Synthetic
                        polypeptide
SEQUENCE: 565
MALPVTALLL PLALLLHAAR PGGGGSCPYS NPSLCGGGGS CPYSNPSLCG GGGSEVQLLE   60
SGGGLVQPGG SLRLSCAASG FTFSSYAMNW VRQAPGKGLE WVSTISGSGG STYYADSVKG  120
RFTISRDNSK NTLYLQMNSL RAEDTAVFYC AIDPEYYDIL TGGDYWGQGT LVTVSSGGGG  180
SGGGGSGGGG GSGGGGSDIQ MTQSPSAMSA SVGDRVTITC RASQGISNYL AWFQQKPGKV  240
PKRLIYAASS LQSGVPSRFS GSGSGTEFTL TISSLQPEDF ATYFCLQHDS FPLTFGGGTK  300
VEIKTTTPAP RPPTPAPTIA SQPLSLRPEA CRPAAGGAVH TRGLDFACDI YIWAPLAGTC  360
GVLLLSLVIT KRGRKKLLYI FKQPFMRPVQ TTQEEDGCSC RFPEEEEGGC ELRVKFSRSA  420
DAPAYQQGQN QLYNELNLGR REEYDVLDKR RGRDPEMGGK PRRKNPQEGL YNELQKDKMA  480
EAYSEIGMKG ERRRGKGHDG LYQGLSTATK DTYDALHMQA LPPR                   524

SEQ ID NO: 566          moltype = DNA   length = 54
FEATURE                 Location/Qualifiers
source                  1..54
                        mol_type = other DNA
                        organism = synthetic construct
                        note = Description of Artificial Sequence: Synthetic
                        oligonucleotide
SEQUENCE: 566
gggtctacat ccggctccgg gaagcccgga agtggcgaag gtagtacaaa gggg          54

SEQ ID NO: 567          moltype = DNA   length = 123
FEATURE                 Location/Qualifiers
source                  1..123
                        mol_type = unassigned DNA
                        organism = Homo sapiens
SEQUENCE: 567
agatccaaaa gaagccgcct gctccatagc gattacatga atatgactcc acgccgccct   60
ggccccacaa ggaaacacta ccagccttac gcaccaccta gagatttcgc tgcctatcgg  120
agc                                                                123

SEQ ID NO: 568          moltype = DNA   length = 126
FEATURE                 Location/Qualifiers
source                  1..126
```

```
                          mol_type = unassigned DNA
                          organism = Homo sapiens
SEQUENCE: 568
aagcgcggca ggaagaagct cctctacatt tttaagcagc cttttatgag gcccgtacag    60
acaacacagg aggaagatgg ctgtagctgc agatttcccg aggaggagga aggtgggtgc   120
gagctg                                                             126

SEQ ID NO: 569        moltype = DNA  length = 336
FEATURE               Location/Qualifiers
source                1..336
                      mol_type = unassigned DNA
                      organism = Homo sapiens
SEQUENCE: 569
agggtgaagt tttccagatc tgcagatgca ccagcgtatc agcagggcca gaaccaactg    60
tataacgagc tcaacctggg acgcagggaa gagtatgacg ttttggacaa gcgcagagga   120
cgggaccctg agatgggtgg caaaccaaga cgaaaaaacc cccaggaggg tctctataat   180
gagctgcaga aggataagat ggctgaagcc tattctgaaa taggcatgaa aggagagcgg   240
agaaggggaa aagggcacga cggtttgtac cagggactca gcactgctac gaaggatact   300
tatgacgctc tccacatgca agccctgcca cctagg                            336

SEQ ID NO: 570        moltype = DNA  length = 1458
FEATURE               Location/Qualifiers
source                1..1458
                      mol_type = other DNA
                      organism = synthetic construct
                      note = Description of Artificial Sequence: Synthetic
                      polynucleotide
SEQUENCE: 570
atggctctgc ccgtcaccgc tctgctgctg cctctggctc tgctgctgca cgccgcacga    60
ccacaggtcc aggtgcagct gcaggagagc ggcccaggcc tggtgaagcc atctgagaca   120
ctgagcctga cctgcacagt gagcgataac tccatctcta attactattg gtcctggatc   180
aggcagcccc ctggcaaggg cctggagtgg atcgcctaca tctactattc tggcaccaca   240
aactataatc ccagcctgaa gtccagagtg accatctccc tggacacatc taagaaccag   300
ttctccctga agctgagctc cgtgaccgca gcagatacag ccgtgactac ttgtgcccgg   360
ctgtttaatt ggggcttcgc ctttgacatc tggggccagg gcaccatggt gacagtgtct   420
agcggaggag gaggaagcgg aggaggaggg tccggaggcg ggggatctga gatcgtgatg   480
acccagtctc cagccacact gtccgtgtct cccggcgaga gggccaccct gagctgcaga   540
gccagccagt ccgtgagctc caacctggcc tggtaccagc agaagcctgg ccaggcacct   600
cggctgctga tctatggagc atccaccagg gccacagaca tccctgcacg cttctctgga   660
agcggatccg gcacagagtt taccctgaca atctctagcc tgcagtctga ggacttcgcc   720
gtgtactatt gtcagcagta caacaattgg ccccctgacc ttggcggcgg cacaaaggtg   780
gagatcaaga ccacaactcc tgcacctagg ccacctaccc cagcacctac aattgctagt   840
cagccactgt cactgcgacc agaggcatgt cgacctgcag ctggaggagc agtgcataca   900
aggggactgg actttgcctg cgatatctac atttgggctc ctctggcagg aacatgtggc   960
gtgctgctga tgagcctggt catcactctg tactgcaagc gaggccggaa gaaactgctg  1020
tatattttca aacagcccct tatgcgacct gtgcagacca cacaggagga agatgggtgc  1080
tcctgtcggt tccccgagga agaggaagga ggctgtgagc tgcgggtcaa gttttccaga  1140
tctgcagacg cccctgctta ccagcagggc cagaaccagc tgtataacga gctgaatctg  1200
gggcggagag aggaatacga cgtgctggat aaaaggcgcg ggagagaccc agaaatgggg  1260
ggaaagccac gacggaaaaa cccccaggag ggactgtaca tgaactgca gaaggataaa  1320
atggcagagg cctattccga aatcgggatg aaggagaaa gaaggcgagg caaaggcacac  1380
gacggactgt accagggct gtctaccgcc acaaaggaca cctatgatgc tctgcatatg  1440
caggcactgc cacccagg                                                1458

SEQ ID NO: 571        moltype = DNA  length = 1455
FEATURE               Location/Qualifiers
source                1..1455
                      mol_type = other DNA
                      organism = synthetic construct
                      note = Description of Artificial Sequence: Synthetic
                      polynucleotide
SEQUENCE: 571
atggctctgc ccgtcaccgc tctgctgctg cctctggctc tgctgctgca cgccgcacga    60
ccacaggtgc agctgcagga gtctggccca ggcctgatga gcccagcca gacactgtcc   120
ctgacctgca cagtgtctgg cggcagcatc agctcctctt actggagctg tatcaggcag   180
cccccctggca agggcctgga gtggatcggc tacatctact attccggcac cacaaactat   240
aatccttccc tgaagtctcg ggtgaccctg tctctggaca caagcaagaa ccagttctcc   300
ctgagactga cctctgtgac agccgccgat accgccgtgt actattgcgc cagagtggcc   360
cccacaggct tctggtttga ctattggggc cagggcaccc tggtgacagt cggga gca   420
ggaggaggaa gcggaggagg agggtccgga ggcgggggat ctgagatcgt gctgacccag   480
tccccaggca cactgtccct gtctcccggc gagagagcca ccctgagctg cagggcctcc   540
cagagagtga gctccaggta cctggcctgg tatcagcaga gcctggccaa gcccccccaga   600
ctgctgatct acgagcatc tagccgcgcc accggaatcc cagaccggtt cagcggatcc   660
ggatctggca gacatcac cctgacaatc tctagactgg agcctgagga gttcgccgtg   720
tactattgtc agcagtatgg caccagccca ctgacatttg gcggcggcac aaaggtggag   780
atcaagacca caactcctgc acctaggcca cctaccccccag cacctacaat tgctagtcag   840
ccactgtcac tgcgaccaga ggcatgtcga cctgcagctg gaggagcagt gcatacaagg   900
ggactggact ttgcctgcga tatctacatt tgggctcctc tggcaggaac atgtggcgtg   960
ctgctgctga gcctggtcat cactctgtac tgcaagcgag gccggaagaa actgctgtat  1020
```

-continued

```
attttcaaac agccctttat gcgacctgtg cagaccacac aggaggaaga tgggtgctcc   1080
tgtcggttcc ccgaggaaga ggaaggaggc tgtgagctgc gggtcaagtt ttccagatct   1140
gcagacgccc ctgcttacca gcagggccag aaccagctgt ataacgagct gaatctggggg  1200
cggagagagg aatacgacgt gctggataaa aggcgcggga gagacccaga aatgggggga   1260
aagccacgac ggaaaaaccc ccaggaggga ctgtacaatg aactgcagaa ggataaaatg   1320
gcagaggcct attccgaaat cgggatgaag ggagaaagaa ggcgaggcaa aggacacgac   1380
ggactgtacc aggggctgtc taccgccaca aaggacacct atgatgctct gcatatgcag   1440
gcactgccac ccagg                                                    1455
```

SEQ ID NO: 572          moltype = DNA  length = 1470
FEATURE                 Location/Qualifiers
source                  1..1470
                        mol_type = other DNA
                        organism = synthetic construct
                        note = Description of Artificial Sequence: Synthetic
                        polynucleotide
SEQUENCE: 572

```
atggctctgc ccgtcaccgc tctgctgctg cctctggctc tgctgctgca cgccgcacga   60
ccacaggtcc agctggtcca gtcaggggcc gaggtgaaga aacctggggc ttctgtgaag   120
gtcagttgca aagctagtgg atactcattc cctgattact atatcaactg ggtgcgccag   180
gcaccaggac agggactgga gtggatggga tggatctact tcgctagcgg caactccgaa   240
tataatcaga agtttacagg cagagtgact atgaccaggg acacaagctc ctctactgcc   300
tatatggagc tgagttcact gcggagtgaa gataccgcag tgtacttctg cgcctctctg   360
tacgactatg attggtattt tgacgtctgg ggacagggca ctatggtgac cgtcagctcc   420
ggaggaggag gaagcggagg aggagggtcc ggaggcgggg gatctgatat cgtgatgaca   480
cagactcccc tgtcactgag cgtcactcca ggagagccag catccatttc ttgtaagtct   540
agtcagtcac tggtgcacag caacggaaat acctacctgc attggtatct gcagaagcct   600
ggccagagcc cacagctgct gatctacaaa gtgtccaata ggttctctgg cgtcccagac   660
cgctttagtg ggtcaggaag cggcgccgat ttcaccctga aaattagccg cgtggaggct   720
gaagacgtgg gcgtctacta ttgcgcagag acaagccacg tcccctggac ttttgggcag   780
ggaaccaagc tggaaatcaa aaccacaact cctgcaccta ggccacctac cccagcacct   840
acaattgcta gtcagccact gtcactgcga ccagaggcat gtcgacctgc agctggagga   900
gcagtgcata caaggggact ggactttgcc tgcgatatct acatttgggc tcctctggca   960
ggaacatgtg gcgtgctgct gctgagcctg gtcatcactc tgtactgcaa gcgaggccgg   1020
aagaaactgc tgtatatttt caaacagccc tttatgcgac ctgtgcagac cacacaggag   1080
gaagatgggt gctcctgtcg gttccccgag gaagaggaag gaggctgtga gctgcgggtc   1140
aagtttttcca gatctgcaga cgccctgctt accagcagg gccagaacca gctgtataac   1200
gagctgaatc tggggcggag agaggaatac gacgtgctgg ataaaaggcg cgggagagac   1260
ccagaaatgg ggggaaagcc acgacggaaa aacccccagg agggactgta caatgaactg   1320
cagaaggata aaatggcaga ggcctattcc gaaatcggga tgaagggaga aagaaggcga   1380
ggcaaaggac acgacggact gtaccagggg ctgtctaccg ccacaaagga cacctatgat   1440
gctctgcata tgcaggcact gccacccagg                                    1470
```

SEQ ID NO: 573          moltype = DNA  length = 1470
FEATURE                 Location/Qualifiers
source                  1..1470
                        mol_type = other DNA
                        organism = synthetic construct
                        note = Description of Artificial Sequence: Synthetic
                        polynucleotide
SEQUENCE: 573

```
atggctctgc ctgtcaccgc tctgctgctg cctctggctc tgctgctgca cgcggcgcgc   60
ccgcaggtgc agctgcagga gtctggccca ggcctggtga gccctctga gacactgagc    120
ctgacctgca cagtgagcga cgattccatc tctaactact attggtcctg gatcaggcag   180
ccccctggca agggcctgga gtggatcggc tacatctcat attccggcac cacaaaccac   240
aatcccagcc tgaagtcccg gctgacaatc tccctggaca aggccaagaa ccagttctct   300
ctgagactga gctccgtgac cgccgccgat acagccgtgt actattgtgc cagagtgttc   360
aactgggggct cgcctttga catctggggc cagggcacca tggtgacagt gtctagcggc   420
ggcggcggct ctggaggagg aggcagcggc ggaggaggct ccggaggcgg cggctctgag  480
atcgtgctga cccagtctcc aggcacactg tctctgagcc ccggcgagag gccccaccct   540
agctgccgcg cctcccagcg gatctctaga acatacctgg cctggtatca gcagaagcct   600
ggccaggccc ccagactgct gatctacgga gcaagcagcc gggccaccgg aatccccgac   660
agattcaccg gctccggctc tggcacagac ttcaccctga caatcagcag actggagcct   720
gaggacttcg ccgtgtacta ttgtcagcag tatggcacct ccccactgac atttggcggc   780
ggcacaaagg tggagatcaa caccacaacc ccagcaccta ggccacctac acctgcacca   840
accatcgcca gccagcctct gtccctgaga ccagaggcct gtaggccagc agcaggagga   900
gcagtgcaca cccggggcct ggacttcgcc tgcgatatct acatctgggc caccactggca  960
ggaacatgtg gcgtgctgct gctgtccctg gtcatcaccc tgtactgcaa gagaggcagg   1020
aagaagctgc tgtatatctt caagcagccc ttcatgagac ccgtgcagac aacccaggag   1080
gaggacggct gcagctgtag gttcccagag gaggaggagg aggatgtga gctgcgcgtg   1140
aagttttccc ggtctgccga tgcacctgca taccagcagg gacagaacca gctgtataac   1200
gagctgaatc tggggccggag agaggagtac gacgtgctgg ataagaggag gggaagggac   1260
cctgagatgg gaggcaagcc tcggagaaag aacccacagg agggcctgta caatgagctg   1320
cagaaggaca gatggccaga ggcctatagc gagatcggaa tgaagggaga gaggcgcggg   1380
ggcaagggac acgatggcct gtatcagggc ctgtcaaccg ctacaaaaga tacctacgat   1440
gctctgcaca tgcaggctct gccaccaaga                                    1470
```

SEQ ID NO: 574          moltype = DNA  length = 1470
FEATURE                 Location/Qualifiers -continued

```
source                  1..1470
                        mol_type = other DNA
                        organism = synthetic construct
                        note = Description of Artificial Sequence: Synthetic
                          polynucleotide
SEQUENCE: 574
atggctctgc ctgtcaccgc tctgctgctg cctctggctc tgctgctgca cgcggcgcgc   60
ccgcaggtgc agctgcagga gagcggccca ggcctggtga agccatctga cacactgagc  120
ctgacctgca cagtgagcga taactccatc tctaattact attggtcctg gatcaggcag  180
ccccctggca agggcctgga gtggatcgcc tacatctact attctggcac cacaaactat  240
aatcccagcc tgaagtccag agtgaccatc tccctggaca catctaagaa ccagttctcc  300
ctgcagctga gctccgtgac agcagcagat gcagccgtgt actattgtgc cagagtgttc  360
cactgggggct tcgcctttga catctggggc cagggcacca tggtgacagt gtctagcggc  420
ggcggcggct ctggaggagg aggcagcggc ggaggaggcc cggaggcgg cggctctgag  480
atcgtgctga cccagagccc aggcacactg tctctgagcc ccggcgagag ggccaccctg  540
tcctgccggg cctctcagag agtgagcaac acatacctgg cctggtatca gcagaatccc  600
ggccaggccc ccagactgct gatctacgga gcaagctcca gggccaccgg aatcccagac  660
cgcttctccg gatctggaag cggcacagac ttcaccctga caatctcccg gctggagcct  720
gaggacttcg ccgtgtacta ttgtcagcag tatggcacct ctccactgac atttggcggc  780
ggcaccaagg tggagatcaa gaccacaacc ccagcaccta ggccacctac acctgcacca  840
accatcgcca gccagcctct gtccctgaga ccagaggcct gtaggccagc agcaggagga  900
gcagtgcaca cccggggggcc ggacttcgcc tgcgatatct acatctgggc accactggca  960
ggaacatgtg gcgtgctgct gctgtccctg gtcatcaccc tgtactgcaa gagaggcagg 1020
aagaagctgc tgtatatctt caagcagccc ttcatgagac ccgtgcagac aacccaggag 1080
gaggacggct gcagctgtag gttcccagag gaggaggagg aggatgtga gctgcgcgtg 1140
aagttttccc ggtctgccga tgcacctgca taccagcagg gacagaacca gctgtataac 1200
gagctgaatc tgggccggag agaggagtac gacgtgctgg ataagaggag gggaaggggac 1260
cctgagatgg gaggcaagcc tcggagaaag aacccacagg agggcctgta caatgagctg 1320
cagaaggaca agatggccga ggcctatagc gagatcggca tgaagggaga gaggcgccgg 1380
ggcaagggac acgatggcct gtatcagggc ctgtcaaccg ctacaaaaga tacctacgat 1440
gctctgcaca tgcaggctct gccaccaaga                                   1470
```

```
SEQ ID NO: 575         moltype = DNA  length = 1455
FEATURE                Location/Qualifiers
source                  1..1455
                        mol_type = other DNA
                        organism = synthetic construct
                        note = Description of Artificial Sequence: Synthetic
                          polynucleotide
SEQUENCE: 575
atggctctgc ccgtcaccgc tctgctgctg cctctggctc tgctgctgca cgccgcacga   60
ccacaggtgc agctgcagga gagcggccca ggcctggtga agccatccga gaccctgtct  120
ctgacctgca cagtgagcaa cgtgtccatc agctcctact attggtcttg gatcaggcag  180
ccccctggca agggactgga gtggatcggc tacatctact atagcggcac cacaaactat  240
aatccctctc tgaagagcag agtgaccatg agcgtggaca catccaagaa ccagttctcc  300
ctgaagctgt ctagcgtgac cgccgccgat acagccgtgt acttttgtgc ccggctgtct  360
aattggggct tcgcctttga catctggggc cagggcacca tggtgacatt ctcctctgga  420
ggaggaggaa gcggaggagg agggtccgga ggcgggggat ctgagatcgt gctgacccag  480
tctccaggca cactgtctct gagccccggc gagagggcca ccctgtcctg cagagcctct  540
cagacaatca gctcctctta cctggcctgg tatcagcaga agcctggcca ggcacctcgg  600
ctgctgatct acggagcaag ctccagggcc accggaatcc cagaccgctt ctcccggatc  660
tctggaagcg gaggatatt cctgacaatc agccggctgg agcctgagga tttcgccgtg  720
tactattgtc agcagtatgg ctggtcccca atcacctttg gccagggcac aaggctggag  780
atcaagacca caactcctgc acctaggcca cctaccccag cacctacaat tgctagtcag  840
ccactgtcac tgcgaccaga ggcatgtcga cctgcagctg gaggagcagt gcatacaagg  900
ggactggact tgcctgcga tatctacatt tgggctcctc tggcaggaac atgtggcgtg  960
ctgctgctga gcctggtcat cactctgtac tgcaagcgag gccggaagaa actgctgtat 1020
attttcaaac agccctttat gcgacctgtg cagaccacac aggaggaaga tgggtgctcc 1080
tgtcggttcc ccgaggaaga ggaaggaggc tgtgagctgc gggtcaagtt ttccagatct 1140
gcagacgccc ctgcttacca gcagggccag aaccagctgt ataacgagct gaatctgggg 1200
cggagagagg aatacgacgt gctgggataaa aggcgcggga gagacccaga atggggggga 1260
aagccacgac ggaaaaaccc ccaggaggga ctgtacaatg aactgcagaa ggataaaatg 1320
gcagaggcct attccgaaat cgggatgaag ggagaaagaa ggcgaggcaa aggacacgac 1380
ggactgtacc aggggctgtc taccgccaca aaggacacct atgatgctct gcatatgcag 1440
gcactgccac ccagg                                                   1455
```

```
SEQ ID NO: 576         moltype = DNA  length = 1473
FEATURE                Location/Qualifiers
source                  1..1473
                        mol_type = other DNA
                        organism = synthetic construct
                        note = Description of Artificial Sequence: Synthetic
                          polynucleotide
SEQUENCE: 576
atggctctgc ccgtcaccgc tctgctgctg cctctggctc tgctgctgca cgccgcacga   60
ccagaggtgc agctggtgga gagcggagga ggactggtgc agcctggcgg atccctgagg  120
ctgtcttgcg cagcaagcgg cttcaccttt agctcctacg acatgcactg ggtgaggcag  180
gcaacaggca agggactgga gtgggtgtcc gccatcggac agccggcga tacctactat  240
cccggctctg tgaagggccg gttcacaatc tccagagaga cgccaagaa ttctctgtat  300
```

```
ctgcagatga acagcctgag ggcaggcgac accgccgtgt actattgtgc cagagccgac   360
cccccttact attactatgg catggacgtg tggggccagg gcaccacagt gacagtgtct   420
agcggaggag gaggaagcgg aggaggaggg tccggaggcg ggggatctga catcgtgatg   480
acccagtccc ctctgtctct gcccgtgaca cctggcgagc cagcctctat cagctgcagg   540
agctcccaga gcctgctgca ctccaacgag tacaattatc tggattggta cctgcagaag   600
cctggccagt cccctcagct gctgatctat ctgggctcta cagggcaag cggagtgcca   660
gacagattct ccggctctgg cagcggcacc gacttcatcc tgaagatctc tcgggtggag   720
gcagaggacg tgggcgtgta ctattgtatg caggccctgg agatcccact gaccttcggc   780
ggaggaacaa aggtggagat caagaccaca actcctgcac ctaggccacc tacccagca   840
cctacaattg ctagtcagcc actgtcactg cgaccagagg catgtcgacc tgcagctgga   900
ggagcagtgc atacaagggg actggacttt gcctgcgata tctacatttg ggctcctctg   960
gcaggaacat gtggcgtgct gctgctgagc ctggtcatca ctctgtactg caagcgaggc  1020
cggaagaaac tgctgtatat tttcaaacag ccctttatgc gacctgtgca gaccacacag  1080
gaggaagatg ggtgctcctg tcggttcccc gaggaagagg aaggaggctg tgagctgcgg  1140
gtcaagtttt ccagatctgc agacgcccct gcttaccagc agggccagaa ccagctgtat  1200
aacgagctga atctggggcg gagagaggaa tacgacgtgc tggataaaag gcgcgggaga  1260
gacccagaaa tggggggaaa gccacgacgg aaaaacccc aggagggact gtacaatgaa  1320
ctgcagaagg ataaaatggc agaggcctat tccgaaatcg ggatgaaggg agaaagaagg  1380
cgaggcaaag gacacgacgg actgtaccag gggctgtcta ccgccacaaa ggacacctat  1440
gatgctctgc atatgcaggc actgccaccc agg                                 1473
```

```
SEQ ID NO: 577          moltype = DNA  length = 1458
FEATURE                 Location/Qualifiers
source                  1..1458
                        mol_type = other DNA
                        organism = synthetic construct
                        note = Description of Artificial Sequence: Synthetic
                        polynucleotide
SEQUENCE: 577
atggctctgc ccgtcaccgc tctgctgctg cctctggctc tgctgctgca cgccgcacga   60
ccacagatca cactgaagga gagcggccca accctggtga agcccaccca gacactgacc  120
ctgacatgca ccttctccgg cttttctctg agcaccagag gcgtgggagt gggatggatc  180
agacagcccc ctggcaaggc cctggagtgg ctggccctga tctactggaa cgacgataag  240
aggtattccc cttctctgca gacacgcctg acaatcacca aggacacccc aaagaaccag  300
gtggtgctga caatgaccaa tatggacccc gtggatacag ccacctacta ttgtgcccgg  360
tctaactggg gcaattggta cttcgcactg tggggaaggg gcacactggt gaccgtgagc  420
tccgaggag gaggaagcgg aggaggaggg tccggaggcg ggggatctga gatcgtgctg  480
acccagtctc cagccacact gtccctgtct cccggcgaga gggccaccct gagctgcaga  540
gccagccagt ccgtgagctc ctacctggcc tggtatcagc agaagcctgg ccaggcacct  600
cggctgctga tctacgacgc cttctatagg gccaccggca tcccagcacg cttctctgga  660
agcggatccg gcacagactt taccctgaca atctctagcc tggagcctga ggatttcgcc  720
gtgtactatt gtcagcaccg gtccaactgg ccaatcacct ttggccaggg cacaaggctg  780
gagatcaaga ccacaactcc tgcacctagg ccacctaccc aattgctagt  840
cagccactgt cactgcgacc agaggcatgt cgacctgcag ctggaggagc agtgcataca  900
aggggactgg actttgcctg cgatatctac atttgggctc tctggcagg aacatgtggc  960
gtgctgctgc tgagcctggt catcactctg tactgcaagc gaggccggaa gaaactgctg 1020
tatattttca aacagccctt tatgcgacct gtgcagacca cacaggagga agatgggtgc 1080
tcctgtcggt tccccgagga gaggaagga ggctgtgagc tgcgggtcaa gttttccaga 1140
tctgcagacg cccctgctta ccagcagggc cagaaccagc tgtataacga gctgaatctg 1200
gggcggagag aggaatacga cgtgctggat aaaaggcgcg gagagaccc agaaatgggg 1260
ggaaagccac gacggaaaaa ccccaggag ggactgtaca atgaactgca gaaggataaa 1320
atggcagagg cctattccga aatcgggatg aagggagaaa gaaggcgagg caaaggacac 1380
gacggactgt accaggggct gtctaccgcc acaaaggaca cctatgatgc tctgcatatg 1440
caggcactgc cacccagg                                                 1458
```

```
SEQ ID NO: 578          moltype = DNA  length = 1470
FEATURE                 Location/Qualifiers
source                  1..1470
                        mol_type = other DNA
                        organism = synthetic construct
                        note = Description of Artificial Sequence: Synthetic
                        polynucleotide
SEQUENCE: 578
atggctctgc ctgtcaccgc tctgctgctg cctctggctc tgctgctgca cgcggcgcgc   60
ccgcaggtgc agctgcagga gagcggccca ggcctggtga gccatctga gaccctgagc  120
ctgacctgca cagtgtccgg cgattccatc tctaactact attggacatg gatcaggcag  180
cccctggca agggactgga gtggatcggc tacatctact attctggcac cacaaactct  240
aatcccagc tgaagagccg ggtgaccgtg tccctggaca caagcaagtc ccagttctct  300
ctgaacctga gctccgtgac cgccgccgat acagccgtt actattgtgc cagagtgttc  360
aacagaggct cgcctttga catctggggc cagggcacca tggtgacagt gtctagcggc  420
ggcggcggct ctgaggagg aggcagcggc ggaggaggct ccggaggcgg cggctctgag  480
atcgtgctga cccagagccc aggcacactg tctctgagcc ccggcgagag ggccaccctg  540
tcctgccggg cctctcagag aatcagcaac acatacctgg cctggtatca gcagaagcct  600
ggccaggccc ccagactgct gatctacgga gcaagctcca gggccaccgg aatcccagac  660
cgcttctccg gatctggaag cggcacagac ttcaccctga caatctccag gctggagcct  720
gaggacttcg cagcctacta ttgtcagcag tatgatacct ctccactgac atttggcggc  780
ggcaccaagt ggagatcaa gaccacaacc ccagcaccta ggccacctac acctgcacca  840
accatcgcca gccagcctct gtccctgaga ccagaggcct gtaggccagc agcaggaga  900
gcagtgcaca cccgggggcct ggacttcgcc tgcgatatct acatctgggc caccactggca  960
```

-continued

```
ggaacatgtg gcgtgctgct gctgtccctg gtcatcaccc tgtactgcaa gagaggcagg   1020
aagaagctgc tgtatatctt caagcagccc ttcatgagac ccgtgcagac aacccaggag   1080
gaggacggct gcagctgtag gttcccagag gaggaggagg gaggatgtga gctgcgcgtg   1140
aagtttccc ggtctgccga tgcacctgca taccagcagg gacagaacca gctgtataac   1200
gagctgaatc tgggccggag agaggagtac gacgtgctga ataagaggag gggaagggac   1260
cctgagatgg gaggcaagcc tcggagaaag aacccacagg agggcctgta caatgagctg   1320
cagaaggaca agatggccga ggcctatagc gagatcggca tgaagggaga gaggcgccgg   1380
ggcaagggac acgatggcct gtatcagggc ctgtcaaccg ctacaaaaga tacctacgat   1440
gctctgcaca tgcaggctct gccaccaaga                                    1470
```

SEQ ID NO: 579          moltype = DNA  length = 1482
FEATURE                 Location/Qualifiers
source                  1..1482
                        mol_type = other DNA
                        organism = synthetic construct
                        note = Description of Artificial Sequence: Synthetic
                        polynucleotide
SEQUENCE: 579

```
atggctctgc ccgtcaccgc tctgctgctg cctctggctc tgctgctgca cgccgcacga   60
ccacaggtga cactgaggga gtctggaccc gccctggtga agcctaccca gacactgacc   120
ctgacatgca ccgtgagcgg cgtgtctctg agcacctccg gcatgtgcgt gagctggatc   180
aggcagccac tgggcaaggc cctggagtgg ctgggcttca tcgattggga cgatgacaag   240
tactataaca caagcctgaa gacacgcctg accatctcca aggacacctc taagaaccag   300
gtggtgctga caatgaccaa tatggatccc gtggacacag ccacctacta ttgcgcccgg   360
atcagaggct actctggcag ctatgatgcc tttgacatct ggggccaggg caccgtggtc   420
atcgtgagct ccggaggagg aggaagcgga ggaggaggtc ccggaggcgg ggatctgac   480
atcgtgatga cccagtcccc tctgtctctg cccgtgacac ctggcgagcc agcctctatc   540
agctgcagga gctcccagag cctgctgcac tccaacggct acaatcacct ggattggtat   600
ctgcagaagc ctggccagtc ccctcaggtg ctgatctacc tgggctctaa cagggcaagc   660
ggagtgccag acagattctc cggatctgga agcggaaccg acttcacct gaagatctct   720
cgggtggagg cagaggacgt gggcgtgtat ttctgtatgc aggccctgca gacccccctg   780
acatttggcg gcggcaccaa ggtggagatc aagaccacaa ctcctgcacc taggccacct   840
accccagcac ctacaattgc tagtcagcca ctgtcactgc gaccagaggc atgtcgacct   900
gcagctggag gagcagtgca tacaagggga ctggactttg cctgcgatat ctacatttgg   960
gctcctctgg caggaacatg tggcgtgctg ctgctgagcc tggtcatcac tctgtactgc   1020
aagcgaggcc ggaagaaact gctgtatatt ttcaaacagc cctttatgcg acctgtgcag   1080
accacacagg aggaagatgg tgtgctcctgt cggttccccg aggaagagga aggaggctgt   1140
gagctgcggg tcaagttttc cagatctgca gacgcccctg cttaccagca gggccagaac   1200
cagctgtata acgagctgaa tctgggtcggg agagaggaat acgacgtgct ggataaaagg   1260
cgcgggagag acccagaaat gggggggaaag ccacgacgga aaaaccccca ggagggactg   1320
tacaatgaac tgcagaagga taaaatggca gaggcctatt ccgaaatcgg gatgaaggga   1380
gaaagaaggc gaggcaaagg acacgacgga ctgtaccagg ggctgtctac cgccacaaag   1440
gacacctatg atgctctgca tatgcaggca ctgccaccca gg                      1482
```

SEQ ID NO: 580          moltype = DNA  length = 1452
FEATURE                 Location/Qualifiers
source                  1..1452
                        mol_type = other DNA
                        organism = synthetic construct
                        note = Description of Artificial Sequence: Synthetic
                        polynucleotide
SEQUENCE: 580

```
atggctctgc ccgtcaccgc tctgctgctg cctctggctc tgctgctgca cgccgcacga   60
ccacaggtga agctgcaggt gtccggccct ggctggtga agccttccga gacactgtct   120
ctgacctgca gcgtgtccgg cggctctatc agctcctact attggtcttg gatcaggcag   180
agcccaggca agggactgga ttggatcggc tacatgtact atagcggcac cacaaactat   240
aatccctctc tgaagagcag agtgacaatc agcgtggaca cctccaagaa ccagttttcc   300
ctgaagctgt ctagcgtgac cgccacagat accgccgtgt actattgtgc cagagtgggc   360
ctgacaggct tctttttcga ctactggggc cagggcacac tggtgaccgt gtcctctgga   420
ggaggaggaa gcggaggagg agggtccgga ggcggggat ctgccatcca gatgacccag   480
tcccctagct ccctgagcgc ctccgtgggc gacaggtga ccatcacatg cagagcctct   540
cagggcatca ggaacgatct gggctggtat cagcagaagc ccggcaaggc cctaagctg   600
ctgatctacg cagcatctag cctgcagtct ggagtgccaa gccggttctc tggaagcgga   660
tccggcaccg actttaccct gacagtgtcc tctctgcaga cagaggactt cgccacatac   720
tattgtctgc aggattacaa ttatccctac acctttggcc agggcacaaa gctggagatc   780
aagaccacaa ctcctgcacc taggccacct accccagcac ctacaattgc tagtcagcca   840
ctgtcactgc gaccagaggc atgtcgacct gcagctggag gagcagtgca tacaagggga   900
ctggactttg cctgcgatat ctacatttgg gctcctctgg caggaacatg tggcgtgctg   960
ctgctgagcc tggtcatcac tctgtactgc aagcgaggcc ggaagaaact gctgtatatt   1020
ttcaaacagc cctttatgcg acctgtgcag accacacagg aggaagatgg tgtgctcctgt   1080
cggttccccg aggaagagga aggaggctgt gagctgcggg tcaagttttc cagatctgca   1140
gacgcccctg cttaccagca gggccagaac cagctgtata acgagctgaa tctgggtcgg   1200
agagaggaat acgacgtgct ggataaaagg cgcgggagag acccagaaat gggggggaaag   1260
ccacgacgga aaaaccccca ggagggactg tacaatgaac tgcagaagga taaaatggca   1320
gaggcctatt ccgaaatcgg gatgaaggga gaaagaaggc gaggcaaagg acacgacgga   1380
ctgtaccagg ggctgtctac cgccacaaag gacacctatg atgctctgca tatgcaggca   1440
ctgccaccca gg                                                       1452
```

SEQ ID NO: 581          moltype = DNA  length = 1443

-continued

```
FEATURE              Location/Qualifiers
source               1..1443
                     mol_type = other DNA
                     organism = synthetic construct
                     note = Description of Artificial Sequence: Synthetic
                     polynucleotide
SEQUENCE: 581
atggctctgc ccgtcaccgc tctgctgctg cctctggctc tgctgctgca cgccgcacga   60
ccacaggtgc agctgcagca gtggggagga ggactgctga agccctccga gaccctgtct  120
ctgacatgcg ccgtgtacgg aggaagctcc tctggaaact attggtcctg gatccggcag  180
cccctggca agagactgga gtggatcggc gagatcaacc acagcggcac cacatcctac   240
aatccttctc tgaagagcag ggtgaccatc tctgtggaca caagcaagaa tcagttctcc  300
ctgaagctga gctccgtgac cgcagcagat acagccgtgt actattgcgc cagaggcgag  360
ctgggaatcg cagacagctg gggacagggc accctggtca cagtgtctag cggaggagga  420
ggaagcggag gaggagggtc cggaggcggg ggatctgata tccagatgac ccagtctccc  480
agcacactgt ccgcctctgt gggcgacagg gtgaccatca catgtcgcgc cagccagtcc  540
atctctcggt ggctggcctg gtaccagcag aagccaggca aggcccccaa gctgctgatc  600
tataaggcct cctctctgga gtccggcgtg ccttctagat tcagcggctc cggctctggc  660
accgagttta ccctgacaat cagctccctg cagccagacg atttcgccac ctactattgt  720
cagcagtaca acagctattc cacctttggc cagggcacaa aggtggagat caagaccaca  780
actcctgcac ctaggccacc tacccagca cctacaattg ctagtcagcc actgtcactg   840
cgaccagagg catgtcgacc tgcagctgga ggagcagtgc atacaagggg actggacttt  900
gcctgcgata tctacatttg ggctcctctg gcaggaacat gtggcgtgct gctgctgagc  960
ctggtcatca ctctgtactg caagcgaggc cggaagaaac tgctgtatat tttcaaacag 1020
ccctttatgc gacctgtgca gaccacacag gaggaagatg ggtgctcctg tcggttcccc 1080
gaggaagagg aaggaggctg tgagctgcgg gtcaagtttt ccagatctgc agacgccct  1140
gcttaccagc agggccagaa ccagctgtat aacgagctga atctgggcg gagagaggaa 1200
tacgacgtgc tggataaaag gcgcgggaga gacccagaaa tggggggaaa gccacgacgg 1260
aaaaacccc aggagggact gtacaatgaa ctgcagaagg ataaaatggc agaggcctat 1320
tccgaaatcg gatgaaggg agaaagaagg cgaggcaaag gacacgacgg actgtaccag 1380
gggctgtcta ccgccacaaa ggacacctat gatgctctgc atatgcaggc actgccaccc 1440
agg                                                                 1443

SEQ ID NO: 582        moltype = DNA   length = 1476
FEATURE              Location/Qualifiers
source               1..1476
                     mol_type = other DNA
                     organism = synthetic construct
                     note = Description of Artificial Sequence: Synthetic
                     polynucleotide
SEQUENCE: 582
atggctctgc ctgtcaccgc tctgctgctg cctctggctc tgctgctgca cgcggcgcgc   60
ccgcagctgc agctgcagga gtccggccct ggcctggtga agccatccga gaccctgtct  120
ctgacctgca cagtgagcgg cggctccatc agctcctcta gctactattg gggctggatc  180
agacagcccc ctggcaaggg actggagtgg atcggcagca tctactattc cggcaacatc  240
taccacaatc cttctctgaa gagccgcgtg tctatcagcg tggacacctc caagaaccag  300
ttctctctga ggctgtcctc tgtgaccgca gcagatacag cagtgtacta ttgcgccagg  360
gagatcatcg tgggagcaac ccactttgac tattgggggc agggcaccct ggtgacagtg  420
agctccggcg gcggcggctc tggaggagga ggcagcggcg gaggaggctc cggaggcggc  480
ggctctgcca tccagatgac acagtcccca tctagcctgt ccgcctctgt gggcgacagg  540
gtgaccatca catgtagagc cagccagggc atcaggaacg atctgggctg gtaccagcag  600
aagccaggca aggcccccga gctgctgatc tatgccgcct cctctctgca gtctggcgtg  660
ccaagcagat cagcggctc cggctctggc accgacttta ccctgacaat cagctccctg   720
cagcccgagg acttcgccac atactattgt ctgcaggatt acaattatcc cctgaccttt  780
ggccctggca caaaggtgga tatcaagacc acaaccccag cacctaggcc acctacacct  840
gcaccaacca tcgccagcca gcctctgtcc ctgagaccag aggcctgtag gccagcagca  900
ggaggagcag tgcacacccg gggcctggac ttcgcctgcg atatctacat ctgggccacca  960
ctggcaggaa catgtggcgt gctgctgctg tccctggtca tcaccctgta ctgcaagaga 1020
ggcaggaaga agctgctgta tatcttcaag cagcccttca tgaggaccgt gcagacaacc 1080
caggaggagg acggctgcag ctgtaggttc ccagaggagg aggaggaggag atgtgagctg 1140
cgcgtgaagt tttcccggtc tgccgatgca cctgcatacc agcagggaca gaaccagctg 1200
tataacgagc tgaatctggg ccggagagag gagtacgacg tgctggataa gaggagggga 1260
agggaccctg agatgggagg caagcctcgg agaaagaacc cacaggaggg cctgtacaat 1320
gagctgcaga aggacaagat ggccgaggcc tatagcgaga tcggcatgaa gggagagagg 1380
cgccggggca agggacacga tggcctgtat cagggcctgt caaccgctac aaaagatacc 1440
tacgatgctc tgcacatgca ggctctgcca ccaaga                             1476

SEQ ID NO: 583        moltype = DNA   length = 1455
FEATURE              Location/Qualifiers
source               1..1455
                     mol_type = other DNA
                     organism = synthetic construct
                     note = Description of Artificial Sequence: Synthetic
                     polynucleotide
SEQUENCE: 583
atggctctgc ccgtcaccgc tctgctgctg cctctggctc tgctgctgca cgccgcacga   60
ccacaggtgc agctgcagca gtggggagca ggactgctga agccctccga gaccctgtct  120
ctgacatgcg ccgtgtacgg aggaagcttc tccggatact attggtcctg gatcaggcag  180
cccctggca agggactgga gtggatcggc gagatcatcc actctggcag ctccaactat  240
```

```
aatccttctc tgaagagccg ggtgtctatc agcgtggaca cctctaagaa ccagttcagc  300
ctgaagctgt ctagcgtgac cgccgccgat acagccgtgt actattgctc cagaggcgag  360
tacggctccg gctctaggtt tgactattgg ggccagggca ccctggtgac agtgtcctct  420
ggaggaggag gaagcggagg aggagggtcc ggaggcgggg gatctgccat ccagatgacc  480
cagtccccaa gctccctgag cgcctccgtg ggcgataggg tggccatcac atgtagggca  540
agccagggaa tcagggacga tctgggctgg taccagcaga agccaggcaa ggcccccaag  600
ctgctgatct atgcagcatc tagcctgcag agcggagtgc catcccggtt ctctggaagc  660
agatccgaca ccgacttcac cctgacaatc tcctctctgc agcctgagga cttcgccaca  720
tactattgtc tgcaggacta cgattatcca ctgacctttg gcggcggcac aaaggtggag  780
atcaagacca caactcctgc acctaggcca cctaccccag cacctacaat tgctagtcag  840
ccactgtcac tgcgaccaga ggcatgtcga cctgcagctg gaggagcagt gcatacaagg  900
ggactggact ttgcctgcga tatctacatt tgggctcctc tggcaggaac atgtggcgtg  960
ctgctgctga gcctggtcat cactctgtac tgcaagcag gccggaagaa actgctgtat  1020
attttcaaac agccctttat gcgacctgtg cagaccacac aggaggaaga tgggtgctcc  1080
tgtcggttcc ccgaggaaga ggaaggaggc tgtgagctgc gggtcaagtt ttccagatct  1140
gcagacgccc ctgcttacca gcagggccag aaccagctgt ataacgagct gaatctgggg  1200
cggagagagg aatacgacgt gctggataaa aggcgcggga gagacccaga aatggggggga  1260
aagccacgac ggaaaaaccc caggaggga ctgtacaatg aactgcagaa ggataaaatg  1320
gcagaggcct attccgaaat cgggatgaag ggagaaagaa ggcgaggcaa aggacacgac  1380
ggactgtacc aggggctgtc taccgccaca aaggacacct atgatgctct gcatatgcag  1440
gcactgccac ccagg                                                    1455
```

```
SEQ ID NO: 584        moltype = DNA   length = 1461
FEATURE               Location/Qualifiers
source                1..1461
                      mol_type = other DNA
                      organism = synthetic construct
                      note = Description of Artificial Sequence: Synthetic
                      polynucleotide
SEQUENCE: 584
atggctctgc ctgtcaccgc tctgctgctg cctctggctc tgctgctgca cgcggcgcgc  60
ccgcaggtgc agctgcagga gtccggccct ggctggtga agccaagcgg caccctgtcc  120
ctgacatgcg ccgtgtctgg cggcagcatc agctccaaca attggtggag ctgggtgagg  180
cagcccctg gcaagggact ggagtggatc ggcgacatcc accactccgg ctctaccaac  240
tacaagccat ccctgaagtc tcgcgtgaca atctctgtgg acaagagcaa gaaccagttc  300
tccctgaatc tgatcagcgt gaccgccgcc gatacagccg tgtactattg cgccagagag  360
gccggcggct actttgacta ttggggccag ggcatcctgg tgaccgtgtc tagcggcggc  420
ggcggctctg aggaggagg cagcggcgga ggaggctccg gaggcggcgg ctctgatatc  480
cagatgaccc agagcccatc cacactgtct gccagcgtgg gcgacaggt gaccatcaca  540
tgtagagcct cccagtctat ctcctcttgg ctggcctggt atcagcagaa gccaggcaag  600
gcccccaagc tgctgatcag caaggcaagc tccctggagt ccggagtgcc atctaggttc  660
agcggatccg gctctggccc tgagtttacc ctgacaatct ctagcctgca gcctgccgat  720
ttcgccacct actattgtca gcagtacaat agctattcca cctttggcca gggcacaaag  780
ctggagatca gaccacaac cccagccacct aggccacta cacctgcacc aaccatcgcc  840
agccagcctc tgtccctgag accagaggcc tgtaggccag cagcaggagg agcagtgcac  900
acccgggggcc tggacttcgc ctgcgatatc tacatctggg caccactggc aggaacatgt  960
ggcgtgctgc tgctgtccct ggtcatcacc ctgtactgca agagaggcag gaagaagctg  1020
ctgtatatct tcaagcagcc cttcatgaga cccgtgcaga aacccaggag ggaggacggc  1080
tgcagctgta ggttcccaga ggaggaggag ggaggatgtg agctgcgcgt gaagtttttcc  1140
cggtctgcca tgcacctgc ataccagcag ggacagaacc agctgtataa cgagctgaat  1200
ctgggcggga gagaggagta cgacgtgctg gataagagga gggaaggga ccctgagatg  1260
ggaggcaagc ctcggagaaa gaacccacac gagggcctgt acaatgagct gcagaaggac  1320
aagatggccg aggcctatag cgagatcggc atgaagggag agaggcgccg gggcaaggga  1380
cacgatggcc tgtatcaggg cctgtcaacc gctacaaaag atacctacga tgctctgcac  1440
atgcaggctc tgccaccaag a                                             1461
```

```
SEQ ID NO: 585        moltype = DNA   length = 1455
FEATURE               Location/Qualifiers
source                1..1455
                      mol_type = other DNA
                      organism = synthetic construct
                      note = Description of Artificial Sequence: Synthetic
                      polynucleotide
SEQUENCE: 585
atggctctgc ccgtcaccgc tctgctgctg cctctggctc tgctgctgca cgccgcacga  60
ccacaggtgc agctgcagca gtggggagca ggactgctga gccctccga cccctgtct  120
ctgacatgcg ccgtgtacgg cggctccttc tctggctact attggacctg gatcagacag  180
ccccctggca agggactgga gtggatcggc gagatcaccc acagcggctc cacaaactat  240
aatccttctc tgaagagcag ggtgtctatc agcgtggaca cctctaagaa ccagttcagc  300
ctgaagctga gctccgtgac cgcagcagat acagccgtgt actattgcgc cagaggcgag  360
tacggatccg gatctcggtt tgactattgg ggccagggca ccctggtgac agtgtctagc  420
ggaggaggag gaagcggagg aggagggtcc ggaggcgggg gatctgccat ccagatgacc  480
cagtccccat cctctctgag cgcctccgtg ggcgataggg tggcaatcac atgtagagcc  540
agccagggaa tcagggacga tctgggctgg taccagcaga agccaggcaa ggccccaag  600
ctgctgatct atgcagcaag ctccctgcag agcggagtgc catccagatt ctctggcagc  660
ggctccgaca ccgacttcac cctgacaatc tctagcctgc agcctgagga cttcgccaca  720
tactattgtc tgcaggacta cgattatcca ctgacctttg gcggcggcac aaaggtggag  780
atcaagacca caactcctgc acctaggcca cctaccccag cacctacaat tgctagtcag  840
ccactgtcac tgcgaccaga ggcatgtcga cctgcagctg gaggagcagt gcatacaagg  900
```

-continued

```
ggactggact ttgcctgcga tatctacatt tgggctcctc tggcaggaac atgtggcgtg   960
ctgctgctga gcctggtcat cactctgtac tgcaagcgag gccggaagaa actgctgtat  1020
attttcaaac agcccttat gcgacctgtg cagaccacac aggaggaaga tgggtgctcc  1080
tgtcggttcc ccgaggaaga ggaaggaggc tgtgagctgc gggtcaagtt ttccagatct  1140
gcagacgccc ctgcttacca gcagggccag aaccagctgt ataacgagct gaatctgggg  1200
cggagagagg aatacgacgt gctggataaa aggcgcggga gagacccaga aatggggggga  1260
aagccacgac ggaaaaaccc ccaggaggga ctgtacaatg aactcagaa ggataaaatg  1320
gcagaggcct attccgaaat cgggatgaag ggagaaagaa ggcgaggcaa aggacacgac  1380
ggactgtacc aggggctgtc taccgccaca aaggacacct atgatgctct gcatatgcag  1440
gcactgccac ccagg                                                    1455
```

SEQ ID NO: 586        moltype = DNA  length = 1455
FEATURE                Location/Qualifiers
source                 1..1455
                        mol_type = other DNA
                        organism = synthetic construct
                        note = Description of Artificial Sequence: Synthetic
                        polynucleotide
SEQUENCE: 586

```
atggctctgc ccgtcaccgc tctgctgctg cctctggctc tgctgctgca cgccgcacga   60
ccacaggtgc agctgcagca gtggggagca ggactgctga agccctccga gaccctgtct  120
ctgacatgcg ccgtgtacgg cggctccttc tctggctact attggtcctg gatcagacag  180
ccccctggca agggactgga gtggatcggc gagatcaccc acagcggctc cacaaactat  240
aatccttctc tgaagagcag ggtgtctatc agcgtggaca cctctaagaa ccagttcagc  300
ctgaagctga gctccgtgac cgcagcagat acagccgtgt actattgcgc cagaggcgag  360
tacggatccg gatctcggtt tgactattgg ggccagggca cctggtgac agtgtctagc  420
ggaggaggag gaagcggagg aggagggtcc ggaggcgggg gatctgccat ccagatgacc  480
cagtccccat cctctctgag cgcctccgtg ggcgataggg tggccctgac atgtagagcc  540
agccagggca tcagggacga tctgggctgg taccagcaga agccaggcaa ggcccccaag  600
ctgctgatct atgcagcaag ctccctgcag agcggagtgc catccagatt ctctggcaac  660
ggctccgaca ccgacttcac cctgacaatc tctagcctgc agcctgagga cttcgccaca  720
tactattgtc tgcaggacta cgattatcca ctgacctttg gcggcggcac aaaggtggag  780
atcaagacca caactcctgc acctaggcca cctacccccag cacctacaat tgctagtcag  840
ccactgtcac tgcgaccaga ggcatgtcga cctgcagctg gaggagcagt gcatacaagg  900
ggactggact ttgcctgcga tatctacatt tgggctcctc tggcaggaac atgtggcgtg  960
ctgctgctga gcctggtcat cactctgtac tgcaagcgag gccggaagaa actgctgtat  1020
attttcaaac agcccttat gcgacctgtg cagaccacac aggaggaaga tgggtgctcc  1080
tgtcggttcc ccgaggaaga ggaaggaggc tgtgagctgc gggtcaagtt ttccagatct  1140
gcagacgccc ctgcttacca gcagggccag aaccagctgt ataacgagct gaatctgggg  1200
cggagagagg aatacgacgt gctggataaa aggcgcggga gagacccaga aatggggggga  1260
aagccacgac ggaaaaaccc ccaggaggga ctgtacaatg aactcagaa ggataaaatg  1320
gcagaggcct attccgaaat cgggatgaag ggagaaagaa ggcgaggcaa aggacacgac  1380
ggactgtacc aggggctgtc taccgccaca aaggacacct atgatgctct gcatatgcag  1440
gcactgccac ccagg                                                    1455
```

SEQ ID NO: 587        moltype = DNA  length = 1458
FEATURE                Location/Qualifiers
source                 1..1458
                        mol_type = other DNA
                        organism = synthetic construct
                        note = Description of Artificial Sequence: Synthetic
                        polynucleotide
SEQUENCE: 587

```
atggctctgc ccgtcaccgc tctgctgctg cctctggctc tgctgctgca cgccgcacga   60
ccacaggtgc agctgcagca gtggggagca ggactgctga agccttctga gaccctgagc  120
ctgacatgcg ccgtgtacgg cggcagcttt tccgcctact attggaactg gatcaggcag  180
ccccctggca agggactgga gtggatcggc gagatcaatc actctggcag caccaactat  240
aatcccagcc tgaagtcccg cgtgaccatc tccgtggaca catctaagaa ccagttttct  300
ctgaatctga ccagcctgac agccgccgat acagccgtgt actattgcgc cagaggcctg  360
gacagctccg gatggtaccc attcgattat tggggccagg gcaccctggt gacagtgtct  420
agcggaggag gaggaagcgg aggaggaggg tccggaggcg ggggatctga catccagatg  480
acccagtccc catccagcgt gagcgcctct gtgggcgata gggtgaccat cacatgtaga  540
gcaagccagg gaatcagctc ctggctggca tggtaccagc agaagccagg caaggccccc  600
aagctgctga tctatgcagc atctagcctg cagagcggag tgccatccag gtttagcgga  660
tccggatctg gaaccgactt caccctgaca atctcctctc tgcagcctga ggacttcgcc  720
acatactatt gtcagcaggc cgattccttc ccttttacct tcggcccagg cacaaaggtg  780
gatatcaaga ccacaactcc tgcacctagg ccacctaccc cagcacctac aattgctagt  840
cagccactgt cactgcgacc agaggcatgt cgacctgcag ctggaggagc agtgcataca  900
aggggactgg actttgcctg cgatatctac atttgggctc ctctggcagg aacatgtgga  960
gtgctgctgc tgagcctggt catcactctg tactgcaagc gaggccggaa gaaactgctg  1020
tatatttttca aacagccctt tatgcgacct gtgcagacca cacaggagga gatgggtgc  1080
tcctgtcggt tccccgagga gaggaagga ggctgtgagc tgcgggtcaa gttttccaga  1140
tctgcagacg cccctgctta ccagcagggc cagaaccagc tgtataacga gctgaatctg  1200
gggcggagag aggaatacga cgtgctggat aaaaggcgcg ggagagaccc agaaatgggg  1260
ggaaagccac gacggaaaaa ccccccaggag ggactgtaca tgaactgca gaaggataaa  1320
atggcagagg cctattccga aatcgggatg aagggagaaa gaaggcgagg caaaggacac  1380
gacggactgt accaggggct gtctaccgcc acaaaggaca cctatgatgc tctgcatatg  1440
caggcactgc cacccagg                                                 1458
```

```
SEQ ID NO: 588          moltype = DNA   length = 1443
FEATURE                 Location/Qualifiers
source                  1..1443
                        mol_type = other DNA
                        organism = synthetic construct
                        note = Description of Artificial Sequence: Synthetic
                        polynucleotide
SEQUENCE: 588
atggctctgc ccgtcaccgc tctgctgctg cctctggctc tgctgctgca cgccgcacga   60
ccacaggtgc agctgcagca gtgggggagca ggactgctga agccaagcga gaccctgtcc   120
ctgacatgcg ccgtgttcgg cggctctttt agcggcgact actggagctg gatcaggcag   180
cccctggca aggggactgga gtggatcggc gagatcaacc actctggcat caccagcttc   240
aatcctccc tgaagtctcg cgtgaccatc tccgtggaca catctaagaa ccagttttcc   300
ctgaagctga gctccgtgac cgcagcagat acagccgtgt actattgcgc cagaggcgag   360
ctgggcatcc ctgacaattg gggccagggc accctggtga cagtgtctag cggaggagga   420
ggaagcggag gaggagggtc cggaggcggg ggatctgata tccagatgac ccagtcccca   480
tctacactga gcgcctccgt gggcgatagg gtgaccatca catgtagagc ctctcagagc   540
atctcccggt ggctggcctg gtaccagcag aagccaggca aggcccccaa gctgctgatc   600
tataaggcat cctctctgga gagcggagtg ccatccaggt tctctggaag cggatccgga   660
accgagttta ccctgacaat cagctccctg cagcctgacg atttcgccac atactattgt   720
cagcagtaca actcttatag caccttggc cagggcacaa aggtggagat caagaccaca   780
actcctgcac ctaggccacc tacccagca cctacaattg ctagtcagcc actgtcactg   840
cgaccagagg catgtcgacc tgcagctgga ggagcagtgc atacaagggg actggacttt   900
gcctgcgata tctacatttg ggctcctctg gcaggaacat gtggcgtgct gctgctgagc   960
ctggtcatca ctctgtactg caagcgaggc cggaagaaac tgctgtatat tttcaaacag   1020
cccttatgc gacctgtgca gaccacacag gaggaagatg ggtgctcctg tcggttcccc   1080
gaggaagagg aaggaggctg tgagctgcgg gtcaagtttt ccagatctgc agacgcccct   1140
gcttaccagc agggccagaa ccagctgtat aacgagctga atctggggcg gagagaggaa   1200
tacgacgtgc tggataaaag gcgcgggaga gacccagaaa tggggggaaa gccacgacgg   1260
aaaaaccccc aggaggagact gtacaatgaa ctgcagaagg ataaaatggc agaggcctat   1320
tccgaaatcg ggatgaaggg agaaagaagg cgaggcaaag gacacgacgg actgtaccag   1380
gggctgtcta ccgccacaaa ggacacctat gatgctctgc atatgcaggc actgccaccc   1440
agg                                                                1443

SEQ ID NO: 589          moltype = DNA   length = 1485
FEATURE                 Location/Qualifiers
source                  1..1485
                        mol_type = other DNA
                        organism = synthetic construct
                        note = Description of Artificial Sequence: Synthetic
                        polynucleotide
SEQUENCE: 589
atggctctgc ctgtcaccgc tctgctgctg cctctggctc tgctgctgca cgcggcgcgc   60
ccgcaggtgc agctgcagga gtccggccct ggcctggtga agccatccgg caccctgtct   120
ctgacatgcg tggtgttcgg cgacagcatc agctcctcta ctggtggtc ctgggtgagg   180
cagcccctg gcaagggact ggagtggatc ggcgaggtgt ccactccgg ctctaccaac   240
tacaatccaa gcctgaagtc ccgcgtgaca atcagcgtgg ataagtccaa gaatcagttt   300
agcctgaagc tgagctccgt gaccgcagca gacacagccg tgtactattg cgccagagcc   360
gcagtggcag gcgccctgga ttattgggga cagggcaccc tggtgacagt gtctagcggc   420
ggcggcggct ctgaggagg aggcagcggc ggaggaggct ccggaggcgg cggctctgac   480
atcgtgatga cccagtctcc cgatagcctg gccgtgtctc tgggcgagag ggcaacaatc   540
aactgtaagt cctctcagag cgtgctgtac agctccaaca ataagaacta cctggcctgg   600
tatcagcaga agcctggcca gcacccaat ctgctggtgt attgggcctc taccagagag   660
agcggagtgc ctgacagatt ctccggagca ggatctggaa cagacttcac cctgacaatc   720
tctagcctgc aggccgagga cgtggccgtg tactattgc agcagtacta tggcacctcc   780
tggacatttg gccagggcac caaggtggag atcaagacca caccccagc acctaggcca   840
cctacacctg caccaaccat cgccagccag cctctgtccc tgagaccaga ggcctgtagg   900
ccagcagcag gaggagcagt gcacacccgg ggcctggact cgcctgcga tatctacatc   960
tgggcaccac tggcaggaac atgtggcgtg ctgctgctgt ccctggtcat cacccctgtac   1020
tgcaagagag gcaggaagaa gctgctgtat atcttcaagc agcccttcat gagaccccgtg   1080
cagacaaccc aggaggagga cggctgcagc tgtaggttcc cagaggagga ggagggagga   1140
tgtgagctgc gcgtgaagtt ttcccggtct gccgatgcac ctgcatacca gcagggacag   1200
aaccagctgt ataacgagct gaatctgggc cggagagagg agtacgacgt gctggataag   1260
aggagGggaa gggaccctga gatgggaggc aagcctcgga gaaagaaccc acaggagggc   1320
ctgtacaatg agctgcagaa ggacaagatg gccgaggcct atagcgagat cggcatgaag   1380
ggagagaggc gccggggcaa gggacacgat ggcctgtatc agggcctgtc aaccgctaca   1440
aaagatacct acgatgctct gcacatgcag gctctgccac caaga                  1485

SEQ ID NO: 590          moltype = DNA   length = 1458
FEATURE                 Location/Qualifiers
source                  1..1458
                        mol_type = other DNA
                        organism = synthetic construct
                        note = Description of Artificial Sequence: Synthetic
                        polynucleotide
SEQUENCE: 590
atggctctgc ccgtcaccgc tctgctgctg cctctggctc tgctgctgca cgccgcacga   60
ccacagatca cactgaggga gagcggccct accctggtga agccaacccca gacactgacc   120
ctgacatgca ccttttccgg cttctccctg tctaccagcg cctgggcgt gggatggatc   180
```

```
aggcagcccc ctggcgaggc cctggagtgg ctggccctga tctactggaa cgacgcgtaag  240
cggtattccc cctctctgaa gtctagactg agcatcacaa aggacacctc caagaaccag  300
gtggtgctga tcatgacaaa tatgggaccca gtgggatacag ccacctacta ttgcgtgcac  360
aggagaatcg cagcccctgg cagcgtgtac tggggacagg gcacactggt gaccgtgagc  420
tccggaggag gaggaagcgg aggaggaggg tccggaggg tcccgggggg tcatctgaatg  480
acccagtctc cttctagcgt gagcgcctcc gtgggcgata gggtgacaat cacctgtcgc  540
gccagccagg gcatctcctc ttggctggcc tggtatcagc agaagccagg caaggcacca  600
aagctgctga tcagcgccgc aagctccctg cagtccggag tgccatctcg gtttttctggc  660
agcggctccg gcacagactt cacactgacc atctctagcc tgcagcccga ggattttgcc  720
acctactatt gtcaccaggc caattccttc cctttttacat tcggccaggg caccaagctg  780
gagatcaaga ccacaactcc tgcacctagg ccacctaccc cagcacctac aattgctagt  840
cagccactgt cactgcgacc agaggcatgt cgacctgcag ctggaggagc agtgcataca  900
agggactgg actttgcctg cgatatctac attttgggctc ctctggcagg aacatgtggc  960
gtgctgctgc tgagcctggt catcactctg tactgcaagc gaggccggaa gaaactgctg  1020
tatatttttca aacagcccctt tatgcgacct gtgcagacca cacaggagga agatgggtgc  1080
tcctgtcggt tccccgagga agaggaagga ggctgtgagc tgcgggtcaa gttttccaga  1140
tctgcagacg ccccctgctta ccagcagggc cagaaccagc tgtataacga gctgaatctg  1200
gggcggagag aggaatacga cgtgctggat aaaaggcgcg gagacccaga atgggggga  1260
ggaaagccac gacggaaaaa cccccaggag ggactgtaca atgaactgca gaaggataaa  1320
atggcagagg cctattccga aatcgggatg aagggagaaa gaaggcgagg caaaggacac  1380
gacggactgt accaggggct gtctaccgcc acaaaggaca cctatgatgc tctgcatatg  1440
caggcactgc cacccagg                                                 1458
```

```
SEQ ID NO: 591          moltype = DNA  length = 1455
FEATURE                 Location/Qualifiers
source                  1..1455
                        mol_type = other DNA
                        organism = synthetic construct
                        note = Description of Artificial Sequence: Synthetic
                        polynucleotide
SEQUENCE: 591
atggctctgc ccgtcaccgc tctgctgctg cctctggctc tgctgctgca cgccgcacga  60
ccacaggtgc agctggtgca gtccggagca gaggtgaaga agcctggcgc ctccgtgaag  120
gtgtcttgca aggtgagcgg ctacaccctg acagagctgt ctatgcactg ggtgcgcaa  180
gcccccggca agggacctga gggaatggga ggattccgac ctgaggatga caagacaatc  240
tacgcccaga agtttcaggg ccgggtgacc atgacagagg acaccagcgc cgatacagcc  300
tatatggagc tgaactctct gcgcagcgag gacaccgccg tgtactattg cgccacactg  360
ctgagggggac tggacgcctt cgacgtgtgg ggacagggaa ccatggtgac agtgagctcc  420
ggaggaggag gaagcggagg aggaggtcc ggaggcgggg gatctgatat ccagatgacc  480
cagtctccat ctagcctgag cgcctccgtg ggcgacaggg tgaccatcac atgtagagcc  540
agccagggca tcaggaacga tctgggctgg taccagcaga agccaggcaa ggcccccaag  600
agactgatct atgcagcatc ctctctgcag tccggagtgc catctaggtt ctctggcagc  660
ggctccggca ccgagtttac cctgacaatc agcacctgc agcctgagga cttcgccacc  720
tactattgtc tgcagcacaa ttcctatcca cggacctttg gccagggcac aaaggtggag  780
atcaagacca caactcctgc acctaggcca cctaccccag cacctacaat tgctagtcag  840
ccactgtcac tgcgaccaga ggcatgtcga cctgcagctg gaggagcagt gcatacaagg  900
ggactgg actttgcctgga tatctacatt tgggctcctc tggcaggaac atgtggcgtg  960
ctgctgctga gcctggtcat cactctgtac tgcaagcgag gccggaagaa actgctgtat  1020
atttttcaaac agcccctttat gcgacctgtg cagaccacac aggaggaaga tgggtgctcc  1080
tgtcggttcc ccgaggaaga ggaagggggc tgtgagctgc gggtcaagtt ttccagatct  1140
gcagacgccc ctgcttacca gcagggccag aaccagctgt ataacgagct gaatctggg  1200
cggagagagg aatacgacgt gctggataaa aggcgcggga gacccagaa tgggggga  1260
aagccacgac ggaaaaaccc ccaggaggga ctgtacaatg aactgcagaa ggataaaatg  1320
gcagaggcct attccgaaat cgggatgaag ggagaaagaa ggcgaggcaa aggacacgac  1380
ggactgtacc aggggctgtc taccgccaca aaggacacct atgatgctct gcatatgcag  1440
gcactgccac ccagg                                                   1455
```

```
SEQ ID NO: 592          moltype = DNA  length = 1458
FEATURE                 Location/Qualifiers
source                  1..1458
                        mol_type = other DNA
                        organism = synthetic construct
                        note = Description of Artificial Sequence: Synthetic
                        polynucleotide
SEQUENCE: 592
atggctctgc ccgtcaccgc tctgctgctg cctctggctc tgctgctgca cgccgcacga  60
ccacaggtgc agctgcagca gtgggggagca ggactgctga gccatccga gaccctgtct  120
ctgacatgcg ccgtgtatgg cggctccttc tctggctact attggcggtg gatcagacag  180
ccccctggca agggactgga gtggatcggc gagatcagcc actccggctc taccaactac  240
aatccctctc tgaagagccg cgtgaccatc agcgtggaca catccaagaa ccagttcagc  300
ctgaagctga gctccgtgac cgcagcagat acagccgtgt actattgcgc cgtgcggggc  360
tactcctatg ctacccccct gtttgactac tggggccagg gcaccctggt gacagtgtct  420
agcggaggag gaggaagcgg aggaggaggg tccggaggcg gggatctga tatccagatg  480
acccagtctcc cttcctctct gagcgcctcc gtgggcgaca gggtgaccat cacatgtcgc  540
gcctctcagg gcatccggaa cgatctgggc tggtatcagc agaagctggg caaggcccca  600
aagagactga tctacgcagc aagctccctg cagtctggag tgccaagcag gttctctgga  660
agcggatccg gaaccgagtt tacctgaca atctctagcc tgcagcctga ggacttcgcc  720
acatactatt gtctgcagta taatagctac ccacggacct tggccaggg cacaaaggtg  780
gagatcaaga ccacaactcc tgcacctagg ccacctaccc cagcacctac aattgctagt  840
```

```
cagccactgt cactgcgacc agaggcatgt cgacctgcag ctggaggagc agtgcataca    900
aggggactgg actttgcctg cgatatctac atttgggctc ctctggcagg aacatgtggc    960
gtgctgctgc tgagcctggt catcactctg tactgcaagc gaggccggaa gaaactgctg   1020
tatattttca aacagcccct tatgcgacct gtgcagacca cacaggagga agatgggtgc   1080
tcctgtcggt tccccgagga agaggaagga ggctgtgagc tgcgggtcaa gttttccaga   1140
tctgcagacg cccctgctta ccagcagggc cagaaccagc tgtataacga gctgaatctg   1200
gggcggagag aggaatacga cgtgctggat aaaaggcgcg ggagagaccc agaaatgggg   1260
ggaaagccac gacggaaaaa cccccaggag ggactgtaca atgaactgca gaaggataaa   1320
atggcagagg cctattccga aatcgggatg aagggagaaa gaaggcgagg caaaggacac   1380
gacggactgt accaggggct gtctaccgcc acaaaggaca cctatgatgc tctgcatatg   1440
caggcactgc cacccagg                                                 1458

SEQ ID NO: 593          moltype = DNA  length = 1443
FEATURE                 Location/Qualifiers
source                  1..1443
                        mol_type = other DNA
                        organism = synthetic construct
                        note = Description of Artificial Sequence: Synthetic
                        polynucleotide
SEQUENCE: 593
atggctctgc ccgtcaccgc tctgctgctg cctctggctc tgctgctgca cgccgcacga     60
ccacaggtgc agctgcagga gagcggccct ggcctggtga agccatccgg caccctgtct    120
ctgacatgcg ccgtgagcgg cgactccatc agctccaact ggtggacatg ggtgaggcag    180
cccCctggca agggactgga gtggatcggc gatatccacc actccggctc taccaactac    240
aatccatctc tgaagagccg cgtgacaatg agcgtggaca agtccgagaa tcagttctcc    300
ctgaagctgt ctagcgtgac cgccgccgat acagccgtgt tttactgcgc cagagacgga    360
ggaggcaccc tggattattg gggccagggc accctggtga cagtgtcctc tggaggagga    420
ggaagcggag gaggagggtc cggaggcggg ggatctgaca tccagatgac ccagagccca    480
tccacactgt ctgccagcgt gggcgatcgg gtgaccatca catgtagagc ctcccagtct    540
atcagctcct ggctggcctg gtaccagcag aagccagaca aggcccccaa gctgctgatc    600
tataaggcat ctaccctgga gagcggagtg ccatccaggt tcagcggatc cggatctggc    660
acagagttta ccctgacaat ctctagcctg cagcctgacg atttcgccac ctactattgt    720
cagcagtaca cggctatag cacctttggc cagggcacaa aggtggagat caagaccaca    780
actcctgcac ctaggccacc tacccagca cctacaattg ctagtcagcc actgtcactg    840
cgaccagagg catgtcgacc tgcagctgga ggagcagtgc atacaaggg actggacttt    900
gcctgcgata tctacatttg ggctcctctg gcaggaacat gtggcgtgct gctgctgagc    960
ctggtcatca ctctgtactg caagcgaggc cggaagaaac tgctgtatat tttcaaacag   1020
cccctttatgc gacctgtgca gaccacacag gaggaagatg ggtgctcctg tcggttcccc   1080
gaggaagagg aaggaggctg tgagctgcgg gtcaagtttt ccagatctgc agacgcccct   1140
gcttaccagc agggccagaa ccagctgtat aacgagctga atctggggcg gagagaggaa   1200
tacgacgtgc tggataaaag gcgcgggaga gacccagaaa tggggggaaa gccacgacgg   1260
aaaaaccccc aggagggact gtacaatgaa ctgcagaagg ataaaatggc agaggcctat   1320
tccgaaatcg ggatgaaggg agaaagaagg cgaggcaaag acacgacgg actgtaccag   1380
gggctgtcta ccgccacaaa ggacacctat gatgctctgc atatgcaggc actgccaccc   1440
agg                                                                 1443

SEQ ID NO: 594          moltype = DNA  length = 1485
FEATURE                 Location/Qualifiers
source                  1..1485
                        mol_type = other DNA
                        organism = synthetic construct
                        note = Description of Artificial Sequence: Synthetic
                        polynucleotide
SEQUENCE: 594
atggcactgc cagtgaccgc cctgctgctg cctctggccc tgctgctgca cgccgccagg     60
cctcaggtgc agctggtgca gtctggcgcc gaggtgaaga agccaggcag ctccgtgaag    120
gtgtcctgca aggcctctgg cggcacattc accaactatt gtatcagctg ggtgagacag    180
gccccaggcc agggactgga gtggatggga ggaatcatcc ccatcttcgg cacccacaaat    240
tatgcccaga cctttcaggg ccgggtgaca atcaccgccg acaagtctac aagcaccgcc    300
tacatggagc tgtctagcct gagatccgag gatacagccg tgtactattg cgccagagac    360
aacggcgata gatactatta cgacatggac gtgtggggcc agggcaccac agtgaccgtg    420
tcctctggag gaggagcag cggcggagga ggctccggag cggcggctc tggcggcggc    480
ggctcccagt ctgtgctgac acagccacct agcgtgtccg ccgcccctgg ccagaaggtg    540
accatctctt gtagcggcag ctcctctaat atcggcaaca attacgtgag ctggtaccag    600
cagctgccag gcacagcccc caagctgctg atctacaaca acaataagag gcctagcggc    660
atcccagatc gcttctccgg ctctaagagc ggcacatccg ccaccctggg catcacagga    720
ctgcagaccg gcgacgaggc agattattac tgcggaacct gggacagctc cctgagcgcc    780
gtggtgtttg gaggaggcac aaagctgacc gtgctgacca caccccctgc ccctaggcca    840
cctaccccag cacctacaat tgctagtcag ccactgtcac tgcgaccaga ggcatgtcga    900
cctgcagctg gaggagcagt gcatacaagg ggactggact ttgcctgcga tatctacatt    960
tgggctcctc tggcaggaac atgtggcgtg ctgctgctga gcctggtcat cactctgtac   1020
tgcaagcgag gccggaagaa actgctgtat attttcaaac agccctttat gcgacctgtg   1080
cagaccacac aggaggaaga tgggtgctcc tgtcggttcc ccgaggaaga ggaaggaggc   1140
tgtgagctgc gggtcaagtt ttccagatct gcagacgccc ctgcttacca gcagggccag   1200
aaccagctgt ataacgagct gaatctgggg cggagagagg aatacgacgt gctggataaa   1260
aggcgcggga gacccaga aatgggggga aagccacgac ggaaaaaccc caggagggga   1320
ctgtacaatg aactgcagaa ggataaaatg gcagaggcct attccgaaat cgggatgaag   1380
ggagaaagaa ggcgaggcaa aggacacgac ggactgtacc aggggctgtc taccgccaca   1440
aaggacacct atgatgctct gcatatgcag gcactgccac ccagg                   1485
```

-continued

```
SEQ ID NO: 595          moltype = DNA   length = 1491
FEATURE                 Location/Qualifiers
source                  1..1491
                        mol_type = other DNA
                        organism = synthetic construct
                        note = Description of Artificial Sequence: Synthetic
                        polynucleotide
SEQUENCE: 595
atggccctgc cagtgaccgc cctgctgctg ccactggccc tgctgctgca cgccgcccgg   60
ccacaggtgc ccctggtgca gagcggagca gaggtgaaga agcccggcag ctccgtgaag  120
gtgagctgca aggcctccgg cggcacattc tccacctatt ctatcagctg ggtgcggcag  180
gcccctggcc agggactgga gtggatggga ggaatcatcc caatcttcgg caccacaaac  240
tatgcccaga agtttcaggg cagggtgaca atcaccgccg acaagtccac atctaccgcc  300
tacatggagc tgtctagcct gaggtccgag gacacagccg tgtactattg tgcccgcgat  360
ggcgagggct cttactatta ctattacgga atggacgtgt ggggacaggg aaccacagtg  420
accgtgtcct ctggcggcgg cggctctgga ggaggaggca gcggcggagg aggctccgga  480
ggcggcggca gccagtccgt gctgacacag ccaccttctg tgagcgccgc ccctggccag  540
aaggtgacca tctcctgctc tggcagctcc tctaatatcg gcaacaatta tgtgagctgg  600
taccagcagc tgcctggcac agccccaaag ctgctgatct acgacaacaa taagcggccc  660
tccggcatcc ctgatagatt cttttggctct aagttcggca caagcgccac cctgggcatc  720
acaggactgc agaccggcga cgaggcagat tattactgtg aacctggga cagctccctg  780
agcgccgtgg tgtttggagg aggcacaaag ctgaccgtgc tgaccacaac ccctgcccct  840
aggccaccta ccccagcacc tacaattgct agtcagccac tgtcactgcg accagaggca  900
tgtcgacctg cagctggagg agcagtgcat acaagggac tggactttgc ctgcgatatc  960
tacatttggg ctcctctggc aggaacatgt ggcgtgctgc tgctgagcct ggtcatcact  1020
ctgtactgca agcgaggccg gaagaaactg ctgtatattt tcaaacagcc ctttatgcga  1080
cctgtgcaga ccacacagga ggaagatggg tgctcctgtc ggttccccga ggaagaggaa  1140
ggaggctgtg agctgcgggt caagtttttcc agatctgcag acgcccctgc ttaccagcag  1200
ggccagaacc agctgtataa cgagctgaat ctggggcgga gagggaata cgacgtgctg  1260
gataaaaggc gcgggagaga cccagaaatg gggggaaagc cacgacggaa aaacccccag  1320
gagggactgt acaatgaact gcagaaggat aaaatggcag aggcctattc cgaaatcggg  1380
atgaaggga aagaaggcg aggcaaagga cacgacggac tgtaccaggg gctgtctacc  1440
gccacaaagg acacctatga tgctctgcat atgcaggcac tgccacccag g  1491

SEQ ID NO: 596          moltype = DNA   length = 1470
FEATURE                 Location/Qualifiers
source                  1..1470
                        mol_type = other DNA
                        organism = synthetic construct
                        note = Description of Artificial Sequence: Synthetic
                        polynucleotide
SEQUENCE: 596
atggcactgc cagtgacagc cctgctgctg cctctggccc tgctgctgca cgccgcccgg   60
ccacaggtgc agctgcagga gtccggccct ggcctggtga agccatctga gaccctgagc  120
ctgacatgta ccgtgtccgg cgattctatc agctcctact attggtcttg gatcaggcag  180
ccccctggcc agggactgga gtggatcggc tacatgtact atagcggcat cacaaactat  240
aatcctagcc tgaagtcccg cgtgaacatc tccctggaca cctctaagaa tcagttcagc  300
ctgaagctgg gctccgtgac agcagcagat accgccgtgt actattgcgc aaggctgtcc  360
gtggcaggct tctactttga ctattggggc cagggcacac tggtgaccgt gtctagcggc  420
ggcggcggct ctgaggagga aggcagcggc ggaggaggca ccggcggcgc ggcctctagg  480
atcgtgctga cacagagccc aggcaccctg agcctgtccc ccggcgagcg ggccacactg  540
agctgtagag cctctcagag cgtgacccgg tcctacctgg cctggtatca gcagaagcca  600
ggccaggccc ccagactgct gatctacggc gcctcctcta gggccacaga catcccagat  660
cgcttctccg gctctggcag cggaaccgac tttacactga ccatcaacag actggagcct  720
gaggatttcg ccgtgtacta ttgccagcag tacggcacaa gcccactgac ctttggcggc  780
ggcaccaagg tggagatcaa gaccacaacc cctgccccta ggccacctac cccagcacct  840
acaattgcta gtcagccact gtcactgcga ccagaggcat gtcgacctgc agctggagga  900
gcagtgcata caaggggact ggactttgcc tgcgatatct catttggcc tcctctggca  960
ggaacatgtg gcgtgctgct gctgagcctg gtcatcactc tgtactgcaa gcgaggccgg  1020
aagaaactgc tgtatatttt caaacagccc tttatgcgac ctgtgcagac cacacaggag  1080
gaagatgggt gctcctgtcg gttccccgag aagaggaag gaggctgtga gctgcgggtc  1140
aagtttttcca gatctgcaga cgcccctgct taccagcagg ccagaacca gctgtataac  1200
gagctgaatc tggggcggag agaggaatac gacgtgctga taaaaggcg cgggagagac  1260
ccagaaatgg ggggaaagcc acgacgaaa aaccccccagg agggactgta caatgaactg  1320
cagaaggata aaatggcaga ggcctattcc gaaatcggga tgaagggaga aagaaggcga  1380
ggcaaggac acgacggact gtaccagggg ctgtctaccg ccacaaagga cacctatgat  1440
gctctgcata tgcaggcact gccacccagg                                   1470

SEQ ID NO: 597          moltype = DNA   length = 1470
FEATURE                 Location/Qualifiers
source                  1..1470
                        mol_type = other DNA
                        organism = synthetic construct
                        note = Description of Artificial Sequence: Synthetic
                        polynucleotide
SEQUENCE: 597
atggcactgc cagtgacagc cctgctgctg cctctggccc tgctgctgca cgccgcccgg   60
ccacaggtgc agctgcagga gagcggccct ggcctggtga agccatctga gaccctgagc  120
```

-continued

```
ctgacatgta ccgtgagctc cgattccatc tctagctact attggtcttg gatcagacag   180
cccctggca agggcctgga gtggatctcc tacatctact attccggcat ctctaactat   240
aatcctagcc tgaagagccg ggtgagcatc tctgtggaca cctccaagaa ccagttttct   300
ctgagactgt cctctgtgac agccgccgat accgccgtgt actattgcgc cagaatcagc   360
gtggccggct tcttttcga caattggggc cagggcacac tggtgaccgt gagctccgga   420
ggaggaggca gcggaggagg aggctccgga ggcggcggct ctggcggcgg cggcagcgag   480
atcatgctga cacagagccc agataccctg agcctgtccc ccggcgaaag ggccacactg   540
tcctgtagag cctctcagag cgtgtctagc tcctacctgg cctggtatca gcagaagcca   600
ggccaggcac ccaggctgct gatctacgga gcatctagca gggccgcagg agtgccagac   660
cgcttttccg gctctggcag cggcaccgat ttcacactga ccatctctcg cctggcccct   720
gaggactttg tggtgtacta ttgccagcag tatggcatct ccccactgac attcggcggc   780
ggcaccaagt ggagatcaa gaccacaacc cctgcccta ggccacctac cccagcacct   840
acaattgcta gtcagccact gtcactgcga ccagaggcag gtcgacctgc agctggagga   900
gcagtgcata caaggggact ggactttgcc tgcgatatct acatttgggc tcctctgtga   960
ggaacatgtg gcgtgctgct gctgagcctg gtcatcactc tgtactgcaa gcgaggccgg  1020
aagaaactgc tgtatattt caaacagccc tttatgcgac ctgtgcagac cacacaggag  1080
gaagatgggg gctcctgtcg gttccccgag aagaggaag gaggctgtga gctgcgggtc  1140
aagtttcca gatctgcaga cgcccctgct taccagcagg gccagaacca gctgtataac  1200
gagctgaatc tggggcggag agaggaatac gacgtgctgg ataaaaggcg cgggagagac  1260
ccagaaatgg ggggaaagcc acgacggaaa aaccccagg agggactgta caatgaactg  1320
cagaaggata aaatggcaga ggcctattcc gaaatcggga tgaagggaga aagaaggcga  1380
ggcaaaggac acgacggact gtaccagggg ctgtctaccg ccacaaagga cacctatgat  1440
gctctgcata tgcaggcact gccacccagg                                  1470
```

```
SEQ ID NO: 598             moltype = DNA  length = 1494
FEATURE                    Location/Qualifiers
source                     1..1494
                           mol_type = other DNA
                           organism = synthetic construct
                           note = Description of Artificial Sequence: Synthetic
                           polynucleotide
SEQUENCE: 598
atggctctgc ctgtcaccgc tctgctgctg cctctggctc tgctgctgca cgcggcgcgc   60
ccgcaggtgc agctgcagca gagcggccct ggcctggtga agcctagcca gacactgtcc  120
ctgacctgtg ccatctctgg cgacagcgtg agctccaaca gcgccacatg gaattggatc  180
aggcagtccc catctcgcgg cctggagtgg ctgggacgga cctactatag atccaagtgg  240
tacgacgatt atgccgtgtc cgtgaagtct cgcatcacaa tcaaccctga cacctccaag  300
aatcacctgt ctctgcacct gaacagcgtg acaccagagg ataccgccgt gtactattgc  360
gcaggaggag gactggtgag cgccctgac ggattcgacg tgtggggcca gggcacaatg  420
gtgaccgtgt ctagcggcgg cggcggctct ggaggaggag gcagcggcgg aggaggctcc  480
ggaggcggcg gctctcagtc cgtgctgaca cagccccctt ctgccagcgg aacacccggc  540
cagcgggtga ccatctcctg ttctggctcc tctagcaaca tcggctccga ccctgtgaat  600
tggtaccagc agctgccagg cacagccccc aagctgctga tctatagcaa caatcagcgg  660
ccttccggcg tgccagatag attcagcggc tccaagtctg gcaccagcgc ctccctggca  720
atctctggac tgcagagcga ggacgaggcc gattactatt gctccgcctg ggacgattct  780
ctgaatggct acgtgtttgg cacaggcacc aaggtgaccg tgctgaccac aacccagca  840
cctaggccac ctacacctgc accaaccatc gccagccagc ctctgtccct gagaccagag  900
gcctgtaggc cagcagcagg aggagcagtg cacaccgggg cctggactt cgcctgcgat  960
atctacatct gggcaccact ggcaggaaca tgtggcgtgc tgctgctgtc cctggtcatc  1020
accctgtact gcaagagagg caggaagaag ctgctgtata tcttcaagca gccccttcatg  1080
agaccgtgc agacaaccca ggaggaggac ggctgcagct gtaggttccc agaggaggag  1140
gaggaggat gtgagctgcg cgtgaagttt tcccggtctg ccgatgcacc tgcataccag  1200
cagggacaga accagctgta taacgagctg aatctggggcc ggagagagga gtacgacgtg  1260
ctggataaga ggagggggaag ggaccctgag atggaggca agcctcggag aaagaaccca  1320
caggaggcc tgtacaatga gctgcagaag gacaagtgcc ccgaggccta tagcgagatc  1380
ggcatgaagg gagagaggcg ccggggcaag ggacacgatg gcctgtatca gggcctgtca  1440
accgctacaa aagataccta cgatgctctg cacatgcagg ctctgccacc aaga         1494
```

```
SEQ ID NO: 599             moltype = DNA  length = 1479
FEATURE                    Location/Qualifiers
source                     1..1479
                           mol_type = other DNA
                           organism = synthetic construct
                           note = Description of Artificial Sequence: Synthetic
                           polynucleotide
SEQUENCE: 599
atggctctgc ctgtcaccgc tctgctgctg cctctggctc tgctgctgca cgcggcgcgc   60
ccgcaggtgc agctggtgca gagcggagca gaggtgaaga agcctggcgc cagcgtgaag  120
gtgtcctgca aggcctctgg ctacacattc accggctatt ctatccactg ggtgcgccag  180
gcccctggcc agggactgga gtggatgggc tggatcaacc caaatagcgg cggcaccttc  240
tacgcccaga gtttcagggg cagggtgaca atgacccgcg acacatctat cagcaccgtg  300
tatatggagc tgagccggct gagatccgac gatacagccg tgtactattg gccagagac   360
ggctggggcg attactatta ctatggactg gacgtgtggg gacagggaac cacagtgacc  420
gtgtccctgg gcggcggcgg ctctggagga ggaggcggag ggggaggag ctccggaggc  480
ggcggctctg atatccagat gacacagagc cctagctccg tgtccgcctc tgtgggcgac  540
agggtgacaa tcacctgcag agcctcccag gatatctcta ctggctggc ctggtaccag  600
cagaagcccg gcaggccccc taagctgctg atctataccg catcctctct gcagggagga  660
gtgccatccc ggttcagcgg ctccggctct ggaacagact tcactgac catcagctcc  720
ctgcagccag aggatctggc cacctactct tgtcagcagg ccaacgtgtt ccctatacaa  780
```

-continued

```
tttggccagg gcaccaagct ggagatcaag accacaaccc cagcacctag gccacctaca  840
cctgcaccaa ccatcgccag ccagcctctg tccctgagac cagaggcctg taggccagca  900
gcaggaggag cagtgcacac ccgggggcctg gacttcgcct gcgatatcta catctgggca  960
ccactggcag gaacatgtgg cgtgctgctg ctgtccctgg tcatcaccct gtactgcaag  1020
agaggcagga agaagctgct gtatatcttc aagcagccct tcatgagacc cgtgcagaca  1080
acccaggagg aggacggctg cagctgtagg ttcccagagg aggaggaggg aggatgtgag  1140
ctgcgcgtga agtttcccg gtctgccgat gcacctgcat accagcaggg acagaaccag  1200
ctgtataacg agctgaatct gggccggaga gaggagtacg acgtgctgga taagaggagg  1260
ggaagggacc ctgagatggg aggcaagcct cggagaaaga acccacagga gggcctgtac  1320
aatgagctgc agaaggacaa gatggccgag gcctatagcg agatcggcat gaagggagag  1380
aggcgccggg gcaagggaca cgatggcctg tatcagggcc tgtcaaccgc tacaaaagat  1440
acctacgatg ctctgcacat gcaggctctg ccaccaaga                         1479
```

SEQ ID NO: 600         moltype = DNA   length = 1479
FEATURE                 Location/Qualifiers
source                  1..1479
                            mol_type = other DNA
                            organism = synthetic construct
                            note = Description of Artificial Sequence: Synthetic
                            polynucleotide SEQUENCE: 600
```
atggctctgc ctgtcaccgc tctgctgctg cctctggctc tgctgctgca cgcggcgcgc  60
ccggaggtgc agctgctgga gtccggcggc ggcctggtgc agccaggcgg ctctctgagg  120
ctgagctgcg cagcatccgg cttcacctttt agctcctacg caatgaactg ggtgcgccag  180
gcccccggca agggactgga gtgggtgtct acaatctctg gcagcggcgg cagcacctac  240
tatgccgact ccgtgaaggg ccggttcaca atctctagag ataacagcaa gaatacctg  300
tacctgcaga tgaacagcct gcgggccgag gacacagccg tgttttattg tgccatcgac  360
ccagagtact atgatatcct gaccggcggc gattattggg gccagggcac actggtgacc  420
gtgtctagcg gcggcggcgg ctctggagga ggaggcagcg gcgaggaggg ctccggaggc  480
ggcggctctg acatccagat gacccagtcc ccatctgccc tgagcgcctc cgtgggcgat  540
agggtgacaa tcacctgccg cgcctcccag ggcatctcta actacctggc ctggttccag  600
cagaagcccg gcaaggtgcc taagcggctg atctatgcag catcctctct gcagagcgga  660
gtgccttcca gattctctgg cagcggctcc ggcacagagt ttacactgac catcagctcc  720
ctgcagcccg aggacttcgc cacctacttt tgtctgcagc acgattcctt ccctctgaca  780
tttggcggcg gcaccaaggt ggagatcaag accacaaccc cagcacctag gccacctaca  840
cctgcaccaa ccatcgccag ccagcctctg tccctgagac cagaggcctg taggccagca  900
gcaggaggag cagtgcacac ccgggggcctg gacttcgcct gcgatatcta catctgggca  960
ccactggcag gaacatgtgg cgtgctgctg ctgtccctgg tcatcaccct gtactgcaag  1020
agaggcagga agaagctgct gtatatcttc aagcagccct tcatgagacc cgtgcagaca  1080
acccaggagg aggacggctg cagctgtagg ttcccagagg aggaggaggg aggatgtgag  1140
ctgcgcgtga agtttcccg gtctgccgat gcacctgcat accagcaggg acagaaccag  1200
ctgtataacg agctgaatct gggccggaga gaggagtacg acgtgctgga taagaggagg  1260
ggaagggacc ctgagatggg aggcaagcct cggagaaaga acccacagga gggcctgtac  1320
aatgagctgc agaaggacaa gatggccgag gcctatagcg agatcggcat gaagggagag  1380
aggcgccggg gcaagggaca cgatggcctg tatcagggcc tgtcaaccgc tacaaaagat  1440
acctacgatg ctctgcacat gcaggctctg ccaccaaga                         1479
```

SEQ ID NO: 601         moltype = DNA   length = 1470
FEATURE                 Location/Qualifiers
source                  1..1470
                            mol_type = other DNA
                            organism = synthetic construct
                            note = Description of Artificial Sequence: Synthetic
                            polynucleotide SEQUENCE: 601
```
atggctctgc ctgtcaccgc tctgctgctg cctctggctc tgctgctgca cgcggcgcgc  60
ccgcaggtgc agctgcagga gtccggccct ggcctggtga agccaagcga gaccctgtcc  120
ctgacatgta ccgtgagctc cgattctatc agcaactact attggagctg gatcaggcag  180
ccccctggca agggactgga gtggatctcc tacatctact attctggcat caccaactat  240
aatccttccc tgaagtctcg cgtgacaatc tctgtggaca ccagcaagaa tcagttcagc  300
ctgaagctgt ctagcgtgac agccgccgat accgccgtgt actattgcgc ccggatcaca  360
gtgaccggct ctactttga ctattggggc agggcacac tggtgaccgt gtcctctggc  420
ggcggcggct ctggaggagg aggcagcggc ggaggaggct ccgaggcgg cggctctgag  480
atcgtgctga cacagtcccc aggcaccctg tccctgtcc ccggcgagcg cgccacactg  540
tcttgtagag ccagccagtc catctctcgg agctacctgg cctggtatca gcagaagcca  600
ggccaggccc ccagacacct gatctacgga gcaagctcca gggccaccgg catccccgac  660
cgcttctccg gctctggcag cggcacagac ttcatcctga ccatctccag actggagcct  720
gaggacttcg ccgtgtacta ttgccagcag tacgataaa gcccactgac ctttggcggc  780
ggcaccaagg tggagatcaa gaccacaacc ccagcaccta aggccgcaca acctgccaca  840
accatcgcca gccagcctct gtccctgaga ccagaggcct gtaggccagc agcaggagga  900
gcagtgcaca cccgggggcct ggacttcgcc tgcgatatct acatctgggc accactggca  960
ggaacatgtg gcgtgctgct gctgtccctg gtcatcaccc tgtactgcaa gagaggcagg  1020
aagaagctgc tgtatatctt caagcagccc ttcatgagac ccgtgcagac aacccaggag  1080
gaggacggct gcagctgtag gttcccagag gaggaggggg aggatgtga gctgcgcgtg  1140
aagtttcccg gtctgccga tgcacctgca taccagcagg gacagaacca gctgtataac  1200
gagctgaatc tgggccggag agaggagtac gacgtgctgg ataagaggag gggaaggggc  1260
cctgagatgg gaggcaagcc tcggagaaag aacccacagg agggcctgta caatgagctg  1320
cagaaggaca agatggccga ggcctatagc gagatcggca tgaagggaga gaggcgccgg  1380
ggcaagggac acgatggcct gtatcagggc ctgtcaaccg ctacaaaaga tacctacgat  1440
```

-continued

```
gctctgcaca tgcaggctct gccaccaaga                                      1470

SEQ ID NO: 602          moltype = DNA   length = 1494
FEATURE                 Location/Qualifiers
source                  1..1494
                        mol_type = other DNA
                        organism = synthetic construct
                        note = Description of Artificial Sequence: Synthetic
                         polynucleotide
SEQUENCE: 602
atggcactgc cagtgacagc cctgctgctg ccactggccc tgctgctgca cgccgcccgg    60
ccacaggtgc agctgcagca gagcggccct ggcctggtga agcctagcca gacactgtcc    120
ctgacctgtg ccatctctgg cgacagcgtg agctccaaca gcgtggtgtg gaattggatc    180
aggcagtccc catctcgcgg cctggagtgg ctgggacgga cctactatag atccaagtgg    240
tacgacgatt atgccgtgtc cgtgaagtct aggatcacaa tcaaccctga caccagcaag    300
aatcagttct ccctgcagct gaactctgtg acaccagagg ataccgccgt gtaccactgc    360
gccagaggcg gaatcgtggg cgcccctgac gcctttgata tctggggcca gggcacaatg    420
gtgaccgtgt ctagcggagg aggaggcagc ggaggaggag gctccggagg cggcggctct    480
ggcggcggcg gcagccagtc cgtgctgacc cagccacctt ctgccagcgg aacacccggc    540
cagcgggtga ccatctcctg ttctggctcc tctagcaaca tcggctctga ccctgtgagc    600
tggtaccagc agttcccagg cacagccccc aagctgctga tctataccaa caatcagcgg    660
cctagcggcg tgccagatcc gttcagcggc tccaagtctg gcacaagcgc ctccctggca    720
atctccggac tgcagtctga ggacgaggcc gattactatt gcgccgcctg ggacgattcc    780
ctgaatggcc acgtgttcgg cacaggcacc aaggtgaccg tgctgaccac aacccccgcc    840
cctaggccac ctaccccagc acctacaatt gctagtcagc cactgtcact gcgaccagag    900
gcatgtcgac ctgcagctgg aggagcagtg catacaaggg gactggactt tgcctgcgat    960
atctacattt gggctcctct ggcaggaaca tgtggcgtgc tgctgctgag cctggtcatc    1020
actctgtact gcaagcgagg ccggaagaaa ctgctgtata ttttcaaaca gcccttatg    1080
cgacctgtgc agaccacaca ggaggaagat gggtgctcct gtcggttccc cgaggaagag    1140
gaaggaggct gtgagctgcg ggtcaagttt tccagatctg cagacgcccc tgcttaccag    1200
cagggccaga accagctgta taacgagctg aatctggggc ggagagagga atacgacgtg    1260
ctggataaaa ggcgcgggag agacccagaa atggggggaa agccacgacg gaaaaacccc    1320
caggagggac tgtacaatga actgcagaag gataaaatgg cagaggccta ttccgaaatc    1380
gggatgaagg gagaaagaag gcgaggcaaa ggacacgacg gactgtacca ggggctgtct    1440
accgccacaa aggacaccta tgatgctctg catatgcagg cactgccacc cagg          1494

SEQ ID NO: 603          moltype = DNA   length = 1494
FEATURE                 Location/Qualifiers
source                  1..1494
                        mol_type = other DNA
                        organism = synthetic construct
                        note = Description of Artificial Sequence: Synthetic
                         polynucleotide
SEQUENCE: 603
atggccctgc cagtgaccgc cctgctgctg ccactggccc tgctgctgca cgccgcccgg    60
ccacaggtgc agctgcagca gtccggccct ggcctggtga agccttctca gacactgagc    120
ctgacctgtg ccatctccgg cgactctgtg agctccaact ctgccgtgtg gaattggatc    180
agacagtccc cctctagagg cctggagtgg ctgggctgga catactatcg gagcaagtac    240
tataacgact acgccgtgag cctgaagtcc agaatcacaa tcaaccctga taccagcaag    300
aatcagttct ccctgcagct gaacagcctg acaccagagg ataccgccgt gtactattgc    360
accaggggcg gaatcgtggg cgcccctgac ggctttgata tctggggcca gggcacaatg    420
gtgaccgtgt ctagcggagg aggaggcagc ggaggaggag gctccggagg cggcggctct    480
ggcggcggcg gcagccagtc cgccctgaca cagccacctt ctgccagcgg aacacccggc    540
cagcgcgtga ccatctcctg ttctggcagc aactccaata tcggctccaa ccctatcaat    600
tggtaccagc agctgccagg cacagccccc aagctgctga tctatagcaa caatcagagg    660
ccttccggcg tgccagaccg cttctctggc agcaagtccg gcacctctgc cagcctggca    720
atctccggac tgcagtctga ggacgaggcc gattactatt gcgcagcatg ggacgatagc    780
ctgaacggac acgtgtttgg cacaggcacc aaggtgaccg tgctgaccac aacccccgcc    840
cctaggccac ctaccccagc acctacaatt gctagtcagc cactgtcact gcgaccagag    900
gcatgtcgac ctgcagctgg aggagcagtg catacaaggg gactggactt tgcctgcgat    960
atctacattt gggctcctct ggcaggaaca tgtggcgtgc tgctgctgag cctggtcatc    1020
actctgtact gcaagcgagg ccggaagaaa ctgctgtata ttttcaaaca gcccttatg    1080
cgacctgtgc agaccacaca ggaggaagat gggtgctcct gtcggttccc cgaggaagag    1140
gaaggaggct gtgagctgcg ggtcaagttt tccagatctg cagacgcccc tgcttaccag    1200
cagggccaga accagctgta taacgagctg aatctggggc ggagagagga atacgacgtg    1260
ctggataaaa ggcgcgggag agacccagaa atggggggaa agccacgacg gaaaaacccc    1320
caggagggac tgtacaatga actgcagaag gataaaatgg cagaggccta ttccgaaatc    1380
gggatgaagg gagaaagaag gcgaggcaaa ggacacgacg gactgtacca ggggctgtct    1440
accgccacaa aggacaccta tgatgctctg catatgcagg cactgccacc cagg          1494

SEQ ID NO: 604          moltype = DNA   length = 1470
FEATURE                 Location/Qualifiers
source                  1..1470
                        mol_type = other DNA
                        organism = synthetic construct
                        note = Description of Artificial Sequence: Synthetic
                         polynucleotide
SEQUENCE: 604
atggcactgc ctgtgacagc cctgctgctg ccactggccc tgctgctgca cgccgcccgg    60
```

-continued

```
ccccaggtgc agctgcagga gagcggccca ggcctggtga agccaagcga gaccctgtcc    120
ctgacatgta ccgtgtctgg cggcagcatc agctcctact attggtcctg gatcagacag    180
tctcctggca agggcctgga gtggatcggc tacgtgtact attccgacat caccaactat    240
aatccatccc tgaagtctag agtgacaatc tctgtggata ccagcaagaa ccagttcagc    300
ctgaacctga acagcgtgac agccgccgac accgccttct acttttgcgc caggatcggc    360
gtggccggct tctactttga ttattgggc  cagggcacac tggtgaccgt gtctagcggc    420
ggcggcggct ctgaggagg  aggcagcggc ggaggaggct ccggcggcgg cggctctgag    480
atcgtgctga cacagagccc agacaccctg agcctgtccc ctggcgagag ggccacactg    540
tcctgtaggg catctcagag cgtgtcccgg agatacctgg ctggtatca  gcagaagcct    600
ggccaggcac ctcgcctgct gatctacgga gcatcctctc gggccacagg catccccgac    660
agattctctg gcagcggctc cggaaccgac ttcaccctga ccatctctag gctggagcca    720
gaggatttcg aggtgtacta ttgccagcag tatggcacat ccccaatcac ctttggccag    780
ggaacccgcc tggagatcaa gaccacaacc cctgcccta  ggccacctac cccagcacct    840
acaattgcta gtcagccact gtcactgcga ccagagcat  gtcgacctgc agctggagga    900
gcagtgcata caaggggact ggactttgcc tgcgatatct acatttgggc tcctctggca    960
ggaacatgtg gcgtgctgct gctgagcctg gtcatcactc tgtactgcaa gcgaggccgg   1020
aagaaactgc tgtatatttt caaacagccc tttatgcgac ctgtgcagac cacacaggag   1080
gaagatgggt gctcctgtcg gttccccgag gaagaggaag gaggctgtga gctgcgggtc   1140
aagtttttcca gatctgcaga cgcccctgct taccagcagg gccagaacca gctgtataac   1200
gagctgaatc tggggcggag agaggaatac gacgtgctgg ataaaaggcg cgggagagac   1260
ccagaaatgt ggggggaaagcc acgacggaaa aaccccagg agggactgta caatgaactg   1320
cagaaggata aaatggcaga ggcctattcc gaaatcggga tgaagggaga agaaggcga    1380
ggcaaaggac acgacggact gtaccagggg ctgtctaccg ccacaaagga cacctatgat   1440
gctctgcata tgcaggcact gccacccagg                                     1470

SEQ ID NO: 605          moltype = DNA  length = 1494
FEATURE                 Location/Qualifiers
source                  1..1494
                        mol_type = other DNA
                        organism = synthetic construct
                        note = Description of Artificial Sequence: Synthetic
                        polynucleotide
SEQUENCE: 605
atggccctgc cagtgaccgc cctgctgctg ccactggccc tgctgctgca cgccgcccgg    60
ccacagatcc agctgcagca gtccggccct ggcctggtga agcctagcca gacactgtcc   120
ctgacctgcg ccatctctgg cgacagcgtg agctccaact ctgccgtgtg gaattggatc   180
aggcagtccc catctcgcgg cctggagtgg ctgggaagga catactatag aagcaagtgg   240
tacaacgact atgccgtgtc cgtgaagtct aggatcacaa tcaagcctga taccgccaag   300
aaccagttct ccctgcagct gaacagcgtg acaccagagg ataccgccgt gtactattc    360
acccgcggcg gaatcgtggg cgcccctgac gcctttgata tctggggcca gggcacaatg    420
gtgaccgtgt ctagcggagg aggaggcagc ggaggaggag gctccggagg cggcggctct    480
ggcggcggc  gcagccagtc cgtgctgaca cagcccccctt ctgccagcgg aacacccggc    540
cagcggtga ccatctcctg ctctggctcc tctagcaaca tcggctccga ccctatcaat    600
tggtaccagc aggtgccagg cacagccccc aagctgctga tctatagcaa caatcagcgg    660
ccttccggcg tgccagatag attcagcggc tccaagtctg gcaccagcgc ctccctggca    720
atctctgac  tgcagagcga ggacgaggcc gattactatt gtgccgcctg ggacgatagc    780
ctgaatggct acgtgtttgg cacaggcacc aaggtgaccg tgctgaccac aacccccgcc    840
cctaggccac ctacccccagc acctacaatt gctagtcagc cactgtcact gcgaccagag    900
gcatgtgcac ctgcagctgg aggagcagtg catacaaggg gactggactt tgcctgcgat    960
atctacattt gggctcctct ggcaggaaca tgtggcgtgc tgctgctgag cctggtcatc   1020
actctgtact gcaagcgagg ccggaagaaa ctgctgtata tttttcaaaca gcccttttatg   1080
cgacctgtgc agaccacaca ggaggaagat gggtgctcct gtcggttccc cgaggaagag   1140
gaaggaggct gtgagctgcg cggtcaagttt tccagatctg cagacgcccc tgcttaccag   1200
cagggccaga accagctgta taacgagctg aatctggggc ggagagagga atacgacgtg   1260
ctggataaaa ggcgcgggag agacccagaa atggggggaa agcccacgacg gaaaaaccc    1320
caggagggac tgtacaatga actgcagaag gataaaatgg cagaggcctta ttccgaaatc   1380
gggatgaagg gagaaagaag gcgaggcaaa ggacacgacg gactgtacca ggggctgtct   1440
accgccacaa aggacaccta tgatgctctg catatgcagg cactgccacc cagg          1494

SEQ ID NO: 606          moltype = DNA  length = 1494
FEATURE                 Location/Qualifiers
source                  1..1494
                        mol_type = other DNA
                        organism = synthetic construct
                        note = Description of Artificial Sequence: Synthetic
                        polynucleotide
SEQUENCE: 606
atggccctgc cagtgaccgc cctgctgctg ccactggccc tgctgctgca cgccgcccgg    60
ccacaggtgc agctgcagca gagcggccct ggcctggtga agcctagcga gacactgtcc   120
ctgacctgtg ccatctctgg cgacagcgtg agctccaaca gcgccacatg gaattggatc   180
aggcagtccc catctcgcgg cctggagtgg ctgggacgga cctactatag atccgagtgg   240
tacaacgact atgccgtgtc cgtgaagtct cggatcacaa tcaaccctga tacctccaag   300
aatcacctgt ctctgcacct gaatagcgtg acaccagagg ataccgccgt gtactattgc   360
gcaggaggag gaatcgtggg cgcccctgac ggattcgacg tgtggggcca gggcacaatg    420
gtgaccgtgt ctagcggagg aggaggctcc ggaggaggag gctctctgcg cggcggcagc   480
ggaggcggcg gcagccagtc cgtgctgaca cagccaccctt ctgccagcgg aacacccggc    540
cagagggtga ccatctcctg ttctggctcc tctagcaaca tcggcagcga ccctgtgatc   600
tggtaccagc agctgccacg cacagccccc aagctgctga tctattccaa caatcagcgg    660
ccttctggcg tgccagatag attcagcggc tccaagtctg gcaccagcgc ctccctggca    720
```

```
atctctggac tgcagagcga ggacgaggcc gattactatt gcgccgcctg ggacgattcc    780
ctgaatggct acgtgtttgg cacaggcacc aaggtgaccg tgctgaccac aaccccgcc    840
cctaggccac ctaccccagc acctacaatt gctagtcagc cactgtcact gcgaccagag    900
gcatgtcgac ctgcagctgg aggagcagtg catacaaggg gactggactt tgcctgcgat    960
atctacattt gggctcctct ggcaggaaca tgtggcgtgc tgctgctgag cctggtcatc    1020
actctgtact gcaagcgagg ccggaagaaa ctgctgtata ttttcaaaca gccctttatg    1080
cgacctgtgc agaccacaca ggaggaagat gggtgctcct gtcggttccc cgaggaagag    1140
gaaggaggct gtgagctgcg ggtcaagttt tccagatctg cagacgcccc tgcttaccag    1200
cagggccaga accagctgta taacgagctg aatctggggc ggagagagga atacgacgtg    1260
ctggataaaa ggcgcgggag agacccagaa atgggggggaa agccacgacg gaaaaacccc    1320
caggagggac tgtacaatga actgcagaag gataaaatgg cagaggccta ttccgaaatc    1380
gggatgaagg gagaaagaag gcgaggcaaa ggacacgacg gactgtacca ggggctgtct    1440
accgccacaa aggacaccta tgatgctctg catatgcagg cactgccacc cagg    1494
```

SEQ ID NO: 607            moltype = DNA  length = 1494
FEATURE                   Location/Qualifiers
source                    1..1494
                          mol_type = other DNA
                          organism = synthetic construct
                          note = Description of Artificial Sequence: Synthetic
                          polynucleotide
SEQUENCE: 607

```
atggcactgc cagtgacagc cctgctgctg ccactggccc tgctgctgca cgccgcccgg    60
ccacaggtgc agctgcagca gagcggccct ggcctggtga agcctagcca gacactgtcc    120
ctgacctgtg ccatctctgg cgacagcgtg agctccaaca gcgccacctg gaattggatc    180
aggcagtccc catctacagg actggagtgg ctggcacgga cctactatag atccaagtgg    240
tacaacgact atgaggtgtc cgtgaagtct cagatcacaa tcaaccctga tacctccaag    300
aatcagttct ctctgcagct gaatagcgtg acaccagagg ataccgccgt gtactattgc    360
gccagaggcg gaatcgtggg cgcccctgac gcctttgata tctgggggcca gggcacaatg    420
gtgaccgtgt ctagcggagg aggaggctcc ggaggaggag gctctggcgg cggcggcagc    480
ggaggcggcg gcagccagtc cgtgctgaca cagcccccct ctgccagcgg aacacccggc    540
cagggagtga ccatctcctg ttctggctcc tctagcaaca tcggcagcaa ccctgtgaat    600
tggtaccagc agctgccagg cacagccccc aagctgctga tctattccaa caatcagagg    660
ccttctggcg tgccagaccg cttcagcgat tccaagtctg gcaccagcgc ctccctggca    720
atctctggac tgcagagcga ggacgaggcc gattactatt gctccgcctg ggacgattgg    780
ctgaatggct acgtgtttgg cacaggcacc aaggtgaccg tgctgaccac aaccccgcc    840
cctaggccac ctaccccagc acctacaatt gctagtcagc cactgtcact gcgaccagag    900
gcatgtcgac ctgcagctgg aggagcagtg catacaaggg gactggactt tgcctgcgat    960
atctacattt gggctcctct ggcaggaaca tgtggcgtgc tgctgctgag cctggtcatc    1020
actctgtact gcaagcgagg ccggaagaaa ctgctgtata ttttcaaaca gccctttatg    1080
cgacctgtgc agaccacaca ggaggaagat gggtgctcct gtcggttccc cgaggaagag    1140
gaaggaggct gtgagctgcg ggtcaagttt tccagatctg cagacgcccc tgcttaccag    1200
cagggccaga accagctgta taacgagctg aatctggggc ggagagagga atacgacgtg    1260
ctggataaaa ggcgcgggag agacccagaa atgggggggaa agccacgacg gaaaaacccc    1320
caggagggac tgtacaatga actgcagaag gataaaatgg cagaggccta ttccgaaatc    1380
gggatgaagg gagaaagaag gcgaggcaaa ggacacgacg gactgtacca ggggctgtct    1440
accgccacaa aggacaccta tgatgctctg catatgcagg cactgccacc cagg    1494
```

SEQ ID NO: 608            moltype = DNA  length = 1467
FEATURE                   Location/Qualifiers
source                    1..1467
                          mol_type = other DNA
                          organism = synthetic construct
                          note = Description of Artificial Sequence: Synthetic
                          polynucleotide
SEQUENCE: 608

```
atggcactgc cagtgacagc cctgctgctg cctctggccc tgctgctgca cgccgccagg    60
cctcaggtgc agctgcagga gtccggccct ggcctggtga agccatccga gaccctgtct    120
ctgacatgca ccgtgtccgg cgattctatc aacaattact tttggagctg gatcagacag    180
cccccctggca agggactgga gtggatcggc tacttctatc acagggggcgg caacaattat    240
aacccaagcc tgaagtcccg cgtgacaatc agcatcgaca cctccaagaa tcagttcagc    300
ctgaacctga cagcgtgac aagcgccgat accgccgtgt actattgtgc ccggctggcc    360
ctggccggct tcttttttcga ctactggggc cagggcacac tggtgaccgt gagctccgga    420
ggaggaggct ccggcggcgg aggctctggc ggcggcggcc ccgaggcggc cggcagcgac    480
atccagatga cacagtctcc aagcaccctg tccgcctctg tgggcgatag ggtgacaatc    540
acctgcagag ccagccagtc catctctagc tggctggcct ggtaccagca gaagccaggc    600
aaggccccca agctgctgat ctataaggcc tcctctctgg agtctggcgt gccaagccgg    660
ttttctggca gcggctccgg cacagagttc acactgacca tcagctccct gcagcccgac    720
gattttgcca cctactattg tcagcagtac aactcttata gcagaacatt cggccagggc    780
accaaggtgg agatcaagac cacaacccct gcccctaggc cacctacccc agcacctaca    840
attgctagtc agccactgtc actgcgacca gaggcatgtc gacctgcagc tggaggagca    900
gtgcatacaa ggggactgga ctttgcctgc gatatctaca tttgggctcc tctggcagga    960
acatgtggcg tgctgctgct gagcctggtc atcactctgt actgcaagcg aggccggaag    1020
aaactgctgt atattttcaa acagcccttt atgcgacctg tgcagaccac acaggaggag    1080
gatgggtgct cctgtcggtt ccccgaggaa gaggaaggag gctgtgagct gcgggtcaag    1140
ttttccagat ctgcagacgc ccctgcttac cagcagggcc agaaccagct gtataacgag    1200
ctgaatctgg ggcggagaga ggaatacgac gtgctggata aaaggcgcgg gagagaccca    1260
gaaatggggg gaaagccacg acggaaaaac ccccaggagg gactgtacaa tgaactgcag    1320
aaggataaaa tggcagaggc ctattccgaa atcgggatga gggagaaag aaggcgaggc    1380
```

-continued

```
aaaggacacg acggactgta ccaggggctg tctaccgcca caaaggacac ctatgatgct  1440
ctgcatatgc aggcactgcc acccagg                                      1467

SEQ ID NO: 609              moltype = DNA  length = 1491
FEATURE                    Location/Qualifiers
source                     1..1491
                           mol_type = other DNA
                           organism = synthetic construct
                           note = Description of Artificial Sequence: Synthetic
                           polynucleotide
SEQUENCE: 609
atggcactgc cagtgacagc cctgctgctg ccactggccc tgctgctgca cgccgcccgg  60
ccacaggtgc ccctggtgca gtccggagca gaggtgaaga agcccggcag ctccgtgaag  120
gtgtcttgca aggccagcgg cggcacattc agcacctaca gcatctcctg ggtgcggcag  180
gcccctggcc agggactgga gtggatggga ggaatcatcc caatcttcgg caccacaaac  240
tacgcccaga agtttcaggg cagagtgaca atcaccgccg acaagtctac aagcaccgcc  300
tatatggagc tgtctagcct gaggtctgag gacaccgccg tgtactattg tgcccgcgat  360
ggcgagggca gctactatta ctattacgga atggacgtgt ggggacaggg aaccacagtg  420
acagtgtcct ctggaggagg aggcagcggc ggaggaggct ccggaggcgg cggctctggc  480
ggcggcggct cccagtctgt gctgacccag ccacctagcg cctccggaac acccggccag  540
agggtgacca tctcttgcag cggcagctcc tctaacatcg gctccaatta cgtgtactgg  600
tatcagcagc tgcctggcac agccccaaag ctgctgatct acagcaacaa tcagcggccc  660
tccggcgtgc ctgacagatt ctccggctct aagagcggca cctccgcctc tctggcaatc  720
tccggactgc gctctgagga cgaggcagat tattactgtg cagcatggga cgatagcctg  780
tccggatggg tgtttggagg aggaacaaag ctgaccgtgc tgaccacaac ccctgcccct  840
aggccaccta ccccagcacc tacaattgct agtcagccac tgtcactgcg accagaggca  900
tgtcgacctg cagctggagg agcagtgcat acaaggggac tggactttgc ctgcgatatc  960
tacatttggg ctcctctggc aggaacatgt ggcgtgctgc tgctgagcct ggtcatcact  1020
ctgtactgca agcgaggccg gaagaaactg ctgtatattt tcaaacagcc ctttatgcga  1080
cctgtgcaga ccacacagga ggaagatggg tgctcctgtc ggttccccga ggaagaggaa  1140
ggaggctgtg agctgcgggt caagttttcc agatctgcag acgcccctgc ttaccagcag  1200
ggccagaacc agctgtataa cgagctgaat ctggggcgga gagaggaata cgacgtgctg  1260
gataaaaggc gcgggagaga cccagaaatg ggggggaaagc cacgacgaa aaaccccag  1320
gagggactgt acaatgaact gcagaaggat aaaatggcag aggcctattc cgaaatcggg  1380
atgaagggag aaagaaggcg aggcaaagga cacgacggac tgtaccaggg gctgtctacc  1440
gccacaaagg acacctatga tgctctgcat atgcaggca ctgccacccag g            1491

SEQ ID NO: 610              moltype = DNA  length = 1482
FEATURE                    Location/Qualifiers
source                     1..1482
                           mol_type = other DNA
                           organism = synthetic construct
                           note = Description of Artificial Sequence: Synthetic
                           polynucleotide
SEQUENCE: 610
atggcactgc cagtgacagc cctgctgctg ccactggccc tgctgctgca cgccgccaga  60
cccgaggtgc agctggtgga gtccggagga ggactggtgc agcctggcgg ctccctgagg  120
ctgtcttgcg cagcaagcgg cttcacctttt agctcctaca gcatgaactg ggtgagacag  180
gcccccggca agggactgga gtgggtgtct tatatctcta gctcctctag cacaatctac  240
tatgccgaca gcgtgaaggg ccggttcacc atctctagag ataacgccaa gaatagcctg  300
tacctgcaga tgaacagcct gagggacgag gatacagccg tgtactattg tgcccgcgat  360
aaggagcgga gatactatta ctatggcatg gacgtgtggg gccagggcac cacagtgacc  420
gtgtcctctg gcggcggcgg ctccggaggc ggcggctctg gaggaggagg cagcggcgga  480
ggaggctccg agatcgtgct gacacagtcc cctgacaccc tgtctctgag cccaggcgag  540
agggccacac tgtcttgcag ggcatcccag tctgtgagca ccacct ggcctggtat  600
cagcagaagc ctggccaggc ccccagactg ctgatctacg agcaagcac ccgggccaca  660
ggcatccctg acagattctc cggctctggc agcggaaccg acttcaccct gaccatctcc  720
aggctggagc cagaggattt tgccgtgtac tattgtcagc agttcggcac aagcccaatc  780
acctttggcc agggaacccg cctggagatc aagaccacaa cccccagccc taggccacct  840
accccagcac ctacaattgc tagtcagcca ctgtcactgc gaccagaggc atgtcgacct  900
gcagctggag gagcagtgca tacaaggga ctggactttg cctgcgatat ctacatttgg  960
gctcctctgg caggaacatg tggcgtgctg ctgctgagcc tggtcatcac tctgtactgc  1020
aagcgaggcc ggaagaaact gctgtatatt ttcaaacagc cctttatgcg acctgtgcag  1080
accacacagg aggaagatgg gtgctcctgt cggttccccg aggaagagga aggaggctgt  1140
gagctgcggg tcaagttttc cagatctgca gacgcccctg cttaccagca gggccagaac  1200
cagctgtata cgagctgaa tctggggcgg agagaggaat acgacgtgct ggataaaagg  1260
cgcgggagag acccagaaat gggggggaaag ccacgacgga aaaacccca ggagggactg  1320
tacaatgaac tgcagaagga taaaatggca gaggcctatt ccgaaatcgg gatgaaggga  1380
gaaagaaggc gaggcaaagg acacgacgga ctgtaccagg ggctgtctac cgccacaaag  1440
gacacctatg atgctctgca tatgcaggca ctgccaccca gg                    1482

SEQ ID NO: 611              moltype = DNA  length = 1494
FEATURE                    Location/Qualifiers
source                     1..1494
                           mol_type = other DNA
                           organism = synthetic construct
                           note = Description of Artificial Sequence: Synthetic
                           polynucleotide
SEQUENCE: 611
```

```
atggcactgc cagtgacagc cctgctgctg ccactggccc tgctgctgca cgccgccaga   60
ccccaggtgc agctgcagca gagcggccct ggcctggtga agcctagcca gaccctgtcc  120
ctggcctgtg ccatctctgg cgacagcgtg agctccaact ccgccatctg gaattggatc  180
aggcagtccc cttctcgcgg cctggagtgg ctgggaggaa catactatcg gtctatgtgg  240
tacaacgact atgccgtgtc cgtgaagtct agaatccaca tcaaccctga tacctccaag  300
aatcagctgt ctctgcagct gaatagcgtg acaccagagg ataccgccgt gtactattgc  360
agccggggcg gaatcgtggg agtgccagac gccttcgata tctggggcca gggcacaatg  420
gtgaccgtgt ctagcggagg aggaggctcc ggaggaggag gctctggcgg cggcggcagc  480
ggaggcggcg gcagccagtc cgtgctgacc cagccacctt ctgccagcgg aacacccggc  540
cagcgggtga ccatctcctg ttctggctcc tctagcaaca tcggcagcaa cacagccaat  600
tggtaccagc agctgccagg caccgcaccc aggctgctga tctatcggaa caatcagaga  660
ccttccggag tgccagaccg cttcagcggc tccaagtctg gcacaagcgc ctccctggcc  720
atctctggcc tgcagagcga ggacgaggcc gattactatt gcgccgcctg ggacgatagc  780
ctgaatggct acgtgtttgg cacaggcacc aaggtgaccg tgctgaccac aaccctgcc  840
cctaggccac ctaccccagc acctacaatt gctagtcagc cactgtcact gcgaccagag  900
gcatgtcgac ctgcagctgg aggagcagtg catacaaggg gactggactt tgcctgcgat  960
atctacattt gggctcctct ggcaggaaca tgtggcgtgc tgctgctgag cctggtcatc 1020
actctgtact gcaagcgagg ccggaagaaa ctgctgtata ttttcaaaca gccctttatg 1080
cgacctgtgc agaccacaca ggaggaagat gggtgctcct gtcggttccc cgaggaaag  1140
gaaggaggct gtgagctgcg ggtcaagttt tccagatctg cagacgcccc tgcttaccag 1200
cagggccaga accagctgta taacgagctg aatctggggc ggagagagga atacgacgtg 1260
ctggataaaa ggcgcgggag agacccagaa atggggggaa aaacacgacg gaaaaacccc 1320
caggagggac tgtacaatga actgcagaag gataaaatgg cagaggccta ttccgaaatc 1380
gggatgaagg gagaaagaag gcgaggcaaa ggacacgacg gactgtacca ggggctgtct 1440
accgccacaa aggacaccta tgatgctctg catatgcagg cactgccacc cagg          1494
```

SEQ ID NO: 612          moltype = DNA  length = 1476
FEATURE                 Location/Qualifiers
source                  1..1476
                        mol_type = other DNA
                        organism = synthetic construct
                        note = Description of Artificial Sequence: Synthetic
                        polynucleotide
SEQUENCE: 612

```
atggcactgc ctgtgacagc cctgctgctg ccactggccc tgctgctgca cgccgcccgg   60
ccacaggtgc agctgcagga gtccggccca ggcctggtga agccatctga gacactgagc  120
ctgacctgca acgtgtctga tggcagcatc agctcctact attggacctg gatcagacag  180
cccctggca agggactgga ctggatcggc tatatcttct acagcggcac cacaaactat  240
aatccctccc tgaagtctag agtgacaatc tccctggaca cctctaagaa tcagtttct  300
ctgaagctga caagcatgac cgccgccgat acagccgtgt actattgcgc caggatcagc  360
gagaagtcct tctattttga ctactggggc agggcacac tggtgaccgt gtctagcgga  420
ggaggaggct ccgaggagg aggctctggc ggcggcggca gcgaggcgg cggctcccag  480
tctgtgctga cccagccacc aagcgcctcc ggaacacctg gccagcgcgt gaccatctct  540
tgtagcggct cctctagcaa catcggctcc aattacgtgt attggtacca gcagctgcct  600
ggcacagccc caaagctgct gatctactcc aacaatcagc ggcccagcgg cgtgcctgat  660
agattctccg gctctaagag cggcacctcc gcctctctgg caatcagcgg actgaggtcc  720
gaggacgagg cagattacta ttgtgcacca tgggacgata gcgtgccggg ccgcgtgttt  780
ggaggaggaa caaagctgac cgtgctgacc acaaccctg ccctaggcc acctaccca  840
gcacctacaa ttgctagtca gccactgtca ctgcgaccag aggcatgtcg acctgcagct  900
ggaggagcag tgcatacaag gggactggac tttgcctgcg atatctacat ttgggctcct  960
ctggcaggaa catgtggcgt gctgctgctg agcctggtca tcactctgta ctgcaagcga 1020
ggccggaaga aactgctgta tattttcaaa cagccctta tgcgacctgt gcagaccaca 1080
caggaggaag atgggtgctc ctgtcggttc cccgaggaag aggaaggagg ctgtgagctg 1140
cgggtcaagt tttccagatc tgcagacgcc cctgcttacc agcagggcca gaaccagctg 1200
tataacgagc tgaatctggg gcggagagag gaatacgacg tgctggataa aaggcgcggg 1260
agagacccag aaatggggggg aaagccacga cggaaaaacc cccaggaggg actgtacaat 1320
gaactgcaga aggataaaat ggcagaggcc tattccgaaa tcgggatgaa gggagaaaga 1380
aggcgaggca aaggacacga cggactgtac caggggctgt ctaccgccac aaaggacacc 1440
tatgatgctc tgcatatgca ggcactgcca cccagg                             1476
```

SEQ ID NO: 613          moltype = DNA  length = 1479
FEATURE                 Location/Qualifiers
source                  1..1479
                        mol_type = other DNA
                        organism = synthetic construct
                        note = Description of Artificial Sequence: Synthetic
                        polynucleotide
SEQUENCE: 613

```
atggccctgc cagtgaccgc cctgctgctg ccactggccc tgctgctgca cgccgccagg   60
ccccaggtgc agctggtgca gagcggagca gaggtgaagc gccctggcgc aagcgtgaag  120
gtgtcctgca aggcctctgg ctatacattc accagctact atatccactg ggtgaggcag  180
gccctggcc agggactgga gtggatgggc gtgatcgtgc catccggcgg ctctatcagc  240
tatgcccaga gtttcaggg cagggtgaca atgacccgcg acacaagcac caacatcgtg  300
tacatggagc tgagctccct gcggtccgag gatacagccg tgtactattg tgccagagac  360
agatactatg gcgattacta ttacggactg gacgtgtggg gacagggaac cacagtgacc  420
gtgtctagcg gcggcggcgg ctctggagga ggaggcagcg gcggaggagg ctccggcggc  480
ggcggctctg acatccagat gacacagtcc ccttcctctc tgtccgcctc tgtgggcgat  540
cgggtgacaa tcacctgcag agcctctcag ggcatcaaca tttcctggc ctggtttcag  600
cagaagcccg gcaaggcccc taagtccctg atctacgcag caagctccct gcagagcgga  660
```

-continued

```
gtgccatcca agttcagcgg ctccggctct ggcacagact ttacactgac catccggtct   720
ctgcagccag aggatttcgc cacctattac tgtcagcact ataatagcta ccccatcaca   780
tttggccagg gcaccagact ggagatcaag accacaaccc ccgcccctag gccacctacc   840
ccagcaccta caattgctag tcagccactg tcactgcgac cagaggcatg tcgacctgca   900
gctggaggag cagtgcatac aaggggactg gactttgcct gcgatatcta catttgggct   960
cctctggcag aacatgtggg cgtgctgctg ctgagcctgg tcatcactct gtactgcaag  1020
cgaggccgga agaaactgct gtatattttc aaacagccct ttatgcgacc tgtgcagacc  1080
acacaggagg aagatgggtg ctcctgtcgg ttccccgagg aagaggaagg aggctgtgag  1140
ctgcgggtca agttttccag atctgcagac gcccctgctt accagcaggg ccagaaccag  1200
ctgtataacg agctgaatct ggggcggaga gaggaatacg acgtgctgga taaaaggcgc  1260
gggagagacc cagaaatggg gggaaagcca cgacggaaaa accccagga gggactgtac  1320
aatgaactgc agaaggataa aatggcagag gcctattccg aaatcgggat gaagggagaa  1380
agaaggcgag gcaaaggaca cgacggactg taccaggggc tgtctaccgc cacaaaggac  1440
acctatgatg ctctgcatat gcaggcactg ccacccagg              1479
```

SEQ ID NO: 614          moltype = DNA  length = 1470
FEATURE                 Location/Qualifiers
source                  1..1470
                        mol_type = other DNA
                        organism = synthetic construct
                        note = Description of Artificial Sequence: Synthetic
                          polynucleotide
SEQUENCE: 614

```
atggcactgc cagtgacagc cctgctgctg cctctggccc tgctgctgca cgccgcccgg   60
ccacaggtgc acctgcagga gtctggccct ggcctggtga agccatctga gacactgagc  120
ctgacatgta ccgtgagcgg cggcagcatc tcccactact attggacctg gatcaggcag  180
cccctggca agggactgga gtggatcggc tacatctact attccggcat caccaacttc  240
tctcctagcc tgaagtctcg cgtgtccatc tctgtggaca gctccaagaa tcagttcagc  300
ctgaacctga cagcgtgac agccgccgat accgccgtgt actattgcgc cggcatctcc  360
ctggccggct tctactttga ctattgggtg cagggcacac tggtgaccgt gtctagcgga  420
ggaggaggca gcggaggagg aggctccgga ggcggcggct ctggcggcgg cggcagcgga  480
atcgtgctga cacagagccc aggcaccctg agcctgtccc ccggcgagcg ggccaccctg  540
tcctgtagag cctctcagag cgtgtcccgg tcttacctgg cctggtatca gcagaagcca  600
ggccaggccc ccagactgct gatctatgga gcatcctcta gggcccacagg agtgccagac  660
cgcttcagcg gctccggctc tggaaccgac ttcaccctga ccatcagccg gctggagcct  720
gaggatttcg ccgtgtttta ctgccagcag tatagcatct ccccactgac attcggcggc  780
ggcaccaagt ggagatcaa gaccacaacc cctgcccta ggccacctac cccagcacct  840
acaattgcta gtcagccact gtcactgcga ccagaggcgt gtcgacctgc agctggagga  900
gcagtgcata caagggggact ggactttgcc tgcgatatct catttgggc tcctctgcag  960
ggaacatgtg gcgtgctgct gctgagcctg gtcatcactc tgtactgcaa gcgaggccgg  1020
aagaaactgc tgtatatttt caaacagccc tttatgcgac ctgtgcagac cacacaggag  1080
gaagatgggt gctcctgtcg gttccccgag gaagaggaag gaggctgtga gctgcgggtc  1140
aagttttcca gatctgcaga cgcccctgct taccagcagg gccagaacca gctgtataac  1200
gagctgaatc tggggcggag agaggaatac gacgtgctgg ataaaaggcg cgggagagac  1260
ccagaaatgg gggggaaagcc acgacggaaa aaccccagg agggactgta caatgaactg  1320
cagaaggata aaatggcaga ggcctattcc gaaatcggga tgaagggaga agaaggcga  1380
ggcaaaggac acgacggact gtaccagggg ctgtctaccg ccacaaagga cacctatgat  1440
gctctgcata tgcaggcact gccacccagg              1470
```

SEQ ID NO: 615          moltype = DNA  length = 1479
FEATURE                 Location/Qualifiers
source                  1..1479
                        mol_type = other DNA
                        organism = synthetic construct
                        note = Description of Artificial Sequence: Synthetic
                          polynucleotide
SEQUENCE: 615

```
atggcactgc ctgtgacagc cctgctgctg ccactggccc tgctgctgca cgccgcccgg   60
ccccaggtgc agctgcagga gtccggccca ggcctggtga agccaagcga gaccctgtcc  120
ctgacatgca ccgtgtccgg cgtgtctatc agctcctact attggagctg gatcaggcag  180
cccccctggca agggactgga gtggatcgc tacatctact attccggcaa caccaattat  240
tctcctagcc tgaagtctcg cgtgacaatc tctgtggaca ccagcaagga tcagctgtct  300
ctgaagctgt ctagcgtgac agccgccgac accgccgtgt actattgcac aaggggcggc  360
agcggaacca tcgacgtgtt cgatatctgg ggacaggaa ccatggtggc cgtgtcctct  420
ggcggcggcg gctccggagg cggcggctct ggaggaggag gcagcggcgg aggaggctcc  480
cagtctgtgc tgacacagcc accaagcgtg tccgcgccc caggccagaa ggtgaccatc  540
tcttgtagcg gcagctcctc taacatcggc aacaattacg tgtcctggta tcagcagctg  600
cctggcacag ccccaaagct gctgatctac gacaacaata agcggcccag cggcatccct  660
gatagattct ccggctctaa gagcggcaca tccgccacc tgggcatcac aggactgcag  720
accggcgacg aggcagatta ctattgtgag acctgggata gctccctgag cgccgtggtg  780
tttggaggag gcacaaagct gaccgtgctg accacaaccc ctgcccctag gccacctacc  840
ccagcaccta caattgctag tcagccactg tcactgcgac cagaggcatg tcgacctgca  900
gctggaggag cagtgcatac aagggggactg gactttgcct gcgatatcta catttgggct  960
cctctggcag aacatgtggg cgtgctgctg ctgagcctgg tcatcactct gtactgcaag  1020
cgaggccgga agaaactgct gtatattttc aaacagccct ttatgcgacc tgtgcagacc  1080
acacaggagg aagatgggtg ctcctgtcgg ttccccgagg aagaggaagg aggctgtgag  1140
ctgcgggtca agttttccag atctgcagac gcccctgctt accagcaggg ccagaaccag  1200
ctgtataacg agctgaatct ggggcggaga gaggaatacg acgtgctgga taaaaggcgc  1260
gggagagacc cagaaatggg gggaaagcca cgacggaaaa accccagga gggactgtac  1320
```

-continued

```
aatgaactgc agaaggataa aatggcagag gcctattccg aaatcgggat gaagggagaa  1380
agaaggcgag gcaaaggaca cgacggactg taccaggggc tgtctaccgc cacaaaggac  1440
acctatgatg ctctgcatat gcaggcactg ccacccagg                         1479

SEQ ID NO: 616          moltype = DNA  length = 1485
FEATURE                 Location/Qualifiers
source                  1..1485
                        mol_type = other DNA
                        organism = synthetic construct
                        note = Description of Artificial Sequence: Synthetic
                         polynucleotide
SEQUENCE: 616
atggcactgc ctgtgacagc cctgctgctg ccactggccc tgctgctgca cgccgcccgg  60
cctcaggtgc agctgcagca gagcggccca ggcctggtga agccatccca gacactgtct  120
ctgacctgcg ccatctccgg cgacaacgtg tccacaaatt ctgccgcctg gaactggatc  180
aggcagagcc catcccgcgg cctggagtgg ctgggctgga cctactatag gagcaagtgg  240
tacaatgact atgccgtgag cctgaagtcc cgcatcaaca tcaatccaga tacctccaag  300
aaccagttct ctctgcagct gaatagcgtg acacccgagg ataccgccgt gtactattgc  360
gcccggtggg tgaacagaga cgtgtttgat atctgggggcc agggcacaat ggtgaccgtg  420
agctccggag gaggaggctc cggcggcgga ggctctggcg gcggcggcag cggaggcggc  480
ggctctcaga gcgccctgac acagccagca tccgtgtctg gcagccctgg ccagagcatc  540
accatctcct gtacaggcac ctctagcgac gtgggctcat acaatctggt gtcttggtat  600
cagcagcacc ccggcaaggc ccctaagctg atgatctacg agggcagcaa gaggccatct  660
ggcgtgagca cagattctc cggctctaag agcggcaata cagcctctct gaccatcagc  720
ggactgcagg cagaggacga ggcagattac tattgctgtt cctatgccgg ctcctctacc  780
tgggtgtttg gcggcggcac aaagctgacc gtgctgacca caacccctgc ccctaggcca  840
cctacccccag cacctacaat tgctagtcag ccactgtcac tgcgaccaga ggcatgtcga  900
cctgcagctg gaggagcagt gcatacaagg ggactggact ttgcctgcga tatctacatt  960
tgggctcctc tggcaggaac atgtggcgtg ctgctgctga gcctggtcat cactctgtac  1020
tgcaagcgag gccggaagaa actgctgtat attttcaaac agcccttttat ggacctgtg  1080
cagaccacac aggaggaaga tgggtgctcc tgtcggttcc ccgaggaaga ggaaggaggc  1140
tgtgagctgc gggtcaagtt ttccagatct gcagacgccc ctgcttacca gcagggccag  1200
aaccagctgt ataacgagct gaatctgggg cggagagagg aatacgacgt gctggataaa  1260
aggcgcggga gacccagat aatgggggga aagccacg ggaaaaaccc ccaggaggga  1320
ctgtacaatg aactgcagaa ggataaaatg gcagaggcct attccgaaat cgggatgaaa  1380
ggagaaagaa ggcgaggcaa aggacacgac ggactgtacc aggggctgtc taccgccaca  1440
aaggacacct atgatgctct gcatatgcag gcactgccac ccagg                  1485

SEQ ID NO: 617          moltype = DNA  length = 1488
FEATURE                 Location/Qualifiers
source                  1..1488
                        mol_type = other DNA
                        organism = synthetic construct
                        note = Description of Artificial Sequence: Synthetic
                         polynucleotide
SEQUENCE: 617
atggccctgc cagtgaccgc cctgctgctg cccctggccc tgctgctgca cgccgccagg  60
ccccaggtgc agctggtgga gtccggagga ggagtggtgc agcctggccg gtctctgaga  120
ctgagctgcg cagcatccgg cttcaccttc agctcctacg gaatgcactg ggtgcggcag  180
accccctggca agggactgga gtgggtggcc gtgatctcct atgacggcaa ctctaattac  240
tatgccgata gcgtgaaggg caggttcaca atctctcgcg acaacagcaa gaataccctg  300
tacctgcaga tgaactctct gcgggccgag gacacagccg tgtactattg tgccagagat  360
ggcgccacag tgaccagcta ctattactat ggcatggacg tgtggggcca gggcaccaca  420
gtgaccgtgt ctagcggagg aggaggcagc ggaggaggag gctccggagg cggcggctct  480
ggcggcggcg gcagcgagat cgtgctgaca cagtcccctg gcaccctgag cctgtcccca  540
ggcgagcggg ccacactgtc ttgcagagcc tctcagagcg tgtccaggac ctacctggcc  600
tggtatcacc agaagcctgg ccaggcacct cgcctgctga tctacggagc atcctctagg  660
gccacaggca tcagcgaccg cttctctggc agcggctccg gaaccgactt caccctgacc  720
atctcccgac tggagcagga ggacttcgcc gtgtactatt gtcagcagta tggcacatcc  780
cccatcacct ttggccaggg caccagactg gagatcaaga ccacaacccc cgccccctagg  840
ccacctaccc cagcacctac aattgctagt cagccactgt cactgcgacc agaggcatgt  900
cgacctgcag ctggaggagc agtgcataca aggggactgg actttgcctg cgatatctac  960
atttgggctc tctggcagg aacatgtggc gtgctgctgc tgagcctggt catcactctg  1020
tactgcaagc gaggccggaa gaaactgctg tatattttca aacagcccct tatggacctg  1080
gtgcagacca cacaggagga agatgggtgc tcctgtcggt tccccgagga agaggaagga  1140
ggctgtgagc tgcgggtcaa gtttttccaga tctgcagacg cccctgctta ccagcagggc  1200
cagaaccagc tgtataacga gctgaatctg ggcggagag aggaatacga cgtgctggat  1260
aaaaggcgcg ggagagaccc agaaatgggg ggaaagccac gacggaaaaa ccccaggag  1320
ggactgtaca atgaactgca gaaggataaa atggcagagg cctattccga aatcgggatg  1380
aagggagaaa gaaggcgagg caaaggacac gacggactg accaggggct gtctaccgcc  1440
acaaaggaca cctatgatgc tctgcatatg caggcactgc cacccagg               1488

SEQ ID NO: 618          moltype = DNA  length = 1503
FEATURE                 Location/Qualifiers
source                  1..1503
                        mol_type = other DNA
                        organism = synthetic construct
                        note = Description of Artificial Sequence: Synthetic
                         polynucleotide
```

-continued

```
SEQUENCE: 618
atggcactgc ctgtgacagc cctgctgctg ccactggccc tgctgctgca cgccgccagg  60
ccccaggtgc agctgcagca gagcggccca ggcctggtga agccatctca gacactgagc 120
ctgacctgcg ccatctctgg cgacagcgtg agctccaact ccgccgtgtg gaattggatc 180
aggcagagcc cttcccgcgg cctggagtgg ctgggacgga cctactatag atctaagtgg 240
tacaacgact atgccgtgtc cgtgaagtct aggatcacaa tcaaccccga tacctcccgc 300
aatcagttct ctctgcagct gaatagcgtg acacctgagg ataccgccgt gtactattgc 360
gccagaggcg gaatcgtggg cgccccagac ggctttgata tctggggcca gggcacaatg 420
gtgaccgtgt ctagcggagg aggaggctcc ggaggaggag gctctggcgg cggcggcagg 480
ggaggcgggg gctccgacat cgtgatgaca cagagccctg attccctggc cgtgtctctg 540
ggcgagaggc aaccatcaa ctgtaagtcc tctcagagcg tgctggacag ctccaacaat 600
aacaattact tcgcctggta tcagcagaga cctggccagc ccctcacct gctgatctac 660
tgggcatcta gccgggagag cggagtgcca gacagattct ctggcagcgg ctccggcaca 720
gacttcaccc tgaccatctc ctctctgcag gccgaggatg tggccgtgta ctattgtcag 780
cagtactatt ccacaccata tacctttggc cagggcacca agctggagat caagaccaca 840
accccccgccc ctaggccacc taccccagca cctacaattg ctagtcagcc actgtcactg 900
cgaccagagg catgtcgacc tgcagctgga ggagcagtgc atacaagggg actggacttt 960
gcctgcgata tctacatttg ggctcctctg gcaggaacat gtggcgtgct gctgctgagc 1020
ctggtcatca ctctgtactg caagcgaggc cggaagaaac tgctgtatat tttcaaacag 1080
cccttatgc gacctgtgca gaccacacag gaggaagatg ggtgctcctg tcggttcccc 1140
gaggaagagg aaggaggctg tgagctgcgg gtcaagtttt ccagatctgc agacgcccct 1200
gcttaccagc agggccagaa ccagctgtat aacgagctga tctggggcg gagagaggaa 1260
tacgacgtgc tggataaaag cgcgcgggaga gacccagaaa tggggggaaa gccacgacgg 1320
aaaaaccccc aggagggact gtacaatgaa ctgcagaagg ataaaatggc agaggcctat 1380
tccgaaatcg ggatgaaggg agaaagaagg cgaggcaaag gacacgacgg actgtaccag 1440
gggctgtcta ccgccacaaa ggacacctat gatgctctgc atatgcaggc actgccaccc 1500
agg                                                              1503

SEQ ID NO: 619      moltype = DNA  length = 1485
FEATURE             Location/Qualifiers
source              1..1485
                    mol_type = other DNA
                    organism = synthetic construct
                    note = Description of Artificial Sequence: Synthetic
                    polynucleotide
SEQUENCE: 619
atggccctgc cagtgaccgc cctgctgctg ccactggccc tgctgctgca cgccgcccgg  60
ccacaggtgc agctgcagca gagcggccct ggcctggtga agcctagcca gacactgtcc 120
ctgacctgcg ccatctctgg cgacagcgtg agctccaaca ccacagcctg gaagtggac 180
agacagtccc cctctaaggg cctggagtgg ctgggctgga catactatag gtccaagtgg 240
tactatgact acaccgtgtc cgtgaagtct cgcatcacaa tcaaccccga tacctccaag 300
aatcagttct ctctgcagct gaatagcgtg acacctgagg ataccgccgt gtactattgc 360
gccaggtgga tcttccacga cgcctttgat atctggggcc agggcacaat ggtgaccgtg 420
tctagcggag gaggaggctc cggaggagga ggctctggcg gcggcggcag cggaggcggc 480
ggcagccagt ccgccctgac acagccacct tctgccagcg gaacacctgg ccagagagtg 540
accatctcct gttctggctc ctctagcaac atcggcagca acaccgtgaa ttggtaccag 600
cagctgccag gcacagcccc caagctgctg atctataccaa acaatcagag gccttccgga 660
gtgccagacc ggttcagcgg ctccaagtct ggcacaagcg cctccctggc catctctggc 720
ctgcagagcg aggacgaggc cgattatttc tgttccacct gggacgattc tctgaatgga 780
cccgtgttcg gaggaggaac aaagctgacc gtgctgacca caaccccagc ccctaggcca 840
cctaccccag cacctacaat tgctagtcag ccactgtcac tgcgaccaga ggcatgtcga 900
cctgcagctg gaggagcagt gcatacaagg ggactggact ttgcctgcga tatctacatt 960
tgggctcctc tggcaggaac atgtggcgtg ctgctgctga gcctggtcat cactctgtac 1020
tgcaagcgag gccggaagaa actgctgtat attttcaaac agccctttat gcgacctgtg 1080
cagaccacac aggaggaaga tgggtgctcc tgtcggttcc ccgaggaaga ggaaggaggc 1140
tgtgagctgc gggtcaagtt ttccagatct gcagacgccc ctgcttacca gcagggccag 1200
aaccagctgt ataacgagct gaatctgggg cggagagagg aatacgacgt gctggataaa 1260
aggcgcggga gagacccaga aatggggggga aagccacgac ggaaaaaccc ccaggaggga 1320
ctgtacaatg aactgcagaa ggataaaatg gcagaggcct attccgaaat cgggatgaag 1380
ggagaaagaa ggcgaggcaa aggacacgac ggactgtacc agggggctgtc taccgccaca 1440
aaggacacct atgatgctct gcatatgcag gcactgccac ccagg                1485

SEQ ID NO: 620      moltype = DNA  length = 1458
FEATURE             Location/Qualifiers
source              1..1458
                    mol_type = other DNA
                    organism = synthetic construct
                    note = Description of Artificial Sequence: Synthetic
                    polynucleotide
SEQUENCE: 620
atggcactgc ctgtgacagc cctgctgctg ccactggccc tgctgctgca cgccgccaga  60
ccccaggtgc agctgcagga gtccggccca ggcctggtga agccaagcga gaccctgtcc 120
ctgacatgca ccgtgtctgg cgacagcatc agctccctgt cttggagctg gatcaggcag 180
acaccaggca ggggcctgga gtggatcggc tacctgtact attccggctc taccgactat 240
aaccccctcc tgaagtctcg cgtgacaatc tctgtggata ccagcaagaa tcagttctct 300
ctgaagctgc ggagcgtggc tgccgccgac acagccctgt actattgcgc cagaggccgg 360
agagcctttg atatctgggg ccagggcaca atggtgaccg tgtctagcgg aggaggaggc 420
tccgaggag gaggctctgg cggcggcggc agcgaggcg cgggctccga catccagatg 480
acccagagcc cttcctctct gagcgcctcc gtgggcgata gggtgacaat cacctgtcgc 540
```

-continued

```
ggctcccagg gcatctctaa ctacctggca tggttccagc agcggcccgg caaggcacct    600
aagtctctga tctatgcagc aagctccctg gagagcggag tgccatccaa gttctctggc    660
agcggctccg gcacagactt tacactgacc atcatcagcc tgcagcccga ggatttcgcc    720
acctactatt gtcagcagta ctataattac cctatcacat ttggccaggg cacccggctg    780
gagatcaaga ccacaacccc tgcccctagg ccacctacca cagcacctac aattgctagt    840
cagccactgt cactgcgacc agaggcatgt cgacctgcag ctggaggagc agtgcataca    900
aggggactgg actttgcctg cgatatctac atttgggctc ctctggcagg aacatgtggc    960
gtgctgctgc tgagcctggt catcactctg tactgcaagc gaggccggaa gaaactgctg   1020
tatattttca aacagcccct tatgcgacct gtgcagacca cacaggagga agatgggtgc   1080
tcctgtcggt tccccgagga agaggaagga ggctgtgagc tgcgggtcaa gttttccaga   1140
tctgcagacg cccctgctta ccagcagggc cagaaccagc tgtataacga gctgaatctg   1200
gggcggagag aggaatacga cgtgctggat aaaaggcgcg ggagagaccc agaaatgggg   1260
ggaaagccac gacggaaaaa cccccaggag ggactgtaca tgaactgca gaaggataaa   1320
atggcagagg cctattccga aatcgggatg aagggagaaa gaaggcgagg caaaggcac   1380
gacggactgt accaggggct gtctaccgcc acaaaggaca cctatgatgc tctgcatatg   1440
caggcactgc cacccagg                                               1458
```

SEQ ID NO: 621              moltype = DNA   length = 1488
FEATURE                     Location/Qualifiers
source                      1..1488
                            mol_type = other DNA
                            organism = synthetic construct
                            note = Description of Artificial Sequence: Synthetic
                            polynucleotide

SEQUENCE: 621

```
atggcactgc ctgtgaccgc cctgctgctg ccactggccc tgctgctgca cgccgcccgg    60
ccacaggtgc agctggtgca gtctggagca gaggtgaaga agcctggcgc aagcgtgaag   120
gtgtcctgca aggcctctgg ctacacattc accggctact atatgcactg ggtgagacag   180
gcccctggcc agggactgga gtggatgggc tggatcaacc ctaatagcgg cggcaccaac   240
tacgcccaga gtttcaggg ccgggtgaca atgaccaagc acaccagcgt gtccacagcc   300
tatatggagc tgagcaggct gacctccgac gatacagcca tctactattg tgccaaggac   360
ggcggcggcg atttctactt ttatggcatg gacgtgtggg gccagggcac cacagtgacc   420
gtgagctccg gcggcggcgg ctctggagga ggaggcagcg gcggaggagg ctccggagga   480
ggcggctctc agaccgtggt gacacaggag ccatctttca gcgtgtcccc cggcggaaca   540
gtgaccctga catgcggcct gtctagcggc tctgtgacaa catcctacta tcctagctgt   600
ttccagcaga cccccggcca ggcacctaga acactgatct actccaccga cacaaggtcc   660
tctggcgtgc cagatcgctt ttctggcagc atcctgggca ataaggccgc cctgaccatc   720
acaggagcac aggccgacga tgagtccgac tactattgcg tgctgtatat gggctccgga   780
atcagcgtgt tcggaggagg caccaagctg acagtgctga ccacaacccc cgcccctagg   840
ccacctaccc cagcacctac aattgctagt cagccactgt cactgcgacc agaggcatgt    900
cgacctgcag ctggaggagc agtgcataca aggggactgg actttgcctg cgatatctac    960
atttgggctc tctggcagg aacatgtggc gtgctgctgc tgagcctggt catcactctg   1020
tactgcaagc gaggccggaa gaaactgctg tatattttca aacagcccct tatgcgacct   1080
gtgcagacca cacaggagga agatgggtgc tcctgtcggt tccccgagga agaggaagga   1140
ggctgtgagc tgcgggtcaa gttttccaga tctgcagacg cccctgctta ccagcagggc   1200
cagaaccagc tgtataacga gctgaatctg gggcggagag aggaatacga cgtgctggat   1260
aaaaggcgcg ggagagaccc agaaatgggg ggaaagccac gacggaaaaa cccccaggag   1320
ggactgtaca tgaactgca gaaggataaa atggcagagg cctattccga aatcgggatg   1380
aagggagaaa gaaggcgagg caaaggcac gacggactgt accaggggct gtctaccgcc   1440
acaaaggaca cctatgatgc tctgcatatg caggcactgc cacccagg                1488
```

SEQ ID NO: 622              moltype = AA   length = 569
FEATURE                     Location/Qualifiers
source                      1..569
                            mol_type = protein
                            organism = synthetic construct
                            note = Description of Artificial Sequence: Synthetic
                            polypeptide

SEQUENCE: 622

```
MALPVTALLL PLALLLHAAR PGGGGSCPYS NPSLCSGGGG SGGGGSQLQL QESGPGLVKP    60
SETLSLTCTV SGGSISSSSY YWGWIRQPPG KGLEWIGSIY YSGNIYHNPS LKSRVSISVD   120
TSKNQFSLRL SSVTAADTAV YYCAREIIVG ATHFDYWGQG TLVTVSSGGG GSGGGGSGGG   180
GSGGGGSAIQ MTQSPSSLSA SVGDRVTITC RASQGIRNDL GWYQQKPGKA PELLIYAASS   240
LQSGVPSRFS GSGSGTDFTL TISSLQPEDF ATYYCLQDYN YPLTFGPGTK VDIKGSGGGG   300
SCPYSNPSLC SGGGGSELPT QGTFSNVSTN VSPAKPTTTA CPYSNPSLCT TTPAPRPPTP   360
APTIASQPLS LRPEACRPAA GGAVHTRGLD FACDIYIWAP LAGTCGVLLL SLVITKRGRK   420
KLLYIFKQPF MRPVQTTQEE DGCSCRFPEE EEGGCELRVK FSRSADAPAY QQGQNQLYNE   480
LNLGRREEYD VLDKRRGRDP EMGGKPRRKN PQEGLYNELQ KDKMAEAYSE IGMKGERRRG   540
KGHDGLYQGL STATKDTYDA LHMQALPPR                                     569
```

SEQ ID NO: 623              moltype = AA   length = 539
FEATURE                     Location/Qualifiers
source                      1..539
                            mol_type = protein
                            organism = synthetic construct
                            note = Description of Artificial Sequence: Synthetic
                            polypeptide

SEQUENCE: 623

```
MALPVTALLL PLALLLHAAR PQLQLQESGP GLVKPSETLS LTCTVSGGSI SSSSYYWGWI    60
```

```
RQPPGKGLEW IGSIYYSGNI YHNPSLKSRV SISVDTSKNQ FSLRLSSVTA ADTAVYYCAR  120
EIIVGATHFD YWGQGTLVTV SSGGGGSGGG GSGGGGSGGG GSAIQMTQSP SSLSASVGDR  180
VTITCRASQG IRNDLGWYQQ KPGKAPELLI YAASSLQSGV PSRFSGSGSG TDFTLTISSL  240
QPEDFATYYC LQDYNYPLTF GPGTKVDIKG SGGGGSCPYS NPSLCSGGGG SCPYSNPSLC  300
SGGGGSTTTA CPYSNPSLCT TTPAPRPPTP APTIASQPLS LRPEACRPAA GGAVHTRGLD  360
FACDIYIWAP LAGTCGVLLL SLVITKRGRK KLLYIFKQPF MRPVQTTQEE DGCSCRFPEE  420
EEGGCELRVK FSRSADAPAY QQGQNQLYNE LNLGRREEYD VLDKRRGRDP EMGGKPRRKN  480
PQEGLYNELQ KDKMAEAYSE IGMKGERRRG KGHDGLYQGL STATKDTYDA LHMQALPPR   539

SEQ ID NO: 624             moltype = AA  length = 527
FEATURE                    Location/Qualifiers
source                     1..527
                           mol_type = protein
                           organism = synthetic construct
                           note = Description of Artificial Sequence: Synthetic
                           polypeptide
SEQUENCE: 624
MALPVTALLL PLALLLHAAR PGGGGSCPYS NPSLCGGGGS QLQLQESGPG LVKPSETLSL  60
TCTVSGGSIS SSSYYWGWIR QPPGKGLEWI GSIYYSGNIY HNPSLKSRVS ISVDTSKNQF  120
SLRLSSVTAA DTAVYYCARE IIVGATHFDY WGQGTLVTVS SGGGGSGGGG SGGGGSGGGG  180
SAIQMTQSPS SLSASVGDRV TITCRASQGI RNDLGWYQQK PGKAPELLIY AASSLQSGVP  240
SRFSGSGSGT DFTLTISSLQ PEDFATYYCL QDYNYPLTFG PGTKVDIKGG GGSCPYSNPS  300
LCGGGGSTTT PAPRPPTPAP TIASQPLSLR PEACRPAAGG AVHTRGLDFA CDIYIWAPLA  360
GTCGVLLLSL VITKRGRKKL LYIFKQPFMR PVQTTQEEDG CSCRFPEEEE GGCELRVKFS  420
RSADAPAYQQ GQNQLYNELN LGRREEYDVL DKRRGRDPEM GGKPRRKNPQ EGLYNELQKD  480
KMAEAYSEIG MKGERRRGKG HDGLYQGLST ATKDTYDALH MQALPPR            527

SEQ ID NO: 625             moltype = AA  length = 522
FEATURE                    Location/Qualifiers
source                     1..522
                           mol_type = protein
                           organism = synthetic construct
                           note = Description of Artificial Sequence: Synthetic
                           polypeptide
SEQUENCE: 625
MALPVTALLL PLALLLHAAR PGGGGSCPYS NPSLCGGGGS CPYSNPSLCG GGGSQLQLQE  60
SGPGLVKPSE TLSLTCTVSG GSISSSSYYW GWIRQPPGKG LEWIGSIYYS GNIYHNPSLK  120
SRVSISVDTS KNQFSLRLSS VTAADTAVYY CAREIIVGAT HFDYWGQGTL VTVSSGGGGS  180
GGGGSGGGGS GGGGSAIQMT VSPSSLSASV GDRVTITCRA SQGIRNDLGW YQQKPGKAPE  240
LLIYAASSLQ SGVPSRFSGS GSGTDFTLTI SSLQPEDFAT YYCLQDYNYP LTFGPGTKVD  300
IKTTTPAPRP PTPAPTIASQ PLSLRPEACR PAAGGAVHTR GLDFACDIYI WAPLAGTCGV  360
LLLSLVITKR GRKKLLYIFK QPFMRPVQTT QEEDGCSCRF PEEEEGGCEL RVKFSRSADA  420
PAYQQGQNQL YNELNLGRRE EYDVLDKRRG RDPEMGGKPR RKNPQEGLYN ELQKDKMAEA  480
YSEIGMKGER RRGKGHDGLY QGLSTATKDT YDALHMQALP PR                 522

SEQ ID NO: 626             moltype = AA  length = 545
FEATURE                    Location/Qualifiers
source                     1..545
                           mol_type = protein
                           organism = synthetic construct
                           note = Description of Artificial Sequence: Synthetic
                           polypeptide
SEQUENCE: 626
MALPVTALLL PLALLLHAAR PQVQLQQSGP GLVKPSQTLS LTCAISGDSV SSNSATWNWI  60
RQSPSRGLEW LGRTYYRSKW YDDYAVSVKS RITINPDTSK NHLSLHLNSV TPEDTAVYYC  120
AGGGLVGAPD GFDVWGQGTM VTVSSGGGGS GGGGSGGGGS GGGGSQSVLT QPPSASGTPG  180
QRVTISCSGS SSNIGSDPVN WYQQLPGTAP KLLIYSNNQR PSGVPDRFSG SKSGTSASLA  240
ISGLQSEDEA DYYCSAWDDS LNGYVFGTGT KVTVLGSGGG GSCPYSNPSL CSGGGGSCPY  300
SNPSLCSGGG GSTTTACPYS NPSLCTTTPA PRPPTPAPTI ASQPLSLRPE ACRPAAGGAV  360
HTRGLDFACD IYIWAPLAGT CGVLLLSLVI TKRGRKKLLY IFKQPFMRPV QTTQEEDGCS  420
CRFPEEEEGG CELRVKFSRS ADAPAYQQGQ NQLYNELNLG RREEYDVLDK RRGRDPEMGG  480
KPRRKNPQEG LYNELQKDKM AEAYSEIGMK GERRRGKGHD GLYQGLSTAT KDTYDALHMQ  540
ALPPR                                                          545

SEQ ID NO: 627             moltype = AA  length = 533
FEATURE                    Location/Qualifiers
source                     1..533
                           mol_type = protein
                           organism = synthetic construct
                           note = Description of Artificial Sequence: Synthetic
                           polypeptide
SEQUENCE: 627
MALPVTALLL PLALLLHAAR PGGGGSCPYS NPSLCGGGGS QVQLQQSGPG LVKPSQTLSL  60
TCAISGDSVS SNSATWNWIR QSPSRGLEWL GRTYYRSKWY DDYAVSVKSR ITINPDTSKN  120
HLSLHLNSVT PEDTAVYYCA GGGLVGAPDG FDVWGQGTMV TVSSGGGGSG GGGSGGGGSG  180
GGGSQSVLTQ PPSASGTPGQ RVTISCSGSS NIGSDPVNWY QQLPGTAPK LLIYSNNQRP  240
SGVPDRFSGS KSGTSASLAI SGLQSEDEAD YYCSAWDDSL NGYVFGTGTK VTVLGGGGSC  300
PYSNPSLCGG GSTTTPAPR PPTPAPTIAS QPLSLRPEAC RPAAGGAVHT RGLDFACDIY  360
IWAPLAGTCG VLLLSLVITK RGRKKLLYIF KQPFMRPVQT TQEEDGCSCR FPEEEEGGCE  420
```

-continued

```
LRVKFSRSAD APAYQQGQNQ LYNELNLGRR EEYDVLDKRR GRDPEMGGKP RRKNPQEGLY  480
NELQKDKMAE AYSEIGMKGE RRRGKGHDGL YQGLSTATKD TYDALHMQAL PPR          533

SEQ ID NO: 628          moltype = AA  length = 528
FEATURE                 Location/Qualifiers
source                  1..528
                        mol_type = protein
                        organism = synthetic construct
                        note = Description of Artificial Sequence: Synthetic
                        polypeptide
SEQUENCE: 628
MALPVTALLL PLALLLHAAR PGGGGSCPYS NPSLCGGGGS CPYSNPSLCG GGGSQVQLQQ  60
SGPGLVKPSQ TLSLTCAISG DSVSSNSATW NWIRQSPSRG LEWLGRTYYR SKWYDDYAVS  120
VKSRITINPD TSKNHLSLHL NSVTPEDTAV YYCAGGGLVG APDGFDVWGQ GTMVTVSSGG  180
GGSGGGGSGG GGSGGGGSQS VLTQPPSASG TPGQRVTISC SGSSSNIGSD PVNWYQQLPG  240
TAPKLLIYSN NQRPSGVPDR FSGSKSGTSA SLAISGLQSE DEADYYCSAW DDSLNGYVFG  300
TGTKVTVLTT TPAPRPPTPA PTIASQPLSL RPEACRPAAG GAVHTRGLDF ACDIYIWAPL  360
AGTCGVLLLS LVITKRGRKK LLYIFKQPFM RPVQTTQEED GCSCRFPEEE EGGCELRVKF  420
SRSADAPAYQ QGQNQLYNEL NLGRREEYDV LDKRRGRDPE MGGKPRRKNP QEGLYNELQK  480
DKMAEAYSEI GMKGERRRGK GHDGLYQGLS TATKDTYDAL HMQALPPR              528

SEQ ID NO: 629          moltype = AA  length = 249
FEATURE                 Location/Qualifiers
source                  1..249
                        mol_type = protein
                        organism = synthetic construct
                        note = Description of Artificial Sequence: Synthetic
                        polypeptide
SEQUENCE: 629
EVQLLESGGG LVQPGGSLRL SCAASGFTFS SYAMNWVRQA PGKGLEWVST ISGSGGSTYY  60
ADSVKGRFTI SRDNSKNTLY LQMNSLRAED TAVFYCAIDP EYYDILTGGD YWGQGTLVTV  120
SSGGGGSGGG GSGGGGSGGG GSDIQMTQSP SAMSASVGDR VTITCRASQG ISNYLAWFQQ  180
KPGKVPKRLI YAASSLQSGV PSRFSGSGSG TEFTLTISSL QPEDFATYFC LQHDSFPLTF  240
GGGTKVEIK                                                         249

SEQ ID NO: 630          moltype = DNA  length = 60
FEATURE                 Location/Qualifiers
source                  1..60
                        mol_type = other DNA
                        organism = synthetic construct
                        note = Description of Artificial Sequence: Synthetic
                        oligonucleotide
SEQUENCE: 630
ggcggcggcg gctctggagg aggaggcagc ggcggaggag gctccggagg cggcggctct  60

SEQ ID NO: 631          moltype = DNA  length = 1467
FEATURE                 Location/Qualifiers
source                  1..1467
                        mol_type = other DNA
                        organism = synthetic construct
                        note = Description of Artificial Sequence: Synthetic
                        polynucleotide
SEQUENCE: 631
atggctctgc ccgtcaccgc tctgctgctg cctctggctc tgctgctgca cgccgcacga  60
ccagaggtgc agctggtgga gagcggagga ggcctggcag agcctggcgg cagcctgagg  120
ctgtcctgcg cagcatctgg cttcaccttt agctcccacg acatgcactg ggtgaggcag  180
gcaacaggca agggcctgga gtgggtgtcc gccatcggaa tcgcaggcga tacctactat  240
tccggctctg tgaagggccg gttcacaatc agcagagaga cgccaagaa ttccctgtac  300
ctgcagatga actctctgag ggccggcgac accgccgtgt actattgtgc cagagccaat  360
tggggcgagg gcgcctttga tatctggggc cagggcacca tggtgacagt gtctagcggc  420
ggcggcggct ctggaggagg aggcagcggc ggaggaggct ccggaggcgg cggctctgac  480
atccagatga cacagtctcc tagctccctg tccgcctctg tgggcgaccg ggtgaccatc  540
acatgcagag ccagccaggg catctccgat tacctggcct ggtatcagca gaagcccggc  600
aagatcccta agctgctgat ctacgcagca tctaccctgc agagcggagt cgccatccgg  660
ttcagcggat ccggatctgg aacagacttt accctgacaa tctctagcct gcagccgag  720
gatgtggcca cctactattg tcagaagtat aactccgtgc cactgacctt cggcggagga  780
acaaaggtgg agatcaagac cacaactcct gcacctaggc cacctacccc agcacctaca  840
attgctagtc agccactgtc actgcgacca gaggcatgtc gacctgcagc tggaggagca  900
gtgcatacaa ggggactgga ctttgcctgc gatatctaca tttgggctcc tctggcagga  960
acatgtggcg tgctgctgct gagcctggtc atcactctgt actgcaagcg aggccggaag  1020
aaactgctgt atatttcaa acagcccttt atgcgacctg tgcagaccac acaggaggaa  1080
gatgggtgct cctgtcggtt ccccgaggaa gaggaaggag ctgtgagct gcgggtcaag  1140
ttttccagat ctgcagacgc ccctgcttac cagcaggggc agaaccagct gtataacgag  1200
ctgaatctgg ggcggagaga ggaatacgac gtgctggata aaaggcgcgg aggacccga  1260
gaaatggggg gaaagccacg acggaaaaac ccccaggagg gactgtacaa tgaactgcag  1320
aaggataaaa tggcagaggc ctattccgaa atcgggatga agggagaaag aaggcgaggc  1380
aaaggacacg acggactgta ccaggggctg tctaccgcca caaggacac ctatgatgct  1440
ctgcatatgc aggcactgcc acccagg                                    1467
```

```
SEQ ID NO: 632          moltype = AA  length = 489
FEATURE                 Location/Qualifiers
source                  1..489
                        mol_type = protein
                        organism = synthetic construct
                        note = Description of Artificial Sequence: Synthetic
                          polypeptide
SEQUENCE: 632
MALPVTALLL PLALLLHAAR PQVQLQESGP GLVKPSETLS LTCTVSDNSI SNYYWSWIRQ   60
PPGKGLEWIA YIYYSGTTNY NPSLKSRVTI SLDTSKNQFS LKLSSVTAAD TAVYYCARLF  120
NWGFAFDIWG QGTMVTVSSG GGGSGGGGSG GGGSGGGGSE IVMTQSPATL SVSPGERATL  180
SCRASQSVSS NLAWYQQKPG QAPRLLIYGA STRATGIPAR FSGSGSGTEF TLTISSLQSE  240
DFAVYYCQQY NNWPLTFGGG TKVEIKTTTP APRPPTPAPT IASQPLSLRP EACRPAAGGA  300
VHTRGLDFAC DIYIWAPLAG TCGVLLLSLV ITLYCKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                         489

SEQ ID NO: 633          moltype = AA  length = 490
FEATURE                 Location/Qualifiers
source                  1..490
                        mol_type = protein
                        organism = synthetic construct
                        note = Description of Artificial Sequence: Synthetic
                          polypeptide
SEQUENCE: 633
MALPVTALLL PLALLLHAAR PQVQLQESGP GLMKPSETLS LTCTVSGGSI SSSYWSCIRQ   60
PPGKGLEWIG YIYYSGTTNY NPSLKSRVTL SLDTSKNQFS LRLTSVTAAD TAVYYCARVA  120
PTGFWFDYWG QGTLVTVSSG GGGSGGGGSG GGGSGGGGSE IVLTQSPGTL SLSPGERATL  180
SCRASQRVSS RYLAWYQQKP GQAPRLLIYG ASSRATGIPD RFSGSGSGTD FTLTISRLEP  240
EEFAVYYCQQ YGTSPLTFGG GTKVEIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                        490

SEQ ID NO: 634          moltype = AA  length = 489
FEATURE                 Location/Qualifiers
source                  1..489
                        mol_type = protein
                        organism = synthetic construct
                        note = Description of Artificial Sequence: Synthetic
                          polypeptide
SEQUENCE: 634
MALPVTALLL PLALLLHAAR PEVQLVESGG GLVQPGGSLR LSCAASGFTF SSHDMHWVRQ   60
ATGKGLEWVS AIGIAGDTYY SGSVKGRFTI SRENAKNSLY LQMNSLRAGD TAVYYCARAN  120
WGEGAFDIWG QGTMVTVSSG GGGSGGGGSG GGGSGGGGSD IQMTQSPSSL SASVGDRVTI  180
TCRASQGISD YLAWYQQKPG KIPKLLIYAA STLQSGVPSR FSGSGSGTDF TLTISSLQPE  240
DVATYYCQKY NSVPLTFGGG TKVEIKTTTP APRPPTPAPT IASQPLSLRP EACRPAAGGA  300
VHTRGLDFAC DIYIWAPLAG TCGVLLLSLV ITLYCKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                         489

SEQ ID NO: 635          moltype = AA  length = 490
FEATURE                 Location/Qualifiers
source                  1..490
                        mol_type = protein
                        organism = synthetic construct
                        note = Description of Artificial Sequence: Synthetic
                          polypeptide
SEQUENCE: 635
MALPVTALLL PLALLLHAAR PQVQLQESGP GLVKPSETLS LTCTVSDDSI SNYYWSWIRQ   60
PPGKGLEWIG YIFYSGTTNH NPSLKSRLTI SLDKAKNQFS LRLSSVTAAD TAVYYCARVF  120
NWGFAFDIWG QGTMVTVSSG GGGSGGGGSG GGGSGGGGSE IVLTQSPGTL SLSPGERATL  180
SCRASQRISR TYLAWYQQKP GQAPRLLIYG ASSRATGIPD RFTGSGSGTD FTLTISRLEP  240
EDFAVYYCQQ YGTSPLTFGG GTKVEINTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                        490

SEQ ID NO: 636          moltype = AA  length = 490
FEATURE                 Location/Qualifiers
source                  1..490
                        mol_type = protein
                        organism = synthetic construct
                        note = Description of Artificial Sequence: Synthetic
                          polypeptide
```

```
SEQUENCE: 636
MALPVTALLL PLALLLHAAR PQVQLQESGP GLVKPSETLS LTCTVSDNSI SNYYWSWIRQ 60
PPGKGLEWIA YIYYSGTTNY NPSLKSRVTI SLDTSKNQFS LQLSSVTAAD AAVYYCARVF 120
HWGFAFDIWG QGTMVTVSSG GGGSGGGGSG GGGSGGGGSE IVLTQSPGTL SLSPGERATL 180
SCRASQRVSN TYLAWYQQNP GQAPRLLIYG ASSRATGIPD RFSGSGSGTD FTLTISRLEP 240
EDFAVYYCQQ YGTSPLTFGG GTKVEIKTTT PAPRPPTPAP TIASQPLSLR PEACRPAAGG 300
AVHTRGLDFA CDIYIWAPLA GTCGVLLLSL VITLYCKRGR KKLLYIFKQP FMRPVQTTQE 360
EDGCSCRFPE EEEGGCELRV KFSRSADAPA YQQGQNQLYN ELNLGRREEY DVLDKRRGRD 420
PEMGGKPRRK NPQEGLYNEL QKDKMAEAYS EIGMKGERRR GKGHDGLYQG LSTATKDTYD 480
ALHMQALPPR                                                       490

SEQ ID NO: 637        moltype = AA  length = 490
FEATURE               Location/Qualifiers
source                1..490
                      mol_type = protein
                      organism = synthetic construct
                      note = Description of Artificial Sequence: Synthetic
                      polypeptide
SEQUENCE: 637
MALPVTALLL PLALLLHAAR PQVQLQESGP GLVKPSETLS LTCTVSNVSI SSYYWSWIRQ 60
PPGKGLEWIG YIYYSGTTNY NPSLKSRVTM SVDTSKNQFS LKLSSVTAAD TAVYFCARLS 120
NWGFAFDIWG QGTMVTFSSG GGGSGGGGSG GGGSGGGGSE IVLTQSPGTL SLSPGERATL 180
SCRASQTISS SYLAWYQQKP GQAPRLLIYG ASSRATGIPD RFSGSGSGTE FTLTISRLEP 240
EDFAVYYCQQ YGWSPITFGQ GTRLEIKTTT PAPRPPTPAP TIASQPLSLR PEACRPAAGG 300
AVHTRGLDFA CDIYIWAPLA GTCGVLLLSL VITLYCKRGR KKLLYIFKQP FMRPVQTTQE 360
EDGCSCRFPE EEEGGCELRV KFSRSADAPA YQQGQNQLYN ELNLGRREEY DVLDKRRGRD 420
PEMGGKPRRK NPQEGLYNEL QKDKMAEAYS EIGMKGERRR GKGHDGLYQG LSTATKDTYD 480
ALHMQALPPR                                                       490

SEQ ID NO: 638        moltype = AA  length = 496
FEATURE               Location/Qualifiers
source                1..496
                      mol_type = protein
                      organism = synthetic construct
                      note = Description of Artificial Sequence: Synthetic
                      polypeptide
SEQUENCE: 638
MALPVTALLL PLALLLHAAR PEVQLVESGG GLVQPGGSLR LSCAASGFTF SSYDMHWVRQ 60
ATGKGLEWVS AIGPAGDTYY PGSVKGRFTI SRENAKNSLY LQMNSLRAGD TAVYYCARAD 120
PPYYYYGMDV WGQGTTVTVS SGGGGSGGGG SGGGGSGGGG SDIVMTQSPL SLPVTPGEPA 180
SISCRSSQSL LHSNEYNYLD WYLQKPGQSP QLLIYLGSNR ASGVPDRFSG SGSGTDFILK 240
ISRVEAEDVG VYYCMQALEI PLTFGGGTKV EIKTTTPAPR PPTPAPTIAS QPLSLRPEAC 300
RPAAGGAVHT RGLDFACDIY IWAPLAGTCG VLLLSLVITL YCKRGRKKLL YIFKQPFMRP 360
VQTTQEEDGC SCRFPEEEEG GCELRVKFSR SADAPAYQQG QNQLYNELNL GRREEYDVLD 420
KRRGRDPEMG GKPRRKNPQE GLYNELQKDK MAEAYSEIGM KGERRRGKGH DGLYQGLSTA 480
TKDTYDALHM QALPPR                                                496

SEQ ID NO: 639        moltype = AA  length = 491
FEATURE               Location/Qualifiers
source                1..491
                      mol_type = protein
                      organism = synthetic construct
                      note = Description of Artificial Sequence: Synthetic
                      polypeptide
SEQUENCE: 639
MALPVTALLL PLALLLHAAR PQITLKESGP TLVKPTQTLT LTCTFSGFSL STRGVGVGWI 60
RQPPGKALEW LALIYWNDDK RYSPSLQTRL TITKDTPKNQ VVLTMTNMDP VDTATYYCAR 120
SNWGNWYFAL WGRGTLVTVS SGGGGSGGGG SGGGGSGGGG SEIVLTQSPA TLSLSPGERA 180
TLSCRASQSV SSYLAWYQQK PGQAPRLLIY DAFYRATGIP ARFSGSGSGT DFTLTISSLE 240
PEDFAVYYCQ HRSNWPITFG QGTRLEIKTT TPAPRPPTPA PTIASQPLSL RPEACRPAAG 300
GAVHTRGLDF ACDIYIWAPL AGTCGVLLLS LVITLYCKRG RKKLLYIFKQ PPMRPVQTTQ 360
EEDGCSCRFP EEEEGGCELR VKFSRSADAP AYQQGQNQLY NELNLGRREE YDVLDKRRGR 420
DPEMGGKPRR KNPQEGLYNE LQKDKMAEAY SEIGMKGERR RGKGHDGLYQ GLSTATKDTY 480
DALHMQALPP R                                                     491

SEQ ID NO: 640        moltype = AA  length = 490
FEATURE               Location/Qualifiers
source                1..490
                      mol_type = protein
                      organism = synthetic construct
                      note = Description of Artificial Sequence: Synthetic
                      polypeptide
SEQUENCE: 640
MALPVTALLL PLALLLHAAR PQVQLQESGP GLVKPSETLS LTCTVSGDSI SNYYWTWIRQ 60
PPGKGLEWIG YIYYSGTTNS NPSLKSRVTV SLDTSKSQFS LNLSSVTAAD TAVYYCARVF 120
NRGFAFDIWG QGTMVTVSSG GGGSGGGGSG GGGSGGGGSE IVLTQSPGTL SLSPGERATL 180
SCRASQRISN TYLAWYQQKP GQAPRLLIYG ASSRATGIPD RFSGSGSGTD FTLTISRLEP 240
EDFAAYYCQQ YDTSPLTFGG GTKVEIKTTT PAPRPPTPAP TIASQPLSLR PEACRPAAGG 300
AVHTRGLDFA CDIYIWAPLA GTCGVLLLSL VITLYCKRGR KKLLYIFKQP FMRPVQTTQE 360
```

-continued

```
EDGCSCRFPE EEEGGCELRV KFSRSADAPA YQQGQNQLYN ELNLGRRREEY DVLDKRRGRD   420
PEMGGKPRRK NPQEGLYNEL QKDKMAEAYS EIGMKGERRR GKGHDGLYQG LSTATKDTYD   480
ALHMQALPPR                                                         490

SEQ ID NO: 641          moltype = AA   length = 499
FEATURE                 Location/Qualifiers
source                  1..499
                        mol_type = protein
                        organism = synthetic construct
                        note = Description of Artificial Sequence: Synthetic
                         polypeptide
SEQUENCE: 641
MALPVTALLL PLALLLHAAR PQVTLRESGP ALVKPTQTLT LTCTVSGVSL STSGMCVSWI   60
RQPLGKALEW LGFIDWDDDK YYNTSLKTRL TISKDTSKNQ VVLTMTNMDP VDTATYYCAR   120
IRGYSGSYDA FDIWGQGTVV IVSSGGGGSG GGGSGGGGSG GGGSDIVMTQ SPLSLPVTPG   180
EPASISCRSS QSLLHSNGYN HLDWYLQKPG QSPQVLIYLG SNRASGVPDR FSGSGSGTDF   240
TLKISRVEAE DVGVYFCMQA LQTPLTFGGG TKVEIKTTTP APRPPTPAPT IASQPLSLRP   300
EACRPAAGGA VHTRGLDFAC DIYIWAPLAG TCGVLLLSLV ITLYCKRGRK KLLYIFKQPF   360
MRPVQTTQEE DGCSCRFPEE EEGGCELRVK FSRSADAPAY QQGQNQLYNE LNLGRRREEYD   420
VLDKRRGRDP EMGGKPRRKN PQEGLYNELQ KDKMAEAYSE IGMKGERRRG KGHDGLYQGL   480
STATKDTYDA LHMQALPPR                                               499

SEQ ID NO: 642          moltype = AA   length = 489
FEATURE                 Location/Qualifiers
source                  1..489
                        mol_type = protein
                        organism = synthetic construct
                        note = Description of Artificial Sequence: Synthetic
                         polypeptide
SEQUENCE: 642
MALPVTALLL PLALLLHAAR PQVQLQVSGP GLVKPSETLS LTCSVSGGSI SSYYWSWIRQ   60
SPGKGLDWIG YMYYSGTTNY NPSLKSRVTI SVDTSKNQFS LKLSSVTATD TAVYYCARVG   120
LTGFFFDYWG QGTLVTVSSG GGGSGGGGSG GGGSGGGGSA IQMTQSPSSL SASVGDRVTI   180
TCRASQGIRN DLGWYQQKPG KAPKLLIYAA SSLQSGVPSR FSGSGSGTDF TLTVSSLQPE   240
DFATYYCLQD YNYPYTFGQG TKLEIKTTTP APRPPTPAPT IASQPLSLRP EACRPAAGGA   300
VHTRGLDFAC DIYIWAPLAG TCGVLLLSLV ITLYCKRGRK KLLYIFKQPF MRPVQTTQEE   360
DGCSCRFPEE EEGGCELRVK FSRSADAPAY QQGQNQLYNE LNLGRRREEYD VLDKRRGRDP   420
EMGGKPRRKN PQEGLYNELQ KDKMAEAYSE IGMKGERRRG KGHDGLYQGL STATKDTYDA   480
LHMQALPPR                                                         489

SEQ ID NO: 643          moltype = AA   length = 486
FEATURE                 Location/Qualifiers
source                  1..486
                        mol_type = protein
                        organism = synthetic construct
                        note = Description of Artificial Sequence: Synthetic
                         polypeptide
SEQUENCE: 643
MALPVTALLL PLALLLHAAR PQVQLQQWGG GLLKPSETLS LTCAVYGGSS SGNYWSWIRQ   60
PPGKRLEWIG EINHSGTTSY NPSLKSRVTI SVDTSKNQFS LKLSSVTAAD TAVYYCARGE   120
LGIADSWGQG TLVTVSSGGG GSGGGGSGGG GSGGGGSDIQ MTQSPSTLSA SVGDRVTITC   180
RASQSISRWL AWYQQKPGKA PKLLIYKASS LESGVPSRFS GSGSGTEFTL TISSLQPDDF   240
ATYYCQQYNS YSTFGQGTKV EIKTTTPAPR PPTPAPTIAS QPLSLRPEAC RPAAGGAVHT   300
RGLDFACDIY IWAPLAGTCG VLLLSLVITL YCKRGRKKLL YIFKQPFMRP VQTTQEEDGC   360
SCRFPEEEEG GCELVKFSR SADAPAYQQG QNQLYNELNL GRRREEYDVLD KRRGRDPEMG   420
GKPRRKNPQE GLYNELQKDK MAEAYSEIGM KGERRRGKGH DGLYQGLSTA TKDTYDALHM   480
QALPPR                                                            486

SEQ ID NO: 644          moltype = AA   length = 492
FEATURE                 Location/Qualifiers
source                  1..492
                        mol_type = protein
                        organism = synthetic construct
                        note = Description of Artificial Sequence: Synthetic
                         polypeptide
SEQUENCE: 644
MALPVTALLL PLALLLHAAR PQLQLQESGP GLVKPSETLS LTCTVSGGSI SSSSYYWGWI   60
RQPPGKGLEW IGSIYYSGNI YHNPSLKSRV SISVDTSKNQ FSLRLSSVTA ADTAVYYCAR   120
EIIVGATHFD YWGQGTLVTV SSGGGGSGGG GSGGGGSGGG GSAIQMTQSP SSLSASVGDR   180
VTITCRASQG IRNDLGWYQQ KPGKAPELLI YAASSLQSGV PSRFSGSGSG TDFTLTISSL   240
QPEDFATYYC LQDYNYPLTF GPGTKVDIKT TTPAPRPPTP APTIASQPLS LRPEACRPAA   300
GGAVHTRGLD FACDIYIWAP LAGTCGVLLL SLVITLYCKR GRKKLLYIFK QPFMRPVQTT   360
QEEDGCSCRF PEEEEGGCEL RVKFSRSADA PAYQQGQNQL YNELNLGRRE EYDVLDKRRG   420
RDPEMGGKPR RKNPQEGLYN ELQKDKMAEA YSEIGMKGER RRGKGHDGLY QGLSTATKDT   480
YDALHMQALP PR                                                     492

SEQ ID NO: 645          moltype = AA   length = 490
FEATURE                 Location/Qualifiers
source                  1..490
```

```
                          mol_type = protein
                          organism = synthetic construct
                          note = Description of Artificial Sequence: Synthetic
                          polypeptide
SEQUENCE: 645
MALPVTALLL PLALLLHAAR PQVQLQQWGA GLLKPSETLS LTCAVYGGSF SGYYWSWIRQ    60
PPGKGLEWIG EIIHSGSSNY NPSLKSRVSI SVDTSKNQFS LKLSSVTAAD TAVYYCSRGE   120
YGSGSRFDYW GQGTLVTVSS GGGGSGGGGS GGGGSGGGGS AIQMTQSPSS LSASVGDRVA   180
ITCRASQGIR DDLGWYQQKP GKAPKLLIYA ASSLQSGVPS RFSGSRSDTD FTLTISSLQP   240
EDFATYYCLQ DYDYPLTFGG GTKVEIKTTT PAPRPPTPAP TIASQPLSLR PEACRPAAGG   300
AVHTRGLDFA CDIYIWAPLA GTCGVLLLSL VITLYCKRGR KKLLYIFKQP FMRPVQTTQE   360
EDGCSCRFPE EEEGGCELRV KFSRSADAPA YQQGQNQLYN ELNLGRREEY DVLDKRRGRD   420
PEMGGKPRRK NPQEGLYNEL QKDKMAEAYS EIGMKGERRR GKGHDGLYQG LSTATKDTYD   480
ALHMQALPPR                                                          490

SEQ ID NO: 646        moltype = AA  length = 487
FEATURE               Location/Qualifiers
source                1..487
                      mol_type = protein
                      organism = synthetic construct
                      note = Description of Artificial Sequence: Synthetic
                      polypeptide
SEQUENCE: 646
MALPVTALLL PLALLLHAAR PQVQLQESGP GLVKPSGTLS LTCAVSGGSI SSNNWWSWVR    60
QPPGKGLEWI GDIHHSGSTN YKPSLKSRVT ISVDKSKNQF SLNLISVTAA DTAVYYCARE   120
AGGYFDYWGQ GILVTVSSGG GGSGGGGSGG GGSGGGGSDI QMTQSPSTLS ASVGDRVTIT   180
CRASQSISSW LAWYQQKPGK APKLLISKAS SLESGVPSRF SGSGSGPEFT LTISSLQPAD   240
FATYYCQQYN SYSTFGQGTK LEIKTTTPAP RPPTPAPTIA SQPLSLRPEA CRPAAGGAVH   300
TRGLDFACDI YIWAPLAGTC GVLLLSLVIT LYCKRGRKKL LYIFKQPFMR PVQTTQEEDG   360
CSCRFPEEEE GGCELRVKFS RSADAPAYQQ GQNQLYNELN LGRREEYDVL DKRRGRDPEM   420
GGKPRRKNPQ EGLYNELQKD KMAEAYSEIG MKGERRRGKG HDGLYQGLST ATKDTYDALH   480
MQALPPR                                                             487

SEQ ID NO: 647        moltype = AA  length = 490
FEATURE               Location/Qualifiers
source                1..490
                      mol_type = protein
                      organism = synthetic construct
                      note = Description of Artificial Sequence: Synthetic
                      polypeptide
SEQUENCE: 647
MALPVTALLL PLALLLHAAR PQVQLQQWGA GLLKPSETLS LTCAVYGGSF SGYYWTWIRQ    60
PPGKGLEWIG EITHSGSTNY NPSLKSRVSI SVDTSKNQFS LKLSSVTAAD TAVYYCARGE   120
YGSGSRFDYW GQGTLVTVSS GGGGSGGGGS GGGGSGGGGS AIQMTQSPSS LSASVGDRVA   180
ITCRASQGIR DDLGWYQQKP GKAPKLLIYA ASSLQSGVPS RFSGSGSDTD FTLTISSLQP   240
EDFATYYCLQ DYDYPLTFGG GTKVEIKTTT PAPRPPTPAP TIASQPLSLR PEACRPAAGG   300
AVHTRGLDFA CDIYIWAPLA GTCGVLLLSL VITLYCKRGR KKLLYIFKQP FMRPVQTTQE   360
EDGCSCRFPE EEEGGCELRV KFSRSADAPA YQQGQNQLYN ELNLGRREEY DVLDKRRGRD   420
PEMGGKPRRK NPQEGLYNEL QKDKMAEAYS EIGMKGERRR GKGHDGLYQG LSTATKDTYD   480
ALHMQALPPR                                                          490

SEQ ID NO: 648        moltype = AA  length = 490
FEATURE               Location/Qualifiers
source                1..490
                      mol_type = protein
                      organism = synthetic construct
                      note = Description of Artificial Sequence: Synthetic
                      polypeptide
SEQUENCE: 648
MALPVTALLL PLALLLHAAR PQVQLQQWGA GLLKPSETLS LTCAVYGGSF SGYYWSWIRQ    60
PPGKGLEWIG EITHSGSTNY NPSLKSRVSI SVDTSKNQFS LKLSSVTAAD TAVYYCARGE   120
YGSGSRFDYW GQGTLVTVSS GGGGSGGGGS GGGGSGGGGS AIQMTQSPSS LSASVGDRVA   180
LTCRASQGIR DDLGWYQQKP GKAPKLLIYA ASSLQSGVPS RFSGSGSDTD FTLTISSLQP   240
EDFATYYCLQ DYDYPLTFGG GTKVEIKTTT PAPRPPTPAP TIASQPLSLR PEACRPAAGG   300
AVHTRGLDFA CDIYIWAPLA GTCGVLLLSL VITLYCKRGR KKLLYIFKQP FMRPVQTTQE   360
EDGCSCRFPE EEEGGCELRV KFSRSADAPA YQQGQNQLYN ELNLGRREEY DVLDKRRGRD   420
PEMGGKPRRK NPQEGLYNEL QKDKMAEAYS EIGMKGERRR GKGHDGLYQG LSTATKDTYD   480
ALHMQALPPR                                                          490

SEQ ID NO: 649        moltype = AA  length = 491
FEATURE               Location/Qualifiers
source                1..491
                      mol_type = protein
                      organism = synthetic construct
                      note = Description of Artificial Sequence: Synthetic
                      polypeptide
SEQUENCE: 649
MALPVTALLL PLALLLHAAR PQVQLQQWGA GLLKPSETLS LTCAVYGGSF SAYYWNWIRQ    60
PPGKGLEWIG EINHSGSTNY NPSLKSRVTI SVDTSKNQFS LNLTSLTAAD TAVYYCARGL   120
```

-continued

```
DSSGWYPFDY WGQGTLVTVS SGGGGSGGGG SGGGGSGGGG SDIQMTQSPS SVSASVGDRV  180
TITCRASQGI SSWLAWYQQK PGKAPKLLIY AASSLQSGVP SRFSGSGSGT DFTLTISSLQ  240
PEDFATYYCQ QADSFPFTFG PGTKVDIKTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYQQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                      491

SEQ ID NO: 650          moltype = AA  length = 486
FEATURE                 Location/Qualifiers
source                  1..486
                        mol_type = protein
                        organism = synthetic construct
                        note = Description of Artificial Sequence: Synthetic
                         polypeptide
SEQUENCE: 650
MALPVTALLL PLALLLHAAR PQVQLQQWGA GLLKPSETLS LTCAVFGGSF SGDYWSWIRQ  60
PPGKGLEWIG EINHSGITSF NPSLKSRVTI SVDTSKNQFS LKLSSVTAAD TAVYYCARGE  120
LGIPDNWGQG TLVTVSSGGG GSGGGGSGGG GSGGGGSDIQ MTQSPSTLSA SVGDRVTITC  180
RASQSISRWL AWYQQKPGKA PKLLIYKASS LESGVPSRFS GSGSGTEFTL TISSLQPDDF  240
ATYYCQQYNS YSTFGQGTKV EIKTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYQQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                            486

SEQ ID NO: 651          moltype = AA  length = 495
FEATURE                 Location/Qualifiers
source                  1..495
                        mol_type = protein
                        organism = synthetic construct
                        note = Description of Artificial Sequence: Synthetic
                         polypeptide
SEQUENCE: 651
MALPVTALLL PLALLLHAAR PQVQLQESGP GLVKPSGTLS LTCVVFGDSI SSSNWWSWVR  60
QPPGKGLEWI GEVFHSGSTN YNPSLKSRVT ISVDKSKNQF SLKLSSVTAA DTAVYYCARA  120
AVAGALDYWG QGTLVTVSSG GGGSGGGGSG GGGSGGGGSD IVMTQSPDSL AVSLGERATI  180
NCKSSQSVLY SSNNKNYLAW YQQKPGQPPN LLVYWASTRE SGVPDRFSGA GSGTDFTLTI  240
SSLQAEDVAV YYCQQYYGTS WTFGQGTKVE IKTTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                  495

SEQ ID NO: 652          moltype = AA  length = 491
FEATURE                 Location/Qualifiers
source                  1..491
                        mol_type = protein
                        organism = synthetic construct
                        note = Description of Artificial Sequence: Synthetic
                         polypeptide
SEQUENCE: 652
MALPVTALLL PLALLLHAAR PQITLRESGP TLVKPTQTLT LTCTFSGFSL STSGLGVGWI  60
RQPPGEALEW LALIYWNDDK RYSPSLKSRL SITKDTSKNQ VVLIMTNMDP VDTATYYCVH  120
RRIAAPGSVY WGQGTLVTVS SGGGGSGGGG SGGGGSGGGG SDIQMTQSPS SVSASVGDRV  180
TITCRASQGI SSWLAWYQQK PGKAPKLLIS AASSLQSGVP SRFSGSGSGT DFTLTISSLQ  240
PEDFATYYCH QANSFPFTFG QGTKLEIKTT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYQQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                      491

SEQ ID NO: 653          moltype = AA  length = 490
FEATURE                 Location/Qualifiers
source                  1..490
                        mol_type = protein
                        organism = synthetic construct
                        note = Description of Artificial Sequence: Synthetic
                         polypeptide
SEQUENCE: 653
MALPVTALLL PLALLLHAAR PQVQLVQSGA EVKKPGASVK VSCKVSGYTL TELSMHWVRQ  60
APGKGPEGMG GFDPEDGKTI YAQKFQGRVT MTEDTSADTA YMELNSLRSE DTAVYYCATL  120
LRGLDAFDVW GQGTMVTVSS GGGGSGGGGS GGGGSGGGGS DIQMTQSPSS LSASVGDRVT  180
ITCRASQGIR NDLGWYQQKP GKAPKRLIYA ASSLQSGVPS RFSGSGSGTE FTLTISTLQP  240
EDFATYYCLQ HNSYPRTFGQ GTKVEIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                        490
```

-continued

```
SEQ ID NO: 654          moltype = AA  length = 491
FEATURE                 Location/Qualifiers
source                  1..491
                        mol_type = protein
                        organism = synthetic construct
                        note = Description of Artificial Sequence: Synthetic
                        polypeptide
SEQUENCE: 654
MALPVTALLL PLALLLHAAR PQVQLQQWGA GLLKPSETLS LTCAVYGGSF SGYYWRWIRQ  60
PPGKGLEWIG EISHSGSTNY NPSLKSRVTI SVDTSKNQFS LKLSSVTAAD TAVYYCAVRG  120
YSYGYPLFDY WGQGTLVTVS SGGGGSGGGG SGGGGSGGGG SDIQMTQSPS SLSASVGDRV  180
TITCRASQGI RNDLGWYQQK LGKAPKRLIY AASSLQSGVP SRFSGSGSGT EFTLTISSLQ  240
PEDFATYYCL QYNSYPRTFG QGTKVEIKTT TPAPRPPTPA PTIASQPLSL RPEACRPAAG  300
GAVHTRGLDF ACDIYIWAPL AGTCGVLLLS LVITLYCKRG RKKLLYIFKQ PPMRPVQTTQ  360
EEDGCSCRFP EEEEGGCELR VKFSRSADAP AYQQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                       491

SEQ ID NO: 655          moltype = AA  length = 486
FEATURE                 Location/Qualifiers
source                  1..486
                        mol_type = protein
                        organism = synthetic construct
                        note = Description of Artificial Sequence: Synthetic
                        polypeptide
SEQUENCE: 655
MALPVTALLL PLALLLHAAR PQVQLQESGP GLVKPSGTLS LTCAVSGDSI SSNWWTWVRQ  60
PPGKGLEWIG DIHHSGSTNY NPSLKSRVTM SVDKSENQFS LKLSSVTAAD TAVFYCARDG  120
GGTLDYWGQG TLVTVSSGGG GSGGGGSGGG GSGGGGSDIQ MTQSPSTLSA SVGDRVTITC  180
RASQSISSWL AWYQQKPGKA PKLLIYKAST LESGVPSRFS GSGSGTEFTL TISSLQPDDF  240
ATYYCQQYNG YSTFGQGTKV EIKTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYQQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                             486

SEQ ID NO: 656          moltype = AA  length = 495
FEATURE                 Location/Qualifiers
source                  1..495
                        mol_type = protein
                        organism = synthetic construct
                        note = Description of Artificial Sequence: Synthetic
                        polypeptide
SEQUENCE: 656
MALPVTALLL PLALLLHAAR PQVQLVQSGA EVKKPGSSVK VSCKASGGTF TNYCISWVRQ  60
APGQGLEWMG GIIPIFGTTN YAQTFQGRVT ITADKSTSTA YMELSSLRSE DTAVYYCARD  120
NGDRYYYDMD VWGQGTTVTV SSGGGGSGGG GSGGGGSGGG GSQSVLTQPP SVSAAPGQKV  180
TISCSGSSSN IGNNYVSWYQ QLPGTAPKLL IYDNNKRPSG IPDRFSGSKS GTSATLGITG  240
LQTGDEADYY CGTWDSSLSA VVFGGGTKLT VLTTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                   495

SEQ ID NO: 657          moltype = AA  length = 497
FEATURE                 Location/Qualifiers
source                  1..497
                        mol_type = protein
                        organism = synthetic construct
                        note = Description of Artificial Sequence: Synthetic
                        polypeptide
SEQUENCE: 657
MALPVTALLL PLALLLHAAR PQVPLVQSGA EVKKPGSSVK VSCKASGGTF STYSISWVRQ  60
APGQGLEWMG GIIPIFGTTN YAQKFQGRVT ITADKSTSTA YMELSSLRSE DTAVYYCARD  120
GEGSYYYYG MDVWGQGTTV TVSSGGGGSG GGGSGGGGSG GGGSQSVLTQ PPSVSAAPGQ  180
KVTISCSGSS NIGNNYVSW YQQLPGTAPK LLIYDNNKRP SGIPDRFFGS KFGTSATLGI  240
TGLQTGDEAD YYCGTWDSSL SAVVFGGGTK LTVLTTTPAP RPPTPAPTIA SQPLSLRPEA  300
CRPAAGGAVH TRGLDFACDI YIWAPLAGTC GVLLLSLVIT LYCKRGRKKL LYIFKQPFMR  360
PVQTTQEEDG CSCRFPEEEE GGCELRVKFS RSADAPAYQQ GQNQLYNELN LGRREEYDVL  420
DKRRGRDPEM GGKPRRKNPQ EGLYNELQKD KMAEAYSEIG MKGERRRGKG HDGLYQGLST  480
ATKDTYDALH MQALPPR                                                 497

SEQ ID NO: 658          moltype = AA  length = 490
FEATURE                 Location/Qualifiers
source                  1..490
                        mol_type = protein
                        organism = synthetic construct
                        note = Description of Artificial Sequence: Synthetic
```

-continued

```
                        polypeptide
SEQUENCE: 658
MALPVTALLL PLALLLHAAR PQVQLQESGP GLVKPSETLS LTCTVSGDSI SSYYWSWIRQ  60
PPGKGLEWIG YMYYSGITNY NPSLKSRVNI SLDTSKNQFS LKLGSVTAAD TAVYYCARLS  120
VAGFYFDYWG QGTLVTVSSG GGGSGGGGSG GGGSGGGGSE IVLTQSPGTL SLSPGERATL  180
SCRASQSVTR SYLAWYQQKP GQAPRLLIYG ASSRATDIPD RFSGSGSGTD FTLTINRLEP  240
EDFAVYYCQQ YGTSPLTFGG GTKVEIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 659          moltype = AA  length = 490
FEATURE                 Location/Qualifiers
source                  1..490
                        mol_type = protein
                        organism = synthetic construct
                        note = Description of Artificial Sequence: Synthetic
                         polypeptide
SEQUENCE: 659
MALPVTALLL PLALLLHAAR PQVQLQESGP GLVKPSETLS LTCTVSSDSI SSYYWSWIRQ  60
PPGKGLEWIS YIYYSGISNY NPSLKSRVSI SVDTSKNQFS LRLSSVTAAD TAVYYCARIS  120
VAGFFFDNWG QGTLVTVSSG GGGSGGGGSG GGGSGGGGSE IMLTQSPDTL SLSPGERATL  180
SCRASQSVSS SYLAWYQQKP GQAPRLLIYG ASSRAAGVPD RFSGSGSGTD FTLTISRLAP  240
EDFVVYYCQQ YGISPLTFGG GTKVEIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 660          moltype = AA  length = 498
FEATURE                 Location/Qualifiers
source                  1..498
                        mol_type = protein
                        organism = synthetic construct
                        note = Description of Artificial Sequence: Synthetic
                         polypeptide
SEQUENCE: 660
MALPVTALLL PLALLLHAAR PQVQLQQSGP GLVKPSQTLS LTCAISGDSV SSNSATWNWI  60
RQSPSRGLEW LGRTYYRSKW YDDYAVSVKS RITINPDTSK NHLSLHLNSV TPEDTAVYYC  120
AGGGLVGAPD GFDVWGQGTM VTVSSGGGGS GGGGSGGGGS GGGGSQSVLT QPPSASGTPG  180
QRVTISCSGS SSNIGSDPVN WYQQLPGTAP KLLIYSNNQR PSGVPDRFSG SKSGTSASLA  240
ISGLQSEDEA DYYCSAWDDS LNGYVFGTGT KVTVLTTTPA PRPPTPAPTI ASQPLSLRPE  300
ACRPAAGGAV HTRGLDFACD IYIWAPLAGT CGVLLLSLVI TLYCKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRRGK GHDGLYQGLS  480
TATKDTYDAL HMQALPPR                                                498

SEQ ID NO: 661          moltype = AA  length = 493
FEATURE                 Location/Qualifiers
source                  1..493
                        mol_type = protein
                        organism = synthetic construct
                        note = Description of Artificial Sequence: Synthetic
                         polypeptide
SEQUENCE: 661
MALPVTALLL PLALLLHAAR PQVQLVQSGA EVKKPGASVK VSCKASGYTF TGYSIHWVRQ  60
APGQGLEWMG WINPNSGGTF YAQKFQGRVT MTRDTSISTV YMELSRLRSD DTAVYYCARD  120
GWGDYYYYGL DVWGQGTTVT VSLGGGGSGG GGSGGGGSGG GGSDIQMTQS PSSVSASVGD  180
RVTITCRASQ DISSWLAWYQ QKPGKAPKLL IYTASSLQGG VPSRFSGSGS GTDFTLTISS  240
LQPEDLATYS CQQANVFPYT FGQGTKLEIK TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                     493

SEQ ID NO: 662          moltype = AA  length = 493
FEATURE                 Location/Qualifiers
source                  1..493
                        mol_type = protein
                        organism = synthetic construct
                        note = Description of Artificial Sequence: Synthetic
                         polypeptide
SEQUENCE: 662
MALPVTALLL PLALLLHAAR PEVQLLESGG GLVQPGGSLR LSCAASGFTF SSYAMNWVRQ  60
APGKGLEWVS TISGSGGSTY YADSVKGRFT ISRDNSKNTL YLQMNSLRAE DTAVFYCAID  120
PEYYDILTGG DYWGQGTLVT VSSGGGGSGG GGSGGGGSGG GGSDIQMTQS PSAMSASVGD  180
RVTITCRASQ GISNYLAWFQ QKPGKVPKRL IYAASSLQSG VPSRFSGSGS GTEFTLTISS  240
LQPEDFATYF CLQHDSFPLT FGGGTKVEIK TTTPAPRPPT PAPTIASQPL SLRPEACRPA  300
```

```
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                      493

SEQ ID NO: 663              moltype = AA  length = 490
FEATURE                     Location/Qualifiers
source                      1..490
                            mol_type = protein
                            organism = synthetic construct
                            note = Description of Artificial Sequence: Synthetic
                             polypeptide
SEQUENCE: 663
MALPVTALLL PLALLLHAAR PQVQLQESGP GLVKPSETLS LTCTVSSDSI SNYYWSWIRQ  60
PPGKGLEWIS YIYYSGITNY NPSLKSRVTI SVDTSKNQFS LKLSSVTAAD TAVYYCARIT  120
VTGFYFDYWG QGTLVTVSSG GGGSGGGGSG GGGSGGGGSE IVLTQSPGTL SLSPGERATL  180
SCRASQSISR SYLAWYQQKP GQAPRHLIYG ASSRATGIPD RFSGSGSGTD FILTISRLEP  240
EDFAVYYCQQ YDTSPLTFGG GTKVEIKTTT PAPRPPTPAP TIASGPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 664              moltype = AA  length = 498
FEATURE                     Location/Qualifiers
source                      1..498
                            mol_type = protein
                            organism = synthetic construct
                            note = Description of Artificial Sequence: Synthetic
                             polypeptide
SEQUENCE: 664
MALPVTALLL PLALLLHAAR PQVQLQQSGP GLVKPSQTLS LTCAISGDSV SSNSVVWNWI  60
RQSPSRGLEW LGRTYYRSKW YDDYAVSVKS RITINPDTSK NQFSLQLNSV TPEDTAVYHC  120
ARGGIVGAPD AFDIWGQGTM VTVSSGGGGS GGGGSGGGGS GGGGSQSVLT QPPSASGTPG  180
QRVTISCSGS SSNIGSDPVS WYQQFPGTAP KLLIYTNNQR PSGVPDRFSG SKSGTSASLA  240
ISGLQSEDEA DYYCAAWDDS LNGHVFGTGT KVTVLTTTPA PRPPTPAPTI ASQPLSLRPE  300
ACRPAAGGAV HTRGLDFACD IYIWAPLAGT CGVLLLSLVI TLYCKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRGK GHDGLYQGLS  480
TATKDTYDAL HMQALPPR                                                498

SEQ ID NO: 665              moltype = AA  length = 498
FEATURE                     Location/Qualifiers
source                      1..498
                            mol_type = protein
                            organism = synthetic construct
                            note = Description of Artificial Sequence: Synthetic
                             polypeptide
SEQUENCE: 665
MALPVTALLL PLALLLHAAR PQVQLQQSGP GLVKPSQTLS LTCAISGDSV SSNSAVWNWI  60
RQSPSRGLEW LGWTYYRSKY YNDYAVSLKS RITINPDTSK NQFSLQLNSL TPEDTAVYYC  120
TRGGIVGAPD GFDIWGQGTM VTVSSGGGGS GGGGSGGGGS GGGGSQSALT QPPSASGTPG  180
QRVTISCSGS NSNIGSNPIN WYQQLPGTAP KLLIYSNNQR PSGVPDRFSG SKSGTSASLA  240
ISGLQSEDEA DYYCAAWDDS LNGHVFGTGT KVTVLTTTPA PRPPTPAPTI ASQPLSLRPE  300
ACRPAAGGAV HTRGLDFACD IYIWAPLAGT CGVLLLSLVI TLYCKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRGK GHDGLYQGLS  480
TATKDTYDAL HMQALPPR                                                498

SEQ ID NO: 666              moltype = AA  length = 490
FEATURE                     Location/Qualifiers
source                      1..490
                            mol_type = protein
                            organism = synthetic construct
                            note = Description of Artificial Sequence: Synthetic
                             polypeptide
SEQUENCE: 666
MALPVTALLL PLALLLHAAR PQVQLQESGP GLVKPSETLS LTCTVSGGSI SSYYWSWIRQ  60
SPGKGLEWIG YVYYSDITNY NPSLKSRVTI SVDTSKNQFS LNLNSVTAAD TAFYFCARIG  120
VAGFYFDYWG QGTLVTVSSG GGGSGGGGSG GGGSGGGGSE IVLTQSPDTL SLSPGERATL  180
SCRASQSVSR RYLAWYQQKP GQAPRLLIYG ASSRATGIPD RFSGSGSGTD FTLTISRLEP  240
EDFEVYYCQQ YGTSPITFGQ GTRLEIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 667              moltype = AA  length = 498
FEATURE                     Location/Qualifiers
```

-continued

```
source                  1..498
                        mol_type = protein
                        organism = synthetic construct
                        note = Description of Artificial Sequence: Synthetic
                          polypeptide
SEQUENCE: 667
MALPVTALLL PLALLLHAAR PQIQLQQSGP GLVKPSQTLS LTCAISGDSV SSNSAVWNWI   60
RQSPSRGLEW LGRTYYRSKW YNDYAVSVKS RITIKPDTAK NQFSLQLNSV TPEDTAVYYF  120
TRGGIVGAPD AFDIWGQGTM VTVSSGGGGS GGGGSGGGGS GGGGSQSVLT QPPSASGTPG  180
QRVTISCSGS SSNIGSDPIN WYQQVPGTAP KLLIYSNNQR PSGVPDRFSG SKSGTSASLA  240
ISGLQSEDEA DYYCAAWDDS LNGYVFGTGT KVTVLTTTPA PRPPTPAPTI ASQPLSLRPE  300
ACRPAAGGAV HTRGLDFACD IYIWAPLAGT CGVLLLSLVI TLYCKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRRGK GHDGLYQGLS  480
TATKDTYDAL HMQALPPR                                                498

SEQ ID NO: 668          moltype = AA  length = 498
FEATURE                 Location/Qualifiers
source                  1..498
                        mol_type = protein
                        organism = synthetic construct
                        note = Description of Artificial Sequence: Synthetic
                          polypeptide
SEQUENCE: 668
MALPVTALLL PLALLLHAAR PQVQLQQSGP GLVKPSETLS LTCAISGDSV SSNSATWNWI   60
RQSPSRGLEW LGRTYYRSEW YNDYAVSVKS RITINPDTSK NHLSLHLNSV TPEDTAVYYC  120
AGGGIVGAPD GFDVWGQGTM VTVSSGGGGS GGGGSGGGGS GGGGSQSVLT QPPSASGTPG  180
QRVTISCSGS SSNIGSDPVI WYQQLPRTAP KLLIYSNNQR PSGVPDRFSG SKSGTSASLA  240
ISGLQSEDEA DYYCAAWDDS LNGYVFGTGT KVTVLTTTPA PRPPTPAPTI ASQPLSLRPE  300
ACRPAAGGAV HTRGLDFACD IYIWAPLAGT CGVLLLSLVI TLYCKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRRGK GHDGLYQGLS  480
TATKDTYDAL HMQALPPR                                                498

SEQ ID NO: 669          moltype = AA  length = 498
FEATURE                 Location/Qualifiers
source                  1..498
                        mol_type = protein
                        organism = synthetic construct
                        note = Description of Artificial Sequence: Synthetic
                          polypeptide
SEQUENCE: 669
MALPVTALLL PLALLLHAAR PQVQLQQSGP GLVKPSQTLS LTCAISGDSV SSNSATWNWI   60
RQSPSTGLEW LARTYYRSKW YNDYEVSVKS QITINPDTSK NQFSLQLNSV TPEDTAVYYC  120
ARGGIVGAPD AFDIWGQGTM VTVSSGGGGS GGGGSGGGGS GGGGSQSVLT QPPSASGTPG  180
QGVTISCSGS SSNIGSNPVN WYQQLPGTAP KLLIYSNNQR PSGVPDRFSD SKSGTSASLA  240
ISGLQSEDEA DYYCSAWDDW LNGYVFGTGT KVTVLTTTPA PRPPTPAPTI ASQPLSLRPE  300
ACRPAAGGAV HTRGLDFACD IYIWAPLAGT CGVLLLSLVI TLYCKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRRGK GHDGLYQGLS  480
TATKDTYDAL HMQALPPR                                                498

SEQ ID NO: 670          moltype = AA  length = 489
FEATURE                 Location/Qualifiers
source                  1..489
                        mol_type = protein
                        organism = synthetic construct
                        note = Description of Artificial Sequence: Synthetic
                          polypeptide
SEQUENCE: 670
MALPVTALLL PLALLLHAAR PQVQLQESGP GLVKPSETLS LTCTVSGDSI NNYFWSWIRQ   60
PPGKGLEWIG YFYHRGGNNY NPSLKSRVTI SIDTSKNQFS LNLNSVTSAD TAVYYCARLA  120
LAGFFFDYWG QGTLVTVSSG GGGSGGGGSG GGGSGGGGSD IQMTQSPSTL SASVGDRVTI  180
TCRASQSISS WLAWYQQKPG KAPKLLIYKA SSLESGVPSR FSGSGSGTEF TLTISSLQPD  240
DFATYYCQQY NSYSRTFGQG TKVEIKTTTP APRPPTPAPT IASQPLSLRP EACRPAAGGA  300
VHTRGLDFAC DIYIWAPLAG TCGVLLLSLV ITLYCKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 671          moltype = AA  length = 497
FEATURE                 Location/Qualifiers
source                  1..497
                        mol_type = protein
                        organism = synthetic construct
                        note = Description of Artificial Sequence: Synthetic
                          polypeptide
SEQUENCE: 671
MALPVTALLL PLALLLHAAR PQVPLVQSGA EVKKPGSSVK VSCKASGGTF STYSISWVRQ   60
```

-continued

```
APGQGLEWMG GIIPIFGTTN YAQKFQGRVT ITADKSTSTA YMELSSLRSE DTAVYYCARD  120
GEGSYYYYYG MDVWGQGTTV TVSSGGGGSG GGGSGGGGSG GGGSQSVLTQ PPSASGTPGQ  180
RVTISCSGSS SNIGSNYVYW YQQLPGTAPK LLIYSNNQRP SGVPDRFSGS KSGTSASLAI  240
SGLRSEDEAD YYCAAWDDSL SGWVFGGGTK LTVLTTTPAP RPPTPAPTIA SQPLSLRPEA  300
CRPAAGGAVH TRGLDFACDI YIWAPLAGTC GVLLLSLVIT LYCKRGRKKL LYIFKQPFMR  360
PVQTTQEEDG CSCRFPEEEE GGCELRVKFS RSADAPAYQQ GQNQLYNELN LGRREEYDVL  420
DKRRGRDPEM GGKPRRKNPQ EGLYNELQKD KMAEAYSEIG MKGERRRGKG HDGLYQGLST  480
ATKDTYDALH MQALPPR                                                 497

SEQ ID NO: 672         moltype = AA  length = 494
FEATURE                Location/Qualifiers
source                 1..494
                       mol_type = protein
                       organism = synthetic construct
                       note = Description of Artificial Sequence: Synthetic
                       polypeptide
SEQUENCE: 672
MALPVTALLL PLALLLHAAR PEVQLVESGG GLVQPGGSLR LSCAASGFTF SSYSMNWVRQ  60
APGKGLEWVS YISSSSSTIY YADSVKGRFT ISRDNAKNSL YLQMNSLRDE DTAVYYCARD  120
KERRYYYYGM DVWGQGTTVT VSSGGGGSGG GGSGGGGSGG GGSEIVLTQS PDTLSLSPGE  180
RATLSCRASQ SVSRRYLAWY QQKPGQAPRL LIYGASSRAT GIPDRFSGSG SGTDFTLTIS  240
RLEPEDFAVY YCQQFGTSPI TFGQGTRLEI KTTTPAPRPP TPAPTIASQP LSLRPEACRP  300
AAGGAVHTRG LDFACDIYIW APLAGTCGVL LLSLVITLYC KRGRKKLLYI FKQPFMRPVQ  360
TTQEEDGCSC RFPEEEEGGC ELRVKFSRSA DAPAYQQGQN QLYNELNLGR REEYDVLDKR  420
RGRDPEMGGK PRRKNPQEGL YNELQKDKMA EAYSEIGMKG ERRRGKGHDG LYQGLSTATK  480
DTYDALHMQA LPPR                                                    494

SEQ ID NO: 673         moltype = AA  length = 498
FEATURE                Location/Qualifiers
source                 1..498
                       mol_type = protein
                       organism = synthetic construct
                       note = Description of Artificial Sequence: Synthetic
                       polypeptide
SEQUENCE: 673
MALPVTALLL PLALLLHAAR PQVQLQQSGP GLVKPSQTLS LACAISGDSV SSNSAIWNWI  60
RQSPSRGLEW LGGTYYRSMW YNDYAVSVKS RITINPDTSK NQLSLQLNSV TPEDTAVYYC  120
SRGGIVGVPD AFDIWGQGTM VTVSSGGGGS GGGGSGGGGS GGGGSQSVLT QPPSASGTPG  180
QRVTISCSGS SSNIGSNTAN WYQQLPGTAP RLLIYRNNQR PSGVPDRFSG SKSGTSASLA  240
ISGLQSEDEA DYYCAAWDDS LNGYVFGTGT KVTVLTTTPA PRPPTPAPTI ASQPLSLRPE  300
ACRPAAGGAV HTRGLDFACD IYIWAPLAGT CGVLLLSLVI TLYCKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRRGK GHDGLYQGLS  480
TATKDTYDAL HMQALPPR                                                498

SEQ ID NO: 674         moltype = AA  length = 492
FEATURE                Location/Qualifiers
source                 1..492
                       mol_type = protein
                       organism = synthetic construct
                       note = Description of Artificial Sequence: Synthetic
                       polypeptide
SEQUENCE: 674
MALPVTALLL PLALLLHAAR PQVQLQESGP GLVKPSETLS LTCNVSDGSI SSYYWTWIRQ  60
PPGKGLDWIG YIFYSGTTNY NPSLKSRVTI SLDTSKNQFS LKLTSMTAAD TAVYYCARIS  120
EKSFYFDYWG QGTLVTVSSG GGGSGGGGSG GGGSGGGGSQ SVLTQPPSAS GTPGQRVTIS  180
CSGSSSNIGS NYVYWYQQLP GTAPKLLIYS NNQRPSGVPD RFSGSKSGTS ASLAISGLRS  240
EDEADYYCAP WDDSLSGRVF GGGTKLTVLT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                      492

SEQ ID NO: 675         moltype = AA  length = 493
FEATURE                Location/Qualifiers
source                 1..493
                       mol_type = protein
                       organism = synthetic construct
                       note = Description of Artificial Sequence: Synthetic
                       polypeptide
SEQUENCE: 675
MALPVTALLL PLALLLHAAR PQVQLVQSGA EVKRPGASVK VSCKASGYTF TSYYIHWVRQ  60
APGQGLEWMG VIVPSGGSIS YAQKFQGRVT MTRDTSTNIV YMELSSLRSE DTAVYYCARD  120
RYYGDYYYGL DVWGQGTTVT VSSGGGGSGG GGSGGGGSGG GGSDIQMTQS PSSLSASVGD  180
RVTITCRASQ GINNFLAWFQ QKPGKAPKSL IYAASSLQSG VPSKFSGSGS GTDFTLTIRS  240
LQPEDFATYY CQHYNSYPIT FGQGTRLEIK TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
```

```
TYDALHMQAL PPR                                                     493

SEQ ID NO: 676           moltype = AA  length = 490
FEATURE                  Location/Qualifiers
source                   1..490
                         mol_type = protein
                         organism = synthetic construct
                         note = Description of Artificial Sequence: Synthetic
                         polypeptide
SEQUENCE: 676
MALPVTALLL PLALLLHAAR PQVHLQESGP GLVKPSETLS LTCTVSGGSI SHYYWTWIRQ  60
PPGKGLEWIG YIYYSGITNF SPSLKSRVSI SVDSSKNQFS LNLNSVTAAD TAVYYCAGIS  120
LAGFYFDYWV QGTLVTVSSG GGGSGGGGSG GGGSGGGGSE IVLTQSPGTL SLSPGERATL  180
SCRASQSVSR SYLAWYQQKP GQAPRLLIYG ASSRATGVPD RFSGSGSGTD FTLTISRLEP  240
EDFAVFYCQQ YSISPLTFGG GTKVEIKTTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                        490

SEQ ID NO: 677           moltype = AA  length = 493
FEATURE                  Location/Qualifiers
source                   1..493
                         mol_type = protein
                         organism = synthetic construct
                         note = Description of Artificial Sequence: Synthetic
                         polypeptide
SEQUENCE: 677
MALPVTALLL PLALLLHAAR PQVQLQESGP GLVKPSETLS LTCTVSGVSI SSYYWSWIRQ  60
PPGKGLEWIA YIYYSGNTNY SPSLKSRVTI SVDTSKDQLS LKLSSVTAAD TAVYYCTRGG  120
SGTIDVFDIW GQGTMVAVSS GGGGSGGGGS GGGGSGGGGS QSVLTQPPSV SAAPGQKVTI  180
SCSGSSSNIG NNYVSWYQQL PGTAPKLLIY DNNKRPSGIP DRFSGSKSGT SATLGITGLQ  240
TGDEADYYCE TWDSSLSAVV FGGGTKLTVL TTTPAPRPPT PAPTIASQPL SLRPEACRPA  300
AGGAVHTRGL DFACDIYIWA PLAGTCGVLL LSLVITLYCK GRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 678           moltype = AA  length = 495
FEATURE                  Location/Qualifiers
source                   1..495
                         mol_type = protein
                         organism = synthetic construct
                         note = Description of Artificial Sequence: Synthetic
                         polypeptide
SEQUENCE: 678
MALPVTALLL PLALLLHAAR PQVQLQQSGP GLVKPSQTLS LTCAISGDNV STNSAAWNWI  60
RQSPSRGLEW LGWTYYRSKW YNDYAVSLKS RININPDTSK NQFSLQLNSV TPEDTAVYYC  120
ARWVNRDVFD IWGQGTMVTV SSGGGGSGGG GSGGGGSGGG GSQSALTQPA SVSGSPGQSI  180
TISCTGTSSD VGSYNLVSWY QQHPGKAPKL MIYEGSKRPS GVSNRFSGSK SGNTASLTIS  240
GLQAEDEADY YCCSYAGSST WVFGGGTKLT VLTTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                  495

SEQ ID NO: 679           moltype = AA  length = 496
FEATURE                  Location/Qualifiers
source                   1..496
                         mol_type = protein
                         organism = synthetic construct
                         note = Description of Artificial Sequence: Synthetic
                         polypeptide
SEQUENCE: 679
MALPVTALLL PLALLLHAAR PQVQLVESGG GVVQPGRSLR LSCAASGFTF SSYGMHWVRQ  60
TPGKGLEWVA VISYDGNSNY YADSVKGRFT ISRDNSKNTL YLQMNSLRAE DTAVYYCARD  120
GATVTSYYYY GMDVWGQGTT VTVSSGGGGS GGGGSGGGGS GGGGSEIVLT QSPGTLSLSP  180
GERATLSCRA SQSVSRTYLA WYHQKPGQAP RLLIYGASSR ATGISDRFSG SGSGTDFTLT  240
ISRLEPEDFA VYYCQQYGTS PITFGQGTRL EIKTTTPAPR PPTPAPTIAS QPLSLRPEAC  300
RPAAGGAVHT RGLDFACDIY IWAPLAGTCG VLLLSLVITL YCKRGRKKLL YIFKQPMRP   360
VQTTQEEDGC SCRFPEEEEG GCELRVKFSR SADAPAYQQG QNQLYNELNL GRREEYDVLD  420
KRRGRDPEMG GKPRRKNPQE GLYNELQKDK MAEAYSEIGM KGERRRGKGH DGLYQGLSTA  480
TKDTYDALHM QALPPR                                                 496

SEQ ID NO: 680           moltype = AA  length = 501
FEATURE                  Location/Qualifiers
source                   1..501
                         mol_type = protein
                         organism = synthetic construct
```

-continued

```
                                 note = Description of Artificial Sequence: Synthetic
                                 polypeptide
SEQUENCE: 680
MALPVTALLL PLALLLHAAR PQVQLQQSGP GLVKPSQTLS LTCAISGDSV SSNSAVWNWI   60
RQSPSRGLEW LGRTYYRSKW YNDYAVSVKS RITINPDTSR NQFSLQLNSV TPEDTAVYYC   120
ARGGIVGAPD GFDIWGQGTM VTVSSGGGGS GGGGSGGGGS GGGGSDIVMT QSPDSLAVSL   180
GERATINCKS SQSVLDSSNN NNYFAWYQQR PGQPPHLLIY WASSRESGVP DRFSGSGSGT   240
DFTLTISSLQ AEDVAVYYCQ QYYSTPYTFG QGTKLEIKTT TPAPRPPTPA PTIASQPLSL   300
RPEACRPAAG GAVHTRGLDF ACDIYIWAPL AGTCGVLLLS LVITLYCKRG RKKLLYIFKQ   360
PFMRPVQTTQ EEDGCSCRFP EEEEGGCELR VKFSRSADAP AYQQGQNQLY NELNLGRREE   420
YDVLDKRRGR DPEMGGKPRR KNPQEGLYNE LQKDKMAEAY SEIGMKGERR RGKGHDGLYQ   480
GLSTATKDTY DALHMQALPP R                                            501

SEQ ID NO: 681           moltype = AA  length = 495
FEATURE                  Location/Qualifiers
source                   1..495
                         mol_type = protein
                         organism = synthetic construct
                         note = Description of Artificial Sequence: Synthetic
                         polypeptide
SEQUENCE: 681
MALPVTALLL PLALLLHAAR PQVQLQQSGP GLVKPSQTLS LTCAISGDSV SSNTTAWKWS   60
RQSPSKGLEW LGWTYYRSKW YYDYTVSVKS RITINPDTSK NQFSLQLNSV TPEDTAVYYC   120
ARWIFHDAFD IWGQGTMVTV SSGGGGSGGG GSGGGGSGGG GSQSALTQPP SASGTPGQRV   180
TISCSGSSSN IGSNTVNWYQ QLPGTAPKLL IYTNNQRPSG VPDRFSGSKS GTSASLAISG   240
LQSEDEADYF CSTWDDSLNG PVFGGGTKLT VLTTTPAPRP PTPAPTIASQ PLSLRPEACR   300
PAAGGAVHTR GLDFACDIYI WAPLAGTCGV LLLSLVITLY CKRGRKKLLY IFKQPFMRPV   360
QTTQEEDGCS CRFPEEEEGG CELRVKFSRS ADAPAYQQGQ NQLYNELNLG RREEYDVLDK   420
RRGRDPEMGG KPRRKNPQEG LYNELQKDKM AEAYSEIGMK GERRRGKGHD GLYQGLSTAT   480
KDTYDALHMQ ALPPR                                                  495

SEQ ID NO: 682           moltype = AA  length = 486
FEATURE                  Location/Qualifiers
source                   1..486
                         mol_type = protein
                         organism = synthetic construct
                         note = Description of Artificial Sequence: Synthetic
                         polypeptide
SEQUENCE: 682
MALPVTALLL PLALLLHAAR PQVQLQESGP GLVKPSETLS LTCTVSGDSI SSLSWSWIRQ   60
TPGEGLEWIG YLYYSGSTDY NPSLKSRVTI SVDTSKNQFS LKLRSVAAAD TALYYCARGR   120
RAFDIWGQGT MVTVSSGGGG SGGGGSGGGG SGGGGSDIQM TQSPSSLSAS VGDRVTITCR   180
GSQGISNYLA WFQQRPGKAP KSLIYAASSL ESGVPSKFSG SGSGTDFTLT IISLQPEDFA   240
TYYCQQYYNY PITFGQGTRL EIKTTTPAPR PPTPAPTIAS QPLSLRPEAC RPAAGGAVHT   300
RGLDFACDIY IWAPLAGTCG VLLLSLVITL YCKRGRKKLL YIFKQPFMRP VQTTQEEDGC   360
SCRFPEEEEG GCELRVKFSR SADAPAYQQG QNQLYNELNL GRREEYDVLD KRRGRDPEMG   420
GKPRRKNPQE GLYNELQKDK MAEAYSEIGM KGERRRGKGH DGLYQGLSTA TKDTYDALHM   480
QALPPR                                                            486

SEQ ID NO: 683           moltype = AA  length = 496
FEATURE                  Location/Qualifiers
source                   1..496
                         mol_type = protein
                         organism = synthetic construct
                         note = Description of Artificial Sequence: Synthetic
                         polypeptide
SEQUENCE: 683
MALPVTALLL PLALLLHAAR PQVQLVQSGA EVKKPGASVK VSCKASGYTF TGYYMHWVRQ   60
APGQGLEWMG WINPNSGGTN YAQKFQGRVT MTRDTSVSTA YMELSRLTSD DTAIYYCAKD   120
GGGDFYFYGM DVWGQGTTVT VSSGGGGSGG GGSGGGGSGG GGSQTVVTQE PSFSVSPGGT   180
VTLTCGLSSG SVSTSYYPSC FQQTPGQAPR TLIYSTDTRS SGVPDRFSGS ILGNKAALTI   240
TGAQADDESD YYCVLYMGSG ISVFGGGTKL TVLTTTPAPR PPTPAPTIAS QPLSLRPEAC   300
RPAAGGAVHT RGLDFACDIY IWAPLAGTCG VLLLSLVITL YCKRGRKKLL YIFKQPFMRP   360
VQTTQEEDGC SCRFPEEEEG GCELRVKFSR SADAPAYQQG QNQLYNELNL GRREEYDVLD   420
KRRGRDPEMG GKPRRKNPQE GLYNELQKDK MAEAYSEIGM KGERRRGKGH DGLYQGLSTA   480
TKDTYDALHM QALPPR                                                  496

SEQ ID NO: 684           moltype = AA  length = 572
FEATURE                  Location/Qualifiers
source                   1..572
                         mol_type = protein
                         organism = synthetic construct
                         note = Description of Artificial Sequence: Synthetic
                         polypeptide
SEQUENCE: 684
MALPVTALLL PLALLLHAAR PGGGGSCPYS NPSLCSGGGG SGGGGSQLQL QESGPGLVKP   60
SETLSLTCTV SGGSISSSSY YWGWIRQPPG KGLEWIGSIY YSGNIYHNPS LKSRVSISVD   120
TSKNQFSLRL SSVTAADTAV YYCAREIIVG ATHFDYWGQG TLVTVSSGGG GSGGGGSGGG   180
GSGGGGSAIQ MTQSPSSLSA SVGDRVTITC RASQGIRNDL GWYQQKPGKA PELLIYAASS   240
```

```
LQSGVPSRFS GSGSGTDFTL TISSLQPEDF ATYYCLQDYN YPLTFGPGTK VDIKGSGGGG    300
SCPYSNPSLC SGGGGSELPT QGTFSNVSTN VSPAKPTTTA CPYSNPSLCT TTPAPRPPTP    360
APTIASQPLS LRPEACRPAA GGAVHTRGLD FACDIYIWAP LAGTCGVLLL SLVITLYCKR    420
GRKKLLYIFK QPFMRPVQTT QEEDGCSCRF PEEEEGGCEL RVKFSRSADA PAYQQGQNQL    480
YNELNLGRRE EYDVLDKRRG RDPEMGGKPR RKNPQEGLYN ELQKDKMAEA YSEIGMKGER    540
RRGKGHDGLY QGLSTATKDT YDALHMQALP PR                                  572

SEQ ID NO: 685          moltype = AA  length = 542
FEATURE                 Location/Qualifiers
source                  1..542
                        mol_type = protein
                        organism = synthetic construct
                        note = Description of Artificial Sequence: Synthetic
                           polypeptide
SEQUENCE: 685
MALPVTALLL PLALLLHAAR PQLQLQESGP GLVKPSETLS LTCTVSGGSI SSSSYYWGWI    60
RQPPGKGLEW IGSIYYSGNI YHNPSLKSRV SISVDTSKNQ FSLRLSSVTA ADTAVYYCAR    120
EIIVGATHFD YWGQGTLVTV SSGGGGSGGG GSGGGGSGGG GSAIQMTQSP SSLSASVGDR    180
VTITCRASQG IRNDLGWYQQ KPGKAPELLI YAASSLQSGV PSRFSGSGSG TDFTLTISSL    240
QPEDFATYYC LQDYNYPLTF GPGTKVDIKG SGGGGSCPYS NPSLCSGGGG SCPYSNPSLC    300
SGGGGSTTTA CPYSNPSLCT TTPAPRPPTP APTIASQPLS LRPEACRPAA GGAVHTRGLD    360
FACDIYIWAP LAGTCGVLLL SLVITLYCKR GRKKLLYIFK QPFMRPVQTT QEEDGCSCRF    420
PEEEEGGCEL RVKFSRSADA PAYQQGQNQL YNELNLGRRE EYDVLDKRRG RDPEMGGKPR    480
RKNPQEGLYN ELQKDKMAEA YSEIGMKGER RRGKGHDGLY QGLSTATKDT YDALHMQALP    540
PR                                                                  542

SEQ ID NO: 686          moltype = AA  length = 530
FEATURE                 Location/Qualifiers
source                  1..530
                        mol_type = protein
                        organism = synthetic construct
                        note = Description of Artificial Sequence: Synthetic
                           polypeptide
SEQUENCE: 686
MALPVTALLL PLALLLHAAR PGGGGSCPYS NPSLCGGGGS QLQLQESGPG LVKPSETLSL    60
TCTVSGGSIS SSSYYWGWIR QPPGKGLEWI GSIYYSGNIY HNPSLKSRVS ISVDTSKNQF    120
SLRLSSVTAA DTAVYYCARE IIVGATHFDY WGQGTLVTVS SGGGGSGGGG SGGGGSGGGG    180
SAIQMTQSPS SLSASVGDRV TITCRASQGI RNDLGWYQQK PGKAPELLIY AASSLQSGVP    240
SRFSGSGSGT DFTLTISSLQ PEDFATYYCL QDYNYPLTFG PGTKVDIKGG GGSCPYSNPS    300
LCGGGGSTTT APRPPTPAP TIASQPLSLR PEACRPAAGG AVHTRGLDFA CDIYIWAPLA    360
GTCGVLLLSL VITLYCKRGR KKLLYIFKQP FMRPVQTTQE EDGCSCRFPE EEEGGCELRV    420
KFSRSADAPA YQQGQNQLYN ELNLGRREEY DVLDKRRGRD PEMGGKPRRK NPQEGLYNEL    480
QKDKMAEAYS EIGMKGERRR GKGHDGLYQG LSTATKDTYD ALHMQALPPR              530

SEQ ID NO: 687          moltype = AA  length = 525
FEATURE                 Location/Qualifiers
source                  1..525
                        mol_type = protein
                        organism = synthetic construct
                        note = Description of Artificial Sequence: Synthetic
                           polypeptide
SEQUENCE: 687
MALPVTALLL PLALLLHAAR PGGGGSCPYS NPSLCGGGGS CPYSNPSLCG GGGSQLQLQE    60
SGPGLVKPSE TLSLTCTVSG GSISSSSYYW GWIRQPPGKG LEWIGSIYYS GNIYHNPSLK    120
SRVSISVDTS KNQFSLRLSS VTAADTAVYY CAREIIVGAT HFDYWGQGTL VTVSSGGGGS    180
GGGGSGGGGS GGGGSAIQMT QSPSSLSASV GDRVTITCRA SQGIRNDLGW YQQKPGKAPE    240
LLIYAASSLQ SGVPSRFSGS GSGTDFTLTI SSLQPEDFAT YYCLQDYNYP LTFGPGTKVD    300
IKTTTPAPRP PTPAPTIASQ PLSLRPEACR PAAGGAVHTR GLDFACDIYI WAPLAGTCGV    360
LLLSLVITLY CKRGRKKLLY IFKQPFMRPV QTTQEEDGC CELRVKFSRS              420
ADAPAYQQGQ NQLYNELNLG RREEYDVLDK RRGRDPEMGG KPRRKNPQEG LYNELQKDKM    480
AEAYSEIGMK GERRRGKGHD GLYQGLSTAT KDTYDALHMQ ALPPR                   525

SEQ ID NO: 688          moltype = AA  length = 548
FEATURE                 Location/Qualifiers
source                  1..548
                        mol_type = protein
                        organism = synthetic construct
                        note = Description of Artificial Sequence: Synthetic
                           polypeptide
SEQUENCE: 688
MALPVTALLL PLALLLHAAR PQVQLQQSGP GLVKPSQTLS LTCAISGDSV SSNSATWNWI    60
RQSPSRGLEW LGRTYYRSKW YDDYAVSVKS RITINPDTSK NHLSLHLNSV TPEDTAVYYC    120
AGGGLVGAPD GFDVWGQGTM VTVSSGGGGS GGGGSGGGGS GGGGSQSVLT QPPSASGTPG    180
QRVTISCSGS SSNIGSDPVN WYQQLPGTAP KLLIYSNNQR PSGVPDRFSG SKSGTSASLA    240
ISGLQSEDEA DYYCSAWDDS LNGYVFGTGT KVTVLGSGGG GSCPYSNPSL CSGGGGSCPY    300
SNPSLCSGGG GSTTTACPYS NPSLCTTTPA PRPPTPAPTI ASQPLSLRPE ACRPAAGGAV    360
HTRGLDFACD IYIWAPLAGT CGVLLLSLVI TLYCKRGRKK LLYIFKQPFM RPVQTTQEED    420
GCSCRFPEEE EGGCELRVKF SRSADAPAYQ QGQNQLYNEL NLGRREEYDV LDKRRGRDPE    480
MGGKPRRKNP QEGLYNELQK DKMAEAYSEI GMKGERRRGK GHDGLYQGLS TATKDTYDAL    540
```

-continued

HMQALPPR                                                                                          548

SEQ ID NO: 689          moltype = AA  length = 536
FEATURE                 Location/Qualifiers
source                  1..536
                        mol_type = protein
                        organism = synthetic construct
                        note = Description of Artificial Sequence: Synthetic
                          polypeptide
SEQUENCE: 689
MALPVTALLL PLALLLHAAR PGGGGSCPYS NPSLCGGGGS QVQLQQSGPG LVKPSQTLSL    60
TCAISGDSVS SNSATWNWIR QSPSRGLEWL GRTYYRSKWY DDYAVSVKSR ITINPDTSKN   120
HLSLHLNSVT PEDTAVYYCA GGGLVGAPDG FDVWGQGTMV TVSSGGGGSG GGGSGGGGSG   180
GGGSQSVLTQ PPSASGTPGQ RVTISCSGSS SNIGSDPVNW YQQLPGTAPK LLIYSNNQRP   240
SGVPDRFSGS KSGTSASLAI SGLQSEDEAD YYCSAWDDSL NGYVFGTGTK VTVLGGGGSC   300
PYSNPSLCGG GGSTTTPAPR PPTPAPTIAS QPLSLRPEAC RPAAGGAVHT RGLDFACDIY   360
IWAPLAGTCG VLLLSLVITL YCKRGRKKLL YIFKQPFMRP VQTTQEEDGC SCRFPEEEEG   420
GCELRVKFSR SADAPAYQQG QNQLYNELNL GRREEYDVLD KRRGRDPEMG GKPRRKNPQE   480
GLYNELQKDK MAEAYSEIGM KGERRRGKGH DGLYQGLSTA TKDTYDALHM QALPPR        536

SEQ ID NO: 690          moltype = AA  length = 531
FEATURE                 Location/Qualifiers
source                  1..531
                        mol_type = protein
                        organism = synthetic construct
                        note = Description of Artificial Sequence: Synthetic
                          polypeptide
SEQUENCE: 690
MALPVTALLL PLALLLHAAR PGGGGSCPYS NPSLCGGGGS CPYSNPSLCG GGGSQVQLQQ    60
SGPGLVKPSQ TLSLTCAISG DSVSSNSATW NWIRQSPSRG LEWLGRTYYR SKWYDDYAVS   120
VKSRITINPD TSKNHLSLHL NSVTPEDTAV YYCAGGGLVG APDGFDVWGQ GTMVTVSSGG   180
GGSGGGGSGG GGSGGGGSQS VLTQPPSASG TPGQRVTISC SGSSSNIGSD PVNWYQQLPG   240
TAPKLLIYSN NQRPSGVPDR FSGSKSGTSA SLAISGLQSE DEADYYCSAW DDSLNGYVFG   300
TGTKVTVLTT TPAPRPPTPA PTIASQPLSL RPEACRPAAG GAVHTRGLDF ACDIYIWAPL   360
AGTCGVLLLS LVITLYCKRG RKKLLYIFKQ PFMRPVQTTQ EEDGCSCRFP EEEEGGCELR   420
VKFSRSADAP AYQQGQNQLY NELNLGRREE YDVLDKRRGR DPEMGGKPRR KNPQEGLYNE   480
LQKDKMAEAY SEIGMKGERR RGKGHDGLYQ GLSTATKDTY DALHMQALPP R            531

SEQ ID NO: 691          moltype = AA  length = 573
FEATURE                 Location/Qualifiers
source                  1..573
                        mol_type = protein
                        organism = synthetic construct
                        note = Description of Artificial Sequence: Synthetic
                          polypeptide
SEQUENCE: 691
MALPVTALLL PLALLLHAAR PGGGGSCPYS NPSLCSGGGG SGGGGSEVQL LESGGGLVQP    60
GGSLRLSCAA SGFTFSSYAM NWVRQAPGKG LEWVSTISGS GGSTYYADSV KGRFTISRDN   120
SKNTLYLQMN SLRAEDTAVF YCAIDPEYYD ILTGGDYWGQ GTLVTVSSGG GGSGGGGSGG   180
GGSGGGGSDI QMTQSPSAMS ASVGDRVTIT CRASQGISNY LAWFQQKPGK VPKRLIYAAS   240
SLQSGVPSRF SGSGSGTEFT LTISSLQPED FATYFCLQHD SFPLTFGGGT KVEIKGSGGG   300
GSCPYSNPSL CSGGGGSELP TQGTFSNVST NVSPAKPTTT ACPYSNPSLC TTTPAPRPPT   360
PAPTIASQPL SLRPEACRPA AGGAVHTRGL DFACDIYIWA PLAGTCGVLL LSLVITLYCK   420
RGRKKLLYIF KQPFMRPVQT TQEEDGCSCR FPEEEEGGCE LRVKFSRSAD APAYQQGQNQ   480
LYNELNLGRR EEYDVLDKRR GRDPEMGGKP RRKNPQEGLY NELQKDKMAE AYSEIGMKGE   540
RRRGKGHDGL YQGLSTATKD TYDALHMQAL PPR                                573

SEQ ID NO: 692          moltype = AA  length = 543
FEATURE                 Location/Qualifiers
source                  1..543
                        mol_type = protein
                        organism = synthetic construct
                        note = Description of Artificial Sequence: Synthetic
                          polypeptide
SEQUENCE: 692
MALPVTALLL PLALLLHAAR PEVQLLESGG GLVQPGGSLR LSCAASGFTF SSYAMNWVRQ    60
APGKGLEWVS TISGSGGSTY YADSVKGRFT ISRDNSKNTL YLQMNSLRAE DTAVFYCAID   120
PEYYDILTGG DYWGQGTLVT VSSGGGGSGG GGSGGGGSGG GGSDIQMTQS PSAMSASVGD   180
RVTITCRASQ GISNYLAWFQ QKPGKVPKRL IYAASSLQSG VPSRFSGSGS GTEFTLTISS   240
LQPEDFATYF CLQHDSFPLT FGGGTKVEIK GSGGGGSCPY SNPSLCSGGG GSCPYSNPSL   300
CSGGGGSTTT ACPYSNPSLC TTTPAPRPPT PAPTIASQPL SLRPEACRPA AGGAVHTRGL   360
DFACDIYIWA PLAGTCGVLL LSLVITLYCK RGRKKLLYIF KQPFMRPVQT TQEEDGCSCR   420
FPEEEEGGCE LRVKFSRSAD APAYQQGQNQ LYNELNLGRR EEYDVLDKRR GRDPEMGGKP   480
RRKNPQEGLY NELQKDKMAE AYSEIGMKGE RRRGKGHDGL YQGLSTATKD TYDALHMQAL   540
PPR                                                                 543

SEQ ID NO: 693          moltype = AA  length = 531
FEATURE                 Location/Qualifiers
source                  1..531

```
                         mol_type = protein
                         organism = synthetic construct
                         note = Description of Artificial Sequence: Synthetic
                           polypeptide
SEQUENCE: 693
MALPVTALLL PLALLLHAAR PGGGGSCPYS NPSLCGGGGS EVQLLESGGG LVQPGGSLRL    60
SCAASGFTFS SYAMNWVRQA PGKGLEWVST ISGSGGSTYY ADSVKGRFTI SRDNSKNTLY   120
LQMNSLRAED TAVFYCAIDP EYYDILTGGD YWGQGTLVTV SSGGGGSGGG GSGGGGSGGG   180
GSDIQMTQSP SAMSASVGDR VTITCRASQG ISNYLAWFQQ KPGKVPKRLI YAASSLQSGV   240
PSRFSGSGSG TEFTLTISSL QPEDFATYFC LQHDSFPLTF GGGTKVEIKG GGGSCPYSNP   300
SLCGGGGSTT TPAPRPPTPA PTIASQPLSL RPEACRPAAG GAVHTRGLDF ACDIYIWAPL   360
AGTCGVLLLS LVITLYCKRG RKKLLYIFKQ PFMRPVQTTQ EEDGCSCRFP EEEEGGCELR   420
VKFSRSADAP AYQQGQNQLY NELNLGRREE YDVLDKRRGR DPEMGGKPRR KNPQEGLYNE   480
LQKDKMAEAY SEIGMKGERR RGKGHDGLYQ GLSTATKDTY DALHMQALPP R            531

SEQ ID NO: 694           moltype = AA  length = 526
FEATURE                  Location/Qualifiers
source                   1..526
                         mol_type = protein
                         organism = synthetic construct
                         note = Description of Artificial Sequence: Synthetic
                           polypeptide
SEQUENCE: 694
MALPVTALLL PLALLLHAAR PGGGGSCPYS NPSLCGGGGS CPYSNPSLCG GGGSEVQLLE    60
SGGGLVQPGG SLRLSCAASG FTFSSYAMNW VRQAPGKGLE WVSTISGSGG STYYADSVKG   120
RFTISRDNSK NTLYLQMNSL RAEDTAVFYC AIDPEYYDIL TGGDYWGQGT LVTVSSGGGG   180
SGGGGSGGGG SGGGGSDIQM TQSPSAMSAS VGDRVTITCR ASQGISNYLA WFQQKPGKVP   240
KRLIYAASSL QSGVPSRFSG SGSGTEFTLT ISSLQPEDFA TYFCLQHDSF PLTFGGGTKV   300
EIKTTTPAPR PPTPAPTIAS QPLSLRPEAC RPAAGGAVHT RGLDFACDIY IWAPLAGTCG   360
VLLLSLVITL YCKRGRKKLL YIFKQPFMRP VQTTQEEDGC SCRFPEEEEG GCELRVKFSR   420
SADAPAYQQG QNQLYNELNL GRREEYDVLD KRRGRDPEMG GKPRRKNPQE GLYNELQKDK   480
MAEAYSEIGM KGERRRGKGH DGLYQGLSTA TKDTYDALHM QALPPR                  526

SEQ ID NO: 695           moltype = AA  length = 12
FEATURE                  Location/Qualifiers
source                   1..12
                         mol_type = protein
                         organism = synthetic construct
                         note = Description of Artificial Sequence: Synthetic peptide
SEQUENCE: 695
GYIFYSGTTN HN                                                        12

SEQ ID NO: 696           moltype = AA  length = 12
FEATURE                  Location/Qualifiers
source                   1..12
                         mol_type = protein
                         organism = synthetic construct
                         note = Description of Artificial Sequence: Synthetic peptide
SEQUENCE: 696
RASQRISNTY LA                                                        12
```

DLL3 TARGETING CHIMERIC ANTIGEN RECEPTORS AND BINDING AGENTS

CROSS REFERENCE TO RELATED APPLICATIONS

This application is a divisional of U.S. application Ser. No. 16/802,822, filed Feb. 27, 2020, which claims the benefit of priority to U.S. Provisional Application No. 62/812,585, filed Mar. 1, 2019; and U.S. Provisional Application No. 62/969,976, filed Feb. 4, 2020, the contents of all of which are hereby incorporated by reference in their entireties.

FIELD

This disclosure relates to DLL3 binding agents and chimeric antigen receptors (CARs) comprising an antigen binding molecule which binds to DLL3, polynucleotides encoding the same, and methods of treating a cancer in a patient using the same.

SEQUENCE LISTING

This application is being filed electronically via Patent Center and includes an electronically submitted sequence listing in .xml format. The .xml file contains a sequence listing entitled "AT-019_04USSL.xml" created on Apr. 27, 2023, and having a size of 923,242 bytes. The sequence listing contained in this .xml file is part of the specification and is incorporated herein by reference in its entirety.

BACKGROUND

Small cell lung cancer (SCLC) is an aggressive form of lung cancer with a poor prognosis and limited therapeutic options. SCLC represents about 10-15% of all new diagnosed lung cancers. The American Cancer Society estimates that about 234,000 new cases of lung cancer will be diagnosed in 2018. Estimated 5-year relative survival rates for SCLC are 31% (for stage I), 19% (for stage II), 8% (for stage III) and 2% (for stage IV). Survival rates for SCLC have remained low for several decades in a large part due to the lack of new therapies to combat this form of lung cancer. Conventional therapeutic treatments for cancer include chemotherapy and radiotherapy. Patients typically respond well to the current front-line therapy, which includes etoposide and cisplatin, but invariably quickly relapse with chemoresistant disease. Prognosis in the relapsed refractory setting is extremely poor, with rapid disease progression and short median survival of less than six months. There remains therefore a great need to develop more targeted and potent therapies for proliferative disorders.

Adoptive transfer of immune cells genetically modified to recognize malignancy-associated antigens is showing promise as a new approach to treating cancer (see, e.g., Brenner et al., Current Opinion in Immunology, 22(2): 251-257 (2010); Rosenberg et al., Nature Reviews Cancer, 8(4): 299-308 (2008)). Immune cells can be genetically modified to express chimeric antigen receptors (CARs), fusion proteins comprised of a DLL3 antigen recognition moiety and T cell activation domains (see, e.g., Eshhar et al., Proc. Natl. Acad. Sci. USA, 90(2): 720-724 (1993), and Sadelain et al., Curr. Opin. Immunol, 21(2): 215-223 (2009)). Immune cells that contain CARs, e.g., CAR-T cells (CAR-Ts), are engineered to endow them with antigen specificity while retaining or enhancing their ability to recognize and kill a target cell.

DLL3 is a non-canonical Notch ligand, functioning in a cell autonomous manner to inhibit Notch signaling, thus blocking cell to cell interactions and internalization of Notch in the target cell. Delta-like ligand 3 (DLL3) is an SCLC tumor marker and has been found to be associated with cancer stem cells. Other indications that implicate DLL3 include melanoma, low grade gliomas, glioblastoma, medullary thyroid cancer, carcinoids, dispersed neuroendocrine tumors in the pancreas, bladder and prostate, testicular cancer, and lung adenocarcinomas with neuroendocrine features. There is a need for treatments for cancer and in particular malignancies involving aberrant expression of DLL3. Provided herein are methods and compositions addressing this need.

SUMMARY

Provided herein are chimeric antigen receptors (CARs) comprising a DLL3 antigen binding domain that specifically binds to DLL3; and immune cells comprising these DLL3-specific CARs, e.g., CAR-T cells. Also provided are methods of making and using these DLL3-specific CARs, and immune cells comprising these DLL3-specific CARs. The DLL-3 targeting CAR T cells described herein demonstrate good transduction efficiency, in vitro phenotype and potent in vitro and in vivo anti-tumor activity.

In one aspect, the present disclosure provides a chimeric antigen receptor comprising an extracellular domain, a transmembrane domain, and an intracellular domain, wherein the extracellular domain comprises a DLL3 antigen binding domain that specifically binds to DLL3, and wherein the antigen binding domain comprises at least one of: (a) a variable heavy chain CDR1 comprising an amino acid sequence selected from the group consisting of SEQ ID NOs 1, 10, 19, 28, 37, 46, 55, 64, 73, 82, 91, 100, 109, 118, 127, 136, 145, 154, 163, 172, 181, 190, 199, 208, 217, 226, 235, 244, 253, 262, 271, 280, 289, 298, 307, 316, 325, 334, 343, 352, 361, 370, 379, 388, 397, 406, 415, 424, 433, 442, 451, and 460; (b) a variable heavy chain CDR2 comprising an amino acid sequence selected from the group consisting of SEQ ID NOs: 2, 11, 20, 38, 47, 56, 65, 74, 83, 92, 101, 110, 119, 128, 137, 146, 155, 164, 173, 182, 191, 200, 209, 218, 227, 236, 245, 254, 263, 272, 281, 290, 299, 308, 317, 326, 335, 344, 353, 362, 371, 380, 389, 398, 407, 416, 425, 434, 443, 452, 461, and 695; (c) a variable heavy chain CDR3 comprising an amino acid sequence selected from the group consisting of SEQ ID NOs 3, 12, 21, 30, 39, 48, 57, 66, 75, 84, 93, 102, 111, 120, 129, 138, 147, 156, 165, 174, 183, 192, 201, 210, 219, 228, 237, 246, 255, 264, 273, 282, 291, 300, 309, 318, 327, 336, 345, 354, 363, 372, 381, 390, 399, 408, 417, 426, 435, 444, 453, and 462; (d) a variable light chain CDR1 comprising an amino acid sequence selected from the group consisting of SEQ ID NOs: 4, 13, 22, 31, 40, 49, 58, 67, 85, 94, 103, 112, 121, 130, 139, 148, 157, 166, 175, 184, 193, 202, 211, 220, 229, 238, 247, 256, 265, 274, 283, 292, 301, 310, 319, 328, 337, 346, 355, 364, 373, 382, 391, 400, 409, 418, 427, 436, 445, 454, 463, and 696; (e) a variable light chain CDR2 comprising an amino acid sequence selected from the group consisting of SEQ ID NOs: 5, 14, 23, 32, 41, 50, 59, 68, 77, 86, 95, 104, 113, 122, 131, 140, 149, 158, 167, 176, 185, 194, 203, 212, 221, 230, 239, 248, 257, 266, 275, 284, 293, 302, 311, 320, 329, 338, 347, 356, 365, 374, 383, 392, 401, 410, 419, 428, 437, 446, 455, and 464; and (f) a variable light chain CDR3 comprising an amino acid sequence selected from the group consisting of SEQ ID NOs: 6, 15, 24, 33, 42, 51, 60, 69, 78, 87, 96, 105, 114, 123, 132, 141, 150, 159, 168, 177, 186, 195, 204, 213, 222, 231, 240, 249, 258, 267, 276, 285, 294, 303, 312, 321, 330, 339, 348, 357, 366, 375, 384, 393, 402, 411, 420, 429, 438, 447, 456, and 465.

In another aspect, the present disclosure provides a chimeric antigen receptor comprising an extracellular domain, a transmembrane domain, and an intracellular domain, wherein the extracellular domain comprises a DLL3 antigen binding domain that specifically binds to DLL3, and wherein the antigen binding domain comprises: (a) a variable heavy chain CDR1 comprising an amino acid sequence selected from the group consisting of SEQ ID NOs: 1, 10, 19, 28, 37, 46, 55, 64, 73, 82, 91, 100, 109, 118, 127, 136, 145, 154, 163, 172, 181, 190, 199, 208, 217, 226, 235, 244, 253, 262, 271, 280, 289, 298, 307, 316, 325, 334, 343, 352, 361, 370, 379, 388, 397, 406, 415, 424, 433, 442, 451, and 460; (b) a variable heavy chain CDR2 comprising an amino acid sequence selected from the group consisting of SEQ ID NOs: 2, 11, 20, 38, 47, 56, 65, 74, 83, 92, 101, 110, 119, 128, 137, 146, 155, 164, 173, 182, 191, 200, 209, 218, 227, 236, 245, 254, 263, 272, 281, 290, 299, 308, 317, 326, 335, 344, 353, 362, 371, 380, 389, 398, 407, 416, 425, 434, 443, 452, and 695461; and (c) a variable heavy chain CDR3 comprising an amino acid sequence selected from the group consisting of SEQ ID NOs: 3, 12, 21, 30, 39, 48, 57, 66, 75, 84, 93, 102, 111, 120, 129, 138, 147, 156, 165, 174, 183, 192, 201, 210, 219, 228, 237, 246, 255, 264, 273, 282, 291, 300, 309, 318, 327, 336, 345, 354, 363, 372, 381, 390, 399, 408, 417, 426, 435, 444, 453, and 462.

In one aspect, the present disclosure provides a chimeric antigen receptor comprising an extracellular domain, a transmembrane domain, and an intracellular domain, wherein the extracellular domain comprises a DLL3 antigen binding domain that specifically binds to DLL3, and wherein the antigen binding domain comprises: (a) a variable light chain CDR1 comprising an amino acid sequence selected from the group consisting of SEQ ID NOs: 4, 13, 22, 31, 40, 49, 58, 67, 85, 94, 103, 112, 121, 130, 139, 148, 157, 166, 175, 184, 193, 202, 211, 220, 229, 238, 247, 256, 265, 274, 283, 292, 301, 310, 319, 328, 337, 346, 355, 364, 373, 382, 391, 400, 409, 418, 427, 436, 445, 454, 463, and 696; (b) a variable light chain CDR2 comprising an amino acid sequence selected from the group consisting of SEQ ID NOs: 5, 14, 23, 32, 41, 50, 59, 68, 77, 86, 95, 104, 113, 122, 131, 140, 149, 158, 167, 176, 185, 194, 203, 212, 221, 230, 239, 248, 257, 266, 275, 284, 293, 302, 311, 320, 329, 338, 347, 356, 365, 374, 383, 392, 401, 410, 419, 428, 437, 446, 455, and 464; and (c) a variable light chain CDR3 comprising an amino acid sequence selected from the group consisting of SEQ ID NOs: 6, 15, 24, 33, 42, 51, 60, 69, 78, 87, 96, 105, 114, 123, 132, 141, 150, 159, 168, 177, 186, 195, 204, 213, 222, 231, 240, 249, 258, 267, 276, 285, 294, 303, 312, 321, 330, 339, 348, 357, 366, 375, 384, 393, 402, 411, 420, 429, 438, 447, 456, and 465.

In another aspect, the present disclosure provides a chimeric antigen receptor comprising an extracellular domain, a transmembrane domain, and an intracellular domain, wherein the extracellular domain comprises a DLL3 antigen binding domain that specifically binds to DLL3, and wherein the antigen binding domain comprises at least one of: (a) a variable heavy chain comprising an amino acid sequence selected from the group consisting of SEQ ID NOs: 7, 16, 25, 34, 43, 52, 61, 70, 79, 88, 97, 106, 115, 124, 133, 142, 151, 160, 169, 178, 187, 196, 205, 214, 223, 232, 241, 250, 259, 268, 277, 286, 295, 304, 313, 322, 331, 340, 349, 358, 367, 376, 385, 394, 403, 412, 421, 430, 439, 448, 457, 466; and (b) a variable light chain comprising an amino acid sequence selected from the group consisting of SEQ ID NOs: 8, 17, 26, 35, 44, 53, 62, 71, 80, 89, 98, 107, 116, 125, 134, 143, 152, 161, 170, 179, 188, 197, 206, 215, 224, 233, 242, 251, 260, 269, 278, 287, 296, 305, 314, 323, 332, 341, 350, 359, 368, 377, 386, 395, 404, 413, 422, 431, 440, 449, 458, and 467, wherein the variable heavy chain and the variable light chain is linked by at least one linker.

In a further aspect, the present disclosure provides a chimeric antigen receptor comprising an extracellular domain, a transmembrane domain, and an intracellular domain, wherein the extracellular domain comprises a DLL3 antigen binding domain that specifically binds to DLL3, and wherein the antigen binding domain comprises: (a) a variable heavy chain comprising an amino acid sequence selected from the group consisting of SEQ ID NOs: 7, 16, 25, 34, 43, 52, 61, 70, 79, 88, 97, 106, 115, 124, 133, 142, 151, 160, 169, 178, 187, 196, 205, 214, 223, 232, 241, 250, 259, 268, 277, 286, 295, 304, 313, 322, 331, 340, 349, 358, 367, 376, 385, 394, 403, 412, 421, 430, 439, 448, 457, and 466; and (b) a variable light chain comprising an amino acid sequence selected from the group consisting of SEQ ID NOs: 8, 17, 26, 35, 44, 53, 62, 71, 80, 89, 98, 107, 116, 125, 134, 143, 152, 161, 170, 179, 188, 197, 206, 215, 224, 233, 242, 251, 260, 269, 278, 287, 296, 305, 314, 323, 332, 341, 350, 359, 368, 377, 386, 395, 404, 413, 422, 431, 440, 449, 458, and 467, wherein the variable heavy chain and the variable light chain is linked by at least one linker.

In one aspect, the present disclosure provides a chimeric antigen receptor comprising an extracellular domain, a transmembrane domain, and an intracellular domain, wherein the extracellular domain comprises a DLL3 antigen binding domain that specifically binds to DLL3, and wherein the antigen binding domain comprises a sequence selected from the group consisting of those scFvs presented in Table 1d.

In another aspect, the present disclosure provides, a chimeric antigen receptor that specifically binds to DLL3, wherein the chimeric antigen receptor comprises an amino acid sequence that is at least about 80%, 85%, 90%, 95%, 96%, 98%, 99% or 100% identical to any one of SEQ ID NOs: 482 to 533 and 632-683. In some embodiments, the chimeric antigen receptor comprises an amino acid sequence of any one of SEQ ID NOs: 482 to 533 and 632-683.

In some embodiments, the present disclosure provides, a chimeric antigen receptor that specifically binds to DLL3, wherein the chimeric antigen receptor comprises an amino acid sequence that is at least about 80%, 85%, 90%, 95%, 96%, 98%, 99% or 100% identical to any one of SEQ ID NOs: 482 to 533 and 632-683, with or without a signal sequence. In some embodiments, the chimeric antigen receptor comprises an amino acid sequence of any one of SEQ ID NOs: 482 to 533 and 632-683, with or without a signal sequence.

In some embodiments, the intracellular domain of the chimeric antigen receptor comprises at least one costimulatory domain.

In some embodiments, the costimulatory domain of the chimeric antigen receptor is a signaling region of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1 (CD1 1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class I molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, CD49D, ITGA6, VLA-6, CD49f, ITGAD, CD1 1d, ITGAE, CD103, ITGAL, CD1 1a, LFA-1, ITGAM, CD1 1b, ITGAX, CD1 1c, ITGB1, CD29, ITGB2, CD18, LFA-1, ITGB7, NKG2D, TNFR2, TRANCE/RANKL, DNAMI (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

In some embodiments, the costimulatory domain comprises a signaling region of CD28.

In some embodiments, the CD28 costimulatory domain comprises SEQ ID NO: 550.

In some embodiments, the costimulatory domain comprises a signaling region of 4-1BB/CD137.

In some embodiments, the 4-1BB/CD137 costimulatory domain comprises SEQ ID NO: 480.

In some embodiments, the intracellular domain comprises at least one activating domain.

In some embodiments, the activating domain comprises CD3.

In some embodiments, the CD3 comprises CD3 zeta.

In some embodiments, the CD3 zeta comprises SEQ ID NO: 481.

In some embodiments, the chimeric antigen receptor is encoded by the polynucleotide sequence of any one of SEQ ID NOs: 571-621 and 631.

In some embodiments, the chimeric antigen receptor further comprises a safety switch.

In some embodiments, the safety switch comprises a CD20 mimotope or a QBEND-10 epitope.

In some embodiments, the safety switch comprises one or more CD20 mimotopes or one or more QBEND-10 epitopes, or combinations thereof.

In some embodiments, the chimeric antigen receptor comprises one or more safety switch in the format of QR3, SR2, RSR, or R2S.

In some embodiments, the chimeric antigen receptor comprises the amino acid sequence that is at least about 80%, 85%, 90%, 95%, 96%, 98%, 99% or 100% identical to any one of SEQ ID NOs: 622-628, 474-476, 565, and 684-694.

In some embodiments, the chimeric antigen receptor comprises the amino acid sequence that is at least about 80%, 85%, 90%, 95%, 96%, 98%, 99% or 100% identical to any one of SEQ ID NOs: 622-628, 474-476, 565, and 684-694, with or without a signal sequence.

In some aspects, the present disclosure provides an isolated polynucleotide encoding any one of the chimeric antigen receptors described herein.

In another aspect, the present disclosure provides a vector comprising the polynucleotide encoding any one of the chimeric antigen receptors described herein.

In some embodiments, the vector is a retroviral vector, a DNA vector, a plasmid, a RNA vector, an adenoviral vector, an adenovirus associated vector, a lentiviral vector, or any combination thereof.

In another aspect, the present disclosure provides an engineered immune cell expressing a chimeric antigen receptors described herein.

In some aspects, the present disclosure provides an engineered immune cell expressing the polynucleotide or vector encoding any one of the chimeric antigen receptors described herein.

In some embodiments, the engineered immune cell is a T cell, tumor infiltrating lymphocyte (TIL), NK cell, TCR-expressing cell, dendritic cell, or NK-T cell.

In some embodiments, the engineered immune cell is an autologous T cell.

In some embodiments, the engineered immune cell is an allogeneic T cell.

In some embodiments, the engineered immune cell is TCR (e.g., TCRα, TCRβ) knocked out.

In one aspect, the present disclosure provides a pharmaceutical composition comprising the engineered immune cell expressing a chimeric antigen receptors described herein.

In some aspects, the present disclosure provides a method of treating a disease or disorder in a subject in need thereof comprising administering to the subject the engineered immune cell or the pharmaceutical composition comprising the engineered immune cell expressing a chimeric antigen receptors described herein.

In some embodiments, the disease or disorder is cancer.

In some embodiments, the disease or disorder is small cell lung cancer.

In some aspects, the present disclosure provides an article of manufacture comprising the engineered immune cell or the pharmaceutical composition comprising the engineered immune cell expressing a chimeric antigen receptors described herein.

In some aspects, the present disclosure provides an anti-DLL3 binding agent disclosed herein.

In some embodiments, the anti-DLL3 binding agent is an antibody, an antibody conjugate, or an antigen-binding fragment thereof, optionally, a F(ab')₂ fragment, a Fab' fragment, a Fab fragment, a Fv fragment, a scFv fragment, a dsFv fragment, or a dAb fragment.

In some embodiments, the binding agent is a monoclonal antibody comprising an IgG constant region.

In some embodiments, the anti-DLL3 binding agent comprises a variable heavy (VH) chain sequence that is at least about 80%, 85%, 90%, 95%, 96%, 98%, 99% or 100% identical to a VH sequence provided in Table 1b.

In some embodiments, the anti-DLL3 binding agent comprises a variable light (VL) chain sequence that is at least about 80%, 85%, 90%, 95%, 96%, 98%, 99% or 100% identical to a VL sequence provided in Table 1c.

In some embodiments, the anti-DLL3 binding agent comprises a sequence that is at least about 80%, 85%, 90%, 95%, 96%, 98%, 99% or 100% identical to an scFv sequence presented in Table 1d.

In some embodiments, the anti-DLL3 binding agent is a fusion protein comprising a scFv fragment fused to an Fc constant region.

In some aspects, the present disclosure provides a pharmaceutical composition comprising the anti-DLL3 binding agent disclosed herein and a pharmaceutically acceptable excipient.

In some aspects, the present disclosure provides a method of treating a disease or disorder in a subject in need thereof comprising administering to the subject an anti-DLL3 binding agent, or a pharmaceutical composition comprising the anti-DLL3 binding agent, as disclosed herein.

In some embodiments, the disease or disorder is cancer. In some embodiments, the disease or disorder is small cell lung cancer.

BRIEF DESCRIPTION OF THE DRAWINGS

FIGS. 2A-2D show the results of epitope mapping experiments. FIG. 2A is a schematic representation of full length and truncated human DLL3 proteins expressed on CHO cells for epitope mapping, and all the proteins were fused at N-terminus with an HA tag for easy detection. FIGS. 2B and 2C show the amino acid sequences of full length and truncated human DLL3 proteins shown in FIG. 2A. FIG. 2D is a series of plots showing the results of epitope mapping of anti-DLL3 antibodies, and examples of anti-DLL3 antibodies recognizing DSL, EGF1 and EGF3 domain, respectively; the x-axis depicts signals from PE channel and the y-axis depicts counts.

FIGS. 3A-3D are a series of plots and tables showing the structure, transduction efficiency of cells from two different donors and the cytotoxic activity of anti-DLL3 CARs. FIG. 3A is a schematic of a construct encoding an anti-DLL3 CAR comprising, from the N-terminus to the C-terminus: anti-DLL3 scFv, the hinge and transmembrane regions from human CD8a, the cytoplasmic region from human 41BB and the cytoplasmic region from human CD3'. FIG. 3B depicts experimental data showing that anti-DLL3 CARs are expressed on the surface of primary T-cells and can recognize recombinant DLL3; the plots are gated on live CD3+ cells and the numbers on the plots are the percentage of cells expressing each anti-DLL3 CAR. FIGS. 3C and 3D show the transduction efficiency of anti-DLL3 CARs comprising the scFv sequences described herein.

FIGS. 4A-4C are a series of plots showing killing data for some anti-DLL3 CARs. FIG. 4A depicts experimental data showing that anti-DLL3 CAR-T cells specifically killed HEK-293T cells expressing human DLL3 but not parental HEK-293T cells in a 3-day cytotoxicity assay at the indicated effector:target (E:T) ratios. T cells that did not express anti-DLL3 CARs (labelled "empty vector") were used as negative control. FIG. 4B depicts experimental data showing that anti-DLL3 CAR-T cells killed SHP-77 and WM266.4 cells that express endogenous DLL3 in a 3-day cytotoxicity assay at indicated effector:target ratios. FIG. 4C depicts experimental data showing that anti-DLL3 CAR-T cells killed DMS 454 and DMS 273 small cell lung cancer cells that express endogenous DLL3 in a 3-day cytotox assay at indicated effector:target ratios. For all plots in FIGS. 4A-4C, One-glo assay system was used to assess target cell viability, n=3.

FIG. 6A depicts serial killing of anti-DLL3 CAR-T cells to DLL3+WM266.4 cells.

Some of the clones remained active on day 12 of the assay. FIG. 6B depicts serial killing of anti-DLL3 CAR-T cells to DMS 454 and WM266.4 cells.

FIG. 9A are schematics showing the structure of CAR designs with 4 different safety switches (QR3, SR2, RSR and R2S). FIG. 9B shows flow cytometry plots demonstrating that anti-DLL3 CARs with safety switches shown in FIG. 9A are expressed on the surface of primary T-cells and can recognize recombinant DLL3. The plots are gated on live CD3+ cells and the numbers on the plots indicate the percentage of cells expressing each anti-DLL3 CAR. FIG. 9C depicts experimental data showing that anti-DLL3 CARs with safety switches are active in serial killing assay.

FIG. 11A shows 8E11-SR2 and 26C8-R2S anti-DLL3 CAR-T cells were stained with recombinant DLL3 and PE conjugated rituximab 14 days after expansion and analyzed using flow cytometry. Numbers in quadrants represent percentage of total T cells. FIG. 11B shows rituximab-mediated complement dependent cytotoxicity (CDC) of 8E11-SR2 and 26C8-R2S anti-DLL3 CAR-T cells. CAR-T cells were incubated for 3 hours with 25% baby rabbit complement and rituximab and cytotoxicity was assessed using flow cytometry.

FIG. 12A shows DLL3 CAR-T cells with safety switches eliminated established SHP-77 small cell lung cancer subcutaneous tumors in mice. FIG. 12B is a plot demonstrating that anti-DLL3 CAR-T cells inhibited the growth of IV injected DMS 273-DLL3 small cell lung cancer tumors.

FIGS. 14A-14F show the experimental design and results of a mouse safety study using subcutaneous LN229-mDLL3 tumor model. FIG. 14A shows the study groups and experiment design. FIG. 14B shows the timing of tissue harvest and tumor volume of animals that received either non-transduced T cells or DLL3 CAR-T cells. FIG. 14C is a table showing the human CD3 staining score of brain and pituitary samples. FIG. 14D is a table showing the histology analysis of harvested brain and pituitary samples. FIG. 14E shows images of pituitary samples stained with anti-vasopressin antibody. FIG. 14F shows images of pituitary samples stained with anti-oxytocin antibody.

FIGS. 15A-15D show the experimental design and results of a mouse safety study using intracranial LN229-mDLL3 tumor model. FIG. 15A shows the study groups and experiment design. FIG. 15B shows the timing of tissue harvest and tumor volume of animals that received non-transduced T cells, DLL3 CAR-T cells or EGFRvIII CAR-T cells. FIG. 15C is a table showing the human CD45 staining score of brain, pituitary and spleen samples. FIG. 15D is a table showing the histology analysis of brain and pituitary samples.

FIG. 16A shows the cytotoxicity readout of the target cells after 3-day of co-culture with DLL3 CAR-T cells, demonstrating that DLL3 CARTs are not cytotoxic against mouse pituitary cells in vitro. FIG. 16B shows the flow cytometry analysis of the surface staining for activation markers CD25 and 41BB of the T cells co-cultured with the targets, demonstrating that mouse pituitary cells do not activate DLL3 CAR-Ts in vitro. FIG. 16C shows the cytokines secreted in the cell culture medium, analyzed by MSD, demonstrating that no cytokines are secreted after co-culturing DLL3 CAR-T cells with mouse pituitary cells in vitro for 3 days

DETAILED DESCRIPTION

Figure 1A:
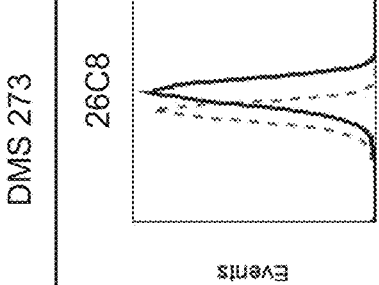
FIGS. 1A-1B are a series of plots showing that purified anti-DLL3 antibodies described herein bind to three DLL3-expressing small cell lung cancer cell lines (SHP-77, DMS 273 and DMS 454). The solid line and dashed line represent staining with anti-DLL3 antibodies or mouse IgG2A isotype control antibody, respectively.

Provided herein are DLL3-specific antibodies and chimeric antigen receptors (CARs). The DLL-3 specific CARs described herein, comprise an extracellular domain, a transmembrane domain, and an intracellular domain, wherein the extracellular domain comprises a DLL3 antigen binding domain that specifically binds to DLL3, and polynucleotides encoding these CARs. Also provided are immune cells comprising these DLL3-specific CARs, e.g., CAR-T cells, and pharmaceutical compositions comprising these immune cells. Methods of making and using these DLL3-specific CARs and immune cells comprising these DLL3-specific CARS are also disclosed, e.g., for the treatment of cancer.

I. DLL-3 Binding Agents

The present disclosure provides DLL-3 binding agents (e.g., molecules comprising a DLL3 antigen binding domain, DLL-3 antibodies or fragments thereof), that specifically bind to DLL-3. As used herein, the term "antibody" refers to a polypeptide that includes canonical immunoglobulin sequence elements sufficient to confer specific binding to a particular target antigen (e.g., DLL-3). As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)-an amino-terminal variable (VH) domain (located at the tips of the Y structure), followed by three constant domains: CHI, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence.

The assignment of amino acids to each of the framework, CDR, and variable domains is typically in accordance with numbering schemes of Kabat numbering (see, e.g., Kabat et al. in Sequences of Proteins of Immunological Interest, 5th Ed., NIH Publication 91-3242, Bethesda Md. 1991), Chothia numbering (see, e.g., Chothia & Lesk, (1987), J Mol Biol 196: 901-917; Al-Lazikani et al., (1997) J Mol Biol 273: 927-948; Chothia et al., (1992) J Mol Biol 227: 799-817; Tramontano et al., (1990) J Mol Biol 215(1): 175-82; and U.S. Pat. No. 7,709,226), contact numbering, or the AbM scheme (Antibody Modeling program, Oxford Molecular).

Accordingly, in some embodiments, the CDRs of the DLL3 binding agents presented herein are numbered according to the Kabat numbering scheme. In other embodiments, the CDRs of the DLL3 binding agents presented herein are numbered according to the Chothia numbering scheme. In other embodiments, the CDRs of the DLL3 binding agents presented herein are numbered according to the contact numbering scheme. In other embodiments, the CDRs of the DLL3 binding agents presented herein are numbered according to the AbM numbering scheme.

Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation.

For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art.

Moreover, the term "antibody" as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof, single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload (e.g., a detectable moiety, a therapeutic moiety, a catalytic moiety, etc), or other pendant group (e.g., poly-ethylene glycol, etc).

Antibodies include antibody fragments. Antibodies also include, but are not limited to, polyclonal monoclonal, chimeric dAb (domain antibody), single chain, $F_{ab}$, $F_a$, $F_{(ab)2}$ fragments, scFvs, and $F_{ab}$ expression libraries. An antibody may be a whole antibody, or immunoglobulin, or an antibody fragment.

As detailed above, whole antibodies consist of two pairs of a "light chain" (LC) and a "heavy chain" (HC) (such light chain (LC)/heavy chain pairs are abbreviated herein as LC/HC). The light chains and heavy chains of such antibodies are polypeptides consisting of several domains. In a whole antibody, each heavy chain comprises a heavy chain variable region (abbreviated herein as HCVR or VH) and a heavy chain constant region. The heavy chain constant region comprises the heavy chain constant domains CHI, CH2 and CH3 (antibody classes IgA, IgD, and IgG) and optionally the heavy chain constant domain CH4 (antibody classes IgE and IgM). Each light chain comprises a light chain variable domain VL and a light chain constant domain CL. The variable domains VH and VL can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (Janeway, C. A., Jr, et al, (2001). Immunobiology, 5th ed., Garland Publishing; and Woof, J., Burton, D., Nat Rev Immunol 4 (2004) 89-99). The two pairs of heavy chain and light chain (HC/LC) are capable of specifically binding to the same antigen. Thus said whole antibody is a bivalent, monospecific antibody. Such "antibodies" include e.g., mouse antibodies, human antibodies, chimeric antibodies, humanized antibodies and genetically engineered antibodies (variant or mutant antibodies) as long as their characteristic properties are retained. In some embodiments, antibodies or binding agents are humanized antibodies, especially as recombinant human or humanized antibodies.

In some embodiments, the antibody or binding agent can be "symmetrical." By "symmetrical" is meant that the antibody or binding agent has the same kind of Fv regions (e.g., the antibody has two Fab regions). In some embodiments, the antibody or binding agent can be "asymmetrical." By "asymmetrical" is meant that the antibody or binding agent has at least two different kinds of Fv regions (e.g., the antibody has: Fab and scFv regions, Fab and scFv2 regions, or Fab-VHH regions). Various asymmetrical antibody or binding agent architectures are known in the art (Brinkman and Kontermann et al. 2017 Mabs (9)(2): 182-212).

As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof, single chain Fvs; polypeptide-Fc fusions; single domain antibodies (e.g., shark single domain antibodies such as IgNAR or fragments thereof); cameloid antibodies; masked antibodies (e.g., Probodies©); Small Modular ImmunoPharmaceuticals ("SMIPs™); single chain or Tandem diabodies (TandAb©); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR©s.

In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments, an antibody agent is or comprises a polypeptide whose amino acid sequence includes at least one CDR (e.g., at least one heavy chain CDR and/or at least one light chain CDR) that is substantially identical to one found in a reference antibody In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

An antibody or antigen binding molecule encoded of the present invention can be single chained or double chained. In some embodiments, the antibody or antigen binding molecule is single chained. In certain embodiments, the antigen binding molecule is selected from the group consisting of an scFv, a Fab, a Fab', a Fv, a F(ab')$_2$, a dAb, and any combination thereof.

In some embodiments, an anti-DLL-3 antibody agent is isolated. In some embodiments, an antibody agent can be purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) (See, e.g., Flatman et al., *J. Chromatogr.*, B 848:79-87 (2007)). In some aspects, the present disclosure provides a composition comprising a DLL-3 binding agent (e.g., a DLL3 specific antibody) and a pharmaceutically acceptable carrier.

In some embodiments, an anti-DLL-3 antibody agent comprises an Fc. Fc domains can interact with cell surface receptors which can allow antibodies to activate the immune system. In IgG, IgA and IgD antibody isotypes, a Fc region is composed of two identical protein fragments, derived from the second and third constant domains of the antibody's two heavy chains; IgM and IgE Fc regions contain three heavy chain constant domains ($C_H$ domains 2-4) in each polypeptide chain. The Fc regions of IgG may bear a highly conserved N-glycosylation site (N297). Glycosylation of the Fc fragment may be essential for Fc receptor-mediated activity. The N-glycans attached to this site can predominantly be core-fucosylated diantennary structures of the complex type.

While the constant regions of the light and heavy chains may not be directly involved in binding of the antibody to an antigen, the constant regions can influence the orientation of the variable regions. The constant regions can also exhibit various effector functions, such as participation in antibody-dependent complement-mediated lysis or antibody-dependent cellular toxicity via interactions with effector molecules and cells.

The disclosed anti-DLL-3 antibody agents can be antibodies of any isotype, including isotype IgA, isotype IgD, isotype IgE, isotype IgG, or isotype IgM. In some embodiments, an anti-DLL-3 antibody contains a IgG1, IgG2, IgG3, or IgG4 constant domain.

Provided herein are DLL3 binding agents (e.g., antibodies) that can bind to various regions or domains of the DLL3 target. The epitope can be, for example, contiguous amino acids of the DLL3 target (linear or contiguous epitope) or come together from two or more non-contiguous regions of the DLL3 target (conformational, non-linear, discontinuous, or non-contiguous epitope). The epitope to which the DLL3 antigen binding domain binds can be determined by various assays, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, flow cytometry, and/or mutagenesis mapping (e.g., site-directed mutagenesis mapping).

Representative DLL3 regions or domains are shown in FIG. 2. Exemplary DLL3 antibodies described herein bind to DLL3 domains provided in Table 1a.

TABLE 1a

| DLL3 Domains to Which Provided Clones Bind | |
| --- | --- |
| Clone Name | Binds to DLL3 Domain (FIG. 2A) |
| 2D3 | EGF3 |
| 5E12 | DSL |
| 26C8 | EGF3 |
| 2A6.C5 | EGF3 |
| 6D8 | EGF1 |
| 7F9 | N-ter |
| 8E11 | EGF3 |
| 9D3 | EGF3 |
| 11H7 | DSL |
| 16H7 | EGF2 |
| 2C3 | EGF2 |
| 4F9 | N-terminus |
| 4G9 | N-terminus |
| 2G1 | EGF5 |
| 3F2 | N-terminus |
| 17A2 | EGF1 |
| 6F8 | EGF5 |
| 9H12-K | EGF4 |
| 4H8 | EGF4 |
| 10G1-K | EGF5 |
| 11A3 | EGF3 |
| 4E6 | EGF3 |

In some embodiments, the DLL3 binding agent comprises a variable heavy chain (VH), wherein the amino acid sequence of the VH is selected from the VH sequences presented in Table 1b. In some embodiments, an anti-DLL-3 binding agent comprises an immunoglobulin heavy chain having at least 60%, 65%, 70%, 75%, 80%, 85%, 90%, 91%, 92%, 93%, 94%, 95%, 96%, 97%, 98%, 99%, or 100%) sequence identity to an amino acid sequence presented in Table 1b.

TABLE 1b

| Heavy Chain Variable Regions (VH) | | |
| --- | --- | --- |
| Clone | VH Sequence | SEQ ID NO: |
| 2D3 | QVQLQESGPGLVKPSETLSLTCTVSDNSISNYYWSWIRQPPGKGLEWI AYIYYSGTTNYNPSLKSRVTISLDTSKNQFSLKLSSVTAADTAVYYCA RLFNWGFAFDIWGQGTMVTVSS | SEQ ID NO: 7 |

TABLE 1b-continued

| | Heavy Chain Variable Regions (VH) | |
| --- | --- | --- |
| Clone | VH Sequence | SEQ ID NO: |
| 5A2 | QVQLQESGPGLMKPSETLSLTCTVSGGSISSSYWSCIRQPPGKGLEWI<br>GYIYYSGTTNYNPSLKSRVTLSLDTSKNQFSLRLTSVTAADTAVYYC<br>ARVAPTGFWFDYWGQGTLVTVSS | SEQ ID NO: 16 |
| 7F9 | EVQLVESGGGLVQPGGSLRLSCAASGFTFSSHDMHWVRQATGKGLE<br>WVSAIGIAGDTYYSGSVKGRFTISRENAKNSLYLQMNSLRAGDTAVY<br>YCARANWGEGAFDIWGQGTMVTVSS | SEQ ID NO: 25 |
| 9D3 | QVQLQESGPGLVKPSETLSLTCTVSDDSISNYYWSWIRQPPGKGLEWI<br>GYIFYSGTTNHNPSLKSRLTISLDKAKNQFSLRLSSVTAADTAVYYCA<br>RVFNWGFAFDIWGQGTMVTVSS | SEQ ID NO: 34 |
| 26C8 | QVQLQESGPGLVKPSETLSLTCTVSDNSISNYYWSWIRQPPGKGLEWI<br>AYIYYSGTTNYNPSLKSRVTISLDTSKNQFSLQLSSVTAADAAVYYC<br>ARVFHWGFAFDIWGQGTMVTVSS | SEQ ID NO: 43 |
| 2A6.C5 | QVQLQESGPGLVKPSETLSLTCTVSNVSISSYYWSWIRQPPGKGLEWI<br>GYIYYSGTTNYNPSLKSRVTMSVDTSKNQFSLKLSSVTAADTAVYFC<br>ARLSNWGFAFDIWGQGTMVTFSS | SEQ ID NO: 52 |
| 5E12 | EVQLVESGGGLVQPGGSLRLSCAASGFTFSSYDMHWVRQATGKGLE<br>WVSAIGPAGDTYYPGSVKGRFTISRENAKNSLYLQMNSLRAGDTAV<br>YYCARADPPYYYYGMDVWGQGTTVTVSS | SEQ ID NO: 61 |
| 6D8 | QITLKESGPTLVKPTQTLTLTCTFSGFSLSTRGVGVGWIRQPPGKALE<br>WLALIYWNDDKRYSPSLQTRLTITKDTPKNQVVLTMTNMDPVDTAT<br>YYCARSNWGNWYFALWGRGTLVTVSS | SEQ ID NO: 70 |
| 8E11 | QVQLQESGPGLVKPSETLSLTCTVSGDSISNYYWTWIRQPPGKGLEWI<br>GYIYYSGTTNSNPSLKSRVTVSLDTSKSQFSLNLSSVTAADTAVYYCA<br>RVFNRGFAFDIWGQGTMVTVSS | SEQ ID NO: 79 |
| 5C1.A4 | QVTLRESGPALVKPTQTLTLTCTVSGVSLSTSGMCVSWIRQPLGKAL<br>EWLGFIDWDDDKYYNTSLKTRLTISKDTSKNQVVLTMTNMDPVDTA<br>TYYCARIRGYSGSYDAFDIWGQGTVVIVSS | SEQ ID NO: 88 |
| 9F7 | QVQLQVSGPGLVKPSETLSLTCSVSGGSISSYYWSWIRQSPGKGLDWI<br>GYMYYSGTTNYNPSLKSRVTISVDTSKNQFSLKLSSVTATDTAVYYC<br>ARVGLTGFFFDYWGQGTLVTVSS | SEQ ID NO: 97 |
| 2C3 | QVQLQQWGGGLLKPSETLSLTCAVYGGSSSGNYWSWIRQPPGKRLE<br>WIGEINHSGTTSYNPSLKSRVTISVDTSKNQFSLKLSSVTAADTAVYY<br>CARGELGIADSWGQGTLVTVSS | SEQ ID NO: 106 |
| 2G1 | QLQLQESGPGLVKPSETLSLTCTVSGGSISSSSYYWGWIRQPPGKGLE<br>WIGSIYYSGNIYHNPSLKSRVSISVDTSKNQFSLRLSSVTAADTAVYY<br>CAREIIVGATHFDYWGQGTLVTVSS | SEQ ID NO: 115 |
| 3E4 | QVQLQQWGAGLLKPSETLSLTCAVYGGSFSGYYWSWIRQPPGKGLE<br>WIGEIIHSGSSNYNPSLKSRVSISVDTSKNQFSLKLSSVTAADTAVYYC<br>SRGEYGSGSRFDYWGQGTLVTVSS | SEQ ID NO: 124 |
| 3F2 | QVQLQESGPGLVKPSGTLSLTCAVSGGSISSNNWWSWVRQPPGKGL<br>EWIGDIHHSGSTNYKPSLKSRVTISVDKSKNQFSLNLISVTAADTAVY<br>YCAREAGGYFDYWGQGILVTVSS | SEQ ID NO: 133 |
| 4F9 | QVQLQQWGAGLLKPSETLSLTCAVYGGSFSGYYWTWIRQPPGKGLE<br>WIGEITHSGSTNYNPSLKSRVSISVDTSKNQFSLKLSSVTAADTAVYY<br>CARGEYGSGSRFDYWGQGTLVTVSS | SEQ ID NO: 142 |
| 4G9 | QVQLQQWGAGLLKPSETLSLTCAVYGGSFSGYYWSWIRQPPGKGLE<br>WIGEITHSGSTNYNPSLKSRVSISVDTSKNQFSLKLSSVTAADTAVYY<br>CARGEYGSGSRFDYWGQGTLVTVSS | SEQ ID NO: 151 |
| 11H7 | QVQLQQWGAGLLKPSETLSLTCAVYGGSFSAYYWNWIRQPPGKGLE<br>WIGEINHSGSTNYNPSLKSRVTISVDTSKNQFSLNLTSLTAADTAVYY<br>CARGLDSSGWYPFDYWGQGTLVTVSS | SEQ ID NO: 160 |
| 16H7 | QVQLQQWGAGLLKPSETLSLTCAVFGGSFSGDYWSWIRQPPGKGLE<br>WIGEINHSGITSFNPSLKSRVTISVDTSKNQFSLKLSSVTAADTAV<br>YYCARGELGIPDNWGQGTLVTVSS | SEQ ID NO: 169 |
| 17A2 | QVQLQESGPGLVKPSGTLSLTCVVFGDSISSSNWWSWVRQPPGKGLE<br>WIGEVFHSGSTNYNPSLKSRVTISVDKSKNQFSLKLSSVTAADTAVY<br>YCARAAVAGALDYWGQGTLVTVSS | SEQ ID NO: 178 |

TABLE 1b-continued

| Heavy Chain Variable Regions (VH) | | |
|---|---|---|
| Clone | VH Sequence | SEQ ID NO: |
| 6H1 | QITLRESGPTLVKPTQTLTLTCTFSGFSLSTSGLGVGWIRQPPGEA LEWLALIYWNDDKRYSPSLKSRLSITKDTSKNQVVLIMTNMDPVDT ATYYCVHRRIAAPGSVYWGQGTLVTVSS | SEQ ID NO: 187 |
| 6H5 | QVQLVQSGAEVKKPGASVKVSCKVSGYTLTELSMHWVRQAPGKGP EGMGGFDpEDGKTIYAQKFQGRVTMTEDTSADTAYMELNSLRSEDT AVYYCATLLRG1DAFDVWGQGTMVTVSS | SEQ ID NO: 196 |
| 10D1 | QVQLQQWGAGLLKPSETLSLTCAVYGGSFSGYYWRWIRQPPGKGLE WIGEISHSGSTNYNPSLKSRVTISVDTSKNQFSLKLSSVTAADTAVYY CAVRGYSYGYPLFDYWGQGTLVTVSS | SEQ ID NO: 205 |
| 11F6 | QVQLQESGPGLVKPSGTLSLTCAVSGDSISSNWWTWVRQPPGKGLE WIGDIHHSGSTNYNPSLKSRVTMSVDKSENQFSLKLSSVTAADTAVF YCARDGGGTLDYWGQGTLVTVSS | SEQ ID NO: 214 |
| 6F8 | QVQLVQSGAEVKKPGSSVKVSCKASGGTFTNYCISWVRQAPGQGLE WMGGIIpIFGTTNYAQTFQGRVTITADKSTSTAYMELSSLRSEDTAVY YCARDNGDRYYYDMDVWGQGTTVTVSS | SEQ ID NO: 223 |
| 3G6-L1 | QVPLVQSGAEVKKPGSSVKVSCKASGGTFSTYSISWVRQAPGQGLE WMGGIIpIFGTTNYAQKFQGRVTITADKSTSTAYMELSSLRSEDTAVY YCARDGEGSYYYYYGMDVWGQGTTVTVSS | SEQ ID NO: 232 |
| 4C6 | QVQLQESGPGLVKPSETLSLTCTVSGDSISSYYWSWIRQPPGKGLEWI GYMYYSGITNYNPSLKSRVNISLDTSKNQFSLKLGSVTAADTAVYYC ARLSVAGFYFDYWGQGTLVTVSS | SEQ ID NO: 241 |
| 4E6 | QVQLQESGPGLVKPSETLSLTCTVSSDSISSYYWSWIRQPPGKGLEWI SYIYYSGISNYNPSLKSRVSISVDTSKNQFSLRLSSVTAADTAVYYCA RISVAGFFFDNWGQGTLVTVSS | SEQ ID NO: 250 |
| 4H8 | QVQLQQSGPGLVKPSQTLSLTCAISGDSVSSNSATWNWIRQSPSRGLE WLGRTYYRSKWYDDYAVSVKSRITINPDTSKNHLSLHLNSVTPEDTA VYYCAGGGLVGAPDGFDVWGQGTMVTVSS | SEQ ID NO: 259 |
| 9H12-K | QVQLVQSGAEVKKPGASVKVSCKASGYTFTGYSIHWVRQAPGQGLE WMGWINPNSGGTFYAQKFQGRVTMTRDTSISTVYMELSRLRSDDTA VYYCARDGWGDYYYYGLDVWGQGTTVTVSL | SEQ ID NO: 268 |
| 10G1-K | EVQLLESGGGLVQPGGSLRLSCAASGFTFSSYAMNWVRQAPGKGLE WVSTISGSGGSTYYADSVKGRFTISRDNSKNTLYLQMNSLRAEDTAV FYCAIDPEYYDILTGGDYWGQGTLVTVSS | SEQ ID NO: 277 |
| 11A3 | QVQLQESGPGLVKPSETLSLTCTVSSDSISNYYWSWIRQPPGKGLEWI SYIYYSGITNYNPSLKSRVTISVDTSKNQFSLKLSSVTAADTAVYYCA RITVTGFYFDYWGQGTLVTVSS | SEQ ID NO: 286 |
| 3B11 | QVQLQQSGPGLVKPSQTLSLTCAISGDSVSSNSVVWNWIRQSPSRGL EWLGRTYYRSKWYDDYAVSVKSRITINPDTSKNQFSLQLNSVTPEDT AVYHCARGGIVGAPDAFDIWGQGTMVTVSS | SEQ ID NO: 295 |
| 5G2 | QVQLQQSGPGLVKPSQTLSLTCAISGDSVSSNSAVWNWIRQSPSRGL EWLGWTYYRSKYYNDYAVSLKSRITINPDTSKNQFSLQLNSLTPEDT AVYYCTRGGIVGAPDGFDIWGQGTMVTVSS | SEQ ID NO: 304 |
| 11E4 | QVQLQESGPGLVKPSETLSLTCTVSGGSISSYYWSWIRQSPGKGLEWI GYVYYSDITNYNPSLKSRVTISVDTSKNQFSLNLNSVTAADTAFYFCA RIGVAGFYFDYWGQGTLVTVSS | SEQ ID NO: 313 |
| 2404.8E11 | QIQLQQSGPGLVKPSQTLSLTCAISGDSVSSNSAVWNWIRQSPSRGLE WLGRTYYRSKWYNDYAVSVKSRITIKPDTAKNQFSLQLNSVTPEDT AVYYFTRGGIVGAPDAFDIWGQGTMVTVSS | SEQ ID NO: 322 |
| 10A2 | QVQLQQSGPGLVKPSETLSLTCAISGDSVSSNSATWNWIRQSPSRGLE WLGRTYYRSEWYNDYAVSVKSRITINPDTSKNHLSLHLNSVTPEDTA VYYCAGGGIVGAPDGFDVWGQGTMVTVSS | SEQ ID NO: 331 |
| 11A8 | QVQLQQSGPGLVKPSQTLSLTCAISGDSVSSNSATWNWIRQSPSTGLE WLARTYYRSKWYNDYEVSVKSQITINPDTSKNQFSLQLNSVTPEDTA VYYCARGGIVGAPDAFDIWGQGTMVTVSS | SEQ ID NO: 340 |
| 4H5 | QVQLQESGPGLVKPSETLSLTCTVSGDSINNYFWSWIRQPPGKGLEWI GYFYHRGGNNYNPSLKSRVTISIDTSKNQFSLNLNSVTSADTAVYYC ARLALAGFFFDYWGQGTLVTVSS | SEQ ID NO: 349 |

TABLE 1b-continued

| Clone | Heavy Chain Variable Regions (VH) | |
|---|---|---|
| | VH Sequence | SEQ ID NO: |
| 3G6-L2 | QVPLVQSGAEVKKPGSSVKVSCKASGGTFSTYSISWVRQAPGQGLE WMGGIIPIFGTTNYAQKFQGRVTITADKSTSTAYMELSSLRSEDTAVY YCARDGEGSYYYYGMDVWGQGTTVTVSS | SEQ ID NO: 358 |
| 3B9 | EVQLVESGGGLVQPGGSLRLSCAASGFTFSSYSMNWVRQAPGKGLE WVSYISSSSSTIYYADSVKGRFTISRDNAKNSLYLQMNSLRDEDTAV YYCARDKERRYYYYGMDVWGQGTTVTVSS | 367 |
| 3F9-L | QVQLQQSGPGLVKPSQTLSLACAISGDSVSSNSAIWNWIRQSPSRGLE WLGGTYYRSMWYNDYAVSVKSRITINPDTSKNQLSLQLNSVTPEDT AVYYCSRGGIVGVPDAFDIWGQGTMVTVSS | SEQ ID NO: 376 |
| 3E10 | QVQLQESGPGLVKPSETLSLTCNVSDGSISSYYWTWIRQPPGKGLDW IGYIFYSGTTNYNPSLKSRVTISLDTSKNQFSLKLTSMTAADTAVYYC ARISEKSFYFDYWGQGTLVTVSS | SEQ ID NO: 385 |
| 3C3 | QVQLVQSGAEVKRPGASVKVSCKASGYTFTSYYIHWVRQAPGQGLE WMGVIVPSGGSISYAQKFQGRVTMTRDTSTNIVYMELSSLRSEDTAV YYCARDRYYGDYYYGLDVWGQGTTVTVSS | SEQ ID NO: 394 |
| 11F4 | QVHLQESGPGLVKPSETLSLTCTVSGGSISHYYWTWIRQPPGKGLEWI GYIYYSGITNFSPSLKSRVSISVDSSKNQFSLNLNSVTAADTAVYYCA GISLAGFYFDYWVQGTLVTVSS | SEQ ID NO: 403 |
| 10E12 | QVQLQESGPGLVKPSETLSLTCTVSGVSISSYYWSWIRQPPGKGLEWI AYIYYSGNTNYSPSLKSRVTISVDTSKDQLSLKLSSVTAADTAVYYCT RGGSGTIDVFDIWGQGTMVAVSS | SEQ ID NO: 412 |
| 4E1 | QVQLQQSGPGLVKPSQTLSLTCAISGDNVSTNSAAWNWIRQSPSRGL EWLGWTYYRSKWYNDYAVSLKSRININPDTSKNQFSLQLNSVTPED TAVYYCARWVNRDVFDIWGQGTMVTVSS | SEQ ID NO: 421 |
| 2404.6H1 | QVQLVESGGGVVQPGRSLRLSCAASGFTFSSYGMHWVRQTPGKGLE WVAVISYDGNSNYYADSVKGRFTISRDNSKNTLYLQMNSLRAEDTA VYYCARDGATVTSYYYYGMDVWGQGTTVTVSS | SEQ ID NO: 430 |
| 2A8-K | QVQLQQSGPGLVKPSQTLSLTCAISGDSVSSNSAVWNWIRQSPSRGL EWLGRTYYRSKWYNDYAVSVKSRITINPDTSRNQFSLQLNSVTPEDT AVYYCARGGIVGAPDGFDIWGQGTMVTVSS | SEQ ID NO: 439 |
| 3B1 | QVQLQQSGPGLVKPSQTLSLTCAISGDSVSSNTTAWKWSRQSPSKGL EWLGWTYYRSKWYYDYTVSVKSRITINPDTSKNQFSLQLNSVTPEDT AVYYCARWIFHDAFDIWGQGTMVTVSS | SEQ ID NO: 448 |
| 9B5 | QVQLQESGPGLVKPSETLSLTCTVSGDSISSLSWSWIRQTPGEGLEWI GYLYYSGSTDYNPSLKSRVTISVDTSKNQFSLKLRSVAAADTALYYC ARGRRAFDIWGQGTMVTVSS | SEQ ID NO: 457 |
| 11A5 | QVQLVQSGAEVKKPGASVKVSCKASGYTFTGYYMHWVRQAPGQGL EWMGWINPNSGGTNYAQKFQGRVTMTRDTSVSTAYMELSRLTSDD TAIYYCAKDGGGDFYFYGMDVWGQGTTVTVSS | SEQ ID NO: 466 |

In some embodiments, the DLL3 binding agent comprises a variable light chain (VL), wherein the amino acid sequence of the VL is selected from the VL sequences presented in Table 1c. In some embodiments, an anti-DLL-3 binding agent comprises an immunoglobulin light chain having at least 60%, 65%, 70%, 75%, 80%, 85%, 90%, 91%, 92%, 93%, 94%, 95%, 96%, 97%, 98%, 99%, or 100%) sequence identity to an amino acid sequence presented in Table 1c.

TABLE 1c

| Clone | Light Chain Variable Regions | |
|---|---|---|
| | VL Sequence | SEQ ID NO: |
| 2D3 | EIVMTQSPATLSVSPGERATLSCRASQSVSSNLAWYQQKPGQAPR LLIYGASTRATGIPARFSGSGSGTEFTLTISSLQSEDFAVYYCQQY NNWPLTFGGGTKVEIK | SEQ ID NO: 8 |
| 5A2 | EIVLTQSPGTLSLSPGERATLSCRASQRVSSRYLAWYQQKPGQAP RLLIYGASSRATGIPDRFSGSGSGTDFTLTISRLEPEEFAVYYCQQ YGTSPLTFGGGTKVEIK | SEQ ID NO: 17 |

TABLE 1c-continued

| Light Chain Variable Regions | | |
| --- | --- | --- |
| Clone | VL Sequence | SEQ ID NO: |
| 7F9 | DIQMTQSPSSLSASVGDRVTITCRASQGISDYLAWYQQKPGKIPK LLIYAASTLQSGVPSRFSGSGSGTDFTLTISSLQPEDVATYYCQKY NSVPLTFGGGTKVEIK | SEQ ID NO: 26 |
| 9D3 | EIVLTQSPGTLSLSPGERATLSCRASQRISRTYLAWYQQKPGQAP RLLIYGASSRATGIPDRFTGSGSGTDFTLTISRLEPEDFAVYYCQQ YGTSPLTFGGGTKVEIN | SEQ ID NO: 35 |
| 26C8 | EIVLTQSPGTLSLSPGERATLSCRASQRVSNTYLAWYQQNPGQAP RLLIYGASSRATGIPDRFSGSGSGTDFTLTISRLEPEDFAVYYCQQ YGTSPLTFGGGTKVEIK | SEQ ID NO: 44 |
| 2A6.C5 | EIVLTQSPGTLSLSPGERATLSCRASQTISSSYLAWYQQKPGQAPR LLIYGASSRATGIPDRFSGSGSGTEFTLTISRLEPEDFAVYYCQQY GWSPITFGQGTRLEIK | SEQ ID NO: 53 |
| 5E12 | DIVMTQSPLSLPVTPGEPASISCRSSQSLLHSNEYNYLDWYLQKP GQSPQLLIYLGSNRASGVPDRFSGSGSGTDFILKISRVEAEDVGVY YCMQALEIPLTFGGGTKVEIK | SEQ ID NO: 62 |
| 6D8 | EIVLTQSPATLSLSPGERATLSCRASQSVSSYLAWYQQKPGQAPR LLIYDAFYRATGIPARFSGSGSGTDFTLTISSLEPEDFAVYYCQHR SNWPITFGQGTRLEIK | SEQ ID NO: 71 |
| 8E11 | EIVLTQSPGTLSLSPGERATLSCRASQRISNTYLAWYQQKPGQAP RLLIYGASSRATGIPDRFSGSGSGTDFTLTISRLEPEDFAAYYCQQ YDTSPLTFGGGTKVEIK | SEQ ID NO: 80 |
| 5C1.A4 | DIVMTQSPLSLPVTPGEPASISCRSSQSLLHSNGYNHLDWYLQKP GQSPQVLIYLGSNRASGVPDRFSGSGSGTDFTLKISRVEAEDVGV YFCMQALQTPLTFGGGTKVEIK | SEQ ID NO: 89 |
| 9F7 | AIQMTQSPSSLSASVGDRVTITCRASQGIRNDLGWYQQKPGKAP KLLIYAASSLQSGVPSRFSGSGSGTDFTLTVSSLQPEDFATYYCLQ DYNYPYTFGQGTKLEIK | SEQ ID NO: 98 |
| 2C3 | DIQMTQSPSTLSASVGDRVTITCRASQSISRWLAWYQQKPGKAPK LLIYKASSLESGVPSRFSGSGSGTEFTLTISSLQPDDFATYYCQQY NSYSTFGQGTKVEIK | SEQ ID NO: 107 |
| 2G1 | AIQMTQSPSSLSASVGDRVTITCRASQGIRNDLGWYQQKPGKAPE LLIYAASSLQSGVPSRFSGSGSGTDFTLTISSLQPEDFATYYCLQD YNYPLTFGPGTKVDIK | SEQ ID NO: 116 |
| 3E4 | AIQMTQSPSSLSASVGDRVAITCRASQGIRDDLGWYQQKPGKAP KLLIYAASSLQSGVPSRFSGSRSDTDFTLTISSLQPEDFATYYCLQ DYDYPLTFGGGTKVEIK | SEQ ID NO: 125 |
| 3F2 | DIQMTQSPSTLSASVGDRVTITCRASQSISSWLAWYQQKPGKAPK LLISKASSLESGVPSRFSGSGSGPEFTLTISSLQPADFATYYCQQYN SYSTFGQGTKLEIK | SEQ ID NO: 134 |
| 4F9 | AIQMTQSPSSLSASVGDRVAITCRASQGIRDDLGWYQQKPGKAP KLLIYAASSLQSGVPSRFSGSGSDTDFTLTISSLQPEDFATYYCLQ DYDYPLTFGGGTKVEIK | SEQ ID NO: 143 |
| 4G9 | AIQMTQSPSSLSASVGDRVALTCRASQGIRDDLGWYQQKPGKAP KLLIYAASSLQSGVPSRFSGSGSDTDFTLTISSLQPEDFATYYCLQ DYDYPLTFGGGTKVEIK | SEQ ID NO: 152 |
| 11H7 | DIQMTQSPSSVSASVGDRVTITCRASQGISSWLAWYQQKPGKAP KLLIYAASSLQSGVPSRFSGSGSGTDFTLTISSLQPEDFATYYCQQ ADSFPFTFGPGTKVDIK | SEQ ID NO: 161 |
| 16H7 | DIQMTQSPSTLSASVGDRVTITCRASQSISRWLAWYQQKPGKAPK LLIYKASSLESGVPSRFSGSGSGTEFTLTISSLQPDDFATYYCQQY NSYSTFGQGTKVEIK | SEQ ID NO: 170 |
| 17A2 | DIVMTQSPDSLAVSLGERATINCKSSQSVLYSSNNKnYLAWYQQ KPGQPPNLLVYWASTRESGVPDRFSGAGSGTDFTLTISSLQAEDV AVYYCQQYYGTSWTFGQGTKVEIK | SEQ ID NO: 179 |
| 6H1 | DIQMTQSPSSVSASVGDRVTITCRASQGISSWLAWYQQKPGKAP KLLISAASSLQSGVPSRFSGSGSGTDFTLTISSLQPEDFATYYCHQ ANSFPFTFGQGTKLEIK | SEQ ID NO: 188 |

TABLE 1c-continued

| Light Chain Variable Regions | | |
| --- | --- | --- |
| Clone | VL Sequence | SEQ ID NO: |
| 6H5 | DIQMTQSPSSLSASVGDRVTITCRASQGIRNDLGWYQQKPGKAP KRLIYAASSLQSGVPSRFSGSGSGTEFTLTISTLQPEDFATYYCLQ HNSYPRTFGQGTKVEIK | SEQ ID NO: 197 |
| 10D1 | DIQMTQSPSSLSASVGDRVTITCRASQGIRNDLGWYQQKLGKAP KRLIYAASSLQSGVPSRFSGSGSGTEFTLTISSLQPEDFATYYCLQ YNSYPRTFGQGTKVEIK | SEQ ID NO: 206 |
| 11F6 | DIQMTQSPSTLSASVGDRVTITCRASQSISSWLAWYQQKPGKAPK LLIYKASTLESGVPSRFSGSGSGTEFTLTISSLQPDDFATYYCQQY NGYSTFGQGTKVEIK | SEQ ID NO: 215 |
| 6F8 | QSVLTQPPSVSAAPGQKVTISCSGSSSNIGNNYVSWYQQLPGTAP KLLIYDNNKRPSGIPDRFSGSKSGTSATLGITGLQTGDEADYYCG TWDSSLSAVVFGGGTKLTVL | SEQ ID NO: 224 |
| 3G6-L1 | QSVLTQPPSVSAAPGQKVTISCSGSSSNIGNNYVSWYQQLPGTAP KLLIYDNNKRPSGIPDRFFGSKFGTSATLGITGLQTGDEADYYCG TWDSSLSAVVFGGGTKLTVL | SEQ ID NO: 233 |
| 4C6 | EIVLTQSPGTLSLSPGERATLSCRASQSVTRSYLAWYQQKPGQAP RLLIYGASSRATDIPDRFSGSGSGTDFTLTINRLEPEDFAVYYCQQ YGTSPLTFGGGTKVEIK | SEQ ID NO: 242 |
| 4E6 | EIMLTQSPDTLSLSPGERATLSCRASQSVSSSYLAWYQQKPGQAP RLLIYGASSRAAGVPDRFSGSGSGTDFTLTISRLAPEDFVVYYCQ QYGISPLTFGGGTKVEIK | SEQ ID NO: 251 |
| 4H8 | QSVLTQPPSASGTPGQRVTISCSGSSSNIGSDPVNWYQQLPGTAPK LLIYSNNQRPSGVPDRFSGSKSGTSASLAISGLQSEDEADYYCSA WDDSLNGYVFGTGTKVTVL | SEQ ID NO: 260 |
| 9H12-K | DIQMTQSPSSVSASVGDRVTITCRASQDISSWLAWYQQKPGKAP KLLIYTASSLQGGVPSRFSGSGSGTDFTLTISSLQPEDLATYSCQQ ANVFPYTFGQGTKLEIK | SEQ ID NO: 269 |
| 10G1-K | DIQMTQSPSAMSASVGDRVTITCRASQGISNYLAWFQQKPGKVP KRLIYAASSLQSGVPSRFSGSGSGTEFTLTISSLQPEDFATYFCLQH DSFPLTFGGGTKVEIK | SEQ ID NO: 278 |
| 11A3 | EIVLTQSPGTLSLSPGERATLSCRASQSISRSYLAWYQQKPGQAPR HLIYGASSRATGIPDRFSGSGSGTDFILTISRLEPEDFAVYYCQQY DTSPLTFGGGTKVEIK | SEQ ID NO: 287 |
| 3B11 | QSVLTQPPSASGTPGQRVTISCSGSSSNIGSDPVSWYQQFPGTAPK LLIYTNNQRPSGVPDRFSGSKSGTSASLAISGLQSEDEADYYCAA WDDSLNGHVFGTGTKVTVL | SEQ ID NO: 296 |
| 5G2 | QSALTQPPSASGTPGQRVTISCSGSNSNIGSNPINWYQQLPGTAPK LLIYSNNQRPSGVPDRFSGSKSGTSASLAISGLQSEDEADYYCAA WDDSLNGHVFGTGTKVTVL | SEQ ID NO: 305 |
| 11E4 | EIVLTQSPDTLSLSPGERATLSCRASQSVSRRYLAWYQQKPGQAP RLLIYGASSRATGIPDRFSGSGSGTDFTLTISRLEPEDFEVYYCQQ YGTSPITFGQGTRLEIK | SEQ ID NO: 314 |
| 2404.8E11 | QSVLTQPPSASGTPGQRVTISCSGSSSNIGSDPINWYQQVPGTAPK LLIYSNNQRPSGVPDRFSGSKSGTSASLAISGLQSEDEADYYCAA WDDSLNGYVFGTGTKVTVL | SEQ ID NO: 323 |
| 10A2 | QSVLTQPPSASGTPGQRVTISCSGSSSNIGSDPVIWYQQLPRTAPK LLIYSNNQRPSGVPDRFSGSKSGTSASLAISGLQSEDEADYYCAA WDDSLNGYVFGTGTKVTVL | SEQ ID NO: 332 |
| 11A8 | QSVLTQPPSASGTPGQGVTISCSGSSSNIGSNPVNWYQQLPGTAP KLLIYSNNQRPSGVPDRFSDSKSGTSASLAISGLQSEDEADYYCSA WDDWLNGYVFGTGTKVTVL | SEQ ID NO: 341 |
| 4H5 | DIQMTQSPSTLSASVGDRVTITCRASQSISSWLAWYQQKPGKAPK LLIYKASSLESGVPSRFSGSGSGTEFTLTISSLQPDDFATYYCQQY NSYSRTFGQGTKVEIK | SEQ ID NO: 350 |
| 3G6-L2 | QSVLTQPPSASGTPGQRVTISCSGSSSNIGSNYVYWYQQLPGTAP KLLIYSNNQRPSGVPDRFSGSKSGTSASLAISGLRSEDEADYYCA AWDDSLSGWVFGGGTKLTVL | SEQ ID NO: 359 |

TABLE 1c-continued

| Light Chain Variable Regions | | |
| --- | --- | --- |
| Clone | VL Sequence | SEQ ID NO: |
| 3B9 | EIVLTQSPDTLSLSPGERATLSCRASQSVSRRYLAWYQQKPGQAP RLLIYGASSRATGIPDRFSGSGSGTDFTLTISRLEPEDFAVYYCQQF GTSPITFGQGTRLEIK | SEQ ID NO: 368 |
| 3F9-L | QSVLTQPPSASGTPGQRVTISCSGSSSNIGSNTANWYQQLPGTAPR LLIYRNNQRPSGVPDRFSGSKSGTSASLAISGLQSEDEADYYCAA WDDSLNGYVFGTGTKVTVL | SEQ ID NO: 377 |
| 3E10 | QSVLTQPPSASGTPGQRVTISCSGSSSNIGSNYVYWYQQLPGTAP KLLIYSNNQRPSGVPDRFSGSKSGTSASLAISGLRSEDEADYYCAP WDDSLSGRVFGGGTKLTVL | SEQ ID NO: 386 |
| 3C3 | DIQMTQSPSSLSASVGDRVTITCRASQGINNFLAWFQQKPGKAPK SLIYAASSLQSGVPSKFSGSGSGTDFTLTIRSLQPEDFATYYCQHY NSYPITFGQGTRLEIK | SEQ ID NO: 395 |
| 11F4 | EIVLTQSPGTLSLSPGERATLSCRASQSVSRSYLAWYQQKPGQAP RLLIYGASSRATGVPDRFSGSGSGTDFTLTISRLEPEDFAVFYCQQ YSISPLTFGGGTKVEIK | SEQ ID NO: 404 |
| 10E12 | QSVLTQPPSVSAAPGQKVTISCSGSSSNIGNNYVSWYQQLPGTAP KLLIYDNNKRPSGIPDRFSGSKSGTSATLGITGLQTGDEADYYCET WDSSLSAVVFGGGTKLTVL | SEQ ID NO: 413 |
| 4E1 | QSALTQPASVSGSPGQSITISCTGTSSDVGSYNLVSWYQQHPGKA PKLMIYEGSKRPSGVSNRFSGSKSGNTASLTISGLQAEDEADYYC CSYAGSSTWVFGGGTKLTVL | SEQ ID NO: 422 |
| 2404.6H1 | EIVLTQSPGTLSLSPGERATLSCRASQSVSRTYLAWYHQKPGQAP RLLIYGASSRATGISDRFSGSGSGTDFTLTISRLEPEDFAVYYCQQ YGTSPITFGQGTRLEIK | SEQ ID NO: 431 |
| 2A8-K | DIVMTQSPDSLAVSLGERATINCKSSQSVLDSSNNNnYFAWYQQR PGQPPHLLIYWASSRESGVPDRFSGSGSGTDFTLTISSLQAEDVAV YYCQQYYSTPYTFGQGTKLEIK | SEQ ID NO: 440 |
| 3B1 | QSALTQPPSASGTPGQRVTISCSGSSSNIGSNTVNWYQQLPGTAP KLLIYTNNQRPSGVPDRFSGSKSGTSASLAISGLQSEDEADYFCST WDDSLNGPVFGGGTKLTVL | SEQ ID NO: 449 |
| 9B5 | DIQMTQSPSSLSASVGDRVTITCRGSQGISNYLAWFQQRPGKAPK SLIYAASSLESGVPSKFSGSGSGTDFTLTIISLQPEDFATYYCQQYY NYPITFGQGTRLEIK | SEQ ID NO: 458 |
| 11A5 | QTVVTQEPSFSVSPGGTVTLTCGLSSGSVSTSYYPSCFQQTPGQAP RTLIYSTDTRSSGVPDRFSGSILGNKAALTITGAQADDESDYYCVL YMGSGISVFGGGTKLTVL | SEQ ID NO: 467 |

Provided herein are DLL3 binding agents (e.g., antibodies), wherein the DLL3 antigen binding domain comprises a variable heavy chain (VH) and a variable light chain, wherein the amino acid sequence of the VH is selected from the VH sequences presented in Table 1b; and the amino acid sequence of the VL is selected from the VL sequences presented in Table 1c.

In some embodiments, the DLL-3 binding agent comprises a heavy chain CDR1, CDR2, and CDR3. In some embodiments, the heavy chain CDR1, CDR2, and CDR3 sequences are selected from the heavy chain CDRs presented in Table 1e.

TABLE 1e

| Heavy Chain CDRs | | |
| --- | --- | --- |
| Clone | CDR1 VH Sequence | SEQ ID NO: |
| 2D3 | NSISNYYWS | SEQ ID NO: 1 |
| 5A2 | GSISSSYWS | SEQ ID NO: 10 |

TABLE 1e-continued

| Heavy Chain CDRs | | |
| --- | --- | --- |
| 7F9 | FTFSSHDMH | SEQ ID NO: 19 |
| 9D3 | DSISNYYWS | SEQ ID NO: 28 |
| 26C8 | NSISNYYWS | SEQ ID NO: 37 |
| 2A6.C5 | VSISSYYWS | SEQ ID NO: 46 |
| 5E12 | FTFSSYDMH | SEQ ID NO: 55 |
| 6D8 | FSLSTRGVGVG | SEQ ID NO: 64 |
| 8E11 | DSISNYYWT | SEQ ID NO: 73 |
| 5C1.A4 | VSLSTSGMCVS | SEQ ID NO: 82 |
| 9F7 | GSISSYYWS | SEQ ID NO: 91 |
| 2C3 | GSSSGNYWS | SEQ ID NO: 100 |

TABLE 1e-continued

Heavy Chain CDRs

| 2G1 | GSISSSSYYWG | SEQ ID NO: 109 |
|---|---|---|
| 3E4 | GSFSGYYWS | SEQ ID NO: 118 |
| 3F2 | GSISSNNWWS | SEQ ID NO: 127 |
| 4F9 | GSFSGYYWT | SEQ ID NO: 136 |
| 4G9 | GSFSGYYWS | SEQ ID NO: 145 |
| 11H7 | GSFSAYYWN | SEQ ID NO: 154 |
| 16H7 | GSFSGDYWS | SEQ ID NO: 163 |
| 17A2 | DSISSSNWWS | SEQ ID NO: 172 |
| 6H1 | FSLSTSGLGVG | SEQ ID NO: 181 |
| 6H5 | YTLTELSMH | SEQ ID NO: 190 |
| 10D1 | GSFSGYYWR | SEQ ID NO: 199 |
| 11F6 | DSISSNWWT | SEQ ID NO: 208 |
| 6F8 | GTFTNYCIS | SEQ ID NO: 217 |
| 3G6-L1 | GTFSTYSIS | SEQ ID NO: 226 |
| 4C6 | DSISSYYWS | SEQ ID NO: 235 |
| 4E6 | DSISSYYWS | SEQ ID NO: 244 |
| 4H8 | DSVSSNSATWN | SEQ ID NO: 253 |
| 9H12-K | YTFTGYSIH | SEQ ID NO: 262 |
| 10G1-K | FTFSSYAMN | SEQ ID NO: 271 |
| 11A3 | DSISNYYWS | SEQ ID NO: 280 |
| 3B11 | DSVSSNSVVWN | SEQ ID NO: 289 |
| 5G2 | DSVSSNSAVWN | SEQ ID NO: 298 |
| 11E4 | GSISSYYWS | SEQ ID NO: 307 |
| 2404.8E11 | DSVSSNSAVWN | SEQ ID NO: 316 |
| 10A2 | DSVSSNSATWN | SEQ ID NO: 325 |
| 11A8 | DSVSSNSATWN | SEQ ID NO: 334 |
| 4H5 | DSINNYFWS | SEQ ID NO: 343 |
| 3G6-L2 | GTFSTYSIS | SEQ ID NO: 352 |
| 3B9 | FTFSSYSMN | SEQ ID NO: 361 |
| 3F9-L | DSVSSNSAIWN | SEQ ID NO: 370 |
| 3E10 | GSISSYYWT | SEQ ID NO: 379 |
| 3C3 | YTFTSYYIH | SEQ ID NO: 388 |
| 11F4 | GSISHYYWT | SEQ ID NO: 397 |
| 10E12 | VSISSYYWS | SEQ ID NO: 406 |
| 4E1 | DNVSTNSAAWN | SEQ ID NO: 415 |
| 2404.6H1 | FTFSSYGMH | SEQ ID NO: 424 |
| 2A8-K | DSVSSNSAVWN | SEQ ID NO: 433 |
| 3B1 | DSVSSNTTAWK | SEQ ID NO: 442 |
| 9B5 | DSISSLSWS | SEQ ID NO: 451 |

TABLE 1e-continued

Heavy Chain CDRs

| 11A5 | YTFTGYYMH | SEQ ID NO: 460 |
|---|---|---|
| Clone | CDR2 VH Sequence | SEQ ID NO: |
| 2D3 | AYIYYSGTTNYN | SEQ ID NO: 2 |
| 5A2 | GYIYYSGTTNYN | SEQ ID NO: 11 |
| 7F9 | SAIGIAGDTYYS | SEQ ID NO: 20 |
| 9D3 | DSISNYYWS | SEQ ID NO: 29 |
|  | GYIFYSGTTNHN | SEQ ID NO: 695 |
| 26C8 | AYIYYSGTTNYN | SEQ ID NO: 38 |
| 2A6.C5 | GYIYYSGTTNYN | SEQ ID NO: 47 |
| 5E12 | SAIGPAGDTYYP | SEQ ID NO: 56 |
| 6D8 | ALIYWNDDKRYS | SEQ ID NO: 65 |
| 8E11 | GYIYYSGTTNSN | SEQ ID NO: 74 |
| 5C1.A4 | GFIDWDDDKYYN | SEQ ID NO: 83 |
| 9F7 | GYMYYSGTTNYN | SEQ ID NO: 92 |
| 2C3 | GEINHSGTTSYN | SEQ ID NO: 101 |
| 2G1 | GSIYYSGNIYHN | SEQ ID NO: 110 |
| 3E4 | GEIIHSGSSNYN | SEQ ID NO: 119 |
| 3F2 | GDIHHSGSTNYK | SEQ ID NO: 128 |
| 4F9 | GEITHSGSTNYN | SEQ ID NO: 137 |
| 4G9 | GEITHSGSTNYN | SEQ ID NO: 146 |
| 11H7 | GEINHSGSTNYN | SEQ ID NO: 155 |
| 16H7 | GEINHSGITSFN | SEQ ID NO: 164 |
| 17A2 | GEVFHSGSTNYN | SEQ ID NO: 173 |
| 6H1 | ALIYWNDDKRYS | SEQ ID NO: 182 |
| 6H5 | GGFDPEDGKTIYA | SEQ ID NO: 191 |
| 10D1 | GEISHSGSTNYN | SEQ ID NO: 200 |
| 11F6 | GDIHHSGSTNYN | SEQ ID NO: 209 |
| 6F8 | GGIIPIFGTTNYA | SEQ ID NO: 218 |
| 3G6-L1 | GGIIPIFGTTNYA | SEQ ID NO: 227 |
| 4C6 | GYMYYSGITNYN | SEQ ID NO: 236 |
| 4E6 | SYIYYSGISNYN | SEQ ID NO: 245 |
| 4H8 | GRTYYRSKWYDDYA | SEQ ID NO: 254 |
| 9H12-K | GWINPNSGGTFYA | SEQ ID NO: 263 |
| 10G1-K | STISGSGGSTYYA | SEQ ID NO: 272 |
| 11A3 | SYIYYSGITNYN | SEQ ID NO: 281 |
| 3B11 | GRTYYRSKWYDDYA | SEQ ID NO: 290 |
| 5G2 | GWTYYRSKYYNDYA | SEQ ID NO: 299 |
| 11E4 | GYVYYSDITNYN | SEQ ID NO: 308 |
| 2404.8E11 | GRTYYRSKWYNDYA | SEQ ID NO: 317 |

TABLE 1e-continued

| Heavy Chain CDRs | | |
|---|---|---|
| 10A2 | GRTYYRSEWYNDYA | SEQ ID NO: 326 |
| 11A8 | ARTYYRSKWYNDYE | SEQ ID NO: 335 |
| 4H5 | GYFYHRGGNNYN | SEQ ID NO: 344 |
| 3G6-L2 | GGIIPIFGTTNYA | SEQ ID NO: 353 |
| 3B9 | SYISSSSSTIYYA | SEQ ID NO: 362 |
| 3F9-L | GGTYYRSMWYNDYA | SEQ ID NO: 371 |
| 3E10 | GYIFYSGTTNYN | SEQ ID NO: 380 |
| 3C3 | GVIVPSGGSISYA | SEQ ID NO: 389 |
| 11F4 | GYIYYSGITNFS | SEQ ID NO: 398 |
| 10E12 | AYIYYSGNTNYS | SEQ ID NO: 407 |
| 4E1 | GWTYYRSKWYNDYA | SEQ ID NO: 416 |
| 2404.6H1 | AVISYDGNSNYYA | SEQ ID NO: 425 |
| 2A8-K | GRTYYRSKWYNDYA | SEQ ID NO: 434 |
| 3B1 | GWTYYRSKWYYDYT | SEQ ID NO: 443 |
| 9B5 | GYLYYSGSTDYN | SEQ ID NO: 452 |

| Clone | CDR3 VH Sequence | SEQ ID NO: |
|---|---|---|
| 11A5 | GWINPNSGGTNYA | SEQ ID NO: 461 |
| 2D3 | CARLFNWGFAFDIW | SEQ ID NO: 3 |
| 5A2 | CARVAPTGFWFDYW | SEQ ID NO: 12 |
| 7F9 | CARANWGEGAFDIW | SEQ ID NO: 21 |
| 9D3 | CARVFNWGFAFDIW | SEQ ID NO: 30 |
| 26C8 | CARVFHWGFAFDIW | SEQ ID NO: 39 |
| 2A6.C5 | CARLSNWGFAFDIW | SEQ ID NO: 48 |
| 5E12 | CARADPPYYYYGMDVW | SEQ ID NO: 57 |
| 6D8 | CARSNWGNWYFALW | SEQ ID NO: 66 |
| 8E11 | CARVFNRGFAFDIW | SEQ ID NO: 75 |
| 5C1.A4 | CARIRGYSGSYDAFDIW | SEQ ID NO: 84 |
| 9F7 | CARVGLTGFFFDYW | SEQ ID NO: 93 |
| 2C3 | CARGELGIADSW | SEQ ID NO: 102 |
| 2G1 | CAREIIVGATHFDYW | SEQ ID NO: 111 |
| 3E4 | CSRGEYGSGSRFDYW | SEQ ID NO: 120 |
| 3F2 | CAREAGGYFDYW | SEQ ID NO: 129 |
| 4F9 | CARGEYGSGSRFDYW | SEQ ID NO: 138 |
| 4G9 | CARGEYGSGSRFDYW | SEQ ID NO: 147 |
| 11H7 | CARGLDSSGWYPFDYW | SEQ ID NO: 156 |
| 16H7 | CARGELGIPDNW | SEQ ID NO: 165 |
| 17A2 | CARAAVAGALDYW | SEQ ID NO: 174 |
| 6H1 | CVHRRIAAPGSVYW | SEQ ID NO: 183 |
| 6H5 | CATLLRGLDAFDVW | SEQ ID NO: 192 |

TABLE 1e-continued

| Heavy Chain CDRs | | |
|---|---|---|
| 10D1 | CAVRGYSYGYPLFDYW | SEQ ID NO: 201 |
| 11F6 | CARDGGGTLDYW | SEQ ID NO: 210 |
| 6F8 | CARDNGDRYYYDMDVW | SEQ ID NO: 219 |
| 3G6-L1 | CARDGEGSYYYYYGMDVW | SEQ ID NO: 228 |
| 4C6 | CARLSVAGFYFDYW | SEQ ID NO: 237 |
| 4E6 | CARISVAGFFFDNW | SEQ ID NO: 246 |
| 4H8 | CAGGGLVGAPDGFDVW | SEQ ID NO: 255 |
| 9H12-K | CARDGWGDYYYYGLDVW | SEQ ID NO: 264 |
| 10G1-K | CAIDPEYYDILTGGDYW | SEQ ID NO: 273 |
| 11A3 | CARITVTGFYFDYW | SEQ ID NO: 282 |
| 3B11 | CARGGIVGAPDAFDIW | SEQ ID NO: 291 |
| 5G2 | CTRGGIVGAPDGFDIW | SEQ ID NO: 300 |
| 11E4 | CARIGVAGFYFDYW | SEQ ID NO: 309 |
| 2404.8E11 | FTRGGIVGAPDAFDIW | SEQ ID NO: 318 |
| 10A2 | CAGGGIVGAPDGFDVW | SEQ ID NO: 327 |
| 11A8 | CARGGIVGAPDAFDIW | SEQ ID NO: 336 |
| 4H5 | CARLALAGFFFDYW | SEQ ID NO: 345 |
| 3G6-L2 | CARDGEGSYYYYYGMDVW | SEQ ID NO: 354 |
| 3B9 | CARDKERRYYYYGMDVW | SEQ ID NO: 363 |
| 3F9-L | CSRGGIVGVPDAFDIW | SEQ ID NO: 372 |
| 3E10 | CARISEKSFYFDYW | SEQ ID NO: 381 |
| 3C3 | CARDRYYGDYYYGLDVW | SEQ ID NO: 390 |
| 11F4 | CAGISLAGFYFDYW | SEQ ID NO: 399 |
| 10E12 | CTRGGSGTIDVFDIW | SEQ ID NO: 408 |
| 4E1 | CARWVNRDVFDIW | SEQ ID NO: 417 |
| 2404.6H1 | CARDGATVTSYYYYGMDVW | SEQ ID NO: 426 |
| 2A8-K | CARGGIVGAPDGFDIW | SEQ ID NO: 435 |
| 3B1 | CARWIFHDAFDIW | SEQ ID NO: 444 |
| 9B5 | CARGRRAFDIW | SEQ ID NO: 453 |
| 11A5 | CAKDGGGDFYFYGMDVW | SEQ ID NO: 462 |

In some embodiments, the DLL-3 binding agent comprises a light chain CDR1, CDR2, and CDR3. In some embodiments, the light chain CDR1, CDR2, and CDR3 sequences are selected from the light chain CDRs presented in Table 1f.

TABLE 1f

| Light Chain CDRs | | |
|---|---|---|
| Clone | CDR1 VL Sequence | SEQ ID NO: |
| 2D3 | RASQSVSSNLA | SEQ ID NO: 4 |
| 5A2 | RASQRVSSRYLA | SEQ ID NO: 13 |

TABLE 1f-continued

| Light Chain CDRs | | |
|---|---|---|
| 7F9 | RASQGISDYLA | SEQ ID NO: 22 |
| 9D3 | RASQRISRTYLA | SEQ ID NO: 31 |
| 26C8 | RASQRVSNTYLA | SEQ ID NO: 40 |
| 2A6.C5 | RASQTISSSYLA | SEQ ID NO: 49 |
| 5E12 | RSSQSLLHSNEYNYLD | SEQ ID NO: 58 |
| 6D8 | RASQSVSSYLA | SEQ ID NO: 67 |
| 8E11 | CARVFNRGFAFDIW | SEQ ID NO: 76 |
|  | RASQRISNTYLA | SEQ ID NO: 696 |
| 5C1.A4 | RSSQSLLHSNGYNHLD | SEQ ID NO: 85 |
| 9F7 | RASQGIRNDLG | SEQ ID NO: 94 |
| 2C3 | RASQSISRWLA | SEQ ID NO: 103 |
| 2G1 | RASQGIRNDLG | SEQ ID NO: 112 |
| 3E4 | RASQGIRDDLG | SEQ ID NO: 121 |
| 3F2 | RASQSISSWLA | SEQ ID NO: 130 |
| 4F9 | RASQGIRDDLG | SEQ ID NO: 139 |
| 4G9 | RASQGIRDDLG | SEQ ID NO: 148 |
| 11H7 | RASQGISSWLA | SEQ ID NO: 157 |
| 16H7 | RASQSISRWLA | SEQ ID NO: 166 |
| 17A2 | KSSQSVLYSSNNKNYLA | SEQ ID NO: 175 |
| 6H1 | RASQGISSWLA | SEQ ID NO: 184 |
| 6H5 | RASQGIRNDLG | SEQ ID NO: 193 |
| 10D1 | RASQGIRNDLG | SEQ ID NO: 202 |
| 11F6 | RASQSISSWLA | SEQ ID NO: 211 |
| 6F8 | SGSSSNIGNNYVS | SEQ ID NO: 220 |
| 3G6-L1 | SGSSSNIGNNYVS | SEQ ID NO: 229 |
| 4C6 | RASQSVTRSYLA | SEQ ID NO: 238 |
| 4E6 | RASQSVSSSYLA | SEQ ID NO: 247 |
| 4H8 | SGSSSNIGSDPVN | SEQ ID NO: 256 |
| 9H12-K | RASQDISSWLA | SEQ ID NO: 265 |
| 10G1-K | RASQGISNYLA | SEQ ID NO: 274 |
| 11A3 | RASQSISRSYLA | SEQ ID NO: 283 |
| 3B11 | SGSSSNIGSDPVS | SEQ ID NO: 292 |
| 5G2 | SGSNSNIGSNPIN | SEQ ID NO: 301 |
| 11E4 | RASQSVSRRYLA | SEQ ID NO: 310 |
| 2404.8E11 | SGSSSNIGSDPIN | SEQ ID NO: 319 |
| 10A2 | SGSSSNIGSDPVI | SEQ ID NO: 328 |
| 11A8 | SGSSSNIGSNPVN | SEQ ID NO: 337 |
| 4H5 | RASQSISSWLA | SEQ ID NO: 346 |
| 3G6-L2 | SGSSSNIGSNYVY | SEQ ID NO: 355 |

TABLE 1f-continued

| Light Chain CDRs | | |
|---|---|---|
| 3B9 | RASQSVSRRYLA | SEQ ID NO: 364 |
| 3F9-L | SGSSSNIGSNTAN | SEQ ID NO: 373 |
| 3E10 | SGSSSNIGSNYVV | SEQ ID NO: 382 |
| 3C3 | RASQGINNFLA | SEQ ID NO: 391 |
| 11F4 | RASQSVSRSYLA | SEQ ID NO: 400 |
| 10E12 | SGSSSNIGNNYVS | SEQ ID NO: 409 |
| 4E1 | TGTSSDVGSYNLVS | SEQ ID NO: 418 |
| 2404.6H1 | RASQSVSRTYLA | SEQ ID NO: 427 |
| 2A8-K | KSSQSVLDSSNNNNYFA | SEQ ID NO: 436 |
| 3B1 | SGSSSNIGSNTVN | SEQ ID NO: 445 |
| 9B5 | RGSQGISNYLA | SEQ ID NO: 454 |
| 11A5 | GLSSGSVSTSYYPS | SEQ ID NO: 463 |

| Clone | CDR2 VL Sequence | SEQ ID NO: |
|---|---|---|
| 2D3 | GASTRAT | SEQ ID NO: 5 |
| 5A2 | GASSRAT | SEQ ID NO: 14 |
| 7F9 | AASTLQS | SEQ ID NO: 23 |
| 9D3 | GASSRAT | SEQ ID NO: 32 |
| 26C8 | GASSRAT | SEQ ID NO: 41 |
| 2A6.C5 | GASSRAT | SEQ ID NO: 50 |
| 5E12 | LGSNRAS | SEQ ID NO: 59 |
| 6D8 | DAFYRAT | SEQ ID NO: 68 |
| 8E11 | GASSRAT | SEQ ID NO: 77 |
| 5C1.A4 | LGSNRAS | SEQ ID NO: 86 |
| 9F7 | AASSLQS | SEQ ID NO: 95 |
| 2C3 | KASSLES | SEQ ID NO: 104 |
| 2G1 | AASSLQS | SEQ ID NO: 113 |
| 3E4 | AASSLQS | SEQ ID NO: 122 |
| 3F2 | KASSLES | SEQ ID NO: 131 |
| 4F9 | AASSLQS | SEQ ID NO: 140 |
| 4G9 | AASSLQS | SEQ ID NO: 149 |
| 11H7 | AASSLQS | SEQ ID NO: 158 |
| 16H7 | KASSLES | SEQ ID NO: 167 |
| 17A2 | WASTRES | SEQ ID NO: 176 |
| 6H1 | AASSLQS | SEQ ID NO: 185 |
| 6H5 | AASSLQS | SEQ ID NO: 194 |
| 10D1 | AASSLQS | SEQ ID NO: 203 |
| 11F6 | KASTLES | SEQ ID NO: 212 |
| 6F8 | DNNKRPS | SEQ ID NO: 221 |
| 3G6-L1 | DNNKRPS | SEQ ID NO: 230 |

TABLE 1f-continued

| Light Chain CDRs | | |
|---|---|---|
| 4C6 | GASSRAT | SEQ ID NO: 239 |
| 4E6 | GASSRAA | SEQ ID NO: 248 |
| 4H8 | SNNQRPS | SEQ ID NO: 257 |
| 9H12-K | TASSLQG | SEQ ID NO: 266 |
| 10G1-K | AASSLQS | SEQ ID NO: 275 |
| 11A3 | GASSRAT | SEQ ID NO: 284 |
| 3B11 | TNNQRPS | SEQ ID NO: 293 |
| 5G2 | SNNQRPS | SEQ ID NO: 302 |
| 11E4 | GASSRAT | SEQ ID NO: 311 |
| 2404.8E11 | SNNQRPS | SEQ ID NO: 320 |
| 10A2 | SNNQRPS | SEQ ID NO: 329 |
| 11A8 | SNNQRPS | SEQ ID NO: 338 |
| 4H5 | KASSLES | SEQ ID NO: 347 |
| 3G6-L2 | SNNQRPS | SEQ ID NO: 356 |
| 3B9 | GASSRAT | SEQ ID NO: 365 |
| 3F9-L | RNNQRPS | SEQ ID NO: 374 |
| 3E10 | SNNQRPS | SEQ ID NO: 383 |
| 3C3 | AASSLQS | SEQ ID NO: 392 |
| 11F4 | GASSRAT | SEQ ID NO: 401 |
| 10E12 | DNNKRPS | SEQ ID NO: 410 |
| 4E1 | EGSKRPS | SEQ ID NO: 419 |
| 2404.6H1 | GASSRAT | SEQ ID NO: 428 |
| 2A8-K | WASSRES | SEQ ID NO: 437 |
| 3B1 | TNNQRPS | SEQ ID NO: 446 |
| 9B5 | AASSLES | SEQ ID NO: 455 |
| 11A5 | STDTRSS | SEQ ID NO: 464 |

| Clone | CDR3 VL Sequence | SEQ ID NO: |
|---|---|---|
| 2D3 | CQQYNNWPLTF | SEQ ID NO: 6 |
| 5A2 | CQQYGTSPLTF | SEQ ID NO: 15 |
| 7F9 | CQKYNSVPLTF | SEQ ID NO: 24 |
| 9D3 | CQQYGTSPLTF | SEQ ID NO: 33 |
| 26C8 | CQQYGTSPLTF | SEQ ID NO: 42 |
| 2A6.C5 | CQQYGWSPITF | SEQ ID NO: 51 |
| 5E12 | CMQALEIPLTF | SEQ ID NO: 60 |
| 6D8 | CQHRSNWPITF | SEQ ID NO: 69 |
| 8E11 | CQQYDTSPLTF | SEQ ID NO: 78 |
| 5C1.A4 | CMQALQTPLTF | SEQ ID NO: 87 |
| 9F7 | CLQDYNYPYTF | SEQ ID NO: 96 |
| 2C3 | CQQYNSYSTF | SEQ ID NO: 105 |

TABLE 1f-continued

| Light Chain CDRs | | |
|---|---|---|
| 2G1 | CLQDYNYPLTF | SEQ ID NO: 114 |
| 3E4 | CLQDYDYPLTF | SEQ ID NO: 123 |
| 3F2 | CQQYNSYSTF | SEQ ID NO: 132 |
| 4F9 | CLQDYDYPLTF | SEQ ID NO: 141 |
| 4G9 | CLQDYDYPLTF | SEQ ID NO: 150 |
| 11H7 | CQQADSFPFTF | SEQ ID NO: 159 |
| 16H7 | CQQYNSYSTF | SEQ ID NO: 168 |
| 17A2 | CQQYYGTSWTF | SEQ ID NO: 177 |
| 6H1 | CHQANSFPFTF | SEQ ID NO: 186 |
| 6H5 | CLQHNSYPRTF | SEQ ID NO: 195 |
| 10D1 | CLQYNSYPRTF | SEQ ID NO: 204 |
| 11F6 | CQQYNGYSTF | SEQ ID NO: 213 |
| 6F8 | CGTWDSSLSAVVF | SEQ ID NO: 222 |
| 3G6-L1 | CGTWDSSLSAVVF | SEQ ID NO: 231 |
| 4C6 | CQQYGTSPLTF | SEQ ID NO: 240 |
| 4E6 | CQQYGISPLTF | SEQ ID NO: 249 |
| 4H8 | CSAWDDSLNGYVF | SEQ ID NO: 258 |
| 9H12-K | CQQANVFPYTF | SEQ ID NO: 267 |
| 10G1-K | CLQHDSFPLTF | SEQ ID NO: 276 |
| 11A3 | CQQYDTSPLTF | SEQ ID NO: 285 |
| 3B11 | CAAWDDSLNGHVF | SEQ ID NO: 294 |
| 5G2 | CAAWDDSLNGHVF | SEQ ID NO: 303 |
| 11E4 | CQQYGTSPITF | SEQ ID NO: 312 |
| 2404.8E11 | CAAWDDSLNGYVF | SEQ ID NO: 321 |
| 10A2 | CAAWDDSLNGYVF | SEQ ID NO: 330 |
| 11A8 | CSAWDDWLNGYVF | SEQ ID NO: 339 |
| 4H5 | CQQYNSYSRTF | SEQ ID NO: 348 |
| 3G6-L2 | CAAWDDSLSGWVF | SEQ ID NO: 357 |
| 3B9 | CQQFGTSPITF | SEQ ID NO: 366 |
| 3F9-L | CAAWDDSLNGYVF | SEQ ID NO: 375 |
| 3E10 | CAPWDDSLSGRVF | SEQ ID NO: 384 |
| 3C3 | CQHYNSYPITF | SEQ ID NO: 393 |
| 11F4 | CQQYSISPLTF | SEQ ID NO: 402 |
| 10E12 | CETWDSSLSAVVF | SEQ ID NO: 411 |
| 4E1 | CCSYAGSSTWVF | SEQ ID NO: 420 |
| 2404.6H1 | CQQYGTSPITF | SEQ ID NO: 429 |
| 2A8-K | CQQYYSTPYTF | SEQ ID NO: 438 |
| 3B1 | CSTWDDSLNGPVF | SEQ ID NO: 447 |

TABLE 1f-continued

| Light Chain CDRs | | |
| --- | --- | --- |
| 9B5 | CQQYYNYPITF | SEQ ID NO: 456 |
| 11A5 | CVLYMGSGISVF | SEQ ID NO: 465 |

The disclosure encompasses modifications to the DLL3 antibody agents comprising the sequences shown in Tables 1b to 1e, including functionally equivalent DLL3 antibody agents having modifications which do not significantly affect their properties and variants which have enhanced or decreased activity and/or affinity. For example, the amino acid sequence may be mutated to obtain a DLL3 antigen binding agent with a desired binding affinity to DLL3. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antigen binding domain removed and a different residue inserted in its place. In some embodiments, sites of interest for substitutional mutagenesis include the hypervariable regions/CDRs, but FR alterations are also contemplated. Conservative substitutions are shown in Table 2 under the heading of "conservative substitutions." If such substitutions result in a change in biological activity, then more substantial changes, denominated "exemplary substitutions" in Table 2, or as further described below in reference to amino acid classes, may be introduced and the products screened.

TABLE 2

Amino Acid Substitutions

| Original Residue (naturally occurring amino acid) | Conservative Substitutions | Exemplary Substitutions |
| --- | --- | --- |
| Ala (A) | Val | Val; Leu; Ile |
| Arg (R) | Lys | Lys; Gln; Asn; Ala |
| Asn (N) | Gln | Gln; His; Asp, Lys; Arg; Ala |
| Asp (D) | Glu | Glu; Asn; Ala |
| Cys (C) | Ser | Ser; Ala |
| Gln (Q) | Asn | Asn; Glu; Ala |
| Glu (E) | Asp | Asp; Gln; Ala |
| Gly (G) | Ala | Ala |
| His (H) | Arg | Asn; Gln; Lys; Arg; Ala |
| Ile (I) | Leu | Leu; Val; Met; Ala; Phe; Norleucine; Ala |
| Leu (L) | Ile | Norleucine; Ile; Val; Met; Ala; Phe |
| Lys (K) | Arg | Arg; Gln; Asn; Ala |

TABLE 2-continued

Amino Acid Substitutions

| Original Residue (naturally occurring amino acid) | Conservative Substitutions | Exemplary Substitutions |
| --- | --- | --- |
| Met (M) | Leu | Leu; Phe; Ile; Ala |
| Phe (F) | Tyr | Leu; Val; Ile; Ala; Tyr |
| Pro (P) | Ala | Ala |
| Ser (S) | Thr | Thr; Ala |
| Thr (T) | Ser | Ser; Ala |
| Trp (W) | Tyr | Tyr; Phe; Ala |
| Tyr (Y) | Phe | Trp; Phe; Thr; Ser; Ala |
| Val (V) | Leu | Ile; Leu; Met; Phe; Ala; Norleucine | i. Antibody Fragments

In one aspect, an anti-DLL-3 antibody agent according to any of the above embodiments can be an antibody fragment. An antibody fragment comprises a portion of an intact antibody, such as the antigen binding or variable region of the intact antibody. Antibody fragments include, but are not limited to, Fab, Fab', Fab'-SH, F(ab')$_2$, Fv, diabody, linear antibodies, multispecific formed from antibody fragments antibodies and scFv fragments, and other fragments described below. In some embodiments, the antibody is a full length antibody, e.g., an intact IgG1 antibody or other antibody class or isotype as described herein. (See, e.g., Hudson et al., Nat. Med., 9: 129-134 (2003); Pluckthun, The Pharmacology of Monoclonal Antibodies, vol. 113, pp. 269-315 (1994); Hollinger et al., Proc. Natl. Acad. Sci. USA, 90: 6444-6448 (1993); WO93/01161; and U.S. Pat. Nos. 5,571,894, 5,869,046, 6,248,516, and 5,587,458). A full length antibody, intact antibody, or whole antibody is an antibody having a structure substantially similar to a native antibody structure or having heavy chains that contain an Fc region as defined herein. Antibody fragments can be made by various techniques, including but not limited to proteolytic digestion of an intact antibody as well as production by recombinant host cells (e.g., E. coli or phage), as known in the art.

An Fv antibody fragment comprises a complete antigen-recognition and antigen-binding site. This fragment may comprise a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

A diabody is a small antibody fragment prepared by constructing an sFv fragment with a short linker (e.g., about 5-10 residues) between the $V_H$ and $V_L$ domains such that interchain but not intra-chain pairing of the V domains is achieved, resulting in a bivalent fragment. Bispecific diabodies are heterodimers of two crossover sFv fragments in which the $V_H$ and $V_L$ domains of the two antibodies are present on different polypeptide chains (See, e.g., EP 404,097; WO 93/11161; and Hollinger et al, Proc. Natl. Acad. Sci. USA, 90:6444-6448 (1993)).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins ($V_H$ and $V_L$, respectively). They are highly expressed in microbial cell culture, show favorable biophysical properties including, for example, but not limited to, solubility and temperature stability, and are well suited to selection and affinity maturation by in vitro selection systems such as, for example, phage display. dAbs are bioactive as monomers and, owing to their small size and inherent stability can be formatted into larger molecules to create drugs with prolonged serum half-lives or other pharmacological activities. (See, e.g., W09425591 and US20030130496).

Fv and scFv are the species have intact combining sites that are devoid of constant regions. Thus, they may be suitable for reduced nonspecific binding during in vivo use. A single-chain Fv (sFv or scFv) is an antibody fragment that comprises the $V_H$ and $V_L$ antibody domains connected into a single polypeptide chain. The sFv polypeptide can further comprise a polypeptide linker between the $V_H$ and $V_L$ domains that enable the sFv to form the desired structure for antigen binding (See, e.g., Pluckthun, The Pharmacology of Monoclonal Antibodies, vol. 113, Rosenburg and Moore eds., Springer-Verlag, New York, pp. 269-315 (1994); Borrebaeck 1995, infra. scFv fusion proteins can be constructed to yield fusion of an effector protein at either the amino or the carboxy terminus of an sFv. The antibody fragment also can be a "linear antibody (See, e.g., U.S. Pat. No. 5,641, 870). Such linear antibody fragments can be monospecific or bispecific. Exemplary DLL3 specific scFvs are provided in Table 1d.

TABLE 1d

Exemplary DLL3 specific scFvs

| Clone | scFv Sequence | SEQ ID NO: |
|---|---|---|
| 2D3 | QVQLQESGPGLVKPSETLSLTCTVSDNSISNYYWSWIRQPPGKGLE WIAYIYYSGTTNYNPSLKSRVTISLDTSKNQFSLKLSSVTAADTAVY YCARLFNWGFAFDIWGQGTMVTVSSGGGGSGGGGSGGGGSGGGG SEIVMTQSPATLSVSPGERATLSCRASQSVSSNLAWYQQKPGQAPRL LIYGASTRATGIPARFSGSGSGTEFTLTISSLQSEDFAVYYCQQYNNW PLTFGGGTKVEIK | SEQ ID NO: 9 |
| 5A2 | QVQLQESGPGLMKPSETLSLTCTVSGGSISSSYWSCIRQPPGKGLEWI GYIYYSGTTNYNPSLKSRVTLSLDTSKNQFSLRLTSVTAADTAVYYC ARVAPTgFWFDYWGQGTLVTVSSGGGGSGGGGSGGGGSGGGGSEI VLTQSPGTLSLSPGERATLSCRASQRVSSRYLAWYQQKPGQAPRLLI YGASSRATGIPDRFSGSGSGTDFTLTISRLEPEEFAVYYCQQYGTSPL TFGGGTKVEIK | SEQ ID NO: 18 |
| 7F9 | EVQLVESGGGLVQPGGSLRLSCAASGFTFSSHDMHWVRQATGKGL EWVSAIGIAGDTYYSGSVKGRFTISRENAKNSLYLQMNSLRAGDTA VYYCARANWGeGAFDIWGQGTMVTVSSGGGGSGGGGSGGGGSGG GGSDIQMTQSPSSLSASVGDRVTITCRASQGISDYLAWYQQKPGKIP KLLIYAASTLQSGVPSRFSGSGSGTDFTLTISSLQPEDVATYYCQKYN SVPLTFGGGTKVEIK | SEQ ID NO: 27 |
| 9D3 | QVQLQESGPGLVKPSETLSLTCTVSDDSISNYYWSWIRQPPGKGLE WIGYIFYSGTTNHNPSLKSRLTISLDKAKNQFSLRLSSVTAADTAVY YCARVFNWgFAFDIWGQGTMVTVSSGGGGSGGGGSGGGGSGGGG SEIVLTQSPGTLSLSPGERATLSCRASQRISRTYLAWYQQKPGQAPRL LIYGASSRATGIPDRFTGSGSGTDFTLTISRLEPEDFAVYYCQQYGTS PLTFGGGTKVEIN | SEQ ID NO: 36 |
| 26C8 | QVQLQESGPGLVKPSETLSLTCTVSDNSISNYYWSWIRQPPGKGLE WIAYIYYSGTTNYNPSLKSRVTISLDTSKNQFSLQLSSVTAADAAVY YCARVFHWgFAFDIWGQGTMVTVSSGGGGSGGGGSGGGGSGGGG SEIVLTQSPGTLSLSPGERATLSCRASQRVSNTYLAWYQQNPGQAPR LLIYGASSRATGIPDRFSGSGSGTDFTLTISRLEPEDFAVYYCQQYGT SPLTFGGGTKVEIK | SEQ ID NO: 45 |
| 2A6.C5 | QVQLQESGPGLVKPSETLSLTCTVSNVSISSYYWSWIRQPPGKGLEW IGYIYYSGTTNYNPSLKSRVTMSVDTSKNQFSLKLSSVTAADTAVYF CARLSNWgFAFDIWGQGTMVTFSSGGGGSGGGGSGGGGSGGGGSEI VLTQSPGTLSLSPGERATLSCRASQTISSSYLAWYQQKPGQAPRLLIY GASSRATGIPDRFSGSGSGTEFTLTISRLEPEDFAVYYCQQYGWSPIT FGQGTRLEIK | SEQ ID NO: 54 |
| 5E12 | EVQLVESGGGLVQPGGSLRLSCAASGFTFSSYDMHWVRQATGKGL EWVSAIGPAGDTYYPGSVKGRFTISRENAKNSLYLQMNSLRAGDTA VYYCARADPPyyyYGMDVWGQGTTVTVSSGGGGSGGGGSGGGGSG GGGSDIVMTQSPLSLPVTPGEPASISCRSSQSLLHSNEYNYLDWYLQ KPGQSPQLLIYLGSNRASGVPDRFSGSGSGTDFILKISRVEAEDVGVY YCMQALEIPLTFGGGTKVEIK | SEQ ID NO: 63 |
| 6D8 | QITLKESGPTLVKPTQTLTLTCTFSGFSLSTrgVGVGWIRQPPGKALE WLALIYWNDDKRYSPSLQTRLTITKDTPKNQVVLTMTNMDPVDTA TYYCARSNWGnWYFALWGRGTLVTVSSGGGGSGGGGSGGGGSGG GGSEIVLTQSPATLSLSPGERATLSCRASQSVSSYLAWYQQKPGQAP RLLIYDAFYRATGIPARFSGSGSGTDFTLTISSLEPEDFAVYYCQHRS NWPITFGQGTRLEIK | SEQ ID NO: 72 |

TABLE 1d-continued

<u>Exemplary DLL3 specific scFvs</u>

| Clone | scFv Sequence | SEQ ID NO: |
|---|---|---|
| 8E11 | QVQLQESGPGLVKPSETLSLTCTVSGDSISNYYWTWIRQPPGKGLE WIGYIYYSGTTNSNPSLKSRVTVSLDTSKSQFSLNLSSVTAADTAVY YCARVFNRgFAFDIWGQGTMVTVSSGGGGSGGGGSGGGGSGGGGS EIVLTQSPGTLSLSPGERATLSCRASQRISNTYLAWYQQKPGQAPRL LIYGASSRATGIPDRFSGSGSGTDFTLTISRLEPEDFAAYYCQQYDTS PLTFGGGTKVEIK | SEQ ID NO: 81 |
| 5C1.A4 | QVTLRESGPALVKPTQTLTLTCTVSGVSLSTsgMCVSWIRQPLGKAL EWLGFIDWDDDKYYNTSLKTRLTISKDTSKNQVVLTMTNMDPVDT ATYYCARIRGYsgsyDAFDIWGQGTVVIVSSGGGGSGGGGSGGGGSG GGGSDIVMTQSPLSLPVTPGEPASISCRSSQSLLHSNGYNHLDWYLQ KPGQSPQVLIYLGSNRASGVPDRFSGSGSGTDFTLKISRVEAEDVGV YFCMQALQTPLTFGGGTKVEIK | SEQ ID NO: 90 |
| 9F7 | QVQLQVSGPGLVKPSETLSLTCSVSGGSISSYYWSWIRQSPGKGLD WIGYMYYSGTTNYNPSLKSRVTISVDTSKNQFSLKLSSVTATDTAV YYCARVGLTgFFFDYWGQGTLVTVSSGGGGSGGGGSGGGGSGGGG SAIQMTQSPSSLSASVGDRVTITCRASQGIRNDLGWYQQKPGKAPKL LIYAASSLQSGVPSRFSGSGSGTDFTLTVSSLQPEDFATYYCLQDYN YPYTFGQGTKLEIK | SEQ ID NO: 99 |
| 2C3 | QVQLQQWGGGLLKPSETLSLTCAVYGGSSSGNYWSWIRQPPGKRL EWIGEINHSGTTSYNPSLKSRVTISVDTSKNQFSLKLSSVTAADTAVY YCARGELGIADSWGQGTLVTVSSGGGGSGGGGSGGGGSGGGGSDI QMTQSPSTLSASVGDRVTITCRASQSISRWLAWYQQKPGKAPKLLIY KASSLESGVPSRFSGSGSGTEFTLTISSLQPDDFATYYCQQYNSYSTF GQGTKVEIK | SEQ ID NO: 108 |
| 2G1 | QLQLQESGPGLVKPSETLSLTCTVSGGSISSssYYWGWIRQPPGKGLE WIGSIYYSGNIYHNPSLKSRVSISVDTSKNQFSLRLSSVTAADTAVYY CAREIIVgaTHFDYWGQGTLVTVSSGGGGSGGGGSGGGGSGGGGSA IQMTQSPSSLSASVGDRVTITCRASQGIRNDLGWYQQKPGKAPELLI YAASSLQSGVPSRFSGSGSGTDFTLTISSLQPEDFATYYCLQDYNYPL TFGPGTKVDIK | SEQ ID NO: 117 |
| 3E4 | QVQLQQWGAGLLKPSETLSLTCAVYGGSFSGYYWSWIRQPPGKGL EWIGEIIHSGSSNYNPSLKSRVSISVDTSKNQFSLKLSSVTAADTAVY YCSRGEYGsgSRFDYWGQGTLVTVSSGGGGSGGGGSGGGGSGGGG SAIQMTQSPSSLSASVGDRVAITCRASQGIRDDLGWYQQKPGKAPK LLIYAASSLQSGVPSRFSGSRSDTDFTLTISSLQPEDFATYYCLQDYD YPLTFGGGTKVEIK | SEQ ID NO: 126 |
| 3F2 | QVQLQESGPGLVKPSGTLSLTCAVSGGSISSnNWWSWVRQPPGKGL EWIGDIHHSGSTNYKPSLKSRVTISVDKSKNQFSLNLISVTAADTAV YYCAREAGGYFDYWGQGILVTVSSGGGGSGGGGSGGGGSGGGGS DIQMTQSPSTLSASVGDRVTITCRASQSISSWLAWYQQKPGKAPKLL ISKASSLESGVPSRFSGSGSGPEFTLTISSLQPADFATYYCQQYNSYST FGQGTKLEIK | SEQ ID NO: 135 |
| 4F9 | QVQLQQWGAGLLKPSETLSLTCAVYGGSFSGYYWTWIRQPPGKGL EWIGEITHSGSTNYNPSLKSRVSISVDTSKNQFSLKLSSVTAADTAVY YCARGEYGsgSRFDYWGQGTLVTVSSGGGGSGGGGSGGGGSGGGG SAIQMTQSPSSLSASVGDRVAITCRASQGIRDDLGWYQQKPGKAPK LLIYAASSLQSGVPSRFSGSGSDTDFTLTISSLQPEDFATYYCLQDYD YPLTFGGGTKVEIK | SEQ ID NO: 144 |
| 4G9 | QVQLQQWGAGLLKPSETLSLTCAVYGGSFSGYYWSWIRQPPGKGL EWIGEITHSGSTNYNPSLKSRVSISVDTSKNQFSLKLSSVTAADTAVY YCARGEYGsgSRFDYWGQGTLVTVSSGGGGSGGGGSGGGGSGGGG SAIQMTQSPSSLSASVGDRVALTCRASQGIRDDLGWYQQKPGKAPK LLIYAASSLQSGVPSRFSGSGSDTDFTLTISSLQPEDFATYYCLQDYD YPLTFGGGTKVEIK | SEQ ID NO: 153 |
| 11H7 | QVQLQQWGAGLLKPSETLSLTCAVYGGSFSAYYWNWIRQPPGKGL EWIGEINHSGSTNYNPSLKSRVTISVDTSKNQFSLNLTSLTAADTAV YYCARGLDSsgwYPFDYWGQGTLVTVSSGGGGSGGGGSGGGGSGG GGSDIQMTQSPSSVSASVGDRVTITCRASQGISSWLAWYQQKPGKA PKLLIYAASSLQSGVPSRFSGSGSGTDFTLTISSLQPEDFATYYCQQA DSFPFTFGPGTKVDIK | SEQ ID NO: 162 |
| 16H7 | QVQLQQWGAGLLKPSETLSLTCAVFGGSFSGDYWSWIRQPPGKGLE WIGEINHSGITSFNPSLKSRVTISVDTSKNQFSLKLSSVTAADTAVYY CARGELGIPDNWGQGTLVTVSSGGGGSGGGGSGGGGSGGGGSDIQ MTQSPSTLSASVGDRVTITCRASQSISRWLAWYQQKPGKAPKLLIYK | SEQ ID NO: 171 |

TABLE 1d-continued

Exemplary DLL3 specific scFvs

| Clone | scFv Sequence | SEQ ID NO: |
|---|---|---|
| | ASSLESGVPSRFSGSGSGTEFTLTISSLQPDDFATYYCQQYNSYSTFG QGTKVEIK | |
| 17A2 | QVQLQESGPGLVKPSGTLSLTCVVFGDSISSsNWWSWVRQPPGKGL EWIGEVFHSGSTNYNPSLKSRVTISVDKSKNQFSLKLSSVTAADTAV YYCARAAVAGALDYWGQGTLVTVSSGGGGSGGGGSGGGGSGGGG SDIVMTQSPDSLAVSLGERATINCKSSQSVLYSSNNKnYLAWYQQKP GQPPNLLVYWASTRESGVPDRFSGAGSGTDFTLTISSLQAEDVAVY YCQQYYGTSWTFGQGTKVEIK | SEQ ID NO: 180 |
| 6H1 | QITLRESGPTLVKPTQTLTLTCTFSGFSLSTsgLGVGWIRQPPGEALE WLALIYWNDDKRYSPSLKSRLSITKDTSKNQVVLIMTNMDPVDTAT YYCVHRRIAaPGSVYWGQGTLVTVSSGGGGSGGGGSGGGGSGGGG SDIQMTQSPSSVSASVGDRVTITCRASQGISSWLAWYQQKPGKAPK LLISAASSLQSGVPSRFSGSGSGTDFTLTISSLQPEDFATYYCHQANSF PFTFGQGTKLEIK | SEQ ID NO: 189 |
| 6H5 | QVQLVQSGAEVKKPGASVKVSCKVSGYTLTELSMHWVRQAPGKG PEGMGGFDpEDGKTIYAQKFQGRVTMTEDTSADTAYMELNSLRSE DTAVYYCATLLRGIDAFDVWGQGTMVTVSSGGGGSGGGGSGGGG SGGGGSDIQMTQSPSSLSASVGDRVTITCRASQGIRNDLGWYQQKP GKAPKRLIYAASSLQSGVPSRFSGSGSGTEFTLTISTLQPEDFATYYC LQHNSYPRTFGQGTKVEIK | SEQ ID NO: 198 |
| 10D1 | QVQLQQWGAGLLKPSETLSLTCAVYGGSFSGYYWRWIRQPPGKGL EWIGEISHSGSTNYNPSLKSRVTISVDTSKNQFSLKLSSVTAADTAVY YCAVRGYSygyPLFDYWGQGTLVTVSSGGGGSGGGGSGGGGSGGGG GSDIQMTQSPSSLSASVGDRVTITCRASQGIRNDLGWYQQKLGKAP KRLIYAASSLQSGVPSRFSGSGSGTEFTLTISSLQPEDFATYYCLQYN SYPRTFGQGTKVEIK | SEQ ID NO: 207 |
| 11F6 | QVQLQESGPGLVKPSGTLSLTCAVSGDSISSNWWTWVRQPPGKGLE WIGDIHHSGSTNYNPSLKSRVTMSVDKSENQFSLKLSSVTAADTAVF YCARDGGGTLDYWGQGTLVTVSSGGGGSGGGGSGGGGSGGGGSD IQMTQSPSTLSASVGDRVTITCRASQSISSWLAWYQQKPGKAPKLLI YKASTLESGVPSRFSGSGSGTEFTLTISSLQPDDFATYYCQQYNGYST FGQGTKVEIK | SEQ ID NO: 216 |
| 6F8 | QVQLVQSGAEVKKPGSSVKVSCKASGGTFTNYCISWVRQAPGQGL EWMGGIIpIFGTTNYAQTFQGRVTITADKSTSTAYMELSSLRSEDTA VYYCARDNGDryyYDMDVWGQGTTVTVSSGGGGSGGGGSGGGGS GGGGSQSVLTQPPSVSAAPGQKVTISCSGSSSNIGNNYVSWYQQLPG TAPKLLIYDNNKRPSGIPDRFSGSKSGTSATLGITGLQTGDEADYYC GTWDSSLSAVVFGGGTKLTVL | SEQ ID NO: 225 |
| 3G6-L1 | QVPLVQSGAEVKKPGSSVKVSCKASGGTFSTYSISWVRQAPGQGLE WMGGIIpIFGTTNYAQKFQGRVTITADKSTSTAYMELSSLRSEDTAV YYCARDGEGsyyyyYGMDVWGQGTTVTVSSGGGGSGGGGSGGGGS GGGGSQSVLTQPPSVSAAPGQKVTISCSGSSSNIGNNYVSWYQQLPG TAPKLLIYDNNKRPSGIPDRFFGSKFGTSATLGITGLQTGDEADYYC GTWDSSLSAVVFGGGTKLTVL | SEQ ID NO: 234 |
| 4C6 | QVQLQESGPGLVKPSETLSLTCTVSGDSISSYYWSWIRQPPGKGLEW IGYMYYSGITNYNPSLKSRVNISLDTSKNQFSLKLGSVTAADTAVYY CARLSVAgFYFDYWGQGTLVTVSSGGGGSGGGGSGGGGSGGGGSE IVLTQSPGTLSLSPGERATLSCRASQSVTRSYLAWYQQKPGQAPRLL IYGASSRATDIPDRFSGSGSGTDFTLTINRLEPEDFAVYYCQQYGTSP LTFGGGTKVEIK | SEQ ID NO: 243 |
| 4E6 | QVQLQESGPGLVKPSETLSLTCTVSSDSISSYYWSWIRQPPGKGLEW ISYIYYSGISNYNPSLKSRVSISVDTSKNQFSLRLSSVTAADTAVYYC ARISVAgFFFDNWGQGTLVTVSSGGGGSGGGGSGGGGSGGGGSEIM LTQSPDTLSLSPGERATLSCRASQSVSSSYLAWYQQKPGQAPRLLIY GASSRAAGVPDRFSGSGSGTDFTLTISRLAPEDFVVYYCQQYGISPLT FGGGTKVEIK | SEQ ID NO: 252 |
| 4H8 | QVQLQQSGPGLVKPSQTLSLTCAISGDSVSSnsATWNWIRQSPSRGLE WLGRTYYRSKwyDDYAVSVKSRITINPDTSKNHLSLHLNSVTPEDTA VYYCAGGGLVgapDGFDVWGQGTMVTVSSGGGGSGGGGSGGGGS GGGGSQSVLTQPPSASGTPGQRVTISCSGSSSNIGSDPVNWYQQLPG TAPKLLIYSNNQRPSGVPDRFSGSKSGTSASLAISGLQSEDEADYYCS AWDDSLNGYVFGTGTKVTVL | SEQ ID NO: 261 |
| 9H12-K | QVQLVQSGAEVKKPGASVKVSCKASGYTFTGYSIHWVRQAPGQGL EWMGWINpNSGGTFYAQKFQGRVTMTRDTSISTVYMELSRLRSDD TAVYYCARDGWGdyyyYGLDVWGQGTTVTVSLGGGGSGGGGSGG | SEQ ID NO: 270 |

TABLE 1d-continued

| Clone | scFv Sequence | SEQ ID NO: |
|---|---|---|
| | GGSGGGGSDIQMTQSPSSVSASVGDRVTITCRASQDISSWLAWYQQ<br>KPGKAPKLLIYTASSLQGGVPSRFSGSGSGTDFTLTISSLQPEDLATY<br>SCQQANVFPYTFGQGTKLEIK | |
| 10G1-K | EVQLLESGGGLVQPGGSLRLSCAASGFTFSSYAMNWVRQAPGKGL<br>EWVSTISgSGGSTYYADSVKGRFTISRDNSKNTLYLQMNSLRAEDTA<br>VFYCAIDPEYydilTGGDYWGQGTLVTVSSGGGGSGGGGSGGGGS<br>GGGGSDIQMTQSPSAMSASVGDRVTITCRASQGISNYLAWFQQKPG<br>KVPKRLIYAASSLQSGVPSRFSGSGSGTEFTLTISSLQPEDFATYFCLQ<br>HDSFPLTFGGGTKVEIK | SEQ ID NO: 279 |
| 11A3 | QVQLQESGPGLVKPSETLSLTCTVSSDSISNYYWSWIRQPPGKGLEW<br>ISYIYYSGITNYNPSLKSRVTISVDTSKNQFSLKLSSVTAADTAVYYC<br>ARITVTgFYFDYWGQGTLVTVSSGGGGSGGGGSGGGGSGGGGSEIV<br>LTQSPGTLSLSPGERATLSCRASQSISRSYLAWYQQKPGQAPRHLIY<br>GASSRATGIPDRFSGSGSGTDFILTISRLEPEDFAVYYCQQYDTSPLTF<br>GGGTKVEIK | SEQ ID NO: 288 |
| 3B11 | QVQLQQSGPGLVKPSQTLSLTCAISGDSVSSnsVVWNWIRQSPSRGL<br>EWLGRTYYRSKwyDDYAVSVKSRITINPDTSKNQFSLQLNSVTPEDT<br>AVYHCARGGIVgapDAFDIWGQGTMVTVSSGGGGSGGGGSGGGGS<br>GGGGSQSVLTQPPSASGTPGQRVTISCSGSSSNIGSDPVSWYQQFPGT<br>APKLLIYTNNQRPSGVPDRFSGSKSGTSASLAISGLQSEDEADYYCA<br>AWDDSLNGHVFGTGTKVTVL | SEQ ID NO: 297 |
| 5G2 | QVQLQQSGPGLVKPSQTLSLTCAISGDSVSSnsAVWNWIRQSPSRGL<br>EWLGWTYYRSKYYndYAVSLKSRITINPDTSKNQFSLQLNSLTPEDT<br>AVYYCTRGGIVgapDGFDIWGQGTMVTVSSGGGGSGGGGSGGGGS<br>GGGGSQSALTQPPSASGTPGQRVTISCSGSNSNIGSNPINWYQQLPGT<br>APKLLIYSNNQRPSGVPDRFSGSKSGTSASLAISGLQSEDEADYYCA<br>AWDDSLNGHVFGTGTKVTVL | SEQ ID NO: 306 |
| 11E4 | QVQLQESGPGLVKPSETLSLTCTVSGGSISSYYWSWIRQSPGKGLEW<br>IGYVYYSDITNYNPSLKSRVTISVDTSKNQFSLNLNSVTAADTAFYF<br>CARIGVAgFYFDYWGQGTLVTVSSGGGGSGGGGSGGGGSGGGGSEI<br>VLTQSPDTLSLSPGERATLSCRASQSVSRRYLAWYQQKPGQAPRLLI<br>YGASSRATGIPDRFSGSGSGTDFTLTISRLEPEDFEVYYCQQYGTSPIT<br>FGQGTRLEIK | SEQ ID NO: 315 |
| 2404.8E11 | QIQLQQSGPGLVKPSQTLSLTCAISGDSVSSnsAVWNWIRQSPSRGLE<br>WLGRTYYRSKwyNDYAVSVKSRITIKPDTAKNQFSLQLNSVTPEDT<br>AVYYFTRGGIVgapDAFDIWGQGTMVTVSSGGGGSGGGGSGGGGSG<br>GGGSQSVLTQPPSASGTPGQRVTISCSGSSSNIGSDPINWYQQVPGTA<br>PKLLIYSNNQRPSGVPDRFSGSKSGTSASLAISGLQSEDEADYYCAA<br>WDDSLNGYVFGTGTKVTVL | SEQ ID NO: 324 |
| 10A2 | QVQLQQSGPGLVKPSETLSLTCAISGDSVSSnsATWNWIRQSPSRGLE<br>WLGRTYYRSEwyNDYAVSVKSRITINPDTSKNHLSLHLNSVTPEDTA<br>VYYCAGGGIVgapDGFDVWGQGTMVTVSSGGGGSGGGGSGGGGSG<br>GGGSQSVLTQPPSASGTPGQRVTISCSGSSSNIGSDPVIWYQQLPRTA<br>PKLLIYSNNQRPSGVPDRFSGSKSGTSASLAISGLQSEDEADYYCAA<br>WDDSLNGYVFGTGTKVTVL | SEQ ID NO: 333 |
| 11A8 | QVQLQQSGPGLVKPSQTLSLTCAISGDSVSSnsATWNWIRQSPSTGLE<br>WLARTYYRSKwyNDYEVSVKSQITINPDTSKNQFSLQLNSVTPEDTA<br>VYYCARGGIVgapDAFDIWGQGTMVTVSSGGGGSGGGGSGGGGSG<br>GGGSQSVLTQPPSASGTPGQRVTISCSGSSSNIGSNPVNWYQQLPGT<br>APKLLIYSNNQRPSGVPDRFSDSKSGTSASLAISGLQSEDEADYYCSA<br>WDDWLNGYVFGTGTKVTVL | SEQ ID NO: 342 |
| 4H5 | QVQLQESGPGLVKPSETLSLTCTVSGDSINNYFWSWIRQPPGKGLE<br>WIGYFYHRGGNNYNPSLKSRVTISIDTSKNQFSLNLNSVTSADTAVY<br>YCARLALAgFFFDYWGQGTLVTVSSGGGGSGGGGSGGGGSGGGGS<br>DIQMTQSPSTLSASVGDRVTITCRASQSISSWLAWYQQKPGKAPKLL<br>IYKASSLESGVPSRFSGSGSGTEFTLTISSLQPDDFATYYCQQYNSYS<br>RTFGQGTKVEIK | SEQ ID NO: 351 |
| 3G6-L2 | QVPLVQSGAEVKKPGSSVKVSCKASGGTFSTYSISWVRQAPGQGLE<br>WMGGIIpIFGTTNYAQKFQGRVTITADKSTSTAYMELSSLRSEDTAV<br>YYCARDGEGsyyyYGMDVWGQGTTVTVSSGGGGSGGGGSGGGGS<br>GGGGSQSVLTQPPSASGTPGQRVTISCSGSSSNIGSNYVYWYQQLPG<br>TAPKLLIYSNNQRPSGVPDRFSGSKSGTSASLAISGLRSEDEADYYCA<br>AWDDSLSGWVFGGGTKLTVL | SEQ ID NO: 360 |
| 3B9 | EVQLVESGGGLVQPGGSLRLSCAASGFTFSSYSMNWVRQAPGKGLE<br>WVSYISsSSSTIYYADSVKGRFTISRDNAKNSLYLQMNSLRDEDTAV | SEQ ID NO: 369 |

TABLE 1d-continued

| Clone | scFv Sequence | SEQ ID NO: |
|---|---|---|
| | YYCARDKERryyyYGMDVWGQGTTVTVSSGGGGSGGGGSGGGGSG<br>GGGSEIVLTQSPDTLSLSPGERATLSCRASQSVSRRYLAWYQQKPGQ<br>APRLLIYGASSRATGIPDRFSGSGSGTDFTLTISRLEPEDFAVYYCQQ<br>FGTSPITFGQGTRLEIK | |
| 3F9-L | QVQLQQSGPGLVKPSQTLSLACAISGDSVSSnsAIWNWIRQSPSRGLE<br>WLGGTYYRSMwyNDYAVSVKSRITINPDTSKNQLSLQLNSVTPEDT<br>AVYYCSRGGIVgvpDAFDIWGQGTMVTVSSGGGGSGGGGSGGGGS<br>GGGGSQSVLTQPPSASGTPGQRVTISCSGSSSNIGSNTANWYQQLPG<br>TAPRLLIYRNNQRPSGVPDRFSGSKSGTSASLAISGLQSEDEADYYC<br>AAWDDSLNGYVFGTGTKVTVL | SEQ ID NO: 378 |
| 3E10 | QVQLQESGPGLVKPSETLSLTCNVSDGSISSYYWTWIRQPPGKGLD<br>WIGYIFYSGTTNYNPSLKSRVTISLDTSKNQFSLKLTSMTAADTAVY<br>YCARISEKsFYFDYWGQGTLVTVSSGGGGSGGGGSGGGGSGGGGS<br>QSVLTQPPSASGTPGQRVTISCSGSSSNIGSNYVYWYQQLPGTAPKL<br>LIYSNNQRPSGVPDRFSGSKSGTSASLAISGLRSEDEADYYCAPWDD<br>SLSGRVFGGGTKLTVL | SEQ ID NO: 387 |
| 3C3 | QVQLVQSGAEVKRPGASVKVSCKASGYTFTSYYIHWVRQAPGQGL<br>EWMGVIVpSGGSISYAQKFQGRVTMTRDTSTNIVYMELSSLRSEDT<br>AVYYCARDRYYgdyyYGLDVWGQGTTVTVSSGGGGSGGGGSGGGG<br>SGGGGSDIQMTQSPSSLSASVGDRVTITCRASQGINNFLAWFQQKPG<br>KAPKSLIYAASSLQSGVPSKFSGSGSGTDFTLTIRSLQPEDFATYYCQ<br>HYNSYPITFGQGTRLEIK | SEQ ID NO: 396 |
| 11F4 | QVHLQESGPGLVKPSETLSLTCTVSGGSISHYYWTWIRQPPGKGLE<br>WIGYIYYSGITNFSPSLKSRVSISVDSSKNQFSLNLNSVTAADTAVYY<br>CAGISLAgFYFDYWVQGTLVTVSSGGGGSGGGGSGGGGSGGGGSEI<br>VLTQSPGTLSLSPGERATLSCRASQSVSRSYLAWYQQKPGQAPRLLI<br>YGASSRATGVPDRFSGSGSGTDFTLTISRLEPEDFAVFYCQQYSISPL<br>TFGGGTKVEIK | SEQ ID NO: 405 |
| 10E12 | QVQLQESGPGLVKPSETLSLTCTVSGVSISSYYWSWIRQPPGKGLEW<br>IAYIYYSGNTNYSPSLKSRVTISVDTSKDQLSLKLSSVTAADTAVYY<br>CTRGGSGtiDVFDIWGQGTMVAVSSGGGGSGGGGSGGGGSGGGGS<br>QSVLTQPPSVSAAPGQKVTISCSGSSSNIGNNYVSWYQQLPGTAPKL<br>LIYDNNKRPSGIPDRFSGSKSGTSATLGITGLQTGDEADYYCETWDS<br>SLSAVVFGGGTKLTVL | SEQ ID NO: 414 |
| 4E1 | QVQLQQSGPGLVKPSQTLSLTCAISGDNVSTnsAAWNWIRQSPSRGL<br>EWLGWTYYRSKwyNDYAVSLKSRININPDTSKNQFSLQLNSVTPED<br>TAVYYCARWVNRDVFDIWGQGTMVTVSSGGGGSGGGGSGGGGSG<br>GGGSQSALTQPASVSGSPGQSITISCTGTSSDVGSYNLVSWYQQHPG<br>KAPKLMIYEGSKRPSGVSNRFSGSKSGNTASLTISGLQAEDEADYYC<br>CSYAGSSTWVFGGGTKLTVL | SEQ ID NO: 423 |
| 2404.6H1 | QVQLVESGGGVVQPGRSLRLSCAASGFTFSSYGMHWVRQTPGKGL<br>EWVAVISYDGNsNYYADSVKGRFTISRDNSKNTLYLQMNSLRAEDT<br>AVYYCARDGATvtsyyyYGMDVWGQGTTVTVSSGGGGSGGGGSGG<br>GGSGGGGSEIVLTQSPGTLSLSPGERATLSCRASQSVSRTYLAWYHQ<br>KPGQAPRLLIYGASSRATGISDRFSGSGSGTDFTLTISRLEPEDFAVY<br>YCQQYGTSPITFGQGTRLEIK | SEQ ID NO: 432 |
| 2A8-K | QVQLQQSGPGLVKPSQTLSLTCAISGDSVSSnsAVWNWIRQSPSRGL<br>EWLGRTYYRSKwyNDYAVSVKSRITINPDTSRNQFSLQLNSVTPEDT<br>AVYYCARGGIVgapDGFDIWGQGTMVTVSSGGGGSGGGGSGGGGS<br>GGGGSDIVMTQSPDSLAVSLGERATINCKSSQSVLDSSNNNnYFAW<br>YQQRPGQPPHLLIYWASSRESGVPDRFSGSGSGTDFTLTISSLQAEDV<br>AVYYCQQYYSTPYTFGQGTKLEIK | SEQ ID NO: 441 |
| 3B1 | QVQLQQSGPGLVKPSQTLSLTCAISGDSVSSntTAWKWSRQSPSKGL<br>EWLGWTYYRSKwyYDYTVSVKSRITINPDTSKNQFSLQLNSVTPEDT<br>AVYYCARWIFHDAFDIWGQGTMVTVSSGGGGSGGGGSGGGGSGG<br>GGSQSALTQPPSASGTPGQRVTISCSGSSSNIGSNTVNWYQQLPGTA<br>PKLLIYTNNQRPSGVPDRFSGSKSGTSASLAISGLQSEDEADYFCSTW<br>DDSLNGPVFGGGTKLTVL | SEQ ID NO: 450 |
| 9B5 | QVQLQESGPGLVKPSETLSLTCTVSGDSISSLSWSWIRQTPGEGLEWI<br>GYLYYSGSTDYNPSLKSRVTISVDTSKNQFSLKLRSVAAADTALYY<br>CARGRRAFDIWGQGTMVTVSSGGGGSGGGGSGGGGSGGGGSDIQ<br>MTQSPSSLSASVGDRVTITCRGSQGISNYLAWFQQRPGKAPKSLIYA<br>ASSLESGVPSKFSGSGSGTDFTLTIISLQPEDFATYYCQQYNYPITFG<br>QGTRLEIK | SEQ ID NO: 459 |

TABLE 1d-continued

Exemplary DLL3 specific scFvs

| Clone | scFv Sequence | SEQ ID NO: |
|-------|---------------|------------|
| 11A5 | QVQLVQSGAEVKKPGASVKVSCKASGYTFTGYYMHWVRQAPGQG LEWMGWINpNSGGTNYAQKFQGRVTMTRDTSVSTAYMELSRLTSD DTAIYYCAKDGGGdfyfYGMDVWGQGTTVTVSSGGGGSGGGGSGG GGSGGGGSQTVVTQEPSFSVSPGGTVTLTCGLSSGSVSTSYYPSCFQ QTPGQAPRTLIYSTDTRSSGVPDRFSGSILGNKAALTITGAQADDESD YYCVLYMGSGISVFGGGTKLTVL | SEQ ID NO: 468 |
| 10G1-K | EVQLLESGGGLVQPGGSLRLSCAASGFTFSSYAMNWVRQAPGKGL EWVSTISgSGGSTYYADSVKGRFTISRDNSKNTLYLQMNSLRAEDTA VFYCAIDPEYydilTGGDYWGQGTLVTVSSGGGGSGGGGSGGGGSG GGGSDIQMTQSPSAMSASVGDRVTITCRASQGISNYLAWFQQKPGK VPKRLIYAASSLQSGVPSRFSGSGSGTEFTLTISSLQPEDFATYFCLQH DSFPLTFGGGTKVEIK | SEQ ID NO: 629 |

In some embodiments, the DLL3 antigen binding domain comprises a scFv comprising a light chain van able (VL) region and the heavy chain variable (VH) region of a DLL3-specific monoclonal antibody joined by a flexible linker. Single chain variable region fragments may be made by linking light and/or heavy chain variable regions by using a linking peptide An example of a linking peptide is the GS linker having the amino acid sequence (GGGGS)$_x$ wherein x is 1, 2, 3, 4, or 5 (SEQ ID NO: 470). In some embodiments, x is 6, 7, 8, 9, 10, 11, 12, 13, 14, 15, or any integer less than about 20. In some embodiments, the linker is (GGGGS)$_4$ (SEQ ID NO: 478). In general, linkers can be short, flexible polypeptides, which in some embodiments are comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In exemplary embodiments, provided herein are DLL3 antigen binding domains comprising: a VH region comprising a VH CDR1, VH CDR2, and VH CDR3 of the VH sequence shown in Table 1b and/or a VL region comprising VL CDR1, VL CDR2, and VL CDR3 of the VL sequence shown in Table 1c. In some embodiments, the VH and VL are linked together by a linker. In some embodiments the linker comprises the amino acid sequence GGGGSGGGGSGGGGSGGGGS (SEQ ID NO: 478). In some embodiments the linker may be encoded by a DNA sequence comprising GGCGGTGGAGGCTCCG-GAGGGGGGGGGCTCTGGCGGAGGGGGCTCC (SEQ ID NO: 564). In some embodiments, the linker may be encoded by a DNA sequence comprising ggcggcggcggcggctctggaggag-gaggcagcggcggaggaggctccggaggcggcggctct (SEQ ID NO: 630). In some embodiments the linker comprises the amino acid sequence GGGGSGGGGSGGGGS (SEQ ID NO: 534). In some embodiments the linker is a scFv Whitlow linker, which may comprise the amino acid sequence GST-SGSGKPGSGEGSTKG (SEQ ID NO: 535). The scFv Whitlow linker may be encoded by a DNA sequence comprising GGGTCTACATCCGGCTCCGGGAAGCCCG-GAAGTGGCGAAGGTAGTACAAAGGGG (SEQ ID NO: 566). In some embodiments, the VH and VL sequences of the scFv's disclosed can be oriented with the VH sequence being located at the N-terminus of the scFv and followed by a linker and then the VL sequence, while in other embodiments the scFv can be oriented with the VL sequence at the N-Terminus and followed by a linker and then the VH sequence.

ii. Chimeric and Humanized Antibodies

In some embodiments, an anti-DLL-3 antibody agent is or comprises a monoclonal antibody, including a chimeric, humanized or human antibody.

In some embodiments, an anti-DLL-3 antibody agent provided herein can be a chimeric antibody (See, e.g., U.S. Pat. No. 4,816,567; and Morrison et al., Proc. Natl. Acad. Sci. USA, 81:6851-6855 (1984)). A chimeric antibody can be an antibody in which a portion of the heavy and/or light chain is derived from a particular source or species, while the remainder of the heavy and/or light chain is derived from a different source or species. In one example, a chimeric antibody can comprise a non-human variable region (e.g., a variable region derived from a mouse, rat, hamster, rabbit, or non-human primate, such as a monkey) and a human constant region. In a further example, a chimeric antibody can be a "class switched" antibody in which the class or subclass has been changed from that of the parent antibody. Chimeric antibodies include antigen-binding fragments thereof.

In some embodiments, a chimeric antibody can be a humanized antibody (See, e.g., Almagro and Fransson, Front. Biosci., 13:1619-1633 (2008); Riechmann et al., Nature, 332:323-329 (1988); Queen et al., Proc. Natl Acad. Sci. USA 86: 10029-10033 (1989); U.S. Pat. Nos. 5,821, 337, 7,527,791, 6,982,321, and 7,087,409; Kashmiri et al., Methods 36:25-34 (2005); Padlan, Mol. Immunol, 28:489-498 (1991); Dall'Acqua et al., Methods, 36:43-60 (2005); Osbourn et al., Methods, 36:61-68 (2005); and Klimka et al., Br. J. Cancer, 83:252-260 (2000)). A humanized antibody is a chimeric antibody comprising amino acid residues from non-human hypervariable regions and amino acid residues from human FRs. In certain embodiments, a humanized antibody will comprise substantially all of at least one, and typically two, variable domains, in which all or substantially all of the hypervariable regions (e.g., CDRs) correspond to those of a non-human antibody, and all or substantially all of the FRs correspond to those of a human antibody. A humanized antibody optionally may comprise at least a portion of an antibody constant region derived from a human antibody.

A non-human antibody can be humanized to reduce immunogenicity to humans, while retaining the specificity and affinity of the parental non-human antibody. A humanized antibody can comprise one or more variable domains comprising one or more CDRs, or portions thereof, derived from a non-human antibody. A humanized antibody can comprise one or more variable domains comprising one or more FRs, or portions thereof, derived from human antibody sequences. A humanized antibody can optionally comprise at least a portion of a human constant region. In some embodiments, one or more FR residues in a humanized antibody are substituted with corresponding residues from a non-human antibody (e.g., the antibody from which the CDR residues are derived), to restore or improve antibody specificity or affinity.

Human framework regions that may be used for humanization include but are not limited to: framework regions selected using a "best-fit" method; framework regions derived from the consensus sequence of human antibodies of a particular subgroup of light or heavy chain variable regions; human mature (somatically mutated) framework regions or human germline framework regions; and framework regions derived from screening FR libraries (See, e.g., Sims et al., J. Immunol, 151:2296 (1993); Carter et al., Proc. Natl. Acad. Sci. USA, 89:4285 (1992); Presta et al., J. Immunol, 151:2623 (1993); Baca et al., J. Biol. Chem., 272: 10678-10684 (1997); and Rosok et al., J. Biol. Chem., 271:22611-22618 (1996)).

iii. Human Antibodies

In some embodiments, an anti-DLL-3 antibody agent provided herein is a human antibody. Human antibodies can be produced using various techniques known in the art (See, e.g., van Dijk and van de Winkel, Curr. Opin. Pharmacol, 5: 368-74 (2001); and Lonberg, Curr. Opin. Immunol, 20:450-459 (2008)). A human antibody can be one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies may be prepared by administering an immunogen (e.g., a DLL-3 protein) to a transgenic animal that has been modified to produce intact human antibodies or intact antibodies with human variable regions in response to antigenic challenge (See, e.g., Lonberg, Nat. Biotech., 23:1117-1125 (2005); U.S. Pat. Nos. 6,075,181, 6,150,584, 5,770,429, and 7,041,870; and U.S. Pat. App. Pub. No. US 2007/0061900). Human variable regions from intact antibodies generated by such animals may be further modified, e.g., by combining with a different human constant region.

Human antibodies can also be made by hybridoma-based methods. For example, human antibodies can be produced from human myeloma and mouse-human heteromyeloma cell lines, using human B-cell hybridoma technology, and other methods (See, e.g., Kozbor, J. Immunol, 133: 3001 (1984); Brodeur et al., Monoclonal Antibody Production Techniques and Applications, pp. 51-63 (1987); Boerner et al., J. Immunol, 147: 86 (1991); Li et al., Proc. Natl. Acad. Sci. USA, 103:3557-3562 (2006); U.S. Pat. No. 7,189,826; Ni, Xiandai Mianyixue, 26(4): 265-268 (2006); Vollmers and Brandlein, Histology and Histopathology, 20(3): 927-937 (2005); and Vollmers and Brandlein, Methods and Findings in Experimental and Clinical Pharmacology, 27(3): 185-91 (2005)). Human antibodies may also be generated by isolating Fv clone variable domain sequences selected from human-derived phage display libraries. Such variable domain sequences may then be combined with a desired human constant region.

Modifications of the oligosaccharide in an antibody can be made, for example, to create antibody variants with certain improved properties. For example, antibody glycosylation variants can have improved CDC function. In some embodiments, the present disclosure can contemplate an antibody variant that possesses some but not all effector functions, which make it a desirable candidate for applications in which the half-life of the antibody in vivo is important yet certain effector functions (such as complement) are unnecessary or deleterious. In vitro and/or in vivo cytotoxicity assays can be conducted to confirm the reduction/depletion of CDC activities.

iv. Antibody Derivatives

In some embodiments, an antibody agent provided herein may be further modified to contain additional nonproteinaceous moieties that are known in the art and readily available. The moieties suitable for derivatization of the antibody can include but are not limited to water soluble polymers. Non-limiting examples of water soluble polymers can include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethyl ene/ maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. The number of polymers attached to the antibody may vary, and if two or more polymers are attached, they can be the same or different molecules.

In some embodiments, conjugates of an antibody and nonproteinaceous moiety that may be selectively heated by exposure to radiation are provided. In some embodiments, the nonproteinaceous moiety can be a carbon nanotube (See, e.g., Kam et al., Proc. Natl. Acad. Sci. USA, 102: 11600-11605 (2005)). The radiation may be of any wavelength, and can include, but is not limited to, wavelengths that do not harm ordinary cells, but which heat the nonproteinaceous moiety to a temperature at which cells proximal to the antibody-nonproteinaceous moiety are killed.

A DLL3 binding agent (e.g., a molecule comprising an antigen binding domain) is said to "specifically bind" its target antigen (e.g., human, cyno or mouse DLL3) when the dissociation constant (Kd) is ~1 nM. The antigen binding domain specifically binds antigen with "high affinity" when the Kd is 1-5 nM, and with "very high affinity" when the Kd is 0.1-0.5 nM. In one embodiment, the antigen binding domain has a Kd of ~1 nM. In one embodiment, the off-rate is $<1\times10^{-5}$. In other embodiments, the antigen binding domains will bind to human DLL3 with a Kd of between about $1\times10^{-7}$ M and $1\times10^{-12}$ M, and in yet another embodiment the antigen binding domains will bind with a Kd between about $1\times10^{-5}$ M and $1\times10^{-12}$ M.

As provided herein, the antigen binding domains of the present disclosure specifically bind mammalian DLL3 (e.g., human DLL3, cyno DLL3 or mouse DLL3). In certain embodiments, a DLL3 antigen binding domain of the present disclosure binds mammalian DLL3 with a Kd of less than $1\times10^{-6}$ M, less than $1\times10^{-7}$ M, less than $1\times10^{-8}$ M, or less than $1\times10^{-9}$ M. In one particular embodiment, the DLL3 antigen binding domains binds mammalian DLL3 (e.g., human DLL3, cyno DLL3 or mouse DLL3) with a Kd of less than $1\times10^{-7}$ M. In another embodiment, the DLL3 antigen binding domains binds mammalian DLL3 (e.g., human DLL3, cyno DLL3 or mouse DLL3) with a Kd of less than $1\times10^{-8}$ M. In some embodiments, the DLL3 antigen binding domains binds mammalian DLL3 (e.g., human DLL3, cyno DLL3) with a Kd of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, or about $5\times10^{-10}$ M. In certain embodiments, the Kd is calculated as the quotient of $K_{off}/K_{on}$, and the $K_{on}$ and $K_{off}$ are determined using a monovalent antibody, such as a Fab fragment, as measured by, e.g., BIAcore® surface plasmon resonance technology. In other embodiments, the Kd is calculated as the quotient of $K_{off}/K_{on}$, and the $K_{on}$ and $K_{off}$ are determined using a bivalent antibody, such as a Fab fragment, as measured by, e.g., BIAcore® surface plasmon resonance technology.

In some embodiments, the DLL3 antigen binding domain binds mammalian DLL3 (e.g., human DLL3, cyno DLL3 or mouse DLL3) with an association rate ($k_{on}$) of less than $1\times10^{-4}$ $M^{-1}$ $s^{-1}$, less than $2\times10^{-4}$ $M^{-1}$ $s^{-1}$, less than $3\times10^{-4}$ $M^{-1}$ $s^{-1}$, less than $4\times10^{-4}$ $M^{-1}$ $s^{-1}$, less than $5\times10^{-4}$ $M^{-1}$ $s^{-1}$, less than $7\times10^{-4}$ $M^{-1}$ $s^{-1}$, less than $8\times10^{-4}$ $M^{-1}$ $s^{-1}$, less than $9\times10^{-4}$ $M^{-1}$ $s^{-1}$, less than $1\times10^{-5}$ $M^{-1}$ $s^{-1}$, less than $2\times10^{-5}$ $M^{-1}$ $s^{-1}$, less than $3\times10^{-5}$ $M^{-1}$ $s^{-1}$, less than $4\times10^{-5}$ $M^{-1}$ $s^{-1}$, less than $5\times10^{-5}$ $M^{-1}$ $s^{-1}$, less than $6\times10^{-5}$ $M^{-1}$ $s^{-1}$, less than $7\times10^{-5}$ $M^{-1}$ $s^{-1}$, less than $8\times10^{-5}$ $M^{-1}$ $s^{-1}$, less than $9\times10^{-5}$ $M^{-1}$ $s^{-1}$, less than $1\times10^{-6}$ $M^{-1}$ $s^{-1}$, less than $2\times10^{-6}$ $M^{-1}$ $s^{-1}$, less than $3\times10^{-6}$ $M^{-1}$ $s^{-1}$, less than $4\times10^{-6}$ $M^{-1}$ $s^{-1}$, less than $5\times10^{-6}$ $M^{-1}$ $s^{-1}$, less than $6\times10^{-6}$ $M^{-1}$ $s^{-1}$, less than $7\times10^{-6}$ $M^{-1}$ $s^{-1}$, less than $8\times10^{-6}$ $M^{-1}$ $s^{-1}$, less than $9\times10^{-6}$ $M^{-1}$ $s^{-1}$, or less than $1\times10^{-7}$ $M^{-1}$ $s^{-1}$. In certain embodiments, the $k_{on}$ is determined using a monovalent antibody, such as a Fab fragment, as measured by, e.g., BIAcore® surface plasmon resonance technology. In other embodiments, the $k_{on}$ is determined using a bivalent antibody as measured by, e.g., BIAcore® surface plasmon resonance technology.

In some embodiments, the DLL3 antigen binding domain binds mammalian DLL3 (e.g., human DLL3, cyno DLL3 or mouse DLL3) with an dissociation rate ($k_{off}$) of less than $1\times10^{-2}$ $s^{-1}$, less than $2\times10^{-2}$ $s^{-1}$, less than $3\times10^{-2}$ $s^{-1}$, less than $4\times10^{-2}$ $s^{-1}$, less than $5\times10^{-2}$ $s^{-1}$, less than $6\times10^{-2}$ $s^{-1}$, less than $7\times10^{-2}$ $s^{-1}$, less than $8\times10^{-2}$ $s^{-1}$, less than $9\times10^{-2}$ $s^{-1}$, less than $1\times10^{-3}$ $s^{-1}$, less than $2\times10^{-3}$ $s^{-1}$, less than $3\times10^{-3}$ $s^{-1}$, less than $4\times10^{-3}$ $s^{-1}$, less than $5\times10^{-3}$ $s^{-1}$, less than $6\times10^{-3}$ $s^{-1}$, less than $7\times10^{-3}$ $s^{-1}$, less than $8\times10^{-3}$ $s^{-1}$, less than $9\times10^{-3}$ $s^{-1}$, less than $1\times10^{-4}$ $s^{-1}$, less than $2\times10^{-4}$ $s^{-1}$, less than $3\times10^{-4}$ $s^{-1}$, less than $4\times10^{-4}$ $s^{-1}$, less than $5\times10^{-4}$ $s^{-1}$, less than $6\times10^{-4}$ $s^{-1}$ less than $7\times10^{-4}$ $s^{-1}$, less than $8\times10^{-4}$ $s^{-1}$, less than $9\times10^{-4}$ $s^{-1}$, less than $1\times10^{-5}$ $s^{-1}$, or less than $5\times10^{-4}$ $s^{-1}$. In certain embodiments, the $k_{off}$ is determined using a monovalent antibody, such as a Fab fragment, as measured by, e.g., BIAcore® surface plasmon resonance technology. In other embodiments, the $k_{off}$ is determined using a bivalent antibody as measured by, e.g., BIAcore® surface plasmon resonance technology.

II. Chimeric Antigen Receptors

As used herein, chimeric antigen receptors (CARs) are proteins that specifically recognize target antigens (e.g., target antigens on cancer cells). When bound to the target antigen, the CAR may activate the immune cell to attack and destroy the cell bearing that antigen (e.g., the cancer cell). CARs may also incorporate costimulatory or signaling domains to increase their potency. See Krause et al., J. Exp. Med., Volume 188, No. 4, 1998 (619-626); Finney et al., *Journal of Immunology*, 1998, 161: 2791-2797, Song et al., Blood 119:696-706 (2012); Kalos et al., *Sci. Transl. Med.* 3:95 (2011); Porter et al., *N. Engl. J. Med.* 365:725-33 (2011), and Gross et al., *Annu. Rev. Pharmacol. Toxicol.* 56:59-83 (2016); U.S. Pat. Nos. 7,741,465, and 6,319,494.

Chimeric antigen receptors described herein comprise an extracellular domain, a transmembrane domain, and an intracellular domain, wherein the extracellular domain comprises a DLL3 antigen binding domain that specifically binds to DLL3. In some embodiments, the DLL-3 specific CAR comprises the following elements from 5' to 3': a signal sequence, a DLL3 antigen binding domain (e.g., an anti-DLL3 scFv), a hinge and transmembrane region, and one or more successive signaling domains. In certain embodiments, the DLL-3 specific CAR comprises the following elements from 5' to 3': a CD8a signal sequence, a DLL3 scFv comprising a DLL3 variable heavy chain and/or variable light chain described herein, a CD8a hinge and transmembrane region, a 41BB cytoplasmic signaling domain, and a CD3ζ cytoplasmic signaling domain. (FIG. 4, Table 7).

In some embodiments, the DLL-3 specific CARs further comprise a safety switches and/or monoclonal antibody specific-epitope.

a. Antigen Binding Domain

As discussed above, the DLL3 CARs described herein comprise an antigen binding domain. An "antigen binding domain" as used herein means any polypeptide that binds a specified target antigen, for example the specified target antigen can be the DLL3 (DLL-3) protein or fragment thereof (referred to interchangeably herein as a "DLL3 antigen", "DLL3 target antigen", or "DLL3 target"). In some embodiments, the antigen binding domain binds to a DLL3 antigen on a tumor cell. In some embodiments, the antigen binding domain binds to a DLL3 antigen on a cell involved in a hyperproliferative disease.

In some embodiments, the antigen binding domain comprises a variable heavy chain, variable light chain, and/or one or more CDRs described herein. In some embodiments, the antigen binding domain is a single chain variable fragment (scFv), comprising light chain CDRs CDR1, CDR2 and CDR3, and heavy chain CDRs CDR1, CDR2 and CDR3.

In some embodiments, DLL-3 specific CARs comprise a VH shown in Table 1b. In some embodiments, DLL-3 specific CARs comprise a VL shown in Table 1c. In some embodiments, DLL-3 specific CARs comprise a heavy chain CDR1, CDR2, CDR3 shown in Table 1e. In some embodiments, DLL-3 specific CARs comprise a light chain CDR1, CDR2, CDR3 shown in Table 1f.

Variants of the antigen binding domains (e.g., variants of the CDRs, VH and/or VL) are also within the scope of the disclosure, e.g., variable light and/or variable heavy chains that each have at least 70-80%, 80-85%, 85-90%, 90-95%, 95-97%, 97-99%, or above 99% identity to the amino acid sequences of the antigen binding domain sequences described herein. In some instances, such molecules include at least one heavy chain and one light chain, whereas in other instances the variant forms contain two variable light chains and two variable heavy chains (or subparts thereof). A skilled artisan will be able to determine suitable variants of the antigen binding domains as set forth herein using well-known techniques. In certain embodiments, one skilled in the art can identify suitable areas of the molecule that may be changed without destroying activity by targeting regions not believed to be important for activity.

In certain embodiments, the polypeptide structure of the antigen binding domains is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen binding domain comprises or consists of avimers.

A DLL3 antigen binding domain is said to be "selective" when it binds to one target more tightly than it binds to a second target.

In some embodiments, the DLL3 antigen binding domain is a scFv. In some embodiments, the DLL3 specific CAR comprises an scFv provided in Table 1d.

In some embodiments, the DLL3 specific CAR comprises a leader or signal peptide; in some embodiments the leader peptide comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence MALPVTALLL-PLALLLHAARP (SEQ ID NO: 477). In some embodiments, the leader peptide comprises the amino acid sequence of SEQ ID NO: 477. In some embodiments, the leader peptide is encoded by a nucleic acid sequence comprising:

(SEQ ID NO: 555)
ATGGCACTCCCCGTAACTGCTCTGCTGCTGCCGTTGGCATTGCTCCTGCAC

GCCGCACGCCCG

In other embodiments, the disclosure relates to isolated polynucleotides encoding any one of the DLL3 antigen binding domains described herein. In some embodiments, the disclosure relates to isolated polynucleotides encoding a DLL3 CAR described in Table 10. Also provided herein are vectors comprising the polynucleotides, and methods of making the same.

TABLE 10

| Polynucleotide Sequences of exemplary DLL3 targeting CARs | | |
|---|---|---|
| SEQ ID NO | CAR Structure | Nucleotide Sequence |
| 570 | CD8α signal sequence, 2D3 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGGTCCAGGTGCAGC TGCAGGAGAGCGGCCCAGGCCTGGTGAAGCCATCTGAG ACACTGAGCCTGACCTGCACCAGTGAGCGATAACTCCATC TCTAATTACTATTGGTCCTGGATCAGGCAGCCCCCTGGC AAGGGCCTGGAGTGGATCGCCTACATCTACTATTCTGGC ACCACAAACTATAATCCCAGCCTGAAGTCCAGAGTGACC ATCTCCCTGGACACATCTAAGAACCAGTTCTCCCTGAAG CTGAGCTCCGTGACCGCAGCAGATACAGCCGTGTACTAT TGTGCCCGGCTGTTTAATTGGGGCTTCGCCTTTGACATCT GGGGCCAGGGCACCATGGTGACAGTGTCTAGCGGAGGA GGAGGAAGCGGAGGAGGAGGGTCCGGAGGCGGGGGAT CTGAGATCGTGATGACCCAGTCTCCAGCCACACTGTCCG TGTCTCCCGGCGAGAGGGCCACCCTGAGCTGCAGAGCC AGCCAGTCCGTGAGCTCCAACCTGGCCTGGTACCAGCAG AAGCCTGGCCAGGCACCTCGGCTGCTGATCTATGGAGCA TCCACCAGGGCCACAGGAATCCCTGCACGCTTCTCTGGA AGCGGATCCGGCACAGAGTTTACCCTGACAATCTCTAGC CTGCAGTCTGAGGACTTCGCCGTGTACTATTGTCAGCAG TACAACAATTGGCCCCTGACCTTTGGCGGCGGCACAAAG GTGGAGATCAAGACCACAACTCCTGCACCTAGGCCACCT ACCCCAGCACCTACAATTGCTAGTCAGCCACTGTCACTG CGACCAGAGGCATGTCGACCTGCAGCTGGAGGAGCAGT GCATACAAGGGGACTGGACTTTGCCTGCGATATCTACAT TTGGGCTCCTCTGGCAGGAACATGTGGCGTGCTGCTGCT GAGCCTGGTCATCACTCTGTACTGCAAGCGAGGCCGGAA GAAACTGCTGTATATTTTCAAACAGCCCTTTATGCGACC TGTGCAGACCACACAGGAGGAAGATGGGTGCTCCTGTC GGTTCCCCGAGGAAGAGGAAGGAGGCTGTGAGCTGCGG GTCAAGTTTTCCAGATCTGCAGACGCCCCTGCTTACCAG CAGGGCCAGAACCAGCTGTATAACGAGCTGAATCTGGG GCGGAGAGAGGAATACGACGTGCTGGATAAAAGGCGCG GGAGAGACCCAGAAATGGGGGGAAAGCCACGACGGAA AAACCCCCAGGAGGGACTGTACAATGAACTGCAGAAGG ATAAAATGGCAGAGGCCTATTCCGAAATCGGGATGAAG GGAGAAAGAAGGCGAGGCAAAGGACACGACGGACTGT ACCAGGGGCTGTCTACCGCCACAAAGGACACCTATGAT GCTCTGCATATGCAGGCACTGCCACCCAGG |
| 571 | CD8α signal sequence, 5A2 scFv, CD8α hinge and transmembrane regions, 41BB | ATGGCTCTGCCCGTCACCGCTCTGCTGCTGCCTCTGGCTC TGCTGCTGCACGCCGCACGACCACAGGTGCAGCTGCAG GAGTCTGGCCCAGGCCTGATGAAGCCCAGCGAGACACT GTCCCTGACCTGCACCAGTGTCTGGCGGCAGCATCAGCTC CTCTTACTGGAGCTGTATCAGGCAGCCCCCTGGCAAGGG CCTGGAGTGGATCGGCTACATCTACTATTCCGGCACCAC AAACTATAATCCTTCCCTGAAGTCTCGGGTGACCCTGTC |

TABLE 10-continued

Polynucleotide Sequences of exemplary DLL3 targeting CARs

| SEQ ID NO | CAR Structure | Nucleotide Sequence |
|---|---|---|
| | cytoplasmic signaling domain, CD3ζ cytoplasmic signaling domain | TCTGGACACAAGCAAGAACCAGTTCTCCCTGAGACTGAC CTCTGTGACAGCCGCCGATACCGCCGTGTACTATTGCGC CAGAGTGGCCCCCACAGGCTTCTGGTTTGACTATTGGGG CCAGGGCACCCTGGTGACAGTGAGCTCCGGAGGAGGAG GAAGCGGAGGAGGAGGGTCCGGAGGCGGGGGATCTGA GATCGTGCTGACCCAGTCCCCAGGCACACTGTCCCTGTC TCCCGGCGAGAGAGCCACCCTGAGCTGCAGGGCCTCCC AGAGAGTGAGCTCCAGGTACCTGGCCTGGTATCAGCAG AAGCCTGGCCAGGCCCCCAGACTGCTGATCTACGGAGC ATCTAGCCGCGCCACCGGAATCCCAGACCGGTTCAGCGG ATCCGGATCTGGCACAGACTTCACCCTGACAATCTCTAG ACTGGAGCCTGAGGAGTTCGCCGTGTACTATTGTCAGCA GTATGGCACCAGCCCACTGACATTTGGCGGCGGCACAA AGGTGGAGATCAAGACCACAACTCCTGCACCTAGGCCA CCTACCCCAGCACCTACAATTGCTAGTCAGCCACTGTCA CTGCGACCAGAGGCATGTCGACCTGCAGCTGGAGGAGC AGTGCATACAAGGGGACTGGACTTTGCCTGCGATATCTA CATTTGGGCTCCTCTGGCAGGAACATGTGGCGTGCTGCT GCTGAGCCTGGTCATCACTCTGTACTGCAAGCGAGGCCG GAAGAAACTGCTGTATATTTTCAAACAGCCCTTTATGCG ACCTGTGCAGACCACACAGGAGGAAGATGGGTGCTCCT GTCGGTTCCCCGAGGAAGAGGAAGGAGGCTGTGAGCTG CGGGTCAAGTTTTCCAGATCTGCAGACGCCCCTGCTTAC CAGCAGGGCCAGAACCAGCTGTATAACGAGCTGAATCT GGGGCGGAGAGAGGAATACGACGTGCTGGATAAAAGGC GCGGGAGAGACCCAGAAATGGGGGGAAAGCCACGACG GAAAAACCCCCAGGAGGGACTGTACAATGAACTGCAGA AGGATAAAATGGCAGAGGCCTATTCCGAAATCGGGATG AAGGGAGAAAGAAGGCGAGGCAAAGGACACGACGGAC TGTACCAGGGGCTGTCTACCGCCACAAAGGACACCTATG ATGCTCTGCATATGCAGGCACTGCCACCCAGG |
| 572 | CD8α signal sequence, 7F9 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGGTCCAGCTGGTCC AGTCAGGGGCCGAGGTGAAGAAACCTGGGGCTTCTGTG AAGGTCAGTTGCAAAGCTAGTGGATACTCATTCCCTGAT TACTATATCAACTGGGTGCGCCAGGCACCAGGACAGGG ACTGGAGTGGATGGGATGGATCTACTTCGCTAGCGGCAA CTCCGAATATAATCAGAAGTTTACAGGCAGAGTGACTAT GACCAGGGACACAAGCTCCTCTACTGCCTATATGGAGCT GAGTTCACTGCGGAGTGAAGATACCGCAGTGTACTTCTG CGCCTCTCTGTACGACTATGATTGGTATTTTGACGTCTGG GGACAGGGCACTATGGTGACCGTCAGCTCCGGAGGAGG AGGAAGCGGAGGAGGAGGGTCCGGAGGCGGGGGATCT GATATCGTGATGACACAGACTCCCCTGTCACTGAGCGTC ACTCCAGGAGAGCCAGCATCCATTTCTTGTAAGTCTAGT CAGTCACTGGTGCACAGCAACGGAAATACCTACCTGCAT TGGTATCTGCAGAAGCCTGGCCAGAGCCCACAGCTGCTG ATCTACAAAGTGTCCAATAGGTTCTCTGGCGTCCCAGAC CGCTTTAGTGGGTCAGGAAGCGGCGCCGATTTCACCCTG AAAATTAGCCGCGTGGAGGCTGAAGACGTGGGCGTCTA CTATTGCGCAGAGACAAGCCACGTCCCCTGGACTTTTGG GCAGGGAACCAAGCTGGAAATCAAAACCACAACTCCTG CACCTAGGCCACCTACCCCAGCACCTACAATTGCTAGTC AGCCACTGTCACTGCGACCAGAGGCATGTCGACCTGCAG CTGGAGGAGCAGTGCATACAAGGGGACTGGACTTTGCC TGCGATATCTACATTTGGGCTCCTCTGGCAGGAACATGT GGCGTGCTGCTGCTGAGCCTGGTCATCACTCTGTACTGC AAGCGAGGCCGGAAGAAACTGCTGTATATTTTCAAACA GCCCTTTATGCGACCTGTGCAGACCACACAGGAGGAAG ATGGGTGCTCCTGTCGGTTCCCCGAGGAAGAGGAAGGA GGCTGTGAGCTGCGGGTCAAGTTTTCCAGATCTGCAGAC GCCCCTGCTTACCAGCAGGGCCAGAACCAGCTGTATAAC GAGCTGAATCTGGGGCGGAGAGAGGAATACGACGTGCT GGATAAAAGGCGCGGGAGAGACCCAGAAATGGGGGGA AAGCCACGACGGAAAAACCCCCAGGAGGGACTGTACAA TGAACTGCAGAAGGATAAAATGGCAGAGGCCTATTCCG AAATCGGGATGAAGGGAGAAAGAAGGCGAGGCAAAGG ACACGACGGACTGTACCAGGGGCTGTCTACCGCCACAA AGGACACCTATGATGCTCTGCATATGCAGGCACTGCCAC CCAGG |
| 631 | CD8α signal sequence, 7F9 | atggctctgcccgtcaccgctctgctgctgcctctggctctgctgctgcacgccgcacgacca gaggtgcagctggtggagagcggaggaggcctggtgcagcctggcggcagcctgaggct |

TABLE 10-continued

| | | |
|---|---|---|

Polynucleotide Sequences of exemplary DLL3 targeting CARs

| SEQ ID NO | CAR Structure | Nucleotide Sequence |
|---|---|---|
| | scFv, CD8α hinge and transmembrane regions, 41BB cytoplasmic signaling domain, CD3ζ cytoplasmic signaling domain | gtcctgcgcagcatctggcttcacctttagctcccacgacatgcactgggtgaggcaggcaac aggcaagggcctggagtgggtgtccgccatcggaatcgcaggcgatacctactattccggct ctgtgaagggccggttcacaatcagcagagagaacgccaagaattccctgtacctgcagatg aactctctgagggccggcgacaccgccgtgtactattgtgccagagccaattggggcgagg gcgcctttgatatctggggccagggcaccatggtgacagtgtctagcggcggcggcggctct ggaggaggaggcagcggcggaggaggctccggaggcggcggctctgacatccagatga cacagtctcctagctccctgtccgcctctgtgggcgaccgggtgaccatcacatgcagagcc agccagggcatctccgattacctggcctggtatcagcagaagcccggcaagatccctaagct gctgatctacgcagcatctaccctgcagagcggagtgccatcccggttcagcggatccggat ctggaacagactttaccctgacaatctctagcctgcagccagaggatgtggccacctactattg tcagaagtataactccgtgccactgaccttcggccggaggaacaaaggtggagatcaagacca caactcctgcacctaggccacctaccccagcacctacaattgctagtcagccactgtcactgc gaccagaggcatgtcgacctgcagctggaggagcagtgcatacaaggggactggactagc ctgcgatatctacatagggctcctctggcaggaacatgtggcgtgctgctgctgagcctggtc atcactctgtactgcaagcgaggccggaagaaactgctgtatattacaaacagccctttatgc gacctgtgcagaccacacaggaggaagatgggtgctcctgtcggttccccgaggaagagg aaggaggctgtgagctgcgggtcaagttaccagatctgcagacgcccctgcttaccagcag ggccagaaccagctgtataacgagctgaatctggggcggagagaggaatacgacgtgctg gataaaaggcgcgggagagacccagaaatgggggaaagccacgacggaaaaaccccc aggagggactgtacaatgaactgcagaaggataaaatggcagaggcctattccgaaatcgg gatgaagggagaaagaaggcgaggcaaaggacacgacggactgtaccaggggctgtcta ccgccacaaaggacacctatgatgctctgcatatgcaggcactgccacccagg |
| 573 | CD8α signal sequence, 9D3 scFv, CD8α hinge and transmembrane regions, 41BB cytoplasmic signaling domain, CD3ζ cytoplasmic signaling domain | ATGGCTCTGCCTGTCACCGCTCTGCTGCTGCCTCTGGCTC TGCTGCTGCACGCGGCGCGCCCGCAGGTGCAGCTGCAG GAGTCTGGCCCAGGCCTGGTGAAGCCCTCTGAGACACTG AGCCTGACCTGCACAGTGAGCGACGATTCCATCTCTAAC TACTATTGGTCCTGGATCAGGCAGCCCCCTGGCAAGGGC CTGGAGTGGATCGGCTACATCTTCTATTCCGGCACCACA AACCACAATCCCAGCCTGAAGTCCCGGCTGACAATCTCC CTGGACAAGGCCAAGAACCAGTTCTCTCTGAGACTGAGC TCCGTGACCGCCGCCGATACAGCCGTGTACTATTGTGCC AGAGTGTTCAACTGGGGCTTCGCCTTTGACATCTGGGGC CAGGGCACCATGGTGACAGTGTCTAGCGGCGGCGGCGG CTCTGGAGGAGGAGGCAGCGGCGGAGGAGGCTCCGGAG GCGGCGGCTCTGAGATCGTGCTGACCCAGTCTCCAGGCA CACTGTCTCTGAGCCCCGGCGAGAGGGCCACCCTGAGCT GCCGCGCCTCCCAGCGGATCTCTAGAACATACCTGGCCT GGTATCAGCAGAAGCCTGGCCAGGCCCCCAGACTGCTG ATCTACGGAGCAAGCAGCCGGGCCACCGGAATCCCCGA CAGATTCACCGGCTCCGGCTCTGGCACAGACTTCACCCT GACAATCAGCAGACTGGAGCCTGAGGACTTCGCCGTGT ACTATTGTCAGCAGTATGGCACCTCCCCACTGACATTTG GCGGCGGCACAAAGGTGGAGATCAACACCACAACCCCA GCACCTAGGCCACCTACACCTGCACCAACCATCGCCAGC CAGCCTCTGTCCCTGAGACCAGAGGCCTGTAGGCCAGCA GCAGGAGGAGCAGTGCACACCCGGGGCCTGGACTTCGC CTGCGATATCTACATCTGGGCACCACTGGCAGGAACATG TGGCGTGCTGCTGCTGTCCCTGGTCATCACCCTGTACTGC AAGAGAGGCAGGAAGAAGCTGCTGTATATCTTCAAGCA GCCCTTCATGAGACCCGTGCAGACAACCCAGGAGGAGG ACGGCTGCAGCTGTAGGTTCCCAGAGGAGGAGGAGGGA GGATGTGAGCTGCGCGTGAAGTTTTCCCGGTCTGCCGAT GCACCTGCATACCAGCAGGGACAGAACCAGCTGTATAA CGAGCTGAATCTGGGCCGGAGAGAGGAGTACGACGTGC TGGATAAGAGGAGGGGAAGGGACCCTGAGATGGGAGGC AAGCCTCGGAGAAAGAACCCACAGGAGGGCCTGTACAA TGAGCTGCAGAAGGACAAGATGGCCGAGGCCTATAGCG AGATCGGCATGAAGGGAGAGAGGCGCCGGGGCAAGGG ACACGATGGCCTGTATCAGGGCCTGTCAACCGCTACAAA AGATACCTACGATGCTCTGCACATGCAGGCTCTGCCACC AAGA |
| 574 | CD8α signal sequence, 26C8 scFv, CD8α hinge and transmembrane regions, 41BB cytoplasmic signaling domain, CD3ζ | ATGGCTCTGCCTGTCACCGCTCTGCTGCTGCCTCTGGCTC TGCTGCTGCACGCGGCGCGCCCGCAGGTGCAGCTGCAG GAGAGCGGCCCAGGCCTGGTGAAGCCATCTGAGACACT GAGCCTGACCTGCACAGTGAGCGATAACTCCATCTCTAA TTACTATTGGTCCTGGATCAGGCAGCCCCCTGGCAAGGG CCTGGAGTGGATCGCCTACATCTACTATTCTGGCACCAC AAACTATAATCCCAGCCTGAAGTCCAGAGTGACCATCTC CCTGGACACATCTAAGAACCAGTTCTCCCTGCAGCTGAG CTCCGTGACAGCAGCAGATGCAGCCGTGTACTATTGTGC CAGAGTGTTCCACTGGGGCTTCGCCTTTGACATCTGGGG CCAGGGCACCATGGTGACAGTGTCTAGCGGCGGCGGCG |

TABLE 10-continued

Polynucleotide Sequences of exemplary DLL3 targeting CARs

| SEQ ID NO | CAR Structure | Nucleotide Sequence |
|---|---|---|
| | cytoplasmic signaling domain | GCTCTGGAGGAGGAGGCAGCGGCGGAGGAGGCTCCGGA GGCGGCGGCTCTGAGATCGTGCTGACCCAGAGCCCAGG CACACTGTCTCTGAGCCCCGGCGAGAGGGCCACCCTGTC CTGCCGGGCCTCTCAGAGAGTGAGCAACACATACCTGGC CTGGTATCAGCAGAATCCCGGCCAGGCCCCCAGACTGCT GATCTACGGAGCAAGCTCCAGGGCCACCGGAATCCCAG ACCGCTTCTCCGGATCTGGAAGCGGCACAGACTTCACCC TGACAATCTCCCGGCTGGAGCCTGAGGACTTCGCCGTGT ACTATTGTCAGCAGTATGGCACCTCTCCACTGACATTTG GCGGCGGCACCAAGGTGGAGATCAAGACCACAACCCCA GCACCTAGGCCACCTACACCTGCACCAACCATCGCCAGC CAGCCTCTGTCCCTGAGACCAGAGGCCTGTAGGCCAGCA GCAGGAGGAGCAGTGCACACCCGGGGCCTGGACTTCGC CTGCGATATCTACATCTGGGCACCACTGGCAGGAACATG TGGCGTGCTGCTGCTGTCCCTGGTCATCACCCTGTACTGC AAGAGAGGCAGGAAGAAGCTGCTGTATATCTTCAAGCA GCCCTTCATGAGACCCGTGCAGACAACCCAGGAGGAGG ACGGCTGCAGCTGTAGGTTCCCAGAGGAGGAGGAGGGA GGATGTGAGCTGCGCGTGAAGTTTTCCCGGTCTGCCGAT GCACCTGCATACCAGCAGGGACAGAACCAGCTGTATAA CGAGCTGAATCTGGGCCGGAGAGAGGGAGTACGACGTGC TGGATAAGAGGAGGGGAAGGGACCCTGAGATGGGGAGGC AAGCCTCGGAGAAAGAACCCACAGGAGGGCCTGTACAA TGAGCTGCAGAAGGACAAGATGGCCGAGGCCTATAGCG AGATCGGCATGAAGGGAGAGAGGCGCCGGGGCAAGGG ACACGATGGCCTGTATCAGGGCCTGTCAACCGCTACAAA AGATACCTACGATGCTCTGCACATGCAGGCTCTGCCACC AAGA |
| 575 | CD8α signal sequence, 2A6.C5 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGGTGCAGCTGCAG GAGAGCGGCCCAGGCCTGGTGAAGCCATCCGAGACCCT GTCTCTGACCTGCACAGTGAGCAACGTGTCCATCAGCTC CTACTATTGGTCTTGGATCAGGCAGCCCCCTGGCAAGGG ACTGGAGTGGATCGGCTACATCTACTATAGCGGCACCAC AAACTATAATCCCTCTCTGAAGAGCAGAGTGACCATGAG CGTGGACACATCCAAGAACCAGTTCTCCCTGAAGCTGTC TAGCGTGACCGCCGCCGATACAGCCGTGTACTTTTGTGC CCGGCTGTCTAATTGGGGCTTCGCCTTTGACATCTGGGG CCAGGGCACCATGGTGACATTCTCCTCTGGAGGAGGAG GAAGCGGAGGAGGAGGGTCCGGAGGCGGGGGATCTGA GATCGTGCTGACCCAGTCTCCAGGCACACTGTCTCTGAG CCCCGGCGAGAGGGCCACCCTGTCCTGCAGAGCCTCTCA GACAATCAGCTCCTCTTACCTGGCCTGGTATCAGCAGAA GCCTGGCCAGGCACCTCGGCTGCTGATCTACGGAGCAAG CTCCAGGGCCACCGGAATCCCAGACCGCTTCTCCGGATC TGGAAGCGGCACAGAGTTTACCCTGACAATCAGCCGGCT GGAGCCTGAGGATTTCGCCGTGTACTATTGTCAGCAGTA TGGCTGGTCCCCAATCACCTTTGGCCAGGGCACAAGGCT GGAGATCAAGACCACAACTCCTGCACCTAGGCCACCTAC CCCAGCACCTACAATTGCTAGTCAGCCACTGTCACTGCG ACCAGAGGCATGTCGACCTGCAGCTGGAGGAGCAGTGC ATACAAGGGGACTGGACTTTGCCTGCGATATCTACATTT GGGCTCCTCTGGCAGGAACATGTGGCGTGCTGCTGCTGA GCCTGGTCATCACTCTGTACTGCAAGCGAGGCCGGAAGA AACTGCTGTATATTTTCAAACAGCCCTTTATGCGACCTGT GCAGACCACACAGGAGGAAGATGGGTGCTCCTGTCGGT TCCCCGAGGAAGAGGAAGGAGGCTGTGAGCTGCGGGTC AAGTTTTCCAGATCTGCAGACGCCCCTGCTTACCAGCAG GGCCAGAACCAGCTGTATAACGAGCTGAATCTGGGGCG GAGAGAGGAATACGACGTGCTGGATAAAAGGCGCGGGA GAGACCCAGAAATGGGGGGAAAGCCACGACGGAAAAA CCCCCAGGAGGGACTGTACAATGAACTGCAGAAGGATA AAATGGCAGAGGCCTATTCCGAAATCGGGATGAAGGGA GAAAGAAGGCGAGGCAAAGGACACGACGGACTGTACCA GGGGCTGTCTACCGCCACAAAGGACACCTATGATGCTCT GCATATGCAGGCACTGCCACCCAGG |
| 576 | CD8α signal sequence, 5E12 scFv, CD8α hinge and transmembrane | ATGGCTCTGCCCGTCACCGCTCTGCTGCTGCCTCTGGCTC TGCTGCTGCACGCCGCACGACCACAGAGGTGCAGCTGGTG GAGAGCGGAGGAGGACTGGTGCAGCCTGGCGGATCCCT GAGGCTGTCTTGCGCAGCAAGCGGCTTCACCTTTAGCTC CTACGACATGCACTGGGTGAGGCAGGCAACAGGCAAGG GACTGGAGTGGGTGTCCGCCATCGGACCAGCCGGCGAT |

TABLE 10-continued

Polynucleotide Sequences of exemplary DLL3 targeting CARs

| SEQ ID NO | CAR Structure | Nucleotide Sequence |
|---|---|---|
| | regions, 41BB cytoplasmic signaling domain, CD3ζ cytoplasmic signaling domain | ACCTACTATCCCGGCTCTGTGAAGGGCCGGTTCACAATC TCCAGAGAGAACGCCAAGAATTCTCTGTATCTGCAGATG AACAGCCTGAGGGCAGGCGACACCGCCGTGTACTATTGT GCCAGAGCCGACCCCCCTTACTATTACTATGGCATGGAC GTGTGGGGCCAGGGCACCACAGTGACAGTGTCTAGCGG AGGAGGAGGAAGCGGAGGAGGAGGGTCCGGAGGCGGG GGATCTGACATCGTGATGACCCAGTCCCCTCTGTCTCTG CCCGTGACACCTGGCGAGCCAGCCTCTATCAGCTGCAGG AGCTCCCAGAGCCTGCTGCACTCCAACGAGTACAATTAT CTGGATTGGTACCTGCAGAAGCCTGGCCAGTCCCCTCAG CTGCTGATCTATCTGGGCTCTAACAGGGCAAGCGGAGTG CCAGACAGATTCTCCGGCTCTGGCAGCGGCACCGACTTC ATCCTGAAGATCTCTCGGGTGGAGGCAGAGGACGTGGG CGTGTACTATTGTATGCAGGCCCTGGAGATCCCACTGAC CTTCGGCGGAGGAACAAAGGTGGAGATCAAGACCACAA CTCCTGCACCTAGGCCACCTACCCCAGCACCTACAATTG CTAGTCAGCCACTGTCACTGCGACCAGAGGCATGTCGAC CTGCAGCTGGAGGAGCAGTGCATACAAGGGGACTGGAC TTTGCCTGCGATATCTACATTTGGGCTCCTCTGGCAGGA ACATGTGGCGTGCTGCTGCTGAGCCTGGTCATCACTCTG TACTGCAAGCGAGGCCGGAAGAAACTGCTGTATATTTTC AAACAGCCCTTTATGCGACCTGTGCAGACCACACAGGA GGAAGATGGGTGCTCCTGTCGGTTCCCCGAGGAAGAGG AAGGAGGCTGTGAGCTGCGGGTCAAGTTTTCCAGATCTG CAGACGCCCCTGCTTACCAGCAGGGCCAGAACCAGCTGT ATAACGAGCTGAATCTGGGGCGGAGAGAGGAATACGAC GTGCTGGATAAAAGGCGCGGGAGAGACCCAGAAATGGG GGGAAAGCCACGACGGAAAAACCCCCAGGAGGGACTGT ACAATGAACTGCAGAAGGATAAAATGGCAGAGGCCTAT TCCGAAATCGGGATGAAGGGAGAAAGAAGGCGAGGCA AAGGACACGACGGACTGTACCAGGGGCTGTCTACCGCC ACAAAGGACACCTATGATGCTCTGCATATGCAGGCACTG CCACCCAGG |
| 577 | CD8α signal sequence, 6D8 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGATCACACTGAAG GAGAGCGGCCCAACCCTGGTGAAGCCCACCCAGACACT GACCCTGACATGCACCTTCTCCGGCTTTTCTCTGAGCACC AGAGGCGTGGGAGTGGGATGGATCAGACAGCCCCCTGG CAAGGCCCTGGAGTGGCTGGCCCTGATCTACTGGAACGA CGATAAGAGGTATTCCCCTTCTCTGCAGACACGCCTGAC AATCACCAAGGACACCCCAAAGAACCAGGTGGTGCTGA CAATGACCAATATGGACCCCGTGGATACAGCCACCTACT ATTGTGCCCGGTCTAACTGGGGCAATTGGTACTTCGCAC TGTGGGGAAGGGGCACACTGGTGACCGTGAGCTCCGGA GGAGGAGGAAGCGGAGGAGGAGGGTCCGGAGGCGGGG GATCTGAGATCGTGCTGACCCAGTCTCCAGCCACACTGT CCCTGTCTCCCGGCGAGAGGGCCACCCTGAGCTGCAGAG CCAGCCAGTCCGTGAGCTCCTACCTGGCCTGGTATCAGC AGAAGCCTGGCCAGGCACCTCGGCTGCTGATCTACGACG CCTTCTATAGGGCCACCGGCATCCCAGCACGCTTCTCTG GAAGCGGATCCGGCACAGACTTTACCCTGACAATCCTA GCCTGGAGCCTGAGGATTCGCCGTGTACTATTGTCAGC ACCGGTCCAACTGGCCAATCACCTTTGGCCAGGGCACAA GGCTGGAGATCAAGACCACAACTCCTGCACCTAGGCCA CCTACCCCAGCACCTACAATTGCTAGTCAGCCACTGTCA CTGCGACCAGAGGCATGTCGACCTGCAGCTGGAGGAGC AGTGCATACAAGGGGACTGGACTTTGCCTGCGATATCTA CATTTGGGCTCCTCTGGCAGGAACATGTGGCGTGCTGCT GCTGAGCCTGGTCATCACTCTGTACTGCAAGCGAGGCCG GAAGAAACTGCTGTATATTTTCAAACAGCCCTTTATGCG ACCTGTGCAGACCACACAGGAGGAAGATGGGTGCTCCT GTCGGTTCCCCGAGGAAGAGGAAGGAGGCTGTGAGCTG CGGGTCAAGTTTTCCAGATCTGCAGACGCCCCTGCTTAC CAGCAGGGCCAGAACCAGCTGTATAACGAGCTGAATCT GGGGCGGAGAGAGGAATACGACGTGCTGGATAAAAGGC GCGGGAGAGACCCAGAAATGGGGGGAAAGCCACGACG GAAAAACCCCCAGGAGGGACTGTACAATGAACTGCAGA AGGATAAAATGGCAGAGGCCTATTCCGAAATCGGGATG AAGGGAGAAAGAAGGCGAGGCAAAGGACACGACGGAC TGTACCAGGGGCTGTCTACCGCCACAAAGGACACCTATG ATGCTCTGCATATGCAGGCACTGCCACCCAGG |

TABLE 10-continued

Polynucleotide Sequences of exemplary DLL3 targeting CARs

| SEQ ID NO | CAR Structure | Nucleotide Sequence |
|---|---|---|
| 578 | CD8α signal sequence, 8E11 scFv, CD8α hinge and transmembrane regions, 41BB cytoplasmic signaling domain, CD3ζ cytoplasmic signaling domain | ATGGCTCTGCCTGTCACCGCTCTGCTGCTGCCTCTGGCTC TGCTGCTGCACGCGGCGCGCCCGCAGGTGCAGCTGCAG GAGAGCGGCCCAGGCCTGGTGAAGCCATCTGAGACCCT GAGCCTGACCTGCACAGTGTCCGGCGATTCCATCTCTAA CTACTATTGGACATGGATCAGGCAGCCCCCTGGCAAGGG ACTGGAGTGGATCGGCTACATCTACTATTCTGGCACCAC AAACTCTAATCCCAGCCTGAAGAGCCGGGTGACCGTGTC CCTGGACACAAGCAAGTCCCAGTTCTCTCTGAACCTGAG CTCCGTGACCGCCGCCGATACAGCCGTGTACTATTGTGC CAGAGTGTTCAACAGAGGCTTCGCCTTTGACATCTGGGG CCAGGGCACCATGGTGACAGTGTCTAGCGGCGGCGGCG GCTCTGGAGGAGGAGGCAGCGGCGGAGGAGGCTCCGGA GGCGGCGGCTCTGAGATCGTGCTGACCCAGAGCCCCAGG CACACTGTCTCTGAGCCCCGGCGAGAGGGCCACCCTGTC CTGCCGGGCCTCTCAGAGAATCAGCAACACATACCTGGC CTGGTATCAGCAGAAGCCTGGCCAGGCCCCCAGACTGCT GATCTACGGAGCAAGCTCCAGGGCCACCGGAATCCCAG ACCGCTTCTCCGGATCTGGAAGCGGCACAGACTTCACCC TGACAATCTCCAGGCTGGAGCCTGAGGACTTCGCAGCCT ACTATTGTCAGCAGTATGATACCTCTCCACTGACATTTG GCGGCGGCACCAAGGTGGAGATCAAGACCACAACCCCA GCACCTAGGCCACCTACACCTGCACCAACCATCGCCAGC CAGCCTCTGTCCCTGAGACCAGAGGCCTGTAGGCCAGCA GCAGGAGGAGCAGTGCACACCCGGGGCCTGGACTTCGC CTGCGATATCTACATCTGGGCACCACTGGCAGGAACATG TGGCGTGCTGCTGCTGTCCCTGGTCATCACCCTGTACTGC AAGAGAGGCAGGAAGAAGCTGCTGTATATCTTCAAGCA GCCCTTCATGAGACCCGTGCAGACAACCCAGGAGGAGG ACGGCTGCAGCTGTAGGTTCCCAGAGGAGGAGGAGGGA GGATGTGAGCTGCGCGTGAAGTTTTCCCGGTCTGCCGAT GCACCTGCATACCAGCAGGGACAGAACCAGCTGTATAA CGAGCTGAATCTGGGCCGGAGAGAGGAGTACGACGTGC TGGATAAGAGGAGGGGAAGGGACCCTGAGATGGGAGGC AAGCCTCGGAGAAAGAACCCACAGGAGGGCCTGTACAA TGAGCTGCAGAAGGACAAGATGGCCGAGGCCTATAGCG AGATCGGCATGAAGGGAGAGAGGCGCCGGGGCAAGGG ACACGATGGCCTGTATCAGGGCCTGTCAACCGCTACAAA AGATACCTACGATGCTCTGCACATGCAGGCTCTGCCACC AAGA |
| 579 | CD8α signal sequence, 5C1.A4 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGGTGACACTGAGG GAGTCTGGACCCGCCCTGGTGAAGCCTACCCAGACACTG ACCCTGACATGCACCGTGAGCGGCGTGTCTCTGAGCACC TCCGGCATGTGCGTGAGCTGGATCAGGCAGCCACTGGGC AAGGCCCTGGAGTGGCTGGGCTTCATCGATTGGGACGAT GACAAGTACTATAACACAAGCCTGAAGACACGCCTGAC CATCTCCAAGGACACCTCTAAGAACCAGGTGGTGCTGAC AATGACCAATATGGATCCCGTGGACACAGCCACCTACTA TTGCGCCCGGATCAGAGGCTACTCTGGCAGCTATGATGC CTTTGACATCTGGGGCCAGGGCACCGTGGTCATCGTGAG CTCCGGAGGAGGAGGAAGCGGAGGAGGAGGGTCCGGA GGCGGGGGATCTGACATCGTGATGACCCAGTCCCCTCTG TCTCTGCCCGTGACACCTGGCGAGCCAGCCTCTATCAGC TGCAGGAGCTCCCAGAGCCTGCTGCACTCCAACGGCTAC AATCACCTGGATTGGTATCTGCAGAAGCCTGGCCAGTCC CCTCAGGTGCTGATCTACCTGGGCTCTAACAGGGCAAGC GGAGTGCCAGACAGATTCTCCGGATCTGGAAGCGGAAC CGACTTCACCCTGAAGATCTCTCGGGTGGAGGCAGAGG ACGTGGGCGTGTATTTCTGTATGCAGGCCCTGCAGACCC CCCTGACATTTGGCGGCGGCACCAAGGTGGAGATCAAG ACCACAACTCCTGCACCTAGGCCACCTACCCCAGCACCT ACAATTGCTAGTCAGCCACTGTCACTGCGACCAGAGGCA TGTCGACCTGCAGCTGGAGGAGCAGTGCATACAAGGGG ACTGGACTTTGCCTGCGATATCTACATTTGGGCTCCTCTG GCAGGAACATGTGGCGTGCTGCTGCTGAGCCTGGTCATC ACTCTGTACTGCAAGCGAGGCCGGAAGAAACTGCTGTAT ATTTTCAAACAGCCCTTTATGCGACCTGTGCAGACCACA CAGGAGGAAGATGGGTGCTCCTGTCGGTTCCCCGAGGA AGAGGAAGGAGGCTGTGAGCTGCGGGTCAAGTTTTCCA GATCTGCAGACGCCCCTGCTTACCAGCAGGGCCAGAACC AGCTGTATAACGAGCTGAATCTGGGGCGGAGAGAGGAA TACGACGTGCTGGATAAAAGGCGCGGGGAGAGACCCAGA |

TABLE 10-continued

| | | |
|---|---|---|
| | Polynucleotide Sequences of exemplary DLL3 targeting CARs | |

| SEQ<br>ID<br>NO | CAR<br>Structure | Nucleotide Sequence |
|---|---|---|
| | | AATGGGGGGAAAGCCACGACGGAAAAACCCCCAGGAG<br>GGACTGTACAATGAACTGCAGAAGGATAAAATGGCAGA<br>GGCCTATTCCGAAATCGGGATGAAGGGAGAAAGAAGGC<br>GAGGCAAAGGACACGACGGACTGTACCAGGGGCTGTCT<br>ACCGCCACAAAGGACACCTATGATGCTCTGCATATGCAG<br>GCACTGCCACCCAGG |
| 580 | CD8α signal<br>sequence, 9F7<br>scFv, CD8α<br>hinge and<br>transmembrane<br>regions,<br>41BB<br>cytoplasmic<br>signaling<br>domain, CD3ζ<br>cytoplasmic<br>signaling<br>domain | ATGGCTCTGCCCGTCACCGCTCTGCTGCTGCCTCTGGCTC<br>TGCTGCTGCACGCCGCACGACCACAGGTGCAGCTGCAG<br>GTGTCCGGCCCTGGCCTGGTGAAGCCTTCCGAGACACTG<br>TCTCTGACCTGCAGCGTGTCCGGCGGCTCTATCAGCTCC<br>TACTATTGGTCTTGGATCAGGCAGAGCCCAGGCAAGGG<br>ACTGGATTGGATCGGCTACATGTACTATAGCGGCACCAC<br>AAACTATAATCCCTCTCTGAAGAGCAGAGTGACAATCAG<br>CGTGGACACCTCCAAGAACCAGTTTTCCCTGAAGCTGTC<br>TAGCGTGACCGCCACAGATACCGCCGTGTACTATTGTGC<br>CAGAGTGGGCCTGACAGGCTTCTTTTTCGACTACTGGGG<br>CCAGGGCACACTGGTGACCGTGTCCTCTGGAGGAGGAG<br>GAAGCGGAGGAGGAGGGTCCGGAGGCGGGGGATCTGCC<br>ATCCAGATGACCCAGTCCCCTAGCTCCCTGAGCGCCTCC<br>GTGGGCGACAGGGTGACCATCACATGCAGAGCCTCTCA<br>GGGCATCAGGAACGATCTGGGCTGGTATCAGCAGAAGC<br>CCGGCAAGGCCCCTAAGCTGCTGATCTACGCAGCATCTA<br>GCCTGCAGTCTGGAGTGCCAAGCCGGTTCTCTGGAAGCG<br>GATCCGGCACCGACTTTACCCTGACAGTGTCCTCTCTGC<br>AGCCAGAGGACTTCGCCACATACTATTGTCTGCAGGATT<br>ACAATTATCCCTACACCTTTGGCCAGGGCACAAAGCTGG<br>AGATCAAGACCACAACTCCTGCACCTAGGCCACCTACCC<br>CAGCACCTACAATTGCTAGTCAGCCACTGTCACTGCGAC<br>CAGAGGCATGTCGACCTGCAGCTGGAGGAGCAGTGCAT<br>ACAAGGGGACTGGACTTTGCCTGCGATATCTACATTTGG<br>GCTCCTCTGGCAGGAACATGTGGCGTGCTGCTGCTGAGC<br>CTGGTCATCACTCTGTACTGCAAGCGAGGCCGGAAGAA<br>ACTGCTGTATATTTTCAAACAGCCCTTTATGCGACCTGTG<br>CAGACCACACAGGAGGAAGATGGGTGCTCCTGTCGGTT<br>CCCCGAGGAAGAGGAAGGAGGCTGTGAGCTGCGGGTCA<br>AGTTTTCCAGATCTGCAGACGCCCCTGCTTACCAGCAGG<br>GCCAGAACCAGCTGTATAACGAGCTGAATCTGGGGCGG<br>AGAGAGGAATACGACGTGCTGGATAAAAGGCGCGGGAG<br>AGACCCAGAAATGGGGGGAAAGCCACGACGGAAAAAC<br>CCCCAGGAGGGGACTGTACAATGAACTGCAGAAGGATAA<br>AATGGCAGAGGCCTATTCCGAAATCGGGATGAAGGGAG<br>AAAGAAGGCGAGGCAAAGGACACGACGGACTGTACCAG<br>GGGCTGTCTACCGCCACAAAGGACACCTATGATGCTCTG<br>CATATGCAGGCACTGCCACCCAGG |
| 581 | CD8α signal<br>sequence, 2C3<br>scFv, CD8α<br>hinge and<br>transmembrane<br>regions,<br>41BB<br>cytoplasmic<br>signaling<br>domain, CD3ζ<br>cytoplasmic<br>signaling<br>domain | ATGGCTCTGCCCGTCACCGCTCTGCTGCTGCCTCTGGCTC<br>TGCTGCTGCACGCCGCACGACCACAGGTGCAGCTGCAG<br>AGTGGGGAGGAGGACTGCTGAAGCCCTCCGAGACCCTG<br>TCTCTGACATGCGCCGTGTACGGAGGAAGCTCCTCTGGA<br>AACTATTGGTCCTGGATCCGGCAGCCCCTGGCAAGAGA<br>CTGGAGTGGATCGGCGAGATCAACCACAGCGGCACCAC<br>ATCCTACAATCCTTCTCTGAAGAGCAGGGTGACCATCTC<br>TGTGGACACAAGCAAGAATCAGTTCTCCCTGAAGCTGAG<br>CTCCGTGACCGCAGCAGATACAGCCGTGTACTATTGCGC<br>CAGAGGCGAGCTGGGAATCGCAGACAGCTGGGGACAGG<br>GCACCCTGGTGACAGTGTCTAGCGGAGGAGGAGGAAGC<br>GGAGGAGGAGGGTCCGGAGGCGGGGGATCTGATATCCA<br>GATGACCCAGTCTCCCAGCACACTGTCCGCCTCTGTGGG<br>CGACAGGGTGACCATCACATGTCGCGCCAGCCAGTCCAT<br>CTCTCGGTGGCTGGCCTGGTACCAGCAGAAGCCAGGCA<br>AGGCCCCCAAGCTGCTGATCTATAAGGCCTCCTCTCTGG<br>AGTCCGGCGTGCCTTCTAGATTCAGCGGCTCCGGCTCTG<br>GCACCGAGTTTACCCTGACAATCAGCTCCCTGCAGCCAG<br>ACGATTTCGCCACCTACTATTGTCAGCAGTACAACAGCT<br>ATTCCACCTTTGGCCAGGGCACAAAGGTGGAGATCAAG<br>ACCACAACTCCTGCACCTAGGCCACCTACCCCAGCACCT<br>ACAATTGCTAGTCAGCCACTGTCACTGCGACCAGAGGCA<br>TGTCGACCTGCAGCTGGAGGAGCAGTGCATACAAGGGG<br>ACTGGACTTTGCCTGCGATATCTACATTTGGGCTCCTCTG<br>GCAGGAACATGTGGCGTGCTGCTGCTGAGCCTGGTCATC<br>ACTCTGTACTGCAAGCGAGGCCGGAAGAAACTGCTGTAT<br>ATTTTCAAACAGCCCTTTATGCGACCTGTGCAGACCACA<br>CAGGAGGAAGATGGGTGCTCCTGTCGGTTCCCCGAGGA |

TABLE 10-continued

Polynucleotide Sequences of exemplary DLL3 targeting CARs

| SEQ ID NO | CAR Structure | Nucleotide Sequence |
|---|---|---|
| | | AGAGGAAGGAGGCTGTGAGCTGCGGGTCAAGTTTTCCA GATCTGCAGACGCCCCTGCTTACCAGCAGGGCCAGAACC AGCTGTATAACGAGCTGAATCTGGGGCGGAGAGAGGAA TACGACGTGCTGGATAAAAGGCGCGGGAGAGACCCAGA AATGGGGGGAAAGCCACGACGGAAAAACCCCCAGGAG GGACTGTACAATGAACTGCAGAAGGATAAAATGGCAGA GGCCTATTCCGAAATCGGGATGAAGGGAGAAAGAAGGC GAGGCAAAGGACACGACGGACTGTACCAGGGGCTGTCT ACCGCCACAAAGGACACCTATGATGCTCTGCATATGCAG GCACTGCCACCCAGG |
| 582 | CD8α signal sequence, 2G1 scFv, CD8α hinge and transmembrane regions, 41BB cytoplasmic signaling domain, CD3ζ cytoplasmic signaling domain | ATGGCTCTGCCTGTCACCGCTCTGCTGCTGCCTCTGGCTC TGCTGCTGCACGCGGCGCGCCCGCAGCTGCAGCTGCAGG AGTCCGGCCCTGGCCTGGTGAAGCCATCCGAGACCCTGT CTCTGACCTGCACAGTGAGCGGCGGCTCCATCAGCTCCT CTAGCTACTATTGGGGCTGGATCAGACAGCCCCCTGGCA AGGGACTGGAGTGGATCGGCAGCATCTACTATTCCGGCA ACATCTACCACAATCCTTCTCTGAAGAGCCGCGTGTCTA TCAGCGTGGACACCTCCAAGAACCAGTTCTCTCTGAGGC TGTCCTCTGTGACCGCAGCAGATACAGCCGTGTACTATT GCGCCAGGGAGATCATCGTGGGAGCAACCCACTTTGACT ATTGGGGCCAGGGCACCCTGGTGACAGTGAGCTCCGGC GGCGGCGGCTCTGGAGGAGGAGGCAGCGGCGGAGGAG GCTCCGGAGGCGGCGGCTCTGCCATCCAGATGACACAGT CCCCATCTAGCCTGTCCGCCTCTGTGGGCGACAGGGTGA CCATCACATGTAGAGCCAGCCAGGGCATCAGGAACGAT CTGGGCTGGTACCAGCAGAAGCCAGGCAAGGCCCCCGA GCTGCTGATCTATGCCGCCTCCTCTCTGCAGTCTGGCGTG CCAAGCAGATTCAGCGGCTCCGGCTCTGGCACCGACTTT ACCCTGACAATCAGCTCCCTGCAGCCCGAGGACTTCGCC ACATACTATTGTCTGCAGGATTACAATTATCCCCTGACC TTTGGCCCTGGCACAAAGGTGGATATCAAGACCACAACC CCAGCACCTAGGCCACCTACACCTGCACCAACCATCGCC AGCCAGCCTCTGTCCCTGAGACCAGAGGCCTGTAGGCCA GCAGCAGGAGGAGCAGTGCACACCCGGGGCCTGGACTT CGCCTGCGATATCTACATCTGGGCACCACTGGCAGGAAC ATGTGGCGTGCTGCTGCTGTCCCTGGTCATCACCCTGTA CTGCAAGAGAGGCAGGAAGAAGCTGCTGTATATCTTCA AGCAGCCCTTCATGAGACCCGTGCAGACAACCCAGGAG GAGGACGGCTGCAGCTGTAGGTTCCCAGAGGAGGAGGA GGGAGGATGTGAGCTGCGCGTGAAGTTTTCCCGGTCTGC CGATGCACCTGCATACCAGCAGGGACAGAACCAGCTGT ATAACGAGCTGAATCTGGGCCGGAGAGAGGAGTACGAC GTGCTGGATAAGAGGAGGGGAAGGGACCCTGAGATGGG AGGCAAGCCTCGGAGAAAGAACCCCACAGGAGGGCCTGT ACAATGAGCTGCAGAAGGACAAGATGGCCGAGGCCTAT AGCGAGATCGGCATGAAGGGAGAGAGGCGCCGGGGCA AGGGACACGATGGCCTGTATCAGGGCCTGTCAACCGCTA CAAAGATACCTACGATGCTCTGCACATGCAGGCTCTGC CACCAAGA |
| 583 | CD8α signal sequence, 3E4 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGGTGCAGCTGCAGC AGTGGGGAGCAGGACTGCTGAAGCCCTCCGAGACCCTG TCTCTGACATGCGCCGTGTACGGAGGAAGCTTCTCCGGA TACTATTGGTCCTGGATCAGGCAGCCCCCTGGCAAGGGA CTGGAGTGGATCGGCGAGATCATCCACTCTGGCAGCTCC AACTATAATCCTTCTCTGAAGAGCCGGGTGTCTATCAGC GTGGACACCTCTAAGAACCAGTTCAGCCTGAAGCTGTCT AGCGTGACCGCCGCCGATACAGCCGTGTACTATTGCTCC AGAGGCGAGTACGGCTCCGGCTCTAGGTTTGACTATTGG GGCCAGGGCACCCTGGTGACAGTGTCCTCTGGAGGAGG AGGAAGCGGAGGAGGAGGGTCCGGAGGCGGGGGATCT GCCATCCAGATGACCCAGTCCCCAAGCTCCCTGAGCGCC TCCGTGGGCGATAGGGTGGCCATCACATGTAGGGCCAAG CCAGGGAATCAGGGACGATCTGGGCTGGTACCAGCAGA AGCCAGGCAAGGCCCCCAAGCTGCTGATCTATGCAGCAT CTAGCCTGCAGAGCGGAGTGCCATCCCGGTTCTCTGGAA GCAGATCCGACACCGACTTCACCCTGACAATCTCCTCTC TGCAGCCTGAGGACTTCGCCACATACTATTGTCTGCAGG ACTACGATTATCCACTGACCTTTGGCGGCGGCACAAAGG TGGAGATCAAGACCACAACTCCTGCACCTAGGCCACCTA CCCCAGCACCTACAATTGCTAGTCAGCCACTGTCACTGC GACCAGAGGCATGTCGACCTGCAGCTGGAGGAGCAGTG |

TABLE 10-continued

Polynucleotide Sequences of exemplary DLL3 targeting CARs

| SEQ ID NO | CAR Structure | Nucleotide Sequence |
|---|---|---|
| | | CATACAAGGGGACTGGACTTTGCCTGCGATATCTACATT TGGGCTCCTCTGGCAGGAACATGTGGCGTGCTGCTGCTG AGCCTGGTCATCACTCTGTACTGCAAGCGAGGCCGGAAG AAACTGCTGTATATTTTCAAACAGCCCTTTATGCGACCT GTGCAGACCACACAGGAGGAAGATGGGTGCTCCTGTCG GTTCCCCGAGGAAGAGGAAGGAGGCTGTGAGCTGCGGG TCAAGTTTTCCAGATCTGCAGACGCCCCTGCTTACCAGC AGGGCCAGAACCAGCTGTATAACGAGCTGAATCTGGGG CGGAGAGAGGAATACGACGTGCTGGATAAAAGGCGCGG GAGAGACCCAGAAATGGGGGGAAAGCCACGACGGAAA AACCCCCAGGAGGGACTGTACAATGAACTGCAGAAGGA TAAAATGGCAGAGGCCTATTCCGAAATCGGGATGAAGG GAGAAGAAGGCGAGGCAAAGGACACGACGGACTGTA CCAGGGGCTGTCTACCGCCACAAAGGACACCTATGATGC TCTGCATATGCAGGCACTGCCACCCAGG |
| 584 | CD8α signal sequence, 3F2 scFv, CD8α hinge and transmembrane regions, 41BB cytoplasmic signaling domain, CD3ζ cytoplasmic signaling domain | ATGGCTCTGCCTGTCACCGCTCTGCTGCTGCCTCTGGCTC TGCTGCTGCACGCGGCGCGCCCGCAGGTGCAGCTGCAG GAGTCCGGCCCTGGCCTGGTGAAGCCAAGCGGCCACCCT GTCCCTGACATGCGCCGTGTCTGGCGGCAGCATCAGCTC CAACAATTGGTGGAGCTGGGTGAGGCAGCCCCCTGGCA AGGGACTGGAGTGGATCGGCGACATCCACCACTCCGGC TCTACCAACTACAAGCCATCCCTGAAGTCTCGCGTGACA ATCTCTGTGGACAAGAGCAAGAACCAGTTCTCCCTGAAT CTGATCAGCGTGACCGCCGCCGATACAGCCGTGTACTAT TGCGCCAGAGAGGCCGGCGGCTACTTTGACTATTGGGGC CAGGGCATCCTGGTGACCGTGTCTAGCGGCGGCGGCGG CTCTGGAGGAGGAGGCAGCGGCGGAGGAGGCTCCGGAG GCGGCGGCTCTGATATCCAGATGACCCAGAGCCCATCCA CACTGTCTGCCAGCGTGGGCGACAGGGTGACCATCACAT GTAGAGCCTCCCAGTCTATCTCCTCTTGGCTGGCCTGGT ATCAGCAGAAGCCAGGCAAGGCCCCCAAGCTGCTGATC AGCAAGGCAAGCTCCCTGGAGTCCGGAGTGCCATCTAG GTTCAGCGGATCCGGCTCTGGCCCTGAGTTTACCCTGAC AATCTCTAGCCTGCAGCCTGCCGATTTCGCCACCTACTA TTGTCAGCAGTACAATAGCTATTCCACCTTTGGCCAGGG CACAAAGCTGGAGATCAAGACCACAACCCCAGCACCTA GGCCACCTACACCTGCACCAACCATCGCCAGCCAGCCTC TGTCCCTGAGACCAGAGGCCTGTAGGCCAGCAGCAGGA GGAGCAGTGCACACCCGGGGCCTGGACTTCGCCTGCGAT ATCTACATCTGGGCACCACTGGCAGGAACATGTGGCGTG CTGCTGCTGTCCCTGGTCATCACCCTGTACTGCAAGAGA GGCAGGAAGAAGCTGCTGTATATCTTCAAGCAGCCCTTC ATGAGACCCGTGCAGACAACCCAGGAGGAGGACGGCTG CAGCTGTAGGTTCCCAGAGGAGGAGGAGGGAGGATGTG AGCTGCGCGTGAAGTTTTCCCGGTCTGCCGATGCACCTG CATACCAGCAGGGACAGAACCAGCTGTATAACGAGCTG AATCTGGGCCGGAGAGAGGAGTACGACGTGCTGGATAA GAGGAGGGGAAGGGACCCTGAGATGGGAGGCAAGCCTC GGAGAAAGAACCCACAGGAGGGCCTGTACAATGAGCTG CAGAAGGACAAGATGGCCGAGGCCTATAGCGAGATCGG CATGAAGGGAGAGAGGCGCCGGGGCAAGGGACACGAT GGCCTGTATCAGGGCCTGTCAACCGCTACAAAAGATACC TACGATGCTCTGCACATGCAGGCTCTGCCACCAAGA |
| 585 | CD8α signal sequence, 4F9 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGGTGCAGCTGCAGC AGTGGGGAGCAGGACTGCTGAAGCCCTCCGAGACCCTG TCTCTGACATGCGCCGTGTACGGCGGCTCCTTCTCTGGCT ACTATTGGACCTGGATCAGACAGCCCCCTGGCAAGGGA CTGGAGTGGATCGGCGAGATCACCCACAGCGGCTCCAC AAACTATAATCCTTCTCTGAAGAGCAGGGTGTGTCTATCAG CGTGGACACCTCTAAGAACCAGTTCAGCCTGAAGCTGAG CTCCGTGACCGCAGCAGATACAGCCGTGTACTATTGCGC CAGAGGCGAGTACGGATCCGGATCTCGGTTTGACTATTG GGGCCAGGGCACCCTGGTGACAGTGTCTAGCGGAGGAG GAGGAAGCGGAGGAGGAGGGTCCGGAGGCGGGGGATC TGCCATCCAGATGACCCAGTCCCCATCCTCTCTGAGCGC CTCCGTGGGCGATAGGGTGGCAATCACATGTAGAGCCA GCCAGGGCATCAGGGACGATCTGGGCTGGTACCAGCAG AAGCCAGGCAAGGCCCCCAAGCTGCTGATCTATGCAGC AAGCTCCCTGCAGAGCGGAGTGCCATCCAGATTCTCTGG CAGCGGCTCCGACACCGACTTCACCCTGACAATCTCTAG CCTGCAGCCTGAGGACTTCGCCACATACTATTGTCTGCA |

TABLE 10-continued

| SEQ ID NO | CAR Structure | Nucleotide Sequence |
|---|---|---|
| | | GGACTACGATTATCCACTGACCTTTGGCGGCGGCACAAA<br>GGTGGAGATCAAGACCACAACTCCTGCACCTAGGCCAC<br>CTACCCCAGCACCTACAATTGCTAGTCAGCCACTGTCAC<br>TGCGACCAGAGGCATGTCGACCTGCAGCTGGAGGAGCA<br>GTGCATACAAGGGGACTGGACTTTGCCTGCGATATCTAC<br>ATTTGGGCTCCTCTGGCAGGAACATGTGGCGTGCTGCTG<br>CTGAGCCTGGTCATCACTCTGTACTGCAAGCGAGGCCGG<br>AAGAAACTGCTGTATATTTTCAAACAGCCCTTTATGCGA<br>CCTGTGCAGACCACACAGGAGGAAGATGGGTGCTCCTG<br>TCGGTTCCCCGAGGAAGAGGAAGGAGGCTGTGAGCTGC<br>GGGTCAAGTTTTCCAGATCTGCAGACGCCCCTGCTTACC<br>AGCAGGGCCAGAACCAGCTGTATAACGAGCTGAATCTG<br>GGGCGGAGAGAGGAATACGACGTGCTGGATAAAAGGCG<br>CGGGAGAGACCCAGAAATGGGGGGAAAGCCACGACGG<br>AAAAACCCCCAGGAGGGACTGTACAATGAACTGCAGAA<br>GGATAAAAATGGCAGAGGCCTATTCCGAAATCGGGATGA<br>AGGGAGAAAGAAGGCGAGGCAAAGGACACGACGGACT<br>GTACCAGGGGCTGTCTACCGCCACAAAGGACACCTATG<br>ATGCTCTGCATATGCAGGCACTGCCACCCAGG |
| 586 | CD8α signal sequence, 4G9 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC<br>TGCTGCTGCACGCCGCACGACCACAGGTGCAGCTGCAGC<br>AGTGGGGAGCAGGACTGCTGAAGCCCTCCGAGACCCTG<br>TCTCTGACATGCGCCGTGTACGGCGGCTCCTTCTCTGGCT<br>ACTATTGGTCCTGGATCAGACAGCCCCCTGGCAAGGGAC<br>TGGAGTGGATCGGCGAGATCACCCACAGCGGCTCCACA<br>AACTATAATCCTTCTCTGAAGAGCAGGGTGTCTATCAGC<br>GTGGACACCTCTAAGAACCAGTTCAGCCTGAAGCTGAGC<br>TCCGTGACCGCCAGCAGATACAGCCGTGTACTATTGCGCC<br>AGAGGCGAGTACGGATCCGGATCTCGGTTTGACTATTGG<br>GGCCAGGGCACCCTGGTGACAGTGTCTAGCGGAGGAGG<br>AGGAAGCGGAGGAGGAGGGTCCGGAGGCGGGGGATCT<br>GCCATCCAGATGACCCAGTCCCCATCCTCTCTGAGCGCC<br>TCCGTGGGCGATAGGGTGGCCCTGACATGTAGAGCCAG<br>CCAGGGCATCAGGGACGATCTGGGCTGGTACCAGCAGA<br>AGCCAGGCAAGGCCCCCAAGCTGCTGATCTATGCAGCA<br>AGCTCCCTGCAGAGCGGAGTGCCATCCAGATTCTCTGGC<br>AGCGGCTCCGACACCGACTTCACCCTGACAATCTCTAGC<br>CTGCAGCCTGAGGACTTCGCCACATACTATTGTCTGCAG<br>GACTACGATTATCCACTGACCTTTGGCGGCGGCACAAAG<br>GTGGAGATCAAGACCACAACTCCTGCACCTAGGCCACCT<br>ACCCCAGCACCTACAATTGCTAGTCAGCCACTGTCACTG<br>CGACCAGAGGCATGTCGACCTGCAGCTGGAGGAGCAGT<br>GCATACAAGGGGACTGGACTTTGCCTGCGATATCTACAT<br>TTGGGCTCCTCTGGCAGGAACATGTGGCGTGCTGCTGCT<br>GAGCCTGGTCATCACTCTGTACTGCAAGCGAGGCCGGAA<br>GAAACTGCTGTATATTTTCAAACAGCCCTTTATGCGACC<br>TGTGCAGACCACACAGGAGGAAGATGGGTGCTCCTGTC<br>GGTTCCCCGAGGAAGAGGAAGGAGGCTGTGAGCTGCGG<br>GTCAAGTTTTCCAGATCTGCAGACGCCCCTGCTTACCAG<br>CAGGGCCAGAACCAGCTGTATAACGAGCTGAATCTGGG<br>GCGGAGAGAGGAATACGACGTGCTGGATAAAAGGCGCG<br>GGAGAGACCCAGAAATGGGGGGAAAGCCACGACGGAA<br>AAACCCCCAGGAGGGACTGTACAATGAACTGCAGAAGG<br>ATAAAAATGGCAGAGGCCTATTCCGAAATCGGGATGAAG<br>GGAGAAAGAAGGCGAGGCAAAGGACACGACGGACTGT<br>ACCAGGGGCTGTCTACCGCCACAAAGGACACCTATGAT<br>GCTCTGCATATGCAGGCACTGCCACCCAGG |
| 587 | CD8α signal sequence, 11H7 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC<br>TGCTGCTGCACGCCGCACGACCACAGGTGCAGCTGCAGC<br>AGTGGGGAGCAGGACTGCTGAAGCCTTCTGAGACCCTG<br>AGCCTGACATGCGCCGTGTACGGCGGCAGCTTTTCCGCC<br>TACTATTGGAACTGGATCAGGCAGCCCCCTGGCAAGGG<br>ACTGGAGTGGATCGGCGAGATCAATCACTCTGGCAGCA<br>CCAACTATAATCCCAGCCTGAAGTCCCGCGTGACCATCT<br>CCGTGGACACATCTAAGAACCAGTTTTCTCTGAATCTGA<br>CCAGCCTGACAGCCGCCGATACAGCCGTGTACTATTGCG<br>CCAGAGGCCTGGACAGCTCCGGATGGTACCCATTCGATT<br>ATTGGGGCCAGGGCACCCTGGTGACAGTGTCTAGCGGA<br>GGAGGAGGAAGCGGAGGAGGAGGGTCCGGAGGCGGGG<br>GATCTGACATCCAGATGACCCAGTCCCCATCCAGCGTGA<br>GCGCCTCTGTGGGCGATAGGGTGACCATCACATGTAGAG<br>CAAGCCAGGGAATCAGCTCCTGGCTGGCATGGTACCAG |

TABLE 10-continued

| | | |
|---|---|---|
| | Polynucleotide Sequences of exemplary DLL3 targeting CARs | |

| SEQ ID NO | CAR Structure | Nucleotide Sequence |
|---|---|---|
| | | CAGAAGCCAGGCAAGGCCCCCAAGCTGCTGATCTATGC |
| | | AGCATCTAGCCTGCAGAGCGGAGTGCCATCCAGGTTTAG |
| | | CGGATCCGGATCTGGAACCGACTTCACCCTGACAATCTC |
| | | CTCTCTGCAGCCTGAGGACTTCGCCACATACTATTGTCA |
| | | GCAGGCCGATTCCTTCCCTTTTACCTTCGGCCCAGGCAC |
| | | AAAGGTGGATATCAAGACCACAACTCCTGCACCTAGGC |
| | | CACCTACCCCAGCACCTACAATTGCTAGTCAGCCACTGT |
| | | CACTGCGACCAGAGGCATGTCGACCTGCAGCTGGAGGA |
| | | GCAGTGCATACAAGGGGACTGGACTTTGCCTGCGATATC |
| | | TACATTTGGGCTCCTCTGGCAGGAACATGTGGCGTGCTG |
| | | CTGCTGAGCCTGGTCATCACTCTGTACTGCAAGCGAGGC |
| | | CGGAAGAAACTGCTGTATATTTTCAAACAGCCCTTTATG |
| | | CGACCTGTGCAGACCACACAGGAGGAAGATGGGTGCTC |
| | | CTGTCGGTTCCCCGAGGAAGAGGAAGGAGGCTGTGAGC |
| | | TGCGGGTCAAGTTTTCCAGATCTGCAGACGCCCCTGCTT |
| | | ACCAGCAGGGCCAGAACCAGCTGTATAACGAGCTGAAT |
| | | CTGGGGCGGAGAGAGGAATACGACGTGCTGGATAAAAG |
| | | GCGCGGGAGAGACCCAGAAATGGGGGGAAAGCCACGA |
| | | CGGAAAAACCCCCAGGAGGGACTGTACAATGAACTGCA |
| | | GAAGGATAAAATGGCAGAGGCCTATTCCGAAATCGGGA |
| | | TGAAGGGAGAAGAAGGCGAGGCAAAGGACACGACGG |
| | | ACTGTACCAGGGGCTGTCTACCGCCACAAAGGACACCTA |
| | | TGATGCTCTGCATATGCAGGCACTGCCACCCAGG |
| 588 | CD8α signal sequence, 16H7 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGGTGCAGCTGCAGC AGTGGGGAGCAGGACTGCTGAAGCCAAGCGAGACCCTG TCCCTGACATGCGCCGTGTTCGGCGGCTCTTTTAGCGGC GACTACTGGAGCTGGATCAGGCAGCCCCCTGGCAAGGG ACTGGAGTGGATCGGCGAGATCAACCACTCTGGCATCAC CAGCTTCAATCCCTCCCTGAAGTCTCGCGTGACCATCTC CGTGGACACATCTAAGAACCAGTTTTCCCTGAAGCTGAG CTCCGTGACCGCAGCAGATACAGCCGTGTACTATTGCGC CAGAGGCGAGCTGGGCATCCCTGACAATTGGGGCCAGG GCACCCTGGTGACAGTGTCTAGCGGAGGAGGAGGAAGC GGAGGAGGAGGGTCCGGAGGCGGGGGATCTGATATCCA GATGACCCAGTCCCCATCTACACTGAGCGCCTCCGTGGG CGATAGGGTGACCATCACATGTAGAGCCTCTCAGAGCAT CTCCCGGTGGCTGGCCTGGTACCAGCAGAAGCCAGGCA AGGCCCCCAAGCTGCTGATCTATAAGGCATCCTCTCTGG AGAGCGGAGTGCCATCCAGGTTCTCTGGAAGCGGATCC GGAACCGAGTTTACCCTGACAATCAGCTCCCTGCAGCCT GACGATTTCGCCACATACTATTGTCAGCAGTACAACTCT TATAGCACCTTTGGCCAGGGCACAAAGGTGGAGATCAA GACCACAACTCCTGCACCTAGGCCACCTACCCCAGCACC TACAATTGCTAGTCAGCCACTGTCACTGCGACCAGAGGC ATGTCGACCTGCAGCTGGAGGAGCAGTGCATACAAGGG GACTGGACTTTGCCTGCGATATCTACATTTGGGCTCCTCT GGCAGGAACATGTGGCGTGCTGCTGCTGAGCCTGGTCAT CACTCTGTACTGCAAGCGAGGCCGGAAGAAACTGCTGT ATATTTTCAAACAGCCCTTTATGCGACCTGTGCAGACCA CACAGGAGGAAGATGGGTGCTCCTGTCGGTTCCCCGAG GAAGAGGAAGGAGGCTGTGAGCTGCGGGTCAAGTTTTC CAGATCTGCAGACGCCCCTGCTTACCAGCAGGGCCAGA ACCAGCTGTATAACGAGCTGAATCTGGGGCGGAGAGAG GAATACGACGTGCTGGATAAAAGGCGCGGGAGAGACCC AGAAATGGGGGGAAAGCCACGACGGAAAAACCCCCAG GAGGGACTGTACAATGAACTGCAGAAGGATAAAATGGC AGAGGCCTATTCCGAAATCGGGATGAAGGGAGAAGAA GGCGAGGCAAAGGACACGACGGACTGTACCAGGGGCTG TCTACCGCCACAAAGGACACCTATGATGCTCTGCATATG CAGGCACTGCCACCCAGG |
| 589 | CD8α signal sequence, 17A2 scFv, CD8α hinge and transmembrane regions, 41BB cytoplasmic signaling domain, CD3ζ | ATGGCTCTGCCTGTCACCGCTCTGCTGCTGCCTCTGGCTC TGCTGCTGCACGCGGCGCGCCCGCAGGTGCAGCTGCAG GAGTCCGGCCCTGGCCTGGTGAAGCCATCCGGCACCCTG TCTCTGACATGCGCTGGTGTTCGGCGACAGCATCAGCTCC TCTAACTGGTGGTCCTGGGTGAGGCAGCCCCCTGGCAAG GGACTGGAGTGGATCGGCGAGGTGTTCCACTCCGGCTCT ACCAACTACAATCCAAGCCTGAAGTCCCGCGTGACAATC AGCGTGGATAAGTCCAAGAATCAGTTTAGCCTGAAGCTG AGCTCCGTGACCGCAGCAGACACAGCCGTGTACTATTGC GCCAGAGCCGCAGTGGCAGGCGCCCTGGATTATTGGGG ACAGGGCACCCTGGTGACAGTGTCTAGCGGCGGCGGCG |

TABLE 10-continued

| SEQ ID NO | CAR Structure | Nucleotide Sequence |
|---|---|---|
| | cytoplasmic signaling domain | GCTCTGGAGGAGGAGGCAGCGGCGGAGGAGGCTCCGGA GGCGGCGGCTCTGACATCGTGATGACCCAGTCTCCCGAT AGCCTGGCCGTGTCTCTGGGCGAGAGGGCAACAATCAA CTGTAAGTCCTCTCAGAGCGTGCTGTACAGCTCCAACAA TAAGAACTACCTGGCCTGGTATCAGCAGAAGCCTGGCCA GCCACCCAATCTGCTGGTGTATTGGGCCTCTACCAGAGA GAGCGGAGTGCCTGACAGATTCTCCGGAGCAGGATCTG GAACAGACTTCACCCTGACAATCTCTAGCCTGCAGGCCG AGGACGTGGCCGTGTACTATTGTCAGCAGTACTATGGCA CCTCCTGGACATTTGGCCAGGGCACCAAGGTGGAGATCA AGACCACAACCCCAGCACCTAGGCCACCTACACCTGCAC CAACCATCGCCAGCCAGCCTCTGTCCCTGAGACCAGAGG CCTGTAGGCCAGCAGCAGGAGGAGCAGTGCACACCCGG GGCCTGGACTTCGCCTGCGATATCTACATCTGGGCACCA CTGGCAGGAACATGTGGCGTGCTGCTGCTGTCCCTGGTC ATCACCCTGTACTGCAAGAGAGGCAGGAAGAAGCTGCT GTATATCTTCAAGCAGCCCTTCATGAGACCCGTGCAGAC AACCCAGGAGGAGGACGGCTGCAGCTGTAGGTTCCCAG AGGAGGAGGAGGGAGGATGTGAGCTGCGCGTGAAGTTT TCCCGGTCTGCCGATGCACCTGCATACCAGCAGGGACAG AACCAGCTGTATAACGAGCTGAATCTGGGCCGGAGAGA GGAGTACGACGTGCTGGATAAGAGGAGGGGAAGGGACC CTGAGATGGGAGGCAAGCCTCGGAGAAAGAACCCACAG GAGGGCCTGTACAATGAGCTGCAGAAGGACAAGATGGC CGAGGCCTATAGCGAGATCGGCATGAAGGGAGAGAGGC GCCGGGGCAAGGGACACGATGGCCTGTATCAGGGCCTG TCAACCGCTACAAAAGATACCTACGATGCTCTGCACATG CAGGCTCTGCCACCAAGA |
| 590 | CD8α signal sequence, 6H1 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGATCACACTGAGG GAGAGCGGCCCTACCCTGGTGAAGCCAACCCAGACACT GACCCTGACATGCACCTTTTCCGGCTTCTCCCTGTCTACC AGCGGCCTGGGCGTGGGATGGGATCAGGCAGCCCCCTGG CGAGGCCCTGGAGTGGCTGGCCCTGATCTACTGGAACGA CGATAAGCGGTATTCCCCCTCTCTGAAGTCTAGACTGAG CATCACAAAGGACACCTCCAAGAACCAGGTGGTGCTGA TCATGACAAATATGGACCCAGTGGATACAGCCACCTACT ATTGCGTGCACAGGAGAATCGCAGCCCCTGGCAGCGTGT ACTGGGGACAGGGCACACTGGTGACCGTGAGCTCCGGA GGAGGAGGAAGCGGAGGAGGAGGGTCCGGAGGCGGGG GATCTGACATCCAGATGACCCAGTCTCCTTCTAGCGTGA GCGCCTCCGTGGGCGATAGGGTGACAATCACCTGTCGCG CCAGCCAGGGCATCTCCTCTTGGCTGGCCTGGTATCAGC AGAAGCCAGGCAAGGCACCAAAGCTGCTGATCAGCGCC GCAAGCTCCCTGCAGTCCGGAGTGCCATCTCGGTTTTCT GGCAGCGGCTCCGGCACAGACTTCACACTGACCATCTCT AGCCTGCAGCCCGAGGATTTTGCCACCTACTATTGTCAC CAGGCCAATTCCTTCCCTTTTACATTCGGCCAGGGCACC AAGCTGGAGATCAAGACCACAACTCCTGCACCTAGGCC ACCTACCCCAGCACCTACAATTGCTAGTCAGCCACTGTC ACTGCGACCAGAGGCATGTCGACCTGCAGCTGGAGGAG CAGTGCATACAAGGGGACTGGACTTTGCCTGCGATATCT ACATTTGGGCTCCTCTGGCAGGAACATGTGGCGTGCTGC TGCTGAGCCTGGTCATCACTCTGTACTGCAAGCGAGGCC GGAAGAAACTGCTGTATATTTTCAAACAGCCCTTTATGC GACCTGTGCAGACCACACAGGAGGAAGATGGGTGCTCC TGTCGGTTCCCCGAGGAAGAGGAAGGAGGCTGTGAGCT GCGGGTCAAGTTTTCCAGATCTGCAGACGCCCCTGCTTA CCAGCAGGGCCAGAACCAGCTGTATAACGAGCTGAATC TGGGGCGGAGAGAGGAATACGACGTGCTGGATAAAAGG CGCGGGAGAGACCCAGAAATGGGGGGGAAAGCCACGAC GGAAAAACCCCCAGGAGGGACTGTACAATGAACTGCAG AAGGATAAAATGGCAGAGGCCTATTCCGAAATCGGGAT GAAGGGAGAAAGAAGGCGAGGCAAAGGACACGACGGA CTGTACCAGGGGCTGTCTACCGCCACAAAGGACACCTAT GATGCTCTGCATATGCAGGCACTGCCACCCAGG |
| 591 | CD8α signal sequence, 6H5 scFv, CD8α hinge and transmembrane regions, | ATGGCTCTGCCCGTCACCGCTCTGCTGCTGCCTCTGGCTC TGCTGCTGCACGCCGCACGACCACAGGTGCAGCTGGTGC AGTCCGGAGCAGAGGTGAAGAAGCCTGGCGCCTCCGTG AAGGTGTCTTGCAAGGTGAGCGGCTACACCCTGACAGA GCTGTCTATGCACTGGGTGCGCCAGGCCCCCGGCAAGGG ACCTGAGGGAATGGGAGGATTCGACCCTGAGGATGGCA |

TABLE 10-continued

| Polynucleotide Sequences of exemplary DLL3 targeting CARs | | |
|---|---|---|

| SEQ ID NO | CAR Structure | Nucleotide Sequence |
|---|---|---|
| | 41BB cytoplasmic signaling domain, CD3ζ cytoplasmic signaling domain | AGACAATCTACGCCCAGAAGTTTCAGGGCCGGGTGACC ATGACAGAGGACACCAGCGCCGATACAGCCTATATGGA GCTGAACTCTCTGCGCAGCGAGGACACCGCCGTGTACTA TTGCGCCACACTGCTGAGGGGACTGGACGCCTTCGACGT GTGGGGACAGGGAACCATGGTGACAGTGAGCTCCGGAG GAGGAGGAAGCGGAGGAGGAGGGTCCGGAGGCGGGGG ATCTGATATCCAGATGACCCAGTCTCCATCTAGCCTGAG CGCCTCCGTGGGCGACAGGGTGACCATCACATGTAGAG CCAGCCAGGGCATCAGGAACGATCTGGGCTGGTACCAG CAGAAGCCAGGCAAGGCCCCCAAGAGACTGATCTATGC AGCATCCTCTCTGCAGTCCGGAGTGCCATCTAGGTTCTC TGGCAGCGGCTCCGGCACCGAGTTTACCCTGACAATCAG CACACTGCAGCCTGAGGACTTCGCCACCTACTATTGTCT GCAGCACAATTCCTATCCACGGACCTTTGGCCAGGGCAC AAAGGTGGAGATCAAGACCACAACTCCTGCACCTAGGC CACCTACCCCAGCACCTACAATTGCTAGTCAGCCACTGT CACTGCGACCAGAGGCATGTCGACCTGCAGCTGGAGGA GCAGTGCATACAAGGGGACTGGACTTTGCCTGCGATATC TACATTTGGGCTCCTCTGGCAGGAACATGTGGCGTGCTG CTGCTGAGCCTGGTCATCACTCTGTACTGCAAGCGAGGC CGGAAGAAACTGCTGTATATTTTCAAACAGCCCTTTATG CGACCTGTGCAGACCACACAGGAGGAAGATGGGTGCTC CTGTCGGTTCCCCGAGGAAGAGGAAGGAGGCTGTGAGC TGCGGGTCAAGTTTTCCAGATCTGCAGACGCCCCTGCTT ACCAGCAGGGCCAGAACCAGCTGTATAACGAGCTGAAT CTGGGGCGGAGAGAGGAATACGACGTGCTGGATAAAAG GCGCGGGAGAGACCCAGAAATGGGGGGAAAGCCACGA CGGAAAAAACCCCCAGGAGGGACTGTACAATGAACTGCA GAAGGATAAAATGGCAGAGGCCTATTCCGAAATCGGGA TGAAGGGAGAAAGAAGGCGAGGCAAAGGACACGACGG ACTGTACCAGGGGCTGTCTACCGCCACAAAGGACACCTA TGATGCTCTGCATATGCAGGCACTGCCACCCAGG |
| 592 | CD8α signal sequence, 10D1 scFv, CD8α hinge and transmembrane regions, 41BB cytoplasmic signaling domain, CD3ζ cytoplasmic signaling domain | ATGGCTCTGCCCGTCACCGCTCTGCTGCTGCCTCTGGCTC TGCTGCTGCACGCCGCACGACCACAGGTGCAGCTGCAGC AGTGGGGAGCAGGACTGCTGAAGCCATCCGAGACCCTG TCTCTGACATGCGCCGTGTATGGCGGCTCCTTCTCTGGCT ACTATTGGCGGTGGATCAGACAGCCCCCTGGCAAGGGA CTGGAGTGGATCGGCGAGATCAGCCACTCCGGCTCTACC AACTACAATCCCTCTCTGAAGAGCCGCGTGACCATCAGC GTGGACACATCCAAGAACCAGTTCAGCCTGAAGCTGAG CTCCGTGACCGCAGCAGATACAGCCGTGTACTATTGCGC CGTGCGGGGCTACTCCTATGGCTACCCCCTGTTTGACTA CTGGGGCCAGGGCACCCTGGTGACAGTGTCTAGCGGAG GAGGAGGAAGCGGAGGAGGAGGGTCCGGAGGCGGGGG ATCTGATATCCAGATGACCCAGTCCCCTTCCTCTCTGAG CGCCTCCGTGGGCGACAGGGTGACCATCACATGTCGCGC CTCTCAGGGCATCCGGAACGATCTGGGCTGGTATCAGCA GAAGCTGGGCAAGGCCCCAAAGAGACTGATCTACGCAG CAAGCTCCCTGCAGTCTGGAGTGCCAAGCAGGTTCTCTG GAAGCGGATCCGGAACCGAGTTTACCCTGACAATCTCTA GCCTGCAGCCTGAGGACTTCGCCACATACTATTGTCTGC AGTATAATAGCTACCCACGGACCTTTGGCCAGGGCACAA AGGTGGAGATCAAGACCACAACTCCTGCACCTAGGCCA CCTACCCCAGCACCTACAATTGCTAGTCAGCCACTGTCA CTGCGACCAGAGGCATGTCGACCTGCAGCTGGAGGAGC AGTGCATACAAGGGGACTGGACTTTGCCTGCGATATCTA CATTTGGGCTCCTCTGGCAGGAACATGTGGCGTGCTGCT GCTGAGCCTGGTCATCACTCTGTACTGCAAGCGAGGCCG GAAGAAACTGCTGTATATTTTCAAACAGCCCTTTATGCG ACCTGTGCAGACCACACAGGAGGAAGATGGGTGCTCCT GTCGGTTCCCCGAGGAAGAGGAAGGAGGCTGTGAGCTG CGGGTCAAGTTTTCCAGATCTGCAGACGCCCCTGCTTAC CAGCAGGGCCAGAACCAGCTGTATAACGAGCTGAATCT GGGGCGGAGAGAGGAATACGACGTGCTGGATAAAAGGC GCGGGAGAGACCCAGAAATGGGGGGAAAGCCACGACG GAAAAACCCCCAGGAGGGACTGTACAATGAACTGCAGA AGGATAAAATGGCAGAGGCCTATTCCGAAATCGGGATG AAGGGAGAAAGAAGGCGAGGCAAAGGACACGACGGAC TGTACCAGGGGCTGTCTACCGCCACAAAGGACACCTATG ATGCTCTGCATATGCAGGCACTGCCACCCAGG |
| 593 | CD8α signal sequence, | ATGGCTCTGCCCGTCACCGCTCTGCTGCTGCCTCTGGCTC TGCTGCTGCACGCCGCACGACCACAGGTGCAGCTGCAG |

TABLE 10-continued

Polynucleotide Sequences of exemplary DLL3 targeting CARs

| SEQ ID NO | CAR Structure | Nucleotide Sequence |
|---|---|---|
| | 11F6 scFv, CD8α hinge and transmembrane regions, 41BB cytoplasmic signaling domain, CD3ζ cytoplasmic signaling domain | GAGAGCGGCCCTGGCCTGGTGAAGCCATCCGGCACCCT GTCTCTGACATGCGCCGTGAGCGGCGACTCCATCAGCTC CAACTGGTGGACATGGGTGAGGCAGCCCCCTGGCAAGG GACTGGAGTGGATCGGCGATATCCACCACTCCGGCTCTA CCAACTACAATCCATCTCTGAAGAGCCGCGTGACAATGA GCGTGGACAAGTCCGAGAATCAGTTCTCCCTGAAGCTGT CTAGCGTGACCGCCGCCGATACAGCCGTGTTTTACTGCG CCAGAGACGGAGGAGGCACCCTGGATTATTGGGGCCAG GGCACCCTGGTGACAGTGTCCTCTGGAGGAGGAGGAAG CGGAGGAGGAGGGTCCGGAGGCGGGGGATCTGACATCC AGATGACCCAGAGCCCATCCACACTGTCTGCCAGCGTGG GCGATCGGGTGACCATCACATGTAGAGCCTCCCAGTCTA TCAGCTCCTGGCTGGCCTGGTACCAGCAGAAGCCAGGCA AGGCCCCCAAGCTGCTGATCTATAAGGCATCTACCCTGG AGAGCGGAGTGCCATCCAGGTTCAGCGGATCCGGATCT GGCACAGAGTTTACCCTGACAATCTCTAGCCTGCAGCCT GACGATTTCGCCACCTACTATTGTCAGCAGTACAACGGC TATAGCACCTTTGGCCAGGGCACAAAGGTGGAGATCAA GACCACAACTCCTGCACCTAGGCCACCTACCCCAGCACC TACAATTGCTAGTCAGCCACTGTCACTGCGACCAGAGGC ATGTCGACCTGCAGCTGGAGGAGCAGTGCATACAAGGG GACTGGACTTTGCCTGCGATATCTACATTTGGGCTCCTCT GGCAGGAACATGTGGCGTGCTGCTGCTGAGCCTGGTCAT CACTCTGTACTGCAAGCGAGGCCGGAAGAAACTGCTGT ATATTTTCAAACAGCCCTTTATGCGACCTGTGCAGACCA CACAGGAGGAAGATGGGTGCTCCTGTCGGTTCCCCGAG GAAGAGGAAGGAGGCTGTGAGCTGCGGGTCAAGTTTTC CAGATCTGCAGACGCCCCTGCTTACCAGCAGGGCCAGA ACCAGCTGTATAACGAGCTGAATCTGGGGCGGAGAGAG GAATACGACGTGCTGGATAAAAGGCGCGGGAGAGACCC AGAAATGGGGGGAAAGCCACGACGGAAAAACCCCCAG GAGGGACTGTACAATGAACTGCAGAAGGATAAAATGGC AGAGGCCTATTCCGAAATCGGGATGAAGGGAGAAAGAA GGCGAGGCAAAGGACACGACGGACTGTACCAGGGGCTG TCTACCGCCACAAAGGACACCTATGATGCTCTGCATATG CAGGCACTGCCACCCAGG |
| 594 | CD8α signal sequence, 6F8 scFv, CD8α hinge and transmembrane regions, 41BB cytoplasmic signaling domain, CD3ζ cytoplasmic signaling domain | ATGGCACTGCCAGTGACCGCCCTGCTGCTGCCTCTGGCC CTGCTGCTGCACGCCGCCAGGCCTCAGGTGCAGCTGGTG CAGTCTGGCGCCGAGGTGAAGAAGCCAGGCAGCTCCGT GAAGGTGTCCTGCAAGGCCTCTGGCGGCACATTCACCAA CTATTGTATCAGCTGGGTGAGACAGGCCCCCAGGCCAGG GACTGGAGTGGATGGGAGGAATCATCCCCATCTTCGGCA CCACAAATTATGCCCAGACCTTTCAGGGCCGGGTGACAA TCACCGCCGACAAGTCTACAAGCACCGCCTACATGGAGC TGTCTAGCCTGAGATCCGAGGATACAGCCGTGTACTATT GCGCCAGAGACAACGGCGATAGATACTATTACGACATG GACGTGTGGGGCCAGGGCACCACAGTGACCGTGTCCTCT GGAGGAGGAGGCAGCGGCGGAGGAGGCTCCGGAGGCG GCGGCTCTGGCGGCGGCGGCTCCCAGTCTGTGCTGACAC AGCCACCTAGCGTGTCCGCCGCCCCTGGCCAGAAGGTGA CCATCTCTTGTAGCGGCAGCTCCTCTAATATCGGCAACA ATTACGTGAGCTGGTACCAGCAGCTGCCAGGCACAGCCC CCAAGCTGCTGATCTACGACAACAATAAGAGGCCTAGC GGCATCCCAGATCGCTTCTCCGGCTCTAAGAGCGGCACA TCCGCCACCCTGGGCATCACAGGACTGCAGACCGGCGA CGAGGCAGATTATTACTGCGGAACCTGGGACAGCTCCCT GAGCGCCGTGGTGTTTGGAGGAGGCACAAAGCTGACCG TGCTGACCACAACCCCTGCCCCTAGGCCACCTACCCCAG CACCTACAATTGCTAGTCAGCCACTGTCACTGCGACCAG AGGCATGTCGACCTGCAGCTGGAGGAGCAGTGCATACA AGGGGACTGGACTTTGCCTGCGATATCTACATTTGGGCT CCTCTGGCAGGAACATGTGGCGTGCTGCTGCTGAGCCTG GTCATCACTCTGTACTGCAAGCGAGGCCGGAAGAAACT GCTGTATATTTTCAAACAGCCCTTTATGCGACCTGTGCA GACCACACAGGAGGAAGATGGGTGCTCCTGTCGGTTCCC CGAGGAAGAGGAAGGAGGCTGTGAGCTGCGGGTCAAGT TTTCCAGATCTGCAGACGCCCCTGCTTACCAGCAGGGCC AGAACCAGCTGTATAACGAGCTGAATCTGGGGCGGAGA GAGGAATACGACGTGCTGGATAAAAGGCGCGGGAGAGA CCCAGAAATGGGGGGAAAGCCACGACGGAAAAACCCCC AGGAGGGACTGTACAATGAACTGCAGAAGGATAAAATG GCAGAGGCCTATTCCGAAATCGGGATGAAGGGAGAAAG AAGGCGAGGCAAAGGACACGACGGACTGTACCAGGGGC |

TABLE 10-continued

Polynucleotide Sequences of exemplary DLL3 targeting CARs

| SEQ ID NO | CAR Structure | Nucleotide Sequence |
|---|---|---|
| | | TGTCTACCGCCACAAAGGACACCTATGATGCTCTGCATA TGCAGGCACTGCCACCCAGG |
| 595 | CD8α signal sequence, 3G6-L1 scFv, CD8α hinge and transmembrane regions, 41BB cytoplasmic signaling domain, CD3ζ cytoplasmic signaling domain | ATGGCCCTGCCAGTGACCGCCCTGCTGCTGCCACTGGCC CTGCTGCTGCACGCCGCCCGGCCACAGGTGCCCCTGGTG CAGAGCGGAGCAGAGGTGAAGAAGCCCGGCAGCTCCGT GAAGGTGAGCTGCAAGGCCTCCGGCGGCACATTCTCCAC CTATTCTATCAGCTGGGTGCGGCAGGCCCCTGGCCAGGG ACTGGAGTGGATGGGAGGAATCATCCCAATCTTCGGCAC CACAAACTATGCCCAGAAGTTTCAGGGCAGGGTGACAA TCACCGCCGACAAGTCCACATCTACCGCCTACATGGAGC TGTCTAGCCTGAGGTCCGAGGACACAGCCGTGTACTATT GTGCCCGCGATGGCGAGGGCTCTTACTATTACTATTACG GAATGGACGTGTGGGGACAGGGAACCACAGTGACCGTG TCCTCTGGCGGCGGCGGCTCTGGAGGAGGAGGCAGCGG CGGAGGAGGCTCCGGAGGCGGCGGCAGCCAGTCCGTGC TGACACAGCCACCTTCTGTGAGCGCCGCCCCTGGCCAGA AGGTGACCATCTCCTGCTCTGGCAGCTCCTCTAATATCG GCAACAATTATGTGAGCTGGTACCAGCAGCTGCCTGGCA CAGCCCCAAAGCTGCTGATCTACGACAACAATAAGCGG CCCTCCGGCATCCCTGATAGATTCTTTGGCTCTAAGTTCG GCACAAGCGCCACCCTGGGCATCACAGGACTGCAGACC GGCGACGAGGCAGATTATTACTGTGGAACCTGGGACAG CTCCCTGAGCGCCGTGGTGTTTGGAGGAGGCACAAAGCT GACCGTGCTGACCACAACCCCTGCCCCTAGGCCACCTAC CCCAGCACCTACAATTGCTAGTCAGCCACTGTCACTGCG ACCAGAGGCATGTCGACCTGCAGCTGGAGGAGCAGTGC ATACAAGGGGACTGGACTTTGCCTGCGATATCTACATTT GGGCTCCTCTGGCAGGAACATGTGGCGTGCTGCTGCTGA GCCTGGTCATCACTCTGTACTGCAAGCGAGGCCGGAAGA AACTGCTGTATATTTTCAAACAGCCCTTTATGCGACCTGT GCAGACCACACAGGAGGAAGATGGGTGCTCCTGTCGGT TCCCCGAGGAAGAGGAAGGAGGCTGTGAGCTGCGGGTC AAGTTTTCCAGATCTGCAGACGCCCCTGCTTACCAGCAG GGCCAGAACCAGCTGTATAACGAGCTGAATCTGGGGCG GAGAGAGGAATACGACGTGCTGGATAAAAGGCGCGGGA GAGACCCAGAAATGGGGGGAAAGCCACGACGGAAAAA CCCCCAGGAGGGACTGTACAATGAACTGCAGAAGGATA AAATGGCAGAGGCCTATTCCGAAATCGGGATGAAGGGA GAAAGAAGGCGAGGCAAAGGACACGACGGACTGTACCA GGGGCTGTCTACCGCCACAAAGGACACCTATGATGCTCT GCATATGCAGGCACTGCCACCCAGG |
| 596 | CD8α signal sequence, 4C6 scFv, CD8α hinge and transmembrane regions, 41BB cytoplasmic signaling domain, CD3ζ cytoplasmic signaling domain | ATGGCACTGCCAGTGACAGCCCTGCTGCTGCCTCTGGCC CTGCTGCTGCACGCCGCCCGGCCACAGGTGCAGCTGCAG GAGTCCGGCCCTGGCCTGGTGAAGCCATCTGAGACCCTG AGCCTGACATGTACCGTGTCCGGCGATTCTATCAGCTCC TACTATTGGTCTTGGATCAGGCAGCCCCCCTGGCAAGGGA CTGGAGTGGATCGGCTACATGTACTATAGCGGCATCACA AACTATAATCCTAGCCTGAAGTCCCGCGTGAACATCTCC CTGGACACCTCTAAGAATCAGTTCAGCCTGAAGCTGGGC TCCGTGACAGCAGCAGATACCGCCGTGTACTATTGCGCA AGGCTGTCCGTGGCAGGCTTCTACTTTGACTATTGGGGC CAGGGCACACTGGTGACCGTGTCTAGCGGCGGCGGCGG CTCTGGAGGAGGAGGCAGCGGCGGAGGAGGCTCCGGCG GCGGCGGCTCTGAGATCGTGCTGACACAGAGCCCAGGC ACCCTGAGCCTGTCCCCCGGCGAGCGGGCCACACTGAGC TGTAGAGCCTCTCAGAGCGTGACCCGGTCCTACCTGGCC TGGTATCAGCAGAAGCCAGGCCAGGCCCCCAGACTGCT GATCTACGGCGCCTCCTCTAGGGCCACAGACATCCCAGA TCGCTTCTCCGGCTCTGGCAGCGGAACCGACTTTACACT GACCATCAACAGACTGGAGCCTGAGGATTTCGCCGTGTA CTATTGCCAGCAGTACGGCACAAGCCCACTGACCTTTGG CGGCGGCACCAAGGTGGAGATCAAGACCACAACCCCTG CCCCTAGGCCACCTACCCCAGCACCTACAATTGCTAGTC AGCCACTGTCACTGCGACCAGAGGCATGTCGACCTGCAG CTGGAGGAGCAGTGCATACAAGGGGACTGGACTTTGCC TGCGATATCTACATTTGGGCTCCTCTGGCAGGAACATGT GGCGTGCTGCTGCTGAGCCTGGTCATCACTCTGTACTGC AAGCGAGGCCGGAAGAAACTGCTGTATATTTTCAAACA GCCCTTTATGCGACCTGTGCAGACCACACAGGAGGAAG ATGGGTGCTCCTGTCGGTTCCCCGAGGAAGAGGAAGGA GGCTGTGAGCTGCGGGTCAAGTTTTCCAGATCTGCAGAC GCCCCTGCTTACCAGCAGGGCCAGAACCAGCTGTATAAC |

TABLE 10-continued

Polynucleotide Sequences of exemplary DLL3 targeting CARs

| SEQ ID NO | CAR Structure | Nucleotide Sequence |
|---|---|---|
| | | GAGCTGAATCTGGGGCGGAGAGAGGAATACGACGTGCT GGATAAAAGGCGCGGGAGAGACCCAGAAATGGGGGGA AAGCCACGACGGAAAAACCCCCAGGAGGGACTGTACAA TGAACTGCAGAAGGATAAAATGGCAGAGGCCTATTCCG AAATCGGGATGAAGGGAGAAAGAAGGCGAGGCAAAGG ACACGACGGACTGTACCAGGGGCTGTCTACCGCCACAA AGGACACCTATGATGCTCTGCATATGCAGGCACTGCCAC CCAGG |
| 597 | CD8α signal sequence, 4E6 scFv, CD8α hinge and transmembrane regions, 41BB cytoplasmic signaling domain, CD3ζ cytoplasmic signaling domain | ATGGCACTGCCAGTGACAGCCCTGCTGCTGCCTCTGGCC CTGCTGCTGCACGCCGCCCGGCCACAGGTGCAGCTGCAG GAGAGCGGCCCTGGCCTGGTGAAGCCATCTGAGACCCT GAGCCTGACATGTACCGTGAGCTCCGATTCCATCTCTAG CTACTATTGGTCTTGGATCAGACAGCCCCCTGGCAAGGG CCTGGAGTGGATCTCCTACATCTACTATTCCGGCATCTCT AACTATAATCCTAGCCTGAAGAGCCGGGTGAGCATCTCT GTGGACACCTCCAAGAACCAGTTTTCTCTGAGACTGTCC TCTGTGACAGCCGCCGATACCGCCGTGTACTATTGCGCC AGAATCAGCGTGGCCGGCTTCTTTTTCGACAATTGGGGC CAGGGCACACTGGTGACCGTGAGCTCCGGAGGAGGAGG CAGCGGAGGAGGAGGCTCCGGAGGCGGCGGCTCTGGCG GCGGCGGCAGCGAGATCATGCTGACACAGAGCCCAGAT ACCCTGAGCCTGTCCCCCGGCGAAAGGGCCACACTGTCC TGTAGAGCCTCTCAGAGCGTGTCTAGCTCCTACCTGGCC TGGTATCAGCAGAAGCCAGGCCAGGCACCCAGGCTGCT GATCTACGGAGCATCTAGCAGGGCCGCAGGAGTGCCAG ACCGCTTTTCCGGCTCTGGCAGCGGCACCGATTTCACAC TGACCATCTCTCGCCTGGCCCCTGAGGACTTTGTGGTGT ACTATTGCCAGCAGTATGGCATCTCCCCACTGACATTCG GCGGCGGCACCAAGGTGGAGATCAAGACCACAACCCCT GCCCCTAGGCCACCTACCCCAGCACCTACAATTGCTAGT CAGCCACTGTCACTGCGACCAGAGGCATGTCGACCTGCA GCTGGAGGAGCAGTGCATACAAGGGGACTGGACTTTGC CTGCGATATCTACATTTGGGCTCCTCTGGCAGGAACATG TGGCGTGCTGCTGCTGAGCCTGGTCATCACTCTGTACTG CAAGCGAGGCCGGAAGAAACTGCTGTATATTTTCAAAC AGCCCTTTATGCGACCTGTGCAGACCACACAGGAGGAA GATGGGTGCTCCTGTCGGTTCCCCGAGGAAGAGGAAGG AGGCTGTGAGCTGCGGGTCAAGTTTTCCAGATCTGCAGA CGCCCCTGCTTACCAGCAGGGCCAGAACCAGCTGTATAA CGAGCTGAATCTGGGGCGGAGAGAGGAATACGACGTGC TGGATAAAAGGCGCGGGAGAGACCCAGAAATGGGGGG AAAGCCACGACGGAAAAACCCCCAGGAGGGACTGTACA ATGAACTGCAGAAGGATAAAATGGCAGAGGCCTATTCC GAAATCGGGATGAAGGGAGAAAGAAGGCGAGGCAAAG GACACGACGGACTGTACCAGGGGCTGTCTACCGCCACA AAGGACACCTATGATGCTCTGCATATGCAGGCACTGCCA CCCAGG |
| 598 | CD8α signal sequence, 4H8 scFv, CD8α hinge and transmembrane regions, 41BB cytoplasmic signaling domain, CD3ζ cytoplasmic signaling domain | ATGGCTCTGCCTGTCACCGCTCTGCTGCTGCCTCTGGCTC TGCTGCTGCACGCGGCGCGCCCGCAGGTGCAGCTGCAGC AGAGCGGCCCTGGCCTGGTGAAGCCTAGCCAGACACTG TCCCTGACCTGTGCCATCTCTGGCGACAGCGTGAGCTCC AACAGCGCCACATGGAATTGGATCAGGCAGTCCCCATCT CGCGGCCTGGAGTGGCTGGGACGGACCTACTATAGATCC AAGTGGTACGACGATTATGCCGTGTCCGTGAAGTCTCGC ATCACAATCAACCCTGACACCTCCAAGAATCACCTGTCT CTGCACCTGAACAGCGTGACACCAGAGGATACCGCCGT GTACTATTGCGCAGGAGGAGGACTGGTGGGCGCCCCTG ACGGATTCGACGTGTGGGGCCAGGGCACAATGGTGACC GTGTCTAGCGGCGGCGGCGGCTCTGGAGGAGGAGGCAG CGGCGGAGGAGGCTCCGGAGGCGGCGGCTCTCAGTCCG TGCTGACACAGCCCCCTTCTGCCAGCGGAACACCCGGCC AGCGGGTGACCATCTCCTGTTCTGGCTCCTCTAGCAACA TCGGCTCCGACCCTGTGAATTGGTACCAGCAGCTGCCAG GCACAGCCCCCAAGCTGCTGATCTATAGCAACAATCAGC GGCCTTCCGGCGTGCCAGATAGATTCAGCGGCTCCAAGT CTGGCACCAGCGCCTCCCTGGCAATCTCTGGACTGCAGA GCGAGGACGAGGCCGATTACTATTGCTCCGCCTGGGACG ATTCTCTGAATGGCTACGTGTTTGGCACAGGCACCAAGG TGACCGTGCTGACCACAACCCCAGCACCTAGGCCACCTA CACCTGCACCAACCATCGCCAGCCAGCCTCTGTCCCTGA GACCAGAGGCCTGTAGGCCAGCAGCAGGAGGAGCAGTG CACACCCGGGGCCTGGACTTCGCCTGCGATATCTACATC |

TABLE 10-continued

Polynucleotide Sequences of exemplary DLL3 targeting CARs

| SEQ ID NO | CAR Structure | Nucleotide Sequence |
|---|---|---|
| | | TGGGCACCACTGGCAGGAACATGTGGCGTGCTGCTGCTG TCCCTGGTCATCACCCTGTACTGCAAGAGAGGCAGGAAG AAGCTGCTGTATATCTTCAAGCAGCCCTTCATGAGACCC GTGCAGACAACCCAGGAGGAGGACGGCTGCAGCTGTAG GTTCCCAGAGGAGGAGGAGGGAGGATGTGAGCTGCGCG TGAAGTTTTCCCGGTCTGCCGATGCCACCTGCATACCAGC AGGGACAGAACCAGCTGTATAACGAGCTGAATCTGGGC CGGAGAGAGGAGTACGACGTGCTGGATAAGAGGAGGGG AAGGGACCCTGAGATGGGAGGCAAGCCTCGGAGAAAGA ACCCACAGGAGGGCCTGTACAATGAGCTGCAGAAGGAC AAGATGGCCGAGGCCTATAGCGAGATCGGCATGAAGGG AGAGAGGCGCGGGGCAAGGGACACGATGGCCTGTATC AGGGCCTGTCAACCGCTACAAAAGATACCTACGATGCTC TGCACATGCAGGCTCTGCCACCAAGA |
| 599 | CD8α signal sequence, 9H12-K scFv, CD8α hinge and transmembrane regions, 41BB cytoplasmic signaling domain, CD3ζ cytoplasmic signaling domain | ATGGCTCTGCCTGTCACCGCTCTGCTGCTGCCTCTGGCTC TGCTGCTGCACGCGGCGCGCCCGCAGGTGCAGCTGGTGC AGAGCGGAGCAGAGGTGAAGAAGCCTGGCGCCAGCGTG AAGGTGTCCTGCAAGGCCTCTGGCTACACAATTCACCGGC TATTCTATCCACTGGGTGCGCCAGGCCCCTGGCCAGGGA CTGGAGTGGATGGGCTGGATCAACCCAAATAGCGGCGG CACCTTCTACGCCCAGAAGTTTCAGGGCAGGGTGACAAT GACCCGCGACACATCTATCAGCACCGTGTATATGGAGCT GAGCCGGCTGAGATCCGACGATACAGCCGTGTACTATTG TGCCAGAGACGGCTGGGGCGATTACTATTACTATGGACT GGACGTGTGGGGACAGGGAACCACAGTGACCGTGTCCC TGGGCGGCGGCGGCTCTGGAGGAGGAGGCAGCGGCGGA GGAGGCTCCGGAGGCGGCGGCTCTGATATCCAGATGAC ACAGAGCCCTAGCTCCGTGTCCGCCTCTGTGGGCGACAG GGTGACAATCACCTGCAGAGCCTCCCAGGATATCTCTAG CTGGCTGGCCTGGTACCAGCAGAAGCCCGGCAAGGCCC CTAAGCTGCTGATCTATACCGCATCCTCTCTGCAGGGAG GAGTGCCATCCCGGTTCAGCGGCTCCGGCTCTGGAACAG ACTTTACACTGACCATCAGCTCCCTGCAGCCAGAGGATC TGGCCACCTACTCTTGTCAGCAGGCCAACGTGTTCCCCT ATACATTTGGCCAGGGCACCAAGCTGGAGATCAAGACC ACAACCCCAGCACCTAGGCCACCTACACCTGCACCAACC ATCGCCAGCCAGCCTCTGTCCCTGAGACCAGAGGCCTGT AGGCCAGCAGCAGGAGGAGCAGTGCACACCCGGGGCCT GGACTTCGCCTGCGATATCTACATCTGGGCACCACTGGC AGGAACATGTGGCGTGCTGCTGCTGTCCCTGGTCATCAC CCTGTACTGCAAGAGAGGCAGGAAGAAGCTGCTGTATA TCTTCAAGCAGCCCTTCATGAGACCCGTGCAGACAACCC AGGAGGAGGACGGCTGCAGCTGTAGGTTCCCAGAGGAG GAGGAGGGAGGATGTGAGCTGCGCGTGAAGTTTTCCCG GTCTGCCGATGCACCTGCATACCAGCAGGGACAGAACC AGCTGTATAACGAGCTGAATCTGGGCCGGAGAGAGGAG TACGACGTGCTGGATAAGAGGAGGGGAAGGGACCCTGA GATGGGAGGCAAGCCTCGGAGAAAGAACCCACAGGAGG GCCTGTACAATGAGCTGCAGAAGGACAAGATGGCCGAG GCCTATAGCGAGATCGGCATGAAGGGAGAGAGGCGCCG GGGCAAGGGACACGATGGCCTGTATCAGGGCCTGTCAA CCGCTACAAAAGATACCTACGATGCTCTGCACATGCAGG CTCTGCCACCAAGA |
| 600 | CD8α signal sequence, 10G1-K scFv, CD8α hinge and transmembrane regions, 41BB cytoplasmic signaling domain, CD3ζ cytoplasmic signaling domain | ATGGCTCTGCCTGTCACCGCTCTGCTGCTGCCTCTGGCTC TGCTGCTGCACGCGGCGCGCCCGGAGGTGCAGCTGCTGG AGTCCGGCGGCGGCCTGGTGCAGCCAGGCGGCTCTCTGA GGCTGAGCTGCGCAGCATCCGGCTTCACCTTTAGCTCCT ACGCAATGAACTGGGTGCGCCAGGCCCCCGGCAAGGGA CTGGAGTGGGTGTCTACAATCTCTGGCAGCGGCGGCAGC ACCTACTATGCCGACTCCGTGAAGGGCCGGTTCACAATC TCTAGAGATAACAGCAAGAATACCCTGTACCTGCAGATG AACAGCCTGCGGGCCGAGGACACAGCCGTGTTTTATTGT GCCATCGACCCAGAGTACTATGATATCCTGACCGGCGGC GATTATTGGGGCCAGGGCACACTGGTGACCGTGTCTAGC GGCGGCGGCGGCTCTGGAGGAGGAGGCAGCGGCGGAGG AGGCTCCGGAGGCGGCGGCTCTGACATCCAGATGACCC AGTCCCCATCTGCCATGAGCGCCTCCGTGGGCGATAGGG TGACAATCACCTGCCGCGCCTCCCAGGGCATCTCTAACT ACCTGGCCTGGTTCCAGCAGAAGCCCGGCAAGGTGCCTA AGCGGCTGATCTATGCAGCATCCTCTCTGCAGAGCGGAG TGCCTTCCAGATTCTCTGGCAGCGGCTCCGGCACAGAGT TTACACTGACCATCAGCTCCCTGCAGCCCGAGGACTTCG |

TABLE 10-continued

Polynucleotide Sequences of exemplary DLL3 targeting CARs

| SEQ ID NO | CAR Structure | Nucleotide Sequence |
|---|---|---|
| | | CCACCTACTTTTGTCTGCAGCACGATTCCTTCCCTCTGAC |
| | | ATTTGGCGGCGGCACCAAGGTGGAGATCAAGACCACAA |
| | | CCCCAGCACCTAGGCCACCTACACCTGCACCAACCATCG |
| | | CCAGCCAGCCTCTGTCCCTGAGACCAGAGGCCTGTAGGC |
| | | CAGCAGCAGGAGGAGCAGTGCACACCCGGGGCCTGGAC |
| | | TTCGCCTGCGATATCTACATCTGGGCACCACTGGCAGGA |
| | | ACATGTGGCGTGCTGCTGCTGTCCCTGGTCATCACCCTG |
| | | TACTGCAAGAGAGGCAGGAAGAAGCTGCTGTATATCTTC |
| | | AAGCAGCCCTTCATGAGACCCGTGCAGACAACCCAGGA |
| | | GGAGGACGGCTGCAGCTGTAGGTTCCCAGAGGAGGAGG |
| | | AGGGAGGATGTGAGCTGCGCGTGAAGTTTTCCCGGTCTG |
| | | CCGATGCACCTGCATACCAGCAGGGACAGAACCAGCTG |
| | | TATAACGAGCTGAATCTGGGCCGGAGAGAGGAGTACGA |
| | | CGTGCTGGATAAGAGGAGGGGAAGGGACCCTGAGATGG |
| | | GAGGCAAGCCTCGGAGAAAGAACCCACAGGAGGGCCTG |
| | | TACAATGAGCTGCAGAAGGACAAGATGGCCGAGGCCTA |
| | | TAGCGAGATCGGCATGAAGGGAGAGAGGCGCCGGGGCA |
| | | AGGGACACGATGGCCTGTATCAGGGCCTGTCAACCGCTA |
| | | CAAAAGATACCTACGATGCTCTGCACATGCAGGCTCTGC |
| | | CACCAAGA |
| 601 | CD8α signal sequence, 11A3 scFv, CD8α hinge and transmembrane regions, 41BB cytoplasmic signaling domain, CD3ζ cytoplasmic signaling domain | ATGGCTCTGCCTGTCACCGCTCTGCTGCTGCCTCTGGCTC |
| | | TGCTGCTGCACGCGGCGCGCCCGCAGGTGCAGCTGCAG |
| | | GAGTCCGGCCCTGGCCTGGTGAAGCCAAGCGAGACCCT |
| | | GTCCCTGACATGTACCGTGAGCTCCGATTCTATCAGCAA |
| | | CTACTATTGGAGCTGGATCAGGCAGCCCCCTGGCAAGGG |
| | | ACTGGAGTGGATCTCCTACATCTACTATTCTGGCATCAC |
| | | CAACTATAATCCTTCCCTGAAGTCTCGCGTGACAATCTC |
| | | TGTGGACACCAGCAAGAATCAGTTCAGCCTGAAGCTGTC |
| | | TAGCGTGACAGCCGCCGATACCGCCGTGTACTATTGCGC |
| | | CCGGATCACAGTGACCGGCTTCTACTTTGACTATTGGGG |
| | | CCAGGGCACACTGGTGACCGTGTCCTCTGGCGGCGGCGG |
| | | CTCTGGAGGAGGAGGCAGCGGCGGAGGAGGCTCCGGAG |
| | | GCGGCGGCTCTGAGATCGTGCTGACACAGTCCCCAGGCA |
| | | CCCTGTCCCTGTCTCCCGGCGAGCGGGCCACACTGTCTT |
| | | GTAGAGCCAGCCAGTCCATCTCTCGGAGCTACCTGGCCT |
| | | GGTATCAGCAGAAGCCAGGCCAGGCCCCCAGACACCTG |
| | | ATCTACGGAGCAAGCTCCAGGGCCACCGGCATCCCCGA |
| | | CCGCTTCTCCGGCTCTGGCAGCGGCACAGACTTCATCCT |
| | | GACCATCTCCAGACTGGAGCCTGAGGACTTCGCCGTGTA |
| | | CTATTGCCAGCAGTACGATACAAGCCCACTGACCTTTGG |
| | | CGGCGGCACCAAGGTGGAGATCAAGACCACAACCCCAG |
| | | CACCTAGGCCACCTACACCTGCACCAACCATCGCCAGCC |
| | | AGCCTCTGTCCCTGAGACCAGAGGCCTGTAGGCAGCAG |
| | | CAGGAGGAGCAGTGCACACCCGGGGCCTGGACTTCGCC |
| | | TGCGATATCTACATCTGGGCACCACTGGCAGGAACATGT |
| | | GGCGTGCTGCTGCTGTCCCTGGTCATCACCCTGTACTGC |
| | | AAGAGAGGCAGGAAGAAGCTGCTGTATATCTTCAAGCA |
| | | GCCCTTCATGAGACCCGTGCAGACAACCCAGGAGGAGG |
| | | ACGGCTGCAGCTGTAGGTTCCCAGAGGAGGAGGAGGGA |
| | | GGATGTGAGCTGCGCGTGAAGTTTTCCCGGTCTGCCGAT |
| | | GCACCTGCATACCAGCAGGGACAGAACCAGCTGTATAA |
| | | CGAGCTGAATCTGGGCCGGAGAGAGGAGTACGACGTGC |
| | | TGGATAAGAGGAGGGGAAGGGACCCTGAGATGGGAGGC |
| | | AAGCCTCGGAGAAAGAACCCACAGGAGGGCCTGTACAA |
| | | TGAGCTGCAGAAGGACAAGATGGCCGAGGCCTATAGCG |
| | | AGATCGGCATGAAGGGAGAGAGGCGCCGGGGCAAGGG |
| | | ACACGATGGCCTGTATCAGGGCCTGTCAACCGCTACAAA |
| | | AGATACCTACGATGCTCTGCACATGCAGGCTCTGCCACC |
| | | AAGA |
| 602 | CD8α signal sequence, 3B11 scFv, CD8α hinge and transmembrane regions, 41BB cytoplasmic signaling domain, CD3ζ cytoplasmic | ATGGCACTGCCAGTGACAGCCCTGCTGCTGCCACTGGCC |
| | | CTGCTGCTGCACGCCGCCGGCCACAGGTGCAGCTGCAG |
| | | CAGAGCGGCCCTGGCCTGGTGAAGCCTAGCCAGACACT |
| | | GTCCCTGACCTGTGCCATCTCTGGCGACAGCGTGAGCTC |
| | | CAACAGCGTGGTGTGGAATTGGATCAGGCAGTCCCCCATC |
| | | TCGCGGCCTGGAGTGGCTGGGACGGACCTACTATAGATC |
| | | CAAGTGGTACGACGATTATGCCGTGTCCGTGAAGTCTAG |
| | | GATCACAATCAACCCTGACACCAGCAAGAATCAGTTCTC |
| | | CCTGCAGCTGAACTCTGTGACACCAGAGGATACCGCCGT |
| | | GTACCACTGCGCCAGAGGCGGAATCGTGGGCGCCCCTG |
| | | ACGCCTTTGATATCTGGGGCCAGGGCACAATGGTGACCG |
| | | TGTCTAGCGGAGGAGGAGGCAGCGGAGGAGGAGGCTCC |

TABLE 10-continued

| Polynucleotide Sequences of exemplary DLL3 targeting CARs | |
|---|---|

| SEQ ID NO | CAR Structure | Nucleotide Sequence |
|---|---|---|
| | signaling domain | GGAGGCGGCGGCTCTGGCGGCGGCGGCAGCCAGTCCGT GCTGACCCAGCCACCTTCTGCCAGCGGAACACCCGGCCA GCGGGTGACCATCTCCTGTTCTGGCTCCTCTAGCAACAT CGGCTCTGACCCTGTGAGCTGGTACCAGCAGTTCCCAGG CACAGCCCCCAAGCTGCTGATCTATACCAACAATCAGCG GCCTAGCGGCGTGCCAGATCGGTTCAGCGGCTCCAAGTC TGGCACAAGCGCCTCCCTGGCAATCTCCGGACTGCAGTC TGAGGACGAGGCCGATTACTATTGCGCCGCCTGGGACG ATTCCCTGAATGGCCACGTGTTCGGCACAGGCACCAAGG TGACCGTGCTGACCACAACCCCCGCCCCTAGGCCACCTA CCCCAGCACCTACAATTGCTAGTCAGCCACTGTCACTGC GACCAGAGGCATGTCGACCTGCAGCTGGAGGAGCAGTG CATACAAGGGGACTGGACTTTGCCTGCGATATCTACATT TGGGCTCCTCTGGCAGGAACATGTGGCGTGCTGCTGCTG AGCCTGGTCATCACTCTGTACTGCAAGCGAGGCCGGAAG AAACTGCTGTATATTTTCAAACAGCCCTTTATGCGACCT GTGCAGACCACACAGGAGGAAGATGGGTGCTCCTGTCG GTTCCCCGAGGAAGAGGAAGGAGGCTGTGAGCTGCGGG TCAAGTTTTCCAGATCTGCAGACGCCCCTGCTTACCAGC AGGGCCAGAACCAGCTGTATAACGAGCTGAATCTGGGG CGGAGAGAGGAATACGACGTGCTGGATAAAAGGCGCGG GAGAGACCCAGAAATGGGGGGAAAGCCACGACGGAAA AACCCCCAGGAGGGACTGTACAATGAACTGCAGAAGGA TAAAATGGCAGAGGCCTATTCCGAAATCGGGATGAAGG GAGAAAGAAGGCGAGGCAAAGGACACGACGGACTGTA CCAGGGGCTGTCTACCGCCACAAAGGACACCTATGATGC TCTGCATATGCAGGCACTGCCACCCAGG |
| 603 | CD8α signal sequence, 5G2 scFv, CD8α hinge and transmembrane regions, 41BB cytoplasmic signaling domain, CD3ζ cytoplasmic signaling domain | ATGGCCCTGCCAGTGACCGCCCTGCTGCTGCCACTGGCC CTGCTGCTGCACGCCGCCCGGCCACAGGTGCAGCTGCAG CAGTCCGGCCCTGGCCTGGTGAAGCCTTCTCAGACACTG AGCCTGACCTGTGCCATCTCCGGCGACTCTGTGAGCTCC AACTCTGCCGTGTGGAATTGGATCAGACAGTCCCCCTCT AGAGGCCTGGAGTGGCTGGGCTGGACATACTATCGGAG CAAGTACTATAACGACTACGCCGTGAGCCTGAAGTCCAG AATCACAATCAACCCTGATACCAGCAAGAATCAGTTCTC CCTGCAGCTGAACAGCCTGACACCAGAGGATACCGCCG TGTACTATTGCACCAGGGGCGGAATCGTGGGCGCCCCTG ACGGCTTTGATATCTGGGGCCAGGGCACAATGGTGACCG TGTCTAGCGGAGGAGGAGGCAGCGGAGGAGGAGGCTCC GGAGGCGGCGGCTCTGGCGGCGGCGGCAGCCAGTCCGC CCTGACACAGCCACCTTCTGCCAGCGGAACACCCGGCCA GCGCGTGACCATCTCCTGTTCTGGCAGCAACTCCAATAT CGGCTCCAACCCTATCAATTGGTACCAGCAGCTGCCAGG CACAGCCCCCAAGCTGCTGATCTATAGCAACAATCAGAG GCCTTCCGGCGTGCCAGACCGCTTCTCTGGCAGCAAGTC CGGCACCTCTGCCAGCCTGGCAATCTCCGGACTGCAGTC TGAGGACGAGGCCGATTACTATTGCGCAGCATGGGACG ATAGCCTGAACGGACACGTGTTTGGCACAGGCACCAAG GTGACCGTGCTGACCACAACCCCCGCCCCTAGGCCACCT ACCCCAGCACCTACAATTGCTAGTCAGCCACTGTCACTG CGACCAGAGGCATGTCGACCTGCAGCTGGAGGAGCAGT GCATACAAGGGGACTGGACTTTGCCTGCGATATCTACAT TTGGGCTCCTCTGGCAGGAACATGTGGCGTGCTGCTGCT GAGCCTGGTCATCACTCTGTACTGCAAGCGAGGCCGGAA GAAACTGCTGTATATTTTCAAACAGCCCTTTATGCGACC TGTGCAGACCACACAGGAGGAAGATGGGTGCTCCTGTC GGTTCCCCGAGGAAGAGGAAGGAGGCTGTGAGCTGCGG GTCAAGTTTTCCAGATCTGCAGACGCCCCTGCTTACCAG CAGGGCCAGAACCAGCTGTATAACGAGCTGAATCTGGG CGCGGAGAGAGGAATACGACGTGCTGGATAAAAGGCGCG GGAGAGACCCAGAAATGGGGGGAAAGCCACGACGGAA AAACCCCCAGGAGGGACTGTACAATGAACTGCAGAAGG ATAAAATGGCAGAGGCCTATTCCGAAATCGGGATGAAG GGAGAAAGAAGGCGAGGCAAAGGACACGACGGACTGT ACCAGGGGCTGTCTACCGCCACAAAGGACACCTATGAT GCTCTGCATATGCAGGCACTGCCACCCAGG |
| 604 | CD8α signal sequence, 11E4 scFv, CD8α hinge and transmembrane | ATGGCACTGCCTGTGACAGCCCTGCTGCTGCCACTGGCC CTGCTGCTGCACGCCGCCCGGCCCCAGGTGCAGCTGCAG GAGAGCGGCCCAGGCCTGGTGAAGCCAAGCGAGACCCT GTCCCTGACATGTACCGTGTCTGGCGGCAGCATCAGCTC CTACTATTGGTCCTGGATCAGACAGTCTCCTGGCAAGGG CCTGGAGTGGATCGGCTACGTGTACTATTCCGACATCAC |

TABLE 10-continued

Polynucleotide Sequences of exemplary DLL3 targeting CARs

| SEQ ID NO | CAR Structure | Nucleotide Sequence |
|---|---|---|
| | regions, 41BB cytoplasmic signaling domain, CD3ζ cytoplasmic signaling domain | CAACTATAATCCATCCCTGAAGTCTAGAGTGACAATCTC TGTGGATACCAGCAAGAACCAGTTCAGCCTGAACCTGA ACAGCGTGACAGCCGCCGACACCGCCTTCTACTTTTGCG CCAGGATCGGCGTGGCCGGCTTCTACTTTGATTATTGGG GCCAGGGCACACTGGTGACCGTGTCTAGCGGCGGCGGC GGCTCTGGAGGAGGAGGCAGCGGCGGAGGAGGCTCCGG CGGCGGCGGCTCTGAGATCGTGCTGACACAGAGCCCAG ACACCCTGAGCCTGTCCCCTGGCGAGAGGGCCACACTGT CCTGTAGGGCATCTCAGAGCGTGTCCCGGAGATACCTGG CCTGGTATCAGCAGAAGCCTGGCCAGGCACCTCGCCTGC TGATCTACGGAGCATCCTCTCGGGCCACAGGCATCCCCG ACAGATTCTCTGGCAGCGGCTCCGGAACCGACTTCACCC TGACCATCTCTAGGCTGGAGCCAGAGGATTTCGAGGTGT ACTATTGCCAGCAGTATGGCACATCCCCAATCACCTTTG GCCAGGGAACCCGCCTGGAGATCAAGACCACAACCCCT GCCCCTAGGCCACCTACCCCAGCACCTACAATTGCTAGT CAGCCACTGTCACTGCGACCAGAGGCATGTCGACCTGCA GCTGGAGGAGCAGTGCATACAAGGGGACTGGACTTTGC CTGCGATATCTACATTTGGGCTCCTCTGGCAGGAACATG TGGCGTGCTGCTGCTGAGCCTGGTCATCACTCTGTACTG CAAGCGAGGCCGGAAGAAACTGCTGTATATTTTCAAAC AGCCCTTTATGCGACCTGTGCAGACCACACAGGAGGAA GATGGGTGCTCCTGTCGGTTCCCCGAGGAAGAGGAAGG AGGCTGTGAGCTGCGGGTCAAGTTTTCCAGATCTGCAGA CGCCCCTGCTTACCAGCAGGGCCAGAACCAGCTGTATAA CGAGCTGAATCTGGGGCGGAGAGAGGAATACGACGTGC TGGATAAAAGGCGCGGGAGAGACCCCAGAAATGGGGGG AAAGCCACGACGGAAAAACCCCCAGGAGGGACTGTACA ATGAACTGCAGAAGGATAAAATGGCAGAGGCCTATTCC GAAATCGGGATGAAGGGAGAAAGAAGGCGAGGCAAAG GACACGACGGACTGTACCAGGGGCTGTCTACCGCCACA AAGGACACCTATGATGCTCTGCATATGCAGGCACTGCCA CCCAGG |
| 605 | CD8α signal sequence, 2404.8E11 scFv, CD8α hinge and transmembrane regions, 41BB cytoplasmic signaling domain, CD3ζ cytoplasmic signaling domain | ATGGCCCTGCCAGTGACCGCCCTGCTGCTGCCACTGGCC CTGCTGCTGCACGCCGCCCGGCCACAGATCCAGCTGCAG CAGTCCGGCCCTGGCCTGGTGAAGCCTAGCCAGACACTG TCCCTGACCTGCGCCATCTCTGGCGACAGCGTGAGCTCC AACTCTGCCGTGTGGAATTGGATCAGGCAGTCCCCCATCT CGCGGCCTGGAGTGGTGGGGAAGGACATACTATAGAAG CAAGTGGTACAACGACTATGCCGTGTCCGTGAAGTCTAG GATCACAATCAAGCCTGATACCGCCAAGAACCAGTTCTC CCTGCAGCTGAACAGCGTGACACCAGAGGATACCGCCG TGTACTATTTCACCCGCGGCGGAATCGTGGGCGCCCCTG ACGCCTTTGATATCTGGGGCCAGGGCACAATGGTGACCG TGTCTAGCGGAGGAGGAGGCAGCGGAGGAGGAGGCTCC GGAGGCGGCGGCTCTGGCGGCGGCGGCAGCCAGTCCGT GCTGACACAGCCCCCTTCTGCCAGCGGAACACCCGGCCA GCGGGTGACCATCTCCTGCTCTGGCTCCTCTAGCAACAT CGGCTCCGACCCTATCAATTGGTACCAGCAGGTGCCAGG CACAGCCCCCAAGCTGCTGATCTATAGCAACAATCAGCG GCCTTCCGGCGTGCCAGATAGATTCAGCGGCTCCAAGTC TGGCACCAGCGCCTCCCTGGCAATCTCTGGACTGCAGAG CGAGGACGAGGCCGATTACTATTGTGCCGCCTGGGACG ATAGCCTGAATGGCTACGTGTTTGGCACAGGCACCAAGG TGACCGTGCTGACCACAACCCCCGCCCCTAGGCCACCTA CCCCAGCACCTACAATTGCTAGTCAGCCACTGTCACTGC GACCAGAGGCATGTCGACCTGCAGCTGGAGGAGCAGTG CATACAAGGGGACTGGACTTTGCCTGCGATATCTACATT TGGGCTCCTCTGGCAGGAACATGTGGCGTGCTGCTGCTG AGCCTGGTCATCACTCTGTACTGCAAGCGAGGCCGGAAG AAACTGCTGTATATTTTCAAACAGCCCTTTATGCGACCT GTGCAGACCACACAGGAGGAAGATGGGTGCTCCTGTCG GTTCCCCGAGGAAGAGGAAGGAGGCTGTGAGCTGCGGG TCAAGTTTTCCAGATCTGCAGACGCCCCTGCTTACCAGC AGGGCCAGAACCAGCTGTATAACGAGCTGAATCTGGGG CGGAGAGAGGAATACGACGTGCTGGATAAAAGGCGCGG GAGAGACCCAGAAATGGGGGGAAAGCCACGACGGAAA AACCCCCAGGAGGGACTGTACAATGAACTGCAGAAGGA TAAAATGGCAGAGGCCTATTCCGAAATCGGGATGAAGG GAGAAAGAAGGCGAGGCAAAGGACACGACGGACTGTA CCAGGGGCTGTCTACCGCCACAAAGGACACCTATGATGC TCTGCATATGCAGGCACTGCCACCCAGG |

TABLE 10-continued

Polynucleotide Sequences of exemplary DLL3 targeting CARs

| SEQ ID NO | CAR Structure | Nucleotide Sequence |
|---|---|---|
| 606 | CD8α signal sequence, 10A2 scFv, CD8α hinge and transmembrane regions, 41BB cytoplasmic signaling domain, CD3ζ cytoplasmic signaling domain | ATGGCCCTGCCAGTGACCGCCCTGCTGCTGCCACTGGCC CTGCTGCTGCACGCCGCCCGGCCACAGGTGCAGCTGCAG CAGAGCGGCCCTGGCCTGGTGAAGCCTAGCGAGACACT GTCCCTGACCTGTGCCATCTCTGGCGACAGCGTGAGCTC CAACAGCGCCACATGGAATTGGATCAGGCAGTCCCCATC TCGCGGCCTGGAGTGGCTGGGACGGACCTACTATAGATC CGAGTGGTACAACGACTATGCCGTGTCCGTGAAGTCTCG GATCACAATCAACCCTGATACCTCCAAGAATCACCTGTC TCTGCACCTGAATAGCGTGACACCAGAGGATACCGCCGT GTACTATTGCGCAGGAGGAGGAATCGTGGGCGCCCCTG ACGGATTCGACGTGTGGGGCCAGGGCACAATGGTGACC GTGTCTAGCGGAGGAGGAGGCTCCGGAGGAGGAGGCTC TGGCGGCGGCGGCAGCGGAGGCGGCGGCAGCCAGTCCG TGCTGACACAGCCACCTTCTGCCAGCGGAACACCCGGCC AGAGGGTGACCATCTCCTGTTCTGGCTCCTCTAGCAACA TCGGCAGCGACCCTGTGATCTGGTACCAGCAGCTGCCAC GCACAGCCCCCAAGCTGCTGATCTATTCCAACAATCAGC GGCCTTCTGGCGTGCCAGATAGATTCAGCGGCTCCAAGT CTGGCACCAGCGCCTCCCTGGCAATCTCTGGACTGCAGA GCGAGGACGAGGCCGATTACTATTGCGCCGCCTGGGAC GATTCCCTGAATGGCTACGTGTTTGGCACAGGCACCAAG GTGACCGTGCTGACCACAACCCCCGCCCCTAGGCCACCT ACCCCAGCACCTACAATTGCTAGTCAGCCACTGTCACTG CGACCAGAGGCATGTCGACCTGCAGCTGGAGGAGCAGT GCATACAAGGGGACTGGACTTTGCCTGCGATATCTACAT TTGGGCTCCTCTGGCAGGAACATGTGGCGTGCTGCTGCT GAGCCTGGTCATCACTCTGTACTGCAAGCGAGGCCGGAA GAAACTGCTGTATATTTTCAAACAGCCCTTTATGCGACC TGTGCAGACCACACAGGAGGAAGATGGGTGCTCCTGTC GGTTCCCCGAGGAAGAGGAAGGAGGCTGTGAGCTGCGG GTCAAGTTTTCCAGATCTGCAGACGCCCCTGCTTACCAG CAGGGCCAGAACCAGCTGTATAACGAGCTGAATCTGGG GCGGAGAGAGGAATACGACGTGCTGGATAAAAGGCGCG GGAGAGACCCAGAAATGGGGGGAAAGCCACGACGGAA AAACCCCCCAGGAGGGACTGTACAATGAACTGCAGAAGG ATAAAATGGCAGAGGCCTATTCCGAAATCGGGATGAAG GGAGAAAGAAGGCGAGGCAAAGGACACGACGGACTGT ACCAGGGGCTGTCTACCGCCACAAAGGACACCTATGAT GCTCTGCATATGCAGGCACTGCCACCCAGG |
| 607 | CD8α signal sequence, 11A8 scFv, CD8α hinge and transmembrane regions, 41BB cytoplasmic signaling domain, CD3ζ cytoplasmic signaling domain | ATGGCACTGCCAGTGACAGCCCTGCTGCTGCCACTGGCC CTGCTGCTGCACGCCGCCCGGCCACAGGTGCAGCTGCAG CAGAGCGGCCCTGGCCTGGTGAAGCCTAGCCAGACACT GTCCCTGACCTGTGCCATCTCTGGCGACAGCGTGAGCTC CAACAGCGCCACCTGGAATTGGATCAGGCAGTCCCCATC TACAGGACTGGAGTGGCTGGCACGGACCTACTATAGATC CAAGTGGTACAACGACTATGAGGTGTCCGTGAAGTCTCA GATCACAATCAACCCTGATACCTCCAAGAATCAGTTCTC TCTGCAGCTGAATAGCGTGACACCAGAGGATACCGCCGT GTACTATTGCGCCAGAGGCGGAATCGTGGGCGCCCCTGA CGCCTTTGATATCTGGGGCCAGGGCACAATGGTGACCGT GTCTAGCGGAGGAGGAGGCTCCGGAGGAGGAGGCTCTG GCGGCGGCGGCAGCGGAGGCGGCGGCAGCCAGTCCGTG CTGACACAGCCCCCTTCTGCCAGCGGAACACCCGGCCAG GGAGTGACCATCTCCTGTTCTGGCTCCTCTAGCAACATC GGCAGCAACCCTGTGAATTGGTACCAGCAGCTGCCAGG CACAGCCCCCAAGCTGCTGATCTATTCCAACAATCAGAG GCCTTCTGGCGTGCCAGACCGCTTCAGCGATTCCAAGTC TGGCACCAGCGCCTCCCTGGCAATCTCTGGACTGCAGAG CGAGGACGAGGCCGATTACTATTGCTCCGCCTGGGACGA TTGGCTGAATGGCTACGTGTTTGGCACAGGCACCAAGGT GACCGTGCTGACCACAACCCCCGCCCCTAGGCCACCTAC CCCAGCACCTACAATTGCTAGTCAGCCACTGTCACTGCG ACCAGAGGCATGTCGACCTGCAGCTGGAGGAGCAGTGC ATACAAGGGGACTGGACTTTGCCTGCGATATCTACATTT GGGCTCCTCTGGCAGGAACATGTGGCGTGCTGCTGCTGA GCCTGGTCATCACTCTGTACTGCAAGCGAGGCCGGAAGA AACTGCTGTATATTTTCAAACAGCCCTTTATGCGACCTGT GCAGACCACACAGGAGGAAGATGGGTGCTCCTGTCGGT TCCCCGAGGAAGAGGAAGGAGGCTGTGAGCTGCGGGTC AAGTTTTCCAGATCTGCAGACGCCCCTGCTTACCAGCAG GGCCAGAACCAGCTGTATAACGAGCTGAATCTGGGGCG GAGAGAGGAATACGACGTGCTGGATAAAAGGCGCGGGA GAGACCCAGAAATGGGGGGAAAGCCACGACGGAAAAA |

TABLE 10-continued

Polynucleotide Sequences of exemplary DLL3 targeting CARs

| SEQ ID NO | CAR Structure | Nucleotide Sequence |
|---|---|---|
| | | CCCCCAGGAGGGACTGTACAATGAACTGCAGAAGGATA AAATGGCAGAGGCCTATTCCGAAATCGGGATGAAGGGA GAAAGAAGGCGAGGCAAAGGACACGACGGACTGTACCA GGGGCTGTCTACCGCCACAAAGGACACCTATGATGCTCT GCATATGCAGGCACTGCCACCCAGG |
| 608 | CD8α signal sequence, 4H5 scFv, CD8α hinge and transmembrane regions, 41BB cytoplasmic signaling domain, CD3ζ cytoplasmic signaling domain | ATGGCACTGCCAGTGACAGCCCTGCTGCTGCCTCTGGCC CTGCTGCTGCACGCCGCCAGGCCTCAGGTGCAGCTGCAG GAGTCCGGCCCTGGCCTGGTGAAGCCATCCGAGACCCTG TCTCTGACATGCACCGTGTCCGGCGATTCTATCAACAAT TACTTTTGGAGCTGGATCAGACAGCCCCCTGGCAAGGGA CTGGAGTGGATCGGCTACTTCTATCACAGGGGCGGCAAC AATTATAACCCAAGCCTGAAGTCCCGCGTGACAATCAGC ATCGACACCTCCAAGAATCAGTTCAGCCTGAACCTGAAC AGCGTGACAAGCGCCGATACCGCCGTGTACTATTGTGCC CGGCTGGCCCTGGCCGGCTTCTTTTTCGACTACTGGGGC CAGGGCACACTGGTGACCGTGAGCTCCGGAGGAGGAGG CTCCGGCGGCGGAGGCTCTGGCGGCGGCGGCTCCGGAG GCGGCGGCAGCGACATCCAGATGACACAGTCTCCAAGC ACCCTGTCCGCCTCTGTGGGCGATAGGGTGACAATCACC TGCAGAGCCAGCCAGTCCATCTCTAGCTGGCTGGCCTGG TACCAGCAGAAGCCAGGCAAGGCCCCCAAGCTGCTGAT CTATAAGGCCTCCTCTCTGGAGTCTGGCGTGCCAAGCCG GTTTTCTGGCAGCGGCTCCGGCACAGAGTTCACACTGAC CATCAGCTCCCTGCAGCCCGACGATTTTGCCACCTACTA TTGTCAGCAGTACAACTCTTATAGCAGAACATTCGGCCA GGGCACCAAGGTGGAGATCAAGACCACAACCCCTGCCC CTAGGCCACCTACCCCAGCACCTACAATTGCTAGTCAGC CACTGTCACTGCGACCAGAGGCATGTCGACCTGCAGCTG GAGGAGCAGTGCATACAAGGGGACTGGACTTTGCCTGC GATATCTACATTTGGGCTCCTCTGGCAGGAACATGTGGC GTGCTGCTGCTGAGCCTGGTCATCACTCTGTACTGCAAG CGAGGCCGGAAGAAACTGCTGTATATTTTTCAAACAGCCC TTTATGCGACCTGTGCAGACCACACAGGAGGAAGATGG GTGCTCCTGTCGGTTCCCCGAGGAAGAGGAAGGAGGCT GTGAGCTGCGGGTCAAGTTTTCCAGATCTGCAGACGCCC CTGCTTACCAGCAGGGCCAGAACCAGCTGTATAACGAG CTGAATCTGGGGCGGAGAGAGGAATACGACGTGCTGGA TAAAAGGCGCGGGAGAGACCCAGAAATGGGGGGAAAG CCACGACGGAAAAACCCCCAGGAGGGACTGTACAATGA ACTGCAGAAGGATAAAATGGCAGAGGCCTATTCCGAAA TCGGGATGAAGGGAGAAAGAAGGCGAGGCAAAGGACA CGACGGACTGTACCAGGGGCTGTCTACCGCCACAAAGG ACACCTATGATGCTCTGCATATGCAGGCACTGCCACCCA GG |
| 609 | CD8α signal sequence, 3G6-L2 scFv, CD8α hinge and transmembrane regions, 41BB cytoplasmic signaling domain, CD3ζ cytoplasmic signaling domain | ATGGCACTGCCAGTGACAGCCCTGCTGCTGCCACTGGCC CTGCTGCTGCACGCCGCCCGGCCACAGGTGCCCCTGGTG CAGTCCGGAGCAGAGGTGAAGAAGCCCGGCAGCTCCGT GAAGGTGTCTTGCAAGGCCAGCGGCGGCACATTCAGCA CCTACAGCATCTCCTGGGTGCGGCAGGCCCCTGGCCAGG GACTGGAGTGGATGGGAGGAATCATCCCAATCTTCGGC ACCACAAACTACGCCCAGAAGTTTCAGGGCAGAGTGAC AATCACCGCCGACAAGTCTACAAGCACCGCCTATATGGA GCTGTCTAGCCTGAGGTCTGAGGACACCGCCGTGTACTA TTGTGCCCGCGATGGCGAGGGCAGCTACTATTACTATTA CGGAATGGACGTGTGGGGACAGGGAACCACAGTGACAG TGTCCTCTGGAGGAGGAGGCAGCGGCGGAGGAGGCTCC GGAGGCGGCGGCTCTGGCGGCGGCGGCTCCCAGTCTGT GCTGACCCAGCCACCTAGCGCCTCCGGAACACCCGGCCA GAGGGTGACCATCTCTTGCAGCGGCAGCTCCTCTAACAT CGGCTCCAATTACGTGTACTGGTATCAGCAGCTGCCTGG CACAGCCCCAAAGCTGCTGATCTACAGCAACAATCAGC GGCCCTCCGGCGTGCCTGACAGATTCTCCGGCTCTAAGA GCGGCACCTCCGCCTCTCTGGCAATCTCCGGACTGCGCT CTGAGGACGAGGCAGATTATTACTGTGCAGCATGGGAC GATAGCCTGTCCGGATGGGTGTTTGGAGGAGGAACAAA GCTGACCGTGCTGACCACAACCCCTGCCCCTAGGCCACC TACCCCAGCACCTACAATTGCTAGTCAGCCACTGTCACT GCGACCAGAGGCATGTCGACCTGCAGCTGGAGGAGCAG TGCATACAAGGGGACTGGACTTTGCCTGCGATATCTACA TTTGGGCTCCTCTGGCAGGAACATGTGGCGTGCTGCTGC TGAGCCTGGTCATCACTCTGTACTGCAAGCGAGGCCGGA AGAAACTGCTGTATATTTTTCAAACAGCCCTTTATGCGAC |

TABLE 10-continued

Polynucleotide Sequences of exemplary DLL3 targeting CARs

| SEQ ID NO | CAR Structure | Nucleotide Sequence |
|---|---|---|
| | | CTGTGCAGACCACACAGGAGGAAGATGGGTGCTCCTGT CGGTTCCCCGAGGAAGAGGAAGGAGGCTGTGAGCTGCG GGTCAAGTTTTCCAGATCTGCAGACGCCCCTGCTTACCA GCAGGGCCAGAACCAGCTGTATAACGAGCTGAATCTGG GGCGGAGAGAGGAATACGACGTGCTGGATAAAAGGCGC GGGAGAGACCCAGAAATGGGGGGAAAGCCACGACGGA AAAACCCCCAGGAGGGACTGTACAATGAACTGCAGAAG GATAAAATGGCAGAGGCCTATTCCGAAATCGGGATGAA GGGAGAAAGAAGGCGAGGCAAAGGACACGACGGACTG TACCAGGGGCTGTCTACCGCCACAAAGGACACCTATGAT GCTCTGCATATGCAGGCACTGCCACCCAGG |
| 610 | CD8α signal sequence, 3B9 scFv, CD8α hinge and transmembrane regions, 41BB cytoplasmic signaling domain, CD3ζ cytoplasmic signaling domain | ATGGCACTGCCAGTGACAGCCCTGCTGCTGCCACTGGCC CTGCTGCTGCACGCCGCCAGACCCGAGGTGCAGCTGGTG GAGTCCGGAGGAGGACTGGTGCAGCCTGGCGGCTCCCT GAGGCTGTCTTGCGCAGCAAGCGGCTTCACCTTTAGCTC CTACAGCATGAACTGGGTGAGACAGGCCCCCGGCAAGG GACTGGAGTGGGTGTCTTATATCTCTAGCTCCTCTAGCA CAATCTACTATGCCGACAGCGTGAAGGGCCGGTTCACCA TCTCTAGAGATAACGCCAAGAATAGCCTGTACCTGCAGA TGAACAGCCTGAGGGACGAGGATACAGCCGTGTACTAT TGTGCCCGCGACAAGGAGCGGAGATACTATTACTATGGC ATGGACGTGTGGGGCCAGGGCACCACAGTGACCGTGTC CTCTGGCGGCGGCGGCTCCGGAGGCGGCGGCTCTGGAG GAGGAGGCAGCGGCGGAGGAGGCTCCGAGATCGTGCTG ACACAGTCCCCTGACACCCTGTCTCTGAGCCCAGGCGAG AGGGCCACACTGTCTTGCAGGGCATCCCAGTCTGTGAGC AGGCGCTACCTGGCCTGGTATCAGCAGAAGCCTGGCCA GGCCCCCAGACTGCTGATCTACGGAGCAAGCAGCCGGG CCACAGGCATCCCTGACAGATTCTCCGGCTCTGGCAGCG GAACCGACTTCACCCTGACCATCTCCAGGCTGGAGCCAG AGGATTTTGCCGTGTACTATTGTCAGCAGTTCGGCACAA GCCCAATCACCTTTGGCCAGGGAACCCGCCTGGAGATCA AGACCACAACCCCAGCCCCTAGGCCACCTACCCCAGCAC CTACAATTGCTAGTCAGCCACTGTCACTGCGACCAGAGG CATGTCGACCTGCAGCTGGAGGAGCAGTGCATACAAGG GGACTGGACTTTGCCTGCGATATCTACATTTGGGCTCCT CTGGCAGGAACATGTGGCGTGCTGCTGCTGAGCCTGGTC ATCACTCTGTACTGCAAGCGAGGCCGGAAGAAACTGCT GTATATTTTCAAACAGCCCTTTATGCGACCTGTGCAGAC CACACAGGAGGAAGATGGGTGCTCCTGTCGGTTCCCCGA GGAAGAGGAAGGAGGCTGTGAGCTGCGGGTCAAGTTTT CCAGATCTGCAGACGCCCCTGCTTACCAGCAGGGCCAGA ACCAGCTGTATAACGAGCTGAATCTGGGCGGAGAGAG GAATACGACGTGCTGGATAAAAGGCGCGGGAGAGACCC AGAAATGGGGGGAAAGCCACGACGGAAAAACCCCCAG GAGGGACTGTACAATGAACTGCAGAAGGATAAAATGGC AGAGGCCTATTCCGAAATCGGGATGAAGGGAGAAAGAA GGCGAGGCAAAGGACACGACGGACTGTACCAGGGGCTG TCTACCGCCACAAAGGACACCTATGATGCTCTGCATATG CAGGCACTGCCACCCAGG |
| 611 | CD8α signal sequence, 3F9-L scFv, CD8α hinge and transmembrane regions, 41BB cytoplasmic signaling domain, CD3ζ cytoplasmic signaling domain | ATGGCACTGCCAGTGACAGCCCTGCTGCTGCCACTGGCC CTGCTGCTGCACGCCGCCAGACCCCAGGTGCAGCTGCAG CAGAGCGGCCCTGGCCTGGTGAAGCCTAGCCAGACCCT GTCCCTGGCTGTGCCATCTCTGGCGACAGCGTGAGCTC CAACTCCGCCATCTGGAATTGGATCAGGCAGTCCCCTTC TCGCGGCCTGGAGTGGCTGGGAGGAACATACTATCGGTC TATGTGGTACAACGACTATGCCGTGTCCGTGAAGTCTAG AATCACAATCAACCCTGATACCTCCAAGAATCAGCTGTC TCTGCAGCTGAATAGCGTGACACCAGAGGATACCGCCGT GTACTATTGCAGCCGGGGCGGAATCGTGGGAGTGCCAG ACGCCTTCGATATCTGGGGCCAGGGCACAATGGTGACCG TGTCTAGCGGAGGAGGAGGCTCCGGAGGAGGAGGCTCT GGCGGCGGCGGCAGCGGAGGCGGCGGCAGCCAGTCCGT GCTGACCCAGCCACCTTCTGCCAGCGGAACACCCGGCCA GCGGGTGACCATCTCCTGTTCTGGCTCCTCTAGCAACAT CGGCAGCAACACAGCCAATTGGTACCAGCAGCTGCCAG GCACCGCACCCAGGCTGCTGATCTATCGGAACAATCAGA GACCTTCCGGAGTGCCAGACCGCTTCAGCGGCTCCAAGT CTGGCACAAGCGCCTCCCTGGCCATCTCTGGCCTGCAGA GCGAGGACGAGGCCGATTACTATTGCGCCGCCTGGGAC GATAGCCTGAATGGCTACGTGTTTGGCACAGGCACCAAG GTGACCGTGCTGACCACAACCCCTGCCCCTAGGCCACCT |

TABLE 10-continued

Polynucleotide Sequences of exemplary DLL3 targeting CARs

| SEQ ID NO | CAR Structure | Nucleotide Sequence |
|---|---|---|
| | | ACCCCAGCACCTACAATTGCTAGTCAGCCACTGTCACTG CGACCAGAGGCATGTCGACCTGCAGCTGGAGGAGCAGT GCATACAAGGGGACTGGACTTTGCCTGCGATATCTACAT TTGGGCTCCTCTGGCAGGAACATGTGGCGTGCTGCTGCT GAGCCTGGTCATCACTCTGTACTGCAAGCGAGGCCGGAA GAAACTGCTGTATATTTTCAAACAGCCCTTTATGCGACC TGTGCAGACCACACAGGAGGAAGATGGGTGCTCCTGTC GGTTCCCCGAGGAAGAGGAAGGAGGCTGTGAGCTGCGG GTCAAGTTTTCCAGATCTGCAGACGCCCCTGCTTACCAG CAGGGCCAGAACCAGCTGTATAACGAGCTGAATCTGGG GCGGAGAGAGGAATACGACGTGCTGGATAAAAGGCGCG GGAGAGACCCAGAAATGGGGGGAAAGCCACGACGGAA AAACCCCCAGGAGGGACTGTACAATGAACTGCAGAAGG ATAAAATGGCAGAGGCCTATTCCGAAATCGGGATGAAG GGAGAAGAAGGCGAGGCAAAGGACACGACGGACTGT ACCAGGGGCTGTCTACCGCCACAAAGGACACCTATGAT GCTCTGCATATGCAGGCACTGCCACCCAGG |
| 612 | CD8α signal sequence, 3E10 scFv, CD8α hinge and transmembrane regions, 41BB cytoplasmic signaling domain, CD3ζ cytoplasmic signaling domain | ATGGCACTGCCTGTGACAGCCCTGCTGCTGCCACTGGCC CTGCTGCTGCACGCCGCCCGGCCACAGGTGCAGCTGCAG GAGTCCGGCCCAGGCCTGGTGAAGCCATCTGAGACACT GAGCCTGACCTGCAACGTGTCTGATGGCAGCATCAGCTC CTACTATTGGACCTGGATCAGACAGCCCCCTGGCAAGGG ACTGGACTGGATCGGCTATATCTTCTACAGCGGCACCAC AAACTATAATCCCTCCCTGAAGTCTAGAGTGACAATCTC CCTGGACACCTCTAAGAATCAGTTTTCTCTGAAGCTGAC AAGCATGACCGCCGCCGATACAGCCGTGTACTATTGCGC CAGGATCAGCGAGAAGTCCTTCTATTTTGACTACTGGGG CCAGGGCACACTGGTGACCGTGTCTAGCGGAGGAGGAG GCTCCGGAGGAGGAGGCTCTGGCGGCGGCGGCAGCGGA GGCGGCGGCTCCCAGTCTGTGCTGACCCAGCCACCAAGC GCCTCCGGAACACCTGGCCAGCGCGTGACCATCTCTTGT AGCGGCTCCTCTAGCAACATCGGCTCCAATTACGTGTAT TGGTACCAGCAGCTGCCTGGCACAGCCCCAAAGCTGCTG ATCTACTCCAACAATCAGCGGCCCAGCGGCGTGCCTGAT AGATTCTCCGGCTCTAAGAGCGGCACCTCCGCCTCTCTG GCAATCAGCGGACTGAGGTCCGAGGACGAGGCAGATTA CTATTGTGCACCATGGGACGATAGCCTGTCCGGCCGCGT GTTTGGAGGAGGAACAAAGCTGACCGTGCTGACCACAA CCCCTGCCCCTAGGCCACCTACCCCCAGCACCTACAATTG CTAGTCAGCCACTGTCACTGCGACCAGAGGCATGTCGAC CTGCAGCTGGAGGAGCAGTGCATACAAGGGGACTGGAC TTTGCCTGCGATATCTACATTTGGGCTCCTCTGGCAGGA ACATGTGGCGTGCTGCTGCTGAGCCTGGTCATCACTCTG TACTGCAAGCGAGGCCGGAAGAAACTGCTGTATATTTTC AAACAGCCCTTTATGCGACCTGTGCAGACCACACAGGA GGAAGATGGGTGCTCCTGTCGGTTCCCCGAGGAAGAGG AAGGAGGCTGTGAGCTGCGGGTCAAGTTTTCCAGATCTG CAGACGCCCCTGCTTACCAGCAGGGCCAGAACCAGCTGT ATAACGAGCTGAATCTGGGGCGGAGAGAGGAATACGAC GTGCTGGATAAAAGGCGCGGGAGAGACCCAGAAATGGG GGGAAAGCCACGACGGAAAAACCCCCAGGAGGGACTGT ACAATGAACTGCAGAAGGATAAAATGGCAGAGGCCTAT TCCGAAATCGGGATGAAGGGAGAAGAAGGCGAGGCA AAGGACACGACGGACTGTACCAGGGGCTGTCTACCGCC ACAAAGGACACCTATGATGCTCTGCATATGCAGGCACTG CCACCCAGG |
| 613 | CD8α signal sequence, 3C3 scFv, CD8α hinge and transmembrane regions, 41BB cytoplasmic signaling domain, CD3ζ cytoplasmic signaling domain | ATGGCCCTGCCAGTGACCGCCCTGCTGCTGCCACTGGCC CTGCTGCTGCACGCCGCCAGGCCCCAGGTGCAGCTGGTG CAGAGCGGAGCAGAGGTGAAGCGCCCTGGCGCAAGCGT GAAGGTGTCCTGCAAGGCCTCTGGCTATACATTCACCAG CTACTATATCCACTGGGTGAGGCAGGCCCCTGGCCAGGG ACTGGAGTGGATGGGCGTGATCGTGCCATCCGGCGGCTC TATCAGCTATGCCCAGAAGTTTCAGGGCAGGGTGACAAT GACCCGCGACACAAGCACCAACATCGTGTACATGGAGC TGAGCTCCCTGCGGTCCGAGGATACAGCCGTGTACTATT GTGCCAGAGACAGATACTATGGCGATTACTATTACGGAC TGGACGTGTGGGGACAGGGAACCACAGTGACCGTGTCT AGCGGCGGCGGCGGCTCTGGAGGAGGAGGCAGCGGCGG AGGAGGCTCCGGCGGCGGCGGCTCTGACATCCAGATGA CACAGTCCCCTTCCTCTCTGTCCGCCTCTGTGGGCGATCG GGTGACAATCACCTGCAGAGCCTCTCAGGGCATCAACA ATTTCCTGGCCTGGTTTCAGCAGAAGCCCGGCAAGGCCC |

TABLE 10-continued

Polynucleotide Sequences of exemplary DLL3 targeting CARs

| SEQ ID NO | CAR Structure | Nucleotide Sequence |
|---|---|---|
| | | CTAAGTCCCTGATCTACGCAGCAAGCTCCCTGCAGAGCG<br>GAGTGCCATCCAAGTTCAGCGGCTCCGGCTCTGGCACAG<br>ACTTTACACTGACCATCCGGTCTCTGCAGCCAGAGGATT<br>TCGCCACCTATTACTGTCAGCACTATAATAGCTACCCCA<br>TCACATTTGGCCAGGGCACCAGACTGGAGATCAAGACC<br>ACAACCCCCGCCCCTAGGCCACCTACCCCAGCACCTACA<br>ATTGCTAGTCAGCCACTGTCACTGCGACCAGAGGCATGT<br>CGACCTGCAGCTGGAGGAGCAGTGCATACAAGGGGACT<br>GGACTTTGCCTGCGATATCTACATTTGGGCTCCTCTGGC<br>AGGAACATGTGGCGTGCTGCTGCTGAGCCTGGTCATCAC<br>TCTGTACTGCAAGCGAGGCCGGAAGAAACTGCTGTATAT<br>TTTCAAACAGCCCTTTATGCGACCTGTGCAGACCACACA<br>GGAGGAAGATGGGTGCTCCTGTCGGTTCCCCGAGGAAG<br>AGGAAGGAGGCTGTGAGCTGCGGGTCAAGTTTTCCAGA<br>TCTGCAGACGCCCCTGCTTACCAGCAGGGCCAGAACCAG<br>CTGTATAACGAGCTGAATCTGGGGCGGAGAGAGGAATA<br>CGACGTGCTGGATAAAAGGCGCGGGAGAGACCCAGAAA<br>TGGGGGGAAAGCCACGACGGAAAAACCCCCAGGAGGG<br>ACTGTACAATGAACTGCAGAAGGATAAAATGGCAGAGG<br>CCTATTCCGAAATCGGGATGAAGGGAGAAAGAAGGCGA<br>GGCAAAGGACACGACGGACTGTACCAGGGGCTGTCTAC<br>CGCCACAAAGGACACCTATGATGCTCTGCATATGCAGGC<br>ACTGCCACCCAGG |
| 614 | CD8α signal sequence, 11F4 scFv, CD8α hinge and transmembrane regions, 41BB cytoplasmic signaling domain, CD3ζ cytoplasmic signaling domain | ATGGCACTGCCAGTGACAGCCCTGCTGCTGCCTCTGGCC<br>CTGCTGCTGCACGCCGCCCGGCCACAGGTGCACCTGCAG<br>GAGTCTGGCCCTGGCCTGGTGAAGCCATCTGAGACACTG<br>AGCCTGACATGTACCGTGAGCGGCGGCAGCATCTCCCAC<br>TACTATTGGACCTGGATCAGGCAGCCCCCTGGCAAGGGA<br>CTGGAGTGGATCGGCTACATCTACTATTCCGGCATCACC<br>AACTTCTCTCCTAGCCTGAAGTCTCGCGTGTCCATCTCTG<br>TGGACAGCTCCAAGAATCAGTTCAGCCTGAACCTGAACA<br>GCGTGACAGCCGCCGATACCGCCGTGTACTATTGCGCCG<br>GCATCTCCCTGGCCGGCTTCTACTTTGACTATTGGGTGCA<br>GGGCACACTGGTGACCGTGTCTAGCGGAGGAGGAGGCA<br>GCGGAGGAGGAGGCTCCGGAGGCGGCGGCTCTGGCGGC<br>GGCGGCAGCGAGATCGTGCTGACACAGAGCCCAGGCAC<br>CCTGAGCCTGTCCCCCGGCGAGCGGGCCACCCTGTCCTG<br>TAGAGCCTCTCAGAGCGTGTCCCGGTCTTACCTGGCCTG<br>GTATCAGCAGAAGCCAGGCCAGGCCCCCAGACTGCTGA<br>TCTATGGAGCATCCTCTAGGGCCACAGGAGTGCCAGACC<br>GCTTCAGCGGCTCCGGCTCTGGAACCGACTTCACCCTGA<br>CCATCAGCCGGCTGGAGCCTGAGGATTTCGCCGTGTTTT<br>ACTGCCAGCAGTATAGCATCTCCCCACTGACATTCGGCG<br>GCGGCACCAAGGTGGAGATCAAGACCACAACCCCTGCC<br>CCTAGGCCACCTACCCCAGCACCTACAATTGCTAGTCAG<br>CCACTGTCACTGCGACCAGAGGCATGTCGACCTGCAGCT<br>GGAGGAGCAGTGCATACAAGGGGACTGGACTTTGCCTG<br>CGATATCTACATTTGGGCTCCTCTGGCAGGAACATGTGG<br>CGTGCTGCTGCTGAGCCTGGTCATCACTCTGTACTGCAA<br>GCGAGGCCGGAAGAAACTGCTGTATATTTTCAAACAGCC<br>CTTTATGCGACCTGTGCAGACCACACAGGAGGAAGATG<br>GGTGCTCCTGTCGGTTCCCCGAGGAAGAGGAAGGAGGC<br>TGTGAGCTGCGGGTCAAGTTTTCCAGATCTGCAGACGCC<br>CCTGCTTACCAGCAGGGCCAGAACCAGCTGTATAACGA<br>GCTGAATCTGGGGCGGAGAGAGGAATACGACGTGCTGG<br>ATAAAAGGCGCGGGAGAGACCCAGAAATGGGGGGAAA<br>GCCACGACGGAAAAACCCCCAGGAGGGACTGTACAATG<br>AACTGCAGAAGGATAAAATGGCAGAGGCCTATTCCGAA<br>ATCGGGATGAAGGGAGAAAGAAGGCGAGGCAAAGGAC<br>ACGACGGACTGTACCAGGGGCTGTCTACCGCCACAAAG<br>GACACCTATGATGCTCTGCATATGCAGGCACTGCCACCC<br>AGG |
| 615 | CD8α signal sequence, 10E12 scFv, CD8α hinge and transmembrane regions, 41BB cytoplasmic signaling | ATGGCACTGCCTGTGACAGCCCTGCTGCTGCCACTGGCC<br>CTGCTGCTGCACGCCGCCCGGCCCCAGGTGCAGCTGCAG<br>GAGTCCGGCCCAGGCCTGGTGAAGCCAAGCGAGACCCT<br>GTCCCTGACATGCACCGTGTCCGGCGTGTCTATCAGCTC<br>CTACTATTGGAGCTGGATCAGGCAGCCCCCTGGCAAGGG<br>ACTGGAGTGGATCGCCTACATCTACTATTCCGGCAACAC<br>CAATTATTCTCCTAGCCTGAAGTCTCGCGTGACAATCTCT<br>GTGGACACCAGCAAGGATCAGCTGTCTCTGAAGCTGTCT<br>AGCGTGACAGCCGCCGACACCGCCGTGTACTATTGCACA<br>AGGGGCGGCAGCGGAACCATCGACGTGTTCGATATCTG |

TABLE 10-continued

Polynucleotide Sequences of exemplary DLL3 targeting CARs

| SEQ ID NO | CAR Structure | Nucleotide Sequence |
|---|---|---|
| | domain, CD3ζ cytoplasmic signaling domain | GGGACAGGGAACCATGGTGGCCGTGTCCTCTGGCGGCG GCGGCTCCGGAGGCGGCGGCTCTGGAGGAGGAGGCAGC GGCGGAGGAGGCTCCCAGTCTGTGCTGACACAGCCACC AAGCGTGTCCGCCGCCCCAGGCCAGAAGGTGACCATCTC TTGTAGCGGCAGCTCCTCTAACATCGGCAACAATTACGT GTCCTGGTATCAGCAGCTGCCTGGCACAGCCCCAAAGCT GCTGATCTACGACAACAATAAGCGGCCCAGCGGCATCC CTGATAGATTCTCCGGCTCTAAGAGCGGCACATCCGCCA CCCTGGGCATCACAGGACTGCAGACCGGCGACGAGGCA GATTACTATTGTGAGACCTGGGATAGCTCCCTGAGCGCC GTGGTGTTTGGAGGAGGCACAAAGCTGACCGTGCTGAC CACAACCCCTGCCCCTAGGCCACCTACCCCAGCACCTAC AATTGCTAGTCAGCCACTGTCACTGCGACCAGAGGCATG TCGACCTGCAGCTGGAGGAGCAGTGCATACAAGGGGAC TGGACTTTGCCTGCGATATCTACATTTGGGCTCCTCTGGC AGGAACATGTGGCGTGCTGCTGCTGAGCCTGGTCATCAC TCTGTACTGCAAGCGAGGCCGGAAGAAACTGCTGTATAT TTTCAAACAGCCCTTTATGCGACCTGTGCAGACCACACA GGAGGAAGATGGGTGCTCCTGTCGGTTCCCCGAGGAAG AGGAAGGAGGCTGTGAGCTGCGGGTCAAGTTTTCCAGA TCTGCAGACGCCCCTGCTTACCAGCAGGGCCAGAACCAG CTGTATAACGAGCTGAATCTGGGGCGGAGAGAGGAATA CGACGTGCTGGATAAAAGGCGCGGGAGAGACCCAGAAA TGGGGGGAAAGCCACGACGGAAAAACCCCCAGGAGGG ACTGTACAATGAACTGCAGAAGGATAAAATGGCAGAGG CCTATTCCGAAATCGGGATGAAGGGAGAAAGAAGGCGA GGCAAAGGACACGACGGACTGTACCAGGGGCTGTCTAC CGCCACAAAGGACACCTATGATGCTCTGCATATGCAGGC ACTGCCACCCAGG |
| 616 | CD8α signal sequence, 4E1 scFv, CD8α hinge and transmembrane regions, 41BB cytoplasmic signaling domain, CD3ζ cytoplasmic signaling domain | ATGGCACTGCCTGTGACAGCCCTGCTGCTGCCACTGGCC CTGCTGCTGCACGCCGCCCGGCCTCAGGTGCAGCTGCAG CAGAGCGGCCCCAGGCCTGGTGAAGCCATCCCAGACACT GTCTCTGACCTGCGCCATCTCCGGCGACAACGTGTCCAC AAATTCTGCCGCCTGGAACTGGATCAGGCAGAGCCCATC CCGCGGCCTGGAGTGGCTGGGCTGACCTACTATAGGA GCAAGTGGTACAATGACTATGCCGTGAGCCTGAAGTCCC GCATCAACATCAATCCAGATACCTCCAAGAACCAGTTCT CTCTGCAGCTGAATAGCGTGACACCCGAGGATACCGCCG TGTACTATTGCGCCCGGTGGGTGAACAGAGACGTGTTTG ATATCTGGGGCCAGGGCACAATGGTGACCGTGAGCTCC GGAGGAGGAGGCTCCGGCGGCGGAGGCTCTGGCGGCGG CGGCAGCGGAGGCGGCGGCTCTCAGAGCGCCCTGACAC AGCCAGCATCCGTGTCTGGCAGCCCTGGCCAGAGCATCA CCATCTCCTGTACAGGCACCTCTAGCGACGTGGGCTCCT ACAATCTGGTGTCTTGGTATCAGCAGCACCCCGGCAAGG CCCCTAAGCTGATGATCTACGAGGGCAGCAAGAGGCCA TCTGGCGTGAGCAACAGATTCTCCGGCTCTAAGAGCGGC AATACAGCCTCTCTGACCATCAGCGGACTGCAGGCAGA GGACGAGGCAGATTACTATTGCTGTTCCTATGCCGGCTC CTCTACCTGGGTGTTTGGCGGCGGCACAAAGCTGACCGT GCTGACCACAACCCCTGCCCCTAGGCCACCTACCCCAGC ACCTACAATTGCTAGTCAGCCACTGTCACTGCGACCAGA GGCATGTCGACCTGCAGCTGGAGGAGCAGTGCATACAA GGGGACTGGACTTTGCCTGCGATATCTACATTTGGGCTC CTCTGGCAGGAACATGTGGCGTGCTGCTGCTGAGCCTGG TCATCACTCTGTACTGCAAGCGAGGCCGGAAGAAACTGC TGTATATTTTCAAACAGCCCTTTATGCGACCTGTGCAGA CCACACAGGAGGAAGATGGGTGCTCCTGTCGGTTCCCCG AGGAAGAGGAAGGAGGCTGTGAGCTGCGGGTCAAGTTT TCCAGATCTGCAGACGCCCCTGCTTACCAGCAGGGCCAG AACCAGCTGTATAACGAGCTGAATCTGGGGCGGAGAGA GGAATACGACGTGCTGGATAAAAGGCGCGGGAGAGACC CAGAAATGGGGGGAAAGCCACGACGGAAAAACCCCCAG GAGGGACTGTACAATGAACTGCAGAAGGATAAAATGGC AGAGGCCTATTCCGAAATCGGGATGAAGGGAGAAAGAA GGCGAGGCAAAGGACACGACGGACTGTACCAGGGGCTG TCTACCGCCACAAAGGACACCTATGATGCTCTGCATATG CAGGCACTGCCACCCAGG |
| 617 | CD8α signal sequence, 2404.6H1 scFv, CD8α | ATGGCCCTGCCAGTGACCGCCCTGCTGCTGCCCCTGGCC CTGCTGCTGCACGCCGCCAGGCCCCAGGTGCAGCTGGTG GAGTCCGGAGGAGGAGTGGTGCAGCCTGGCCGGTCTCT GAGACTGAGCTGCGCAGCATCCGGCTTCACCTTCAGCTC |

TABLE 10-continued

Polynucleotide Sequences of exemplary DLL3 targeting CARs

| SEQ ID NO | CAR Structure | Nucleotide Sequence |
|---|---|---|
| | hinge and transmembrane regions, 41BB cytoplasmic signaling domain, CD3ζ cytoplasmic signaling domain | CTACGGAATGCACTGGGTGCGGCAGACCCCTGGCAAGG GACTGGAGTGGGTGGCCGTGATCTCCTATGACGGCAACT CTAATTACTATGCCGATAGCGTGAAGGGCAGGTTCACAA TCTCTCGCGACAACAGCAAGAATACCCTGTACCTGCAGA TGAACTCTCTGCGGGCCGAGGACACAGCCGTGTACTATT GTGCCAGAGATGGCGCCACAGTGACCAGCTACTATTACT ATGGCATGGACGTGTGGGGCCAGGGCACCACAGTGACC GTGTCTAGCGGAGGAGGAGGCAGCGGAGGAGGAGGCTC CGGAGGCGGCGGCTCTGGCGGCGGCGGCAGCGAGATCG TGCTGACACAGTCCCCTGGCACCCTGAGCCTGTCCCCAG GCGAGCGGGCCACACTGTCTTGCAGAGCCTCTCAGAGCG TGTCCAGGACCTACCTGGCCTGGTATCACCAGAAGCCTG GCCAGGCACCTCGCCTGCTGATCTACGGAGCATCCTCTA GGGCCACAGGCATCAGCGACCGCTTCTCTGGCAGCGGCT CCGGAACCGACTTCACCCTGACCATCTCCCGGCTGGAGC CAGAGGACTTCGCCGTGTACTATTGTCAGCAGTATGGCA CATCCCCCATCACCTTTGGCCAGGGCACCAGACTGGAGA TCAAGACCACAACCCCCGCCCCTAGGCCACCTACCCCAG CACCTACAATTGCTAGTCAGCCACTGTCACTGCGACCAG AGGCATGTCGACCTGCAGCTGGAGGAGCAGTGCATACA AGGGGACTGGACTTTGCCTGCGATATCTACATTTGGGCT CCTCTGGCAGGAACATGTGGCGTGCTGCTGCTGAGCCTG GTCATCACTCTGTACTGCAAGCGAGGCCGGAAGAAACT GCTGTATATTTTCAAACAGCCCTTTATGCGACCTGTGCA GACCACACAGGAGGAAGATGGGTGCTCCTGTCGGTTCCC CGAGGAAGAGGAAGGAGGCTGTGAGCTGCGGGTCAAGT TTTCCAGATCTGCAGACGCCCCTGCTTACCAGCAGGGCC AGAACCAGCTGTATAACGAGCTGAATCTGGGGCGGAGA GAGGAATACGACGTGCTGGATAAAAGGCGCGGGAGAGA CCCAGAAATGGGGGGGAAAGCCACGACGGAAAAACCCCC AGGAGGGACTGTACAATGAACTGCAGAAGGATAAAATG GCAGAGGCCTATTCCGAAATCGGGATGAAGGGAGAAAG AAGGCGAGGCAAAGGACACGACGGACTGTACCAGGGGC TGTCTACCGCCACAAAGGACACCTATGATGCTCTGCATA TGCAGGCACTGCCACCCAGG |
| 618 | CD8α signal sequence, 2A8 scFv, CD8α hinge and transmembrane regions, 41BB cytoplasmic signaling domain, CD3ζ cytoplasmic signaling domain | ATGGCACTGCCTGTGACAGCCCTGCTGCTGCCACTGGCC CTGCTGCTGCACGCCGCCAGGCCCCAGGTGCAGCTGCAG CAGAGCGGCCCCAGGCCTGGTGAAGCCATCTCAGACACT GAGCCTGACCTGCGCCATCTCTGGCGACAGCGTGAGCTC CAACTCCGCCGTGTGGAATTGGATCAGGCAGAGCCCTTC CCGCGGCCTGGAGTGGCTGGGACGGACCTACTATAGATC TAAGTGGTACAACGACTATGCCGTGTCCGTGAAGTCTAG GATCACAATCAACCCCGATACCTCCCGCAATCAGTTCTC TCTGCAGCTGAATAGCGTGACACCTGAGGATACCGCCGT GTACTATTGCGCCAGAGGCGGAATCGTGGGCGCCCCAG ACGGCTTTGATATCTGGGGCCAGGGCACAATGGTGACCG TGTCTAGCGGAGGAGGAGGCTCCGGAGGAGGAGGCTCT GGCGGCGGCGGCAGCGGAGGCGGCGGCTCCGACATCGT GATGACACAGAGCCCTGATTCCCTGGCCGTGTCTCTGGG CGAGAGGGCAACCATCAACTGTAAGTCCTCTCAGAGCGT GCTGGACAGCTCCAACAATAACAATTACTTCGCCTGGTA TCAGCAGAGACCTGGCCAGCCCCCTCACCTGCTGATCTA CTGGGCATCTAGCCGGGAGAGCGGAGTGCCAGACAGAT TCTCTGGCAGCGGCTCCGGCACAGACTTCACCCTGACCA TCTCCTCTCTGCAGGCCGAGGATGTGGCCGTGTACTATT GTCAGCAGTACTATTCCACACCATATACCTTTGGCCAGG GCACCAAGCTGGAGATCAAGACCACAACCCCCGCCCCT AGGCCACCTACCCCAGCACCTACAATTGCTAGTCAGCCA CTGTCACTGCGACCAGAGGCATGTCGACCTGCAGCTGGA GGAGCAGTGCATACAAGGGGACTGGACTTTGCCTGCGA TATCTACATTTGGGCTCCTCTGGCAGGAACATGTGGCGT GCTGCTGCTGAGCCTGGTCATCACTCTGTACTGCAAGCG AGGCCGGAAGAAACTGCTGTATATTTTCAAACAGCCCTT TATGCGACCTGTGCAGACCACACAGGAGGAAGATGGGT GCTCCTGTCGGTTCCCCGAGGAAGAGGAAGGAGGCTGT GAGCTGCGGGTCAAGTTTTCCAGATCTGCAGACGCCCCT GCTTACCAGCAGGGCCAGAACCAGCTGTATAACGAGCT GAATCTGGGGCGGAGAGAGGAATACGACGTGCTGGATA AAAGGCGCGGGAGAGACCCAGAAATGGGGGGGAAAGCC ACGACGGAAAAACCCCCAGGAGGGACTGTACAATGAAC TGCAGAAGGATAAAATGGCAGAGGCCTATTCCGAAATC GGGATGAAGGGAGAAAGAAGGCGAGGCAAAGGACACG |

TABLE 10-continued

Polynucleotide Sequences of exemplary DLL3 targeting CARs

| SEQ ID NO | CAR Structure | Nucleotide Sequence |
|---|---|---|
| | | ACGGACTGTACCAGGGGCTGTCTACCGCCACAAAGGAC ACCTATGATGCTCTGCATATGCAGGCACTGCCACCCAGG |
| 619 | CD8α signal sequence, 3B1 scFv, CD8α hinge and transmembrane regions, 41BB cytoplasmic signaling domain, CD3ζ cytoplasmic signaling domain | ATGGCCCTGCCAGTGACCGCCCTGCTGCTGCCACTGGCC CTGCTGCTGCACGCCGCCCGGCCACAGGTGCAGCTGCAG CAGAGCGGCCCTGGCCTGGTGAAGCCTAGCCAGACACT GTCCCTGACCTGCACCGTCTCTGGCGACAGCGTGAGCTC CAACACCACAGCCTGGAAGTGGAGCAGACAGTCCCCCT CTAAGGGCCTGGAGTGGCTGGGCTGGACATACTATAGGT CCAAGTGGTACTATGACTACACCGTGTCCGTGAAGTCTC GCATCACAATCAACCCCGATACCTCCAAGAATCAGTTCT CTCTGCAGCTGAATAGCGTGACACCTGAGGATACCGCCG TGTACTATTGCGCCAGGTGGATCTTCCACGACGCCTTTG ATATCTGGGGCCAGGGCACAATGGTGACCGTGTCTAGCG GAGGAGGAGGCTCCGGAGGAGGAGGCTCTGGCGGCGGC GGCAGCGGAGGCGGCGGCAGCCAGTCCGCCCTGACACA GCCACCTTCTGCCAGCGGAACACCTGGCCAGAGAGTGA CCATCTCCTGTTCTGGCTCCTCTAGCAACATCGGCAGCA ACACCGTGAATTGGTACCAGCAGCTGCCAGGCACAGCC CCCAAGCTGCTGATCTATACCAACAATCAGAGGCCTTCC GGAGTGCCAGACCGGTTCAGCGGCTCCAAGTCTGGCAC AAGCGCCTCCCTGGCCATCTCTGGCCTGCAGAGCGAGGA CGAGGCCGATTATTTCTGTTCCACCTGGGACGATTCTCT GAATGGACCCGTGTTCGGAGGAGGAACAAAGCTGACCG TGCTGACCACAACCCCAGCCCCTAGGCCACCTACCCCAG CACCTACAATTGCTAGTCAGCCACTGTCACTGCGACCAG AGGCATGTCGACCTGCAGCTGGAGGAGCAGTGCATACA AGGGGACTGGACTTTGCCTGCGATATCTACATTTGGGCT CCTCTGGCAGGAACATGTGGCGTGCTGCTGCTGAGCCTG GTCATCACTCTGTACTGCAAGCGAGGCCGGAAGAAACT GCTGTATATTTTCAAACAGCCCTTTATGCGACCTGTGCA GACCACACAGGAGGAAGATGGGTGCTCCTGTCGGTTCCC CGAGGAAGAGGAAGGAGGCTGTGAGCTGCGGGTCAAGT TTTCCAGATCTGCAGACGCCCCTGCTTACCAGCAGGGCC AGAACCAGCTGTATAACGAGCTGAATCTGGGGCGGAGA GAGGAATACGACGTGCTGGATAAAAGGCGCGGGAGAGA CCCAGAAATGGGGGGAAAGCCACGACGGAAAAACCCCC AGGAGGGACTGTACAATGAACTGCAGAAGGATAAAATG GCAGAGGCCTATTCCGAAATCGGGATGAAGGGAGAAAG AAGGCGAGGCAAAGGACACGACGGACTGTACCAGGGGC TGTCTACCGCCACAAAGGACACCTATGATGCTCTGCATA TGCAGGCACTGCCACCCAGG |
| 620 | CD8α signal sequence, 9B5 scFv, CD8α hinge and transmembrane regions, 41BB cytoplasmic signaling domain, CD3ζ cytoplasmic signaling domain | ATGGCACTGCCTGTGACAGCCCTGCTGCTGCCACTGGCC CTGCTGCTGCACGCCGCCCAGACCCCAGGTGCAGCTGCAG GAGTCCGGCCCAGGCCTGGTGAAGCCAAGCGAGACCCT GTCCCTGACATGCACCGTGTCTGGCGACAGCATCAGCTC CCTGTCTTGGAGCTGGATCAGGCAGACACCAGGCGAGG GCCTGGAGTGGATCGGCTACCTGTACTATTCCGGCTCTA CCGACTATAACCCCTCCCTGAAGTCTCGCGTGACAATCT CTGTGGATACCAGCAAGAATCAGTTCTCTCTGAAGCTGC GGAGCGTGGCTGCCGCCGACACAGCCCTGTACTATTGCG CCAGAGGCCGGAGAGCCTTTGATATCTGGGGCCAGGGC ACAATGGTGACCGTGTCTAGCGGAGGAGGAGGCTCCGG AGGAGGAGGCTCTGGCGGCGGCGGCAGCGGAGGCGGCG GCTCCGACATCCAGATGACCCAGAGCCCTTCCTCTCTGA GCGCCTCCGTGGGCGATAGGGTGACAATCACCTGTCGCG GCTCCCAGGGCATCTCTAACTACCTGGCATGGTTCCAGC AGCGGCCCGGCAAGGCACCTAAGTCTCTGATCTATGCAG CAAGCTCCCTGGAGAGCGGAGTGCCATCCAAGTTCTCTG GCAGCGGCTCCGGCACAGACTTTACACTGACCATCATCA GCCTGCAGCCCGAGGATTTCGCCACCTACTATTGTCAGC AGTACTATAATTACCCTATCACATTTGGCCAGGGCACCC GGCTGGAGATCAAGACCACAACCCCTGCCCCTAGGCCA CCTACCCCAGCACCTACAATTGCTAGTCAGCCACTGTCA CTGCGACCAGAGGCATGTCGACCTGCAGCTGGAGGAGC AGTGCATACAAGGGGACTGGACTTTGCCTGCGATATCTA CATTTGGGCTCCTCTGGCAGGAACATGTGGCGTGCTGCT GCTGAGCCTGGTCATCACTCTGTACTGCAAGCGAGGCCG GAAGAAACTGCTGTATATTTTCAAACAGCCCTTTATGCG ACCTGTGCAGACCACACAGGAGGAAGATGGGTGCTCCT GTCGGTTCCCCGAGGAAGAGGAAGGAGGCTGTGAGCTG CGGGTCAAGTTTTCCAGATCTGCAGACGCCCCTGCTTAC CAGCAGGGCCAGAACCAGCTGTATAACGAGCTGAATCT |

Polynucleotide Sequences of exemplary DLL3 targeting CARs

TABLE 10-continued

| Polynucleotide Sequences of exemplary DLL3 targeting CARs | | |
| --- | --- | --- |

SEQ
ID CAR
NO Structure     Nucleotide Sequence

```
                GGGGCGGAGAGAGGAATACGACGTGCTGGATAAAAGGC
                GCGGGAGAGACCCAGAAATGGGGGGAAAGCCACGACG
                GAAAAACCCCCAGGAGGGACTGTACAATGAACTGCAGA
                AGGATAAAATGGCAGAGGCCTATTCCGAAATCGGGATG
                AAGGGAGAAAGAAGGCGAGGCAAAGGACACGACGGAC
                TGTACCAGGGGCTGTCTACCGCCACAAAGGACACCTATG
                ATGCTCTGCATATGCAGGCACTGCCACCCAGG

621 CD8α signal   ATGGCACTGCCTGTGACCGCCCTGCTGCTGCCACTGGCC
    sequence,    CTGCTGCTGCACGCCGCCCGGCCACAGGTGCAGCTGGTG
    11A5 scFv,   CAGTCTGGAGCAGAGGTGAAGAAGCCTGGCGCAAGCGT
    CD8α hinge   GAAGGTGTCCTGCAAGGCCTCTGGCTACACATTCACCGG
    and          CTACTATATGCACTGGGTGAGACAGGCCCCTGGCCAGGG
    transmembrane ACTGGAGTGGATGGGCTGGATCAACCCTAATAGCGGCG
    regions,     GCACCAACTACGCCCAGAAGTTTCAGGGCCGGGTGACA
    41BB         ATGACCAGAGACACCAGCGTGTCCACAGCCTATATGGA
    cytoplasmic  GCTGAGCAGGCTGACCTCCGACGATACAGCCATCTACTA
    signaling    TTGTGCCAAGGACGGCGGCGGCGATTTCTACTTTTATGG
    domain, CD3ζ CATGGACGTGTGGGGCCAGGGCACCACAGTGACCGTGA
    cytoplasmic  GCTCCGGCGGCGGCGGCTCTGGAGGAGGAGGCAGCGGC
    signaling    GGAGGAGGCTCCGGAGGAGGCGGCTCTCAGACCGTGGT
    domain       GACACAGGAGCCATCTTTCAGCGTGTCCCCCGGCGGAAC
                 AGTGACCCTGACATGCGGCCTGTCTAGCGGCTCTGTGAG
                 CACATCCTACTATCCTAGCTGTTTCCAGCAGACCCCCGG
                 CCAGGCACCTAGAACACTGATCTACTCCACCGACACAAG
                 GTCCTCTGGCGTGCCAGATCGCTTTTCTGGCAGCATCCT
                 GGGCAATAAGGCCGCCCTGACCATCACAGGAGCACAGG
                 CCGACGATGAGTCCGACTACTATTGCGTGCTGTATATGG
                 GCTCCGGAATCAGCGTGTTCGGAGGAGGCACCAAGCTG
                 ACAGTGCTGACCACAACCCCCGCCCCTAGGCCACCTACC
                 CCAGCACCTACAATTGCTAGTCAGCCACTGTCACTGCGA
                 CCAGAGGCATGTCGACCTGCAGCTGGAGGAGCAGTGCA
                 TACAAGGGGACTGGACTTTGCCTGCGATATCTACATTTG
                 GGCTCCTCTGGCAGGAACATGTGGCGTGCTGCTGCTGAG
                 CCTGGTCATCACTCTGTACTGCAAGCGAGGCCGGAAGAA
                 ACTGCTGTATATTTTCAAACAGCCCTTTATGCGACCTGTG
                 CAGACCACACAGGAGGAAGATGGGTGCTCCTGTCGGTT
                 CCCCGAGGAAGAGGAAGGAGGCTGTGAGCTGCGGGTCA
                 AGTTTTCCAGATCTGCAGACGCCCCTGCTTACCAGCAGG
                 GCCAGAACCAGCTGTATAACGAGCTGAATCTGGGGCGG
                 AGAGAGGAATACGACGTGCTGGATAAAAGGCGCGGGAG
                 AGACCCAGAAATGGGGGGAAAGCCACGACGGAAAAAC
                 CCCCAGGAGGGACTGTACAATGAACTGCAGAAGGATAA
                 AATGGCAGAGGCCTATTCCGAAATCGGGATGAAGGGAG
                 AAAGAAGGCGAGGCAAAGGACACGACGGACTGTACCAG
                 GGGCTGTCTACCGCCACAAAGGACACCTATGATGCTCTG
                 CATATGCAGGCACTGCCACCCAGG
``` b. Safety Switches and Monoclonal Antibody Specific-Epitopes

Safety Switches

It will be appreciated that adverse events may be minimized by transducing the immune cells (containing one or more CARs) with a suicide gene. It may also be desired to incorporate an inducible "on" or "accelerator" switch into the immune cells. Suitable techniques include use of inducible caspase-9 (U.S. Appl. 2011/0286980) or a thymidine kinase, before, after or at the same time, as the cells are transduced with the CAR construct of the present disclosure. Additional methods for introducing suicide genes and/or "on" switches include TALENS, zinc fingers, RNAi, siRNA, shRNA, antisense technology, and other techniques known in the art.

In accordance with the disclosure, additional on-off or other types of control switch techniques may be incorporated herein. These techniques may employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US2015/0266973, US2016/0046700, U.S. Pat. No. 8,486,693, US 2014/0171649, and US 2012/0130076, the contents of which are further incorporated by reference herein in their entirety.

In some embodiments, the CAR-immune cell (e.g., CAR-T cell) of the disclosure comprises a polynucleotide encoding a suicide polypeptide, such as for example RQR8. See, e.g., WO2013153391A, which is hereby incorporated by reference in its entirety. In CAR-immune cell (e.g., CAR-T cell) cells comprising the polynucleotide, the suicide polypeptide is expressed at the surface of a CAR-immune cell (e.g., CAR-T cell). In some embodiments, the suicide polypeptide comprises the amino acid sequence shown in SEQ ID NO: 552:

(SEQ ID NO: 552)
CPYSNPSLCSGGGGSELPTQGTFSNVSTNVSPAKPTTTACPYSNPSLCSG

GGGSPAPRPPTPAPTIASQPLSLRPEACRPAAGGAVHTRGLDFACDIYIW

APLAGTCGVLLLSLVITLYCNHRNRRRVCKCPRPVV.

The suicide polypeptide may also comprise a signal peptide at the amino terminus—for example, MGTSLLCW-MALCLLGADHADA (SEQ ID NO: 553). In some embodiments, the suicide polypeptide comprises the amino acid sequence shown in SEQ ID NO: 554, which includes the signal sequence of SEQ ID NO: 553:

(SEQ ID NO: 554)
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDIYIWAPLAGTCGVLLLSLVITLYCNHRNRRRVC

KCPRPVV.

When the suicide polypeptide is expressed at the surface of a CAR-immune cell (e.g., CAR-T cell), binding of rituximab to the R epitopes of the polypeptide causes lysis of the cell. More than one molecule of rituximab may bind per polypeptide expressed at the cell surface. Each R epitope of the polypeptide may bind a separate molecule of rituximab. Deletion of DLL3-specific CAR-immune cell (e.g., CAR-T cell) may occur in vivo, for example by administering rituximab to a patient. The decision to delete the transferred cells may arise from undesirable effects being detected in the patient which are attributable to the transferred cells, such as for example, when unacceptable levels of toxicity are detected.

In some embodiments, a suicide polypeptide is expressed on the surface of the cell. In some embodiments, a suicide polypeptide is included in the CAR construct. In some embodiments, a suicide polypeptide is not part of the DLL3 CAR construct.

In some embodiments, the extracellular domain of any one of the DLL3-specific CARs disclosed herein may comprise one or more epitopes specific for (i.e., specifically recognized by) a monoclonal antibody. These epitopes are also referred to herein as mAb-specific epitopes. Exemplary mAb-specific epitopes are disclosed in International Patent Publication No. WO 2016/120216, which is incorporated herein in its entirety. In these embodiments, the extracellular domain of the CARs comprise antigen binding domains that specifically bind to DLL3 and one or more epitopes that bind to one or more monoclonal antibodies (mAbs). CARs comprising the mAb-specific epitopes can be single-chain or multi-chain.

The inclusion of epitopes specific for monoclonal antibodies in the extracellular domain of the CARs described herein allows sorting and depletion of engineered immune cells expressing the CARs. In some embodiments, this feature also promotes recovery of endogenous DLL3-expressing cells that were depleted by administration of engineered immune cells expressing the CARs. In some embodiments, allowing for depletion provides a safety switch in case of deleterious effects, e.g., upon administration to a subject.

Accordingly, in some embodiments, the present disclosure relates to a method for sorting and/or depleting the engineered immune cells endowed with the CARs comprising mAb-specific epitopes and a method for promoting recovery of endogenous DLL3-expressing cells.

Several epitope-monoclonal antibody couples can be used to generate CARs comprising monoclonal antibody specific epitopes; in particular, those already approved for medical use, such as CD20 epitope/rituximab as a non-limiting example.

The disclosure also encompasses methods for sorting the engineered immune cells endowed with the DLL3-specific CARs expressing the mAb-specific epitope(s) and therapeutic methods where the activation of the engineered immune cells endowed with these CARs is modulated by depleting the cells using an antibody that targets the external ligand binding domain of said CARs. Table 4 provides exemplary mimotope sequences that can be inserted into the extracellular domains of any one of the CARs of the disclosure.

TABLE 4

| Exemplary mimotope sequences | | |
|---|---|---|
| Rituximab | | |
| Mimotope | SEQ ID NO: 536 | CPYSNPSLC |
| Palivizumab | | |
| Epitope | SEQ ID NO: 537 | NSELLSLINDMPITNDQKKLMSNN |
| Cetuximab | | |
| Mimotope 1 | SEQ ID NO: 538 | CQFDLSTRRLKC |
| Mimotope 2 | SEQ ID NO: 539 | CQYNLSSRALKC |
| Mimotope 3 | SEQ ID NO: 540 | CVWQRWQKSYVC |
| Mimotope 4 | SEQ ID NO: 541 | CMWDRFSRWYKC |
| Nivolumab | | |
| Epitope 1 | SEQ ID NO: 542 | SFVLNWYRMSPSNQTDKLAAFPEDR |
| Epitope 2 | SEQ ID NO: 543 | SGTYLCGAISLAPKAQIKE |
| QBEND-10 | | |
| Epitope | SEQ ID NO: 544 | ELPTQGTFSNVSTNVSPAKPTTTA |
| | SEQ ID NO: 471 | ELPTQGTFSNVSTNVS |
| Alemtuzumab | | |
| Epitope | SEQ ID NO: 545 | GQNDTSQTSSPS |

In some embodiments, the extracellular binding domain of the CAR comprises the following sequence:

$V_1$-$L_1$-$V_2$-(L)$_x$-Epitope1-(L)$_x$-;

$V_1$-$L_1$-$V_2$-(L)$_x$-Epitope1-(L)$_x$-Epitope2-(L)$_x$-;

$V_1$-$L_1$-$V_2$-(L)$_x$-Epitope1-(L)$_x$-Epitope2-(L)$_x$-Epitope3-(L)$_x$-;

(L)$_x$-Epitope1-(L)$_x$-$V_1$-$L_1$-$V_2$;

(L)$_x$-Epitope1-(L)$_x$-Epitope2-(L)$_x$-$V_1$-$L_1$-$V_2$;

Epitope1-(L)$_x$-Epitope2-(L)$_x$-Epitope3-(L)$_x$-$V_1$-$L_1$-$V_2$;

(L)$_x$-Epitope1-(L)$_x$-$V_1$-$L_1$-$V_2$-(L)$_x$-Epitope2-(L)$_x$;

(L)$_x$-Epitope1-(L)$_x$-$V_1$-$L_1$-$V_2$-(L)$_x$-Epitope2-(L)$_x$-Epitope3-(L)$_x$-;

(L)$_x$-Epitope1-(L)$_x$-$V_1$-$L_1$-$V_2$-(L)$_x$-Epitope2-(L)$_x$-Epitope3-(L)$_x$-Epitope4-(L)$_x$-;

$(L)_x$-Epitope1-$(L)_x$-Epitope2-$(L)_x$-$V_1$-$L_1$-$V_2$-$(L)_x$-
   Epitope3-$(L)_x$-;

$(L)_x$-Epitope1-$(L)_x$-Epitope2-$(L)_x$-$V_1$-$L_1$-$V_2$-$(L)_x$-
   Epitope3-$(L)_x$-Epitope4-$(L)_x$-;

$V_1$-$(L)_x$-Epitope1-$(L)_x$-$V_2$;

$V_1$-$(L)_x$-Epitope1-$(L)_x$-$V_2$-$(L)_x$-Epitope2-$(L)_x$;

$V_1$-$(L)_x$-Epitope1-$(L)_x$-$V_2$-$(L)_x$-Epitope2-$(L)_x$-Epitope3-
   $(L)_x$;

$V_1$-$(L)_x$-Epitope1-$(L)_x$-$V_2$-$(L)_x$-Epitope2-$(L)_x$-Epitope3-
   $(L)_x$-Epitope4-$(L)_x$;

$(L)_x$-Epitope1-$(L)_x$-$V_1$-$(L)_x$-Epitope2-$(L)_x$-$V_2$; or, $(L)_x$-Epitope1-$(L)_x$-$V_1$-$(L)_x$-Epitope2-$(L)_x$-$V_2$-$(L)_x$-
   Epitope3-$(L)_x$;

wherein, $V_1$ is $V_L$ and $V_2$ is $V_H$ or $V_1$ is $V_H$ and $V_2$ is $V_L$;

$L_1$ is a linker suitable to link the $V_H$ chain to the $V_L$ chain;

Epitope 1, Epitope 2, Epitope 3 and Epitope 4 are mAb-
   specific epitopes and can be identical or c. Hinge Domain The extracellular domain of the CARS of the disclosure may comprise a "hinge" domain (or hinge region). The term generally to any polypeptide that functions to link the transmembrane domain in a CAR to the extracellular antigen binding domain in a CAR. In particular, hinge domains can be used to provide more flexibility and accessibility for the extracellular antigen binding domain.

A hinge domain may comprise up to 300 amino acids—in some embodiments 10 to 100 amino acids or in some embodiments 25 to 50 amino acids. The hinge domain may be derived from all or part of naturally occurring molecules, such as from all or part of the extracellular region of CD8, CD4, CD28, 4-1BB, or IgG (in particular, the hinge region of an IgG; it will be appreciated that the hinge region may contain some or all of a member of the immunoglobulin family such as IgG1, IgG2, IgG3, IgG4, IgA, IgD, IgE, IgM, or fragment thereof), or from all or part of an antibody heavy-chain constant region. Alternatively, the A domain may be a synthetic sequence that corresponds to a naturally occurring A sequence or may be an entirely synthetic A sequence. In some embodiments said A domain is a part of human CD8α chain (e.g., NP_001139345.1). In another particular embodiment, said hinge and transmembrane domains comprise a part of human CD8α chain. In some embodiments, the hinge domain of CARs described herein comprises a subsequence of CD8α, CD28, an IgG1, IgG4, PD-1 or an FcγRIIIα, in particular the hinge region of any of an CD8α, CD28, an IgG1, IgG4, PD-1 or an FcγRIIIα. In some embodiments, the hinge domain comprises a human CD8α hinge, a human IgG1 hinge, a human IgG4, a human PD-1 or a human FcγRIIIα hinge. In some embodiments the CARs disclosed herein comprise a scFv, CD8α human hinge and transmembrane domains, the CD3ζ signaling domain, and 4-1BB signaling domain. Table 5 provides amino acid sequences for exemplary hinges provided herein.

TABLE 5

Exemplary hinges

| Domain | Amino Acid Sequence | SEQ ID NO: |
|---|---|---|
| FcγRIIIα hinge | GLAVSTISSFFPPGYQ | 546 |
| CD8α hinge | TTTPAPRPPTPAPTIASQPLSLRPEACRPAAGG AVHTRGLDFACD | 547 |

TABLE 5-continued

Exemplary hinges

| Domain | Amino Acid Sequence | SEQ ID NO: |
|---|---|---|
| IgG1 hinge | EPKSPDKTHTCPPCPAPPVAGPSVFLFPPKPKD TLMIARTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK | 548 |

In certain embodiments, the hinge region comprises an amino acid sequence that is at least about 75%, at least about 80%, at least about 85%, at least about 90%, at least about 95%, at least about 96%, at least about 97%, at least about 98%, at least about 99%, or 100% identical to the extracellular domain amino acid sequences set forth herein in Table 5.

d. Transmembrane Domain

The CARs of the disclosure are designed with a transmembrane domain that is fused to the extracellular domain of the CAR. It can similarly be fused to the intracellular domain of the CAR. In some instances, the transmembrane domain can be selected or modified by amino acid substitution to avoid binding of such domains to the transmembrane domains of the same or different surface membrane proteins to minimize interactions with other members of the receptor complex. In some embodiments, short linkers may form linkages between any or some of the extracellular, transmembrane, and intracellular domains of the CAR.

Suitable transmembrane domains for a CAR disclosed herein have the ability to (a) be expressed at the surface an immune cell such as, for example without limitation, a lymphocyte cell, such as a T helper ($T_h$) cell, cytotoxic T ($T_c$) cell, T regulatory ($T_{reg}$) cell, or Natural killer (NK) cells, and/or (b) interact with the extracellular antigen binding domain and intracellular signaling domain for directing the cellular response of an immune cell against a target cell.

The transmembrane domain may be derived either from a natural or from a synthetic source. Where the source is natural, the domain may be derived from any membrane-bound or transmembrane protein.

Transmembrane regions of particular use in this disclosure may be derived from (comprise, or correspond to) CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 1d, ITGAE, CD103, ITGAL, CD1 1a, LFA-1, ITGAM, CD1 1b, ITGAX, CD1 1c, ITGB1, CD29, ITGB2, CD18, LFA-1, ITGB7, NKG2D, TNFR2, TRANCE/ RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

As non-limiting examples, the transmembrane region can be a derived from, or be a portion of a T cell receptor such as α, β, γ or δ, polypeptide constituting CD3 complex, IL-2 receptor p55 (a chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1).

In some embodiments, the transmembrane domain in the CAR of the disclosure is a CD8α transmembrane domain. In some embodiments, the transmembrane domain in the CAR of the disclosure is a CD8α transmembrane domain comprising the amino acid sequence IYI-WAPLAGTCGVLLLSLVIT (SEQ ID NO: 549). In some embodiments, the CD8α transmembrane domain comprises the nucleic acid sequence that encodes the transmembrane amino acid sequence of SEQ ID NO: 549. In some embodiments, the hinge and transmembrane domain in the CAR of the disclosure is a CD8α hinge and transmembrane domain comprising the amino acid sequence of SEQ ID NO: 479.

In some embodiments, the transmembrane domain in the CAR of the disclosure is a CD28 transmembrane domain. In some embodiments, the transmembrane domain in the CAR of the disclosure is a CD28 transmembrane domain comprising the amino acid sequence of FWVLVVVGGVLA-CYSLLVTVAFIIFWV (SEQ ID NO: 550). In some embodiments, the CD28 transmembrane domain comprises the nucleic acid sequence that encodes the transmembrane amino acid sequence of SEQ ID NO: 550.

e. Intracellular Domain

The intracellular (cytoplasmic) domain of the CARs of the disclosure can provide activation of at least one of the normal effector functions of the immune cell comprising the CAR, e.g., Signal 1/activation and/or Signal 2/costimulation. Effector function of a T cell, for example, may refer to cytolytic activity or helper activity, including the secretion of cytokines. In some embodiments, an activating intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability.

It will be appreciated that suitable (e.g., activating) intracellular domains include, but are not limited to signaling domains derived from (or corresponding to) CD3 zeta, CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 1d, ITGAE, CD103, ITGAL, CD1 1a, LFA-1, ITGAM, CD1 1b, ITGAX, CD1 1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

The intracellular domains of the CARs of the disclosure may incorporate, in addition to the activating domains described above, costimulatory signaling domains (interchangeably referred to herein as costimulatory molecules) to increase their potency. Costimulatory domains can provide a signal in addition to the primary signal provided by an activating molecule as described herein.

It will be appreciated that suitable costimulatory domains within the scope of the disclosure can be derived from (or correspond to) for example, CD28, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD1 1a/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNFR, integrin, signaling lymphocytic activation molecule, BTLA, Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. It will be appreciated that additional costimulatory molecules, or fragments thereof, not listed above are within the scope of the disclosure.

In some embodiments, the intracellular/cytoplasmic domain of the CAR can be designed to comprise the 41BB/CD137 domain by itself or combined with any other desired intracellular domain(s) useful in the context of the CAR of the disclosure. The complete native amino acid sequence of 41BB/CD137 is described in NCBI Reference Sequence: NP_001552.2. The complete native 41BB/CD137 nucleic acid sequence is described in NCBI Reference Sequence: NM_001561.5.

In some embodiments, the intracellular/cytoplasmic domain of the CAR can be designed to comprise the CD28 domain by itself or combined with any other desired intracellular domain(s) useful in the context of the CAR of the disclosure. The complete native amino acid sequence of CD28 is described in NCBI Reference Sequence:

NP_006130.1. The complete native CD28 nucleic acid sequence is described in NCBI Reference Sequence: NM_006139.1.

In some embodiments, the intracellular/cytoplasmic domain of the CAR can be designed to comprise the CD3 zeta domain by itself or combined with any other desired intracellular domain(s) useful in the context of the CAR of the disclosure. In some embodiments, the intracellular signaling domain of the CAR can comprise the CD3ζ signaling domain which has amino acid sequence with at least about 70%, at least 80%, at least 90%, 95%, 97%, or 99% sequence identity with an amino acid sequence shown in SEQ ID NO: 481 in Table 7. For example, the intracellular domain of the CAR can comprise a CD3 zeta chain portion and a portion of a costimulatory signaling molecule. The intracellular signaling sequences within the intracellular signaling portion of the CAR of the disclosure may be linked to each other in a random or specified order. In some embodiments, the intracellular domain is designed to comprise the activating domain of CD3 zeta and a signaling domain of CD28. In some embodiments, the intracellular domain is designed to comprise the activating domain of CD3 zeta and a costimulatory/signaling domain of 4-1BB.

In some embodiments, the 4-1BB (intracellular domain) comprises the amino acid sequence KRGRKKLLY-IFKQPFMRPVQTTQEEDGCSCRFPEEEEGGCEL (SEQ ID NO: 480). In some embodiments, the 4-1BB (intracellular domain) is encoded by the nucleic acid sequence:

```
                              (SEQ ID NO: 568)
AAGCGCGGCAGGAAGAAGCTCCTCTACATTTTTAAGCAGCCTTTTATGAG

GCCCGTACAGACAACACAGGAGGAAGATGGCTGTAGCTGCAGATTTCCCG

AGGAGGAGGAAGGTGGGTGCGAGCTG.
```

In some embodiments, the intracellular domain in the CAR is designed to comprise a portion of CD28 and CD3 zeta, wherein the intracellular CD28 comprises the nucleic acid sequence set forth in SEQ ID NO: 567.

```
                              (SEQ ID NO: 567)
AGATCCAAAAGAAGCCGCCTGCTCCATAGCGATTACATGAATATGACTCC

ACGCCGCCCTGGCCCCACAAGGAAACACTACCAGCCTTACGCACCACCTA

GAGATTTCGCTGCCTATCGGAGC.
```

In some embodiments, the intracellular domain in the CAR is designed to comprise the amino acid sequence RSKRSRLLHSDYMNMTPRRPGPTRKHYQPYAPPRD-FAAYRS (SEQ ID NO: 551). The CD3 zeta amino acid sequence may comprise SEQ ID NO: 481 or 469 and the nucleic acid sequence may comprise SEQ ID NO: 569:

```
                              (SEQ ID NO: 569)
AGGGTGAAGTTTTCCAGATCTGCAGATGCACCAGCGTATCAGCAGGGCCA

GAACCAACTGTATAACGAGCTCAACCTGGGACGCAGGGAAGAGTATGACG

TTTTGGACAAGCGCAGAGGACGGGACCCTGAGATGGGTGGCAAACCAAGA

CGAAAAAACCCCCAGGAGGGTCTCTATAATGAGCTGCAGAAGGATAAGAT

GGCTGAAGCCTATTCTGAAATAGGCATGAAAGGAGAGCGGAGAAGGGGAA

AAGGGCACGACGGTTTGTACCAGGGACTCAGCACTGCTACGAAGGATACT

TATGACGCTCTCCACATGCAAGCCCTGCCACCTAGG.
```

In some embodiments the intracellular signaling domain of the CAR of the disclosure comprises a domain of a co-stimulatory molecule. In some embodiments, the intracellular signaling domain of a CAR of the disclosure comprises a part of co-stimulatory molecule selected from the group consisting of fragment of 4-1BB (GenBank: AAA53133.) and CD28 (NP_006130.1). In some embodiments, the intracellular signaling domain of the CAR of the disclosure comprises amino acid sequence which comprises at least 70%, at least 80%, at least 90%, 95%, 97%, or 99% sequence identity with an amino acid sequence shown in SEQ ID NO: 480 and SEQ ID NO: 551. In some embodiments, the intracellular signaling domain of the CAR of the disclosure comprises amino acid sequence which comprises at least 70%, at least 80%, at least 90%, 95%, 97%, or 99% sequence identity with an amino acid sequence shown in SEQ ID NO: 480 and/or at least 70%, at least 80%, at least 90%, 95%, 97%, or 99% sequence identity with an amino acid sequence shown in SEQ ID NO: 551.

In exemplary embodiments, a CAR of the disclosure comprises, from N-terminus to C-terminus: a (cleavable) CD8α signal sequence, a DLL3 scFv, a CD8α hinge and transmembrane region, a 4-1BB cytoplasmic (costimulatory) signaling domain, and a CD3ζ cytoplasmic (stimulatory) signaling domain.

III. Immune Cells Comprising CARs a. Immune Cells

Provided herein are engineered immune cells expressing the CARs of the disclosure (e.g., CAR-T cells).

In some embodiments, an engineered immune cell comprises a population of CARs, each CAR comprising different extracellular antigen-binding domains. In some embodiments, an immune cell comprises a population of CARs, each CAR comprising the same extracellular antigen-binding domains.

The engineered immune cells can be allogeneic or autologous.

In some embodiments, the engineered immune cell is a T cell (e.g., inflammatory T lymphocyte, cytotoxic T lymphocyte, regulatory T lymphocyte (Treg), helper T lymphocyte, tumor infiltrating lymphocyte (TIL)), natural killer T cell (NKT), TCR-expressing cell, dendritic cell, killer dendritic cell, a mast cell, or a B-cell. In some embodiments, the cell can be derived from the group consisting of CD4+ T-lymphocytes and CD8+ T-lymphocytes. In some exemplary embodiments, the engineered immune cell is a T cell. In some exemplary embodiments, the engineered immune cell is a gamma delta T cell. In some exemplary embodiments, the engineered immune cell is a macrophage. In some exemplary embodiments, the engineered immune cell is a natural killer (NK) cell.

In some embodiments, the engineered immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells.

In some embodiments, the cell is obtained or prepared from peripheral blood. In some embodiments, the cell is obtained or prepared from peripheral blood mononuclear cells (PBMCs). In some embodiments, the cell is obtained or prepared from bone marrow. In some embodiments, the cell is obtained or prepared from umbilical cord blood. In some embodiments, the cell is a human cell.

In some embodiments, the cell is transfected or transduced by the nucleic acid vector using a method selected from the group consisting of electroporation, sonoporation, biolistics (e.g., Gene Gun), lipid transfection, polymer transfection, nanoparticles, viral transfection (e.g., retrovirus, lentivirus, AAV) or polyplexes.

In some embodiments, the engineered immune cells expressing at their cell surface membrane a DLL3-specific CAR of the disclosure comprise a percentage of stem cell memory and central memory cells greater than 10%, 20%, 30%, 40%, 50%, 60%, 70%, 80%, 90%, or 100%. In some embodiments, the engineered immune cells expressing at their cell surface membrane a DLL3-specific CAR of the disclosure comprise a percentage of stem cell memory and central memory cells of about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 15% to about 100%, about 15% to about 90%, about 15% to about 80%, about 15% to about 70%, about 15% to about 60%, about 15% to about 50%, about 15% to about 40%, about 15% to about 30%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 90%, about 70% to about 80%, about 80% to about 100%, about 80% to about 90%, about 90% to about 100%, about 25% to about 50%, about 75% to about 100%, or about 50% to about 75%.

In some embodiments, the immune cell is an inflammatory T-lymphocyte that expresses any one of the CARs described herein. In some embodiments, the immune cell is a cytotoxic T-lymphocyte that expresses any one of the CARs described herein. In some embodiments, the immune cell is a regulatory T-lymphocyte that expresses any one of the CARs described herein. In some embodiments, the immune cell is a helper T-lymphocyte that expresses any one of the CARs described herein.

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor, from a patient diagnosed with cancer or from a patient diagnosed with an infection. In some embodiments, cells can be part of a mixed population of cells which present different phenotypic characteristics.

Also provided herein are cell lines obtained from a transformed immune cell (e.g., T-cell) according to any of the above-described methods. Also provided herein are modified cells resistant to an immunosuppressive treatment. In some embodiments, an isolated cell according to the disclosure comprises a polynucleotide encoding a CAR.

The immune cells of the disclosure can be activated and expanded, either prior to or after genetic modification of the immune cells, using methods as generally known. Generally, the engineered immune cells of the disclosure can be expanded, for example, by contacting with an agent that stimulates a CD3 TCR complex and a costimulatory molecule on the surface of the T-cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations may be stimulated in vitro by contact with, for example, an anti-CD3 antibody such as an OKT3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody (e.g., an OKT3 antibody) and an anti-CD28 antibody, under conditions appropriate for stimulating proliferation of the T cells. The anti-CD3 antibody and an anti-CD28 antibody can be disposed on a bead, such as a plastic or magnetic bead, or plate or other substrate. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$, IL-4, IL-7, GM-CSF, IL-10, IL-2, IL-15, TGFbeta, and TNF, or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells (e.g., IL-7 and/or IL-15). Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics. In some embodiments, the cells of the disclosure can be expanded by co-culturing with tissue or cells. The cells can also be expanded in vivo, for example in the subject's blood after administering the cell into the subject.

In some embodiments, an engineered immune cell according to the present disclosure may comprise one or more disrupted or inactivated genes. In some embodiments, an engineered immune cell according to the present disclosure comprises one disrupted or inactivated gene selected from the group consisting of CD52, DLL3, GR, PD-1, CTLA-4, LAG3, TIM3, BTLA, BY55, TIGIT, B7H5, LAIR1, SIGLEC10, 2B4, HLA, TCRα and TCRβ and/or expresses a CAR, a multi-chain CAR and/or a pTα transgene. In some embodiments, an isolated cell comprises polynucleotides encoding polypeptides comprising a multi-chain CAR. In some embodiments, the isolated cell according to the present disclosure comprises two disrupted or inactivated genes selected from the group consisting of:

CD52 and GR, CD52 and TCRα, CDR52 and TCRβ, DLL3 and CD52, DLL3 and TCRα, DLL3 and TCRβ, GR and TCRα, GR and TCRβ, TCRα and TCRβ, PD-1 and TCRα, PD-1 and TCRβ, CTLA-4 and TCRα, CTLA-4 and TCRβ, LAG3 and TCRα, LAG3 and TCRβ, TIM3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ and/or expresses a CAR, a multi-chain CAR and a pTα transgene. In some embodiments the method comprises disrupting or inactivating one or more genes by introducing into the cells a endonuclease able to selectively inactivate a gene by selective DNA cleavage. In some embodiments the endonuclease can be, for example, a zinc finger nuclease (ZFN), megaTAL nuclease, meganuclease, transcription activator-like effector nuclease (TALE-nuclease/TALEN), or CRISPR (e.g., Cas9) endonuclease.

In some embodiments, TCR is rendered not functional in the cells according to the disclosure by disrupting or inactivating TCRα gene and/or TCRβ gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, susceptible to be obtained by this method are encompassed in the scope of the present disclosure. Modified cells disclosed herein can be used in for treating patients in need thereof against Host versus Graft (HvG) rejection and Graft versus Host Disease (GvHD); therefore in the scope of the present disclosure is a method of treating patients in need thereof against Host versus Graft (HvG) rejection and Graft versus Host Disease (GvHD) comprising treating said patient by administering to said patient an effective amount of modified cells comprising disrupted or inactivated TCRα and/or TCRβ genes.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, cyclophosphamide, and cytarabine, alone or in combination. PNAs are metabolized by deoxycytidine kinase (dCK) into mono-, di-, and tri-phosphate PNA. Their tri-phosphate forms compete with ATP for DNA synthesis, act as pro-apoptotic agents, and are potent inhibitors of ribonucleotide reductase (RNR), which is involved in trinucleotide production. Provided herein are DLL3-specific CAR-T cells comprising a disrupted or inactivated dCK gene. In some embodiments, the dCK knockout cells are made by transfection of T cells using polynucleotides encoding specific TAL-nuclease directed against dCK genes by, for example, electroporation of mRNA. The dCK knockout DLL3-specific CAR-T cells are resistant to PNAs, including for example clorofarabine and/or fludarabine, and maintain T cell cytotoxic activity toward DLL3-expressing cells.

In some embodiments, isolated cells or cell lines of the disclosure can comprise a pTα or a functional variant thereof. In some embodiments, an isolated cell or cell line can be further genetically modified by disrupting or inactivating the TCRα gene.

The disclosure also provides engineered immune cells comprising any of the CAR polynucleotides described herein. In some embodiments, a CAR can be introduced into an immune cell as a transgene via a plasmid vector. In some embodiments, the plasmid vector can also contain, for example, a selection marker which provides for identification and/or selection of cells which received the vector.

CAR polypeptides may be synthesized in situ in the cell after introduction of polynucleotides encoding the CAR polypeptides into the cell. Alternatively, CAR polypeptides may be produced outside of cells, and then introduced into cells. Methods for introducing a polynucleotide construct into cells are known in the art. In some embodiments, stable transformation methods (e.g., using a lentiviral vector) can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides may be introduced into a cell by any suitable means such as for example, recombinant viral vectors (e.g., retroviruses, adenoviruses), liposomes, and the like. Transient transformation methods include, for example without limitation, microinjection, electroporation or particle bombardment. Polynucleotides may be included in vectors, such as for example plasmid vectors or viral vectors.

In some embodiments, isolated nucleic acids are provided comprising a promoter operably linked to a first polynucleotide encoding a DLL3 antigen binding domain, at least one costimulatory molecule, and an activating domain. In some embodiments, the nucleic acid construct is contained within a viral vector. In some embodiments, the viral vector is selected from the group consisting of retroviral vectors, murine leukemia virus vectors, SFG vectors, adenoviral vectors, lentiviral vectors, adeno-associated virus (AAV) vectors, Herpes virus vectors, and vaccinia virus vectors. In some embodiments, the nucleic acid is contained within a plasmid.

b. Methods of Making

Provided herein are methods of making the CARs and the CAR-containing immune cells of the disclosure.

A variety of known techniques can be utilized in making the polynucleotides, polypeptides, vectors, antigen binding domains, immune cells, compositions, and the like according to the disclosure.

Prior to the in vitro manipulation or genetic modification of the immune cells described herein, the cells may be obtained from a subject. The cells expressing a DLL3 CAR may be derived from an allogenic or autologous process.

i. Source Material

In some embodiments, the immune cells comprise T cells. T cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain embodiments, T cells can be obtained from a unit of blood collected from the subject using any number of techniques known to the skilled person, such as FICOLL™ separation.

Cells may be obtained from the circulating blood of an individual by apheresis. The apheresis product typically contains lymphocytes, including T cells, monocytes, granulocytes, B cells, other nucleated white blood cells, red blood cells, and platelets. In certain embodiments, the cells collected by apheresis may be washed to remove the plasma fraction, and placed in an appropriate buffer or media for subsequent processing.

In certain embodiments, T cells are isolated from PBMCs by lysing the red blood cells and depleting the monocytes, for example, using centrifugation through a PERCOLL™ gradient. A specific subpopulation of T cells, (e.g., CD28+, CD4+, CDS+, CD45RA−, CD45RO+, CDS+, CD62−, CD95−, CD95+, IL2Rβ+, IL2Rβ−, CCR7+, CCR7−, CDL−, CD62L+ and combinations thereof) can be further isolated by positive or negative selection techniques known in the art. In one example the subpopulation of T cells is CD45RA+, CD95−, IL-2RP−, CCR7+, CD62L+. In one example the subpopulation of T cells is CD45RA+, CD95+, IL-2RP+, CCR7+, CD62L+. In one example the subpopulation of T cells is CD45RO+, CD95+, IL-2RP+, CCR7+, CD62L+. In one example the subpopulation of T cells is CD45RO+, CD95+, IL-2RP+, CCR7−, CD62L−. In one example the subpopulation of T cells is CD45RA+, CD95+, IL-2RP+, CCR7−, CD62L−. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present disclosure.

PBMCs may be used directly for genetic modification with the immune cells (such as CARs or TCRs) using methods as described herein. In certain embodiments, after isolating the PBMCs, T lymphocytes can be further isolated and both cytotoxic and helper T lymphocytes can be sorted into naive, memory, and effector T cell subpopulations either before or after genetic modification and/or expansion.

In some embodiments, CD8+ cells are further sorted into naive, stem cell memory, central memory, and effector cells by identifying characteristic cell surface antigens that are associated with each of these types of CD8+ cells. In some embodiments, the expression of phenotypic markers of central memory T cells include CD45RO, CD62L, CCR7, CD28, CD3, and CD127 and are negative for granzyme B. In some embodiments, stem cell memory T cells are CD45RO−, CD62L+, CD8+ T cells, central memory T cells are CD45RO+, CD62L+, CD8+ T cells. In some embodiments, effector T cells are negative for CD62L, CCR7, CD28, and CD127, and positive for granzyme B and perforin.

In certain embodiments, CD4+ T cells are further sorted into subpopulations. For example, CD4+T helper cells can be sorted into naive, central memory, and effector cells by identifying cell populations that have characteristic cell surface antigens.

iii. Stem Cell-Derived Immune Cells

In some embodiments, the immune cells may be derived from stem cells, such as a progenitor cell, a bone barrow stem cell, an inducible pluripotent stem cell, an iPSC, a hematopoietic stem cell, and a mesenchymal stem cell. iPS cells and other types of stem cells may be cultivated immortal cell lines or isolated directly from a patient. Various methods for isolating, developing, and/or cultivating stem cells are known in the art and may be used to practice the present invention.

In some embodiments, the immune cell is an induced pluripotent stem cell (iPSC) derived from a reprogrammed T-cell. In some embodiments, the source material may be an induced pluripotent stem cell (iPSC) derived from a T cell or non-T cell. The source material may alternatively be a B cell, or any other cell from peripheral blood mononuclear cell isolates, hematopoietic progenitor, hematopoietic stem cell, mesenchymal stem cell, adipose stem cell, or any other somatic cell type.

ii. Genetic Modification of Isolated Cells

The immune cells, such as T cells, can be genetically modified following isolation using known methods, or the immune cells can be activated and expanded (or differentiated in the case of progenitors) in vitro prior to being genetically modified. In some embodiments, the isolated immune cells are genetically modified to reduce or eliminate expression of endogenous TCRα and/or CD52. In some embodiments, the cells are genetically modified using gene editing technology (e.g., CRISPR/Cas9, CRISPR/CAS12, a zinc finger nuclease (ZFN), a TALEN, a MegaTAL, a meganuclease) to reduce or eliminate expression of endogenous proteins (e.g., TCRα and/or CD52). In another embodiment, the immune cells, such as T cells, are optionally further genetically modified with the chimeric antigen receptors described herein (e.g., transduced with a viral vector comprising one or more nucleotide sequences encoding a CAR) and then are activated and/or expanded in vitro.

Methods for activating and expanding T cells are known in the art and are described, for example, in U.S. Pat. Nos. 6,905,874; 6,867,041; 6,797,514; and PCT WO2012/079000, the contents of which are hereby incorporated by reference in their entirety. Generally, such methods include contacting PBMC or isolated T cells with a stimulatory molecule and a costimulatory molecule, such as anti-CD3 and anti-CD28 antibodies, generally attached to a plastic or magnetic bead or other surface, in a culture medium with appropriate cytokines, such as IL-2. Anti-CD3 and anti-CD28 antibodies attached to the same bead serve as a "surrogate" antigen presenting cell (APC). One example is the Dynabeads® system, which is a CD3/CD28 activator/stimulator system for physiological activation of human T cells. In other embodiments, the T cells may be activated and stimulated to proliferate with feeder cells and appropriate antibodies and cytokines using methods such as those described in U.S. Pat. Nos. 6,040,177; 5,827,642; and WO2012129514, the contents of which are hereby incorporated by reference in their entirety.

Certain methods for making the constructs and engineered immune cells of the disclosure are described in PCT application PCT/US15/14520, the contents of which are hereby incorporated by reference in their entirety.

It will be appreciated that PBMCs can further include other cytotoxic lymphocytes such as NK cells or NKT cells. An expression vector carrying the coding sequence of a chimeric receptor as disclosed herein can be introduced into a population of human donor T cells, NK cells or NKT cells. Successfully transduced T cells that carry the expression vector can be sorted using flow cytometry to isolate CD3 positive T cells and then further propagated to increase the number of these CAR expressing T cells in addition to cell activation using anti-CD3 antibodies and IL-2 or other methods known in the art as described elsewhere herein. Standard procedures are used for cryopreservation of T cells expressing the CAR for storage and/or preparation for use in a human subject. In one embodiment, the in vitro transduction, culture and/or expansion of T cells are performed in the absence of non-human animal derived products such as fetal calf serum and fetal bovine serum. In an embodiment, cryopreservation can comprise freezing in a suitable medium, such as CryoStor® CS10, CryoStor® CS2 or CryoStor® CS5 (BioLife Solutions).

For cloning of polynucleotides, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vector provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells, and more specifically human cells.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for viral transfection and transformation of cells for expression of a vector of interest are well known in the art. In a further embodiment, a mixture of different expression vectors can be used in genetically modifying a donor population of immune effector cells wherein each vector encodes a different CAR as disclosed herein. The resulting transduced immune effector cells form a mixed population of engineered cells, with a proportion of the engineered cells expressing more than one different CARs.

In one embodiment, the disclosure provides a method of storing genetically engineered cells expressing CARs which target a DLL3 protein. In an embodiment this involves cryopreserving the immune cells such that the cells remain viable upon thawing. In an embodiment, cryopreservation can comprise freezing in a suitable medium, such as CryoStor® CS10, CryoStor® CS2 or CryoStor® CS5 (BioLife Solutions). A fraction of the immune cells expressing the CARs can be cryopreserved by methods known in the art to provide a permanent source of such cells for the future treatment of patients afflicted with a malignancy. When needed, the cryopreserved transformed immune cells can be thawed, grown and expanded for more such cells.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

iv. Allogeneic CAR T Cells

In brief, the process for manufacturing allogeneic CAR T therapy, or AlloCARs™ involves harvesting healthy, selected, screened and tested T cells from healthy donors. Allogeneic T cells are gene editing to reduce the risk of graft versus host disease (GvHD) and to prevent allogeneic rejection. A selected T cell receptor gene (e.g., TCRα, TCRβ) is knocked out to avoid GvHD. The CD52 gene can also be knocked out to render the CAR T product resistant to anti-CD52 antibody treatment. Anti-CD52 antibody treatment can therefore be used to lymphodeplete the host immune system and allow the CAR T cells to stay engrafted to achieve full therapeutic impact. Next, the T cells are engineered to express CARs, which recognize certain cell surface proteins (e.g., DLL-3) that are expressed in hematologic or solid tumors. The engineered T cells then undergo a purification step and are ultimately cryopreserved in vials for delivery to patients.

v. Autologous CAR T Cells

Autologous chimeric antigen receptor (CAR) T cell therapy, involves collecting a patient's own cells (e.g., white blood cells, including T cells) and genetically engineering the T cells to express CARs that recognize a target antigen expressed on the cell surface of one or more specific cancer cells and kill cancer cells. The engineered cells are then cryopreserved and subsequently administered to the patient from which the cells were removed for engineering.

IV. Methods of Treatment

The disclosure comprises methods for treating or preventing a condition associated with undesired and/or elevated DLL3 levels in a patient, comprising administering to a patient in need thereof an effective amount of at least one CAR, or immune-cell comprising a CAR disclosed herein.

Methods are provided for treating diseases or disorders, including cancer. In some embodiments, the disclosure relates to creating a T cell-mediated immune response in a subject, comprising administering an effective amount of the engineered immune cells of the present application to the subject. In some embodiments, the T cell-mediated immune response is directed against a target cell or cells. In some embodiments, the engineered immune cell comprises a chimeric antigen receptor (CAR). In some embodiments, the target cell is a tumor cell. In some aspects the disclosure comprises a method for treating or preventing a malignancy, said method comprising administering to a subject in need thereof an effective amount of at least one isolated antigen binding domain described herein. In some aspects, the disclosure comprises a method for treating or preventing a malignancy, said method comprising administering to a subject in need thereof an effective amount of at least one immune cell, wherein the immune cell comprises at least one chimeric antigen receptor, and/or isolated antigen binding domain as described herein. The CAR containing immune cells of the disclosure can be used to treat malignancies involving aberrant expression of DLL3. In some embodiments, CAR containing immune cells of the disclosure can be used to treat such malignancies as small cell lung cancer, melanoma, low grade gliomas, glioblastoma, medullary thyroid cancer, carcinoids, dispersed neuroendocrine tumors in the pancreas, bladder and prostate, testicular cancer, and lung adenocarcinomas with neuroendocrine features. In exemplary embodiments, the CAR-containing immune cells, e.g., the anti-DLL3 CAR-T cells of the disclosure, are used to treat small cell lung cancer.

Also provided are methods for reducing the size of a tumor in a subject, comprising administering to the subject an engineered cell of the present disclosure to the subject, wherein the cell comprises a chimeric antigen receptor comprising a DLL3 antigen binding domain and binds to a DLL3 antigen on the tumor.

In some embodiments, the subject has a solid tumor, or a blood malignancy such as lymphoma or leukemia. In some embodiments, the engineered cell is delivered to a tumor bed, such as a tumor bed found in small cell lung cancer. In some embodiments, the cancer is present in the bone marrow of the subject. In some embodiments, the engineered cells are autologous immune cells, e.g., autologous T cells. In some embodiments, the engineered cells are allogeneic immune cells, e.g., allogeneic T cells. In some embodiments, the engineered cells are heterologous immune cells, e.g., heterologous T cells. In some embodiments, the engineered cells are transfected or transduced ex vivo. As used herein, the term "in vitro cell" refers to any cell that is cultured ex vivo.

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner (e.g., a physician or clinician), such as in human subjects during clinical trials, in animal model systems predictive of efficacy in humans, or by assaying the activity of the agent in in vitro assays.

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Desired treatment total amounts of cells in the composition comprise at least 2 cells (for example, at least one CD8+ T cell and at least one CD4+ T cell, or two CD8+ T cells, or two CD4+ T cells) or is more typically greater than $10^2$ cells, and up to $10^6$, up to and including $10^8$ or $10^9$ cells and can be $10^{10}$ or $10^{12}$ or more cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^1$, $10^9$, $10^{10}$, $10^{11}$, or $10^{12}$ cells. In some aspects of the present disclosure, particularly since all the infused cells will be redirected to a particular target antigen (e.g., DLL3), lower numbers of cells, in the range of $10^6$/kilogram ($10^6$-$10^{11}$ per patient) may be administered. CAR treatments may be administered multiple times at dosages within these ranges. The cells may be autologous, allogeneic, or heterologous to the patient undergoing therapy.

In some embodiments, the therapeutically effective amount of the CAR T cells is about $1 \times 10^5$ cells/kg, about $2 \times 10^5$ cells/kg, about $3 \times 10^5$ cells/kg, about $4 \times 10^5$ cells/kg, about $5 \times 10^5$ cells/kg, about $6 \times 10^5$ cells/kg, about $7 \times 10^5$ cells/kg, about $8 \times 10^5$ cells/kg, about $9 \times 10^5$ cells/kg, $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $2 \times 10^7$ cells/kg, about $3 \times 10^7$ cells/kg, about $4 \times 10^7$ cells/kg, about $5 \times 10^7$ cells/kg, about $6 \times 10^7$ cells/kg, about $7 \times 10^7$ cells/kg, about $8 \times 10^7$ cells/kg, or about $9 \times 10^7$ cells/kg.

In some embodiments, target doses for CAR+/CAR-T+ cells range from about $1 \times 10^6$ to about $1 \times 10^{10}$ cells/kg, for example about $1 \times 10^6$ cells/kg, about $1 \times 10^7$ cells/kg, about $1 \times 10^8$ cells/kg, about $1 \times 10^9$ cells/kg or about $1 \times 10^{10}$ cells/kg. It will be appreciated that doses above and below this range may be appropriate for certain subjects, and appropriate dose levels can be determined by the healthcare provider as needed. Additionally, multiple doses of cells can be provided in accordance with the disclosure.

In some aspects the disclosure comprises a pharmaceutical composition comprising at least one antigen binding domain as described herein and a pharmaceutically acceptable excipient. In some embodiments, the pharmaceutical composition further comprises an additional active agent.

The CAR expressing cell populations of the present disclosure may be administered either alone, or as a pharmaceutical composition in combination with diluents and/or with other components such as IL-2 or other cytokines or cell populations. Pharmaceutical compositions of the present disclosure may comprise a CAR expressing cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

The pharmaceutical compositions (solutions, suspensions or the like), may include one or more of the following: sterile diluents such as water for injection, saline solution, preferably physiological saline, Ringer's solution, isotonic sodium chloride, fixed oils such as synthetic mono- or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. For therapeutic applications, an injectable pharmaceutical composition is preferably sterile.

In some embodiments, upon administration to a patient, engineered immune cells expressing at their cell surface any one of the DLL3-specific CARs described herein may reduce, kill or lyse endogenous DLL3-expressing cells of the patient. In one embodiment, a percentage reduction or lysis of DLL3-expressing endogenous cells or cells of a cell line expressing DLL3 by engineered immune cells expressing any one of the DLL3-specific CARs described herein is at least about or greater than 10%, 15%, 20%, 25%, 30%, 35%, 40%, 45%, 50%, 55%, 60%, 65%, 70%, 75%, 80%, 85%, 90%, or 95%. In one embodiment, a percentage reduction or lysis of DLL3-expressing endogenous cells or cells of a cell line expressing DLL3 by engineered immune cells expressing any one of the DLL3-specific CARs described herein is about 5% to about 95%, about 10% to about 95%, about 10% to about 90%, about 10% to about 80%, about 10% to about 70%, about 10% to about 60%, about 10% to about 50%, about 10% to about 40%, about 20% to about 90%, about 20% to about 80%, about 20% to about 70%, about 20% to about 60%, about 20% to about 50%, about 25% to about 75%, or about 25% to about 60%. In one embodiment, the endogenous DLL3-expressing cells are endogenous DLL3-expressing bone marrow cells.

In one embodiment, the percent reduction or lysis of target cells, e.g., a cell line expressing DLL3, by engineered immune cells expressing at their cell surface membrane a DLL3-specific CAR of the disclosure can be measured using the assay disclosed herein.

The methods can further comprise administering one or more chemotherapeutic agents to a patient prior to administering the engineered cells provided herein. In certain embodiments, the chemotherapeutic agent is a lymphodepleting (preconditioning) chemotherapeutic. For example, methods of conditioning a patient in need of a T cell therapy comprising administering to the patient specified beneficial doses of cyclophosphamide (between 200 mg/m²/day and 2000 mg/m²/day, about 100 mg/m²/day and about 2000 mg/m²/day; e.g., about 100 mg/m²/day, about 200 mg/m²/day, about 300 mg/m²/day, about 400 mg/m²/day, about 500 mg/m²/day, about 600 mg/m²/day, about 700 mg/m²/day, about 800 mg/m²/day, about 900 mg/m²/day, about 1000 mg/m²/day, about 1500 mg/m²/day or about 2000 mg/m²/day) and specified doses of fludarabine (between 20 mg/m²/day and 900 mg/m²/day, between about 10 mg/m²/day and about 900 mg/m²/day; e.g., about 10 mg/m²/day, about 20 mg/m²/day, about 30 mg/m²/day, about 40 mg/m²/day, about 40 mg/m²/day, about 50 mg/m²/day, about 60 mg/m²/day, about 70 mg/m²/day, about 80 mg/m²/day, about 90 mg/m²/day, about 100 mg/m²/day, about 500 mg/m²/day or about 900 mg/m²/day). An exemplary dosing regimen involves treating a patient comprising administering daily to the patient about 300 mg/m²/day of cyclophosphamide in combination or before or after administering about 30 mg/m²/day of fludarabine for three days prior to administration of a therapeutically effective amount of engineered T cells to the patient.

In some embodiments, notably in the case when the engineered cells provided herein have been gene edited to eliminate or minimize surface expression of CD52, lymphodepletion further comprises administration of an anti-CD52 antibody, such as alemtuzumab. In some embodiments, the CD52 antibody is administered at a dose of about 1-20 mg/day IV, e.g., about 13 mg/day IV for 1, 2, 3 or more days. The antibody can be administered in combination with, before, or after administration of other elements of a lymphodepletion regime (e.g., cyclophosphamide and/or fludarabine).

In other embodiments, the antigen binding domain, transduced (or otherwise engineered) cells and the chemotherapeutic agent are administered each in an amount effective to treat the disease or condition in the subject.

In certain embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RF S2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell, polypeptide, or nucleic acid. In other embodiments, the chemotherapeutic agent is administered from about 1-7 days, about 1 to about 4 weeks or from about 1 week to about 1 month, about 1 week to about 2 months, about 1 week to about 3 months, about 1 week to about 6 months, about 1 week to about 9 months, or about 1 week to about 12 months after the administration of the engineered cell, polypeptide, or nucleic acid. In other embodiments, the chemotherapeutic agent is administered at least 1 month before administering the cell, polypeptide, or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (Opdivo®), pembrolizumab (Keytruda®), pembrolizumab, pidilizumab, and atezolizumab.

Additional therapeutic agents suitable for use in combination with the disclosure include, but are not limited to, ibrutinib (Imbruvica®), ofatumumab (Arzerra®, rituximab (Rituxan®), bevacizumab (Avastin®), trastuzumab (Herceptin®), trastuzumab emtansine (KADCYLA®, imatinib (Gleevec®), cetuximab (Erbitux®, panitumumab) (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition comprising CAR-containing immune cells may be administered with a therapeutic regimen to prevent or reduce cytokine release syndrome (CRS) or neurotoxicity. The therapeutic regimen to prevent cytokine release syndrome (CRS) or neurotoxicity may include lenzilumab, tocilizumab, atrial natriuretic peptide (ANP), anakinra, iNOS inhibitors (e.g., L-NIL or 1400W). In additional embodiments, the composition comprising CAR-containing immune cells can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, IL-21 a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

V. Methods of Sorting and Depletion

In some embodiments, provided are methods for in vitro sorting of a population of immune cells, wherein a subset of the population of immune cells comprises engineered immune cells expressing any one of the DLL3-specific CARs comprising epitopes specific for monoclonal antibodies (e.g., exemplary mimotope sequences). The method comprises contacting the population of immune cells with a monoclonal antibody specific for the epitopes and selecting the immune cells that bind to the monoclonal antibody to obtain a population of cells enriched in engineered immune cells expressing the DLL3-specific CAR.

In some embodiments, said monoclonal antibody specific for said epitope is optionally conjugated to a fluorophore. In this embodiment, the step of selecting the cells that bind to the monoclonal antibody can be done by Fluorescence Activated Cell Sorting (FACS).

In some embodiments, said monoclonal antibody specific for said epitope is optionally conjugated to a magnetic particle. In this embodiment, the step of selecting the cells that bind to the monoclonal antibody can be done by Magnetic Activated Cell Sorting (MACS).

In some embodiments, the mAb used in the method for sorting immune cells expressing the CAR is chosen from alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and/or ustekinumab. In some embodiments, said mAb is rituximab. In another embodiment, said mAb is QBEND-10.

In some embodiments, the population CAR-expressing immune cells obtained when using the method for in vitro sorting CAR-expressing immune cells described above, comprises at least 70%, 75%, 80%, 85%, 90%, 95% of CAR-expressing immune cells. In some embodiments, the population of CAR-expressing immune cells obtained when using the method for in vitro sorting CAR-expressing immune cells, comprises at least 85% CAR-expressing immune cells.

In some embodiments, the population of CAR-expressing immune cells obtained when using the method for in vitro sorting CAR-expressing immune cells described above shows increased cytotoxic activity in vitro compared with the initial (non-sorted) cell population. In some embodiments, said cytotoxic activity in vitro is increased by 10%, 20%, 30% or 50%. In some embodiments, the immune cells are T-cells.

In some embodiments, the mAbs are previously bound onto a support or surface. Non-limiting examples of solid support may include a bead, agarose bead, a plastic bead a magnetic bead, a plastic welled plate, a glass welled plate, a ceramic welled plate, a column, or a cell culture bag.

The CAR-expressing immune cells to be administered to the recipient may be enriched in vitro from the source population. Methods of expanding source populations may include selecting cells that express an antigen such as CD34 antigen, using combinations of density centrifugation, immuno-magnetic bead purification, affinity chromatography, and fluorescent activated cell sorting.

Flow cytometry is may be used to quantify specific cell types within a population of cells. In general, flow cytometry is a method for quantitating components or structural features of cells primarily by optical means. Since different cell types can be distinguished by quantitating structural features, flow cytometry and cell sorting can be used to count and sort cells of different phenotypes in a mixture.

A flow cytometry analysis involves two primary steps: 1) labeling selected cell types with one or more labeled markers, and T) determining the number of labeled cells relative to the total number of cells in the population. In some embodiments, the method of labeling cell types includes binding labeled antibodies to markers expressed by the specific cell type. The antibodies may be either directly labeled with a fluorescent compound or indirectly labeled using, for example, a fluorescent-labeled second antibody which recognizes the first antibody.

In a some embodiments, the method used for sorting T cells expressing CAR is the Magnetic-Activated Cell Sorting (MACS). Magnetic-activated cell sorting (MACS) is a method for separation of various cell populations depending on their surface antigens (CD molecules) by using super-paramagnetic nanoparticles and columns. MACS may be used to obtain a pure cell population. Cells in a single-cell suspension may be magnetically labeled with microbeads. The sample is applied to a column composed of ferromagnetic spheres, which are covered with a cell-friendly coating allowing fast and gentle separation of cells. The unlabeled cells pass through while the magnetically labeled cells are retained within the column. The flow-through can be collected as the unlabeled cell fraction. After a washing step, the column is removed from the separator, and the magnetically labeled cells are eluted from the column.

Detailed protocol for the purification of specific cell population such as T-cell can be found in Basu S et al. (2010). (Basu S, Campbell H M, Dittel B N, Ray A. Purification of specific cell population by fluorescence activated cell sorting (FACS). J Vis Exp. (41): 1546).

In some aspects the present disclosure provides a method for depleting DLL3 specific CAR-expressing immune cells by in vivo depletion. in vivo depletion may include the administration of a treatment (e.g., a molecule that binds an epitope on the CAR) to a mammalian organism aiming to stop the proliferation of the CAR-expressing immune cells by inhibition or elimination.

One aspect of the invention is related to a method for in vivo depleting an engineered immune cell expressing a DLL3 CAR comprising a mAb specific epitope, comprising contacting said engineered immune cell or said CAR-expressing immune cell with at least one epitope-specific mAb. Another aspect of the invention relates to a method for in vivo depleting CAR-expressing immune cell which comprises a chimeric scFv (e.g., formed by insertion of a mAb-specific epitope) by contacting said engineered immune cell with epitope-specific antibodies. In some embodiments, the immune cells are T-cells and/or the antibodies are monoclonal.

According to one embodiment, the in vivo depletion of the immune engineered cells is performed on engineered immune cells which has been previously sorted using the in vitro method of the present invention. In this case, the same infused mAb may be used. In some embodiments, the mAb-specific antigen is CD20 antigen and the epitope-specific mAb is rituximab. In some embodiments, the invention relates to a method for in vivo depleting an engineered immune cell expressing a CAR comprising an mAb-specific epitope (CAR-expressing immune cell) in a patient comprising contacting said CAR-expressing immune cell with at least one epitope-specific mAb.

In some embodiments, the step of contacting said engineered immune cell or said CAR-expressing immune cell with at least one epitope-specific mAb comprises infusing the patient with epitope-specific mAb (e.g., rituximab). In some embodiments, the amount of epitope-specific mAb administered to the patient is sufficient to eliminate at least 20%, 30%, 40%, 50%, 60%, 70%, 80% or 90% of the CAR-expressing immune cell in the patient.

In some embodiments, the step of contacting said engineered immune cell or said CAR-expressing immune cell with at least one epitope-specific mAb comprises infusing the patient with about 375 mg/m$^2$ of rituximab, once or several times. In some embodiments, the mAb (e.g., rituximab) is administered once weekly.

In some embodiments, when immune cells expressing a CAR comprising an mAb-specific epitope (CAR-expressing immune cells) are depleted in a complement dependent cytotoxicity (CDC) assay using epitope-specific mAb, the amount of viable CAR-expressing immune cells decreases. In some embodiments, the amount of viable CAR-expressing immune cells decreases by at least 10%, 20%, 30%, 40%, 50%, 60%, 70%, 80% or 90%. In some embodiments, said mAb-specific epitope is a CD20 epitope or mimotope and/or the epitope-specific mAb is rituximab.

In certain embodiments, the in vivo depletion of CAR-engineered immune cells is performed by infusing bi-specific antibodies. By definition, a bispecific monoclonal antibody (BsAb) is an artificial protein that is composed of fragments of two different monoclonal antibodies and consequently binds to two different types of antigen. These BsAbs and their use in immunotherapy have been reviewed in Muller D and Kontermann R. E. (2010) Bispecific Antibodies for Cancer Immunotherapy, BioDrugs 24 (2): 89-98.

According to another particular embodiment, the infused bi-specific mAb is able to bind both the mAb-specific epitope borne on engineered immune cells expressing the chimeric scFv and to a surface antigen on an effector and cytotoxic cell (e.g., immune cells such as lymphocytes, macrophages, dendritic cells, natural killer cells (NK Cell), cytotoxic T lymphocytes (CTL)). By doing so, the depletion of engineered immune cells triggered by the BsAb may occur through antibody-dependent cellular cytotoxicity (ADCC). (Deo Y M, Sundarapandiyan K, Keler T, Wallace P K, and Graziano R F, (2000), Journal of Immunology, 165 (10):5954-5961]).

In some embodiments, a cytotoxic drug is coupled to the epitope-specific mAbs which may be used to deplete CAR-expressing immune cells. By combining targeting capabilities of monoclonal antibodies with the cancer-killing ability of cytotoxic drugs, antibody-drug conjugate (ADC) allows a sensitive discrimination between healthy and diseased tissue when compared to the use of the drug alone. Market approvals were received for several ADCs; the technology for making them—particularly on linkers—are described in (Payne, G. (2003) Cancer Cell 3:207-212; Trail et al (2003) Cancer Immunol. Immunother. 52:328-337; Syrigos and Epenetos (1999) Anticancer Research 19:605-614; Niculescu-Duvaz and Springer (1997) Adv. Drug Del. Rev. 26:151-172; U.S. Pat. No. 4,975,278).

In some embodiments, the epitope-specific mAb to be infused is conjugated beforehand with a molecule able to promote complement dependent cytotoxicity (CDC). Therefore, the complement system helps or complements the ability of antibodies to clear pathogens from the organism. When stimulated an activation cascade is triggered as a massive amplification of the response and activation of the cell-killing membrane attack complex. Different molecule may be used to conjugate the mAb, such as glycans (Courtois, A, Gac-Breton, S., Berthou, C, Guezennec, J., Bordron, A. and Boisset, C. (2012), Complement dependent cytotoxicity activity of therapeutic antibody fragments may be acquired by immunogenic glycan coupling, Electronic Journal of Biotechnology ISSN: 0717-3458; http://www.ejbio-technology.info DOI: 10.2225/vol15-issue5).

VI. Kits and Articles of Manufacture

The present application provides kits comprising any one of the DLL3 containing CARs or DLL3 CAR containing immune cells described herein, and pharmaceutical compositions of the same. In an embodiment of a kit the engineered CAR cells are frozen in a suitable medium, such as CryoStor® CS10, CryoStor® CS2 or CryoStor® CS5 (BioLife Solutions).

In some exemplary embodiments, a kit of the disclosure comprises allogeneic DLL3 CAR-containing T-cells and a CD52 antibody for administering to the subject a lymphodepletion regiment and a CAR-T regimen.

The present application also provides articles of manufacture comprising any one of the therapeutic compositions or kits described herein. Examples of an article of manufacture include vials (e.g., sealed vials).

EXAMPLES

Example 1: Generation and Testing of DLL3 Targeting Antibodies

The monoclonal antibodies to be used in accordance with the invention may be made by the hybridoma method first described by Kohler and Milstein, Nature 256:495, 1975, or may be made by recombinant DNA methods such as described in U.S. Pat. No. 4,816,567. Anti-DLL3 antibodies were first screened in Flag-DLL3 (adipogen) ELISA and then screened in FACS to determine binding to HEK-293T cells with or without human DLL3 expression.

Figure 1B:
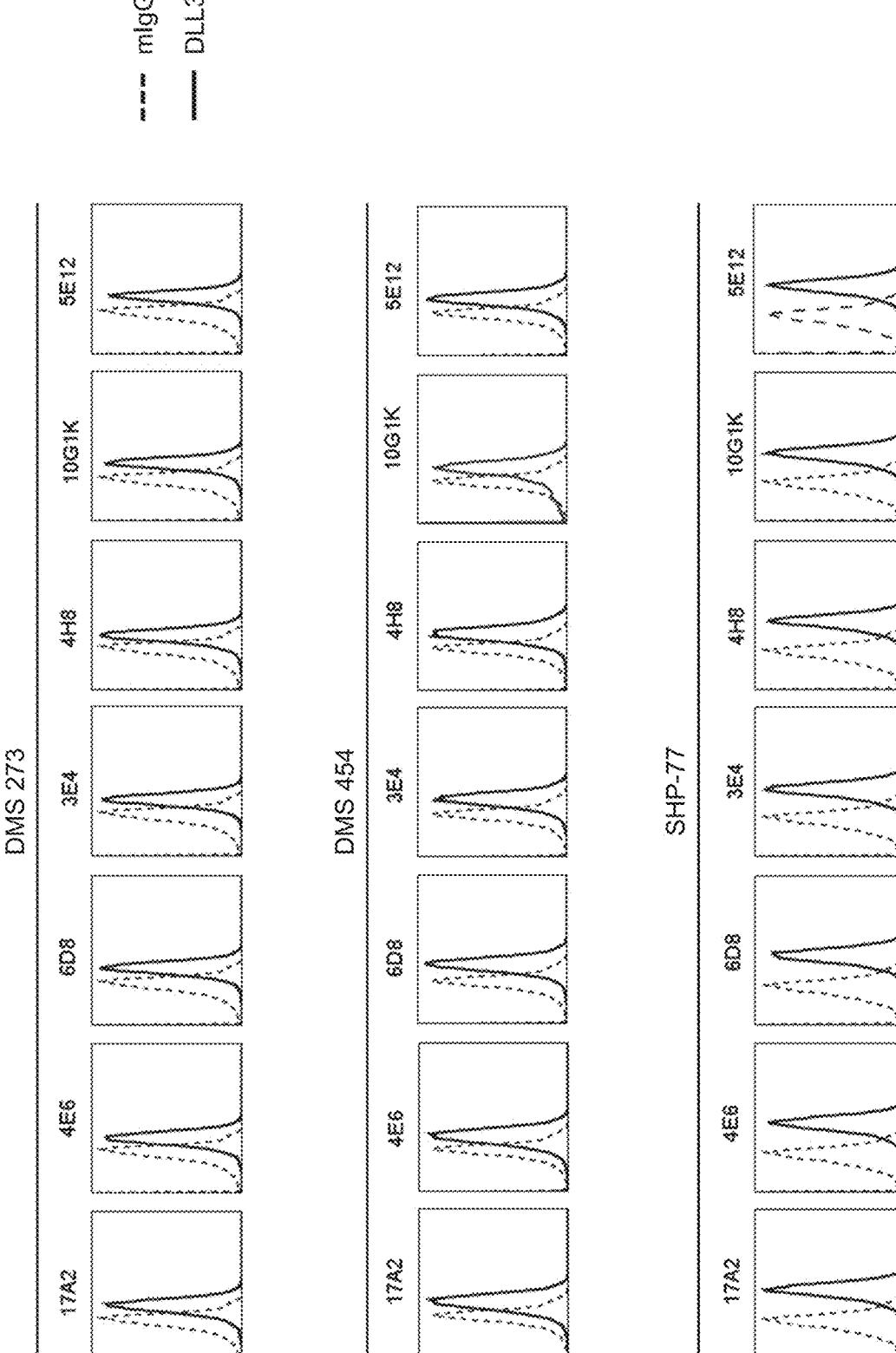

To test if the DLL3 specific antibodies can recognize cells that express endogenous DLL3, DMS 273 (Sigma, cat #95062830), DMS 454 (Sigma, cat #95062832), and SHP-77 (ATCC, cat #CRL-2195) cells were stained with 2 ug/ml of purified DLL3 antibodies with mouse IgG2A backbone (mIgG2a) or control mIgG2a antibody in PBS supplemented with 1% BSA. Bound DLL3 antibodies were detected with PE labelled anti-mouse IgG antibody (Biolegend, cat #405307). The samples were analyzed by flow cytometry. Representative images showing binding of DLL3 antibodies to DMS 273, DMS 454 and SHP-77 cells are included in FIG. 1.

Example 2: Determination of Kinetics and Affinity of Anti-DLL3 Antibodies Toward DLL3

This example determines the binding kinetics and affinity of various anti-DLL3 antibodies at 37° C. as both full-length monoclonal antibodies (IgG) and scFvs toward human, cynomolgus monkey (cyno) and mouse DLL3. For the scFvs, the variable regions of the anti-DLL3 antibodies derived from their respective hybridoma were cloned flanking a $(GGGGS)_3$ (SEQ ID NO: 472) or $(GGGGS)_4$ (SEQ ID NO: 478) linker followed by part of the hinge and Fc from a modified human IgG2 sequence resulting in a scFv-Fc fusion which was expressed using Expi293. The extracellular domain (ECD) from human, cyno and mouse DLL3 was fused with a C-terminal 8×His epitope tag (SEQ ID NO: 473) and Avi tag, expressed using Expi293 then purified by immobilized metal affinity chromatography (IMAC) followed by size exclusion chromatography (SEC).

The antibody binding kinetics were determined by surface plasmon resonance (Biacore™ surface plasmon resonance (SPR) system, GE Healthcare Bio-Sciences, Pittsburgh Pa.). The antibodies diluted in HBS-T+ running buffer (0.01 M HEPES pH 7.4, 0.15 M NaCl, 0.05% v/v Tween20, 1 mg/mL BSA) were captured on a CM4 chip immobilized with an antibody specific for the anti-DLL3 antibody constant domains. Purified DLL3 was serially diluted into HBS-T+, injected for 2 min at 30 uL/min and a dissociation time of 10 min then the surface regenerated with either 10 mM Glycine-HCl pH 1.7 or phosphoric acid between injections. Kinetic association rates (kon) and dissociation rates (koff) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_d$) values are calculated as $k_{off}/k_{on}$.

The kinetics and affinity parameters for tested anti-DLL3 antibodies are shown in Table 8A. Specifically, Table 8A shows the affinity of anti-DLL3 antibodies (either as IgG or scFv-Fc fusion) to human, cyno and mouse DLL3. The last column shows which extracellular domain of human DLL3 each of anti-DLL3 antibodies recognizes.

TABLE 8A

| | Affinity of anti-DLL3 antibodies | | | | |
| --- | --- | --- | --- | --- | --- |
| Clones | IgG affinity to huDLL3 (nM) | ScFv affinity to huDLL3 (nM) | ScFv affinity to cynoDLL3 (nM) | ScFv affinity to msDLL3 (nM) | Binding domain |
| 2D3 | 5.47 | ND | ND | ND | EGF3 |
| 5E12 | 7.76 | ND | ND | ND | DSL |

TABLE 8A-continued

| | Affinity of anti-DLL3 antibodies | | | | |
|---|---|---|---|---|---|
| Clones | IgG affinity to huDLL3 (nM) | ScFv affinity to huDLL3 (nM) | ScFv affinity to cynoDLL3 (nM) | ScFv affinity to msDLL3 (nM) | Binding domain |
| 26C8 | 5.54 | 5.53 | 4.51 | 3.05 | EGF3 |
| 2A6.C5 | 23.4 | 48.4 | 46.8 | 42.1 | EGF3 |
| 6D8 | <1.42 | <1.2 | NB | <1.5 | EGF1 |
| 7F9 | 12.67 | 27.3 | >250 | NB | N-ter |
| 8E11 | 5.86 | 11.2 | 10.5 | 7.03 | EGF3 |
| 9D3 | 21.1 | 23.3 | 21.8 | 7.19 | EGF3 |
| 2G1 | 38.1 | 17.2 | 20.5 | 2.61 | EGF5 |
| 3F2 | 14.8 | 8.18 | 6.81 | N | N-ter |
| 17A2 | 5.49 | 3.82 | <0.97 | N | EGF1 |
| 6F8 | 26.5 | 40.8 | NB | 19.3 | EGF5 |
| 9H12-K | ND | 186 | NB | NB | EGF4 |
| 4H8 | 18.5 | 23.3 | 27.0 | 18.6 | EGF4 |
| 10G1-K | ND | 26.3 | 28.8 | 27.7 | EGF5 |
| 11A3 | 4.8 | ND | ND | ND | EGF3 |

N-ter = N-terminus
ND = Not Determined
NB = No Binding

Example 3: Generation of CHO Cells Expressing Full Length and Truncated DLL3

A panel of CHO cells expressing full length and a variety of truncated human DLL3 were used to determine which domain each DLL3 targeting antibody recognizes. The extracellular domain of human DLL3 can be subdivided into different sub-domains that are defined by the following amino acid positions: Signal peptide: 1-26; N-terminus (N-ter): 27-175; DSL: 176-215; EGF1:215-249; EGF2:274-310; EGF3:312-351; EGF4:353-389; EGF5: 391-427; and EGF6: 429-465.

To generate truncated DLL3 proteins used for epitope mapping, the sequences of the respective 8 extracellular domains (signal peptide plus N-terminus, DSL, EGF1, EGF2, EGF3, EGF4, EGF5 and EGF6) of human DLL3 were deleted one by one from the antigen, starting from the N-terminus. Table 6 shows the truncated DLL3 proteins that were generated (also see FIGS. 2A-2D).

TABLE 6

| Truncated DLL3 proteins | |
|---|---|
| Name/ Component | Sequence |
| Human DLL3 complete ECD (SEQ ID NO: 556) | METDTLLLWVLLLWVPGSTGYPYDVPDYAGMLAG VFELQIHSFGPGPGPGAPRSPCSARLPCRLFFRV CLKPGLSEEAAESPCALGAALSARGPVYTEQPGA PAPDLPLPDGLLQVPFRDAWPGTFSFIIETWREE LGDQIGGPAWSLLARVAGRRRLAAGGPWARDIQR AGAWELRFSYRARCEPPAVGTACTRLCRPRSAPS RCGPGLRPCAPLEDECEAPLVCRAGCSPEHGFCE QPGECRCLEGWTGPLCTVPVSTSSCLSPRGPSSA TTGCLVPGPGPCDGNPCANGGSCSETPRSFECTC PRGFYGLRCEVSGVTCADGPCFNGGLCVGGADPD SAYICHCPPGFQGSNCEKRVDRCSLQPCRNGGLC LDLGHALRCRCRAGFAGPRCEHDLDDCAGRACAN GGTCVEGGGAHRCSCALGFGGRDCRERADPCAAR PCAHGGRCYAHFSGLVCACAPGYMGARCEFPVHP DGASALPAAPPGLRPGDPQRYLLPPALGLLVAAG VAGAALLLVHVRRRGHSQDAGSRLLAGTPEPSVH ALPDALNNLRTQEGSGDGPSSSVDWNRPEDVDPQ GIYVISAPSIYAREVATPLFPPLHTGRAGQRQHL LFPYPSSILSVK |

TABLE 6-continued

| Truncated DLL3 proteins | |
|---|---|
| Name/ Component | Sequence |
| Human DLL3 DSL-EGF6 (SEQ ID NO: 557) | METDTLLLWVLLLWVPGSTGYPYDVPDYAGMLGSA RCEPPAVGTACTRLCRPRSAPSRCGPGLRPCAPLE DECEAPLVCRAGCSPEHGFCEQPGECRCLEGWTGP LCTVPVSTSSCLSPRGPSSATTGCLVPGPGPCDGN PCANGGSCSETPRSFECTCPRGFYGLRCEVSGVTC ADGPCFNGGLCVGGADPDSAYICHCPPGFQGSNCE KRVDRCSLQPCRNGGLCLDLGHALRCRCRAGFAGP RCEHDLDDCAGRACANGGTCVEGGGAHRCSCALGF GGRDCRERADPCAARPCAHGGRCYAHFSGLVCACA PGYMGARCEFPVHPDGASALPAAPPGLRPGDPQRY LLPPALGLLVAAGVAGAALLLVHVRRRGHSQDAGS RLLAGTPEPSVHALPDALNNLRTQEGSGDGPSSSV DWNRPEDVDPQGIYVISAPSIYAREVATPLFPPLH TGRAGQRQHLLFPYPSSILSVK |
| Human DLL3 EGF1-EGF6 (SEQ ID NO: 558) | METDTLLLWVLLLWVPGSTGYPYDVPDYAGMLGSA PLVCRAGCSPEHGFCEQPGECRCLEGWTGPLCTVP VSTSSCLSPRGPSSATTGCLVPGPGPCDGNPCANG GSCSETPRSFECTCPRGFYGLRCEVSGVTCADGPC FNGGLCVGGADPDSAYICHCPPGFQGSNCEKRVDR CSLQPCRNGGLCLDLGHALRCRCRAGFAGPRCEHD LDDCAGRACANGGTCVEGGGAHRCSCALGFGGRDC RERADPCAARPCAHGGRCYAHFSGLVCACAPGYMG ARCEFPVHPDGASALPAAPPGLRPGDPQRYLLPPA LGLLVAAGVAGAALLLVHVRRRGHSQDAGSRLLAG TPEPSVHALPDALNNLRTQEGSGDGPSSSVDWNRP EDVDPQGIYVISAPSIYAREVATPLFPPLHTGRAG QRQHLLFPYPSSILSVK |
| Human DLL3 EGF2-EGF6 (SEQ ID NO: 559) | METDTLLLWVLLLWVPGSTGYPYDVPDYAGMLGSG PGPCDGNPCANGGSCSETPRSFECTCPRGFYGLRC EVSGVTCADGPCFNGGLCVGGADPDSAYICHCPPG FQGSNCEKRVDRCSLQPCRNGGLCLDLGHALRCRC RAGFAGPRCEHDLDDCAGRACANGGTCVEGGGAHR CSCALGFGGRDCRERADPCAARPCAHGGRCYAHFS GLVCACAPGYMGARCEFPVHPDGASALPAAPPGLR PGDPQRYLLPPALGLLVAAGVAGAALLLVHVRRRG HSQDAGSRLLAGTPEPSVHALPDALNNLRTQEGSG DGPSSSVDWNRPEDVDPQGIYVISAPSIYAREVAT PLFPPLHTGRAGQRQHLLFPYPSSILSVK |
| Human DLL3 EGF3-EGF6 (SEQ ID NO: 560) | METDTLLLWVLLLWVPGSTGYPYDVPDYAGMLGSS GVTCADGPCFNGGLCVGGADPDSAYICHCPPGFQG SNCEKRVDRCSLQPCRNGGLCLDLGHALRCRCRAG FAGPRCEHDLDDCAGRACANGGTCVEGGGAHRCSC ALGFGGRDCRERADPCAARPCAHGGRCYAHFSGLV CACAPGYMGARCEFPVHPDGASALPAAPPGLRPGD PQRYLLPPALGLLVAAGVAGAALLLVHVRRRGHSQ DAGSRLLAGTPEPSVHALPDALNNLRTQEGSGDGP SSSVDWNRPEDVDPQGIYVISAPSIYAREVATPLF PPLHTGRAGQRQHLLFPYPSSILSVK |
| Human DLL3 EGF4-EGF6 (SEQ ID NO: 561) | METDTLLLWVLLLWVPGSTGYPYDVPDYAGMLGSR VDRCSLQPCRNGGLCLDLGHALRCRCRAGFAGPRC EHDLDDCAGRACANGGTCVEGGGAHRCSCALGFGG RDCRERADPCAARPCAHGGRCYAHFSGLVCACAPG YMGARCEFPVHPDGASALPAAPPGLRPGDPQRYLL PPALGLLVAAGVAGAALLLVHVRRRGHSQDAGSRL LAGTPEPSVHALPDALNNLRTQEGSGDGPSSSVDW NRPEDVDPQGIYVISAPSIYAREVATPLFPPLHTG RAGQRQHLLFPYPSSILSVK |
| Human DLL3 EGF5-EGF6 (SEQ ID NO: 562) | METDTLLLWVLLLWVPGSTGYPYDVPDYAGMLGSD LDDCAGRACANGGTCVEGGGAHRCSCALGFGGRDC RERADPCAARPCAHGGRCYAHFSGLVCACAPGYMG ARCEFPVHPDGASALPAAPPGLRPGDPQRYLLPPA LGLLVAAGVAGAALLLVHVRRRGHSQDAGSRLLAG TPEPSVHALPDALNNLRTQEGSGDGPSSSVDWNRP EDVDPQGIYVISAPSIYAREVATPLFPPLH TGRAGQRQHLLFPYPSSILSVK |
| Human DLL3 EGF6 | METDTLLLWVLLLWVPGSTGYPYDVPDYAGMLGSR ADPCAARPCAHGGRCYAHFSGLVCACAPGYMGARC |

TABLE 6-continued

Truncated DLL3 proteins

| Name/ Component | Sequence |
|---|---|
| (SEQ ID NO: 563) | EFPVHPDGASALPAAPPGLRPGDPQRYLLPPALGL LVAAGVAGAALLLVHVRRRGHSQDAGSRLLAGTPE PSVHALPDALNNLRTQEGSGDGPSSSVDWNRPEDV DPQGIYVISAPSIYAREVATPLFPPLHTGRAGQRQ HLLFPYPSSILSVK |

To establish CHO cells expressing full length and truncated human DLL3 with an N-terminal H-A tag, the coding sequences for frill length human DLL3 (SEQ ID NO: 556; GeneBank record NM_016941) and the 7 HA-tagged truncated human DLL3 (SEQ ID NOs: 557 to 563) were cloned into pLVX—SFFV-Puro-P2A-TetO3G vector (Clontech). A lentivirus encoding either the frill length or truncated human DLL3s were generated by co-transfecting 293T cells with the pLVX—SFFV-Puro-P2A-TetO3G vectors with psPAX2 and pMD2G vectors. Two days after transfection, supernatant containing viral particles were collected and used to transduce CHO cells together with 5 ug/ml of polybrene.

Figure 2A:
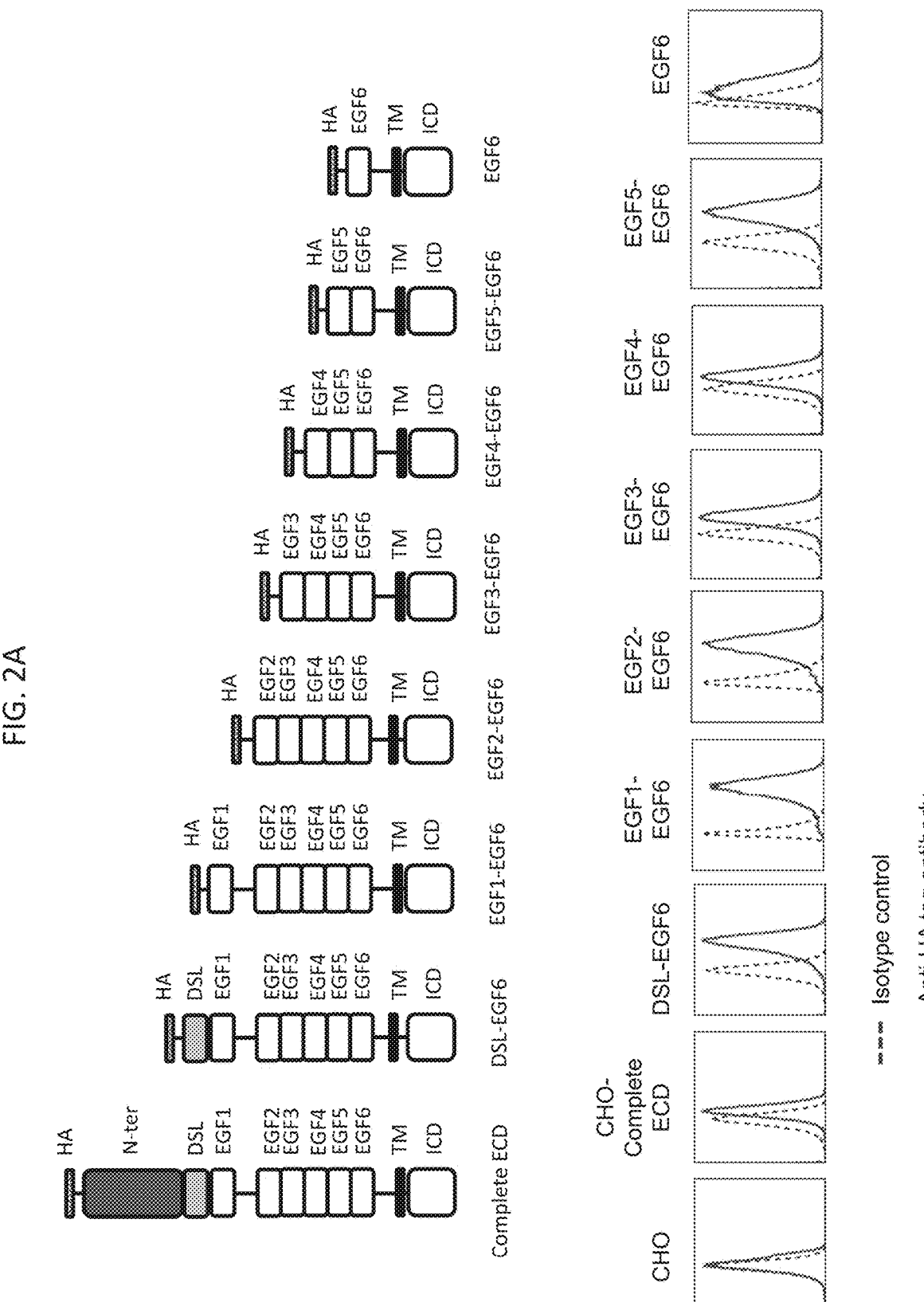
Figure 2D:
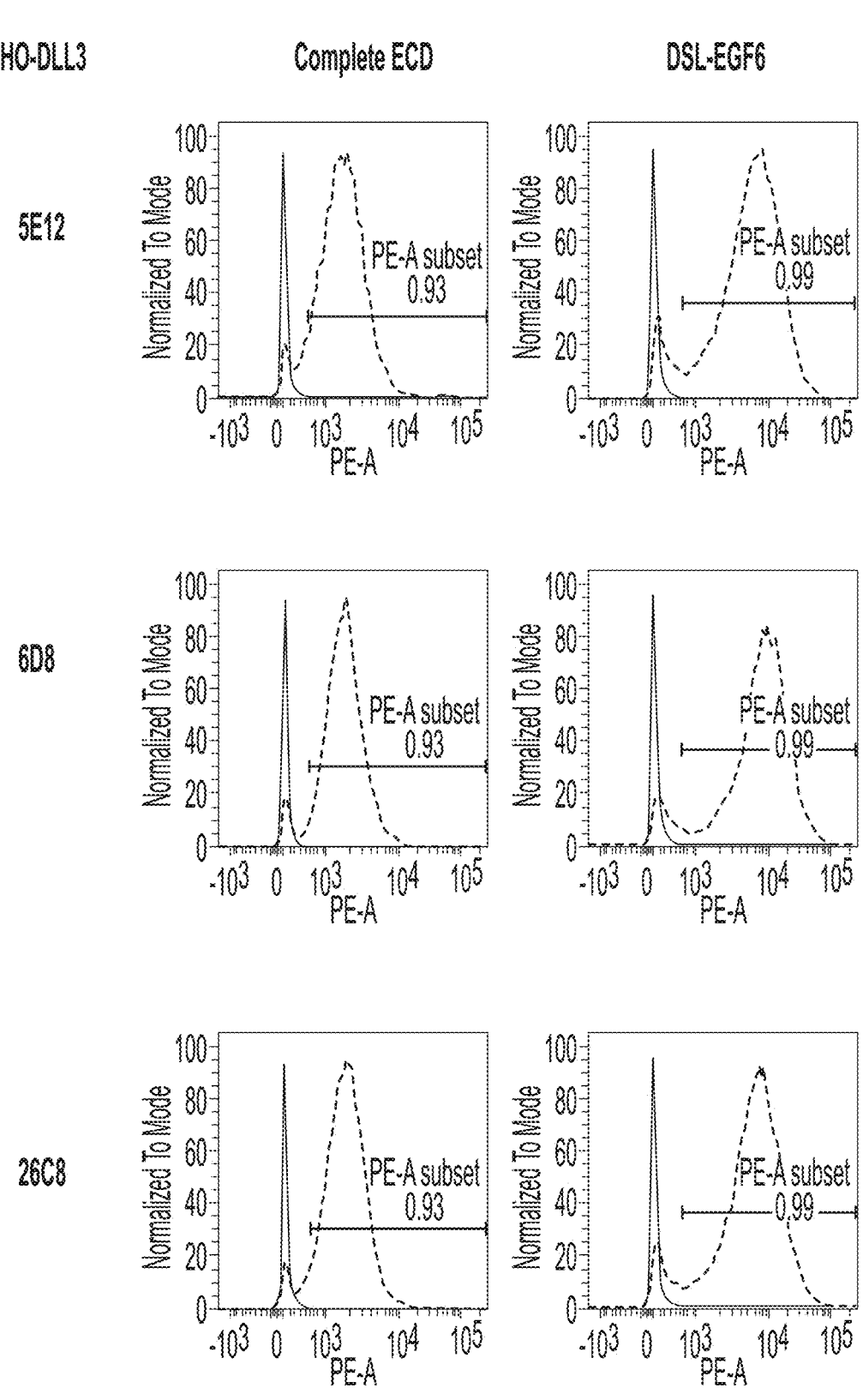
Figure 2D:
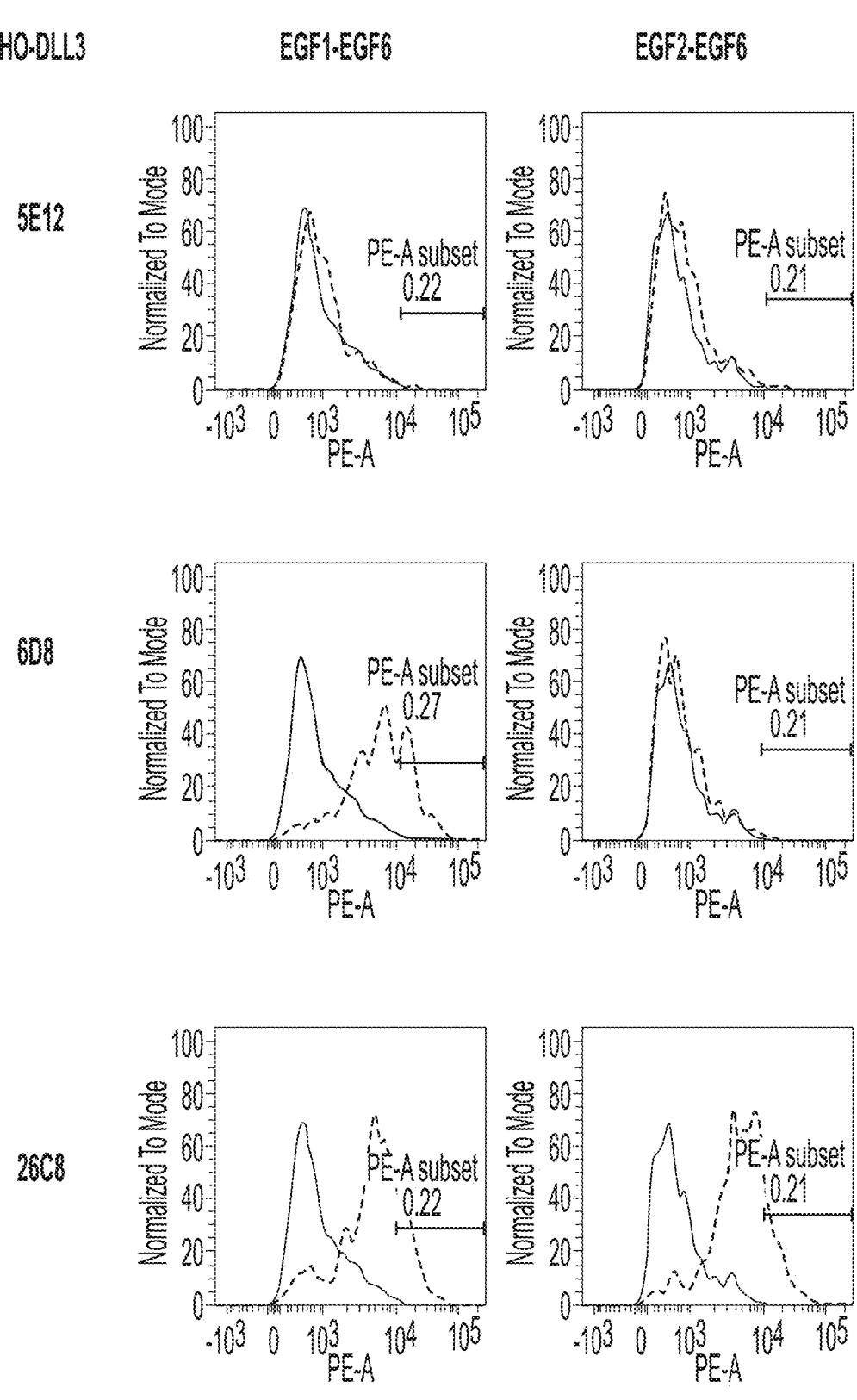
Figure 2D:
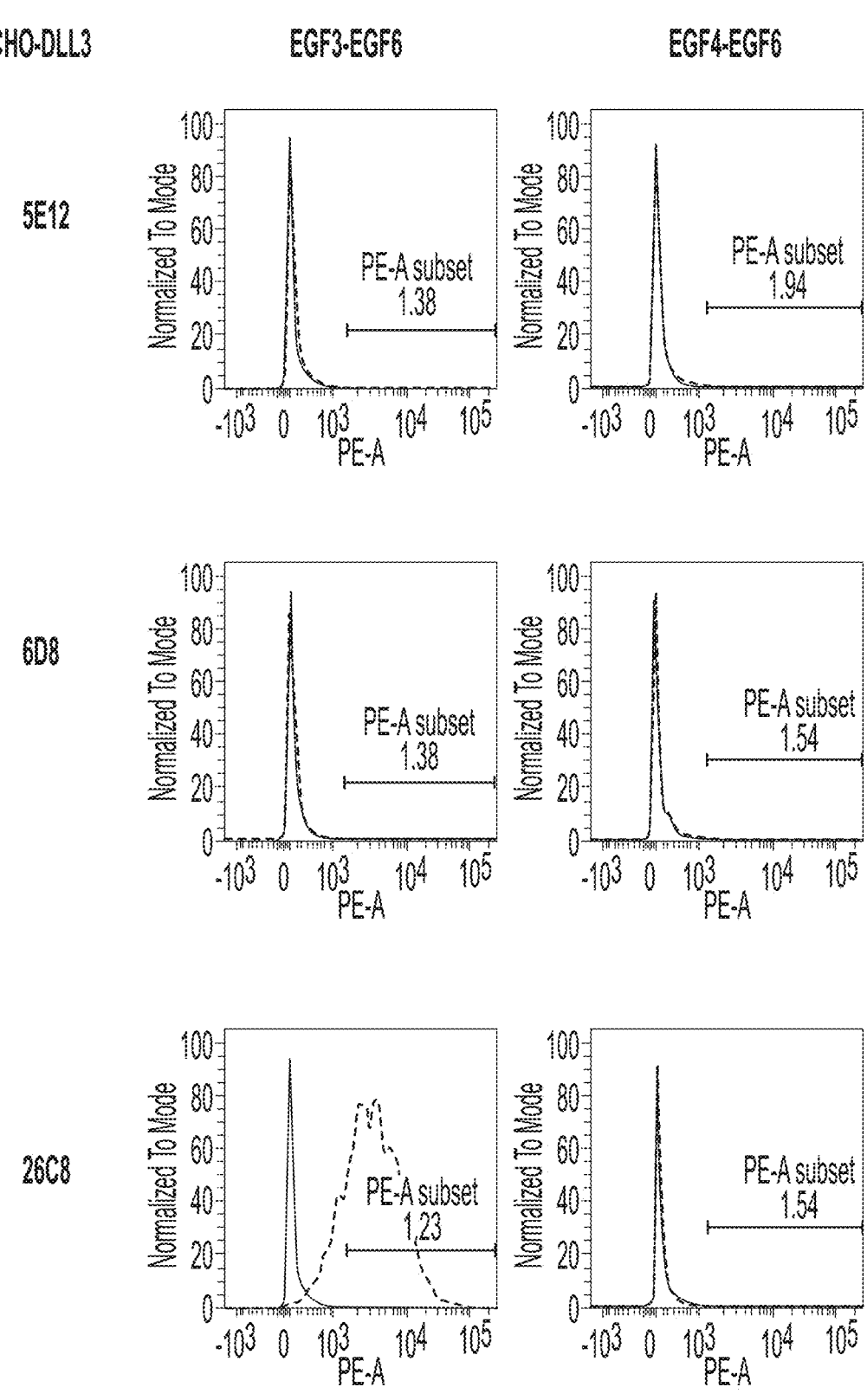
Figure 2D:
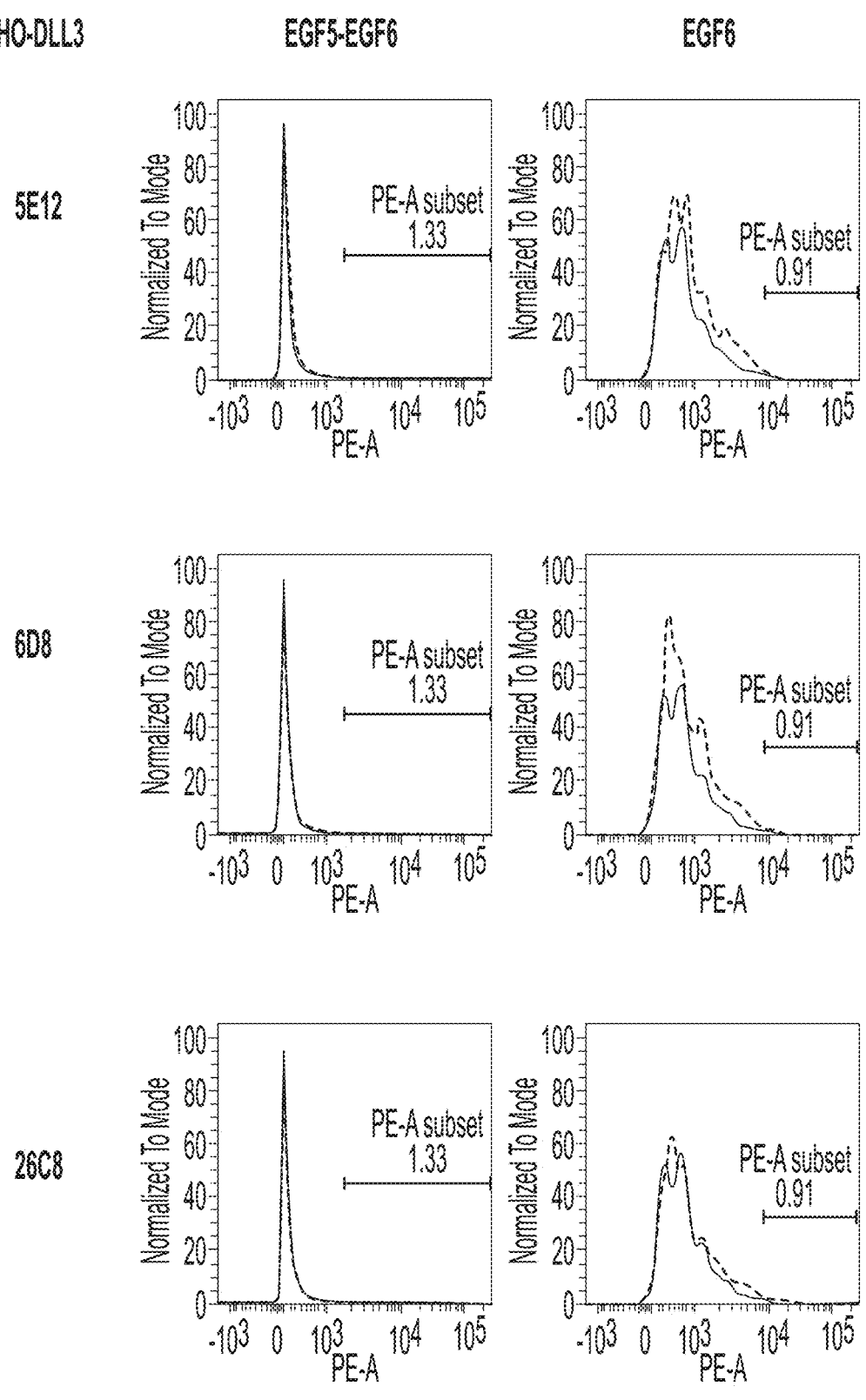

The expression of full length and truncated DLL3 was verified in a FACS assay using PE conjugated anti-HA antibody (Biolegend, cat #901518). As negative control, cells were incubated with isotype-matched and PE-labelled antibody (Biolegend, cat #400111) instead of anti-HA antibody. The bottom panel of FIG. 2A shows the expression of full length and truncated DLL3 on CHO cells.

Example 4: Epitope Mapping of DLL3 Targeting Antibodies

CHO cells expressing full length and truncated DLL3 were stained with hybridoma supernatant or purified DLL3 antibodies in PBS+1% BSA. Bound DLL3 antibodies were detected with PE labelled anti-mouse IgG antibody (Biolegend, cat #405307). The samples were analyzed by flow cytometry. The binding domain for each clone was determined using the panel of CHO expressing full length or truncated DLL3 described in Example 2. Flow cytometry analysis demonstrated that, for example, if a clone binds to all truncated proteins including EGF3 but not to any truncated protein without EGF3, then such clone recognizes EGF3. As shown in the representative images in FIG. 2D, anti-DLL3 antibodies recognize DSL, EGF1 and EGF3 domains, respectively. Signals from the PE channel are shown on the x-axis and counts are shown on the y-axis.

Example 5: Generation of DLL3 Specific CAR-T Cells

This example describes the construction of anti-DLL3 chimeric antigen receptors (CARs).

The anti-DLL3 antibodies listed in Table 1a were reformatted to CARs. The amino acid sequences of the heavy chain variable regions and light chain variable regions of these antibodies (Table 1b and Table 1c) were used to design single chain variable fragments (scFvs) (Table 1d) having the following general structure: heavy chain variable region-linker-light chain variable region. The linker had the following amino acid sequences GGGGSGGGGSGGGGSGGGGS (SEQ ID NO: 478).

Protein sequences encoding chimeric antigen receptor were designed to contain the following elements from 5' to 3' (FIG. 3A, Table 7): the CD8α signal sequence (SEQ ID NO: 477), an anti-DLL3 scFv, hinge and transmembrane regions of the human CD8α molecule (SEQ ID NO: 479), the cytoplasmic portion of the 41BB molecule (SEQ ID NO: 291) and the cytoplasmic portion of the CD3ζ molecule (SEQ ID NO: 292).

TABLE 7

CAR amino acid sequences

| SEQ ID NO: | Name/ Component | Sequence |
|---|---|---|
| 477 | CD8α signal sequence | MALPVTALLLPLALLLHAARP |
| 478 | linker | GGGGSGGGGSGGGGSGGGGS |
| 479 | CD8α hinge and transmembrane regions | TTTPAPRPPTPAPTIASQPLSLRPEACRPAAGGAVHTRGLDFAC DIYIWAPLAGTCGVLLLSLVIT |
| 480 | 41BB cytoplasmic signaling domain | KRGRKKLLYIFKQPFMRPVQTTQEEDGCSCRFPEEEEGGCEL |
| 481 | CD3ζ cytoplasmic signaling domain | LRVKFSRSADAPAYQQGQNQLYNELNLGRREEYDVLDKRRG RDPEMGGKPRRKNPQEGLYNELQKDKMAEAYSEIGMKGERR RGKGHDGLYQGLSTATKDTYDALHMQALPPR |
| 469 | CD3ζ cytoplasmic signaling domain | LRVKFSRSADAPAYKQGQNQLYNELNLGRREEYDVLDKRRG RDPEMGGKPRRKNPQEGLYNELQKDKMAEAYSEIGMKGERR RGKGHDGLYQGLSTATKDTYDALHMQALPPR |
| 482 | CD8α signal sequence, 2D3 scFv, CD8α hinge and transmembrane regions, 41BB cytoplasmic signaling domain, | MALPVTALLLPLALLLHAARPQVQLQESGPGLVKPSETLSLTC TVSDNSISNYYWSWIRQPPGKGLEWIAYIYYSGTTNYNPSLKS RVTISLDTSKNQFSLKLSSVTAADTAVYYCARLFNWGFAFDI WGQGTMVTVSSGGGGSGGGGSGGGGSGGGGSEIVMTQSPAT LSVSPGERATLSCRASQSVSSNLAWYQQKPGQAPRLLIYGAST RATGIPARFSGSGSGTEFTLTISSLQSEDFAVYYCQQYNNWPLT FGGGTKVEIKTTTPAPRPPTPAPTIASQPLSLRPEACRPAAGGA |

TABLE 7-continued

CAR amino acid sequences

| SEQ ID NO: | Name/ Component | Sequence |
|---|---|---|
| | CD3ζ cytoplasmic signaling domain | VHTRGLDFACDIYIWAPLAGTCGVLLLSLVITKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |
| 483 | CD8α signal sequence, 5A2 scFv, CD8α hinge and transmembrane regions, 41BB cytoplasmic signaling domain, CD3ζ cytoplasmic signaling domain | MALPVTALLLPLALLLHAARPQVQLQESGPGLMKPSETLSLTC TVSGGGSISSSYWSCIRQPPGKGLEWIGYIYYSGTTNYNPSLKSR VTLSLDTSKNQFSLRLTSVTAADTAVYYCARVAPTGFWFDYW GQGTLVTVSSGGGGSGGGGSGGGGSGGGGSEIVLTQSPGTLS LSPGERATLSCRASQRVSSRYLAWYQQKPGQAPRLLIYGASSR ATGIPDRFSGSGSGTDFTLTISRLEPEEFAVYYCQQYGTSPLTF GGGTKVEIKTTTPAPRPPTPAPTIASQPLSLRPEACRPAAGGAV HTRGLDFACDIYIWAPLAGTCGVLLLSLVITKRGRKKLLYIFK QPFMRPVQTTQEEDGCSCRFPEEEEGGCELRVKFSRSADAPAY QQGQNQLYNELNLGRREEYDVLDKRRGRDPEMGGKPRRKNP QEGLYNELQKDKMAEAYSEIGMKGERRRGKGHDGLYQGLST ATKDTYDALHMQALPPR |
| 484 | CD8α signal sequence, 7F9 scFv, CD8α hinge and transmembrane regions, 41BB cytoplasmic signaling domain, CD3ζ cytoplasmic signaling domain | MALPVTALLLPLALLLHAARPEVQLVESGGGLVQPGGSLRLS CAASGFTFSSHDMHWVRQATGKGLEWVSAIGIAGDTYYSGS VKGRFTISRENAKNSLYLQMNSLRAGDTAVYYCARANWGEG AFDIWGQGTMVTVSSGGGGSGGGGSGGGGSGGGGSDIQMTQ SPSSLSASVGDRVTITCRASQGISDYLAWYQQKPGKIPKLLIYA ASTLQSGVPSRFSGSGSGTDFTLTISSLQPEDVATYYCQKYNSV PLTFGGGTKVEIKTTTPAPRPPTPAPTIASQPLSLRPEACRPAAG GAVHTRGLDFACDIYIWAPLAGTCGVLLLSLVITKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 485 | CD8α signal sequence, 9D3 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSDDSISNYYWSWIRQPPGKGLEWIGYIFYSGTTNHNPSLKS RLTISLDKAKNQFSLRLSSVTAADTAVYYCARVFNWGFAFDI WGQGTMVTVSSGGGGSGGGGSGGGGSGGGGSEIVLTQSPGT LSLSPGERATLSCRASQRISRTYLAWYQQKPGQAPRLLIYGAS SRATGIPDRFTGSGSGTDFTLTISRLEPEDFAVYYCQQYGTSPL TFGGGTKVEINTTTPAPRPPTPAPTIASQPLSLRPEACRPAAGG AVHTRGLDFACDIYIWAPLAGTCGVLLLSLVITKRGRKKLLYI FKQPFMRPVQTTQEEDGCSCRFPEEEEGGCELRVKFSRSADAP AYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 486 | CD8α signal sequence, 26C8 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSDNSISNYYWSWIRQPPGKGLEWIAYIYYSGTTNYNPSLKS RVTISLDTSKNQFSLQLSSVTAADAAVYYCARVFHWGFAFDI WGQGTMVTVSSGGGGSGGGGSGGGGSGGGGSEIVLTQSPGT LSLSPGERATLSCRASQRVSNTYLAWYQQNPGQAPRLLIYGAS SRATGIPDRFSGSGSGTDFTLTISRLEPEDFAVYYCQQYGTSPL TFGGGTKVEIKTTTPAPRPPTPAPTIASQPLSLRPEACRPAAGG AVHTRGLDFACDIYIWAPLAGTCGVLLLSLVITKRGRKKLLYI FKQPFMRPVQTTQEEDGCSCRFPEEEEGGCELRVKFSRSADAP AYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 487 | CD8α signal sequence, 2A6.C5 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSNVSISSYYWSWIRQPPGKGLEWIGYIYYSGTTNYNPSLKS RVTMSVDTSKNQFSLKLSSVTAADTAVYFCARLSNWGFAFDI WGQGTMVTFSSGGGGSGGGGSGGGGSGGGGSEIVLTQSPGTL SLSPGERATLSCRASQTISSSYLAWYQQKPGQAPRLLIYGASSR ATGIPDRFSGSGSGTEFTLTISRLEPEDFAVYYCQQYGWSPITF GQGTRLEIKTTTPAPRPPTPAPTIASQPLSLRPEACRPAAGGAV HTRGLDFACDIYIWAPLAGTCGVLLLSLVITKRGRKKLLYIFK QPFMRPVQTTQEEDGCSCRFPEEEEGGCELRVKFSRSADAPAY QQGQNQLYNELNLGRREEYDVLDKRRGRDPEMGGKPRRKNP QEGLYNELQKDKMAEAYSEIGMKGERRRGKGHDGLYQGLST ATKDTYDALHMQALPPR |
| 488 | CD8α signal sequence, 5E12 scFv, CD8α hinge | MALPVTALLLPLALLLHAARPEVQLVESGGGLVQPGGSLRLS CAASGFTFSSYDMHWVRQATGKGLEWVSAIGPAGDTYYPGS VKGRFTISRENAKNSLYLQMNSLRAGDTAVYYCARADPPYYY |

TABLE 7-continued

CAR amino acid sequences

| SEQ ID NO: | Name/ Component | Sequence |
|---|---|---|
| | and transmembrane regions, 41BB cytoplasmic signaling domain, CD3ζ cytoplasmic signaling domain | YGMDVWGQGTTVTVSSGGGGSGGGGSGGGGSGGGGSDIVM TQSPLSLPVTPGEPASISCRSSQSLLHSNEYNYLDWYLQKPGQS PQLLIYLGSNRASGVPDRFSGSGSGTDFILKISRVEAEDVGVYY CMQALEIPLTFGGGTKVEIKTTTPAPRPPTPAPTIASQPLSLRPE ACRPAAGGAVHTRGLDFACDIYIWAPLAGTCGVLLLSLVITKR GRKKLLYIFKQPFMRPVQTTQEEDGCSCRFPEEEEGGCELRVK FSRSADAPAYQQGQNQLYNELNLGRREEYDVLDKRRGRDPE MGGKPRRKNPQEGLYNELQKDKMAEAYSEIGMKGERRRGK GHDGLYQGLSTATKDTYDALHMQALPPR |
| 489 | CD8α signal sequence, 6D8 scFv, CD8α hinge and transmembrane regions, 41BB cytoplasmic signaling domain, CD3ζ cytoplasmic signaling domain | MALPVTALLLPLALLLHAARPQITLKESGPTLVKPTQTLTLTCT FSGFSLSTrgVGVGWIRQPPGKALEWLALIYWNDDKRYSPSLQ TRLTITKDTPKNQVVLTMTNMDPVDTATYYCARSNWGnWYF ALWGRGTLVTVSSGGGGSGGGGSGGGGSGGGGSEIVLTQSPA TLSLSPGERATLSCRASQSVSSYLAWYQQKPGQAPRLLIYDAF YRATGIPARFSGSGSGTDFTLTISSLEPEDFAVYYCQHRSNWPI TFGQGTRLEIKTTTPAPRPPTPAPTIASQPLSLRPEACRPAAGGA VHTRGLDFACDIYIWAPLAGTCGVLLLSLVITKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |
| 490 | CD8α signal sequence, 8E11 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGDSISNYYWTWIRQPPGKGLEWIGYIYYSGTTNSNPSLKS RVTVSLDTSKSQFSLNLSSVTAADTAVYYCARVFNRgFAFDIW GQGTMVTVSSGGGGSGGGGSGGGGSGGGGSEIVLTQSPGTLS LSPGERATLSCRASQRISNTYLAWYQQKPGQAPRLLIYGASSR ATGIPDRFSGSGSGTDFTLTISRLEPEDPAAYYCQQYDTSPLTF GGGTKVEIKTTTPAPRPPTPAPTIASQPLSLRPEACRPAAGGAV HTRGLDFACDIYIWAPLAGTCGVLLLSLVITKRGRKKLLYIFK QPFMRPVQTTQEEDGCSCRFPEEEEGGCELRVKFSRSADAPAY QQGQNQLYNELNLGRREEYDVLDKRRGRDPEMGGKPRRKNP QEGLYNELQKDKMAEAYSEIGMKGERRRGKGHDGLYQGLST ATKDTYDALHMQALPPR |
| 491 | CD8α signal sequence, 5C1.A4 scFv, CD8α hinge and transmembrane regions, 41BB cytoplasmic signaling domain, CD3ζ cytoplasmic signaling domain | MALPVTALLLPLALLLHAARPQVTLRESGPALVKPTQTLTLTC TVSGVSLSTsgMCVSWIRQPLGKALEWLGFIDWDDDKYYNTS LKTRLTISKDTSKNQVVLTMTNMDPVDTATYYCARIRGYsgsy DAFDIWGQGTVVIVSSGGGGSGGGGSGGGGSGGGGSDIVM QSPLSLPVTPGEPASISCRSSQSLLHSNGYNHLDWYLQKPGQSP QVLIYLGSNRASGVPDRFSGSGSGTDFTLKISRVEAEDVGVYF CMQALQTPLTFGGGTKVEIKTTTPAPRPPTPAPTIASQPLSLRP EACRPAAGGAVHTRGLDFACDIYIWAPLAGTCGVLLLSLVITK RGRKKLLYIFKQPFMRPVQTTQEEDGCSCRFPEEEEGGCELRV KFSRSADAPAYQQGQNQLYNELNLGRREEYDVLDKRRGRDP EMGGKPRRKNPQEGLYNELQKDKMAEAYSEIGMKGERRRGK GHDGLYQGLSTATKDTYDALHMQALPPR |
| 492 | CD8α signal sequence, 9F7 scFv, CD8α hinge and transmembrane regions, 41BB cytoplasmic signaling domain, CD3ζ cytoplasmic signaling domain | MALPVTALLLPLALLLHAARPQVQLQVSGPGLVKPSETLSLTC SVSGGSISSYYWSWIRQSPGKGLDWIGYMYYSGTTNYNPSLK SRVTISVDTSKNQFSLKLSSVTATDTAVYYCARVGLTgFFFDY WGQGTLVTVSSGGGGSGGGGSGGGGSGGGGSAIQMTQSPSSL SASVGDRVTITCRASQGIRNDLGWYQQKPGKAPKLLIYAASSL QSGVPSRFSGSGSGTDFTLTVSSLQPEDFATYYCLQDYNYPYT FGQGTKLEIKTTTPAPRPPTPAPTIASQPLSLRPEACRPAAGGA VHTRGLDFACDIYIWAPLAGTCGVLLLSLVITKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |
| 493 | CD8α signal sequence, 2C3 scFv, CD8α hinge and transmembrane regions, 41BB cytoplasmic signaling domain, CD3ζ cytoplasmic signaling domain | MALPVTALLLPLALLLHAARPQVQLQQWGGGLLKPSETLSLT CAVYGGSSSGNYWSWIRQPPGKRLEWIGEINHSGTTSYNPSLK SRVTISVDTSKNQFSLKLSSVTAADTAVYYCARGELGIADSWG QGTLVTVSSGGGGSGGGGSGGGGSGGGGSDIQMTQSPSTLSA SVGDRVTITCRASQSISRWLAWYQQKPGKAPKLLIYKASSLES GVPSRFSGSGSGTEFTLTISSLQPDDFATYYCQQYNSYSTFGQG TKVEIKTTTPAPRPPTPAPTIASQPLSLRPEACRPAAGGAVHTR GLDFACDIYIWAPLAGTCGVLLLSLVITKRGRKKLLYIFKQPF MRPVQTTQEEDGCSCRFPEEEEGGCELRVKFSRSADAPAYQQ GQNQLYNELNLGRREEYDVLDKRRGRDPEMGGKPRRKNPQE GLYNELQKDKMAEAYSEIGMKGERRRGKGHDGLYQGLSTAT KDTYDALHMQALPPR |

TABLE 7-continued

| CAR amino acid sequences | |
|---|---|

| SEQ ID NO: | Name/ Component | Sequence |
|---|---|---|
| 494 | CD8α signal sequence, 2G1 scFv, CD8α hinge and transmembrane regions, 41BB cytoplasmic signaling domain, CD3ζ cytoplasmic signaling domain | MALPVTALLLPLALLLHAARPQLQLQESGPGLVKPSETLSLTC TVSGGSISSssYYWGWIRQPPGKGLEWIGSIYYSGNIYHNPSLK SRVSISVDTSKNQFSLRLSSVTAADTAVYYCAREIIVgaTHFDY WGQGTLVTVSSGGGGSGGGGSGGGGSGGGGSAIQMTQSPSSL SASVGDRVTITCRASQGIRNDLGWYQQKPGKAPELLIYAASSL QSGVPSRFSGSGSGTDFTLTISSLQPEDFATYYCLQDYNYPLTF GPGTKVDIKTTTPAPRPPTPAPTIASQPLSLRPEACRPAAGGAV HTRGLDFACDIYIWAPLAGTCGVLLLSLVITKRGRKKLLYIFK QPFMRPVQTTQEEDGCSCRFPEEEEGGCELRVKFSRSADAPAY QQGQNQLYNELNLGRREEYDVLDKRRGRDPEMGGKPRRKNP QEGLYNELQKDKMAEAYSEIGMKGERRRGKGHDGLYQGLST ATKDTYDALHMQALPPR |
| 495 | CD8α signal sequence, 3E4 scFv, CD8α hinge and transmembrane regions, 41BB cytoplasmic signaling domain, CD3ζ cytoplasmic signaling domain | MALPVTALLLPLALLLHAARPQVQLQQWGAGLLKPSETLSLT CAVYGGSFSGYYWSWIRQPPGKGLEWIGEIIHSGSSNYNPSLK SRVSISVDTSKNQFSLKLSSVTAADTAVYYCSRGEYGsgSRFDY WGQGTLVTVSSGGGGSGGGGSGGGGSGGGGSAIQMTQSPSSL SASVGDRVAITCRASQGIRDDLGWYQQKPGKAPKLLIYAASS LQSGVPSRFSGSRSDTDFTLTISSLQPEDFATYYCLQDYDYPLT FGGGTKVEIKTTTPAPRPPTPAPTIASQPLSLRPEACRPAAGGA VHTRGLDFACDIYIWAPLAGTCGVLLLSLVITKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |
| 496 | CD8α signal sequence, 3F2 scFv, CD8α hinge and transmembrane regions, 41BB cytoplasmic signaling domain, CD3ζ cytoplasmic signaling domain | MALPVTALLLPLALLLHAARPQVQLQESGPGLVKPSGTLSLTC AVSGGSISSnNWWSWVRQPPGKGLEWIGDIHHSGSTNYKPSL KSRVTISVDKSKNQFSLNLISVTAADTAVYYCAREAGGYFDY WGQGILVTVSSGGGGSGGGGSGGGGSGGGGSDIQMTQSPSTL SASVGDRVTITCRASQSISSWLAWYQQKPGKAPKLLISKASSL ESGVPSRFSGSGSGPEFTLTISSLQPADFATYYCQQYNSYSTFG QGTKLEIKTTTPAPRPPTPAPTIASQPLSLRPEACRPAAGGAVH TRGLDFACDIYIWAPLAGTCGVLLLSLVITKRGRKKLLYIFKQP FMRPVQTTQEEDGCSCRFPEEEEGGCELRVKFSRSADAPAYQ QGQNQLYNELNLGRREEYDVLDKRRGRDPEMGGKPRRKNPQ EGLYNELQKDKMAEAYSEIGMKGERRRGKGHDGLYQGLSTA TKDTYDALHMQALPPR |
| 497 | CD8α signal sequence, 4F9 scFv, CD8α hinge and transmembrane regions, 41BB cytoplasmic signaling domain, CD3ζ cytoplasmic signaling domain | MALPVTALLLPLALLLHAARPQVQLQQWGAGLLKPSETLSLT CAVYGGSFSGYYWTWIRQPPGKGLEWIGEITHSGSTNYNPSL KSRVSISVDTSKNQFSLKLSSVTAADTAVYYCARGEYGsgSRF DYWGQGTLVTVSSGGGGSGGGGSGGGGSGGGGSAIQMTQSP SSLSASVGDRVAITCRASQGIRDDLGWYQQKPGKAPKLLIYA ASSLQSGVPSRFSGSGSDTDFTLTISSLQPEDFATYYCLQDYDY PLTFGGGTKVEIKTTTPAPRPPTPAPTIASQPLSLRPEACRPAAG GAVHTRGLDFACDIYIWAPLAGTCGVLLLSLVITKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 498 | CD8α signal sequence, 4G9 scFv, CD8α hinge and transmembrane regions, 41BB cytoplasmic signaling domain, CD3ζ cytoplasmic signaling domain | MALPVTALLLPLALLLHAARPQVQLQQWGAGLLKPSETLSLT CAVYGGSFSGYYWSWIRQPPGKGLEWIGEITHSGSTNYNPSLK SRVSISVDTSKNQFSLKLSSVTAADTAVYYCARGEYGsgSRFD YWGQGTLVTVSSGGGGSGGGGSGGGGSGGGGSAIQMTQSPS SLSASVGDRVALTCRASQGIRDDLGWYQQKPGKAPKLLIYAA SSLQSGVPSRFSGSGSDTDFTLTISSLQPEDFATYYCLQDYDYP LTFGGGTKVEIKTTTPAPRPPTPAPTIASQPLSLRPEACRPAAG GAVHTRGLDFACDIYIWAPLAGTCGVLLLSLVITKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 499 | CD8α signal sequence, 11H7 scFv, CD8α hinge and transmembrane regions, 41BB cytoplasmic signaling domain, CD3ζ cytoplasmic | MALPVTALLLPLALLLHAARPQVQLQQWGAGLLKPSETLSLT CAVYGGSFSAYYWNWIRQPPGKGLEWIGEINHSGSTNYNPSL KSRVTISVDTSKNQFSLNLTSLTAADTAVYYCARGLDSsgwYP FDYWGQGTLVTVSSGGGGSGGGGSGGGGSGGGGSDIQMTQS PSSVSASVGDRVTITCRASQGISSWLAWYQQKPGKAPKLLIYA ASSLQSGVPSRFSGSGSGTDFTLTISSLQPEDFATYYCQQADSF PFTFGPGTKVDIKTTTPAPRPPTPAPTIASQPLSLRPEACRPAAG GAVHTRGLDFACDIYIWAPLAGTCGVLLLSLVITKRGRKKLLY |

TABLE 7-continued

| CAR amino acid sequences | | |
|---|---|---|

| SEQ ID NO: | Name/ Component | Sequence |
|---|---|---|
| | signaling domain | IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 500 | CD8α signal sequence, 16H7 scFv, CD8α hinge and transmembrane regions, 41BB cytoplasmic signaling domain, CD3ζ cytoplasmic signaling domain | MALPVTALLLPLALLLHAARPQVLQQWGAGLLKPSETLSLT CAVFGGSFSGDYWSWIRQPPGKGLEWIGEINHSGITSFNPSLKS RVTISVDTSKNQFSLKLSSVTAADTAVYYCARGELGIPDNWG QGTLVTVSSGGGGSGGGGSGGGGSGGGGSDIQMTQSPSTLSA SVGDRVTITCRASQSISRWLAWYQQKPGKAPKLLIYKASSLES GVPSRFSGSGSGTEFTLTISSLQPDDFATYYCQQYNSYSTFGQG TKVEIKTTTPAPRPPTPAPTIASQPLSLRPEACRPAAGGAVHTR GLDFACDIYIWAPLAGTCGVLLLSLVITKRGRKKLLYIFKQPF MRPVQTTQEEDGCSCRFPEEEEGGCELRVKFSRSADAPAYQQ GQNQLYNELNLGRREEYDVLDKRRGRDPEMGGKPRRKNPQE GLYNELQKDKMAEAYSEIGMKGERRRGKGHDGLYQGLSTAT KDTYDALHMQALPPR |
| 501 | CD8α signal sequence, 17A2 scFv, CD8α hinge and transmembrane regions, 41BB cytoplasmic signaling domain, CD3ζ cytoplasmic signaling domain | MALPVTALLLPLALLLHAARPQVLQESGPGLVKPSGTLSLTC VVFGDSISSsNWWSWVRQPPGKGLEWIGEVFHSGSTNYNPSL KSRVTISVDKSKNQFSLKLSSVTAADTAVYYCARAAVAGALD YWGQGTLVTVSSGGGGSGGGGSGGGGSGGGGSDIVMTQSPD SLAVSLGERATINCKSSQSVLYSSNNKNYLAWYQQKPGQPPN LLVYWASTRESGVPDRFSGAGSGTDFTLTISSLQAEDVAVYYC QQYYGTSWTFGQGTKVEIKTTTPAPRPPTPAPTIASQPLSLRPE ACRPAAGGAVHTRGLDFACDIYIWAPLAGTCGVLLLSLVITKR GRKKLLYIFKQPFMRPVQTTQEEDGCSCRFPEEEEGGCELRVK FSRSADAPAYQQGQNQLYNELNLGRREEYDVLDKRRGRDPE MGGKPRRKNPQEGLYNELQKDKMAEAYSEIGMKGERRRGK GHDGLYQGLSTATKDTYDALHMQALPPR |
| 502 | CD8α signal sequence, 6H1 scFv, CD8α hinge and transmembrane regions, 41BB cytoplasmic signaling domain, CD3ζ cytoplasmic signaling domain | MALPVTALLLPLALLLHAARPQITLRESGPTLVKPTQTLTLTCT FSGFSLSTsgLGVGWIRQPPGEALEWLALIYWNDDKRYSPSLK SRLSITKDTSKNQVVLIMTNMDPVDTATYYCVHRRIAaPGSVY WGQGTLVTVSSGGGGSGGGGSGGGGSGGGGSDIQMTQSPSS VSASVGDRVTITCRASQGISSWLAWYQQKPGKAPKLLISAASS LQSGVPSRFSGSGSGTDFTLTISSLQPEDFATYYCHQANSFPFT FGGQGTKLEIKTTTPAPRPPTPAPTIASQPLSLRPEACRPAAGGA VHTRGLDFACDIYIWAPLAGTCGVLLLSLVITKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |
| 503 | CD8α signal sequence, 6H5 scFv, CD8α hinge and transmembrane regions, 41BB cytoplasmic signaling domain, CD3ζ cytoplasmic signaling domain | MALPVTALLLPLALLLHAARPQVQLVQSGAEVKKPGASVKVS CKVSGYTLTELSMHWVRQAPGKGPEGMGGFDpEDGKTIYAQ KFQGRVTMTEDTSADTAYMELNSLRSEDTAVYYCATLLRG1D AFDVWGQGTMVTVSSGGGGSGGGGSGGGGSGGGGSDIQMT QSPSSLSASVGDRVTITCRASQGIRNDLGWYQQKPGKAPKRLI YAASSLQSGVPSRFSGSGSGTEFTLTISTLQPEDFATYYCLQHN SYPRTFGQGTKVEIKTTTPAPRPPTPAPTIASQPLSLRPEACRPA AGGAVHTRGLDFACDIYIWAPLAGTCGVLLLSLVITKRGRKK LLYIFKQPFMRPVQTTQEEDGCSCRFPEEEEGGCELRVKFSRS ADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 504 | CD8α signal sequence, 10D1 scFv, CD8α hinge and transmembrane regions, 41BB cytoplasmic signaling domain, CD3ζ cytoplasmic signaling domain | MALPVTALLLPLALLLHAARPQVQLQQWGAGLLKPSETLSLT CAVYGGSFSGYYWRWIRQPPGKGLEWIGEISHSGSTNYNPSL KSRVTISVDTSKNQFSLKLSSVTAADTAVYYCAVRGYSygyPLF DYWGQGTLVTVSSGGGGSGGGGSGGGGSGGGGSDIQMTQSP SSLSASVGDRVTITCRASQGIRNDLGWYQQKLGKAPKRLIYA ASSLQSGVPSRFSGSGSGTEFTLTISSLQPEDFATYYCLQYNSY PRTFGQGTKVEIKTTTPAPRPPTPAPTIASQPLSLRPEACRPAAG GAVHTRGLDFACDIYIWAPLAGTCGVLLLSLVITKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 505 | CD8α signal sequence, 11F6 scFv, CD8α hinge and transmembrane | MALPVTALLLPLALLLHAARPQVQLQESGPGLVKPSGTLSLTC AVSGDSISSNWWTWVRQPPGKGLEWIGDIHHSGSTNYNPSLK SRVTMSVDKSENQFSLKLSSVTAADTAVFYCARDGGGTLDY WGQGTLVTVSSGGGGSGGGGSGGGGSGGGGSDIQMTQSPST |

TABLE 7-continued

CAR amino acid sequences

| SEQ ID NO: | Name/ Component | Sequence |
|---|---|---|
| | regions, 41BB cytoplasmic signaling domain, CD3ζ cytoplasmic signaling domain | LSASVGDRVTITCRASQSISSWLAWYQQKPGKAPKLLIYKAST LESGVPSRFSGSGSGTEFTLTISSLQPDDFATYYCQQYNGYSTF GQGTKVEIKTTTPAPRPPTPAPTIASQPLSLRPEACRPAAGGAV HTRGLDFACDIYIWAPLAGTCGVLLLSLVITKRGRKKLLYIFK QPFMRPVQTTQEEDGCSCRFPEEEEGGCELRVKFSRSADAPAY QQGQNQLYNELNLGRREEYDVLDKRRGRDPEMGGKPRRKNP QEGLYNELQKDKMAEAYSEIGMKGERRRGKGHDGLYQGLST ATKDTYDALHMQALPPR |
| 506 | CD8α signal sequence, 6F8 scFv, CD8α hinge and transmembrane regions, 41BB cytoplasmic signaling domain, CD3ζ cytoplasmic signaling domain | MALPVTALLLPLALLLHAARPQVQLVQSGAEVKKPGSSVKVS CKASGGTFTNYCISWVRQAPGQGLEWMGGIIpIFGTTNYAQTF QGRVTITADKSTSTAYMELSSLRSEDTAVYYCARDNGDryyYD MDVWGQGTTVTVSSGGGGSGGGGSGGGGSGGGGSQSVLTQP PSVSAAPGQKVTISCSGSSSNIGNNYVSWYQQLPGTAPKLLIY DNNKRPSGIPDRFSGSKSGTSATLGITGLQTGDEADYYCGTWD SSLSAVVFGGGTKLTVLTTTPAPRPPTPAPTIASQPLSLRPEACR PAAGGAVHTRGLDFACDIYIWAPLAGTCGVLLLSLVITKRGR KKLLYIFKQPFMRPVQTTQEEDGCSCRFPEEEEGGCELRVKFS RSADAPAYQQGQNQLYNELNLGRREEYDVLDKRRGRDPEMG GKPRRKNPQEGLYNELQKDKMAEAYSEIGMKGERRRGKGHD GLYQGLSTATKDTYDALHMQALPPR |
| 507 | CD8α signal sequence, 3G6-L1 scFv, CD8α hinge and transmembrane regions, 41BB cytoplasmic signaling domain, CD3ζ cytoplasmic signaling domain | MALPVTALLLPLALLLHAARPQVPLVQSGAEVKKPGSSVKVS CKASGGTFSTYSISWVRQAPGQGLEWMGGIIpIFGTTNYAQKF QGRVTITADKSTSTAYMELSSLRSEDTAVYYCARDGEGsyyyY YGMDVWGQGTTVTVSSGGGGSGGGGSGGGGSGGGGSQSVL TQPPSVSAAPGQKVTISCSGSSSNIGNNYVSWYQQLPGTAPKL LIYDNNKRPSGIPDRFFGSKFGTSATLGITGLQTGDEADYYCGT WDSSLSAVVFGGGTKLTVLTTTPAPRPPTPAPTIASQPLSLRPE ACRPAAGGAVHTRGLDFACDIYIWAPLAGTCGVLLLSLVITKR GRKKLLYIFKQPFMRPVQTTQEEDGCSCRFPEEEEGGCELRVK FSRSADAPAYQQGQNQLYNELNLGRREEYDVLDKRRGRDPE MGGKPRRKNPQEGLYNELQKDKMAEAYSEIGMKGERRRGK GHDGLYQGLSTATKDTYDALHMQALPPR |
| 508 | CD8α signal sequence, 4C6 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGDSISSYYWSWIRQPPGKGLEWIGYMYYSGITNYNPSLKS RVNISLDTSKNQFSLKLGSVTAADTAVYYCARLSVAgFYFDY WGQGTLVTVSSGGGGSGGGGSGGGGSGGGGSEIVLTQSPGTL SLSPGERATLSCRASQSVTRSYLAWYQQKPGQAPRLLIYGASS RATDIPDRFSGSGSGTDFTLTINRLEPEDFAVYYCQQYGTSPLT FGGGTKVEIKTTTPAPRPPTPAPTIASQPLSLRPEACRPAAGGA VHTRGLDFACDIYIWAPLAGTCGVLLLSLVITKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |
| 509 | CD8α signal sequence, 4E6 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSSDSISSYYWSWIRQPPGKGLEWISYIYYSGISNYNPSLKSR VSISVDTSKNQFSLRLSSVTAADTAVYYCARISVAgFFFDNWG QGTLVTVSSGGGGSGGGGSGGGGSGGGGSEIMLTQSPDTLSL SPGERATLSCRASQSVSSSYLAWYQQKPGQAPRLLIYGASSRA AGVPDRFSGSGSGTDFTLTISRLAPEDFVVYYCQQYGISPLTFG GGTKVEIKTTTPAPRPPTPAPTIASQPLSLRPEACRPAAGGAVH TRGLDFACDIYIWAPLAGTCGVLLLSLVITKRGRKKLLYIFKQP FMRPVQTTQEEDGCSCRFPEEEEGGCELRVKFSRSADAPAYQ QGQNQLYNELNLGRREEYDVLDKRRGRDPEMGGKPRRKNPQ EGLYNELQKDKMAEAYSEIGMKGERRRGKGHDGLYQGLSTA TKDTYDALHMQALPPR |
| 510 | CD8α signal sequence, 4H8 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSnsATWNWIRQSPSRGLEWLGRTYYRSKwyDDYAV SVKSRITINPDTSKNHLSLHLNSVTPEDTAVYYCAGGGLVgapD GFDVWGQGTMVTVSSGGGGSGGGGSGGGGSGGGGSQSVLT QPPSASGTPGQRVTISCSGSSSNIGSDPVNWYQQLPGTAPKLLI YSNNQRPSGVPDRFSGSKSGTSASLAISGLQSEDEADYYCSAW DDSLNGYVFGTGTKVTVLTTTPAPRPPTPAPTIASQPLSLRPEA CRPAAGGAVHTRGLDFACDIYIWAPLAGTCGVLLLSLVITKRG RKKLLYIFKQPFMRPVQTTQEEDGCSCRFPEEEEGGCELRVKF SRSADAPAYQQGQNQLYNELNLGRREEYDVLDKRRGRDPEM GGKPRRKNPQEGLYNELQKDKMAEAYSEIGMKGERRRGKGH DGLYQGLSTATKDTYDALHMQALPPR |

TABLE 7-continued

| CAR amino acid sequences | |
|---|---|

| SEQ ID NO: | Name/ Component | Sequence |
|---|---|---|
| 511 | CD8α signal sequence, 9H12-K scFv, CD8α hinge and transmembrane regions, 41BB cytoplasmic signaling domain, CD3ζ cytoplasmic signaling domain | MALPVTALLLPLALLLHAARPQVQLVQSGAEVKKPGASVKVS CKASGYTFTGYSIHWVRQAPGQGLEWMGWINpNSGGTFYAQ KFQGRVTMTRDTSISTVYMELSRLRSDDTAVYYCARDGWGdy yyYGLDVWGQGTTVTVSLGGGGSGGGGSGGGGSGGGGSDIQ MTQSPSSVSASVGDRVTITCRASQDISSWLAWYQQKPGKAPK LLIYTASSLQGGVPSRFSGSGSGTDFTLTISSLQPEDLATYSCQQ ANVFPYTFGQGTKLEIKTTTPAPRPPTPAPTIASQPLSLRPEACR PAAGGAVHTRGLDFACDIYIWAPLAGTCGVLLLSLVITKRGR KKLLYIFKQPFMRPVQTTQEEDGCSCRFPEEEEGGCELRVKFS RSADAPAYQQGQNQLYNELNLGRREEYDVLDKRRGRDPEMG GKPRRKNPQEGLYNELQKDKMAEAYSEIGMKGERRRGKGHD GLYQGLSTATKDTYDALHMQALPPR |
| 512 | CD8α signal sequence, 10G1-K scFv, CD8α hinge and transmembrane regions, 41BB cytoplasmic signaling domain, CD3ζ cytoplasmic signaling domain | MALPVTALLLPLALLLHAARPEVQLLESGGGLVQPGGSLRLSC AASGFTFSSYAMNWVRQAPGKGLEWVSTISgSGGSTYYADSV KGRFTISRDNSKNTLYLQMNSLRAEDTAVFYCAIDPEYydilTG GDYWGQGTLVTVSSGGGGSGGGGSGGGGSGGGGSDIQMT QSPSAMSASVGDRVTITCRASQGISNYLAWFQQKPGKVPKRLI YAASSLQSGVPSRFSGSGSGTEFTLTISSLQPEDFATYFCLQHD SFPLTFGGGTKVEIKTTTPAPRPPTPAPTIASQPLSLRPEACRPA AGGAVHTRGLDFACDIYIWAPLAGTCGVLLLSLVITKRGRKK LLYIFKQPFMRPVQTTQEEDGCSCRFPEEEEGGCELRVKFSRS ADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 513 | CD8α signal sequence, 11A3 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSSDSISNYYWSWIRQPPGKGLEWISYIYYSGITNYNPSLKSR VTISVDTSKNQFSLKLSSVTAADTAVYYCARITVTgFYFDYWG QGTLVTVSSGGGGSGGGGSGGGGSGGGGSEIVLTQSPGTLSLS PGERATLSCRASQSISRSYLAWYQQKPGQAPRHLIYGASSRAT GIPDRFSGSGSGTDFILTISRLEPEDFAVYYCQQYDTSPLTFGG GTKVEIKTTTPAPRPPTPAPTIASQPLSLRPEACRPAAGGAVHT RGLDFACDIYIWAPLAGTCGVLLLSLVITKRGRKKLLYIFKQPF MRPVQTTQEEDGCSCRFPEEEEGGCELRVKFSRSADAPAYQQ GQNQLYNELNLGRREEYDVLDKRRGRDPEMGGKPRRKNPQE GLYNELQKDKMAEAYSEIGMKGERRRGKGHDGLYQGLSTAT KDTYDALHMQALPPR |
| 514 | CD8α signal sequence, 3B11 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSnsVVWNWIRQSPSRGLEWLGRTYYRSKwyDDYA VSVKSRITINPDTSKNQFSLQLNSVTPEDTAVYHCARGGIVgap DAFDIWGQGTMVTVSSGGGGSGGGGSGGGGSGGGGSQSVLT QPPSASGTPGQRVTISCSGSSSNIGSDPVSWYQQFPGTAPKLLI YTNNQRPSGVPDRFSGSKSGTSASLAISGLQSEDEADYYCAA WDDSLNGHVFGTGTKVTVLTTTPAPRPPTPAPTIASQPLSLRPE ACRPAAGGAVHTRGLDFACDIYIWAPLAGTCGVLLLSLVITKR GRKKLLYIFKQPFMRPVQTTQEEDGCSCRFPEEEEGGCELRVK FSRSADAPAYQQGQNQLYNELNLGRREEYDVLDKRRGRDPE MGGKPRRKNPQEGLYNELQKDKMAEAYSEIGMKGERRRGK GHDGLYQGLSTATKDTYDALHMQALPPR |
| 515 | CD8α signal sequence, 5G2 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSnsAVWNWIRQSPSRGLEWLGWTYYRSKYYndYA VSLKSRITINPDTSKNQFSLQLNSLTPEDTAVYYCTRGGIVgapD GFDIWGQGTMVTVSSGGGGSGGGGSGGGGSGGGGSQSALTQ PPSASGTPGQRVTISCSGSNSNIGSNPINWYQQLPGTAPKLLIYS NNQRPSGVPDRFSGSKSGTSASLAISGLQSEDEADYYCAAWD DSLNGHVFGTGTKVTVLTTTPAPRPPTPAPTIASQPLSLRPEAC RPAAGGAVHTRGLDFACDIYIWAPLAGTCGVLLLSLVITKRGR KKLLYIFKQPFMRPVQTTQEEDGCSCRFPEEEEGGCELRVKFS RSADAPAYQQGQNQLYNELNLGRREEYDVLDKRRGRDPEMG GKPRRKNPQEGLYNELQKDKMAEAYSEIGMKGERRRGKGHD GLYQGLSTATKDTYDALHMQALPPR |
| 516 | CD8α signal sequence, 11E4 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGGSISSYYWSWIRQSPGKGLEWIGYVYYSDITNYNPSLKS RVTISVDTSKNQFSLNLNSVTAADTAFYFCARIGVAgFYFDYW GQGTLVTVSSGGGGSGGGGSGGGGSGGGGSEIVLTQSPDTLS LSPGERATLSCRASQSVSRRYLAWYQQKPGQAPRLLIYGASSR ATGIPDRFSGSGSGTDFTLTISRLEPEDFEVYYCQQYGTSPITFG QGTRLEIKTTTPAPRPPTPAPTIASQPLSLRPEACRPAAGGAVH TRGLDFACDIYIWAPLAGTCGVLLLSLVITKRGRKKLLYIFKQP FMRPVQTTQEEDGCSCRFPEEEEGGCELRVKFSRSADAPAYQ |

TABLE 7-continued

CAR amino acid sequences

| SEQ ID NO: | Name/ Component | Sequence |
|---|---|---|
| | | QGQNQLYNELNLGRREEYDVLDKRRGRDPEMGGKPRRKNPQ<br>EGLYNELQKDKMAEAYSEIGMKGERRRGKGHDGLYQGLSTA<br>TKDTYDALHMQALPPR |
| 517 | CD8α signal sequence, 2404.8E11 scFv, CD8α hinge and transmembrane regions, 41BB cytoplasmic signaling domain, CD3ζ cytoplasmic signaling domain | MALPVTALLLPLALLLHAARPQIQLQQSGPGLVKPSQTLSLTC<br>AISGDSVSSnsAVWNWIRQSPSRGLEWLGRTYYRSKwyNDYA<br>VSVKSRITIKPDTAKNQFSLQLNSVTPEDTAVYYFTRGGIVgap<br>DAFDIWGQGTMVTVSSGGGGSGGGGSGGGGSGGGGSQSVLT<br>QPPSASGTPGQRVTISCSGSSSNIGSDPINWYQQVPGTAPKLLI<br>YSNNQRPSGVPDRFSGSKSGTSASLAISGLQSEDEADYYCAA<br>WDDSLNGYVFGTGTKVTVLTTTPAPRPPTPAPTIASQPLSLRPE<br>ACRPAAGGAVHTRGLDFACDIYIWAPLAGTCGVLLLSLVITKR<br>GRKKLLYIFKQPFMRPVQTTQEEDGCSCRFPEEEEGGCELRVK<br>FSRSADAPAYQQGQNQLYNELNLGRREEYDVLDKRRGRDPE<br>MGGKPRRKNPQEGLYNELQKDKMAEAYSEIGMKGERRRGK<br>GHDGLYQGLSTATKDTYDALHMQALPPR |
| 518 | CD8α signal sequence, 10A2 scFv, CD8α hinge and transmembrane regions, 41BB cytoplasmic signaling domain, CD3ζ cytoplasmic signaling domain | MALPVTALLLPLALLLHAARPQVQLQQSGPGLVKPSETLSLTC<br>AISGDSVSSnsATWNWIRQSPSRGLEWLGRTYYRSEwyNDYAV<br>SVKSRITINPDTSKNHLSLHLNSVTPEDTAVYYCAGGGIVgapD<br>GFDVWGQGTMVTVSSGGGGSGGGGSGGGGSGGGGSQSVLT<br>QPPSASGTPGQRVTISCSGSSSNIGSDPVIWYQQLPRTAPKLLIY<br>SNNQRPSGVPDRFSGSKSGTSASLAISGLQSEDEADYYCAA<br>DDSLNGYVFGTGTKVTVLTTTPAPRPPTPAPTIASQPLSLRPEA<br>CRPAAGGAVHTRGLDFACDIYIWAPLAGTCGVLLLSLVITKRG<br>RKKLLYIFKQPFMRPVQTTQEEDGCSCRFPEEEEGGCELRVKF<br>SRSADAPAYQQGQNQLYNELNLGRREEYDVLDKRRGRDPEM<br>GGKPRRKNPQEGLYNELQKDKMAEAYSEIGMKGERRRGKGH<br>DGLYQGLSTATKDTYDALHMQALPPR |
| 519 | CD8α signal sequence, 11A8 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC<br>AISGDSVSSnsATWNWIRQSPSTGLEWLARTYYRSKwyNDYEV<br>SVKSQITINPDTSKNQFSLQLNSVTPEDTAVYYCARGGIVgapD<br>AFDIWGQGTMVTVSSGGGGSGGGGSGGGGSGGGGSQSVLTQ<br>PPSASGTPGQVTISCSGSSSNIGSNPVNWYQQLPGTAPKLLIY<br>SNNQRPSGVPDRFSDSKSGTSASLAISGLQSEDEADYYCAAW<br>DWLNGYVFGTGTKVTVLTTTPAPRPPTPAPTIASQPLSLRPEA<br>CRPAAGGAVHTRGLDFACDIYIWAPLAGTCGVLLLSLVITKRG<br>RKKLLYIFKQPFMRPVQTTQEEDGCSCRFPEEEEGGCELRVKF<br>SRSADAPAYQQGQNQLYNELNLGRREEYDVLDKRRGRDPEM<br>GGKPRRKNPQEGLYNELQKDKMAEAYSEIGMKGERRRGKGH<br>DGLYQGLSTATKDTYDALHMQALPPR |
| 520 | CD8α signal sequence, 4H5 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC<br>TVSGDSINNYFWSWIRQPPGKGLEWIGYFYHRGGNNYNPSLK<br>SRVTISIDTSKNQFSLNLNSVTSADTAVYYCARLALALAgFFFDY<br>WGQGTLVTVSSGGGGSGGGGSGGGGSGGGGSGSDIQMTQSPST<br>LSASVGDRVTITCRASQSISSWLAWYQQKPGKAPKLLIYKASS<br>LESGVPSRFSGSGSGTEFTLTISSLQPDDFATYYCQQYNSYSRT<br>FGQGTKVEIKTTTPAPRPPTPAPTIASQPLSLRPEACRPAAGGA<br>VHTRGLDFACDIYIWAPLAGTCGVLLLSLVITKRGRKKLLYIF<br>KQPFMRPVQTTQEEDGCSCRFPEEEEGGCELRVKFSRSADAPA<br>YQQGQNQLYNELNLGRREEYDVLDKRRGRDPEMGGKPRRK<br>NPQEGLYNELQKDKMAEAYSEIGMKGERRRGKGHDGLYQGL<br>STATKDTYDALHMQALPPR |
| 521 | CD8α signal sequence, 3G6-L2 scFv, CD8α hinge and transmembrane regions, 41BB cytoplasmic signaling domain, CD3ζ cytoplasmic signaling domain | MALPVTALLLPLALLLHAARPQVPLVQSGAEVKKPGSSVKVS<br>CKASGGTFSTYSISWVRQAPGQGLEWMGGIIpIFGTTNYAQKF<br>QGRVTITADKSTSTAYMELSSLRSEDTAVYYCARDGEGsyyyy<br>YGMDVWGQGTTVTVSSGGGGSGGGGSGGGGSGGGGSQSVL<br>TQPPSASGTPGQRVTISCSGSSSNIGSNYVYWYQQLPGTAPKL<br>LIYSNNQRPSGVPDRFSGSKSGTSASLAISGLRSEDEADYYCAA<br>WDDSLSGWVFGGGTKLTVLTTTPAPRPPTPAPTIASQPLSLRPE<br>ACRPAAGGAVHTRGLDFACDIYIWAPLAGTCGVLLLSLVITKR<br>GRKKLLYIFKQPFMRPVQTTQEEDGCSCRFPEEEEGGCELRVK<br>FSRSADAPAYQQGQNQLYNELNLGRREEYDVLDKRRGRDPE<br>MGGKPRRKNPQEGLYNELQKDKMAEAYSEIGMKGERRRGK<br>GHDGLYQGLSTATKDTYDALHMQALPPR |
| 522 | CD8α signal sequence, 3B9 scFv, CD8α hinge and transmembrane regions, 41BB | MALPVTALLLPLALLLHAARPEVQLVESGGGLVQPGGSLRLS<br>CAASGFTFSSYSMNWVRQAPGKGLEWVSYISsSSSTIYYADSV<br>KGRFTISRDNAKNSLYLQMNSLRDEDTAVYYCARDKERryyyY<br>GMDVWGQGTTVTVSSGGGGSGGGGSGGGGSGGGGSEIVLTQ<br>SPDTLSLSPGERATLSCRASQSVSRRYLAWYQQKPGQAPRLLI |

TABLE 7-continued

CAR amino acid sequences

| SEQ ID NO: | Name/Component | Sequence |
|---|---|---|
| | cytoplasmic signaling domain, CD3ζ cytoplasmic signaling domain | YGASSRATGIPDRFSGSGSGTDFTLTISRLEPEDFAVYYCQQFG TSPITFGQGTRLEIKTTTPAPRPPTPAPTIASQPLSLRPEACRPAA GGAVHTRGLDFACDIYIWAPLAGTCGVLLLSLVITKRGRKKLL YIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR |
| 523 | CD8α signal sequence, 3F9-L scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLA CAISGDSVSSnsAIWNWIRQSPSRGLEWLGGTYYRSMwyNDYA VSVKSRITINPDTSKNQLSLQLNSVTPEDTAVYYCSRGGIVgvp DAFDIWGQGTMVTVSSGGGGSGGGGSGGGGSGGGGSQSVLT QPPSASGTPGQRVTISCSGSSSNIGSNTANWYQQLPGTAPRLLI YRNNQRPSGVPDRFSGSKSGTSASLAISGLQSEDEADYYCAA WDDSLNGYVFGTGTKVTVLTTTPAPRPPTPAPTIASQPLSLRPE ACRPAAGGAVHTRGLDFACDIYIWAPLAGTCGVLLLSLVITKR GRKKLLYIFKQPFMRPVQTTQEEDGCSCRFPEEEEGGCELRVK FSRSADAPAYQQGQNQLYNELNLGRREEYDVLDKRRGRDPE MGGKPRRKNPQEGLYNELQKDKMAEAYSEIGMKGERRRGK GHDGLYQGLSTATKDTYDALHMQALPPR |
| 524 | CD8α signal sequence, 3E10 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC NVSDGSISSYYWTWIRQPPGKGLDWIGYIFYSGTTNYNPSLKS RVTISLDTSKNQFSLKLTSMTAADTAVYYCARISEKsFYFDYW GQGTLVTVSSGGGGSGGGGSGGGGSGGGGSQSVLTQPPSASG TPGQRVTISCSGSSSNIGSNYVYWYQQLPGTAPKLLIYSNNQR PSGVPDRFSGSKSGTSASLAISGLRSEDEADYYCAPWDDSLSG RVFGGGTKLTVLTTTPAPRPPTPAPTIASQPLSLRPEACRPAAG GAVHTRGLDFACDIYIWAPLAGTCGVLLLSLVITKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 525 | CD8α signal sequence, 3C3 scFv, CD8α hinge and transmembrane regions, 41BB cytoplasmic signaling domain, CD3ζ cytoplasmic signaling domain | MALPVTALLLPLALLLHAARPQVQLVQSGAEVKRPGASVKVS CKASGYTFTSYYIHWVRQAPGQGLEWMGVIVpSGGSISYAQK FQGRVTMTRDTSTNIVYMELSSLRSEDTAVYYCARDRYYgdyy YGLDVWGQGTTVTVSSGGGGSGGGGSGGGGSGGGGSDIQMT QSPSSLSASVGDRVTITCRASQGINNFLAWFQQKPGKAPKSLIY AASSLQSGVPSKFSGSGSGTDFTLTIRSLQPEDFATYYCQHYNS YPITFGQGTRLEIKTTTPAPRPPTPAPTIASQPLSLRPEACRPAA GGAVHTRGLDFACDIYIWAPLAGTCGVLLLSLVITKRGRKKLL YIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR |
| 526 | CD8α signal sequence, 11F4 scFv, CD8α hinge and transmembrane regions, 41BB cytoplasmic signaling domain, CD3ζ cytoplasmic signaling domain | MALPVTALLLPLALLLHAARPQVHLQESGPGLVKPSETLSLTC TVSGGSISHYYWTWIRQPPGKGLEWIGYIYYSGITNFSPSLKSR VSISVDSSKNQFSLNLNSVTAADTAVYYCAGISLAgFYFDYWV QGTLVTVSSGGGGSGGGGSGGGGSGGGGSEIVLTQSPGTLSLS PGERATLSCRASQSVSRSYLAWYQQKPGQAPRLLIYGASSRAT GVPDRFSGSGSGTDFTLTISRLEPEDFAVFYCQQYSISPLTFGG GTKVEIKTTTPAPRPPTPAPTIASQPLSLRPEACRPAAGGAVHT RGLDFACDIYIWAPLAGTCGVLLLSLVITKRGRKKLLYIFKQPF MRPVQTTQEEDGCSCRFPEEEEGGCELRVKFSRSADAPAYQQ GQNQLYNELNLGRREEYDVLDKRRGRDPEMGGKPRRKNPQE GLYNELQKDKMAEAYSEIGMKGERRRGKGHDGLYQGLSTAT KDTYDALHMQALPPR |
| 527 | CD8α signal sequence, 10E12 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGVSISSYYWSWIRQPPGKGLEWIAYIYYSGNTNYSPSLKS RVTISVDTSKDQLSLKLSSVTAADTAVYYCTRGGSGtiDVFDIW GQGTMVAVSSGGGGSGGGGSGGGGSGGGGSQSVLTQPPSVS AAPGQKVTISCSGSSSNIGNNYVSWYQQLPGTAPKLLIYDNNK RPSGIPDRFSGSKSGTSATLGITGLQTGDEADYYCETWDSSLSA VVFGGGTKLTVLTTTPAPRPPTPAPTIASQPLSLRPEACRPAAG GAVHTRGLDFACDIYIWAPLAGTCGVLLLSLVITKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |

TABLE 7-continued

CAR amino acid sequences

| SEQ ID NO: | Name/ Component | Sequence |
|---|---|---|
| 528 | CD8α signal sequence, 4E1 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDNVSTnsAAWNWIRQSPSRGLEWLGWTYYRSKwyNDYA VSLKSRININPDTSKNQFSLQLNSVTPEDTAVYYCARWVNRD VFDIWGQGTMVTVSSGGGGSGGGGSGGGGSGGGGSQSALTQ PASVSGSPGQSITISCTGTSSDVGSYNLVSWYQQHPGKAPKLM IYEGSKRPSGVSNRFSGSKSGNTASLTISGLQAEDEADYYCCS YAGSSTWVFGGGTKLTVLTTTPAPRPPTPAPTIASQPLSLRPEA CRPAAGGAVHTRGLDFACDIYIWAPLAGTCGVLLLSLVITKRG RKKLLYIFKQPFMRPVQTTQEEDGCSCRFPEEEEGGCELRVKF SRSADAPAYQQGQNQLYNELNLGRREEYDVLDKRRGRDPEM GGKPRRKNPQEGLYNELQKDKMAEAYSEIGMKGERRRGKGH DGLYQGLSTATKDTYDALHMQALPPR |
| 529 | CD8α signal sequence, 2404.6H1 scFv, CD8α hinge and transmembrane regions, 41BB cytoplasmic signaling domain, CD3ζ cytoplasmic signaling domain | MALPVTALLLPLALLLHAARPQVQLVESGGGVVQPGRSLRLS CAASGFTFSSYGMHWVRQTPGKGLEWVAVISYDGNsNYYAD SVKGRFTISRDNSKNTLYLQMNSLRAEDTAVYYCARDGATvts yyyYGMDVWGQGTTVTVSSGGGGSGGGGSGGGGSGGGGSEI VLTQSPGTLSLSPGERATLSCRASQSVSRTYLAWYHQKPGQAP RLLIYGASSRATGISDRFSGSGSGTDFTLTISRLEPEDFAVYYCQ QYGTSPITFGQGTRLEIKTTTPAPRPPTPAPTIASQPLSLRPEAC RPAAGGAVHTRGLDFACDIYIWAPLAGTCGVLLLSLVITKRGR KKLLYIFKQPFMRPVQTTQEEDGCSCRFPEEEEGGCELRVKFS RSADAPAYQQGQNQLYNELNLGRREEYDVLDKRRGRDPEMG GKPRRKNPQEGLYNELQKDKMAEAYSEIGMKGERRRGKGHD GLYQGLSTATKDTYDALHMQALPPR |
| 530 | CD8α signal sequence, 2A8 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSnsAVWNWIRQSPSRGLEWLGRTYYRSKwyNDYA VSVKSRITINPDTSRNQFSLQLNSVTPEDTAVYYCARGGIVgap DGFDIWGQGTMVTVSSGGGGSGGGGSGGGGSGGGGSDIVMT QSPDSLAVSLGERATINCKSSQSVLDSSNNNnYFAWYQQRPGQ PPHLLIYWASSRESGVPDRFSGSGSGTDFTLTISSLQAEDVAVY YCQQYYSTPYTFGQGTKLEIKTTTPAPRPPTPAPTIASQPLSLRP EACRPAAGGAVHTRGLDFACDIYIWAPLAGTCGVLLLSLVITK RGRKKLLYIFKQPFMRPVQTTQEEDGCSCRFPEEEEGGCELRV KFSRSADAPAYQQGQNQLYNELNLGRREEYDVLDKRRGRDP EMGGKPRRKNPQEGLYNELQKDKMAEAYSEIGMKGERRRGK GHDGLYQGLSTATKDTYDALHMQALPPR |
| 531 | CD8α signal sequence, 3B1 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSntTAWKWSRQSPSKGLEWLGWTYYRSKwyYDYT VSVKSRITINPDTSKNQFSLQLNSVTPEDTAVYYCARWIFHDA FDIWGQGTMVTVSSGGGGSGGGGSGGGGSGGGGSQSALTQP PSASGTPGQRVTISCSGSSSNIGSNTVNWYQQLPGTAPKLLIYT NNQRPSGVPDRFSGSKSGTSASLAISGLQSEDEADYFCSTWDD SLNGPVFGGGTKLTVLTTTPAPRPPTPAPTIASQPLSLRPEACRP AAGGAVHTRGLDFACDIYIWAPLAGTCGVLLLSLVITKRGRK KLLYIFKQPFMRPVQTTQEEDGCSCRFPEEEEGGCELRVKFSR SADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 532 | CD8α signal sequence, 9B5 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGDSISSLSWSWIRQTPGEGLEWIGYLYYSGSTDYNPSLKS RVTISVDTSKNQFSLKLRSVAAADTALYYCARGRRAFDIWGQ GTMVTVSSGGGGSGGGGSGGGGSGGGGSDIQMTQSPSSLSAS VGDRVTITCRGSQGISNYLAWFQQRPGKAPKSLIYAASSLESG VPSKFSGSGSGTDFTLTIISLQPEDFATYYCQQYYNYPITFGQG TRLEIKTTTPAPRPPTPAPTIASQPLSLRPEACRPAAGGAVHTR GLDFACDIYIWAPLAGTCGVLLLSLVITKRGRKKLLYIFKQPF MRPVQTTQEEDGCSCRFPEEEEGGCELRVKFSRSADAPAYQQ GQNQLYNELNLGRREEYDVLDKRRGRDPEMGGKPRRKNPQE GLYNELQKDKMAEAYSEIGMKGERRRGKGHDGLYQGLSTAT KDTYDALHMQALPPR |
| 533 | CD8α signal sequence, 11A5 scFv, CD8α hinge and transmembrane regions, 41BB cytoplasmic signaling domain, CD3ζ cytoplasmic | MALPVTALLLPLALLLHAARPQVQLVQSGAEVKKPGASVKVS CKASGYTFTGYYMHWVRQAPGQGLEWMGWINpNSGGTNYA QKFQGRVTMTRDTSVSTAYMELSRLTSDDTAIYYCAKDGGGd fyfYGMDVWGQGTTVTVSSGGGGSGGGGSGGGGSGGGGSQT VVTQEPSFSVSPGGTVTLTCGLSSGSVSTSYYPSCFQQTPGQAP RTLIYSTDTRSSGVPDRFSGSILGNKAALTITGAQADDESDYYC VLYMGSGISVFGGGTKLTVLTTTPAPRPPTPAPTIASQPLSLRP EACRPAAGGAVHTRGLDFACDIYIWAPLAGTCGVLLLSLVITK |

TABLE 7-continued

CAR amino acid sequences

| SEQ ID NO: | Name/ Component | Sequence |
|---|---|---|
| | signaling domain | RGRKKLLYIFKQPFMRPVQTTQEEDGCSCRFPEEEEGGCELRV KFSRSADAPAYQQGQNQLYNELNLGRREEYDVLDKRRGRDP EMGGKPRRKNPQEGLYNELQKDKMAEAYSEIGMKGERRRGK GHDGLYQGLSTATKDTYDALHMQALPPR |
| 632 | CD8α signal sequence, 2D3 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSDNSISNYYWSWIRQPPGKGLEWIAYIYYSGTTNYNPSLKS RVTISLDTSKNQFSLKLSSVTAADTAVYYCARLFNWGFAFDI WGQGTMVTVSSGGGGSGGGGSGGGGSGGGGSEIVMTQSPAT LSVSPGERATLSCRASQSVSSNLAWYQQKPGQAPRLLIYGAST RATGIPARFSGSGSGTEFTLTISSLQSEDFAVYYCQQYNNWPLT FGGGTKVEIKTTTPAPRPPTPAPTIASQPLSLRPEACRPAAGGA VHTRGLDFACDIYIWAPLAGTCGVLLLSLVITLYCKRGRKKLL YIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR |
| 633 | CD8α signal sequence, 5A2 scFv, CD8α hinge and transmembrane regions, 41BB cytoplasmic signaling domain, CD3ζ cytoplasmic signaling domain | MALPVTALLLPLALLLHAARPQVQLQESGPGLMKPSETLSLTC TVSGGSISSSYWSCIRQPPGKGLEWIGYIYYSGTTNYNPSLKSR VTLSLDTSKNQFSLRLTSVTAADTAVYYCARVAPTgFWFDYW GQGTLVTVSSGGGGSGGGGSGGGGSGGGGSEIVLTQSPGTLS LSPGERATLSCRASQRVSSRYLAWYQQKPGQAPRLLIYGASSR ATGIPDRFSGSGSGTDFTLTISRLEPEEFAVYYCQQYGTSPLTF GGGTKVEIKTTTPAPRPPTPAPTIASQPLSLRPEACRPAAGGAV HTRGLDFACDIYIWAPLAGTCGVLLLSLVITLYCKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 634 | CD8α signal sequence, 7F9 scFv, CD8α hinge and transmembrane regions, 41BB cytoplasmic signaling domain, CD3ζ cytoplasmic signaling domain | MALPVTALLLPLALLLHAARPEVQLVESGGGLVQPGGSLRLS CAASGFTFSSHDMHWVRQATGKGLEWVSAIGIAGDTYYSGS VKGRFTISRENAKNSLYLQMNSLRAGDTAVYYCARANWGeG AFDIWGQGTMVTVSSGGGGSGGGGSGGGGSGGGGSDIQMTQ SPSSLSASVGDRVTITCRASQGISDYLAWYQQKPGKIPKLLIYA ASTLQSGVPSRFSGSGSGTDFTLTISSLQPEDVATYYCQKYNSV PLTFGGGTKVEIKTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFSR SADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 635 | CD8α signal sequence, 9D3 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSDDSISNYYWSWIRQPPGKGLEWIGYIFYSGTTNHNPSLKS RLTISLDKAKNQFSLRLSSVTAADTAVYYCARVFNWgFAFDI WGQGTMVTVSSGGGGSGGGGSGGGGSGGGGSEIVLTQSPGT LSLSPGERATLSCRASQRISRTYLAWYQQKPGQAPRLLIYGAS SRATGIPDRFTGSGSGTDFTLTISRLEPEDFAVYYCQQYGTSPL TFGGGTKVEINTTTPAPRPPTPAPTIASQPLSLRPEACRPAAGG AVHTRGLDFACDIYIWAPLAGTCGVLLLSLVITLYCKRGRKKL LYIFKQPFMRPVQTTQEEDGCSCRFPEEEEGGCELRVKFSRSA DAPAYQQGQNQLYNELNLGRREEYDVLDKRRGRDPEMGGKP RRKNPQEGLYNELQKDKMAEAYSEIGMKGERRRGKGHDGLY QGLSTATKDTYDALHMQALPPR |
| 636 | CD8α signal sequence, 26C8 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSDNSISNYYWSWIRQPPGKGLEWIAYIYYSGTTNYNPSLKS RVTISLDTSKNQFSLQLSSVTAADAAVYYCARVFHWgFAFDI WGQGTMVTVSSGGGGSGGGGSGGGGSGGGGSEIVLTQSPGT LSLSPGERATLSCRASQRVSNTYLAWYQQNPGQAPRLLIYGAS SRATGIPDRFSGSGSGTDFTLTISRLEPEDFAVYYCQQYGTSPL TFGGGTKVEIKTTTPAPRPPTPAPTIASQPLSLRPEACRPAAGG AVHTRGLDFACDIYIWAPLAGTCGVLLLSLVITLYCKRGRKKL LYIFKQPFMRPVQTTQEEDGCSCRFPEEEEGGCELRVKFSRSA DAPAYQQGQNQLYNELNLGRREEYDVLDKRRGRDPEMGGKP RRKNPQEGLYNELQKDKMAEAYSEIGMKGERRRGKGHDGLY QGLSTATKDTYDALHMQALPPR |
| 637 | CD8α signal sequence, 2A6.C5 scFv, CD8α hinge and transmembrane | MALPVTALLLPLALLLHAARPQVQLQESGPGLVKPSETLSLTC TVSNVSISSYYWSWIRQPPGKGLEWIGYIYYSGTTNYNPSLKS RVTMSVDTSKNQFSLKLSSVTAADTAVYFCARLSNWgFAFDI WGQGTMVTFSSGGGGSGGGGSGGGGSGGGGSEIVLTQSPGTL |

TABLE 7-continued

CAR amino acid sequences

| SEQ ID NO: | Name/ Component | Sequence |
|---|---|---|
| | regions, 41BB cytoplasmic signaling domain, CD3ζ cytoplasmic signaling domain | SLSPGERATLSCRASQTISSSYLAWYQQKPGQAPRLLIYGASSR ATGIPDRFSGSGSGTEFTLTISRLEPEDFAVYYCQQYGWSPITF GQGTRLEIKTTTPAPRPPTPAPTIASQPLSLRPEACRPAAGGAV HTRGLDFACDIYIWAPLAGTCGVLLLSLVITLYCKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 638 | CD8α signal sequence, 5E12 scFv, CD8α hinge and transmembrane regions, 41BB cytoplasmic signaling domain, CD3ζ cytoplasmic signaling domain | MALPVTALLLPLALLLHAARPEVQLVESGGGLVQPGGSLRLS CAASGFTFSSYDMHWVRQATGKGLEWVSAIGPAGDTYYPGS VKGRFTISRENAKNSLYLQMNSLRAGDTAVYYCARADPPyyy YGMDVWGQGTTVTVSSGGGGSGGGGSGGGGSGGGGSDIVM TQSPLSLPVTPGEPASISCRSSQSLLHSNEYNYLDWYLQKPGQS PQLLIYLGSNRASGVPDRFSGSGSGTDFILKISRVEAEDVGVYY CMQALEIPLTFGGGTKVEIKTTTPAPRPPTPAPTIASQPLSLRPE ACRPAAGGAVHTRGLDFACDIYIWAPLAGTCGVLLLSLVITLY CKRGRKKLLYIFKQPFMRPVQTTQEEDGCSCRFPEEEEGGCEL RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR |
| 639 | CD8α signal sequence, 6D8 scFv, CD8α hinge and transmembrane regions, 41BB cytoplasmic signaling domain, CD3ζ cytoplasmic signaling domain | MALPVTALLLPLALLLHAARPQITLKESGPTLVKPTQTLTLTCT FSGFSLSTrgVGVGWIRQPPGKALEWLALIYWNDDKRYSPSLQ TRLTITKDTPKNQVVLTMTNMDPVDTATYYCARSNWGnWYF ALWGRGTLVTVSSGGGGSGGGGSGGGGSGGGGSEIVLTQSPA TLSLSPGERATLSCRASQSVSSYLAWYQQKPGQAPRLLIYDAF YRATGIPARFSGSGSGTDFTLTISSLEPEDFAVYYCQHRSNWPI TFGQGTRLEIKTTTPAPRPPTPAPTIASQPLSLRPEACRPAAGGA VHTRGLDFACDIYIWAPLAGTCGVLLLSLVITLYCKRGRKKLL YIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR |
| 640 | CD8α signal sequence, 8E11 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGDSISNYYWTWIRQPPGKGLEWIGYIYYSGTTNSNPSLKS RVTVSLDTSKSQFSLNLSSVTAADTAVYYCARVFNRgFAFDIW GQGTMVTVSSGGGGSGGGGSGGGGSGGGGSEIVLTQSPGTLS LSPGERATLSCRASQRISNTYLAWYQQKPGQAPRLLIYGASSR ATGIPDRFSGSGSGTDFTLTISRLEPEDFAAYYCQQYDTSPLTF GGGTKVEIKTTTPAPRPPTPAPTIASQPLSLRPEACRPAAGGAV HTRGLDFACDIYIWAPLAGTCGVLLLSLVITLYCKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 641 | CD8α signal sequence, 5C1.A4 scFv, CD8α hinge and transmembrane regions, 41BB cytoplasmic signaling domain, CD3ζ cytoplasmic signaling domain | MALPVTALLLPLALLLHAARPQVTLRESGPALVKPTQTLTLTC TVSGVSLSTsgMCVSWIRQPLGKALEWLGFIDWDDDKYYNTS LKTRLTISKDTSKNQVVLTMTNMDPVDTATYYCARIRGYsgsy DAFDIWGQGTVVIVSSGGGGSGGGGSGGGGSGGGGSDIVMT QSPLSLPVTPGEPASISCRSSQSLLHSNGYNHLDWYLQKPGQSP QVLIYLGSNRASGVPDRFSGSGSGTDFTLKISRVEAEDVGVYF CMQALQTPLTFGGGTKVEIKTTTPAPRPPTPAPTIASQPLSLRP EACRPAAGGAVHTRGLDFACDIYIWAPLAGTCGVLLLSLVITL YCKRGRKKLLYIFKQPFMRPVQTTQEEDGCSCRFPEEEEGGCE LRVKFSRSADAPAYQQGQNQLYNELNLGRREEYDVLDKRRG RDPEMGGKPRRKNPQEGLYNELQKDKMAEAYSEIGMKGERR RGKGHDGLYQGLSTATKDTYDALHMQALPPR |
| 642 | CD8α signal sequence, 9F7 scFv, CD8α hinge and transmembrane regions, 41BB cytoplasmic signaling domain, CD3ζ cytoplasmic signaling domain | MALPVTALLLPLALLLHAARPQVQLQVSGPGLVKPSETLSLTC SVSGGSISSYYWSWIRQSPGKGLDWIGYMYYSGTTNYNPSLK SRVTISVDTSKNQFSLKLSSVTATDTAVYYCARVGLTgFFFDY WGQGTLVTVSSGGGGSGGGGSGGGGSGGGGSAIQMTQSPSSL SASVGDRVTITCRASQGIRNDLGWYQQKPGKAPKLLIYAASSL QSGVPSRFSGSGSGTDFTLTVSSLQPEDFATYYCLQDYNYPYT FGQGTKLEIKTTTPAPRPPTPAPTIASQPLSLRPEACRPAAGGA VHTRGLDFACDIYIWAPLAGTCGVLLLSLVITLYCKRGRKKLL YIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR |

TABLE 7-continued

| CAR amino acid sequences | | |
|---|---|---|
| SEQ ID NO: | Name/ Component | Sequence |
| 643 | CD8α signal sequence, 2C3 scFv, CD8α hinge and transmembrane regions, 41BB cytoplasmic signaling domain, CD3ζ cytoplasmic signaling domain | MALPVTALLLPLALLLHAARPQVQLQQWGGGLLKPSETLSLT CAVYGGSSSGNYWSWIRQPPGKRLEWIGEINHSGTTSYNPSLK SRVTISVDTSKNQFSLKLSSVTAADTAVYYCARGELGIADSWG QGTLVTVSSGGGGSGGGGSGGGGSGGGGSDIQMTQSPSTLSA SVGDRVTITCRASQSISRWLAWYQQKPGKAPKLLIYKASSLES GVPSRFSGSGSGTEFTLTISSLQPDDFATYYCQQYNSYSTFGQG TKVEIKTTTPAPRPPTPAPTIASQPLSLRPEACRPAAGGAVHTR GLDFACDIYIWAPLAGTCGVLLLSLVITLYCKRGRKKLLYIFK QPFMRPVQTTQEEDGCSCRFPEEEEGGCELRVKFSRSADAPAY QQGQNQLYNELNLGRREEYDVLDKRRGRDPEMGGKPRRKNP QEGLYNELQKDKMAEAYSEIGMKGERRRGKGHDGLYQGLST ATKDTYDALHMQALPPR |
| 644 | CD8α signal sequence, 2G1 scFv, CD8α hinge and transmembrane regions, 41BB cytoplasmic signaling domain, CD3ζ cytoplasmic signaling domain | MALPVTALLLPLALLLHAARPQLQLQESGPGLVKPSETLSLTC TVSGGSISSssYYWGWIRQPPGKGLEWIGSIYYSGNIYHNPSLK SRVSISVDTSKNQFSLRLSSVTAADTAVYYCAREIIVgaTHFDY WGQGTLVTVSSGGGGSGGGGSGGGGSGGGGSAIQMTQSPSSL SASVGDRVTITCRASQGIRNDLGWYQQKPGKAPELLIYAASSL QSGVPSRFSGSGSGTDFTLTISSLQPEDFATYYCLQDYNYPLTF GPGTKVDIKTTTPAPRPPTPAPTIASQPLSLRPEACRPAAGGAV HTRGLDFACDIYIWAPLAGTCGVLLLSLVITLYCKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 645 | CD8α signal sequence, 3E4 scFv, CD8α hinge and transmembrane regions, 41BB cytoplasmic signaling domain, CD3ζ cytoplasmic signaling domain | MALPVTALLLPLALLLHAARPQVQLQQWGAGLLKPSETLSLT CAVYGGSFSGYYWSWIRQPPGKGLEWIGEIIHSGSSNYNPSLK SRVSISVDTSKNQFSLKLSSVTAADTAVYYCSRGEYGsgSRFDY WGQGTLVTVSSGGGGSGGGGSGGGGSGGGGSAIQMTQSPSSL SASVGDRVAITCRASQGIRDDLGWYQQKPGKAPKLLIYAASS LQSGVPSRFSGSRSDTDFTLTISSLQPEDFATYYCLQDYDYPLT FGGGTKVEIKTTTPAPRPPTPAPTIASQPLSLRPEACRPAAGGA VHTRGLDFACDIYIWAPLAGTCGVLLLSLVITLYCKRGRKKLL YIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR |
| 646 | CD8α signal sequence, 3F2 scFv, CD8α hinge and transmembrane regions, 41BB cytoplasmic signaling domain, CD3ζ cytoplasmic signaling domain | MALPVTALLLPLALLLHAARPQVQLQESGPGLVKPSGTLSLTC AVSGGSISSnNWWSWVRQPPGKGLEWIGDIHHSGSTNYKPSL KSRVTISVDKSKNQFSLNLISVTAADTAVYYCAREAGGYFDY WGQGILVTVSSGGGGSGGGGSGGGGSGGGGSDIQMTQSPSTL SASVGDRVTITCRASQSISSWLAWYQQKPGKAPKLLISKASSL ESGVPSRFSGSGSGPEFTLTISSLQPADFATYYCQQYNSYSTFG QGTKLEIKTTTPAPRPPTPAPTIASQPLSLRPEACRPAAGGAVH TRGLDFACDIYIWAPLAGTCGVLLLSLVITLYCKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |
| 647 | CD8α signal sequence, 4F9 scFv, CD8α hinge and transmembrane regions, 41BB cytoplasmic signaling domain, CD3ζ cytoplasmic signaling domain | MALPVTALLLPLALLLHAARPQVQLQQWGAGLLKPSETLSLT CAVYGGSFSGYYWTWIRQPPGKGLEWIGEITHSGSTNYNPSL KSRVSISVDTSKNQFSLKLSSVTAADTAVYYCARGEYGsgSRF DYWGQGTLVTVSSGGGGSGGGGSGGGGSGGGGSAIQMTQSP SSLSASVGDRVAITCRASQGIRDDLGWYQQKPGKAPKLLIYA ASSLQSGVPSRFSGSGSDTDFTLTISSLQPEDFATYYCLQDYDY PLTFGGGTKVEIKTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFSR SADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 648 | CD8α signal sequence, 4G9 scFv, CD8α hinge and transmembrane regions, 41BB cytoplasmic signaling domain, CD3ζ cytoplasmic signaling domain | MALPVTALLLPLALLLHAARPQVQLQQWGAGLLKPSETLSLT CAVYGGSFSGYYWSWIRQPPGKGLEWIGEITHSGSTNYNPSLK SRVSISVDTSKNQFSLKLSSVTAADTAVYYCARGEYGsgSRFD YWGQGTLVTVSSGGGGSGGGGSGGGGSGGGGSAIQMTQSPS SLSASVGDRVALTCRASQGIRDDLGWYQQKPGKAPKLLIYAA SSLQSGVPSRFSGSGSDTDFTLTISSLQPEDFATYYCLQDYDYP LTFGGGTKVEIKTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFSR |

TABLE 7-continued

| | CAR amino acid sequences | |
|---|---|---|

| SEQ ID NO: | Name/ Component | Sequence |
|---|---|---|
| | | SADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 649 | CD8α signal sequence, 11H7 scFv, CD8α hinge and transmembrane regions, 41BB cytoplasmic signaling domain, CD3ζ cytoplasmic signaling domain | MALPVTALLLPLALLLHAARPQVQLQQWGAGLLKPSETLSLT CAVYGGSFSAYYWNWIRQPPGKGLEWIGEINHSGSTNYNPSL KSRVTISVDTSKNQFSLNLTSLTAADTAVYYCARGLDSsgwYP FDYWGQGTLVTVSSGGGGSGGGGSGGGGSGGGGSDIQMTQS PSSVSASVGDRVTITCRASQGISSWLAWYQQKPGKAPKLLIYA ASSLQSGVPSRFSGSGSGTDFTLTISSLQPEDFATYYCQQADSF PFTFGPGTKVDIKTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFSR SADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 650 | CD8α signal sequence, 16H7 scFv, CD8α hinge and transmembrane regions, 41BB cytoplasmic signaling domain, CD3ζ cytoplasmic signaling domain | MALPVTALLLPLALLLHAARPQVQLQQWGAGLLKPSETLSLT CAVFGGSFSGDYWSWIRQPPGKGLEWIGEINHSGITSFNPSLKS RVTISVDTSKNQFSLKLSSVTAADTAVYYCARGELGIPDNWG QGTLVTVSSGGGGSGGGGSGGGGSGGGGSDIQMTQSPSTLSA SVGDRVTITCRASQSISRWLAWYQQKPGKAPKLLIYKASSLES GVPSRFSGSGSGTEFTLTISSLQPDDFATYYCQQYNSYSTFGQG TKVEIKTTTPAPRPPTPAPTIASQPLSLRPEACRPAAGGAVHTR GLDFACDIYIWAPLAGTCGVLLLSLVITLYCKRGRKKLLYIFK QPFMRPVQTTQEEDGCSCRFPEEEEGGCELRVKFSRSADAPAY QQGQNQLYNELNLGRREEYDVLDKRRGRDPEMGGKPRRKNP QEGLYNELQKDKMAEAYSEIGMKGERRRGKGHDGLYQGLST ATKDTYDALHMQALPPR |
| 651 | CD8α signal sequence, 17A2 scFv, CD8α hinge and transmembrane regions, 41BB cytoplasmic signaling domain, CD3ζ cytoplasmic signaling domain | MALPVTALLLPLALLLHAARPQVQLQESGPGLVKPSGTLSLTC VVFGDSISSsNWWSWVRQPPGKGLEWIGEVFHSGSTNYNPSL KSRVTISVDKSKNQFSLKLSSVTAADTAVYYCARAAVAGALD YWGQGTLVTVSSGGGGSGGGGSGGGGSGGGGSDIVMTQSPD SLAVSLGERATINCKSSQSVLYSSNNKNYLAWYQQKPGQPPN LLVYWASTRESGVPDRFSGAGSGTDFTLTISSLQAEDVAVYYC QQYYGTSWTFGQGTKVEIKTTTPAPRPPTPAPTIASQPLSLRPE ACRPAAGGAVHTRGLDFACDIYIWAPLAGTCGVLLLSLVITLY CKRGRKKLLYIFKQPFMRPVQTTQEEDGCSCRFPEEEEGGCEL RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR |
| 652 | CD8α signal sequence, 6H1 scFv, CD8α hinge and transmembrane regions, 41BB cytoplasmic signaling domain, CD3ζ cytoplasmic signaling domain | MALPVTALLLPLALLLHAARPQITLRESGPTLVKPTQTLTLTCT FSGFSLSTsgLGVGWIRQPPGEALEWLALIYWNDDKRYSPSLK SRLSITKDTSKNQVVLIMTNMDPVDTATYYCVHRRIAaPGSVY WGQGTLVTVSSGGGGSGGGGSGGGGSGGGGSDIQMTQSPSS VSASVGDRVTITCRASQGISSWLAWYQQKPGKAPKLLISAASS LQSGVPSRFSGSGSGTDFTLTISSLQPEDFATYYCHQANSFPFT FGGQGTKLEIKTTTPAPRPPTPAPTIASQPLSLRPEACRPAAGGA VHTRGLDFACDIYIWAPLAGTCGVLLLSLVITLYCKRGRKKLL YIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR |
| 653 | CD8α signal sequence, 6H5 scFv, CD8α hinge and transmembrane regions, 41BB cytoplasmic signaling domain, CD3ζ cytoplasmic signaling domain | MALPVTALLLPLALLLHAARPQVQLVQSGAEVKKPGASVKVS CKVSGYTLTELSMHWVRQAPGKGPEGMGGFDpEDGKTIYAQ KFQGRVTMTEDTSADTAYMELNSLRSEDTAVYYCATLLRGlD AFDVWGQGTMVTVSSGGGGSGGGGSGGGGSGGGGSDIQMT QSPSSLSASVGDRVTITCRASQGIRNDLGWYQQKPGKAPKRLI YAASSLQSGVPSRFSGSGSGTEFTLTISTLQPEDFATYYCLQHN SYPRTFGQGTKVEIKTTTPAPRPPTPAPTIASQPLSLRPEACRPA AGGAVHTRGLDFACDIYIWAPLAGTCGVLLLSLVITLYCKRG RKKLLYIFKQPFMRPVQTTQEEDGCSCRFPEEEEGGCELRVKF SRSADAPAYQQGQNQLYNELNLGRREEYDVLDKRRGRDPEM GGKPRRKNPQEGLYNELQKDKMAEAYSEIGMKGERRRGKGH DGLYQGLSTATKDTYDALHMQALPPR |
| 654 | CD8α signal sequence, 10D1 scFv, CD8α hinge and transmembrane regions, 41BB | MALPVTALLLPLALLLHAARPQVQLQQWGAGLLKPSETLSLT CAVYGGSFSGYYWRWIRQPPGKGLEWIGEISHSGSTNYNPSL KSRVTISVDTSKNQFSLKLSSVTAADTAVYYCAVRGYSygyPLF DYWGQGTLVTVSSGGGGSGGGGSGGGGSGGGGSDIQMTQSP SSLSASVGDRVTITCRASQGIRNDLGWYQQKLGKAPKRLIYA |

TABLE 7-continued

CAR amino acid sequences

| SEQ ID NO: | Name/ Component | Sequence |
|---|---|---|
| | cytoplasmic signaling domain, CD3ζ cytoplasmic signaling domain | ASSLQSGVPSRFSGSGSGTEFTLTISSLQPEDFATYYCLQYNSY PRTFGQGTKVEIKTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFSR SADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 655 | CD8α signal sequence, 11F6 scFv, CD8α hinge and transmembrane regions, 41BB cytoplasmic signaling domain, CD3ζ cytoplasmic signaling domain | MALPVTALLLPLALLLHAARPQVQLQESGPGLVKPSGTLSLTC AVSGDSISSNWWTWVRQPPGKGLEWIGDIHHSGSTNYNPSLK SRVTMSVDKSENQFSLKLSSVTAADTAVFYCARDGGSTLDY WGQGTLVTVSSGGGGSGGGGSGGGGSGGGGSDIQMTQSPST LSASVGDRVTITCRASQSISSWLAWYQQKPGKAPKLLIYKAST LESGVPSRFSGSGSGTEFTLTISSLQPDDFATYYCQQYNGYSTF GQGTKVEIKTTTPAPRPPTPAPTIASQPLSLRPEACRPAAGGAV HTRGLDFACDIYIWAPLAGTCGVLLLSLVITLYCKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQ GLSTATKDTYDALHMQALPPR |
| 656 | CD8α signal sequence, 6F8 scFv, CD8α hinge and transmembrane regions, 41BB cytoplasmic signaling domain, CD3ζ cytoplasmic signaling domain | MALPVTALLLPLALLLHAARPQVQLVQSGAEVKKPGSSVKVS CKASGGTFTNYCISWVRQAPGQGLEWMGGIIpIFGTTNYAQTF QGRVTITADKSTSTAYMELSSLRSEDTAVYYCARDNGDryyYD MDVWGQGTTVTVSSGGGGSGGGGSGGGGSGGGGSQSVLTQP PSVSAAPGQKVTISCSGSSSNIGNNYVSWYQQLPGTAPKLLIY DNNKRPSGIPDRFSGSKSGTSATLGITGLQTGDEADYYCGTWD SSLSAVVFGGGTKLTVLTTTPAPRPPTPAPTIASQPLSLRPEACR PAAGGAVHTRGLDFACDIYIWAPLAGTCGVLLLSLVITLYCKR GRKKLLYIFKQPFMRPVQTTQEEDGCSCRFPEEEEGGCELRVK FSRSADAPAYQQGQNQLYNELNLGRREEYDVLDKRRGRDPE MGGKPRRKNPQEGLYNELQKDKMAEAYSEIGMKGERRRGK GHDGLYQGLSTATKDTYDALHMQALPPR |
| 657 | CD8α signal sequence, 3G6-L1 scFv, CD8α hinge and transmembrane regions, 41BB cytoplasmic signaling domain, CD3ζ cytoplasmic signaling domain | MALPVTALLLPLALLLHAARPQVPLVQSGAEVKKPGSSVKVS CKASGGTFSTYSISWVRQAPGQGLEWMGGIIpIFGTTNYAQKF QGRVTITADKSTSTAYMELSSLRSEDTAVYYCARDGEGsyyyy YGMDVWGQGTTVTVSSGGGGSGGGGSGGGGSGGGGSQSVL TQPPSVSAAPGQKVTISCSGSSSNIGNNYVSWYQQLPGTAPKL LIYDNNKRPSGIPDRFFGSKFGTSATLGITGLQTGDEADYYCGT WDSSLSAVVFGGGTKLTVLTTTPAPRPPTPAPTIASQPLSLRPE ACRPAAGGAVHTRGLDFACDIYIWAPLAGTCGVLLLSLVITLY CKRGRKKLLYIFKQPFMRPVQTTQEEDGCSCRFPEEEEGGCEL RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR |
| 658 | CD8α signal sequence, 4C6 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGDSISSYYWSWIRQPPGKGLEWIGYMYYSGITNYNPSLKS RVNISLDTSKNQFSLKLGSVTAADTAVYYCARLSVAgFYFDY WGQGTLVTVSSGGGGSGGGGSGGGGSGGGGSEIVLTQSPGTL SLSPGERATLSCRASQSVTRSYLAWYQQKPGQAPRLLIYGASS RATDIPDRFSGSGSGTDFTLTINRLEPEDFAVYYCQQYGTSPLT FGGGTKVEIKTTTPAPRPPTPAPTIASQPLSLRPEACRPAAGGA VHTRGLDFACDIYIWAPLAGTCGVLLLSLVITLYCKRGRKKLL YIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR |
| 659 | CD8α signal sequence, 4E6 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSSDSISSYYWSWIRQPPGKGLEWISYIYYSGISNYNPSLKSR VSISVDTSKNQFSLRLSSVTAADTAVYYCARISVAgFFFDNWG QGTLVTVSSGGGGSGGGGSGGGGSGGGGSEIMLTQSPDTLSL SPGERATLSCRASQSVSSSYLAWYQQKPGQAPRLLIYGASSRA AGVPDRFSGSGSGTDFTLTISRLAPEDFVVYYCQQYGISPLTFG GGTKVEIKTTTPAPRPPTPAPTIASQPLSLRPEACRPAAGGAVH TRGLDFACDIYIWAPLAGTCGVLLLSLVITLYCKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |

TABLE 7-continued

| SEQ ID NO: | Name/ Component | Sequence |
|---|---|---|
| 660 | CD8α signal sequence, 4H8 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSnsATWNWIRQSPSRGLEWLGRTYYRSKwyDDYAV SVKSRITINPDTSKNHLSLHLNSVTPEDTAVYYCAGGGLVgapD GFDVWGQGTMVTVSSGGGGSGGGGSGGGGSGGGGSQSVLT QPPSASGTPGQRVTISCSGSSSNIGSDPVNWYQQLPGTAPKLLI YSNNQRPSGVPDRFSGSKSGTSASLAISGLQSEDEADYYCSAW DDSLNGYVFGTGTKVTVLTTTPAPRPPTPAPTIASQPLSLRPEA CRPAAGGAVHTRGLDFACDIYIWAPLAGTCGVLLLSLVITLYC KRGRKKLLYIFKQPFMRPVQTTQEEDGCSCRFPEEEEGGCELR VKFSRSADAPAYQQGQNQLYNELNLGRREEYDVLDKRRGRD PEMGGKPRRKNPQEGLYNELQKDKMAEAYSEIGMKGERRRG KGHDGLYQGLSTATKDTYDALHMQALPPR |
| 661 | CD8α signal sequence, 9H12-K scFv, CD8α hinge and transmembrane regions, 41BB cytoplasmic signaling domain, CD3ζ cytoplasmic signaling domain | MALPVTALLLPLALLLHAARPQVQLVQSGAEVKKPGASVKVS CKASGYTFTGYSIHWVRQAPGQGLEWMGWINpNSGGTFYAQ KFQGRVTMTRDTSISTVYMELSRLRSDDTAVYYCARDGWGdy yyYGLDVWGQGTTVTVSLGGGGSGGGGSGGGGSGGGGSDIQ MTQSPSSVSASVGDRVTITCRASQDISSWLAWYQQKPGKAPK LLIYTASSLQGGVPSRFSGSGSGTDFTLTISSLQPEDLATYSCQQ ANVFPYTFGQGTKLEIKTTTPAPRPPTPAPTIASQPLSLRPEACR PAAGGAVHTRGLDFACDIYIWAPLAGTCGVLLLSLVITLYCKR GRKKLLYIFKQPFMRPVQTTQEEDGCSCRFPEEEEGGCELRVK FSRSADAPAYQQGQNQLYNELNLGRREEYDVLDKRRGRDPE MGGKPRRKNPQEGLYNELQKDKMAEAYSEIGMKGERRRGK GHDGLYQGLSTATKDTYDALHMQALPPR |
| 662 | CD8α signal sequence, 10G1-K scFv, CD8α hinge and transmembrane regions, 41BB cytoplasmic signaling domain, CD3ζ cytoplasmic signaling domain | MALPVTALLLPLALLLHAARPEVQLLESGGGLVQPGGSLRLSC AASGFTFSSYAMNWVRQAPGKGLEWVSTISgSGGSTYYADSV KGRFTISRDNSKNTLYLQMNSLRAEDTAVFYCAIDPEYydilTG GDYWGQGTLVTVSSGGGGSGGGGSGGGGSGGGGSDIQMTQS PSAMSASVGDRVTITCRASQSISNYLAWFQQKPGKVPKRLIYA ASSLQSGVPSRFSGSGSGTEFTLTISSLQPEDFATYFCLQHDSFP LTFGGGTKVEIKTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFSR SADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 663 | CD8α signal sequence, 11A3 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSSDSISNYYWSWIRQPPGKGLEWISYIYYSGITNYNPSLKSR VTISVDTSKNQFSLKLSSVTAADTAVYYCARITVTgFYFDYWG QGTLVTVSSGGGGSGGGGSGGGGSGGGGSEIVLTQSPGTLSLS PGERATLSCRASQSISRSYLAWYQQKPGQAPRHLIYGASSRAT GIPDRFSGSGSGTDFILTISRLEPEDFAVYYCQQYDTSPLTFGG GTKVEIKTTTPAPRPPTPAPTIASQPLSLRPEACRPAAGGAVHT RGLDFACDIYIWAPLAGTCGVLLLSLVITLYCKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |
| 664 | CD8α signal sequence, 3B11 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSnsVVWNWIRQSPSRGLEWLGRTYYRSKwyDDYA VSVKSRITINPDTSKNQFSLQLNSVTPEDTAVYHCARGGIVgap DAFDIWGQGTMVTVSSGGGGSGGGGSGGGGSGGGGSQSVLT QPPSASGTPGQRVTISCSGSSSNIGSDPVSWYQQFPGTAPKLLI YTNNQRPSGVPDRFSGSKSGTSASLAISGLQSEDEADYYCAA WDDSLNGHVFGTGTKVTVLTTTPAPRPPTPAPTIASQPLSLRPE ACRPAAGGAVHTRGLDFACDIYIWAPLAGTCGVLLLSLVITLY CKRGRKKLLYIFKQPFMRPVQTTQEEDGCSCRFPEEEEGGCEL RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR |
| 665 | CD8α signal sequence, 5G2 scFv, CD8α hinge and transmembrane regions, 41BB cytoplasmic signaling domain, CD3ζ cytoplasmic | MALPVTALLLPLALLLHAARPQVQLQQSGPGLVKPSQTLSLTC AISGDSVSSnsAVWNWIRQSPSRGLEWLGWTYYRSKYYndYA VSLKSRITINPDTSKNQFSLQLNSLTPEDTAVYYCTRGGIVgapD GFDIWGQGTMVTVSSGGGGSGGGGSGGGGSGGGGSQSALTQ PPSASGTPGQRVTISCSGSNSNIGSNPINWYQQLPGTAPKLLIYS NNQRPSGVPDRFSGSKSGTSASLAISGLQSEDEADYYCAAWD DSLNGHVFGTGTKVTVLTTTPAPRPPTPAPTIASQPLSLRPEAC RPAAGGAVHTRGLDFACDIYIWAPLAGTCGVLLLSLVITLYCK |

TABLE 7-continued

CAR amino acid sequences

| SEQ ID NO: | Name/ Component | Sequence |
|---|---|---|
| | signaling domain | RGRKKLLYIFKQPFMRPVQTTQEEDGCSCRFPEEEEGGCELRV KFSRSADAPAYQQGQNQLYNELNLGRREEYDVLDKRRGRDP EMGGKPRRKNPQEGLYNELQKDKMAEAYSEIGMKGERRRGK GHDGLYQGLSTATKDTYDALHMQALPPR |
| 666 | CD8α signal sequence, 11E4 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGGGSISSYYWSWIRQSPGKGLEWIGYVYYSDITNYNPSLKS RVTISVDTSKNQFSLNLNSVTAADTAFYFCARIGVAgFYFDYW GQGTLVTVSSGGGGSGGGGSGGGGSGGGGSEIVLTQSPDTLS LSPGERATLSCRASQSVSRRYLAWYQQKPGQAPRLLIYGASSR ATGIPDRFSGSGSGTDFTLTISRLEPEDFEVYYCQQYGTSPITFG QGTRLEIKTTTPAPRPPTPAPTIASQPLSLRPEACRPAAGGAVH TRGLDFACDIYIWAPLAGTCGVLLLSLVITLYCKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |
| 667 | CD8α signal sequence, 2404.8E11 scFv, CD8α hinge and transmembrane regions, 41BB cytoplasmic signaling domain, CD3ζ cytoplasmic signaling domain | MALPVTALLLPLALLLHAARPQIQLQQSGPGLVKPSQTLSLTC AISGDSVSSnsAVWNWIRQSPSRGLEWLGRTYYRSKwyNDYA VSVKSRITIKPDTAKNQFSLQLNSVTPEDTAVYYFTRGGIVgap DAFDIWGQGTMVTVSSGGGGSGGGGSGGGGSGGGGSQSVLT QPPSASGTPGQRVTISCSGSSSNIGSDPINWYQQVPGTAPKLLI YSNNQRPSGVPDRFSGSKSGTSASLAISGLQSEDEADYYCAA WDDSLNGYVFGTGTKVTVLTTTPAPRPPTPAPTIASQPLSLRPE ACRPAAGGAVHTRGLDFACDIYIWAPLAGTCGVLLLSLVITLY CKRGRKKLLYIFKQPFMRPVQTTQEEDGCSCRFPEEEEGGCEL RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR |
| 668 | CD8α signal sequence, 10A2 scFv, CD8α hinge and transmembrane regions, 41BB cytoplasmic signaling domain, CD3ζ cytoplasmic signaling domain | MALPVTALLLPLALLLHAARPQVQLQQSGPGLVKPSETLSLTC AISGDSVSSnsATWNWIRQSPSRGLEWLGRTYYRSEwyNDYAV SVKSRITINPDTSKNHLSLHLNSVTPEDTAVYYCAGGGIVgapD GFDVWGQGTMVTVSSGGGGSGGGGSGGGGSGGGGSQSVLT QPPSASGTPGQRVTISCSGSSSNIGSDPVIWYQQLPRTAPKLLIY SNNQRPSGVPDRFSGSKSGTSASLAISGLQSEDEADYYCAAW DDSLNGYVFGTGTKVTVLTTTPAPRPPTPAPTIASQPLSLRPEA CRPAAGGAVHTRGLDFACDIYIWAPLAGTCGVLLLSLVITLYC KRGRKKLLYIFKQPFMRPVQTTQEEDGCSCRFPEEEEGGCELR VKFSRSADAPAYQQGQNQLYNELNLGRREEYDVLDKRRGRD PEMGGKPRRKNPQEGLYNELQKDKMAEAYSEIGMKGERRRG KGHDGLYQGLSTATKDTYDALHMQALPPR |
| 669 | CD8α signal sequence, 11A8 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSnsATWNWIRQSPSTGLEWLARTYYRSKwyNDYEV SVKSQITINPDTSKNQFSLQLNSVTPEDTAVYYCARGGIVgapD AFDIWGQGTMVTVSSGGGGSGGGGSGGGGSGGGGSQVLTQ PPSASGTPGQGVTISCSGSSSNIGSNPVNWYQQLPGTAPKLLIY SNNQRPSGVPDRFSDSKSGTSASLAISGLQSEDEADYYCSAWD DWLNGYVFGTGTKVTVLTTTPAPRPPTPAPTIASQPLSLRPEA CRPAAGGAVHTRGLDFACDIYIWAPLAGTCGVLLLSLVITLYC KRGRKKLLYIFKQPFMRPVQTTQEEDGCSCRFPEEEEGGCELR VKFSRSADAPAYQQGQNQLYNELNLGRREEYDVLDKRRGRD PEMGGKPRRKNPQEGLYNELQKDKMAEAYSEIGMKGERRRG KGHDGLYQGLSTATKDTYDALHMQALPPR |
| 670 | CD8α signal sequence, 4H5 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGDSINNYFWSWIRQPPGKGLEWIGYFYHRGGNNYNPSLK SRVTISIDTSKNQFSLNLNSVTSADTAVYYCARLALALAgFFFDY WGQGTLVTVSSGGGGSGGGGSGGGGSGGGGSDIQMTQSPST LSASVGDRVTITCRASQSISSWLAWYQQKPGKAPKLLIYKASS LESGVPSRFSGSGSGTEFTLTISSLQPDDFATYYCQQYNSYSRT FGQGTKVEIKTTTPAPRPPTPAPTIASQPLSLRPEACRPAAGGA VHTRGLDFACDIYIWAPLAGTCGVLLLSLVITLYCKRGRKKLL YIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR |
| 671 | CD8α signal sequence, 3G6-L2 scFv, CD8α hinge and transmembrane | MALPVTALLLPLALLLHAARPQVPLVQSGAEVKKPGSSVKVS CKASGGTFSTYSISWVRQAPGQGLEWMGGIIpIFGTTNYAQKF QGRVTITADKSTSTAYMELSSLRSEDTAVYYCARDGEGsyyyy YGMDVWGQGTTVTVSSGGGGSGGGGSGGGGSGGGGSQSVL |

TABLE 7-continued

CAR amino acid sequences

| SEQ ID NO: | Name/ Component | Sequence |
|---|---|---|
| | regions, 41BB cytoplasmic signaling domain, CD3ζ cytoplasmic signaling domain | TQPPSASGTPGQRVTISCSGSSSNIGSNYVYWYQQLPGTAPKL LIYSNNQRPSGVPDRFSGSKSGTSASLAISGLRSEDEADYYCAA WDDSLSGWVFGGGTKLTVLTTTPAPRPPTPAPTIASQPLSLRPE ACRPAAGGAVHTRGLDFACDIYIWAPLAGTCGVLLLSLVITLY CKRGRKKLLYIFKQPFMRPVQTTQEEDGCSCRFPEEEEGGCEL RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR |
| 672 | CD8α signal sequence, 3B9 scFv, CD8α hinge and transmembrane regions, 41BB cytoplasmic signaling domain, CD3ζ cytoplasmic signaling domain | MALPVTALLLPLALLLHAARPEVQLVESGGGLVQPGGSLRLS CAASGFTFSSYSMNWVRQAPGKGLEWVSYISsSSSTIYYADSV KGRFTISRDNAKNSLYLQMNSLRDEDTAVYYCARDKERryyyY GMDVWGQGTTVTVSSGGGGSGGGGSGGGGSGGGGSEIVLTQ SPDTLSLSPGERATLSCRASQSVSRRYLAWYQQKPGQAPRLLI YGASSRATGIPDRFSGSGSGTDFTLTISRLEPEDFAVYYCQQFG TSPITFGQGTRLEIKTTTPAPRPPTPAPTIASQPLSLRPEACRPAA GGAVHTRGLDFACDIYIWAPLAGTCGVLLLSLVITLYCKRGR KKLLYIFKQPFMRPVQTTQEEDGCSCRFPEEEEGGCELRVKFS RSADAPAYQQGQNQLYNELNLGRREEYDVLDKRRGRDPEMG GKPRRKNPQEGLYNELQKDKMAEAYSEIGMKGERRRGKGHD GLYQGLSTATKDTYDALHMQALPPR |
| 673 | CD8α signal sequence, 3F9-L scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLA CAISGDSVSSnsAIWNWIRQSPSRGLEWLGGTYYRSMwyNDYA VSVKSRITINPDTSKNQLSLQLNSVTPEDTAVYYCSRGGIVgvp DAFDIWGQGTMVTVSSGGGGSGGGGSGGGGSGGGGSQSVLT QPPSASGTPGQRVTISCSGSSSNIGSNTANWYQQLPGTAPKLLI YRNNQRPSGVPDRFSGSKSGTSASLAISGLQSEDEADYYCAA WDDSLNGYVFGTGTKVTVLTTTPAPRPPTPAPTIASQPLSLRPE ACRPAAGGAVHTRGLDFACDIYIWAPLAGTCGVLLLSLVITLY CKRGRKKLLYIFKQPFMRPVQTTQEEDGCSCRFPEEEEGGCEL RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR |
| 674 | CD8α signal sequence, 3E10 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC NVSDGSISSYYWTWIRQPPGKGLDWIGYIFYSGTTNYNPSLKS RVTISLDTSKNQFSLKLTSMTAADTAVYYCARISEKsFYFDYW GQGTLVTVSSGGGGSGGGGSGGGGSGGGGSQSVLTQPPSASG TPGQRVTISCSGSSSNIGSNYVYWYQQLPGTAPKLLIYSNNQR PSGVPDRFSGSKSGTSASLAISGLRSEDEADYYCAPWDDSLSG RVFGGGTKLTVLTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFSR SADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 675 | CD8α signal sequence, 3C3 scFv, CD8α hinge and transmembrane regions, 41BB cytoplasmic signaling domain, CD3ζ cytoplasmic signaling domain | MALPVTALLLPLALLLHAARPQVQLVQSGAEVKRPGASVKVS CKASGYTFTSYYIHWVRQAPGQGLEWMGVIVpSGGGSISYAQK FQGRVTMTRDTSTNIVYMELSSLRSEDTAVYYCARDRYYgdyy YGLDVWGQGTTVTVSSGGGGSGGGGSGGGGSGGGGSDIQMT QSPSSLSASVGDRVTITCRASQGINNFLAWFQQKPGKAPKSLIY AASSLQSGVPSKFSGSGSGTDFTLTIRSLQPEDFATYYCQHYNS YPITFGQGTRLEIKTTTPAPRPPTPAPTIASQPLSLRPEACRPAA GGAVHTRGLDFACDIYIWAPLAGTCGVLLLSLVITLYCKRGR KKLLYIFKQPFMRPVQTTQEEDGCSCRFPEEEEGGCELRVKFS RSADAPAYQQGQNQLYNELNLGRREEYDVLDKRRGRDPEMG GKPRRKNPQEGLYNELQKDKMAEAYSEIGMKGERRRGKGHD GLYQGLSTATKDTYDALHMQALPPR |
| 676 | CD8α signal sequence, 11F4 scFv, CD8α hinge and transmembrane regions, 41BB cytoplasmic signaling domain, CD3ζ cytoplasmic signaling domain | MALPVTALLLPLALLLHAARPQVHLQESGPGLVKPSETLSLTC TVSGGSISHYYWTWIRQPPGKGLEWIGYIYYSGITNFSPSLKSR VSISVDSSKNQFSLNLNSVTAADTAVYYCAGISLAgFYFDYWV QGTLVTVSSGGGGSGGGGSGGGGSGGGGSEIVLTQSPGTLSLS PGERATLSCRASQSVSRSYLAWYQQKPGQAPRLLIYGASSRAT GVPDRFSGSGSGTDFTLTISRLEPEDFAVFYCQQYSISPLTFGG GTKVEIKTTTPAPRPPTPAPTIASQPLSLRPEACRPAAGGAVHT RGLDFACDIYIWAPLAGTCGVLLLSLVITLYCKRGRKKLLYIF KQPFMRPVQTTQEEDGCSCRFPEEEEGGCELRVKFSRSADAPA YQQGQNQLYNELNLGRREEYDVLDKRRGRDPEMGGKPRRK NPQEGLYNELQKDKMAEAYSEIGMKGERRRGKGHDGLYQGL STATKDTYDALHMQALPPR |

TABLE 7-continued

CAR amino acid sequences

| SEQ ID NO: | Name/ Component | Sequence |
|---|---|---|
| 677 | CD8α signal sequence, 10E12 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGVSISSYYWSWIRQPPGKGLEWIAYIYYSGNTNYSPSLKS RVTISVDTSKDQLSLKLSSVTAADTAVYYCTRGGSGtiDVFDIW GQGTMVAVSSGGGGSGGGGSGGGGSGGGGSQSVLTQPPSVS AAPGQKVTISCSGSSSNIGNNYVSWYQQLPGTAPKLLIYDNNK RPSGIPDRFSGSKSGTSATLGITGLQTGDEADYYCETWDSSLSA VVFGGGTKLTVLTTTPAPRPPTPAPTIASQPLSLRPEACRPAAG GAVHTRGLDFACDIYIWAPLAGTCGVLLLSLVITLYCKRGRK KLLYIFKQPFMRPVQTTQEEDGCSCRFPEEEEGGCELRVKFSR SADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 678 | CD8α signal sequence, 4E1 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDNVSTnsAAWNWIRQSPSRGLEWLGWTYYRSKwyNDYA VSLKSRININPDTSKNQFSLQLNSVTPEDTAVYYCARWVNRD VFDIWGQGTMVTVSSGGGGSGGGGSGGGGSGGGGSQSALTQ PASVSGSPGQSITISCTGTSSDVGSYNLVSWYQQHPGKAPKLM IYEGSKRPSGVSNRFSGSKSGNTASLTISGLQAEDEADYYCCS YAGSSTWVFGGGTKLTVLTTTPAPRPPTPAPTIASQPLSLRPEA CRPAAGGAVHTRGLDFACDIYIWAPLAGTCGVLLLSLVITLYC KRGRKKLLYIFKQPFMRPVQTTQEEDGCSCRFPEEEEGGCELR VKFSRSADAPAYQQGQNQLYNELNLGRREEYDVLDKRRGRD PEMGGKPRRKNPQEGLYNELQKDKMAEAYSEIGMKGERRRG KGHDGLYQGLSTATKDTYDALHMQALPPR |
| 679 | CD8α signal sequence, 2404.6H1 scFv, CD8α hinge and transmembrane regions, 41BB cytoplasmic signaling domain, CD3ζ cytoplasmic signaling domain | MALPVTALLLPLALLLHAARPQVQLVESGGGVVQPGRSLRLS CAASGFTFSSYGMHWVRQTPGKGLEWVAVISYDGNsNYYAD SVKGRFTISRDNSKNTLYLQMNSLRAEDTAVYYCARDGATvts yyyYGMDVWGQGTTVTVSSGGGGSGGGGSGGGGSGGGGSEI VLTQSPGTLSLSPGERATLSCRASQSVSRTYLAWYHQKPGQAP RLLIYGASSRATGISDRFSGSGSGTDFTLTISRLEPEDFAVYYCQ QYGTSPITFGQGTRLEIKTTTPAPRPPTPAPTIASQPLSLRPEAC RPAAGGAVHTRGLDFACDIYIWAPLAGTCGVLLLSLVITLYCK RGRKKLLYIFKQPFMRPVQTTQEEDGCSCRFPEEEEGGCELRV KFSRSADAPAYQQGQNQLYNELNLGRREEYDVLDKRRGRDP EMGGKPRRKNPQEGLYNELQKDKMAEAYSEIGMKGERRRGK GHDGLYQGLSTATKDTYDALHMQALPPR |
| 680 | CD8α signal sequence, 2A8 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSnsAVWNWIRQSPSRGLEWLGRTYYRSKwyNDYA VSVKSRITINPDTSRNQFSLQLNSVTPEDTAVYYCARGGIVgap DGFDIWGQGTMVTVSSGGGGSGGGGSGGGGSGGGGSDIVMT QSPDSLAVSLGERATINCKSSQSVLDSSNNNnYFAWYQQRPGQ PPHLLIYWASSRESGVPDRFSGSGSGTDFTLTISSLQAEDVAVY YCQQYYSTPYTFGQGTKLEIKTTTPAPRPPTPAPTIASQPLSLRP EACRPAAGGAVHTRGLDFACDIYIWAPLAGTCGVLLLSLVITL YCKRGRKKLLYIFKQPFMRPVQTTQEEDGCSCRFPEEEEGGCE LRVKFSRSADAPAYQQGQNQLYNELNLGRREEYDVLDKRRG RDPEMGGKPRRKNPQEGLYNELQKDKMAEAYSEIGMKGERR RGKGHDGLYQGLSTATKDTYDALHMQALPPR |
| 681 | CD8α signal sequence, 3B1 scFv, CD8α hinge and transmembrane regions, 41BB cytoplasmic signaling domain, CD3ζ cytoplasmic signaling domain | MALPVTALLLPLALLLHAARPQVQLQQSGPGLVKPSQTLSLTC AISGDSVSSntTAWKWSRQSPSKGLEWLGWTYYRSKwyYDYT VSVKSRITINPDTSKNQFSLQLNSVTPEDTAVYYCARWIFHDA FDIWGQGTMVTVSSGGGGSGGGGSGGGGSGGGGSQSALTQP PSASGTPGQRVTISCSGSSSNIGSNTVNWYQQLPGTAPKLLIYT NNQRPSGVPDRFSGSKSGTSASLAISGLQSEDEADYFCSTWDD SLNGPVFGGGTKLTVLTTTPAPRPPTPAPTIASQPLSLRPEACRP AAGGAVHTRGLDFACDIYIWAPLAGTCGVLLLSLVITLYCKR GRKKLLYIFKQPFMRPVQTTQEEDGCSCRFPEEEEGGCELRVK FSRSADAPAYQQGQNQLYNELNLGRREEYDVLDKRRGRDPE MGGKPRRKNPQEGLYNELQKDKMAEAYSEIGMKGERRRGK GHDGLYQGLSTATKDTYDALHMQALPPR |
| 682 | CD8α signal sequence, 9B5 scFv, CD8α hinge and transmembrane regions, 41BB cytoplasmic signaling domain, CD3ζ cytoplasmic signaling domain | MALPVTALLLPLALLLHAARPQVQLQESGPGLVKPSETLSLTC TVSGDSISSLSWSWIRQTPGEGLEWIGYLYYSGSTDYNPSLKS RVTISVDTSKNQFSLKLRSVAAADTALYYCARGRRAFDIWGQ GTMVTVSSGGGGSGGGGSGGGGSGGGGSDIQMTQSPSSLSAS VGDRVTITCRGSQGISNYLAWFQQRPGKAPKSLIYAASSLESG VPSKFSGSGSGTDFTLTIISLQPEDFATYYCQQYYNYPITFGQG TRLEIKTTTPAPRPPTPAPTIASQPLSLRPEACRPAAGGAVHTR GLDFACDIYIWAPLAGTCGVLLLSLVITLYCKRGRKKLLYIFK QPFMRPVQTTQEEDGCSCRFPEEEEGGCELRVKFSRSADAPAY |

TABLE 7-continued

CAR amino acid sequences

| SEQ ID NO: | Name/ Component | Sequence |
|---|---|---|
| | | QQGQNQLYNELNLGRREEYDVLDKRRGRDPEMGGKPRRKNP QEGLYNELQKDKMAEAYSEIGMKGERRRGKGHDGLYQGLST ATKDTYDALHMQALPPR |
| 683 | CD8α signal sequence, 11A5 scFv, CD8α hinge and transmembrane regions, 41BB cytoplasmic signaling domain, CD3ζ cytoplasmic signaling domain | MALPVTALLLPLALLLHAARPQVQLVQSGAEVKKPGASVKVS CKASGYTFTGYYMHWVRQAPGQGLEWMGWINpNSGGTNYA QKFQGRVTMTRDTSVSTAYMELSRLTSDDTAIYYCAKDGGGd fyfYGMDVWGQGTTVTVSSGGGGSGGGGSGGGGSGGGGSQT VVTQEPSFSVSPGGTVTLTCGLSSGSVSTSYYPSCFQQTPGQAP RTLIYSTDTRSSGVPDRFSGSILGNKAALTITGAQADDESDYYC VLYMGSGISVFGGGTKLTVLTTTPAPRPPTPAPTIASQPLSLRP EACRPAAGGAVHTRGLDFACDIYIWAPLAGTCGVLLLSLVITL YCKRGRKKLLYIFKQPFMRPVQTTQEEDGCSCRFPEEEEGGCE LRVKFSRSADAPAYQQGQNQLYNELNLGRREEYDVLDKRRG RDPEMGGKPRRKNPQEGLYNELQKDKMAEAYSEIGMKGERR RGKGHDGLYQGLSTATKDTYDALHMQALPPR |

Figure 3A:
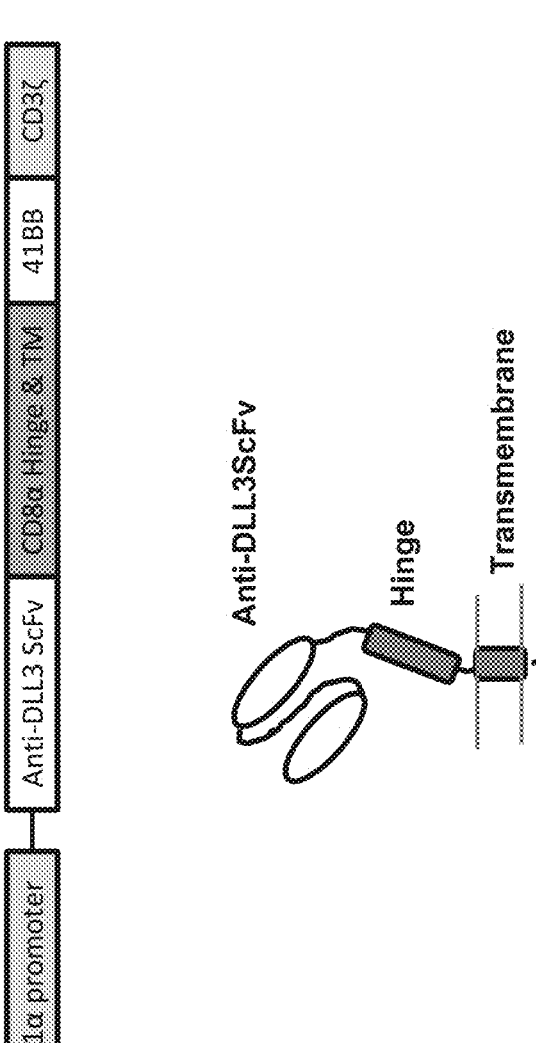

A schematic of the CAR structure is set forth in FIG. 3A. Representative CAR sequences reformatted from anti-DLL3 clones are included in SEQ ID NO 482 to 533. Codon-optimized DLL3 CAR sequences were synthesized and subcloned into the following lentiviral vectors pLVX-EF1a-DLL3 CAR (Clontech) using the XmaI (5') and MluI (3') restriction sites.

To generate DLL3 CAR-T cells, PBMCs were first purified from buffy coat samples using Ficoll gradient density medium (Ficoll Paque PLUS/GE Healthcare Life Sciences). T cells were purified from PBMCs using a commercially available T cell isolation kit (Miltenyi Biotec, Cat #130-096-535). Alternatively, primary human T cells can be directly purified from LeukoPak (StemCell Technologies).

To make lentivirus encoding DLL3 CARs, HEK-293T cells were plated at 0.4 million cells per mL in 2 mL of DMEM (Gibco) supplemented with 10% FBS (Hyclone or JR Scientific) per well of a 6-well plate on Day 0. On Day 1, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK-293T. Purified T cells were activated in X-Vivo-15 medium (Lonza) supplemented with 100 IU/mL human IL-2 (Miltenyi Biotec), 10% FBS (Hyclone), and human T Trans-Act (Miltenyi Biotec, Cat #130-111-160, 1:100 dilution). On Day 2, the media from each well of the 6-well plate was replaced with 2 mL per well of T cell transduction media, i.e., X-Vivo-15 supplemented with 10% FBS. On Day 3, T cells were resuspended at 0.5 million cells per mL in 1 mL of T cell transduction media per well of a Grex-24 plate (Wilson Wolf, cat #80192M). The lentiviral supernatants from HEK293T cells were harvested and passed through a 0.45 micron filter (EMD Millipore) to remove cell debris, and then added to the T cells along with 100 IU/mL human IL-2. On Day 5, 4.5 mL of T cell expansion media, i.e., X-Vivo-15 supplemented with 5% human AB serum (Gemini Bio) was added to each well of a Grex-24 plate. On Day 9 and Day 13, transduction efficiency was determined by detecting the percentage of T cells that recognize recombinant DLL3 (Adipogen) using flow cytometry. Cells were expanded into larger flasks or G-Rex vessels (Wilson Wolf) as needed using T cell expansion media. On Day 14, DLL3 CAR-T cells were cryopreserved. Percentage of cells stained with recombinant DLL3 was normalized across clones right before cryopreservation.

To determine the percentage of T cells that were successfully transduced with DLL3 CAR, T cells were first incubated with 1 ug/ml Flag tagged recombinant DLL3 (Adipogen) in PBS+1% BSA for 20 minutes at 4 C. Then cells were washed with PBS+1% BSA, stained with PE labelled anti-Flag antibodies (Biolegend, Cat #637310) and analyzed using flow cytometry.

Figure 3B:
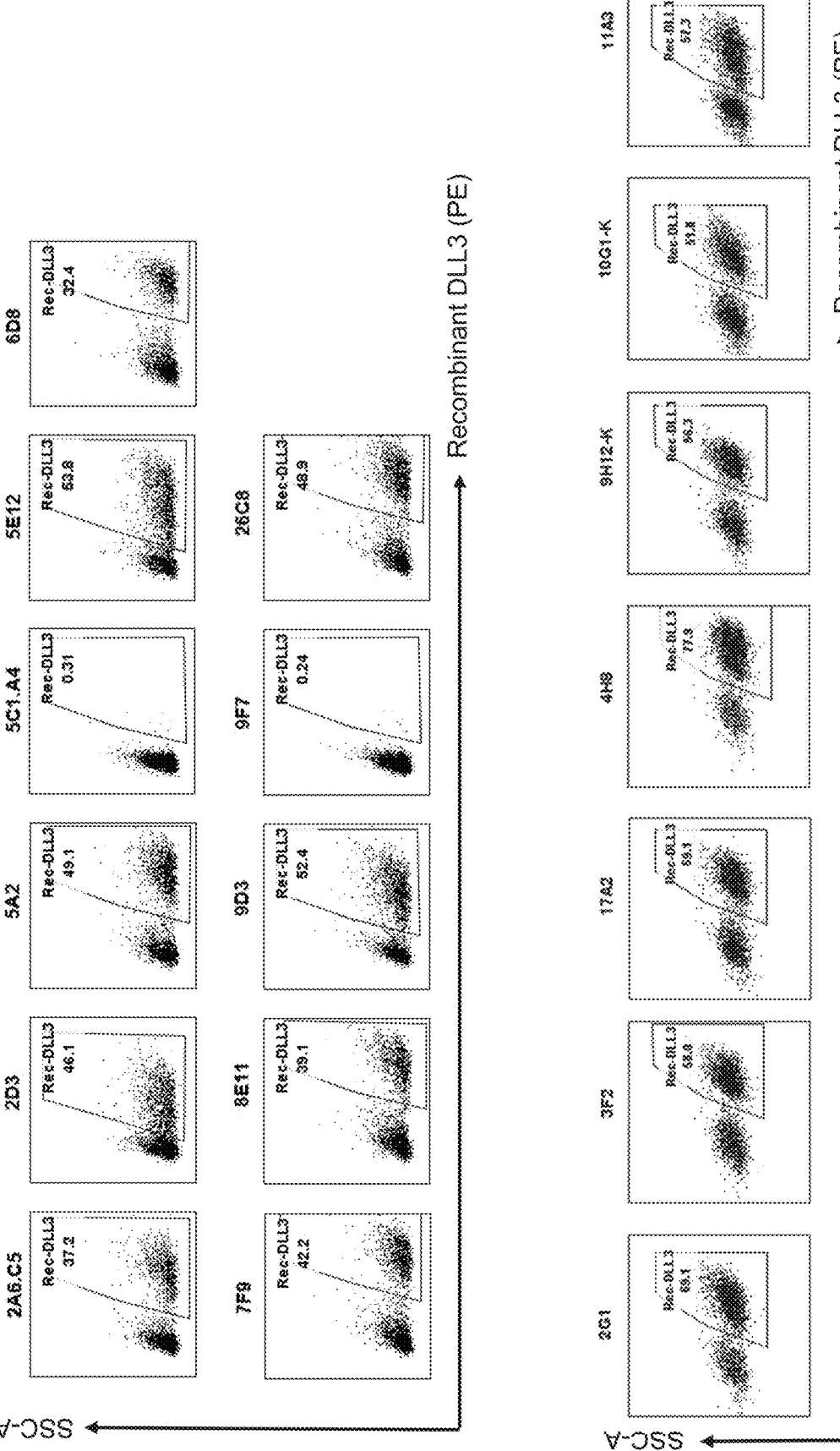

Examples of DLL3 CAR-T cells are shown in FIG. 3B. FIG. 3B shows experimental data, showing anti-DLL3 CARs are expressed on the surface of primary T-cells and can recognize recombinant DLL3. The plots are gated on live CD3+ cells. The numbers on the plots are the percentage of cells expressing each anti-DLL3 CAR.

Example 6: In Vitro Characterization

This example describes experiments used to determine the specificity and in vitro activity of CARs for DLL3.

SHP-77, WM266.4, DMS 454 and DMS 273 are DLL3+ cells lines that were purchased from ATCC or Sigma. HEK-293T is a DLL3 negative cell line. To express human DLL3 in HEK-293T, lentivirus encoding full length human DLL3 was used to transduce HEK-293T cells.

To test DLL3-specific killing, firefly luciferase expressing HEK-293T cells with or without human DLL3 expression were then plated at a seeding density of 5,000 cells per well in 96-well assay plates (Costar). DLL3 CAR-T cells were thawed and added to plated HEK-293T cells with or without human DLL3 expression at effector:target (E:T) ratio ranging from 1:9 to 9:1 in T cell expansion media, i.e., X-Vivo-15 supplemented with 5% human AB serum (Gemini Bio). Cell viability was measured after 72 hours using one-glo assay kit (Promega). Representative DLL3 CAR-T cells demonstrated potent killing on HEK-293T-DLL3 cells but did not show detectable activity in HEK-293T parental cells (FIG. 4A).

To test the cytotoxic activity of DLL3 CAR-T cells against cell lines that express endogenous DLL3, DLL3 CAR-T cells were incubated with firefly luciferase labelled DLL3+ SHP-77, WM266.4, DMS 454 or DMS 273 cells at effector:target (E:T) ratio ranting from 1:9 to 9:1 in T cell expansion media, i.e., X-Vivo-15 supplemented with 5% human AB serum (Gemini Bio). Cell viability was measured after 72 hours using one-glo assay kit (Promega). Each condition was assayed in 3 replicates. Average percentage of live cells and standard deviation were plated (FIG. 4B and FIG. 4C).

Figure 4A:
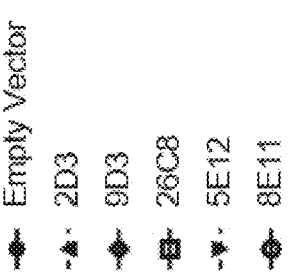
Figure 4A:
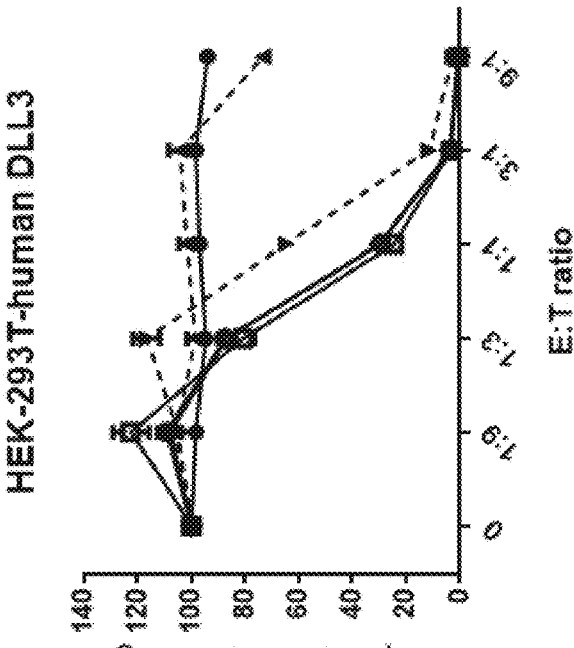
Figure 4A:
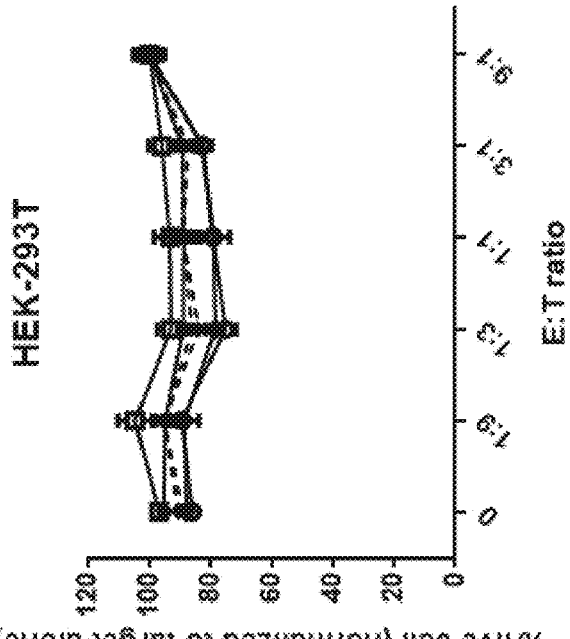

FIG. 4A shows experimental data showing anti-DLL3 CAR-T cells specifically killed HEK-293T cells expressing human DLL3 but not parental HEK-293T cells in a 3-day cytotox assay at indicated effector:target ratios. T cells that didn't express anti-DLL3 CARs (labelled empty vector) were used as negative control.

Figure 4B:
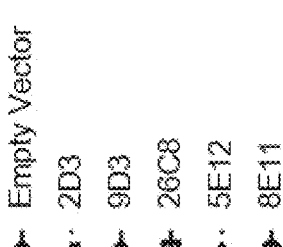
Figure 4B:
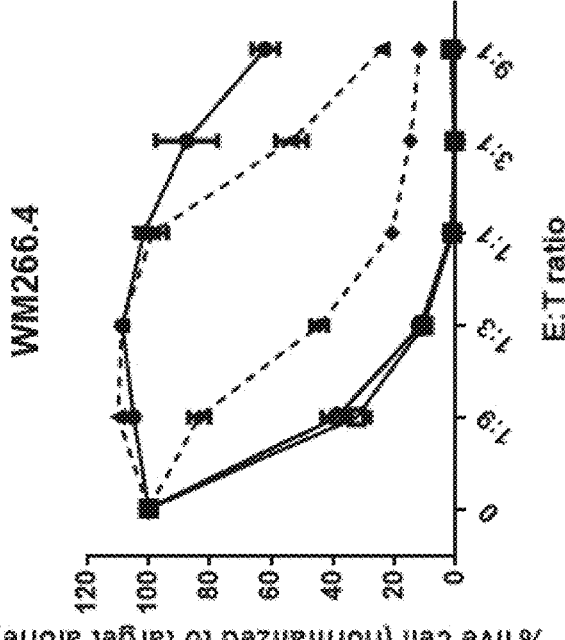
Figure 4B:
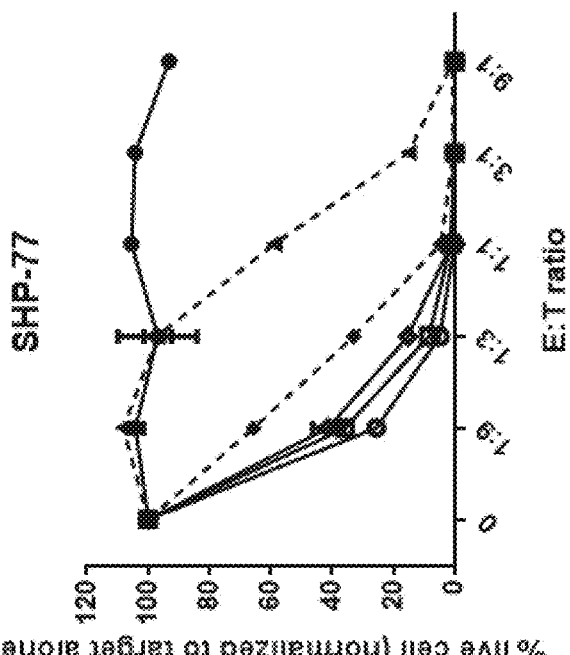

FIG. 4B shows experimental data showing anti-DLL3 CAR-T cells killed SHP-77 and WM266.4 cells that expresses endogenous DLL3 in a 3-day cytotox assay at indicated effector:target ratios.

FIG. 4C shows experimental data showing anti-DLL3 CAR-T cells killed DMS 454 and DMS 273 small cell lung cancer cells that expresses endogenous DLL3 in a 3-day cytotox assay at indicated effector:target ratios. For all plots in FIG. 4C, One-glo assay system was used to assess target cell viability, n=3.

Figure 5:
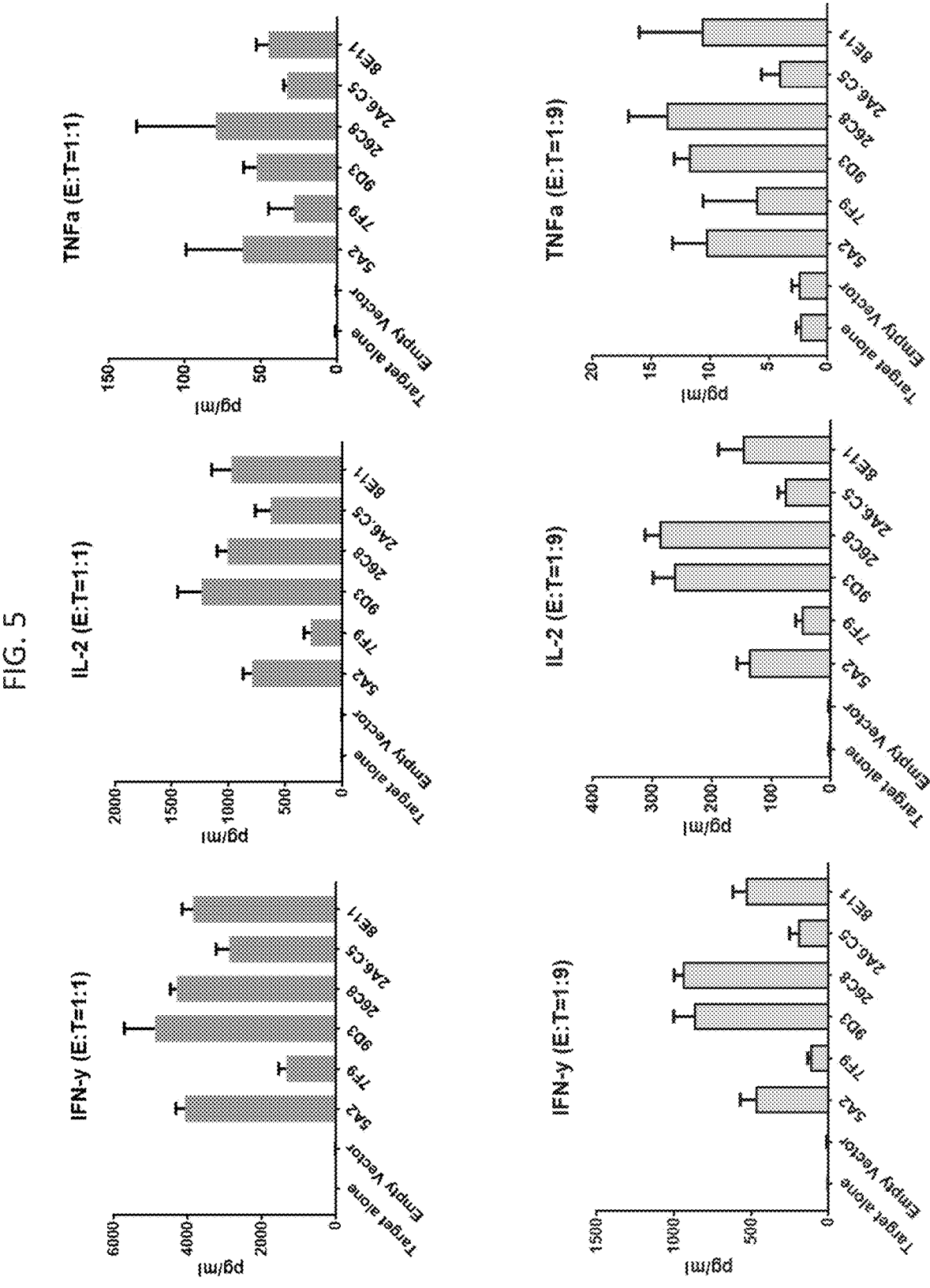
FIG. 5 is a series of bar graphs showing that anti-DLL3 CAR-T cells released cytokines after co-incubation with DLL3-expressing SHP-77 cell line when CAR-T cells and SHP-77 cells were incubated at 1:1 or 1:9 effector:target ratio for 24 hours. Supernatant was collected and IFN-γ, IL-2 and TNF-α levels were measured using proinflammory 9-plex kit from MSD, n=3.

To measure cytokines secreted from DLL3 CAR-T cells, DLL3 CAR-T cells were incubated with DLL3+ SHP-77 cells at effector:target (E:T) ratio of 1:1 or 1:9 in T cell expansion media, i.e., X-Vivo-15 supplemented with 5% human AB serum (Gemini Bio). 24 hours later, tissue culture supernatant was collected and the levels of 3 cytokines [interferon gamma (IFN-$\gamma$), tumor necrosis factor alpha (TNF-$\alpha$), and IL-2] in the supernatants were measured using human proinflammatory tissue culture 9-plex assay (MSD) following manufacturer's protocol. FIG. 5 shows Anti-DLL3 CAR-T cells released cytokines after co-incubation with DLL3-expressing SHP-77 cell line. CAR-T cells and SHP-77 cells were incubated at 1:1 or 1:9 effector:target ratio for 24 hours, n=3.

Example 7: Serial Killing Assay

A serial killing assay involves repeated exposure of CAR-T cells to their target causing the CAR-T cells to undergo proliferation and in certain cases, differentiation and exhaustion. This assay was used to select optimal clones with high target cell lysis and proliferative abilities after several rounds of exposure to target cells.

Figure 6A:
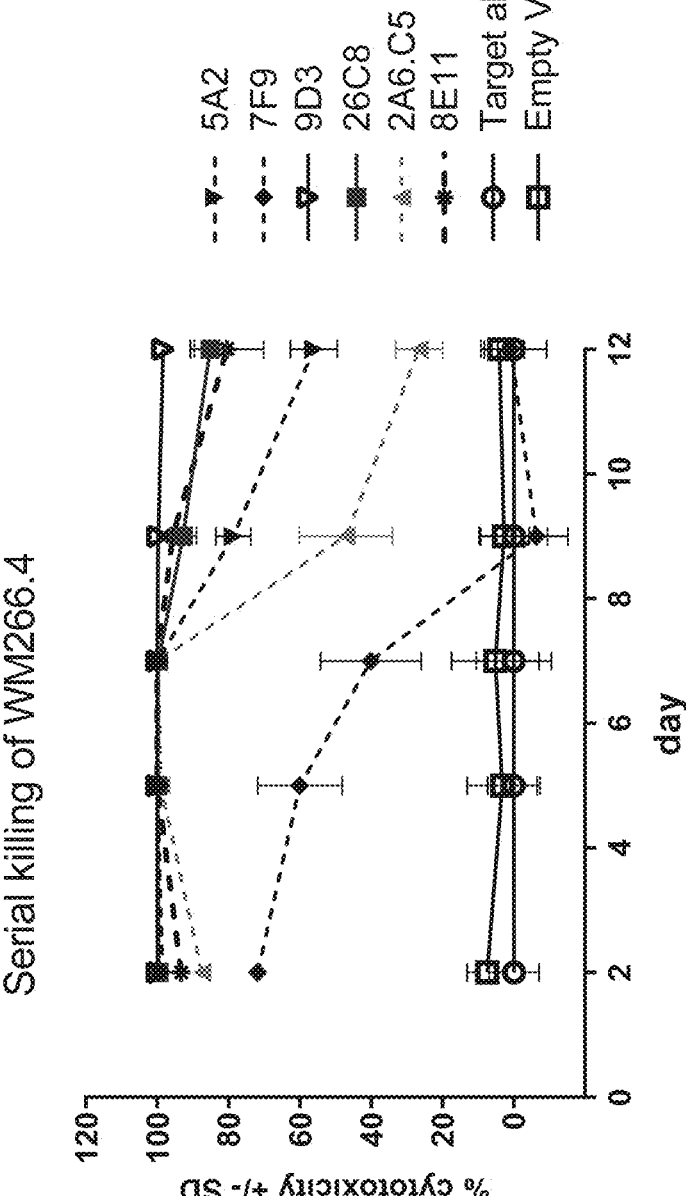
FIGS. 6A-6B are plots showing experimental data of a serial killing assay after repeated exposure of anti-DLL3 CAR-T cells to DLL3+ cell lines.
Figure 6B:
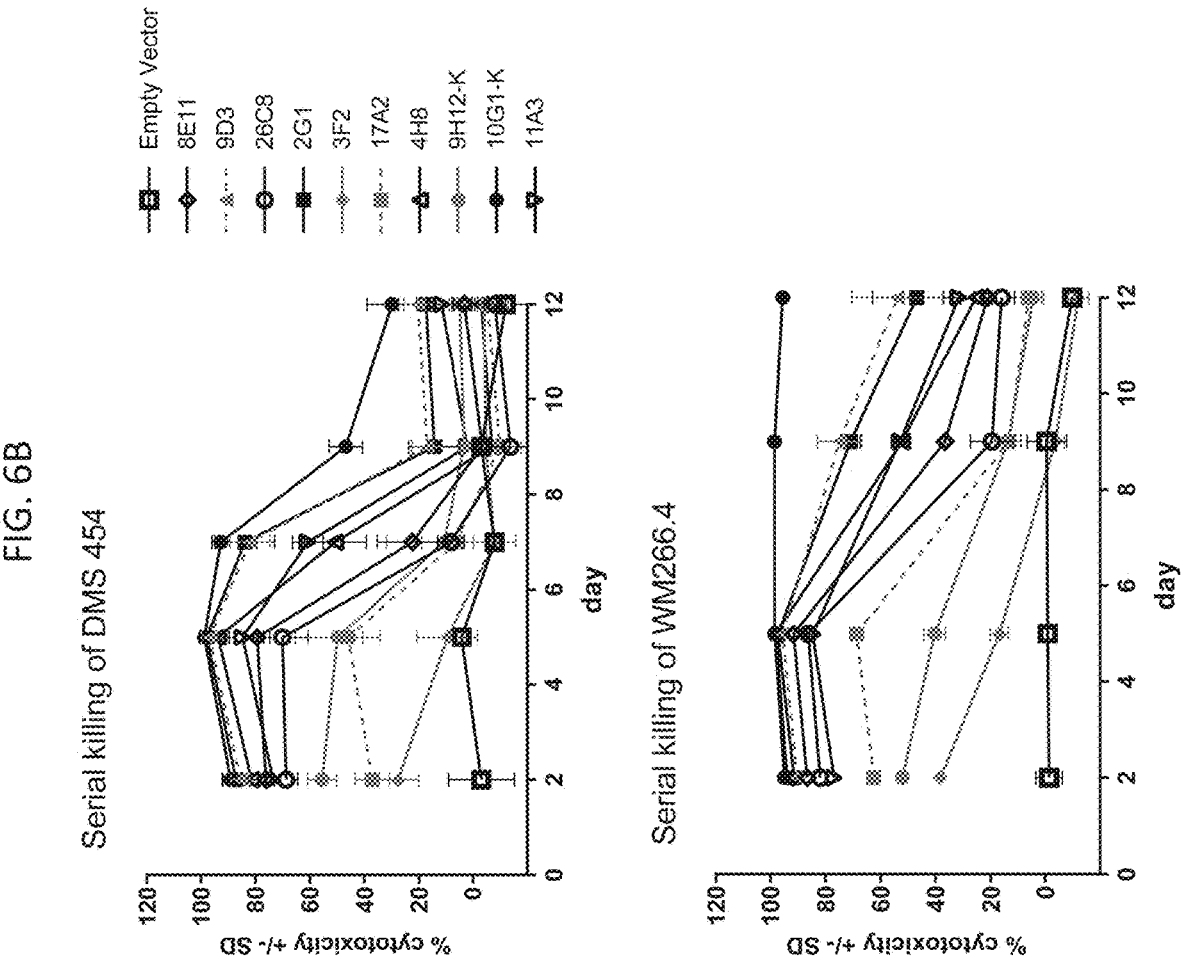
Figure 6C:
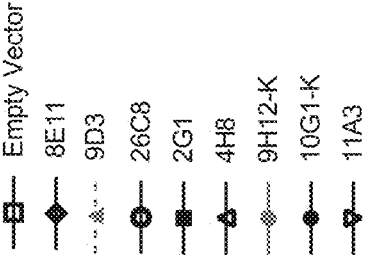
FIG. 6C depicts serial killing of anti-DLL3 CAR-Ts to DMS 273 small cell lung cancer line. For all plots in FIGS. 6A-6C, one-glo assay or Cell-Titer-glo system was used to assess target cell viability, n=3-5.
Figure 6C:
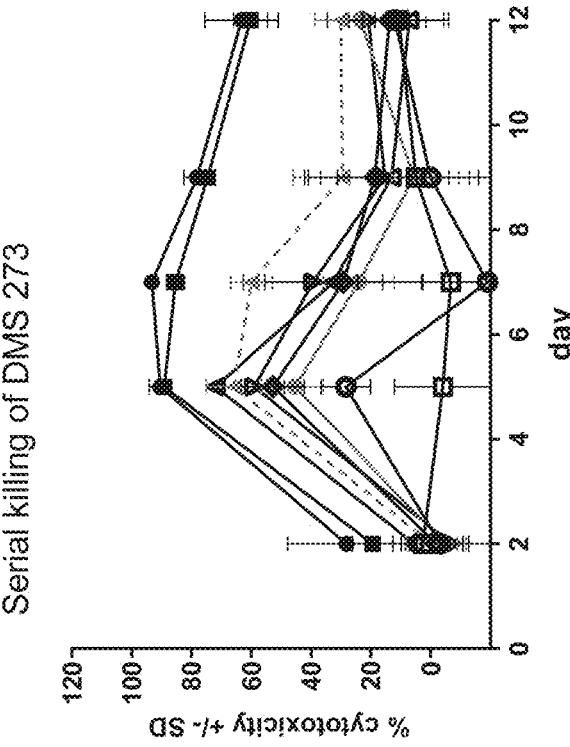

One the first day of the assay, 5,000 firefly luciferase labelled WM266.4, DMS 454 or DMS 273 cells that are known to express DLL3 were seeded in 96-well plates with white wall and flat clear bottom in 100 ul X-Vivo-15 medium with 5% of human serum. After target cells attached to the bottom of the plates, DLL3 CAR-T cells were thawed and added to plated target cells at an effector:target (E:T) ratio of 1:1 in X-VIVO medium with 5% of human serum. Every 2 days thereafter, 100 μl medium containing DLL3 CAR-T cells were transferred to freshly plated target cells and percentage lysis of previously plated target cells were determined using one-glo assay system or CellTiter-glo system (Promega). Each condition was assayed in 3 to 6 replicates. Average percentage of lysis and standard deviation were plated (FIGS. 6A-6C). Optimal clones were those with highest target cell lysis during the entire assay on day 12. These data show experimental data of serial killing assay to show that after repeated exposure of anti-DLL3 CAR-T cells to DLL3+WM266.4 cells, some of the clones remained active. One-glo assay system or CellTiter-glo was used at each indicated time point to assess target cell viability, n=3-6.

Example 8: In Vivo Activity

Figure 7A:
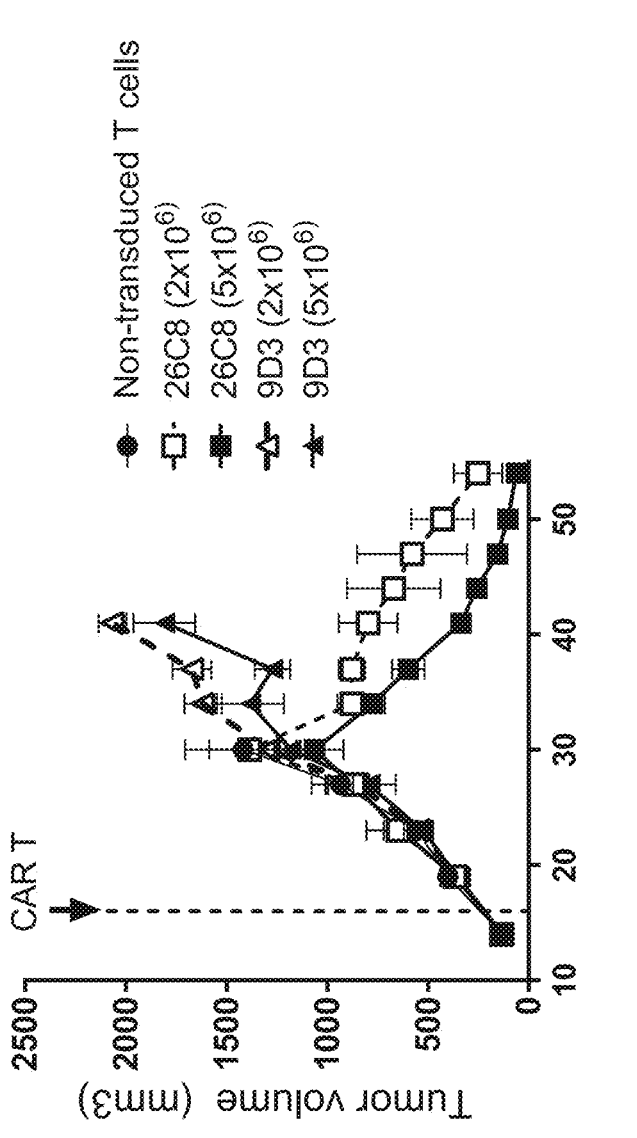
FIGS. 7A-7B are plots demonstrating that anti-DLL3 CAR-T cells eliminated established SHP-77 small cell lung cancer subcutaneous tumors in mice in a dose dependent manner.
Figure 7B:
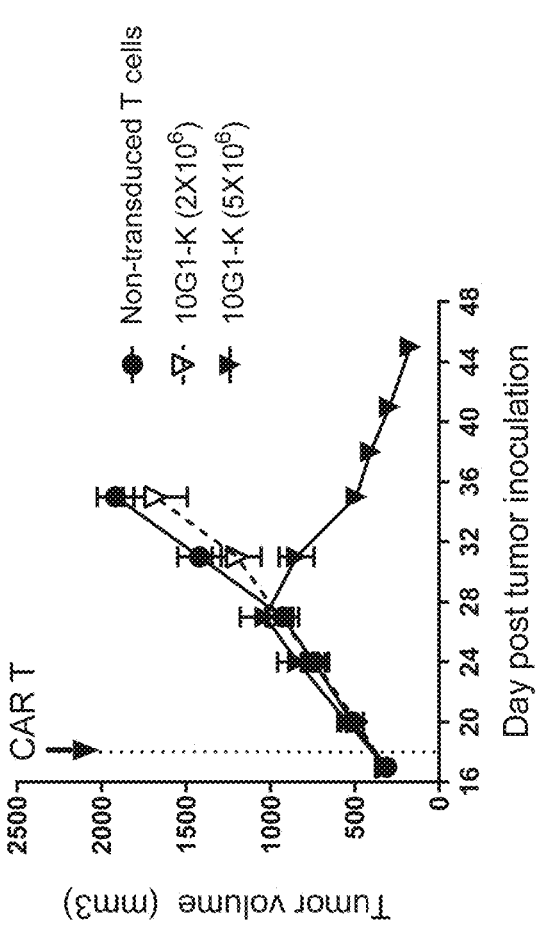

To test the anti-tumor activity of DLL3 CAR-T cells, SHP-77 tumor bearing NSG mice were used. SHP-77 cells were obtained from a frozen stock vial, thawed and counted according to standard procedure. Cells were diluted to $50\times10^6$ viable cells/mL in complete growth medium (RPMI+10% FBS). Cell suspension was kept on ice until implantation. Immediately before implanting, cells were mixed 1:1 with BD Matrigel Matrix (cat #354234) and 200 μL of cells/matrigel suspension containing $5\times10^6$ SHP-77 cells was injected per mouse subcutaneously. Tumor growth was monitored by caliper measurements using a digital caliper starting from Day 5 post-implantation. Tumor size was calculated using the formula Tumor volume=(width^2× length/2). Mice were randomized into groups of 5 based on tumor volume about two weeks post-implantation. Average tumor volume per group was 314 mm$^3$ or less. One day after mice were randomized, Non-transduced T cells and DLL3 CAR-T cells were thawed and counted according to standard procedure. Cells were resuspended in RPMI+10% FBS and injected at doses 2 or 5 million CAR+ cells/mouse by tail vein IV injection in a volume of 200 uL/mouse. Tumors continued to be monitored every 3-4 days until the end of the study. 26C8 and 10G1-K DLL3 CAR-T cells induced tumor inhibition in a dose dependent manner (FIG. 7A-7B) FIG. 7A-7B shows experimental data showing anti-DLL3 CAR-T cells can eliminate established small cell lung cancer tumors in mice in a dose dependent manner.

Figure 8:
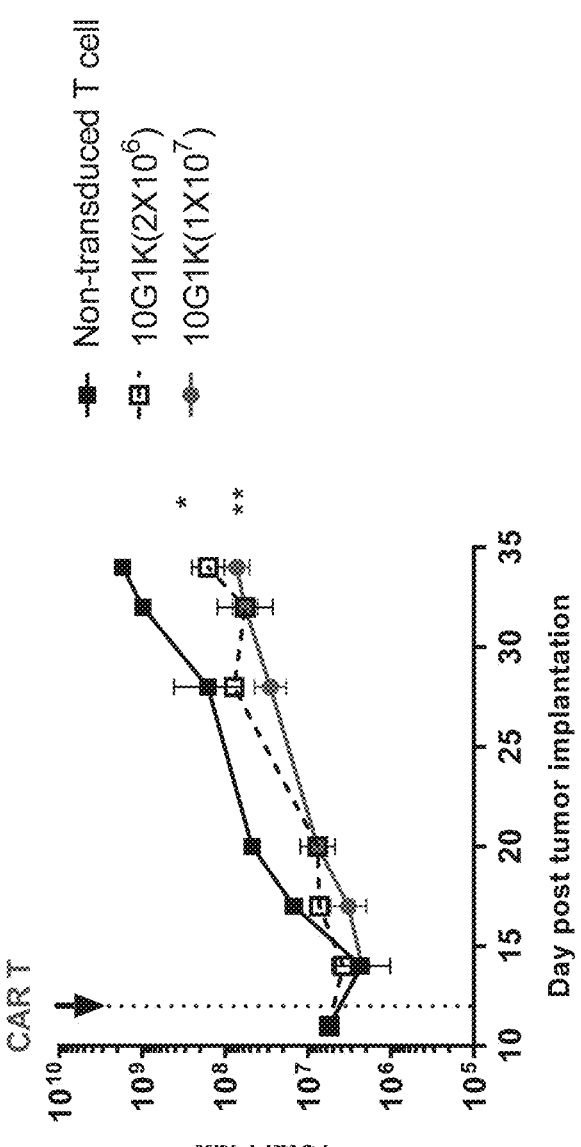
FIG. 8 is a plot demonstrating that 10G1-K anti-DLL3 CAR-T cells inhibited the growth of established IV injected SHP-77 small cell lung cancer tumors in a dose dependent manner. Statistical analysis was done using ANOVA with repeated measures (Dunnett's multiple comparisons), day 14-day 28, n=4-5. *, p<0.05. **, p<0.01.

To test anti-tumor activity of DLL3 CAR-T cells in models that show metastasis similar to human disease, SHP-77 tumors were established with tail vein injection. Tumors were observed in lung, liver, brain, kidney and spleen. Specifically, SHP-77 cells were thawed and diluted to $40\times10^6$ viable cells/mL in complete growth medium (RPMI+10% FBS). Cell suspension was kept on ice until implantation and 200 uL of cell suspension was injected per mouse by tail vein IV. On day 7 post-implantation, 200 uL Luciferin (15 mg/mL) was injected and tumor growth was monitored by IVIS imaging. Mice were randomized into groups of 5 based on Total Flux on Day 11 post-implantation. On Day 12 post-implantation, CAR-Ts were thawed and counted according to standard procedure. Cells were resuspended in RPMI+10% FBS and injected at 2 or 7 million CAR+ cells per mouse by tail vein IV injection in a volume of 200 uL per mouse. Tumors continued to be monitored every 3-4 days until the end of the study. As shown in FIG. 8, 10G1-K anti-DLL3 CAR-T cells can inhibit established small cell lung cancer tumors in mice in a dose dependent manner.

Example 9: Anti-DLL3 CAR Constructs with a Safety Switch

This example describes the construction, expression and cytotoxic activity of anti-DLL3 CAR with safety switch. The anti-DLL3 CARs in Table 6 were reformatted to include different safety switches structures listed below (Table 8B).

TABLE 8B

| Structure of safety switches | |
| --- | --- |
| Format | Structure |
| QR3 | CD8α signal sequence-linker-CD20 mimotope-linker-anti-DLL3 ScFv-linker-CD20 mimotope-linker-QBEND-10 epitope-linker-CD20 mimotope-hinge and transmembrane regions of human CD8 α molecule-41BB signaling domain-CD3ζ signaling domain |
| SR2 | CD8α signal sequence-anti-DLL3 ScFv-linker-CD20 mimotope-linker-CD20 mimotope-linker-hinge and transmembrane regions of human CD8 α molecule-41BB signaling domain-CD3ζ signaling domain |
| RSR | CD8α signal sequence-linker-CD20 mimotope-linker-anti-DLL3 ScFv-linker-CD20 mimotope-linker-hinge and transmembrane regions of human CD8 α molecule-41BB signaling domain-CD3ζ signaling domain |
| R2S | CD8α signal sequence-linker-CD20 mimotope-linker-CD20 mimotope-linker-anti-DLL3 ScFv-linker-hinge and |

TABLE 8B-continued

| Structure of safety switches | |
| --- | --- |
| Format | Structure |
| | transmembrane regions of human CD8 α molecule-41BB signaling domain-CD3ζ signaling domain |

Protein sequences encoding anti-DLL3 CAR constructs including a safety switch are shown in Table 9. Exemplary safety switch constructs may comprise the CD8α signal sequence (SEQ ID NO: 477), an anti-DLL3 scFv described herein, CD20 mimotope (SEQ ID NO: 536), QBEND-10 epitope (SEQ ID NO: 544), hinge and transmembrane regions of the human CD8α molecule (SEQ ID NO: 479), the cytoplasmic portion of the 4-1BB molecule (SEQ ID NO: 291) and the cytoplasmic portion of the CD3ζ molecule (SEQ ID NO: 292).

TABLE 9

CAR and safety switch amino acid sequences

| SEQ ID NO | Name/Component | Sequence |
| --- | --- | --- |
| 622 | 2G1-QR3 CD8α signal sequence, CD20 mimotope, 2G1 ScFv, CD20 mimotope, QBEND-10 epitope, CD20 mimotope, hinge and transmembrane regions of human CD8 α molecule, 41BB signaling domain, CD3ζ signaling domain | MALPVTALLLPLALLLHAARPGGGGSCPYSNPSLCSGGGGSG GGGSQLQLQESGPGLVKPSETLSLTCTVSGGSISSSSYYWGWI RQPPGKGLEWIGSIYYSGNIYHNPSLKSRVSISVDTSKNQFSLR LSSVTAADTAVYYCAREIIVGATHFDYWGQGTLVTVSSGGGG SGGGGSGGGGSGGGGSAIQMTQSPSSLSASVGDRVTITCRASQ GIRNDLGWYQQKPGKAPELLIYAASSLQSGVPSRFSGSGSGTD FTLTISSLQPEDFATYYCLQDYNYPLTFGPGTKVDIKGSGGGGS CPYSNPSLCSGGGGSELPTQGTFSNVSTNVSPAKPTTTACPYSN PSLCTTTPAPRPPTPAPTIASQPLSLRPEACRPAAGGAVHTRGL DFACDIYIWAPLAGTCGVLLLSLVITKRGRKKLLYIFKQPFMRP VQTTQEEDGCSCRFPEEEEGGCELRVKFSRSADAPAYQQGQN QLYNELNLGRREEYDVLDKRRGRDPEMGGKPRRKNPQEGLY NELQKDKMAEAYSEIGMKGERRRGKGHDGLYQGLSTATKDT YDALHMQALPPR |
| 623 | 2G1-SR2 CD8α signal sequence, 2G1 ScFv, CD20 mimotope, CD20 mimotope, hinge and transmembrane regions of human CD8 α molecule, 41BB signaling domain, CD3ζ signaling domain | MALPVTALLLPLALLLHAARPQLQLQESGPGLVKPSETLSLTC TVSGGSISSSSYYWGWIRQPPGKGLEWIGSIYYSGNIYHNPSLK SRVSISVDTSKNQFSLRLSSVTAADTAVYYCAREIIVGATHFDY WGQGTLVTVSSGGGGSGGGGSGGGGSGGGGSAIQMTQSPSSL SASVGDRVTITCRASQGIRNDLGWYQQKPGKAPELLIYAASSL QSGVPSRFSGSGSGTDFTLTISSLQPEDFATYYCLQDYNYPLTF GPGTKVDIKGSGGGGSCPYSNPSLCSGGGGSCPYSNPSLCSGG GGSTTTACPYSNPSLCTTTPAPRPPTPAPTIASQPLSLRPEACRP AAGGAVHTRGLDFACDIYIWAPLAGTCGVLLLSLVITKRGRK KLLYIFKQPFMRPVQTTQEEDGCSCRFPEEEEGGCELRVKFSRS ADAPAYQQGQNQLYNELNLGRREEYDVLDKRRGRDPEMGG KPRRKNPQEGLYNELQKDKMAEAYSEIGMKGERRRGKGHDG LYQGLSTATKDTYDALHMQALPPR |
| 624 | 2G1-RSR CD8α signal sequence, CD20 mimotope, 2G1 ScFv, CD20 mimotope, hinge and transmembrane regions of human CD8 α molecule, 41BB signaling domain, CD3ζ signaling domain | MALPVTALLLPLALLLHAARPGGGGSCPYSNPSLCGGGGSQL QLQESGPGLVKPSETLSLTCTVSGGSISSSSYYWGWIRQPPGKG LEWIGSIYYSGNIYHNPSLKSRVSISVDTSKNQFSLRLSSVTAA DTAVYYCAREIIVGATHFDYWGQGTLVTVSSGGGGSGGGGSG GGGSGGGGSAIQMTQSPSSLSASVGDRVTITCRASQGIRNDLG WYQQKPGKAPELLIYAASSLQSGVPSRFSGSGSGTDFTLTISSL QPEDFATYYCLQDYNYPLTFGPGTKVDIKGGGGSCPYSNPSLC GGGGSTTTPAPRPPTPAPTIASQPLSLRPEACRPAAGGAVHTRG LDFACDIYIWAPLAGTCGVLLLSLVITKRGRKKLLYIFKQPFM RPVQTTQEEDGCSCRFPEEEEGGCELRVKFSRSADAPAYQQG QNQLYNELNLGRREEYDVLDKRRGRDPEMGGKPRRKNPQEG LYNELQKDKMAEAYSEIGMKGERRRGKGHDGLYQGLSTATK DTYDALHMQALPPR |
| 625 | 2G1-R2S CD8α signal sequence, CD20 mimotope, CD20 mimotope, 2G1 ScFv, hinge and transmembrane | MALPVTALLLPLALLLHAARPGGGGSCPYSNPSLCGGGGSCP YSNPSLCGGGGSQLQLQESGPGLVKPSETLSLTCTVSGGSISSS SYYWGWIRQPPGKGLEWIGSIYYSGNIYHNPSLKSRVSISVDTS KNQFSLRLSSVTAADTAVYYCAREIIVGATHFDYWGQGTLVT VSSGGGGSGGGGSGGGGSGGGGSAIQMTQSPSSLSASVGDRV TITCRASQGIRNDLGWYQQKPGKAPELLIYAASSLQSGVPSRFS GSGSGTDFTLTISSLQPEDFATYYCLQDYNYPLTFGPGTKVDIK |

TABLE 9-continued

| | CAR and safety switch amino acid sequences | |
|---|---|---|

| SEQ ID NO | Name/Component | Sequence |
|---|---|---|
| | regions of human CD8 α molecule, 41BB signaling domain, CD3ζ signaling domain | TTTPAPRPPTPAPTIASQPLSLRPEACRPAAGGAVHTRGLDFAC DIYIWAPLAGTCGVLLLSLVITKRGRKKLLYIFKQPFMRPVQTT QEEDGCSCRFPEEEEGGCELRVKFSRSADAPAYQQGQNQLYN ELNLGRREEYDVLDKRRGRDPEMGGKPRRKNPQEGLYNELQ KDKMAEAYSEIGMKGERRRGKGHDGLYQGLSTATKDTYDAL HMQALPPR |
| 626 | 4H8-SR2 CD8α signal sequence, 4H8 ScFv, CD20 mimotope, CD20 mimotope, hinge and transmembrane regions of human CD8 α molecule, 41BB signaling domain, CD3ζ signaling domain | MALPVTALLLPLALLLHAARPQVQLQQSGPGLVKPSQTLSLTC AISGDSVSSNSATWNWIRQSPSRGLEWLGRTYYRSKWYDDYA VSVKSRITINPDTSKNHLSLHLNSVTPEDTAVYYCAGGGLVGA PDGFDVWGQGTMVTVSSGGGGSGGGGSGGGGSGGGGSQSVL TQPPSASGTPGQRVTISCSGSSSNIGSDPVNWYQQLPGTAPKLL IYSNNQRPSGVPDRFSGSKSGTSASLAISGLQSEDEADYYCSA WDDSLNGYVFGTGTKVTVLGSGGGGSCPYSNPSLCSGGGGSC PYSNPSLCSGGGGSTTTACPYSNPSLCTTTPAPRPPTPAPTIASQ PLSLRPEACRPAAGGAVHTRGLDFACDIYIWAPLAGTCGVLLL SLVITKRGRKKLLYIFKQPFMRPVQTTQEEDGCSCRFPEEEEGG CELRVKFSRSADAPAYQQGQNQLYNELNLGRREEYDVLDKR RGRDPEMGGKPRRKNPQEGLYNELQKDKMAEAYSEIGMKGE RRRGKGHDGLYQGLSTATKDTYDALHMQALPPR |
| 627 | 4H8-RSR CD8α signal sequence, CD20 mimotope, 4H8 ScFv, CD20 mimotope, hinge and transmembrane regions of human CD8 α molecule, 41BB signaling domain, CD3ζ signaling domain | MALPVTALLLPLALLLHAARPGGGGSCPYSNPSLCGGGGSQV QLQQSGPGLVKPSQTLSLTCAISGDSVSSNSATWNWIRQSPSR GLEWLGRTYYRSKWYDDYAVSVKSRITINPDTSKNHLSLHLN SVTPEDTAVYYCAGGGLVGAPDGFDVWGQGTMVTVSSGGG GSGGGGSGGGGSGGGGSQSVLTQPPSASGTPGQRVTISCSGSS SNIGSDPVNWYQQLPGTAPKLLIYSNNQRPSGVPDRFSGSKSG TSASLAISGLQSEDEADYYCSAWDDSLNGYVFGTGTKVTVLG GGGSCPYSNPSLCGGGGSTTTPAPRPPTPAPTIASQPLSLRPEAC RPAAGGAVHTRGLDFACDIYIWAPLAGTCGVLLLSLVITKRGR KKLLYIFKQPFMRPVQTTQEEDGCSCRFPEEEEGGCELRVKFS RSADAPAYQQGQNQLYNELNLGRREEYDVLDKRRGRDPEMG GKPRRKNPQEGLYNELQKDKMAEAYSEIGMKGERRRGKGHD GLYQGLSTATKDTYDALHMQALPPR |
| 628 | 4H8-R2S CD8α signal sequence, CD20 mimotope, CD20 mimotope, 4H8 ScFv, hinge and transmembrane regions of human CD8 α molecule, 41BB signaling domain, CD3ζ signaling domain | MALPVTALLLPLALLLHAARPGGGGSCPYSNPSLCGGGGSCP YSNPSLCGGGGSQVQLQQSGPGLVKPSQTLSLTCAISGDSVSS NSATWNWIRQSPSRGLEWLGRTYYRSKWYDDYAVSVKSRITI NPDTSKNHLSLHLNSVTPEDTAVYYCAGGGLVGAPDGFDVW GQGTMVTVSSGGGGSGGGGSGGGGSGGGGSQSVLTQPPSAS GTPGQRVTISCSGSSSNIGSDPVNWYQQLPGTAPKLLIYSNNQR PSGVPDRFSGSKSGTSASLAISGLQSEDEADYYCSAWDDSLNG YVFGTGTKVTVLTTTPAPRPPTPAPTIASQPLSLRPEACRPAAG GAVHTRGLDFACDIYIWAPLAGTCGVLLLSLVITKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQG LSTATKDTYDALHMQALPPR |
| 474 | 10G1K-QR3 CD8α signal sequence, CD20 mimotope, 10G1-K ScFv, CD20 mimotope, QBEND-10 epitope, CD20 mimotope, hinge and transmembrane regions of human CD8 α molecule, 41BB signaling domain, CD3ζ signaling domain | MALPVTALLLPLALLLHAARPGGGGSCPYSNPSLCSGGGGSG GGGSEVQLLESGGGLVQPGGSLRLSCAASGFTFSSYAMNWVR QAPGKGLEWVSTISGSGGSTYYADSVKGRFTISRDNSKNTLYL QMNSLRAEDTAVFYCAIDPEYYDILTGGDYWGQGTLVTVSSG GGGSGGGGSGGGGSGGGGSDIQMTQSPSAMSASVGDRVTIT CRASQGISNYLAWFQQKPGKVPKRLIYAASSLQSGVPSRFSGS GSGTEFTLTISSLQPEDFATYFCLQHDSFPLTFGGGTKVEIKGS GGGGSCPYSNPSLCSGGGGSELPTQGTFSNVSTNVSPAKPTTT ACPYSNPSLCTTTPAPRPPTPAPTIASQPLSLRPEACRPAAGGA VHTRGLDFACDIYIWAPLAGTCGVLLLSLVITKRGRKKLLYIF KQPFMRPVQTTQEEDGCSCRFPEEEEGGCELRVKFSRSADAPA YQQGQNQLYNELNLGRREEYDVLDKRRGRDPEMGGKPRRKN PQEGLYNELQKDKMAEAYSEIGMKGERRRGKGHDGLYQGLS TATKDTYDALHMQALPPR |
| 475 | 10G1-K-SR2 CD8α signal sequence, 10G1-K ScFv, CD20 mimotope, CD20 mimotope, hinge and transmembrane regions of human CD8 α molecule, 41BB signaling | MALPVTALLLPLALLLHAARPEVQLLESGGGLVQPGGSLRLSC AASGFTFSSYAMNWVRQAPGKGLEWVSTISGSGGSTYYADSV KGRFTISRDNSKNTLYLQMNSLRAEDTAVFYCAIDPEYYDILT GGDYWGQGTLVTVSSGGGGSGGGGSGGGGSGGGGSDIQMT QSPSAMSASVGDRVTITCRASQGISNYLAWFQQKPGKVPKRLI YAASSLQSGVPSRFSGSGSGTEFTLTISSLQPEDFATYFCLQHD SFPLTFGGGTKVEIKGSGGGGSCPYSNPSLCSGGGGSCPYSNPS LCSGGGGSTTTACPYSNPSLCTTTPAPRPPTPAPTIASQPLSLRP EACRPAAGGAVHTRGLDFACDIYIWAPLAGTCGVLLLSLVITK RGRKKLLYIFKQPFMRPVQTTQEEDGCSCRFPEEEEGGCELRV |

TABLE 9-continued

CAR and safety switch amino acid sequences

| SEQ ID NO | Name/Component | Sequence |
|---|---|---|
| | domain, CD3ζ signaling domain | KFSRSADAPAYQQGQNQLYNELNLGRREEYDVLDKRRGRDP EMGGKPRRKNPQEGLYNELQKDKMAEAYSEIGMKGERRRGK GHDGLYQGLSTATKDTYDALHMQALPPR |
| 476 | 10G1-K RSR CD8α signal sequence, CD20 mimotope, 10G1-K ScFv, CD20 mimotope, hinge and transmembrane regions of human CD8 α molecule, 41BB signaling domain, CD3ζ signaling domain | MALPVTALLLPLALLLHAARPGGGGSCPYSNPSLCGGGGSEV QLLESGGGLVQPGGSLRLSCAASGFTFSSYAMNWVRQAPGKG LEWVSTISGSGGSTYYADSVKGRFTISRDNSKNTLYLQMNSLR AEDTAVFYCAIDPEYYDILTGGDYWGQGTLVTVSSGGGGSGG GGSGGGGSGGGGSDIQMTQSPSAMSASVGDRVTITCRASQG ISNYLAWFQQKPGKVPKRLIYAASSLQSGVPSRFSGSGSGTEFT LTISSLQPEDFATYFCLQHDSFPLTFGGGTKVEIKGGGGSCPYS NPSLCGGGGSTTTPAPRPPTPAPTIASQPLSLRPEACRPAAGGA VHTRGLDFACDIYIWAPLAGTCGVLLLSLVITKRGRKKLLYIF KQPFMRPVQTTQEEDGCSCRFPEEEEGGCELRVKFSRSADAPA YQQGQNQLYNELNLGRREEYDVLDKRRGRDPEMGGKPRRKN PQEGLYNELQKDKMAEAYSEIGMKGERRRGKGHDGLYQGLS TATKDTYDALHMQALPPR |
| 565 | 10G1-K-R2S CD8α signal sequence, CD20 mimotope, CD20 mimotope, 10G1-K ScFv, hinge and transmembrane regions of human CD8 α molecule, 41BB signaling domain, CD3ζ signaling domain | MALPVTALLLPLALLLHAARPGGGGSCPYSNPSLCGGGGSCP YSNPSLCGGGGSEVQLLESGGGLVQPGGSLRLSCAASGFTFSS YAMNWVRQAPGKGLEWVSTISGSGGSTYYADSVKGRFTISRD NSKNTLYLQMNSLRAEDTAVFYCAIDPEYYDILTGGDYWGQG TLVTVSSGGGGSGGGGSGGGGSGGGGSDIQMTQSPSAMSAS VGDRVTITCRASQGISNYLAWFQQKPGKVPKRLIYAASSLQSG VPSRFSGSGSGTEFTLTISSLQPEDFATYFCLQHDSFPLTFGGGT KVEIKTTTPAPRPPTPAPTIASQPLSLRPEACRPAAGGAVHTRG LDFACDIYIWAPLAGTCGVLLLSLVITKRGRKKLLYIFKQPFM RPVQTTQEEDGCSCRFPEEEEGGCELRVKFSRSADAPAYQQG QNQLYNELNLGRREEYDVLDKRRGRDPEMGGKPRRKNPQEG LYNELQKDKMAEAYSEIGMKGERRRGKGHDGLYQGLSTATK DTYDALHMQALPPR |
| 684 | 2G1-QR3 CD8α signal sequence, CD20 mimotope, 2G1 ScFv, CD20 mimotope, QBEND-10 epitope, CD20 mimotope, hinge and transmembrane regions of human CD8 α molecule, 41BB signaling domain, CD3ζ signaling domain | MALPVTALLLPLALLLHAARPGGGGSCPYSNPSLCSGGGGSG GGGSQLQLQESGPGLVKPSETLSLTCTVSGGSISSSSYYWGWI RQPPGKGLEWIGSIYYSGNIYHNPSLKSRVSISVDTSKNQFSLR LSSVTAADTAVYYCAREIIVGATHFDYWGQGTLVTVSSGGGG SGGGGSGGGGSGGGGSAIQMTQSPSSLSASVGDRVTITCRASQ GIRNDLGWYQQKPGKAPELLIYAASSLQSGVPSRFSGSGSGTD FTLTISSLQPEDFATYYCLQDYNYPLTFGPGTKVDIKGSGGGGS CPYSNPSLCSGGGGSELPTQGTFSNVSTNVSPAKPTTTACPYSN PSLCTTTPAPRPPTPAPTIASQPLSLRPEACRPAAGGAVHTRGL DFACDIYIWAPLAGTCGVLLLSLVITLYCKRGRKKLLYIFKQPF MRPVQTTQEEDGCSCRFPEEEEGGCELRVKFSRSADAPAYQQ GQNQLYNELNLGRREEYDVLDKRRGRDPEMGGKPRRKNPQE GLYNELQKDKMAEAYSEIGMKGERRRGKGHDGLYQGLSTAT KDTYDALHMQALPPR |
| 685 | 2G1-SR2 CD8α signal sequence, 2G1 ScFv, CD20 mimotope, CD20 mimotope, hinge and transmembrane regions of human CD8 α molecule, 41BB signaling domain, CD3ζ signaling domain | MALPVTALLLPLALLLHAARPQLQLQESGPGLVKPSETLSLTC TVSGGSISSSSYYWGWIRQPPGKGLEWIGSIYYSGNIYHNPSLK SRVSISVDTSKNQFSLRLSSVTAADTAVYYCAREIIVGATHFDY WGQGTLVTVSSGGGGSGGGGSGGGGSGGGGSAIQMTQSPSSL SASVGDRVTITCRASQGIRNDLGWYQQKPGKAPELLIYAASSL QSGVPSRFSGSGSGTDFTLTISSLQPEDFATYYCLQDYNYPLTF GPGTKVDIKGSGGGGSCPYSNPSLCSGGGGSCPYSNPSLCSGG GGSTTTACPYSNPSLCTTTPAPRPPTPAPTIASQPLSLRPEACRP AAGGAVHTRGLDFACDIYIWAPLAGTCGVLLLSLVITLYCKR GRKKLLYIFKQPFMRPVQTTQEEDGCSCRFPEEEEGGCELRVK FSRSADAPAYQQGQNQLYNELNLGRREEYDVLDKRRGRDPE MGGKPRRKNPQEGLYNELQKDKMAEAYSEIGMKGERRRGKG HDGLYQGLSTATKDTYDALHMQALPPR |
| 686 | 2G1-RSR CD8α signal sequence, CD20 mimotope, 2G1 ScFv, CD20 mimotope, hinge and transmembrane regions of human CD8 α molecule, 41BB signaling domain, CD3ζ signaling domain | MALPVTALLLPLALLLHAARPGGGGSCPYSNPSLCGGGGSQL QLQESGPGLVKPSETLSLTCTVSGGSISSSSYYWGWIRQPPGKG LEWIGSIYYSGNIYHNPSLKSRVSISVDTSKNQFSLRLSSVTAA DTAVYYCAREIIVGATHFDYWGQGTLVTVSSGGGGSGGGGSA GGGSGGGGSAIQMTQSPSSLSASVGDRVTITCRASQGIRNDLG WYQQKPGKAPELLIYAASSLQSGVPSRFSGSGSGTDFTLTISSL QPEDFATYYCLQDYNYPLTFGPGTKVDIKGGGGSCPYSNPSLC GGGGSTTTPAPRPPTPAPTIASQPLSLRPEACRPAAGGAVHTRG LDFACDIYIWAPLAGTCGVLLLSLVITLYCKRGRKKLLYIFKQP FMRPVQTTQEEDGCSCRFPEEEEGGCELRVKFSRSADAPAYQ QGQNQLYNELNLGRREEYDVLDKRRGRDPEMGGKPRRKNPQ EGLYNELQKDKMAEAYSEIGMKGERRRGKGHDGLYQGLSTA TKDTYDALHMQALPPR |

TABLE 9-continued

CAR and safety switch amino acid sequences

| SEQ ID NO | Name/Component | Sequence |
|---|---|---|
| 687 | 2G1-R2S CD8α signal sequence, CD20 mimotope, CD20 mimotope, 2G1 ScFv, hinge and transmembrane regions of human CD 8α molecule, 41BB signaling domain, CD3ζ signaling domain | MALPVTALLLPLALLLHAARPGGGGSCPYSNPSLCGGGGSCP YSNPSLCGGGGSQLQLQESGPGLVKPSETLSLTCTVSGGSISSS SYYWGWIRQPPGKGLEWIGSIYYSGNIYHNPSLKSRVSISVDTS KNQFSLRLSSVTAADTAVYYCAREIIVGATHFDYWGQGTLVT VSSGGGGSGGGGSGGGGSGGGGSAIQMTQSPSSLSASVGDRV TITCRASQGIRNDLGWYQQKPGKAPELLIYAASSLQSGVPSRFS GSGSGTDFTLTISSLQPEDFATYYCLQDYNYPLTFGPGTKVDIK TTTPAPRPPTPAPTIASQPLSLRPEACRPAAGGAVHTRGLDFAC DIYIWAPLAGTCGVLLLSLVITLYCKRGRKKLLYIFKQPFMRP VQTTQEEDGCSCRFPEEEEGGCELRVKFSRSADAPAYQQGQN QLYNELNLGRREEYDVLDKRRGRDPEMGGKPRRKNPQEGLY NELQKDKMAEAYSEIGMKGERRRGKGHDGLYQGLSTATKDT YDALHMQALPPR |
| 688 | 4H8-SR2 CD8α signal sequence, 4H8 ScFv, CD20 mimotope, hinge and transmembrane regions of human CD8 α molecule, 41BB signaling domain, CD3ζ signaling domain | MALPVTALLLPLALLLHAARPQVQLQQSGPGLVKPSQTLSLTC AISGDSVSSNSATWNWIRQSPSRGLEWLGRTYYRSKWYDDYA VSVKSRITINPDTSKNHLSLHLNSVTPEDTAVYYCAGGGLVGA PDGFDVWGQGTMVTVSSGGGGSGGGGSGGGGSGGGGSQSVL TQPPSASGTPGQRVTISCSGSSSNIGSDPVNWYQQLPGTAPKLL IYSNNQRPSGVPDRFSGSKSGTSASLAISGLQSEDEADYYCSA WDDSLNGYVFGTGTKVTVLGSGGGGSCPYSNPSLCSGGGGSC PYSNPSLCSGGGGSTTTACPYSNPSLCTTTPAPRPPTPAPTIASQ PLSLRPEACRPAAGGAVHTRGLDFACDIYIWAPLAGTCGVLLL SLVITLYCKRGRKKLLYIFKQPFMRPVQTTQEEDGCSCRFPEEE EGGCELRVKFSRSADAPAYQQGQNQLYNELNLGRREEYDVL DKRRGRDPEMGGKPRRKNPQEGLYNELQKDKMAEAYSEIGM KGERRRGKGHDGLYQGLSTATKDTYDALHMQALPPR |
| 689 | 4H8-RSR CD8α signal sequence, CD20 mimotope, 4H8 ScFv, CD20 mimotope, hinge and transmembrane regions of human CD8 α molecule, 41BB signaling domain, CD3ζ signaling domain | MALPVTALLLPLALLLHAARPGGGGSCPYSNPSLCGGGGSQV QLQQSGPGLVKPSQTLSLTCAISGDSVSSNSATWNWIRQSPSR GLEWLGRTYYRSKWYDDYAVSVKSRITINPDTSKNHLSLHLN SVTPEDTAVYYCAGGGLVGAPDGFDVWGQGTMVTVSSGGGG GSGGGGSGGGGSGGGGSQSVLTQPPSASGTPGQRVTISCSGSS SNIGSDPVNWYQQLPGTAPKLLIYSNNQRPSGVPDRFSGSKSG TSASLAISGLQSEDEADYYCSAWDDSLNGYVFGTGTKVTVLG GGGSCPYSNPSLCGGGGSTTTPAPRPPTPAPTIASQPLSLRPEAC RPAAGGAVHTRGLDFACDIYIWAPLAGTCGVLLLSLVITLYCK RGRKKLLYIFKQPFMRPVQTTQEEDGCSCRFPEEEEGGCELRV KFSRSADAPAYQQGQNQLYNELNLGRREEYDVLDKRRGRDP EMGGKPRRKNPQEGLYNELQKDKMAEAYSEIGMKGERRRGK GHDGLYQGLSTATKDTYDALHMQALPPR |
| 690 | 4H8-R2S CD8α signal sequence, CD20 mimotope, CD20 mimotope, 4H8 ScFv, hinge and transmembrane regions of human CD8 α molecule, 41BB signaling domain, CD3ζ signaling domain | MALPVTALLLPLALLLHAARPGGGGSCPYSNPSLCGGGGSCP YSNPSLCGGGGSQVQLQQSGPGLVKPSQTLSLTCAISGDSVSS NSATWNWIRQSPSRGLEWLGRTYYRSKWYDDYAVSVKSRITI NPDTSKNHLSLHLNSVTPEDTAVYYCAGGGLVGAPDGFDVW GQGTMVTVSSGGGGSGGGGSGGGGSGGGGSQSVLTQPPSAS GTPGQRVTISCSGSSSNIGSDPVNWYQQLPGTAPKLLIYSNNQR PSGVPDRFSGSKSGTSASLAISGLQSEDEADYYCSAWDDSLNG YVFGTGTKVTVLTTTPAPRPPTPAPTIASQPLSLRPEACRPAAG GAVHTRGLDFACDIYIWAPLAGTCGVLLLSLVITLYCKRGRKK LLYIFKQPFMRPVQTTQEEDGCSCRFPEEEEGGCELRVKFSRSA DAPAYQQGQNQLYNELNLGRREEYDVLDKRRGRDPEMGGK RRKNPQEGLYNELQKDKMAEAYSEIGMKGERRRGKGHDGLY QGLSTATKDTYDALHMQALPPR |
| 691 | 10G1K-QR3 CD8α signal sequence,CD20 mimotope, 10G1-K ScFv, CD20 mimotope, QBEND-10 epitope, CD20 mimotope, hinge and transmembrane regions of human CD8 α molecule, 41BB signaling domain, CD3ζ signaling domain | MALPVTALLLPLALLLHAARPGGGGSCPYSNPSLCSGGGGSG GGGSEVQLLESGGGLVQPGGSLRLSCAASGFTFSSYAMNWVR QAPGKGLEWVSTISGSGGSTYYADSVKGRFTISRDNSKNTLYL QMNSLRAEDTAVFYCAIDPEYYDILTGGDYWGQGTLVTVSSG GGGSGGGGSGGGGSGGGGSDIQMTQSPSAMSASVGDRVTITC RASQGISNYLAWFQQKPGKVPKRLIYAASSLQSGVPSRFSGSG SGTEFTLTISSLQPEDFATYFCLQHDSFPLTFGGGTKVEIKGSG GGGSCPYSNPSLCSGGGGSELPTQGTFSNVSTNVSPAKPTTTA CPYSNPSLCTTTPAPRPPTPAPTIASQPLSLRPEACRPAAGGAV HTRGLDFACDIYIWAPLAGTCGVLLLSLVITLYCKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQG LSTATKDTYDALHMQALPPR |
| 692 | 10G1-K-SR2 CD8α signal | MALPVTALLLPLALLLHAARPEVQLLESGGGLVQPGGSLRLSC AASGFTFSSYAMNWVRQAPGKGLEWVSTISGSGGSTYYADSV |

TABLE 9-continued

CAR and safety switch amino acid sequences

| SEQ ID NO | Name/Component | Sequence |
|---|---|---|
| | sequence, 10G1-K ScFv, CD20 mimotope, CD20 mimotope, hinge and transmembrane regions of human CD8 α molecule, 41BB signaling domain, CD3ζ signaling domain | KGRFTISRDNSKNTLYLQMNSLRAEDTAVFYCAIDPEYYDILT GGDYWGQGTLVTVSSGGGGSGGGGSGGGGSGGGGSDIQMTQ SPSAMSASVGDRVTITCRASQGISNYLAWFQQKPGKVPKRLIY AASSLQSGVPSRFSGSGSGTEFTLTISSLQPEDFATYFCLQHDSF PLTFGGGTKVEIKGSGGGGSCPYSNPSLCSGGGGSCPYSNPSLC SGGGGSTTTACPYSNPSLCTTTPAPRPPTPAPTIASQPLSLRPEA CRPAAGGAVHTRGLDFACDIYIWAPLAGTCGVLLLSLVITLYC KRGRKKLLYIFKQPFMRPVQTTQEEDGCSCRFPEEEEGGCELR VKFSRSADAPAYQQGQNQLYNELNLGRREEYDVLDKRRGRD PEMGGKPRRKNPQEGLYNELQKDKMAEAYSEIGMKGERRRG KGHDGLYQGLSTATKDTYDALHMQALPPR |
| 693 | 10G1-K RSR CD8α signal sequence, CD20 mimotope, 10G1-K ScFv, CD20 mimotope, hinge and transmembrane regions of human CD8 α molecule, 41BB signaling domain, CD3ζ signaling domain | MALPVTALLLPLALLLHAARPGGGGSCPYSNPSLCGGGGSEV QLLESGGGLVQPGGSLRLSCAASGFTFSSYAMNWVRQAPGKG LEWVSTISGSGGSTYYADSVKGRFTISRDNSKNTLYLQMNSLR AEDTAVFYCAIDPEYYDILTGGDYWGQGTLVTVSSGGGGSGG GGSGGGGSGGGGSDIQMTQSPSAMSASVGDRVTITCRASQGIS NYLAWFQQKPGKVPKRLIYAASSLQSGVPSRFSGSGSGTEFTL TISSLQPEDFATYFCLQHDSFPLTFGGGTKVEIKGGGGSCPYSN PSLCGGGGSTTTPAPRPPTPAPTIASQPLSLRPEACRPAAGGAV HTRGLDFACDIYIWAPLAGTCGVLLLSLVITLYCKRGRKKLLY IFKQPFMRPVQTTQEEDGCSCRFPEEEEGGCELRVKFSRSADA PAYQQGQNQLYNELNLGRREEYDVLDKRRGRDPEMGGKPRR KNPQEGLYNELQKDKMAEAYSEIGMKGERRRGKGHDGLYQG LSTATKDTYDALHMQALPPR |
| 694 | 10G1-K-R2S CD8α signal sequence, CD20 mimotope, CD20 mimotope, 10G1-K ScFv, hinge and transmembrane regions of human CD8 α molecule, 41BB signaling domain, CD3ζ signaling domain | MALPVTALLLPLALLLHAARPGGGGSCPYSNPSLCGGGGSCP YSNPSLCGGGGSEVQLLESGGGLVQPGGSLRLSCAASGFTFSS YAMNWVRQAPGKGLEWVSTISGSGGSTYYADSVKGRFTISRD NSKNTLYLQMNSLRAEDTAVFYCAIDPEYYDILTGGDYWGQG TLVTVSSGGGGSGGGGSGGGGSGGGGSDIQMTQSPSAMSASV GDRVTITCRASQGISNYLAWFQQKPGKVPKRLIYAASSLQSGV PSRFSGSGSGTEFTLTISSLQPEDFATYFCLQHDSFPLTFGGGTK VEIKTTTPAPRPPTPAPTIASQPLSLRPEACRPAAGGAVHTRGL DFACDIYIWAPLAGTCGVLLLSLVITLYCKRGRKKLLYIFKQPF MRPVQTTQEEDGCSCRFPEEEEGGCELRVKFSRSADAPAYQQ GQNQLYNELNLGRREEYDVLDKRRGRDPEMGGKPRRKNPQE GLYNELQKDKMAEAYSEIGMKGERRRGKGHDGLYQGLSTAT KDTYDALHMQALPPR |

Figure 9A:
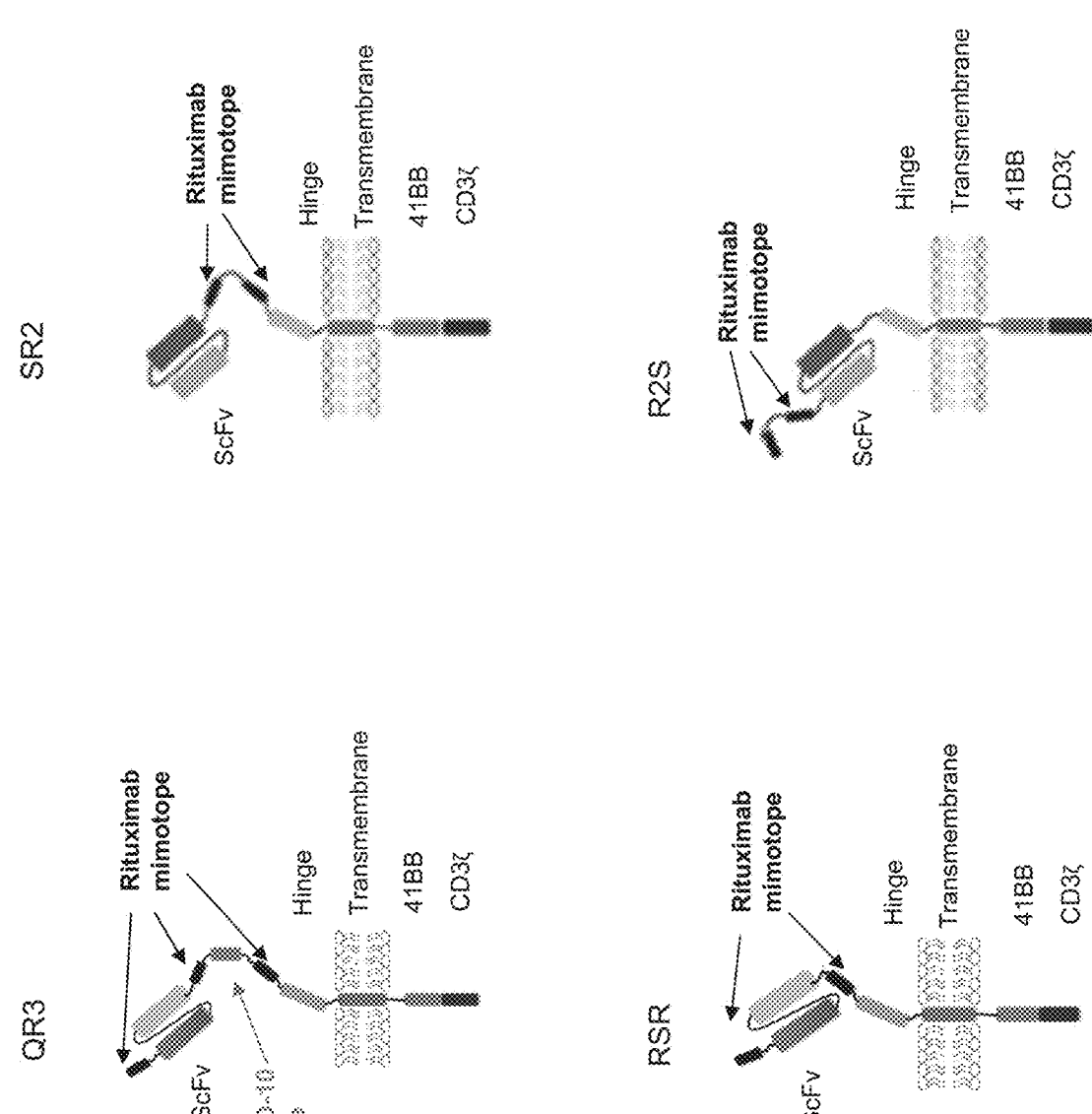
FIGS. 9A-9C depict the structure, transduction efficiency of primary T-cells and the cytotoxic activity of anti-DLL3 CARs with safety switch.
Figure 9B:
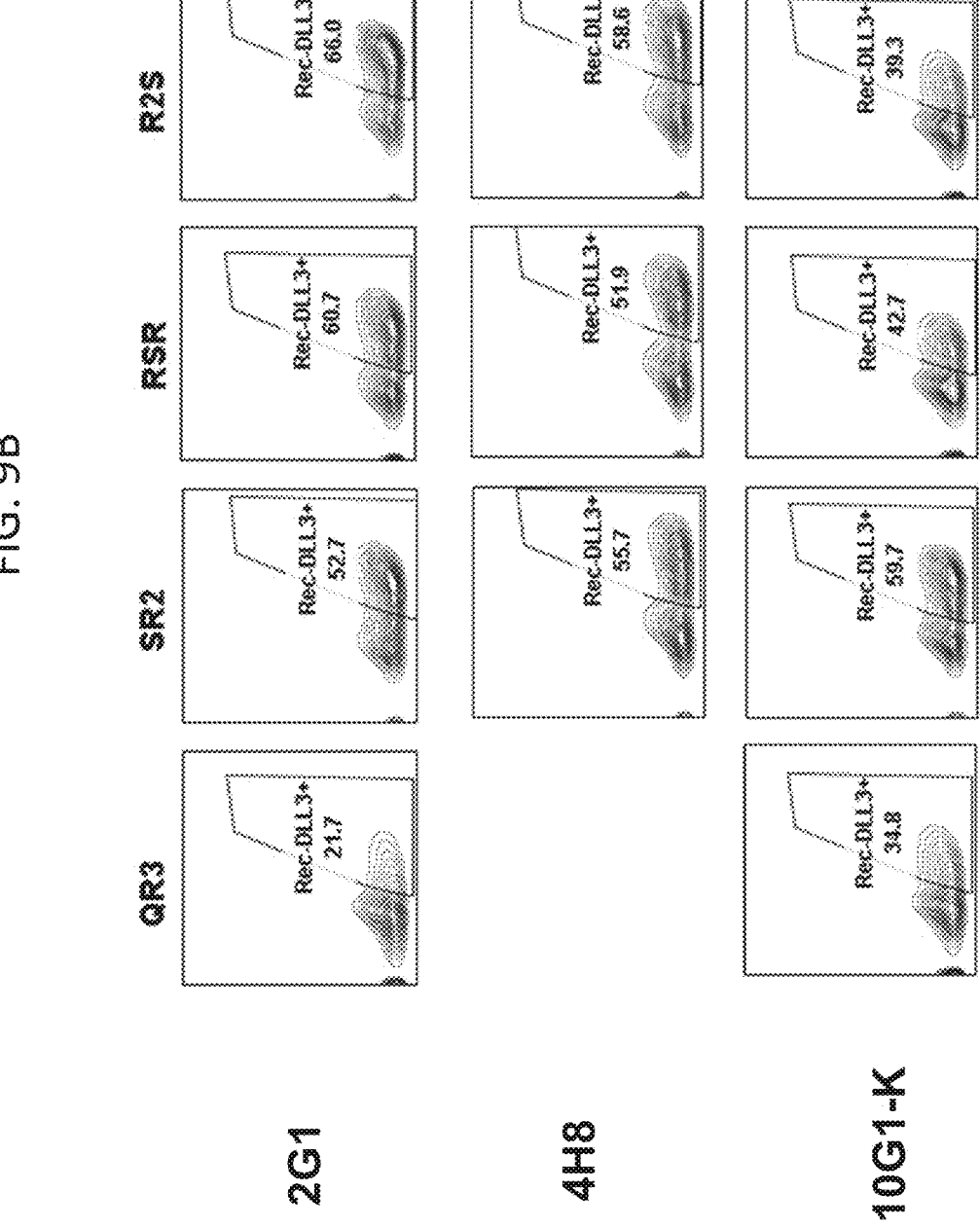
Figure 9C:
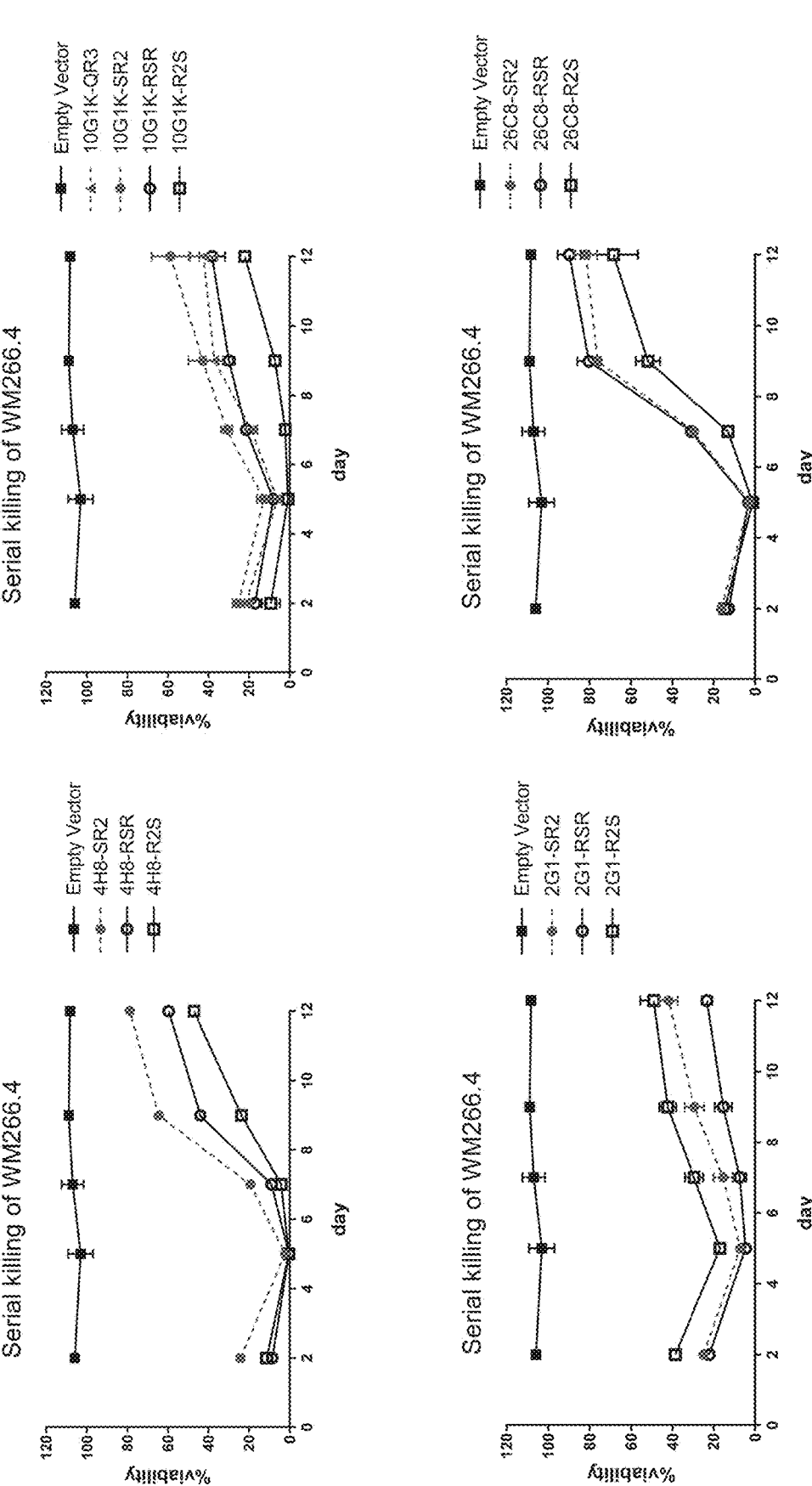

CAR-Ts were generated using methods described in Example 5 and their cytotoxic activity were examined using methods described in Example 7. FIG. 9A are plots showing the structure of four different safety switches. FIG. 9B depicts experimental flow cytometry data showing that anti-DLL3 CARs 2G1, 4H8 and 10G1-K with safety switches are expressed on the surface of primary T-cells and can recognize recombinant DLL3. The plots are gated on live CD3+ cells and the numbers on the plots are the percentage of cells expressing each anti-DLL3 CAR. FIG. 9C depicts experimental data showing that anti-DLL3 CARs with safety switches are active in serial killing assay of DLL3+WM266.4 cell line.

Example 10: Cytotoxicity Against Small Cell Lung Cancer PDX Models

Small cell lung cancer PDX models were purchased from Crown Bioscience. To examine DLL3 expression of cell surface, frozen vials of PDX models were thawed and 200,000 cells were used for each staining sample. The expression of DLL3 was verified in a FACS assay using PE conjugated anti-DLL3 antibody. Brilliant violet 421 conjugated anti-human CD45 and anti-mouse CD45 antibodies were added in the same staining sample to exclude human and mouse lymphocytes.

Figure 10B:
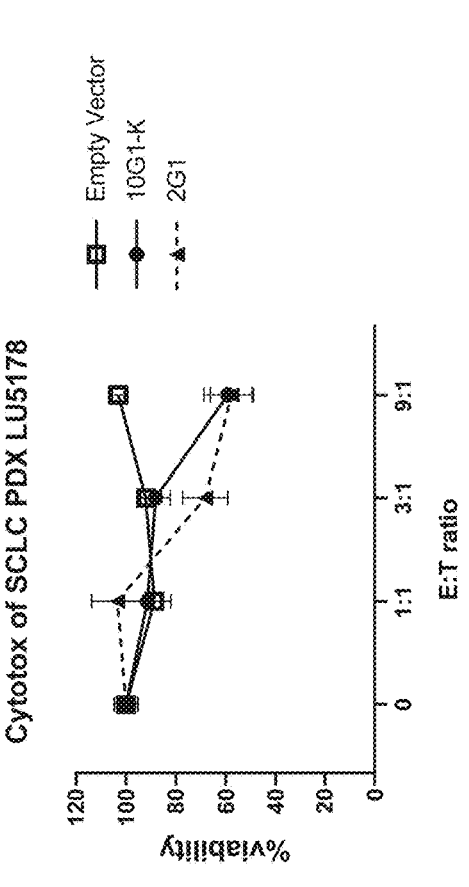
FIG. 10B shows experimental data showing anti-DLL3 CAR-Ts show cytotoxic activity against the same two PDX models.
Figure 10B:
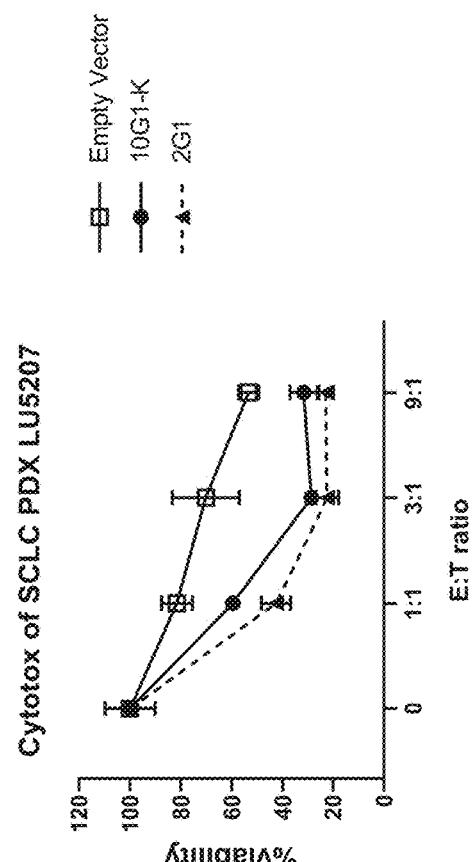
Figure 10A:
FIG. 10A depicts plots showing that two small cell lung cancer patient-derived xenograft (PDX) models express DLL3 on cell surface. Solid line and dashed line represent staining with anti-DLL3 antibodies or fluorescence minus one (FMO), respectively.
Figure 10A:
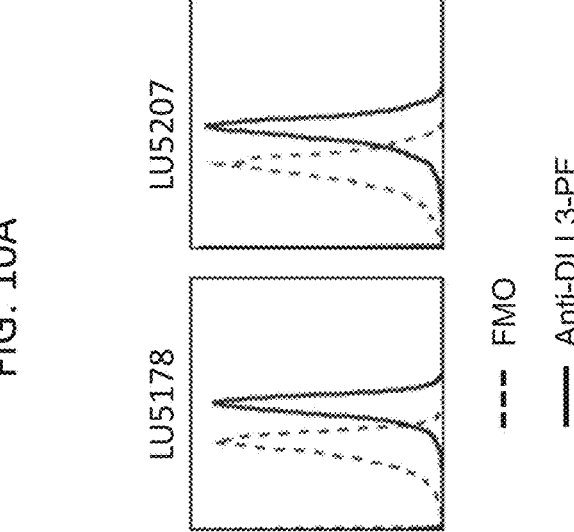

FIG. 10A depicts experimental data showing DLL3 is expressed on the surface of two small cell lung cancer PDX models. FIG. 10B shows experimental data showing anti-DLL3 CAR-T cells killed the same two small cell lung PDX models in a 3-day cytotoxicity assay at indicated effector: target ratios. T cells that didn't express anti-DLL3 CARs (labelled empty vector) were used as negative control.

Figures 11A, 11B:
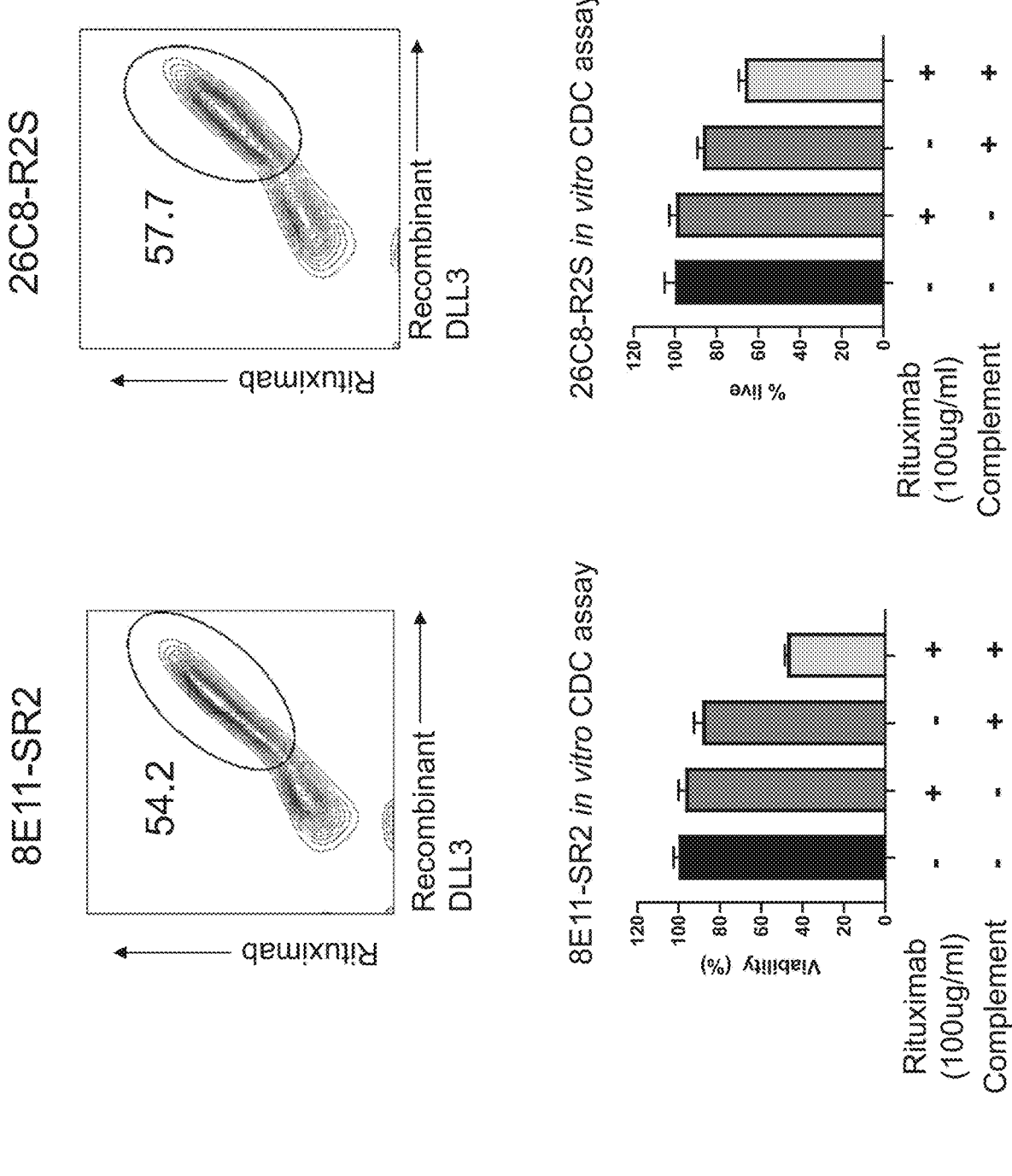
FIGS. 11A-11B show safety switches allow detection and depletion of DLL3 CAR-T cells with rituximab.

Example 11: In Vitro Detection and Depletion of DLL3 CAR-T Cells Using Rituximab-Based Safety-Switch In order to deplete or turn off CAR T cells in the event of unwanted activity, a rituximab off-switch was developed by insertion of rituximab mimotopes at varying location in the extracellular region of the CARs as described in Example 9. Complement-dependent cytotoxicity assay was used to evaluate rituximab-dependent in vitro depletion of DLL3 CAR-T cells. In this assay, frozen CAR-T cells were thawed and $1 \times 10^5$ cells were incubated in RPMI 1640 medium supplemented with 10% FBS in 96-well plates. Cells were incubated for 3 hours in the absence or presence of 25% baby rabbit complement (Cedarlane, CL3441-S) and rituximab antibodies (produced in-house; 100 mg/mL). Cells were stained with recombinant DLL3 (Adipogen) and cytotoxicity was analyzed by flow cytometry. FIG. 11A depicts experimental data showing anti-DLL3 CAR-T cells can be detected by both recombinant DLL3 and rituximab staining. FIG. 11B depicts experimental data showing DLL3 CAR-T cells were depleted in vitro in a rituximab-dependent and complement-dependent manner.

Example 12: In Vivo Activity of Anti-DLL3 CAR-T Cells with a Safety Switch

Figure 12A:
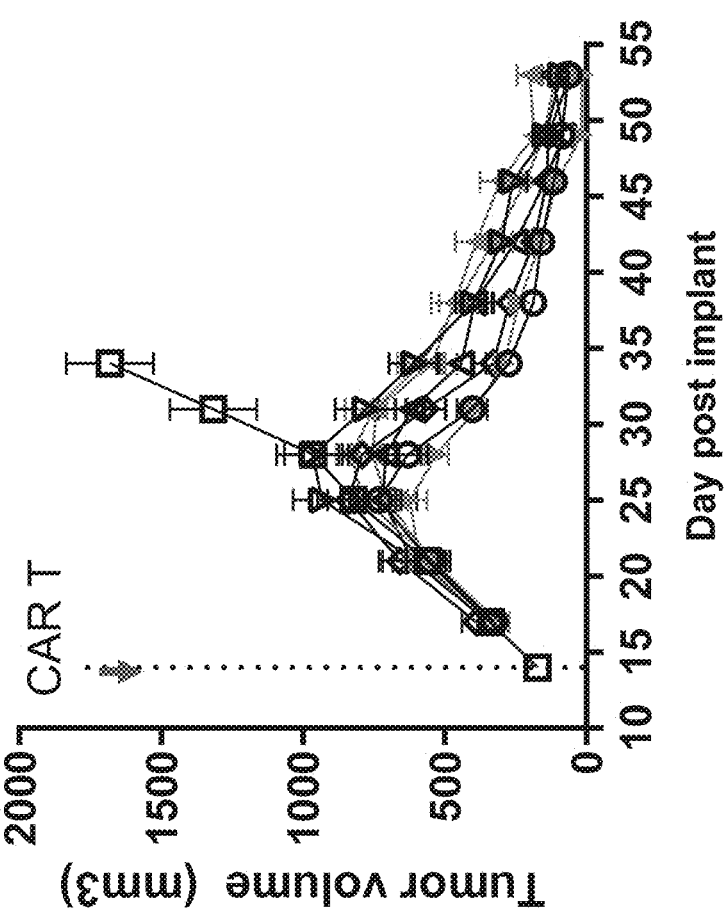
FIGS. 12A-12B depict plots demonstrating that anti-DLL3 CAR-T cells with safety switches inhibited the growth of subcutaneous or IV injected small cell lung cancer tumors.

To test the anti-tumor activity of DLL3 CAR-T cells with a safety switch, SHP-77 tumor bearing NSG mice were used. SHP-77 cells were thawed from a frozen vial, counted and diluted. $50 \times 10^6$ viable cells/mL in RPMI medium/matrigel suspension was injected per mouse subcutaneously. Tumor growth was monitored by caliper measurements using a digital caliper starting from Day 5 post-implantation. Tumor size was calculated using the formula Tumor volume=(width^2×length/2). Mice were randomized into groups of 8 based on tumor volume about 14 days post-implantation. Average tumor volume per group was 178 mm³. On the same day after mice were randomized, Non-transduced T cells and DLL3 CAR-T cells were thawed and counted according to standard procedure. Cells were resuspended in RPMI at $5 \times 10^6$ CAR+ cells/mouse by tail vein IV injection in a volume of 200 uL/mouse. Tumors continued to be monitored every 3-4 days until the end of the study. All groups of DLL3 CAR-T cells with safety switch induced significant tumor inhibition and complete or near complete elimination of detectable tumor by Day 50 (FIG. 12A).

Figure 12B:
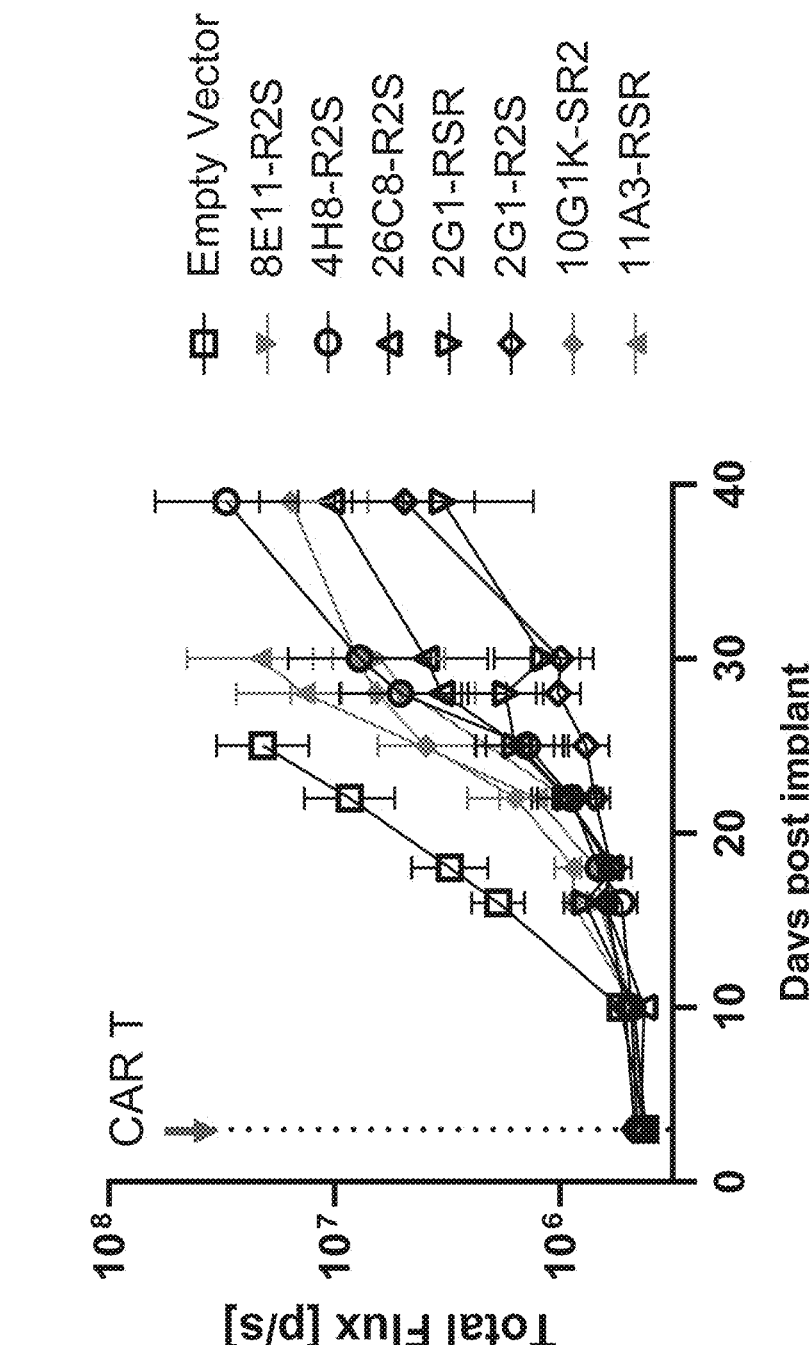

To test anti-tumor activity of DLL3 CAR-T cells in models that show metastasis like human disease, DMS 273 small cell lung tumors expressing exogenous DLL3 (DMS 273-DLL3) were established with tail vein injection. Specifically, DMS 273-DLL3 cells were thawed and diluted to $5 \times 10^5$ viable cells/mL in RPMI medium. 200 uL of cell suspension was injected per mouse by tail vein IV. On day 3 post-implantation, mice were randomized into groups of 9. On the same day, DLL3 CAR-Ts were thawed, counted and resuspended in RPMI medium at $5 \times 10^6$ CAR+ cells per mouse by tail vein IV injection in a volume of 200 uL per mouse. Tumors continued to be monitored every 3-4 days using IVIS imaging system until the end of the study. As shown in FIG. 12B, multiple different DLL3 CARs with different rituximab-based safety switches were effective against metastatic tumors.

Example 13: Mouse Safety Study Using Non-Tumor Bearing Animals

Figures 13A, 13B:
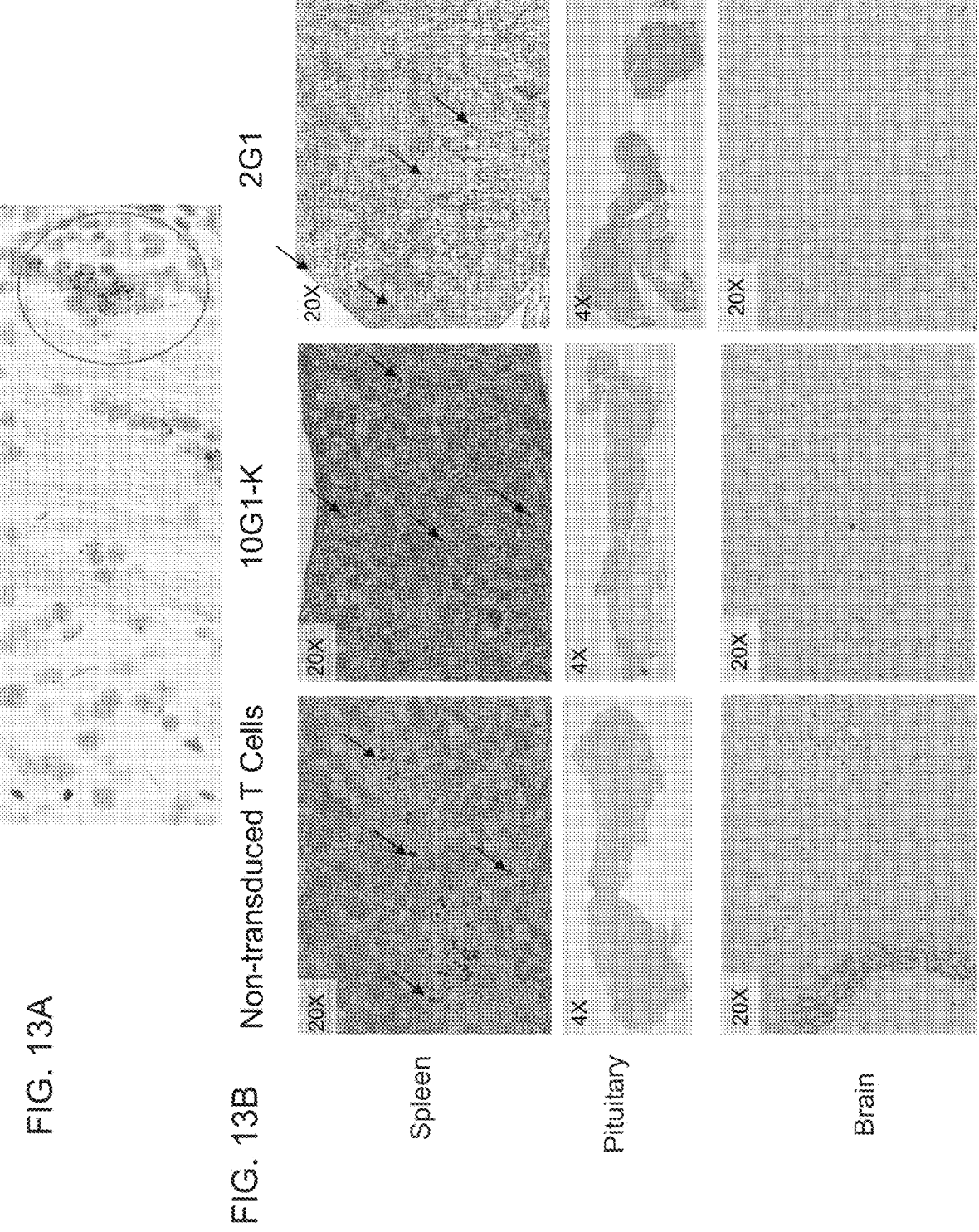
FIG. 13A shows a representative image of mouse DLL3 RNA expression in the brain of NSG mice. Circle indicates clusters of mouse DLL3 RNA.
FIG. 13B shows anti-human CD3 staining of spleen, pituitary and brain samples of animals dosed with non-transduced T cells, 10G1-K DLL3 CAR-T cells or 2G1 DLL3 CAR-T cells. Arrows indicate CD3 positive cells in spleens.

DLL3 RNA has been reported in human brain and pituitary (GTex). Similarly, mouse DLL3 RNA has also been reported in pituitary (Bio-GPS). To understand DLL3 RNA expression in mouse brain, brains from three NSG mice were fixed in 10% neutral buffered formalin (NBF), embedded, serially sectioned at 4-6 microns, and analyzed in an RNAscope®LS Red ISH assay (ACDBio). DLL3 RNA was detected at low levels in brain samples of NSG mice. FIG. 13A shows a representative image of the mouse DLL3 RNA staining observed in this assay.

To understand the potential toxicity liabilities of DLL3 RNA expression in the brain and pituitary, non-transduced T cells, $8 \times 10^6$ 10G1-K DLL3 CAR-T cells, or $8 \times 10^6$ 2G1 DLL3 CAR-T cells were IV injected into NSG mice. Seven days after injection, spleens, brains and pituitaries were harvested, fixed in 10% NBF, embedded, serially sectioned at 4-6 microns, and stained with anti-human CD3 antibody (Abcam, ab52959, 1:500 dilution) to detect human T cells by immunohistochemistry. Although T cells were detected in spleens from all animals, they were not detected in brain or pituitary samples (FIG. 13B). Thus, although DLL3 RNA was detected at a low level in non-tumor bearing NSG mice, DLL3 CAR-T cells were not detected in the brain or pituitary samples of the mice.

Example 14: Mouse Safety Study Using Animals Bearing Subcutaneous Tumor

Figure 14A:
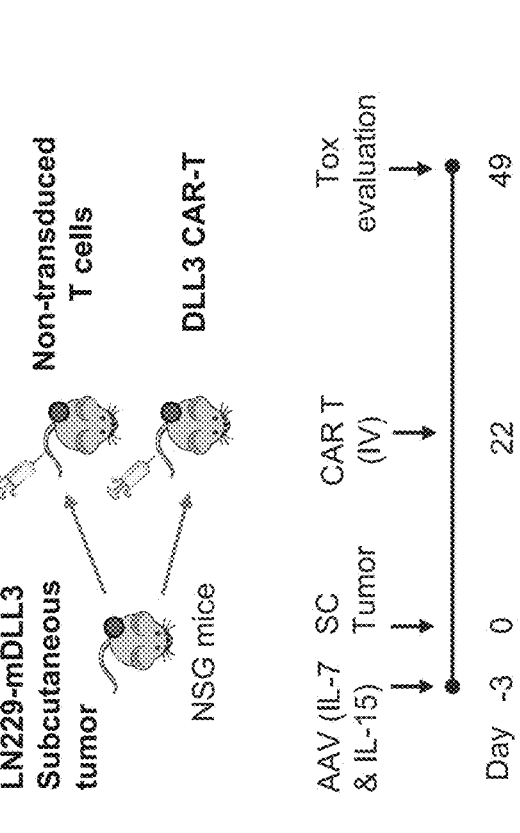
Figure 14B:

To further evaluate potential brain and pituitary toxicity liabilities, DLL3 CAR-T cells were injected into NSG mice bearing subcutaneous LN229 tumors that express exogenous mouse DLL3 (LN229-mDLL3). In this model, activation of CAR-T by tumor cells may lead to increased sensitivity and activity against potential DLL3-expressing normal tissues. The experiment design is shown in FIG. 14A. Three days before tumor implantation (day −3), adeno-associated viruses (AAV) encoding IL-7 & IL-15 (Vigene Biosciences) were injected through tail vein to support CAR-T cell expansion and persistence. LN229-mDLL3 cells were then thawed from a frozen vial and diluted to $4.25 \times 10^7$ cells/mL in complete growth medium (RPMI+10% FBS). Cell suspension was kept on ice until implantation. Immediately before implanting, cells were mixed 1:1 with BD Matrigel Matrix (cat #354234) and 200 µL of cells/matrigel suspension containing $4.25 \times 10^6$ LN229-mDLL3 cells was injected per mouse subcutaneously. Tumor growth was monitored by caliper measurements using a digital caliper starting from Day 8 post-implantation. Tumor size was calculated using the formula Tumor volume=(width^2×length/2). On day 22 post implantation, mice were randomized into groups of 5 based on tumor volume and serum concentration of IL-7 and IL-15. On the same day (day 22), non-transduced T cells and mouse cross-reactive 10G1-K DLL3 CAR-T cells were thawed and resuspended in RPMI+10% FBS and injected at $1 \times 10^7$ CAR+ cells/mouse by tail vein IV injection in a volume of 200 uL/mouse. Tumors continued to be monitored every 3-4 days until the end of the study and robust anti-tumor activity with DLL3 CAR T treatment was observed (FIG. 14B).

On day 49, when animals that received DLL3 CAR-T cells were tumor free, brain tissues from animals were fixed in 10% NBF and embedded to reveal the ventricular system, including the lateral, third and fourth ventricles, such that the three sections were placed into a single block that was serially sectioned at 4-6 microns, and stained with hematoxylin and eosin (H&E) or stained to detect human-specific CD3 (hCD3) by immunohistochemistry. Pituitary glands were fixed in 10% NBF, processed and stained with H&E or immunohistochemically stained to demonstrate hCD3. The H&E slides were examined microscopically and histopathologic findings were scored by a pathologist using a standard system. Administration of DLL3 CAR-T cells resulted in abundant hCD3-staining T cells in the pituitary pars intermedia and nervosa with relatively few T cells in the pars distalis (FIG. 14C and data not shown). Sparse-to-moderately low or moderate-to-moderately high hCD3 staining of T cells was present in brain neuropil and vasculature (as circulating T cells) (FIG. 14C and data not shown). No other pituitary or brain findings were present (FIGS. 14C-D). To understand the functional consequences of T cell infiltration, two hormones released in the pars nervosa, vasopressin and oxytocin, were stained using immunohistochemistry. For vasopressin detection, samples were stained with anti-vasopressin antibody (ImmunoStar, 20069) at 1/7,000 dilution for 1 hour at room temperature and then with Rabbit-on-Rodent HRP-Polymer (Biocare Medical) for 30 minutes at room temperature. For oxytocin detection, samples were stained with anti-oxytocin antibody (ImmunoStar, 20068) at 193 194

Figures 14E, 14F:
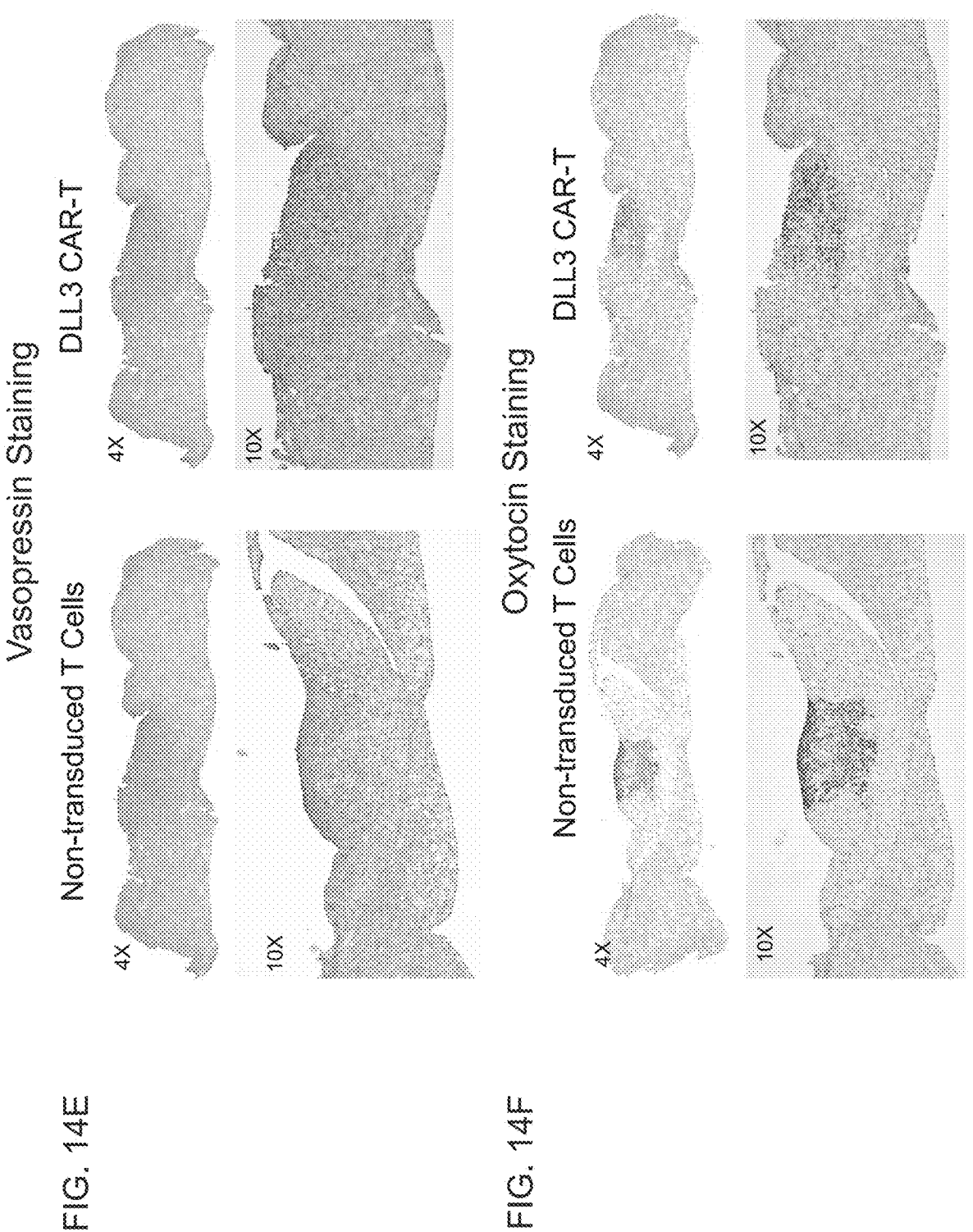

1/10,000 dilution for 15 minutes at room temperature and then with Rabbit-on-Rodent HRP-Polymer (Biocare Medical) for 30 minutes at room temperature. Both hormones can be detected in the pituitary pars nervosa of animals that received non-transduced T cells or DLL3 CAR-T cells, suggesting that hormone producing neurons in this region remained functional (FIGS. 14E-F). Thus, no tissue damage was seen in the samples based on the pathological evaluation and hormone staining.

Example 15: Mouse Safety Study Using Animals Bearing Intracranial Tumors

Figures 15A, 15B:
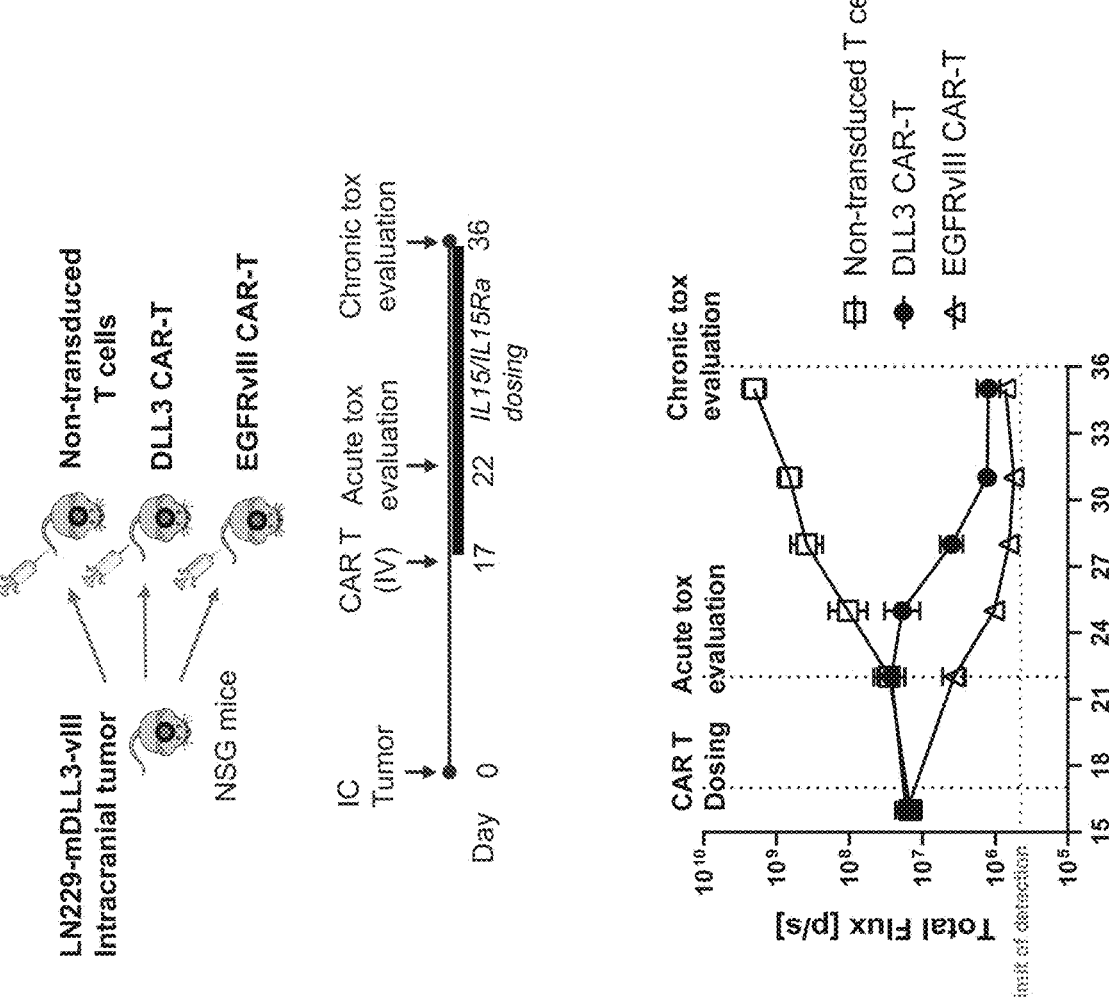

To promote T cell infiltration into the brain and further understand potential brain toxicity, NSG mice bearing intracranial LN229 tumors that express exogenous mouse DLL3 and human EGFRvIII (LN229-mDLL3-vIII) were used. The experiment design is shown in FIG. 15A. LN229-mDLL3 cells were thawed from a frozen vial and diluted to $1 \times 10^7$ viable cells/mL in RPMI. Then 3 µL of cell suspension containing $3 \times 10^4$ LN229-mDLL3 cells was injected per mouse intracranially. Tumor growth was monitored by IVIS imaging system. On day 17 post implantation, mice were randomized into groups of 10 based on tumor volume. On the same day (day 17), TCR knocked-out, non-transduced T cells, 10G1-K DLL3 CAR-T cells, and EGFRvIII CAR-T cells were thawed and resuspended in RPMI and injected at $1 \times 10^7$ CAR+ cells/mouse by tail vein IV injection in a volume of 200 uL/mouse. EGFRvIII CAR-T cells were included as control to evaluate potential inflammation caused by tumor lysis in the brain. In order to support CAR-T cell expansion and persistence, 0.5 ug IL-15 (Peprotech AF-200-15) and 3 ug IL-15Ra Fc fusion protein (R&D Systems 7194-IR) were given to each animal twice weekly starting on day 17 until the end of the study. Tumors continued to be monitored every 3-4 days until the end of the study and clear anti-tumor activity was observed (FIG. 15B). On day 22 and 38, brain tissues from all animals were trimmed, processed, and embedded to reveal the ventricular system, including the lateral, third and fourth ventricles, such that the three sections were placed into a single block that was serially sectioned at 4-6 microns, and stained with H&E or stained to detect human-specific CD45 (hCD45) by immunohistochemistry. Pituitary gland tissues were processed to include pars nervosa, intermedia, and distalis, and stained with H&E or immunohistochemically stained to detect hCD45 as the marker for human T cells.

On day 22, animals that received non-transduced T cells or 10G1-K DLL3 CAR-T cells had rare/sparse hCD45 staining T cells in the brain or pituitary gland (data not shown). On the other hand, for animals treated with EGFRvIII CAR-T cells, hCD45+ staining ranged from rare/sparse to moderately low or moderate-to-moderately high in areas of infiltrate/gliosis or glioma, consistent with anti-tumor activity in this group (data not shown). On day 38, animals that received non-transduced T cells or EGFRvIII CAR-T cells had rare/sparse hCD45+ staining in the brain and pituitary gland. Animals that received 10G1-K DLL3 CAR-T cells had minimal or mild mononuclear cell infiltrate in the pituitary gland, primarily in the pars intermedia and nervosa (FIGS. 15C-D). Also, these animals had slightly more (moderately low) hCD45+ staining associated with the small foci of glioma compared with the rare/sparse staining in other areas of the brain (vasculature of the brain, choroid plexus, and meninges), consistent with anti-tumor activity in this group as shown in FIG. 15B.

Example 16: In Vitro Cytotoxicity of Disassociated Mouse Pituitary Cells

To directly test whether the DLL3 CARTs are active against the pituitary, mouse pituitaries from NSG mice were harvested under aseptic conditions for in vitro analysis. Tissues were dissociated by 3 rounds of incubations at 37 C in 1 mL dissociation mix [5 mL DMEM, high glucose, GlutaMax (Gibco, cat #10564), 50 uL Enzyme H, 5 uL Enzyme R, 6.25 uL Enzyme A (Miltenyi tumor dissociation kit #130-095-929)] followed by mechanical dissociation using trituration. Single cells were transferred to complete medium (DMEM, high glucose, GlutaMax, 20%, 1× Insulin-Transferrin-Selenium Solution, 1×MEM Non-Essential Amino Acids, 1× Penicillin-Streptomycin) and pooled following each round. Cells were pelleted and treated with ACK lysis buffer for 3 min at RT, followed by neutralization in complete medium. The cell suspension was filtered through a 70u filter and centrifuged to remove buffer. Cells were counted and plated in 96-well plate in complete medium at $5 \times 10^4$ cells per well and let to recover for 3 days before CAR-T cells were added. At the time CAR-T cells are added, the expected target density is $1 \times 10^4$ cells per well. For controls, DLL3$^+$ cells (DMS-273) and DLL3$^-$ cells (293T) were plated at the same densities. 10G1-K and 2G1 DLL3 CAR-T cells were added at E:T=9:1, 3:1, and 1:1 and co-cultured with targets for 3 days. At the end of 3 day co-culture, the media was separated from the wells and centrifuged to pellet out the T cells. The target cells were treated with 50 uL/well Cell Titer Glo (Promega, G7570) for 10 minutes and analyzed in SpectraMax plate reader for cytotox readout.

Figure 16A:
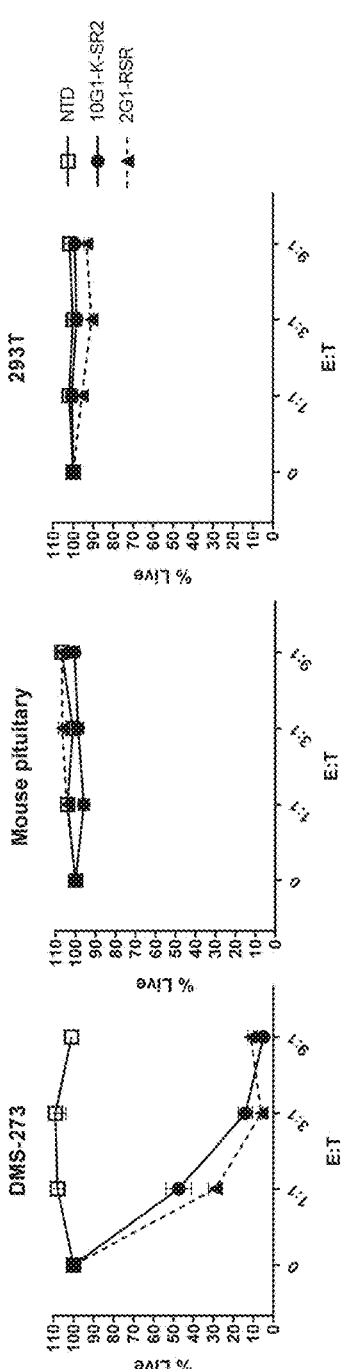
FIGS. 16A-16C show the experimental data of the in vitro cytotoxicity of dissociated mouse pituitary cells.
Figure 16B:
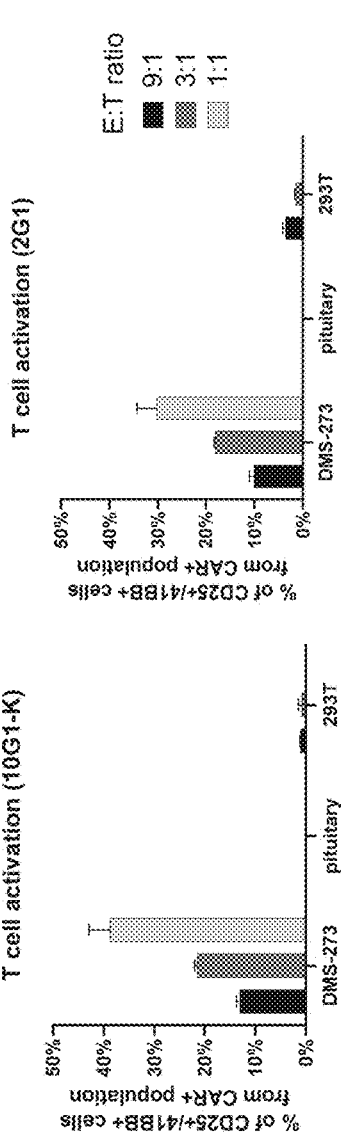
Figure 16C:
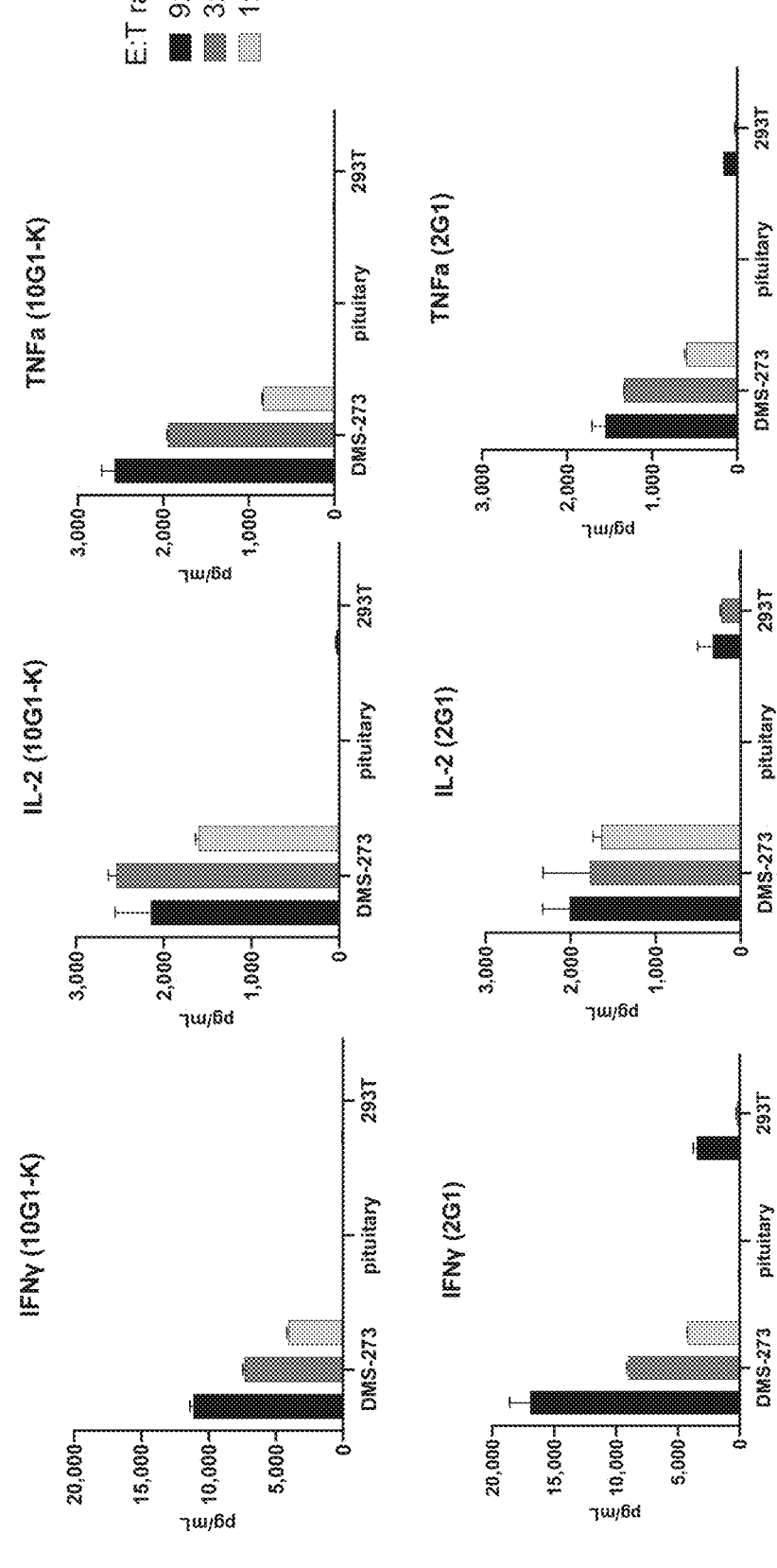

FIG. 16A depicts experimental data showing that although DLL3 CAR-T cells are active against DLL3+ DMS 273 cell line, they are not cytotoxic against mouse pituitary cells in vitro. The T cells were pooled and stained for activation markers (41BB and CD25) for analysis by flow cytometry. FIG. 16B depicts that mouse pituitary cells do not activate DLL3 CAR-T cells in vitro. The supernatant was frozen at −80 C and then thawed for cytokine analysis using Human TH1/TH2 10-Plex Tissue Culture Kit (Meso Scale Discovery, K15010B). FIG. 16C depicts that although both 10G1-K and 2G1 DLL3 CAR-T cells secrete interferon-gamma (IFNγ), tumor necrosis factor alpha (TNF-α), and IL-2 when co-cultured with DLL3+ DMS 273 cell line, there is no cytokine secretion after co-culturing DLL3 CAR-T cells with mouse pituitary cells. Thus, DLL3 CAR-T cells were not cytotoxic against pituitary cells in vitro.

What is claimed is:

1. An isolated polynucleotide encoding a chimeric antigen receptor comprising an extracellular domain, a hinge domain, a transmembrane domain, and an intracellular domain, wherein the extracellular domain comprises a DLL3 antigen binding domain that specifically binds to DLL3, and wherein the antigen binding domain comprises:
   (a) a variable heavy chain CDR1 comprising the amino acid sequence shown as SEQ ID NO: 109;
   (b) a variable heavy chain CDR2 comprising the amino acid sequence shown as SEQ ID NO: 110;
   (c) a variable heavy chain CDR3 comprising the amino acid sequence shown as SEQ ID NO: 111;
   (d) a variable light chain CDR1 comprising the amino acid sequence shown as SEQ ID NO: 112;
   (e) a variable light chain CDR2 comprising the amino acid sequence shown as SEQ ID NO: 113; and
   (f) a variable light chain CDR3 comprising the amino acid sequence shown as SEQ ID NO: 114.

2. A vector comprising the polynucleotide of claim 1.

3. The isolated polynucleotide of claim 1, wherein the hinge domain is a selected from a CD8 hinge domain, a CD4 hinge domain, a CD28 hinge domain, a 4-1BB hinge domain, or an IgG hinge domain.

4. The isolated polynucleotide of claim 1, wherein the hinge domain is a CD8 hinge domain.

5. The isolated polynucleotide of claim 4, wherein the CD8 hinge domain is a CD8alpha hinge domain.

6. The isolated polynucleotide of claim 1, wherein the hinge domain is a CD28 hinge domain.

7. The isolated polynucleotide of claim 1, wherein the transmembrane domain is selected from a CD8 transmembrane domain, a CD4 transmembrane domain, a CD28 transmembrane domain, or a 4-1BB transmembrane domain.

8. The isolated polynucleotide of claim 1, wherein the transmembrane domain is a CD8 transmembrane domain.

9. The isolated polynucleotide of claim 8, wherein the CD8 transmembrane domain is a CD8alpha transmembrane domain.

10. The isolated polynucleotide of claim 1, wherein the transmembrane domain is a CD28 transmembrane domain.

11. The isolated polynucleotide of claim 1, wherein the antigen binding domain comprises:
   (a) a variable heavy chain comprising the amino acid sequence shown as SEQ ID NO: 115; and (b) a variable light chain comprising the amino acid sequence shown as SEQ ID NO: 116, wherein the variable heavy chain and the variable light chain is linked by at least one linker.

12. The isolated polynucleotide of claim 1, wherein the antigen binding domain comprises the scFv sequence shown as SEQ ID NO: 117.

13. The isolated polynucleotide of claim 1, wherein the chimeric antigen receptor comprises an amino acid sequence that is 100% identical to SEQ ID NO: 644.

14. The isolated polynucleotide of claim 1, wherein the intracellular domain comprises one or two costimulatory domains.

15. The isolated polynucleotide of claim 14, wherein the costimulatory domains are a signaling region of CD28, OX-40, or 4-1BB/CD137.

16. The isolated polynucleotide of claim 15, wherein the 4-1BB/CD137 costimulatory domain comprises SEQ ID NO: 480.

17. The isolated polynucleotide of claim 1, wherein the intracellular domain comprises at least one activating domain.

18. The isolated polynucleotide of claim 17, wherein the intracellular domain comprising at least one activating domain comprises CD3zeta.

19. The isolated polynucleotide of claim 18, wherein the CD3zeta comprises SEQ ID NO: 481.

20. The isolated polynucleotide of claim 1, further comprising a safety switch.

21. The isolated polynucleotide of claim 1, wherein the chimeric antigen receptor comprises one or more safety switches in the format of a) QR3 comprising CD8alpha signal sequence-linker-CD20 mimotope-linker-anti-DLL3 scFv-linker-CD20 mimotope-linker-QBEND-10 epitope-linker-CD20 mimotope-hinge and transmembrane regions of human CD8alpha molecule-41BB signaling domain-CD3zeta signaling domain, b) SR2 comprising CD8alpha signal sequence-anti-DLL3 ScFv-linker-CD20 mimotope-linker-CD20 mimotope-linker-hinge and transmembrane regions of human CD8alpha molecule-4-1BB signaling domain-CD3zeta signaling domain, c) RSR comprising CD8alpha signal sequence-linker-CD20 mimotope-linker-anti-DLL3 scFv-linker-CD20 mimotope-linker-hinge and transmembrane regions of human CD8alpha molecule-4-1BB signaling domain-CD3zeta signaling domain, or d) R2S comprising CD8alpha signal sequence-linker-CD20 mimotope-linker-CD20 mimotope-linker-anti-DLL3 scFv-linker-hinge and transmembrane regions of human CD8alpha molecule-4-1BB signaling domain-CD3zeta signaling domain.

22. The isolated polynucleotide of claim 20, wherein the chimeric antigen receptor comprises the amino acid sequence shown as SEQ ID NO: 686.

23. An engineered immune cell expressing the vector of claim 2.

24. An isolated polynucleotide encoding an anti-DLL3 binding agent comprising an antigen binding domain of an antibody that specifically binds to DLL3, wherein the antigen binding domain comprises:

(a) a variable heavy chain CDR1 comprising the amino acid sequence shown as SEQ ID NO: 109;

(b) a variable heavy chain CDR2 comprising the amino acid sequence shown as SEQ ID NO: 110;

(c) a variable heavy chain CDR3 comprising the amino acid sequence shown as SEQ ID NO: 111;

(d) a variable light chain CDR1 comprising the amino acid sequence shown as SEQ ID NO: 112;

(e) a variable light chain CDR2 comprising the amino acid sequence shown as SEQ ID NO: 113; and (f) a variable light chain CDR3 comprising the amino acid sequence shown as SEQ ID NO: 114.

25. The isolated polynucleotide of claim 24, wherein the binding agent is an antibody, an antibody conjugate, or an antigen-binding fragment thereof, wherein the antigen-binding fragment thereof is a F(ab')2 fragment, a Fab' fragment, a Fab fragment, a Fv fragment, a scFv fragment, or a dsFv fragment.

26. The isolated polynucleotide of claim 25, wherein the binding agent is a monoclonal antibody comprising an IgG constant region.

* * * * *